US012662469B2

(12) United States Patent
Zhang et al.

(10) Patent No.: US 12,662,469 B2
(45) Date of Patent: Jun. 23, 2026

(54) CYCLIC UREAS

(71) Applicant: SIRONAX LTD, Grand Cayman (KY)

(72) Inventors: Zhiyuan Zhang, Beijing (CN); Yaning Su, Beijing (CN); Jianguang Han, Beijing (CN); Hanying Ruan, Beijing (CN); Ying Li, Beijing (CN); Guozheng Wang, Beijing (CN); Wendong Liu, Beijing (CN); Chong Zhang, Beijing (CN); Leiming Liang, Beijing (CN)

(73) Assignee: SIRONAX LTD, Grand Cayman (KY)

( * ) Notice: Subject to any disclaimer, the term of this patent is extended or adjusted under 35 U.S.C. 154(b) by 946 days.

(21) Appl. No.: 17/325,200

(22) Filed: May 19, 2021

(65) Prior Publication Data

US 2021/0292305 A1 Sep. 23, 2021

Related U.S. Application Data

(63) Continuation of application No. PCT/CN2019/119795, filed on Nov. 20, 2019.

(30) Foreign Application Priority Data

Nov. 20, 2018 (WO) ................ PCT/CN2018/116553

(51) Int. Cl.

| | |
|---|---|
| ***C07D 403/12*** | (2006.01) |
| ***C07D 231/06*** | (2006.01) |
| ***C07D 401/06*** | (2006.01) |
| ***C07D 401/14*** | (2006.01) |
| ***C07D 403/06*** | (2006.01) |
| ***C07D 403/14*** | (2006.01) |
| ***C07D 405/12*** | (2006.01) |
| ***C07D 413/06*** | (2006.01) |
| ***C07D 413/12*** | (2006.01) |
| ***C07D 413/14*** | (2006.01) |
| ***C07D 417/12*** | (2006.01) |
| ***C07D 471/04*** | (2006.01) |
| ***C07D 487/04*** | (2006.01) |
| ***C07D 495/04*** | (2006.01) |
| ***C07D 513/04*** | (2006.01) |

(52) U.S. Cl.

CPC ......... *C07D 403/12* (2013.01); *C07D 231/06* (2013.01); *C07D 401/06* (2013.01); *C07D 401/14* (2013.01); *C07D 403/06* (2013.01); *C07D 403/14* (2013.01); *C07D 405/12* (2013.01); *C07D 413/06* (2013.01); *C07D 413/12* (2013.01); *C07D 413/14* (2013.01); *C07D 417/12* (2013.01); *C07D 471/04* (2013.01); *C07D 487/04* (2013.01); *C07D 495/04* (2013.01); *C07D 513/04* (2013.01)

(58) Field of Classification Search

CPC .................................................... C07D 403/12

See application file for complete search history.

(56) References Cited

U.S. PATENT DOCUMENTS

| | | | |
|---|---|---|---|
| 4,839,376 | A | 6/1989 | Hiroyuki et al. |
| 6,159,990 | A | 12/2000 | Lagu et al. |
| 6,756,394 | B1 | 6/2004 | Yuan et al. |
| 8,278,344 | B2 | 10/2012 | Cuny et al. |
| 9,974,762 | B2 | 5/2018 | Zhang et al. |
| 10,092,529 | B2 | 10/2018 | Zhang et al. |
| 2003/0083386 | A1 | 5/2003 | Yuan et al. |
| 2004/0259884 | A1 | 12/2004 | Haley et al. |
| 2009/0099242 | A1 | 4/2009 | Cuny et al. |
| 2010/0317701 | A1 | 12/2010 | Cuny et al. |
| 2011/0144169 | A1 | 6/2011 | Cuny et al. |
| 2012/0122889 | A1 | 5/2012 | Yuan et al. |
| 2012/0309795 | A1 | 12/2012 | Cuny et al. |
| 2016/0168128 | A1 | 6/2016 | Rammer et al. |
| 2017/0290790 | A1 | 10/2017 | Zhang et al. |
| 2021/0350581 | A1 | 11/2021 | Kamada et al. |

FOREIGN PATENT DOCUMENTS

| | | | |
|---|---|---|---|
| CN | 102316735 | A | 1/2012 |
| CN | 107108492 | A | 8/2017 |
| CN | 108602809 | A | 9/2018 |
| CO | 20170013709 | A2 | 3/2018 |
| EP | 1193259 | A1 | 4/2002 |
| JP | S6479157 | A | 3/1989 |

(Continued)

OTHER PUBLICATIONS

Hsu et al., "Development and Optimization of Piperidyl-1,2,3-Triazole Ureas as Selective Chemical Probes of Endocannabinoid Biosynthesis", J Med Chem., Nov. 14, 2014 (Year: 2014).*

Annibaletto et al., "Multicomponent Catalytic Enantioselective Synthesis of Isoxazolidin-5-Ones", Advanced Synthesis and Catalysis, Jul. 26, 2021 (Year: 2021).*

Holler, N. et al., Fas triggers an alternative, caspase-8-independent cell death pathway using the kinase RIP as effector molecule, *Nature Immunology*, 2000, 1(6), pp. 489-495.

Degterev, A. et al., Identification of RIP1 kinase as a specific cellular target of necrostatins, *Nature Chemical Biology*, 2008, 4(5), pp. 313-321.

Dunai, Z., et al., Necroptosis: Biochemical, Physiological and Pathological Aspects, *Pathology & Oncology Research*, 2011, 17(4), pp. 791-800.

(Continued)

*Primary Examiner* — Andrew D Kosar

*Assistant Examiner* — Gillian A Hutter

(74) *Attorney, Agent, or Firm* — Troutman Pepper Locke LLP

(57) ABSTRACT

The invention provides amides that inhibit cellular necrosis and/or human receptor interacting protein 1 kinase (RIP1), including corresponding sulfonamides, and pharmaceutically acceptable salts, hydrates and stereoisomers thereof. The compounds are employed in pharmaceutical compositions, and methods of making and use, including treating a person in need thereof with an effective amount of the compound or composition, and detecting a resultant improvement in the person's health or condition.

20 Claims, No Drawings

(56) References Cited

FOREIGN PATENT DOCUMENTS

| | | | | | |
|---|---|---|---|---|---|
| JP | H04230367 | A | | 8/1992 | |
| JP | 2005526091 | A | | 9/2005 | |
| JP | 2006527712 | A | | 12/2006 | |
| JP | 2006527756 | A | | 12/2006 | |
| JP | 2010513519 | A | | 4/2010 | |
| NC | 20200015153 | A2 | | 3/2011 | |
| NC | 20200015156 | A2 | | 2/2021 | |
| WO | WO 9857940 | A1 | | 12/1998 | |
| WO | WO 2000078730 | A1 | | 12/2000 | |
| WO | WO 03079973 | A2 | | 10/2003 | |
| WO | WO 2004100946 | A1 | | 11/2004 | |
| WO | WO 2004110996 | A1 | | 12/2004 | |
| WO | WO 2009023272 | A1 | | 2/2009 | |
| WO | WO-2010074588 | A2 | * | 7/2010 | ......... A61K 31/4178 |
| WO | WO 2010075290 | A1 | | 7/2010 | |
| WO | WO 2010075561 | A1 | | 7/2010 | |
| WO | WO 2012125544 | A2 | | 9/2012 | |
| WO | 2016101885 | A1 | | 6/2016 | |
| WO | WO 2016101887 | A1 | | 6/2016 | |
| WO | WO 2017096301 | A1 | | 6/2017 | |
| WO | 2017004500 | A1 | | 7/2017 | |
| WO | 17136727 | A1 | | 8/2017 | |
| WO | 2018192416 | A1 | | 10/2018 | |
| WO | 2019213445 | A1 | | 11/2019 | |
| WO | 2019213447 | A1 | | 11/2019 | |
| WO | 2020013531 | A1 | | 1/2020 | |

OTHER PUBLICATIONS

Degterev, A. et al., Chemical inhibitor of nonapoptotic cell death with therapeutic potential for ischemic brain injury, *Nature Chemical Biology*, 2005, 1(2), pp. 112-119.

Manguso, R. T. et al., In vivo CRISPR screening identifies Ptpn2 as a cancer immunotherapy target, *Nature*, 2017, 547(7664), pp. 413-418.

Wang, W. et al., RIP1 Kinase Drives Macrophage-Mediated Adaptive Immune Tolerance in Pancreatic Cancer, *Cancer Cell*, 2018, 34(5), pp. 757-774.

Berge, S. M., et al., Pharmaceutical Salts, *Journal of Pharmaceutical Sciences*, 1977, 66(1), pp. 1-19.

Cox, C. D. et al., Kinesin spindle protein (KSP) inhibitors. Part 4: Structure-based design of 5-alkylamino-3,5-diaryl-4,5-dihydropyrazoles as potent, water-soluble inhibitors of the mitotic kinesin KSP, *Bioorganic & Medicinal Chemistry Letters*, 2006, 16(12), pp. 3175-3179.

Sebastian, J., Dihydropyrazole and dihydropyrrole structures based design of Kif15 inhibitors as novel therapeutic agents for cancer, *Computational Biology and Chemistry*, 2017, 68, pp. 164-174.

He, S., et al, Small Molecules Simultaneously Inhibiting p53-Murine Double Minute 2 (MDM2) Interaction and Histone Deacetylases (HDACs): Discovery of Novel Multitargeting Antitumor Agents, *Journal of Medicinal Chemistry*, 2018, 61, pp. 7245-7260.

Wu, R., et al., Highly Sensitive Spectroscopic Detection of Chiral Molecular Structures by 77Se NMR Spectroscopy, Spectroscopy, Jan. 1, 1996, vol. 11, No. 6, pp. 37-42.

International Search Report and Written Opinion in counterpart PCT application No. PCT/CN2019/119795, mailed Feb. 19, 2020.

Supplementary European Search Report in counterpart European patent application No. EP19886719, dated Nov. 17, 2021.

C. Cox et al., Two-step synthesis of β-alkyl chalcones and their use in the synthesis of 3,5-diaryl-5-alkyl-4,5-dihydropyrazoles, Tetrahedron Letters, 45(7), 1489-1493, (2004).

Y. Ren et al., Discovery of a Highly Potent, Selective, and Metabolically Stable Inhibitor of Receptor-Interacting Protein 1 (RIP1) for the Treatment of Systemic Inflammatory Response Syndrome, Journal of Medicinal Chemistry, 60(3), 972-986 (2016).

RN 2184622-52-2 listed in STN Registry dated Dec. 15, 2004.

RN 797795-40-5 etc. listed in STN Registry dated Mar. 5, 2018.

* cited by examiner

CYCLIC UREAS

INTRODUCTION

Tumor necrosis factor alpha (TNF-α)-induced NF-κB activation plays a central role in the immune system and inflammatory responses. Receptor-interacting protein 1 (RIP1) is a multi-functional signal transducer involved in mediating nuclear factor κB (NF-κB) activation, apoptosis, and necroptosis. The kinase activity of RIP1 is critically involved in mediating necroptosis, a caspase-independent pathway of necrotic cell death. Holler et al. Nat Immunol 2000; 1: 489-495; Degterev et al. Nat Chem Biol 2008; 4: 313-321.

Necroptosis plays a role in various pathological forms of cell death, including ischemic brain injury, neurodegenerative diseases and viral infections. Dunai, et al., December 2011, Pathol. Oncol. Res.: POR 17 (4): 791-800. Necrostatin-1 (Nec-1), a small molecule inhibitor of RIP1 kinase activity, can block necroptosis. Degterev et al. Nat Chem Biol 2005; 1: 112-119.

RIP1 can contribute to D-1 immunotherapy resistance (e.g. Manguso et al., 2017 Nature 547, 413-418) and can act as a checkpoint kinase governing tumor immunity (e.g. Wang et al, Cancer Cell 34, 757-774, Nov. 12, 2018).

Related patent publications include: U.S. Pat. No. 9,974,762, U.S. Ser. No. 10/092,529, U.S. Pat. Nos. 6,756,394, 8,278,344, US2012122889, US2009099242, US2010317701, US2011144169, US20030083386, US20120309795, WO2009023272, WO2010075290, WO2010075561, WO2012125544.

SUMMARY OF THE INVENTION

The invention provides compounds that are inhibitors of necrosis, ferroptosis, human receptor interacting protein 1 kinase (RIP1) or related indications, and prodrugs thereof, which are hydrolyzed, typically in the gut or blood, to yield the corresponding inhibitors. The inhibitors provide unexpectedly exceptional metabolic stability, evidenced by liver microsome data and PK data.

In an aspect the invention provides a compound that is an inhibitor of necrosis, ferroptosis, human RIP1, or related indications, or sulfonamide or prodrug thereof, the compound of structure:

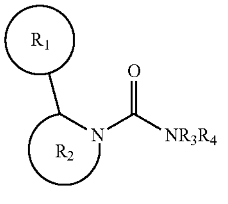

wherein:

- $R_1$ is a C3-C14 cyclic or hetero-cyclic moiety, particularly substituted or unsubstituted, 0-3 heteroatom C3-C9 cycloalkyl, cycloalkenyl, or cycloalkynyl; or substituted or unsubstituted, 0-3 heteroatom C5-C14 aryl;
- $R_2$ is a C3-C14 hetero-cyclic moiety, particularly substituted or unsubstituted, 1-3 heteroatom C3-C9 cycloalkyl, cycloalkenyl, or cycloalkynyl; or substituted or unsubstituted, 1-3 heteroatom C5-C14 aryl; and
- $R_3$ and $R_4$ are independently H, substituted or unsubstituted, 0-3 heteroatom hydrocarbyl or substituted heteroatom, wherein $R_3$ and $R_4$ are optionally linked to form a 3-8 membered ring with 1-3 heteroatoms: N or N and N/S/O;

wherein if $R_3$ is H, $R_4$ is other than H or phenyl (excluding cmpd 17 of US2012122889); or a corresponding sulfonamide of the amide compound, or a pharmaceutically acceptable salt, hydrate or stereoisomer the compound or corresponding sulfonamide.

In embodiments:

$R_1$ is (a) substituted or unsubstituted phenyl;
- (b) substituted or unsubstituted 2-, 3- or 4-pyridine;
- (c) substituted or unsubstituted naphthyl or 3-azanaphthyl;
- (d) substituted or unsubstituted 0-3 heteroatom cyclohexyl, cyclopentyl; or
- (e) substituted or unsubstituted 0-3 heteroatom cyclopentene or cyclopentadiene;

$R_1$ is substituted or unsubstituted: phenyl, cyclohexyl, furan, thiophene or azole;

$R_1$ is substituted or unsubstituted: phenyl or cyclohexyl;

$R_1$ is substituted or unsubstituted phenyl;

$R_1$ is fluoro-substituted (e.g. 3,5 difluorophenyl) or unsubstituted phenyl;

$R_2$ is a substituted or unsubstituted C3-C6 saturated or unsaturated ring with 1-3 heteroatom(s): N or N and N/S/O;

$R_2$ is a substituted or unsubstituted C3-C6 saturated ring with 1-3 heteroatom(s): N or N and N/S/O:
- N, e.g. aziridine, azetidine, pyrrolidine, piperidine;
- N and O, e.g. oxaziridine, isoxaziridine, oxazetidine, oxazolidine, oxazinane;
- N and S, e.g. thiaziridine, thiazetidine, thiazolidine, thiazinane;
- N and N, e.g. diaziridine, diazetidine, diazolidine (pyrazolidine), diazinane;

$R_2$ is a substituted or unsubstituted C3-C6 unsaturated ring comprising 1-3 heteroatom(s): N or N and N/S/O:
- N, e.g. pyrrole, dihydropyrrole, pyridine, dihydropyridine, tetrahydropyridine;
- N and N/S/O, e.g. azole (e.g. pyrazole, dihydropyrazole, imidazole, triazole, tetrazole, pentazole, oxazole, isoxazole, thiazole or isothiazole), pyrimidine, oxazine, thiazine, triazine, ozadiazine, thiadiazine;

$R_2$ is a substituted or unsubstituted C5 saturated or unsaturated ring (e.g. cycloalkyl, cycloalkenyl, or aryl) with 1-3 heteroatom(s): N or N and N/S/O;

$R_2$ is pyrrolidine, dihydro-pyrazole or isoxazolidine;

$R_3$ and $R_4$ are unlinked, $R_3$ is H or C1-C4 alkyl and $R_4$ is a C3-C14 cyclic or hetero-cyclic moiety, particularly substituted or unsubstituted, 0-3 heteroatom C3-C9 cycloalkyl, cycloalkenyl, or cycloalkynyl; or substituted or unsubstituted, 0-3 heteroatom C5-C14 aryl;

$R_3$ and $R_4$ are unlinked, $R_3$ is H or Me and $R_4$ is a substituted or unsubstituted, 0-3 heteroatom C4-C9 ring;

$R_3$ and $R_4$ are unlinked, $R_3$ is H or Me and $R_4$ is C4-6 cycloalky or pyrrolidine;

$R_3$ and $R_4$ are linked to form a 4-8 membered ring comprising 1-3 heteroatoms: N or N and N/S/O;

$R_3$ and $R_4$ are linked to form a 4-6 membered N-containing, heterocycloalkyl ring, optionally fused to a second ring (e.g. phenyl, to form e.g. isoindoline);

$R_3$ and $R_4$ are linked to form a 4-6 membered N-containing, heterocycloalkyl ring linked to a through a linker L (e.g. $-CH_2-$, $-O-$, $-CH-$) to $R_5$ wherein $R_5$ is a C3-C14 cyclic or hetero-cyclic moiety, particularly substituted or unsubstituted, 0-3 heteroatom C3-C9 cycloalkyl, cycloalkenyl, or cycloalkynyl; or substituted or unsubstituted, 0-3 heteroatom C5-C14 aryl;

L is —$CH_2$—.

L is —O—;

L is —CH—;

$R_5$ is (a) substituted or unsubstituted phenyl;

(b) substituted or unsubstituted 2-, 3- or 4-pyridine;

(c) substituted or unsubstituted naphthyl or 3-azanaphthyl;

(d) substituted or unsubstituted 0-3 heteroatom cyclohexyl, cyclopentyl; or (e) substituted or unsubstituted 0-3 heteroatom cyclopentene or cyclopentadiene;

$R_5$ is substituted or unsubstituted: phenyl, cyclohexyl, furan, thiophene or azole;

$R_5$ is substituted or unsubstituted: phenyl or cyclohexyl;

$R_5$ is substituted or unsubstituted phenyl;

$R_5$ is fluoro-substituted (e.g. 3,5 difluorophenyl) or unsubstituted phenyl; and/or the compound comprises a structure of Table 1.

In another aspect the invention provides a pharmaceutical composition comprising a therapeutically effective amount of a subject compound in unit dosage form and one or more pharmaceutically acceptable excipients.

In another aspect the invention provides use of a subject compound or composition in the manufacture of a medicament for inhibiting necrosis, ferroptosis, and/or human receptor interacting protein 1 kinase (RIP1), in a person in need thereof.

In another aspect the invention provides a subject compound or composition for use in inhibiting necrosis, ferroptosis, and/or human receptor interacting protein 1 kinase (RIP1), in a person in need thereof, or in the manufacture of a medicament for RIP1 in a person in need thereof.

In another aspect the invention provides a method of inhibiting necrosis, ferroptosis, and/or human receptor interacting protein 1 kinase (RIP1), comprising administering to a person in need thereof a subject compound or composition.

In embodiments the related indications are such as brain injury, neurodegenerative diseases, viral infections, immune tolerance, and cancer e.g. promote tumor immunity in pancreatic cancer and melanoma.

The invention encompasses all combination of the particular embodiments recited herein, as if each combination had been laboriously recited.

DESCRIPTION OF PARTICULAR EMBODIMENTS OF THE INVENTION

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The term "alkyl" refers to a hydrocarbon group selected from linear and branched saturated hydrocarbon groups of 1-18, or 1-12, or 1-6 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

Lower alkyl means 1-8, preferably 1-6, more preferably 1-4 carbon atoms; lower alkenyl or alkynyl means 2-8, 2-6 or 2-4 carbon atoms.

The term "alkenyl" refers to a hydrocarbon group selected from linear and branched hydrocarbon groups comprising at least one C═C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halogen" or "halo" refers to F, Cl, Br or I.

The term "heteroalkyl" refers to alkyl comprising at least one heteroatom.

The term "heteroaryl" refers to a group selected from:

5- to 7-membered aromatic, monocyclic rings comprising 1, 2, 3 or 4 heteroatoms selected from N, O, and S, with the remaining ring atoms being carbon;

8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1, 1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicylclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

In embodiments substituents are selected from optionally substituted heteroatom and optionally substituted, optionally hetero-, optionally cyclic C1-C18 hydrocarbyl, particularly wherein the optionally substituted, optionally hetero-, optionally cyclic C1-C18 hydrocarbyl is optionally-substituted, optionally hetero-, optionally cyclic alkyl, alkenyl or alkynyl, or optionally-substituted, optionally hetero-aryl; and/or the optionally substituted heteroatom is halogen, optionally substituted hydroxyl (such as alkoxy, aryloxy), optionally substituted acyl (such as formyl, alkanoyl, carbamoyl, carboxyl, amido), optionally substituted amino (such as amino, alkylamino, dialkylamino, amido, sulfamidyl), optionally substituted thiol (such as mercapto, alkylthiol, aryl thiol), optionally substituted sulfinyl or sulfonyl (such as alkylsulfinyl, arylsulfinyl, alkyl sulfonyl, arylsulfonyl), nitro, or cyano.

In embodiments, substituents are selected from: halogen, —R', —OR', =O, =NR', =N—OR', —NR'R", —SR', —SiR'R"R"', —OC(O)R', —C(O)R', —CO2R', —CONR'R", —OC(O)NR'R", —NR"C(O)R', —NR'—C(O)NR"R'", —NR'—SO2NR'", —NR"CO2R', —NH—C(NH2)=NH, —NR'C(NH2)=NH, —NH—C(NH2)=NR', —S(O)R', —SO2R', —SO2NR'R", —NR"SO2R, —CN and —NO2, —N3, —CH(Ph)2, perfluoro(C1-C4)alkoxy and perfluoro(C1-C4)alkyl, in a number ranging from zero to three, with those groups having zero, one or two substituents being particularly preferred. R', R" and R'" each independently refer to hydrogen, unsubstituted (C1-C8)alkyl and heteroalkyl, (C1-C8)alkyl and heteroalkyl substituted with one to three halogens, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. Hence, —NR'R" includes 1-pyrrolidinyl and 4-morpholinyl, "alkyl" includes groups such as trihaloalkyl (e.g., —CF3 and —CH2CF3), and when the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl".

Preferred substituents are selected from: halogen, —R', —OR', =O, —NR'R", —SR', —SiR'R"R'", —OC(O)R', —C(O)R', —CO2R', —CONR'R", —OC(O)NR'R", —NR"C(O)R', —NR"CO2R', —NR'—SO2NR"R'", —S(O)R', —SO2R', —SO2NR'R", —NR"SO2R, —CN and —NO2, perfluoro(C1-C4)alkoxy and perfluoro(C1-C4)alkyl, where R' and R" are as defined above.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, 0-3 heteroatom C1-C6 alkyl, substituted or unsubstituted, 0-3 heteroatom C2-C6 alkenyl, substituted or unsubstituted, 0-3 heteroatom C2-C6 alkynyl, or substituted or unsubstituted, 0-3 heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or triflurommethyl ether (OCF3).

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —$CH_2$C(O)— groups (keto forms) may undergo tautomerism to form hydroxyl —CH═C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents. Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)$n-COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" refers to administering at least one compound and/or at least one stereoisomer thereof, and/or at least one pharmaceutically acceptable salt thereof to a subject in recognized need thereof.

An "effective amount" refers to an amount of at least one compound and/or at least one stereoisomer thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent $R^{16}$" herein includes from 1 to 4, such as from 1 to 3, further as 1 or 2, substituents selected from the list of $R^{16}$ as described herein.

The subject compounds and stereoisomers thereof, and pharmaceutically acceptable salts thereof may be employed alone or in combination with at least one other therapeutic agent for treatment. In some embodiments, the compounds, stereoisomers thereof, and pharmaceutically acceptable salts thereof can be used in combination with at least one additional therapeutic agent. The compound and/or one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the compound and/or one pharmaceutically acceptable salt disclosed herein.

Also provided is a composition comprising a subject compound and stereoisomers thereof, and pharmaceutically acceptable salts thereof, and at least one pharmaceutically acceptable carrier.

The composition comprising a subject compound and stereoisomers thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The subject compounds and stereoisomers thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The subject compounds and stereoisomers thereof, and pharmaceutically acceptable salts thereof disclosed herein can also be administered parenterally, in sterile liquid dosage forms, such as dispersions, suspensions or solutions. Other dosages forms that can also be used to administer the subject compounds and stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene gycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in *Remington's Pharmaceutical Sciences*, A. Osol, a standard reference text in the art.

For administration by inhalation, the subject compounds and stereoisomers thereof, and pharmaceutically acceptable salts thereof may be conveniently delivered in the form of an aerosol spray presentation from pressurized packs or nebulisers. The subject compounds and stereoisomers thereof, and pharmaceutically acceptable salts thereof may also be delivered as powders, which may be formulated and the powder composition may be inhaled with the aid of an insufflation powder inhaler device. One exemplary delivery system for inhalation can be metered dose inhalation (MDI) aerosol, which may be formulated as a suspension or solution of a subject compound and stereoisomers thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the subject compound and stereoisomers thereof, and pharmaceutically acceptable salts thereof in an appropriate ophthalmic vehicle, such that the subject compound and stereoisomers thereof, and at least one pharmaceutically acceptable salts thereof is maintained in contact with the ocular surface for a sufficient time period to allow the compound to penetrate the corneal and internal regions of the eye.

Useful pharmaceutical dosage-forms for administration of the subject compounds and stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the subject compound and stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the compound, stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound, stereoisomers thereof, and pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound, stereoisomers thereof, and pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound, stereoisomers thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The compounds, stereoisomers thereof, and pharmaceutically acceptable salt thereof disclosed herein can be administered as the sole active ingredient or in combination with at least one second active ingredient.

The subject compounds are incorporated into pharmaceutical compositions or formulations. The compositions will contain pharmaceutically acceptable diluents and/or carriers, i. e. diluents or carriers that are physiologically compatible and substantially free from pathogenic impurities. Suitable excipients or carriers and methods for preparing administrable compositions are known or apparent to those skilled in the art and are described in more detail in such publications as Remington's Pharmaceutical Science, Mack Publishing Co, NJ (1991). The compositions may also be in the form of controlled release or sustained release compositions as known in the art. For many applications the subject compounds are administered for morning/daytime dosing, with off period at night.

The subject compounds may be used per se, or in the form of their pharmaceutically acceptable salts, such as hydrochlorides, hydrobromides, acetates, sulfates, citrates, carbonates, trifluoroacetates and the like. When compounds contain relatively acidic functionalities, salts can be obtained by addition of the desired base, either neat or in a suitable inert solvent. Examples of pharmaceutically acceptable base addition salts include sodium, potassium, calcium, ammonium, organic amino, or magnesium salts, or the like. When compounds contain relatively basic functionalities, salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al, "Pharmaceutical Salts", Journal of Pharmaceutical Science, 1977, 66, 1-19).

The neutral forms of the compounds may be regenerated by contacting the salt with a base or acid, and isolating the parent compound in the conventional manner. The parent form of the compound differs from the various salt forms in certain physical properties, such as solubility in polar solvents, but otherwise the salts are equivalent to the parent form of the compound for the purposes of this invention.

In addition to salt forms, this invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity.

Certain compounds of the invention can exist in unsolvated forms as well as solvated forms, including hydrated forms. In general, the solvated forms are equivalent to unsolvated forms and are intended to be encompassed within the scope of the present invention. Certain compounds of the invention may exist in multiple crystalline or amorphous forms. In general, all physical forms are equivalent for the uses contemplated by the present invention and are intended to be within the scope of the invention.

Some of the subject compounds possess asymmetric carbon atoms (optical centers) or double bonds; the racemates, diastereomers, geometric isomers and individual isomers are all intended to be encompassed within the scope of the present invention.

The compounds of the invention may also contain unnatural proportions of atomic isotopes at one or more of the atoms that constitute such compounds, such as deuterium, e.g. $-CD_3$, $CD_2H$ or $CDH_2$ in place of methyl. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

The compounds are generally administered in a "therapeutically effective amount", i.e. the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The contacting is generally effected by administering to the subject an effective amount of one or more compounds having the general formula I (supra), including the various embodiments described above. Generally administration is adjusted to achieve a therapeutic dosage of about 0.1 to 50, preferably 0.5 to 10, more preferably 1 to 10 mg/kg, though optimal dosages are compound specific, and generally empirically determined for each compound.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the mimetic is usually a minor component (from about 0.1 to about 50% by weight or preferably from about 1 to about 40% by weight) with the remainder being various vehicles or carriers and processing aids helpful for forming the desired dosing form. Unit dosage formulations are preferably about of 5, 10, 25, 50, 100, 250, 500, or 1,000 mg per unit. In a particular embodiment, unit dosage forms are packaged in a multipack adapted for sequential use, such as blisterpack comprising sheets of at least 6, 9 or 12 unit dosage forms.

The subject compositions may also be coformulated and/or coadministered with a different compound to treat programmed cell death.

TABLE 1

| Active Compounds | |
|---|---|
| 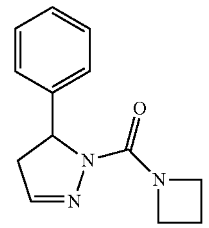 [SMILES: O=C(N1CCC1)N1N=CCC1c1ccccc1] | 1 |

TABLE 1-continued
| Active Compounds | |
|---|---|
| 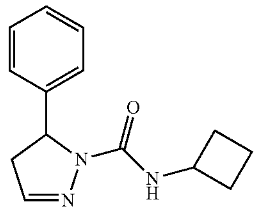 [SMILES: O=C(NC1CCC1)N1N=CCC1c1ccccc1] | 2 |
| 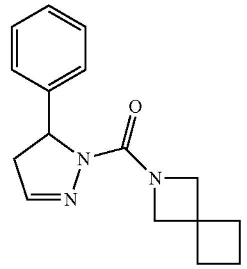 [SMILES: O=C(N1CC2(CCC2)C1)N1N=CCC1c1ccccc1] | 3 |
| 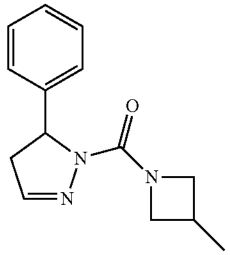 [SMILES: CC1CN(C(=O)N2N=CCC2c2ccccc2)C1] | 4 |
| 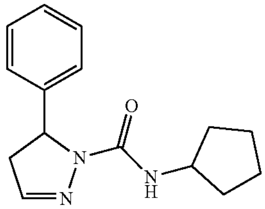 [SMILES: O=C(NC1CCCC1)N1N=CCC1c1ccccc1] | 5 |
| 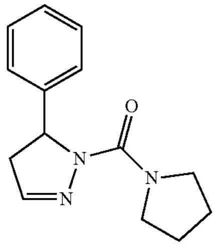 [SMILES: O=C(N1CCCC1)N1N=CCC1c1ccccc1] | 6 |
| 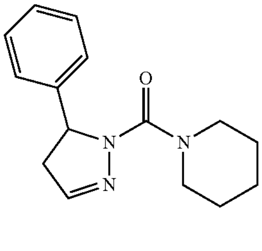 [SMILES: O=C(N1CCCCC1)N1N=CCC1c1ccccc1] | 7 |

TABLE 1-continued
| Active Compounds | |
|---|---|
| 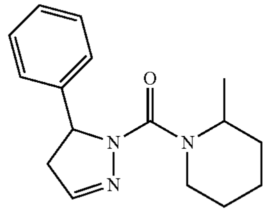 [SMILES: CC1CCCCN1C(=O)N1N=CCC1c1ccccc1] | 8 |
| 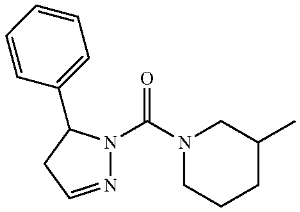 [SMILES: CC1CCCN(C(=O)N2N=CCC2c2ccccc2)C1] | 9 |
| 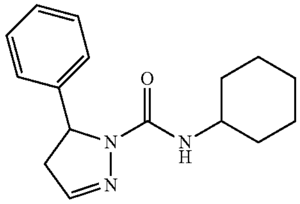 | 10 |
| 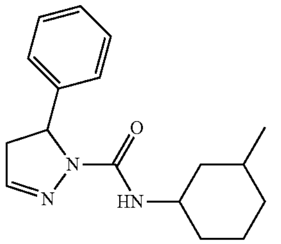 [SMILES: CC1CCCC(NC(=O)N2N=CCC2c2ccccc2)C1] | 11 |
| 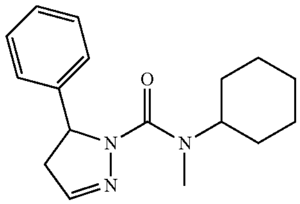 [SMILES: CN(C(=O)N1N=CCC1c1ccccc1)C1CCCCC1] | 12 |
| 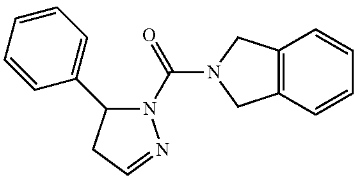 [SMILES: O=C(N1Cc2ccccc2C1)N1N=CCC1c1ccccc1] | 13 |
| 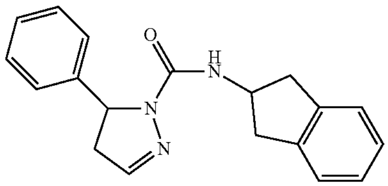 [SMILES: O=C(NC1Cc2ccccc2C1)N1N=CCC1c1ccccc1] | 14 |

TABLE 1-continued
| Active Compounds | |
|---|---|
| 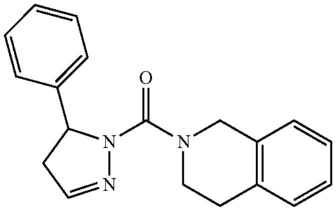 [SMILES: O=C(N1CCc2ccccc2C1)N1N=CCC1c1ccccc1] | 15 |
| 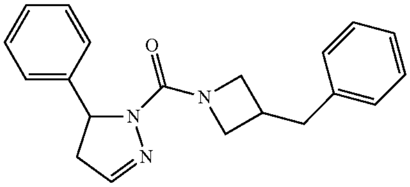 [SMILES: O=C(N1CC(Cc2ccccc2)C1)N1N=CCC1c1ccccc1] | 16 |
| 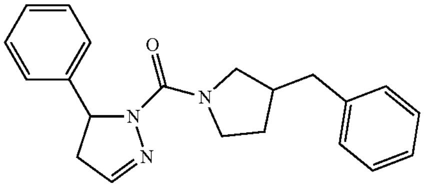 [SMILES: O=C(N1CCC(Cc2ccccc2)C1)N1N=CCC1c1ccccc1] | 17 |
| 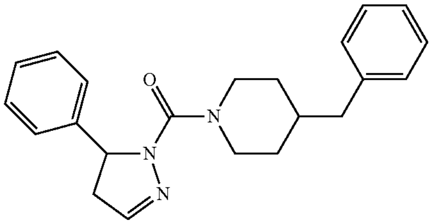 [SMILES: O=C(N1CCC(Cc2ccccc2)CC1)N1N=CCC1c1ccccc1] | 18 |
| 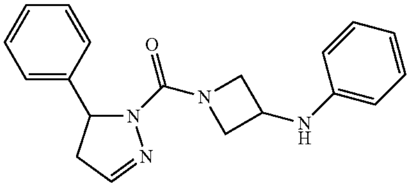 [SMILES: O=C(N1CC(Nc2ccccc2)C1)N1N=CCC1c1ccccc1] | 19 |
| 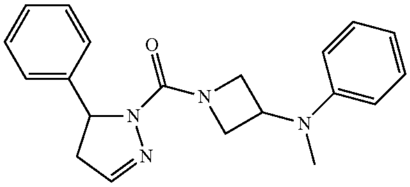 [SMILES: CN(c1ccccc1)C1CN(C(=O)N2N=CCC2c2ccccc2)C1] | 20 |
| 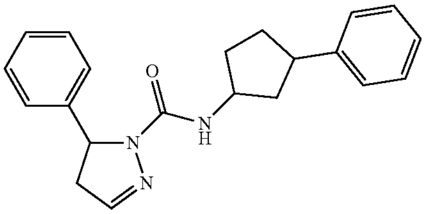 [SMILES: O=C(NC1CCC(c2ccccc2)C1)N1N=CCC1c1ccccc1] | 21 |

TABLE 1-continued
| Active Compounds | |
|---|---|
| 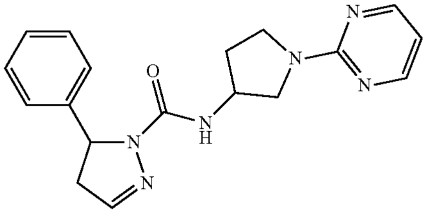 [SMILES: O=C(NC1CCN(c2ncccn2)C1)N1N=CCC1c1ccccc1] | 22 |
| 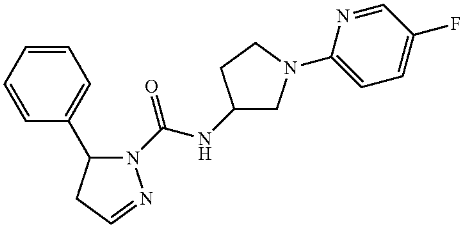 [SMILES: O=C(NC1CCN(c2ccc(F)cn2)C1)N1N=CCC1c1ccccc1] | 23 |
| 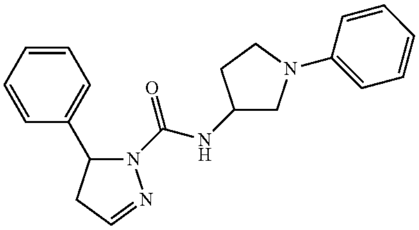 [SMILES: O=C(NC1CCN(c2ccccc2)C1)N1N=CCC1c1ccccc1] | 24 |
| 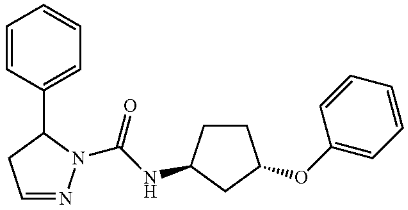 [SMILES: O=C(N[C@H]1CC[C@H](Oc2ccccc2)C1)N1N=CCC1c1ccccc1] | 25 |
| 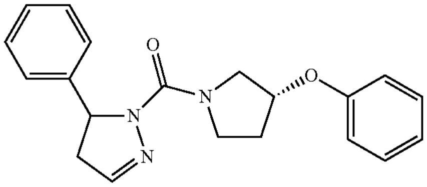 [SMILES: O=C(N1CC[C@@H](Oc2ccccc2)C1)N1N=CCC1c1ccccc1] | 26A |
| 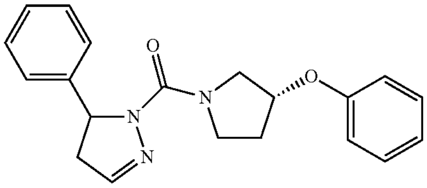 [SMILES: O=C(N1CC[C@@H](Oc2ccccc2)C1)N1N=CCC1c1ccccc1] | 26B |
| 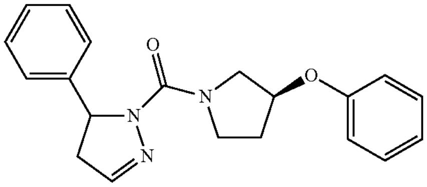 [SMILES: O=C(N1CC[C@H](Oc2ccccc2)C1)N1N=CCC1c1ccccc1] | 27A |

TABLE 1-continued
| Active Compounds | |
|---|---|
| 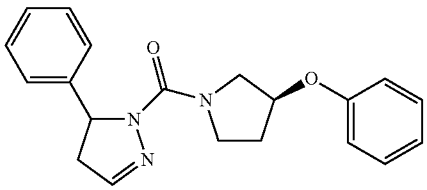 [SMILES: O=C(N1CC[C@H](Oc2ccccc2)C1)N1N=CCC1c1ccccc1] | 27B |
| 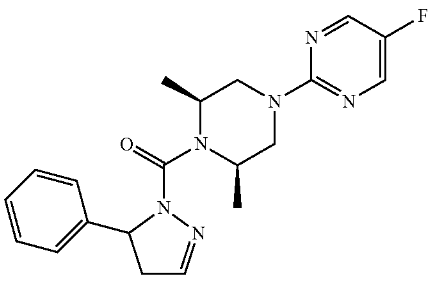 [SMILES: C[C@@H]1CN(c2ncc(F)cn2)C[C@H](C)N1C(=O)N1N=CCC1c1ccccc1] | 28 |
| 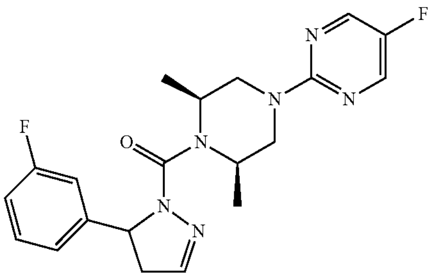 [SMILES: C[C@@H]1CN(c2ncc(F)cn2)C[C@H](C)N1C(=O)N1N=CCC1c1cccc(F)c1] | 29 |
| 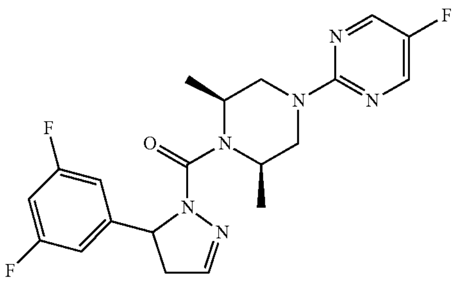 [SMILES: C[C@@H]1CN(c2ncc(F)cn2)C[C@H](C)N1C(=O)N1N=CCC1c1cc(F)cc(F)c1] | 30 |
| 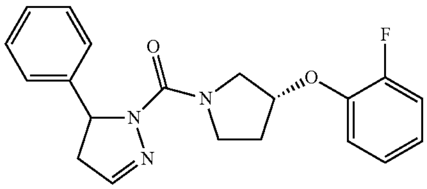 [SMILES: O=C(N1CC[C@@H](Oc2ccccc2F)C1)N1N=CCC1c1ccccc1] | 31 |
| 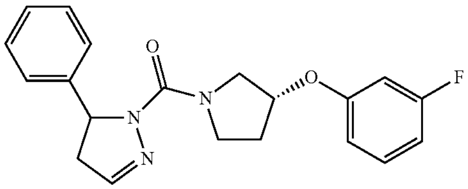 [SMILES: O=C(N1CC[C@@H](Oc2cccc(F)c2)C1)N1N=CCC1c1ccccc1] | 32 |

TABLE 1-continued
| Active Compounds | |
|---|---|
| 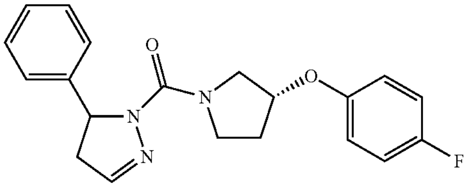 [SMILES: O=C(N1CC[C@@H](Oc2ccc(F)cc2)C1)N1N=CCC1c1ccccc1] | 33 |
| 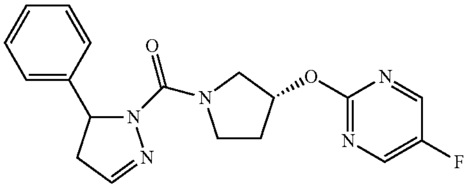 | 34 |
| 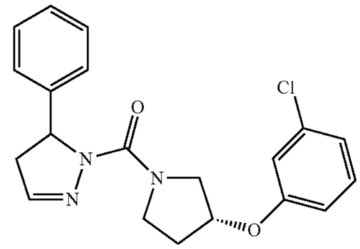 [SMILES: O=C(N1CC[C@@H](Oc2cccc(Cl)c2)C1)N1N=CCC1c1ccccc1] | 35 |
| 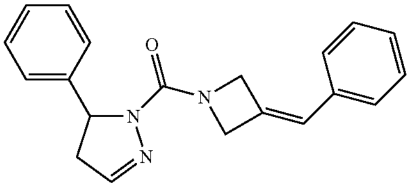 [SMILES: O=C(N1CC(=Cc2ccccc2)C1)N1N=CCC1c1ccccc1] | 36 |
| 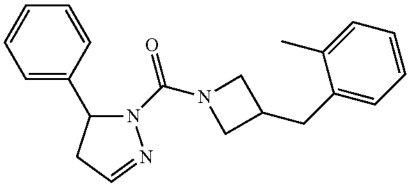 | 37 |
| 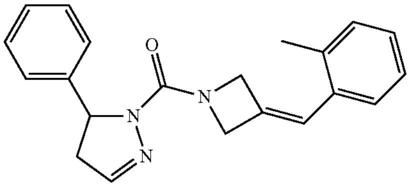 [SMILES: Cc1ccccc1C=C1CN(C(=O)N2N=CCC2c2ccccc2)C1] | 38 |
| 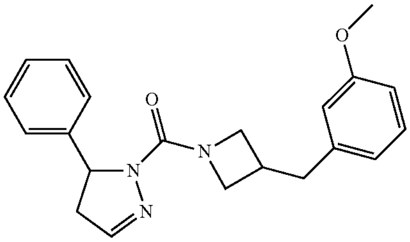 [SMILES: COc1cccc(CC2CN(C(=O)N3N=CCC3c3ccccc3)C2)c1] | 39 |

TABLE 1-continued
| Active Compounds |
| --- |
| 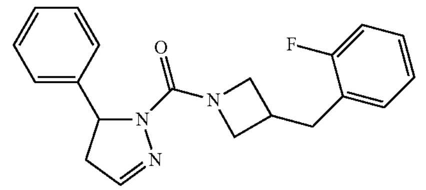 [SMILES: O=C(N1CC(Cc2ccccc2F)C1)N1N=CCC1c1ccccc1] 40 |
| 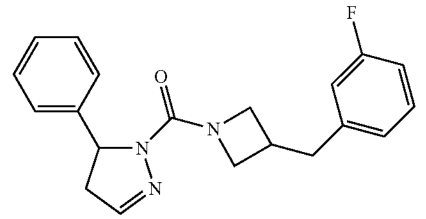 [SMILES: O=C(N1CC(Cc2cccc(F)c2)C1)N1N=CCC1c1ccccc1] 41 |
| 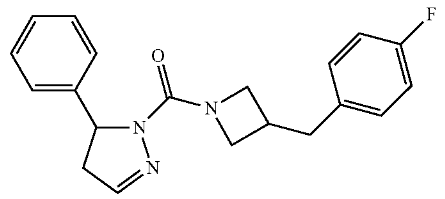 [SMILES: O=C(N1CC(Cc2ccc(F)cc2)C1)N1N=CCC1c1ccccc1] 42 |
| 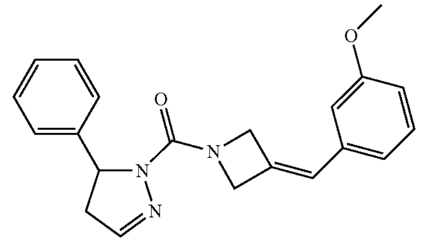 [SMILES: COc1cccc(C=C2CN(C(=O)N3N=CCC3c3ccccc3)C2)c1] 43 |
| 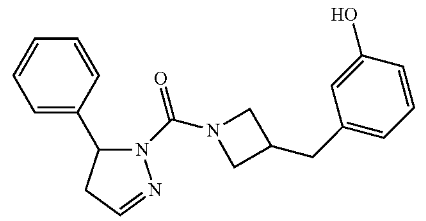 [SMILES: O=C(N1CC(Cc2cccc(O)c2)C1)N1N=CCC1c1ccccc1] 44 |
| 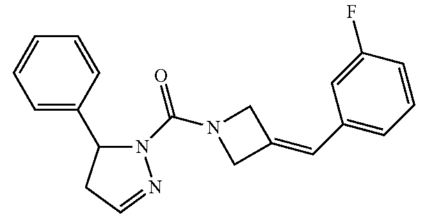 [SMILES: O=C(N1CC(=Cc2cccc(F)c2)C1)N1N=CCC1c1ccccc1] 45 |
| 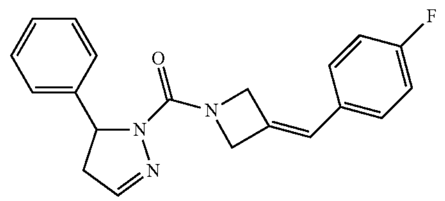 [SMILES: O=C(N1CC(=Cc2ccc(F)cc2)C1)N1N=CCC1c1ccccc1] 46 |

TABLE 1-continued
| Active Compounds | |
|---|---|
| 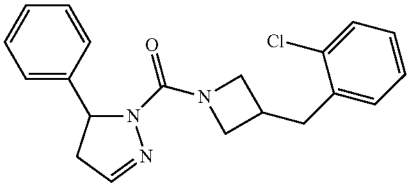 | 47 |
| 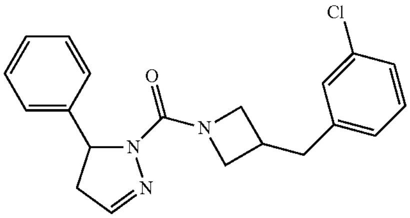 | 48 |
| 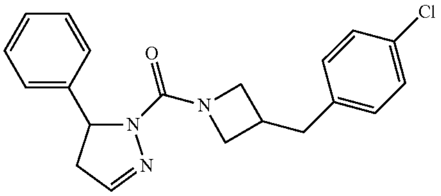 [SMILES: O=C(N1CC(Cc2ccc(Cl)cc2)C1)N1N=CCC1c1ccccc1] | 49 |
| 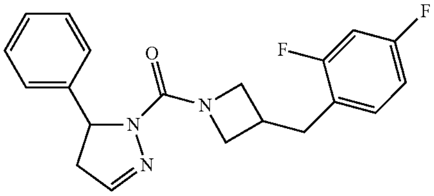 [SMILES: O=C(N1CC(Cc2ccc(F)cc2F)C1)N1N=CCC1c1ccccc1] | 50 |
| 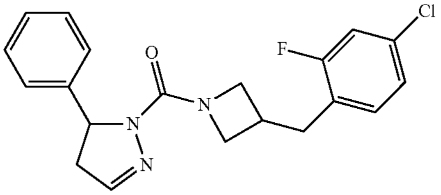 | 51 |
| 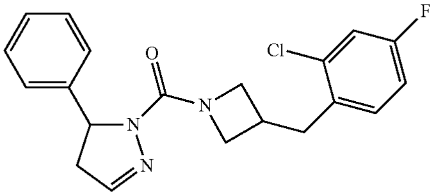 [SMILES: O=C(N1CC(Cc2ccc(F)cc2Cl)C1)N1N=CCC1c1ccccc1] | 52 |
| 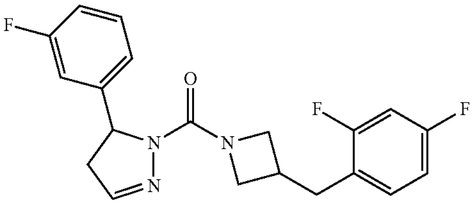 [SMILES: O=C(N1CC(Cc2ccc(F)cc2F)C1)N1N=CCC1c1cccc(F)c1] | 53 |

TABLE 1-continued
| Active Compounds | |
|---|---|
| 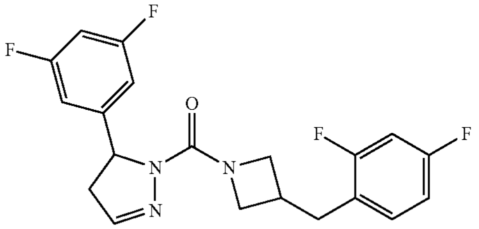 [SMILES: O=C(N1CC(Cc2ccc(F)cc2F)C1)N1N=CCC1c1cc(F)cc(F)c1] | 54 |
| 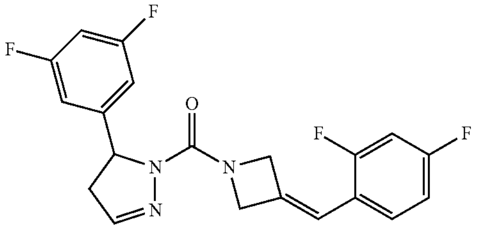 [SMILES: O=C(N1CC(=Cc2ccc(F)cc2F)C1)N1N=CCC1c1cc(F)cc(F)c1] | 55 |
| 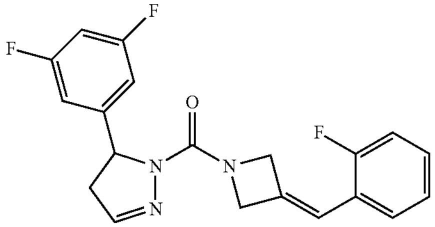 [SMILES: O=C(N1CC(=Cc2ccccc2F)C1)N1N=CCC1c1cc(F)cc(F)c1] | 56 |
| 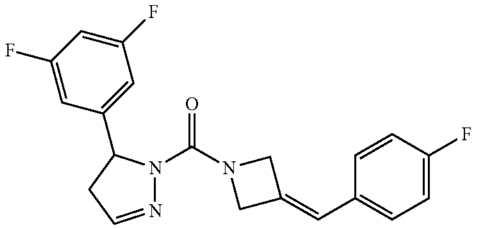 [SMILES: O=C(N1CC(=Cc2ccc(F)cc2)C1)N1N=CCC1c1cc(F)cc(F)c1] | 57 |
| 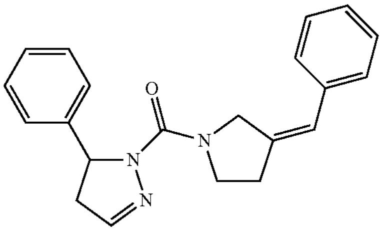 [SMILES: O=C(N1CC/C(=C/c2ccccc2)C1)N1N=CCC1c1ccccc1] | 58 |
| 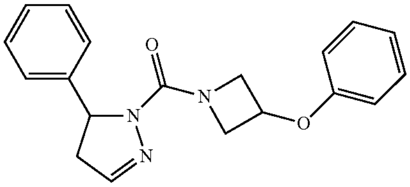 | 59 |
| 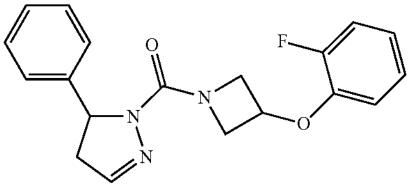 | 60 |

TABLE 1-continued
| Active Compounds | |
|---|---|
| 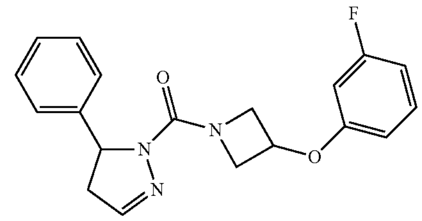 [SMILES: O=C(N1CC(Oc2cccc(F)c2)C1)N1N=CCC1c1ccccc1] | 61 |
| 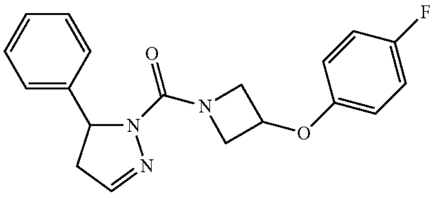 [SMILES: O=C(N1CC(Oc2ccc(F)cc2)C1)N1N=CCC1c1ccccc1] | 62 |
| 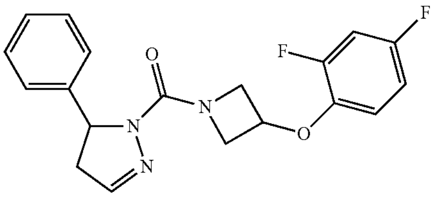 [SMILES: O=C(N1CC(Oc2ccc(F)cc2F)C1)N1N=CCC1c1ccccc1] | 63 |
| 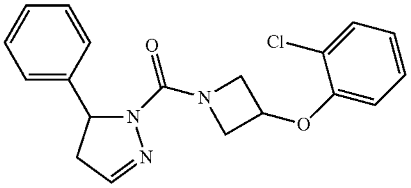 [SMILES: O=C(N1CC(Oc2ccccc2Cl)C1)N1N=CCC1c1ccccc1] | 64 |
| 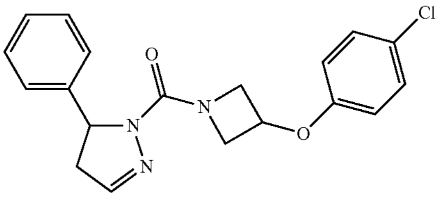 | 65 |
| 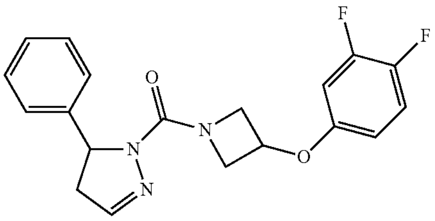 [SMILES: O=C(N1CC(Oc2ccc(F)c(F)c2)C1)N1N=CCC1c1ccccc1] | 66 |
| 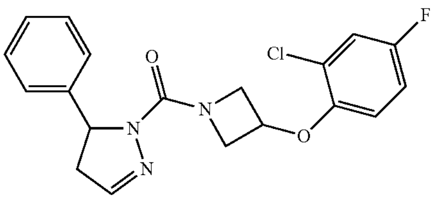 [SMILES: O=C(N1CC(Oc2ccc(F)cc2Cl)C1)N1N=CCC1c1ccccc1] | 67 |

TABLE 1-continued
| Active Compounds | |
|---|---|
| 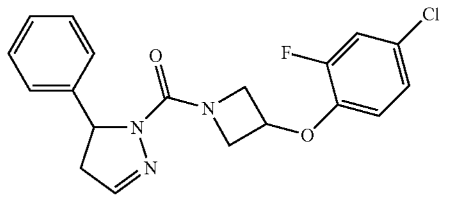 [SMILES: O=C(N1CC(Oc2ccc(Cl)cc2F)C1)N1N=CCC1c1ccccc1] | 68 |
| 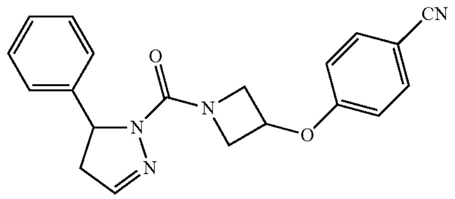 [SMILES: N#Cc1ccc(OC2CN(C(=O)N3N=CCC3c3ccccc3)C2)cc1] | 69 |
| 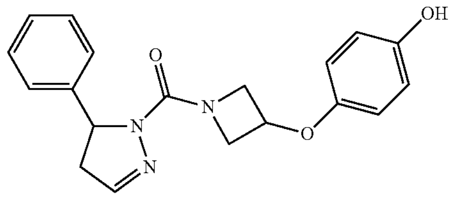 [SMILES: O=C(N1CC(Oc2ccc(O)cc2)C1)N1N=CCC1c1ccccc1] | 70 |
| 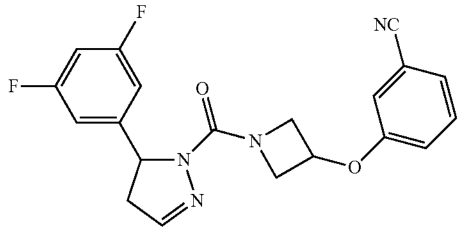 [SMILES: N#Cc1cccc(OC2CN(C(=O)N3N=CCC3c3cc(F)cc(F)c3)C2)c1] | 71 |
| 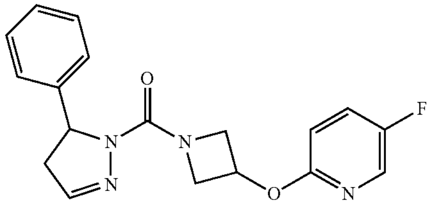 [SMILES: O=C(N1CC(Oc2ccc(F)cn2)C1)N1N=CCC1c1ccccc1] | 72 |
| 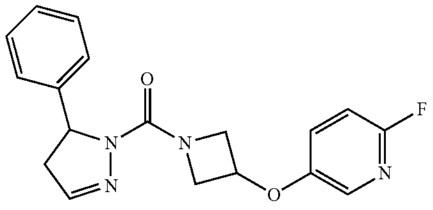 [SMILES: O=C(N1CC(Oc2ccc(F)nc2)C1)N1N=CCC1c1ccccc1] | 73 |
| 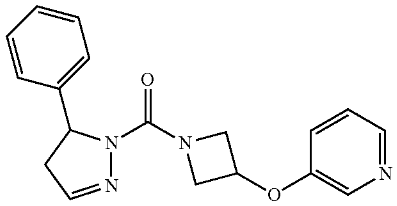 [SMILES: O=C(N1CC(Oc2cccnc2)C1)N1N=CCC1c1ccccc1] | 74 |

TABLE 1-continued
| Active Compounds |
| --- |
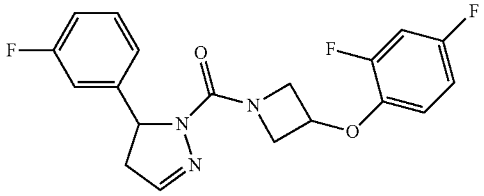 [SMILES: O=C(N1CC(Oc2ccc(F)cc2F)C1)N1N=CCC1c1cccc(F)c1]
75
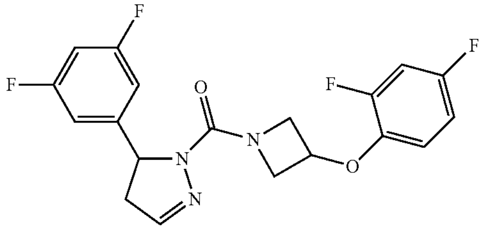 [SMILES: O=C(N1CC(Oc2ccc(F)cc2F)C1)N1N=CCC1c1cc(F)cc(F)c1]
76
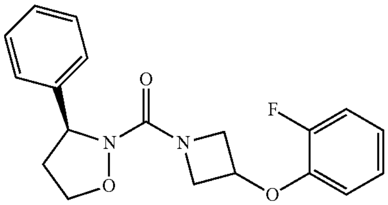 [SMILES: O=C(N1CC(Oc2ccccc2F)C1)N1OCC[C@H]1c1ccccc1]
77
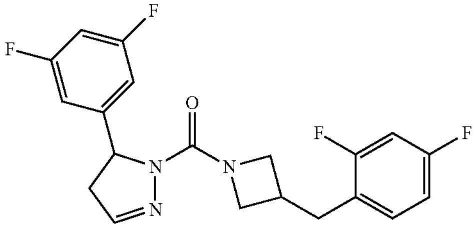 [SMILES: O=C(N1CC(Cc2ccc(F)cc2F)C1)N1N=CCC1c1cc(F)cc(F)c1]
78
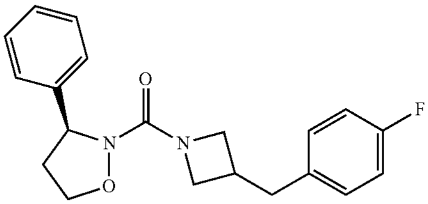 [SMILES: O=C(N1CC(Cc2ccc(F)cc2)C1)N1OCC[C@H]1c1ccccc1]
79
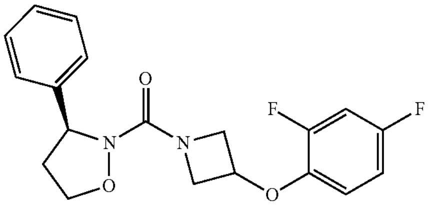 [SMILES: O=C(N1CC(Oc2ccc(F)cc2F)C1)N1OCC[C@H]1c1ccccc1]
80
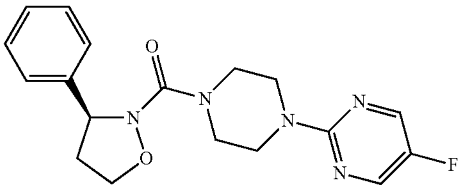 [SMILES: O=C(N1CCN(c2ncc(F)cn2)CC1)N1OCC[C@H]1c1ccccc1]
81

TABLE 1-continued
| Active Compounds |
| --- |
| 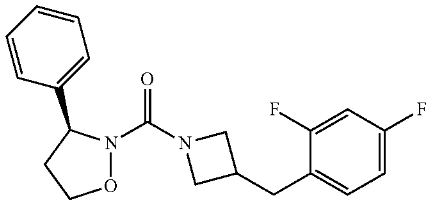 [SMILES: O=C(N1CC(Cc2ccc(F)cc2F)C1)N1OCC[C@H]1c1ccccc1] 82 |
| 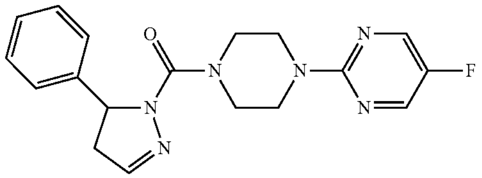 [SMILES: O=C(N1CCN(c2ncc(F)cn2)CC1)N1N=CCC1c1ccccc1] 83 |
| 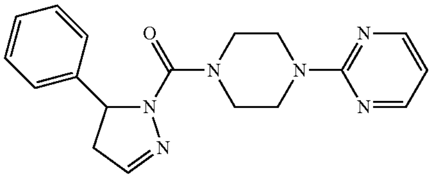 84 |
| 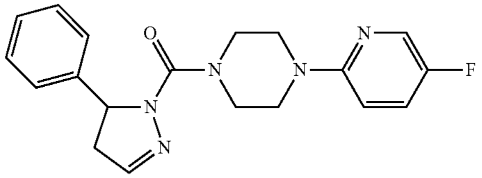 [SMILES: O=C(N1CCN(c2ccc(F)cn2)CC1)N1N=CCC1c1ccccc1] 85 |
| 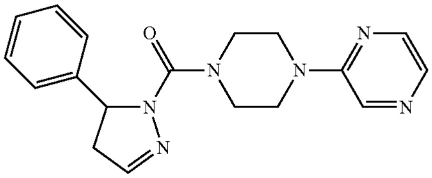 [SMILES: O=C(N1CCN(c2cnccn2)CC1)N1N=CCC1c1ccccc1] 86 |
| 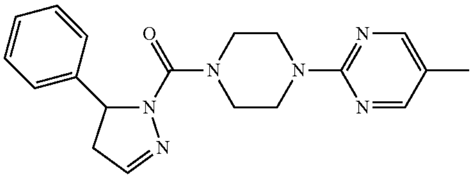 [SMILES: Cc1cnc(N2CCN(C(=O)N3N=CCC3c3ccccc3)CC2)nc1] 87 |
| 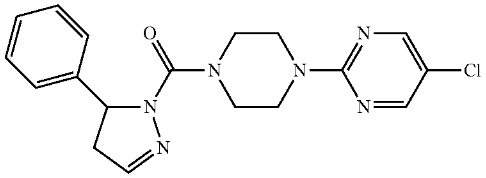 [SMILES: O=C(N1CCN(c2ncc(Cl)cn2)CC1)N1N=CCC1c1ccccc1] 88 |
| 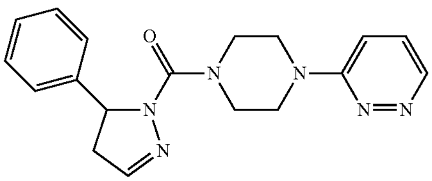 [SMILES: O=C(N1CCN(c2cccnn2)CC1)N1N=CCC1c1ccccc1] 89 |

TABLE 1-continued
| Active Compounds | |
|---|---|
| 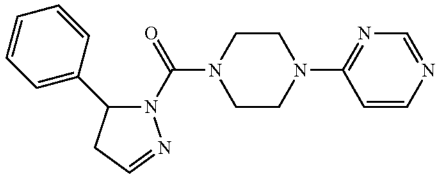 | 90 |
| 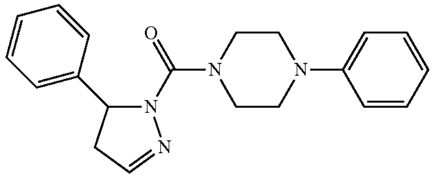 [SMILES: O=C(N1CCN(c2ccccc2)CC1)N1N=CCC1c1ccccc1] | 91 |
| 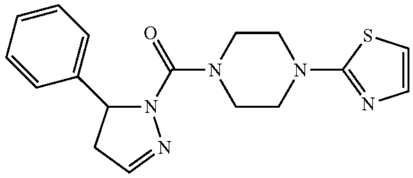 [SMILES: O=C(N1CCN(c2nccs2)CC1)N1N=CCC1c1ccccc1] | 92 |
| 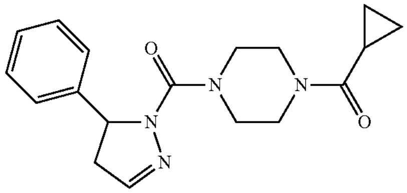 [SMILES: O=C(C1CC1)N1CCN(C(=O)N2N=CCC2c2ccccc2)CC1] | 93 |
| 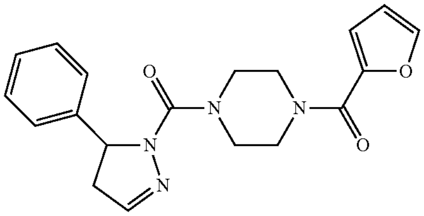 [SMILES: O=C(c1ccco1)N1CCN(C(=O)N2N=CCC2c2ccccc2)CC1] | 94 |
| 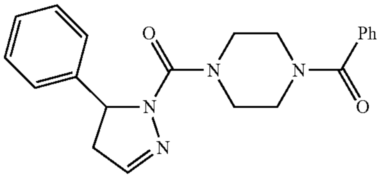 [SMILES: O=C(c1ccccc1)N1CCN(C(=O)N2N=CCC2c2ccccc2)CC1] | 95 |
| 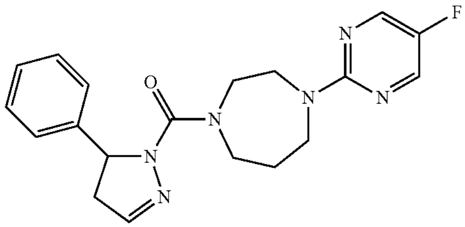 [SMILES: O=C(N1CCCN(c2ncc(F)cn2)CC1)N1N=CCC1c1ccccc1] | 96 |

TABLE 1-continued
| Active Compounds |
| --- |
| 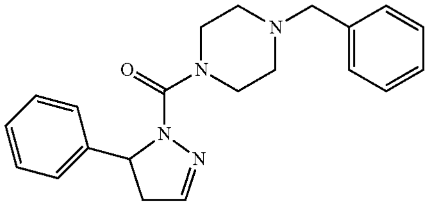 [SMILES: O=C(N1CCN(Cc2ccccc2)CC1)N1N=CCC1c1ccccc1] 97 |
| 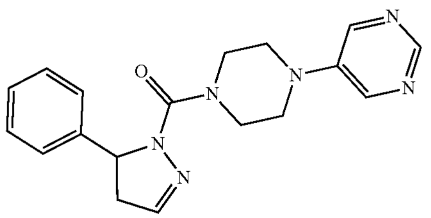 [SMILES: O=C(N1CCN(c2cncnc2)CC1)N1N=CCC1c1ccccc1] 98 |
| 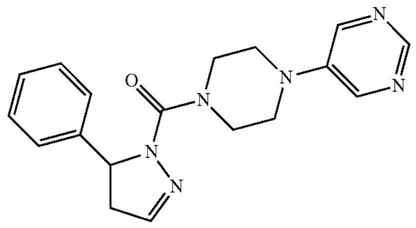 [SMILES: O=C(N1CCN(c2cncnc2)CC1)N1N=CCC1c1ccccc1] 99 |
| 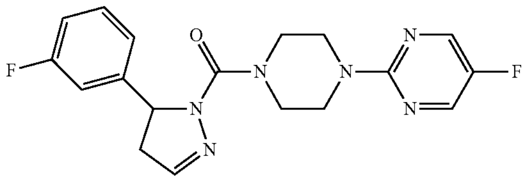 [SMILES: O=C(N1CCN(c2ncc(F)cn2)CC1)N1N=CCC1c1cccc(F)c1] 100 |
| 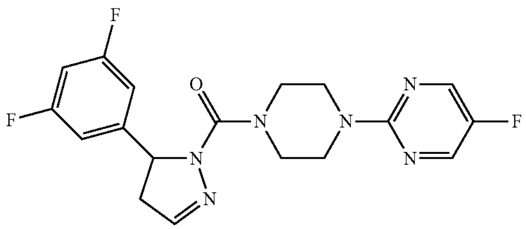 [SMILES: O=C(N1CCN(c2ncc(F)cn2)CC1)N1N=CCC1c1cc(F)cc(F)c1] 101 |
| 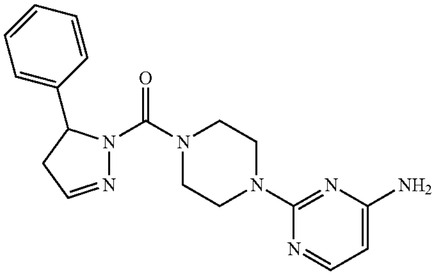 [SMILES: Nc1ccnc(N2CCN(C(=O)N3N=CCC3c3ccccc3)CC2)n1] 102 |

TABLE 1-continued
| Active Compounds | |
|---|---|
| 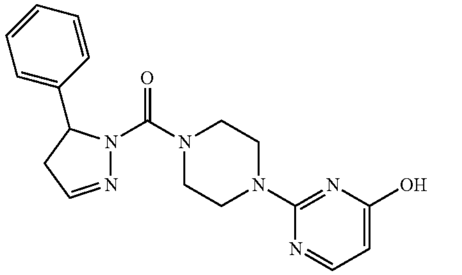 [SMILES: O=C(N1CCN(c2nccc(O)n2)CC1)N1N=CCC1c1ccccc1] | 103 |
| 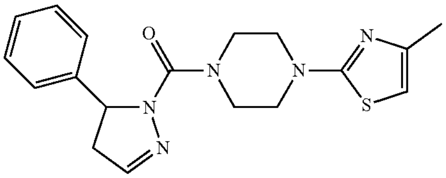 [SMILES: Cc1csc(N2CCN(C(=O)N3N=CCC3c3ccccc3)CC2)n1] | 104 |
| 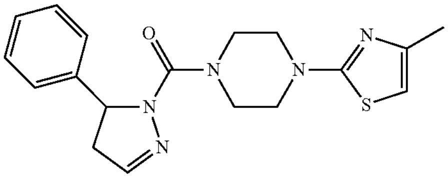 [SMILES: Cc1csc(N2CCN(C(=O)N3N=CCC3c3ccccc3)CC2)n1] | 105 |
| 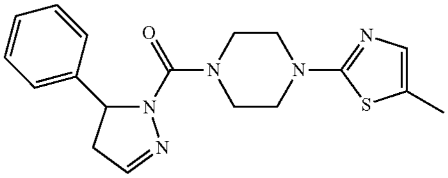 [SMILES: Cc1cnc(N2CCN(C(=O)N3N=CCC3c3ccccc3)CC2)s1] | 106 |
| 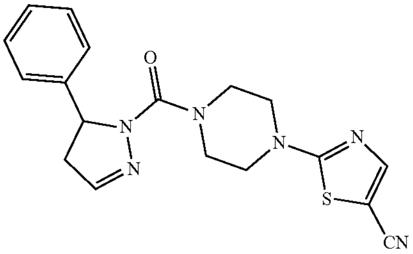 [SMILES: N#Cc1cnc(N2CCN(C(=O)N3N=CCC3c3ccccc3)CC2)s1] | 107 |
| 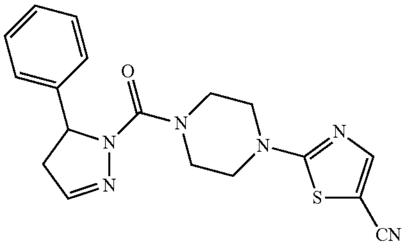 [SMILES: N#Cc1cnc(N2CCN(C(=O)N3N=CCC3c3ccccc3)CC2)s1] | 108 |
| 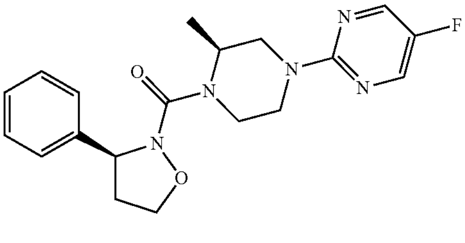 [SMILES: C[C@H]1CN(c2ncc(F)cn2)CCN1C(=O)N1OCC[C@H]1c1ccccc1] | 109 |

TABLE 1-continued
| Active Compounds | |
|---|---|
| 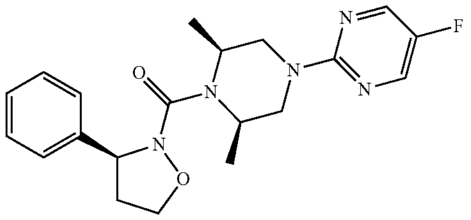 [SMILES: C[C@@H]1CN(c2ncc(F)cn2)C[C@H](C)N1C(=O)N1OCC[C@H]1c1ccccc1] | 110 |
| 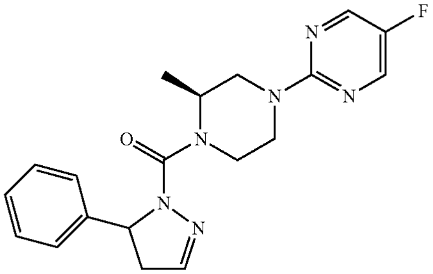 [SMILES: C[C@H]1CN(c2ncc(F)cn2)CCN1C(=O)N1N=CCC1c1ccccc1] | 111A |
| 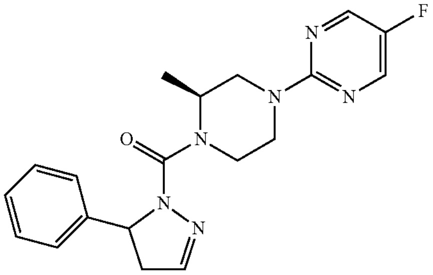 | 111B |
| 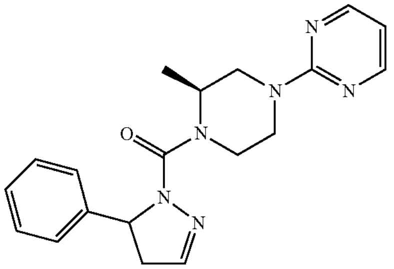 [SMILES: C[C@H]1CN(c2ncccn2)CCN1C(=O)N1N=CCC1c1ccccc1] | 112A |
| 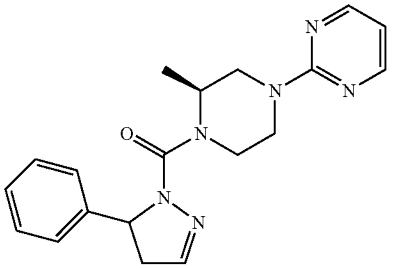 [SMILES: C[C@H]1CN(c2ncccn2)CCN1C(=O)N1N=CCC1c1ccccc1] | 112B |

TABLE 1-continued
| Active Compounds | |
|---|---|
| 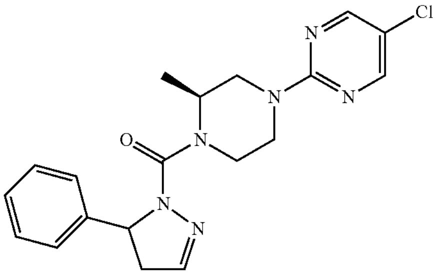 [SMILES: C[C@H]1CN(c2ncc(Cl)cn2)CCN1C(=O)N1N=CCC1c1ccccc1] | 113A |
| 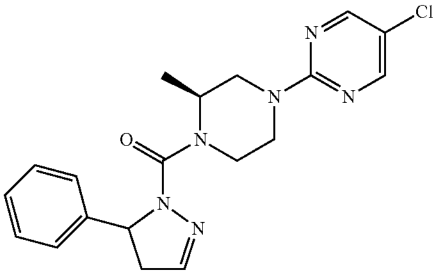 [SMILES: C[C@H]1CN(c2ncc(Cl)cn2)CCN1C(=O)N1N=CCC1c1ccccc1] | 113B |
| 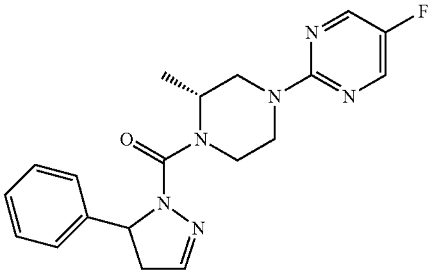 [SMILES: C[C@@H]1CN(c2ncc(F)cn2)CCN1C(=O)N1N=CCC1c1ccccc1] | 114A |
| 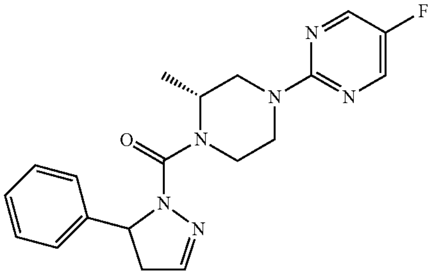 [SMILES: C[C@@H]1CN(c2ncc(F)cn2)CCN1C(=O)N1N=CCC1c1ccccc1] | 114B |
| 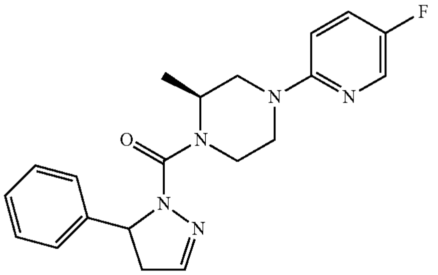 [SMILES: C[C@H]1CN(c2ccc(F)cn2)CCN1C(=O)N1N=CCC1c1ccccc1] | 115A |
| 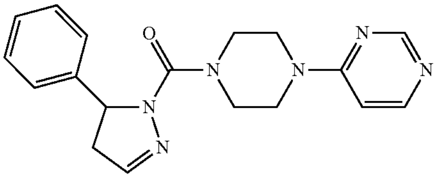 [SMILES: O=C(N1CCN(c2ccncn2)CC1)N1N=CCC1c1ccccc1] | 115B |

TABLE 1-continued
| Active Compounds | |
|---|---|
| 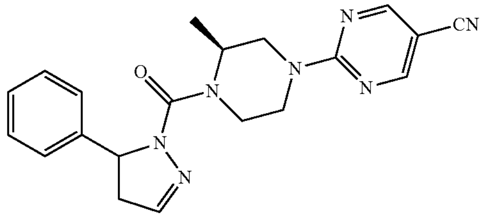 [SMILES: C[C@H]1CN(c2ncc(C#N)cn2)CCN1C(=O)N1N=CCC1c1ccccc1] | 116A |
| 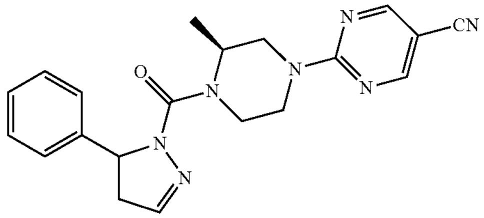 [SMILES: C[C@H]1CN(c2ncc(C#N)cn2)CCN1C(=O)N1N=CCC1c1ccccc1] | 116B |
| 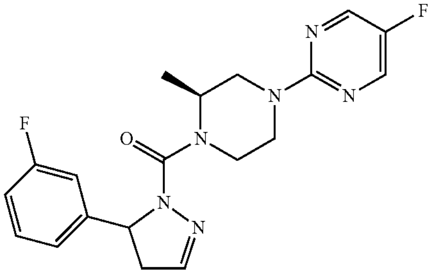 [SMILES: C[C@H]1CN(c2ncc(F)cn2)CCN1C(=O)N1N=CCC1c1cccc(F)c1] | 117A |
| 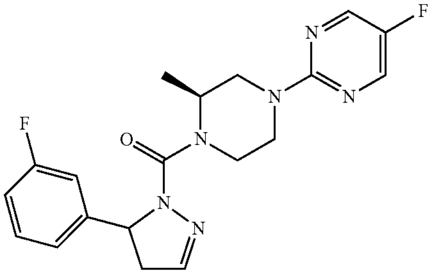 [SMILES: C[C@H]1CN(c2ncc(F)cn2)CCN1C(=O)N1N=CCC1c1cccc(F)c1] | 117B |
| 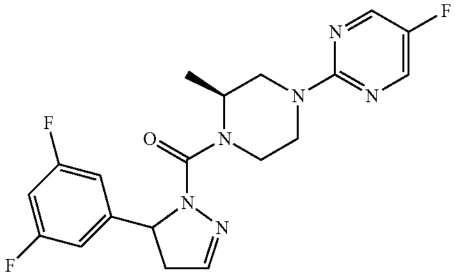 [SMILES: C[C@H]1CN(c2ncc(F)cn2)CCN1C(=O)N1N=CCC1c1cc(F)cc(F)c1] | 118A |
| 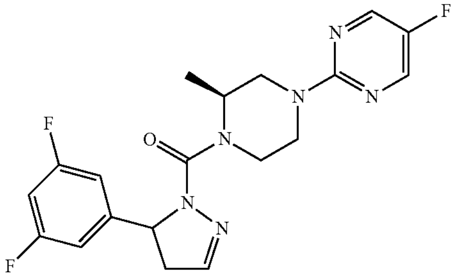 [SMILES: C[C@H]1CN(c2ncc(F)cn2)CCN1C(=O)N1N=CCC1c1cc(F)cc(F)c1] | 118B |

TABLE 1-continued
| Active Compounds |
|---|
| 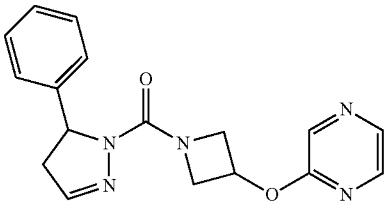 [SMILES: O=C(N1CC(Oc2cnccn2)C1)N1N=CCC1c1ccccc1] 119 |
| 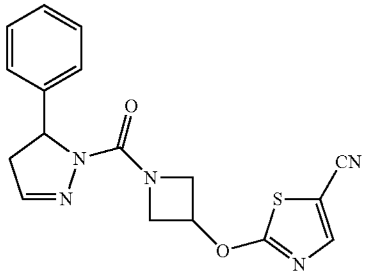 [SMILES: N#Cc1cnc(OC2CN(C(=O)N3N=CCC3c3ccccc3)C2)s1] 120 |
| 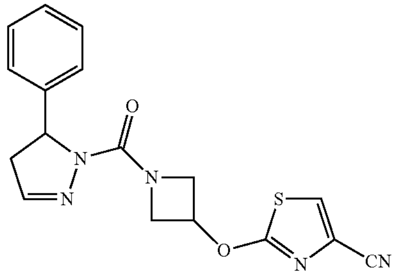 [SMILES: N#Cc1csc(OC2CN(C(=O)N3N=CCC3c3ccccc3)C2)n1] 121 |
| 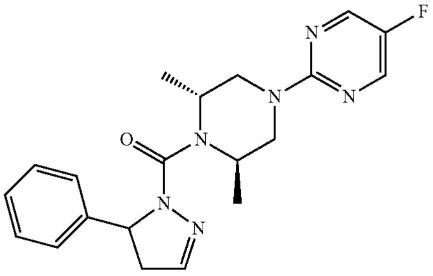 [SMILES: C[C@@H]1CN(c2ncc(F)cn2)C[C@@H](C)N1C(=O)N1N=CCC1c1ccccc1] 122 |
| 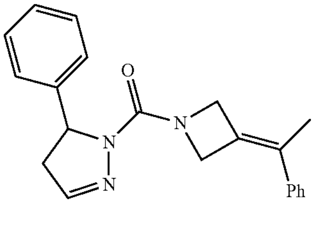 [SMILES: CC(=C1CN(C(=O)N2N=CCC2c2ccccc2)C1)c1ccccc1] 123 |
| 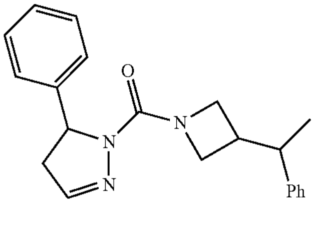 [SMILES: CC(c1ccccc1)C1CN(C(=O)N2N=CCC2c2ccccc2)C1] 124 |

TABLE 1-continued
| Active Compounds | |
|---|---|
| 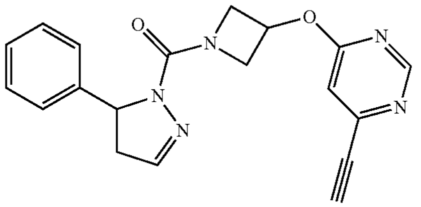 [SMILES: C#Cc1cc(OC2CN(C(=O)N3N=CCC3c3ccccc3)C2)ncn1] | 125 |
| 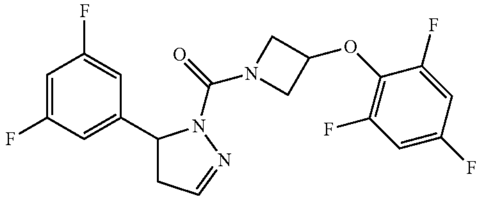 [SMILES: O=C(N1CC(Oc2c(F)cc(F)cc2F)C1)N1N=CCC1c1cc(F)cc(F)c1] | 126 |
| 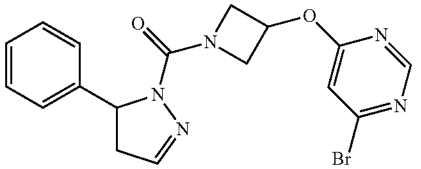 [SMILES: O=C(N1CC(Oc2cc(Br)ncn2)C1)N1N=CCC1c1ccccc1] | 127 |
| 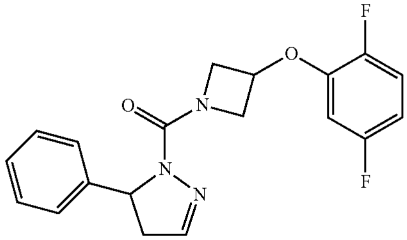 [SMILES: O=C(N1CC(Oc2cc(F)ccc2F)C1)N1N=CCC1c1ccccc1] | 128 |
| 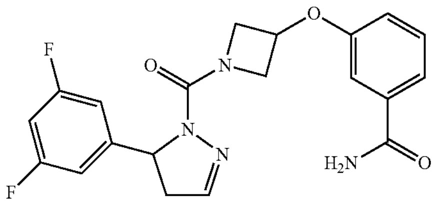 [SMILES: NC(=O)c1cccc(OC2CN(C(=O)N3N=CCC3c3cc(F)cc(F)c3)C2)c1] | 129 |
| 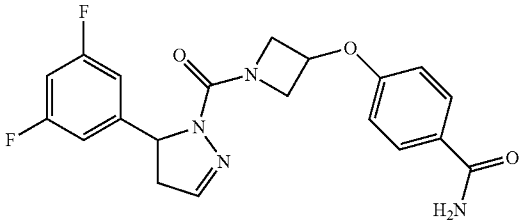 [SMILES: NC(=O)c1ccc(OC2CN(C(=O)N3N=CCC3c3cc(F)cc(F)c3)C2)cc1] | 130 |
| 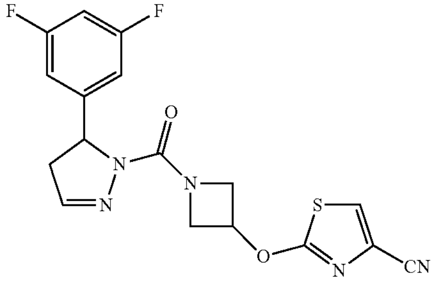 [SMILES: N#Cc1csc(OC2CN(C(=O)N3N=CCC3c3cc(F)cc(F)c3)C2)n1] | 131 |

TABLE 1-continued
| Active Compounds |
| --- |
| 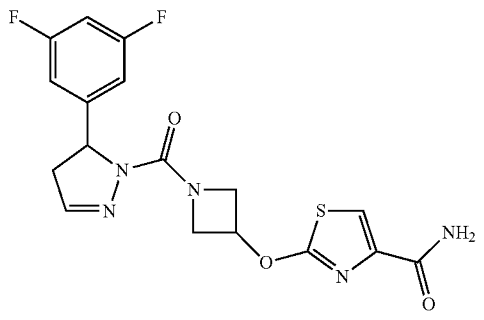 [SMILES: NC(=O)c1csc(OC2CN(C(=O)N3N=CCC3c3cc(F)cc(F)c3)C2)n1] 132 |
| 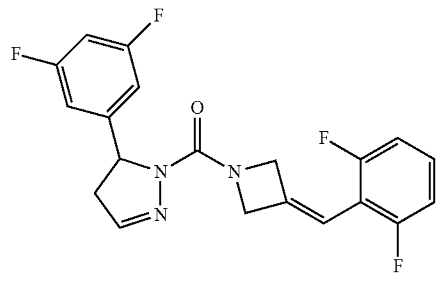 [SMILES: O=C(N1CC(=Cc2c(F)cccc2F)C1)N1N=CCC1c1cc(F)cc(F)c1] 133 |
| 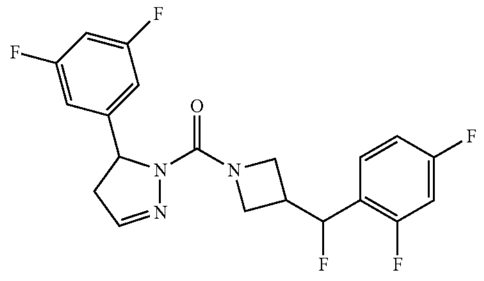 [SMILES: O=C(N1CC(C(F)c2ccc(F)cc2F)C1)N1N=CCC1c1cc(F)cc(F)c1] 134 |
| 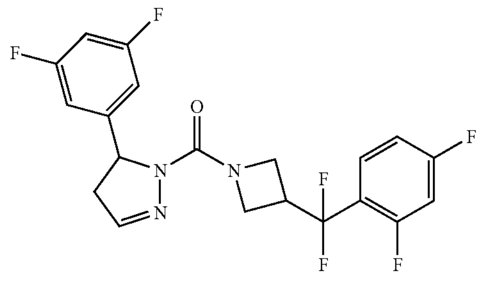 [SMILES: O=C(N1CC(C(F)(F)c2ccc(F)cc2F)C1)N1N=CCC1c1cc(F)cc(F)c1] 135 |
| 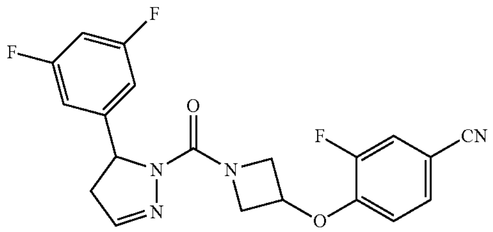 [SMILES: N#Cc1ccc(OC2CN(C(=O)N3N=CCC3c3cc(F)cc(F)c3)C2)c(F)c1] 136 |

TABLE 1-continued
| Active Compounds | |
|---|---|
| 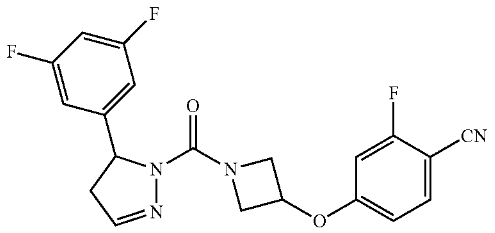 [SMILES: N#Cc1ccc(OC2CN(C(=O)N3N=CCC3c3cc(F)cc(F)c3)C2)cc1F] | 137 |
| 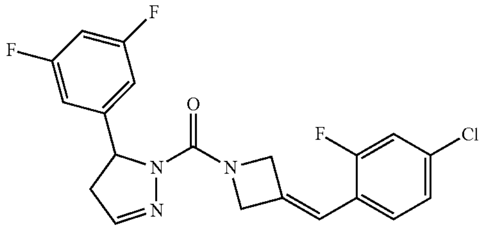 [SMILES: O=C(N1CC(=Cc2ccc(Cl)cc2F)C1)N1N=CCC1c1cc(F)cc(F)c1] | 138 |
| 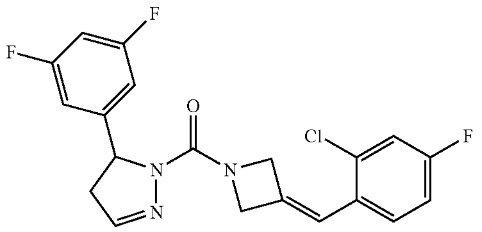 [SMILES: O=C(N1CC(=Cc2ccc(F)cc2Cl)C1)N1N=CCC1c1cc(F)cc(F)c1] | 139 |
| 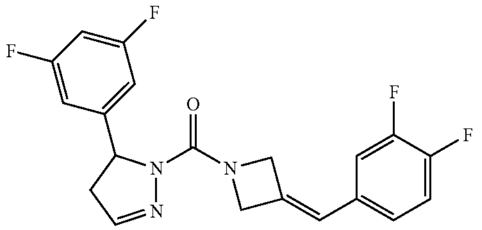 [SMILES: O=C(N1CC(=Cc2ccc(F)c(F)c2)C1)N1N=CCC1c1cc(F)cc(F)c1] | 140 |
| 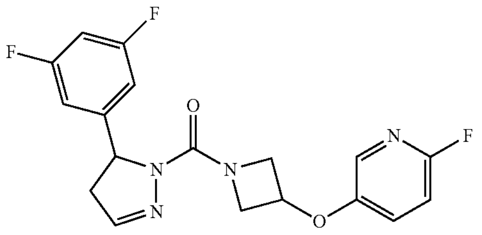 [SMILES: O=C(N1CC(Oc2ccc(F)nc2)C1)N1N=CCC1c1cc(F)cc(F)c1] | 141 |
| 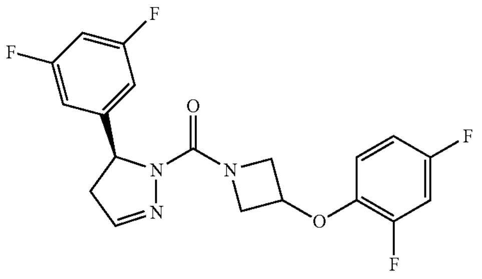 [SMILES: O=C(N1CC(Oc2ccc(F)cc2F)C1)N1N=CC[C@H]1c1cc(F)cc(F)c1] | 142 |

TABLE 1-continued
| Active Compounds | |
|---|---|
| 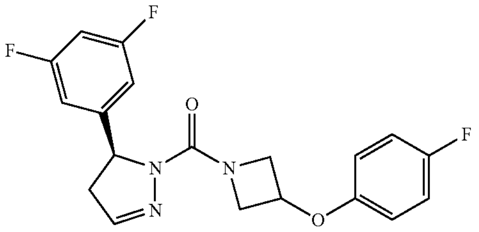 | 143 |
| 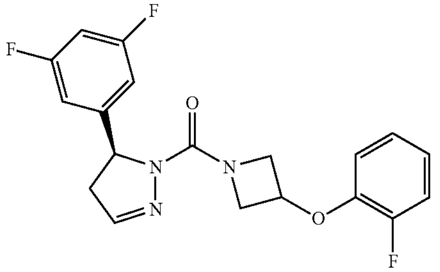 [SMILES: O=C(N1CC(Oc2ccccc2F)C1)N1N=CC[C@H]1c1cc(F)cc(F)c1] | 144 |
| 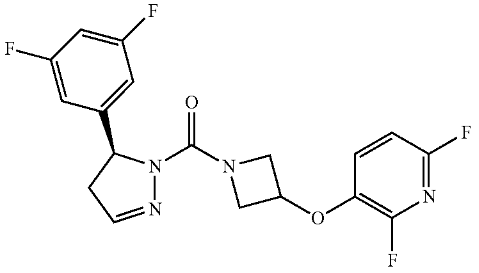 | 145 |
| 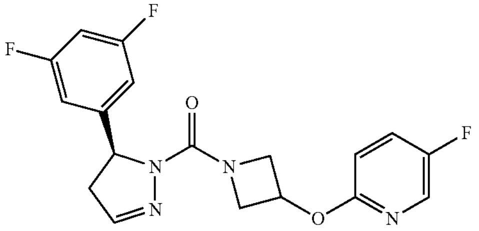 [SMILES: O=C(N1CC(Oc2ccc(F)cn2)C1)N1N=CC[C@H]1c1cc(F)cc(F)c1] | 146 |
| 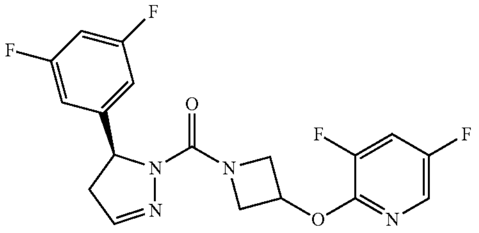 [SMILES: O=C(N1CC(Oc2ncc(F)cc2F)C1)N1N=CC[C@H]1c1cc(F)cc(F)c1] | 147 |
| 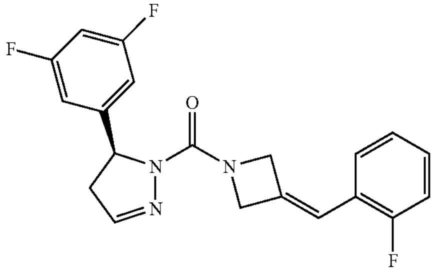 [SMILES: O=C(N1CC(=Cc2ccccc2F)C1)N1N=CC[C@H]1c1cc(F)cc(F)c1] | 148 |

TABLE 1-continued
Active Compounds
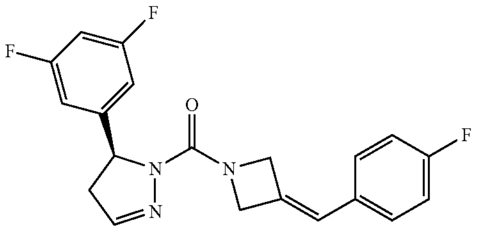 [SMILES: O=C(N1CC(=Cc2ccc(F)cc2)C1)N1N=CC[C@H]1c1cc(F)cc(F)c1]
149
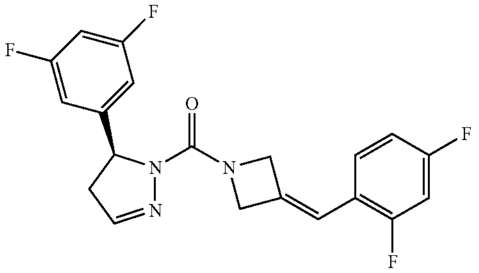 [SMILES: O=C(N1CC(=Cc2ccc(F)cc2F)C1)N1N=CC[C@H]1c1cc(F)cc(F)c1]
150
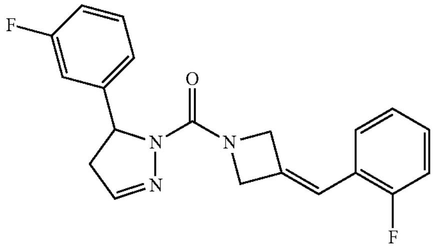 [SMILES: O=C(N1CC(=Cc2ccccc2F)C1)N1N=CCC1c1cccc(F)c1]
151
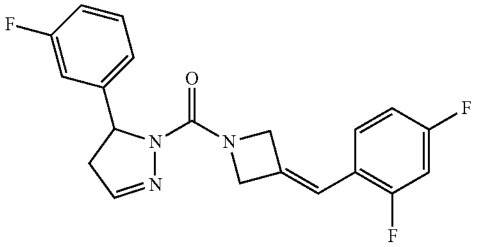 [SMILES: O=C(N1CC(=Cc2ccc(F)cc2F)C1)N1N=CCC1c1cccc(F)c1]
152
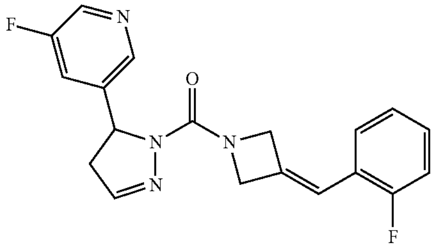 [SMILES: O=C(N1CC(=Cc2ccccc2F)C1)N1N=CCC1c1cncc(F)c1]
153
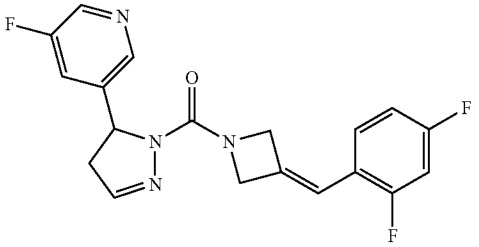 [SMILES: O=C(N1CC(=Cc2ccc(F)cc2F)C1)N1N=CCC1c1cncc(F)c1]
154

TABLE 1-continued
| Active Compounds | |
|---|---|
| 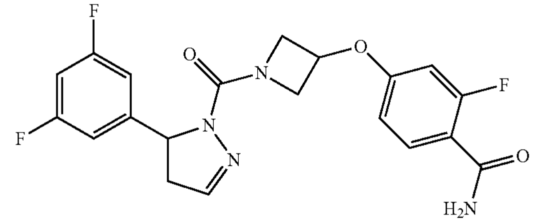 | 155 |
| 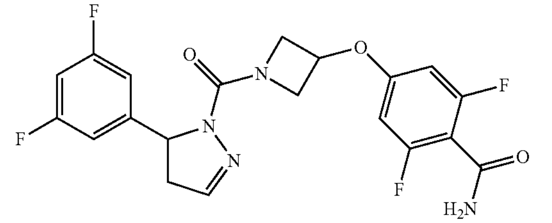 [SMILES: NC(=O)c1c(F)cc(OC2CN(C(=O)N3N=CCC3c3cc(F)cc(F)c3)C2)cc1F] | 156 |
| 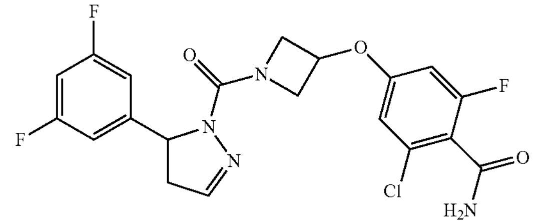 [SMILES: NC(=O)c1c(F)cc(OC2CN(C(=O)N3N=CCC3c3cc(F)cc(F)c3)C2)cc1Cl] | 157 |
| 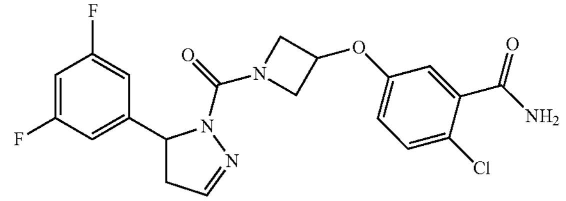 [SMILES: NC(=O)c1cc(OC2CN(C(=O)N3N=CCC3c3cc(F)cc(F)c3)C2)ccc1Cl] | 158 |
| 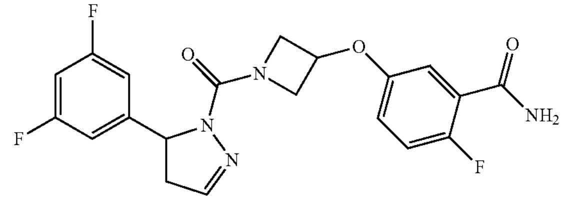 [SMILES: NC(=O)c1cc(OC2CN(C(=O)N3N=CCC3c3cc(F)cc(F)c3)C2)ccc1F] | 159 |
| 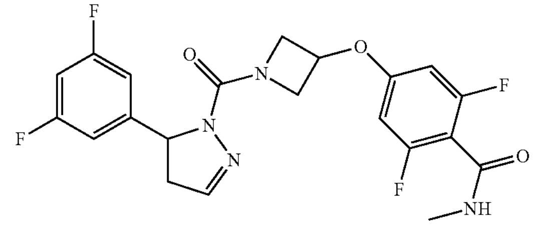 [SMILES: CNC(=O)c1c(F)cc(OC2CN(C(=O)N3N=CCC3c3cc(F)cc(F)c3)C2)cc1F] | 160 |
| 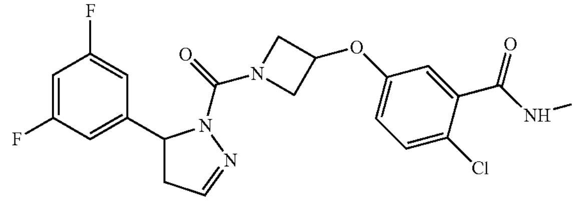 [SMILES: CNC(=O)c1cc(OC2CN(C(=O)N3N=CCC3c3cc(F)cc(F)c3)C2)ccc1Cl] | 161 |

TABLE 1-continued
| Active Compounds |
|---|
| 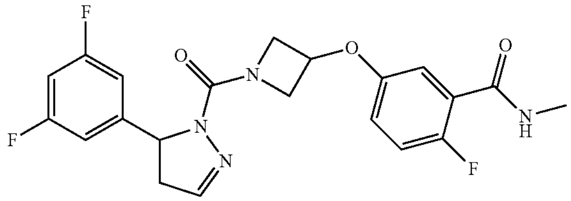 [SMILES: CNC(=O)c1cc(OC2CN(C(=O)N3N=CCC3c3cc(F)cc(F)c3)C2)ccc1F] 162 |
| 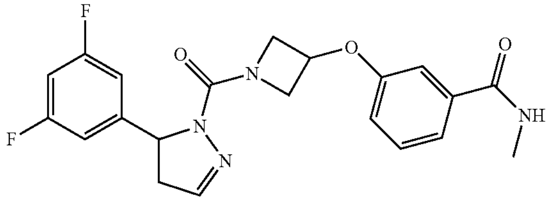 [SMILES: CNC(=O)c1cccc(OC2CN(C(=O)N3N=CCC3c3cc(F)cc(F)c3)C2)c1] 163 |
| 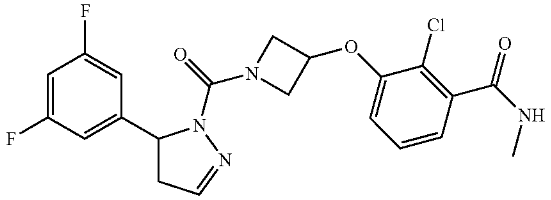 [SMILES: CNC(=O)c1cccc(OC2CN(C(=O)N3N=CCC3c3cc(F)cc(F)c3)C2)c1Cl] 164 |
| 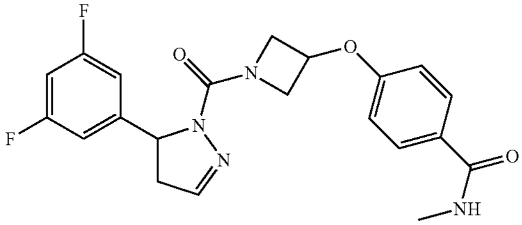 [SMILES: CNC(=O)c1ccc(OC2CN(C(=O)N3N=CCC3c3cc(F)cc(F)c3)C2)cc1] 165 |
| 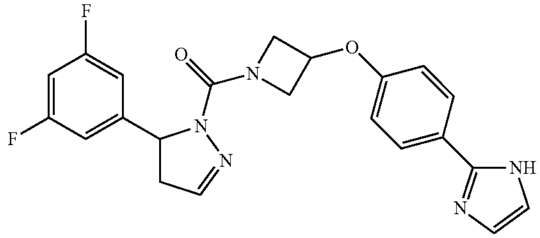 [SMILES: O=C(N1CC(Oc2ccc(-c3ncc[nH]3)cc2)C1)N1N=CCC1c1cc(F)cc(F)c1] 166 |
| 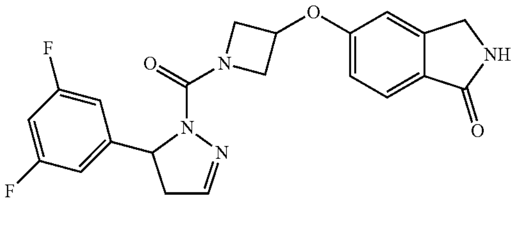 [SMILES: O=C1NCc2cc(OC3CN(C(=O)N4N=CCC4c4cc(F)cc(F)c4)C3)ccc21] 167 |
| 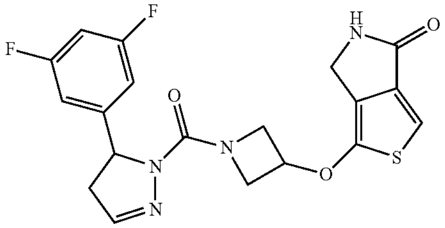 [SMILES: O=C1NCc2c1csc2OC1CN(C(=O)N2N=CCC2c2cc(F)cc(F)c2)C1] 168 |

TABLE 1-continued
| Active Compounds | |
|---|---|
| 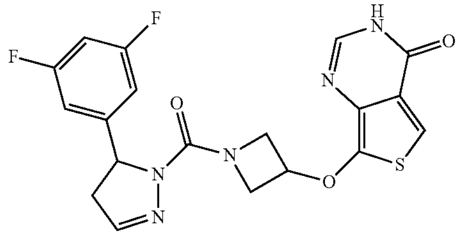 [SMILES: O=C(N1CC(Oc2scc3c(=O)[nH]cnc23)C1)N1N=CCC1c1cc(F)cc(F)c1] | 169 |
| 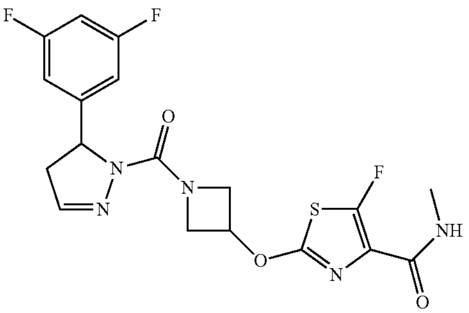 [SMILES: CNC(=O)c1nc(OC2CN(C(=O)N3N=CCC3c3cc(F)cc(F)c3)C2)oc1F] | 170 |
| 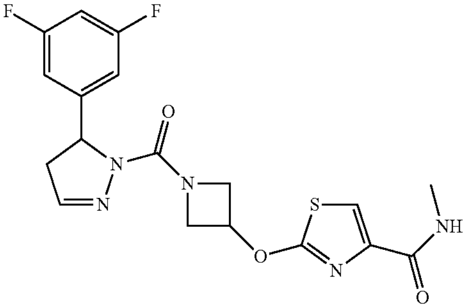 [SMILES: CNC(=O)c1coc(OC2CN(C(=O)N3N=CCC3c3cc(F)cc(F)c3)C2)n1] | 171 |
| 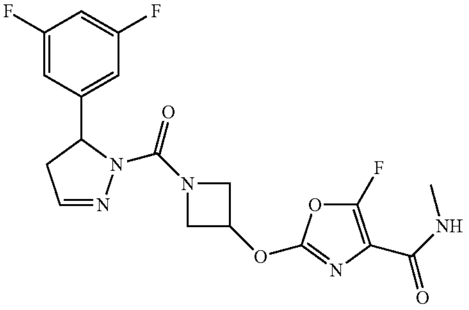 | 172 |
| 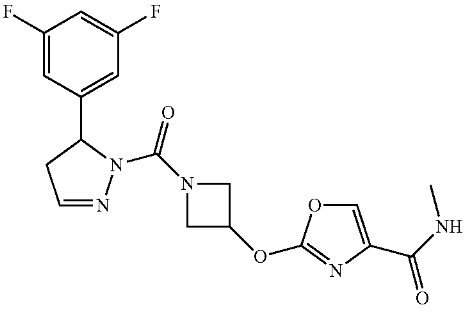 | 173 |

TABLE 1-continued
| Active Compounds | |
|---|---|
| 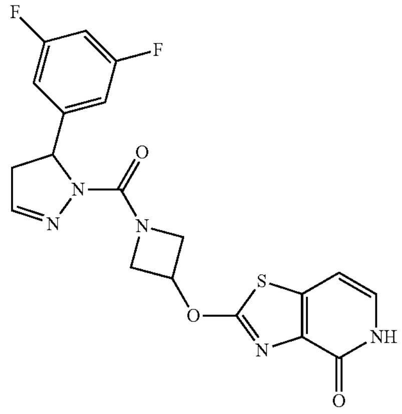 [SMILES: O=C(N1CC(Oc2nc3c(=O)[nH]ccc3s2)C1)N1N=CCC1c1cc(F)cc(F)c1] | 174 |
| 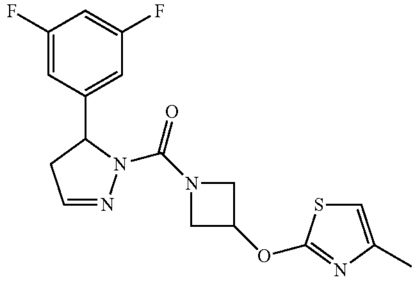 [SMILES: Cc1csc(OC2CN(C(=O)N3N=CCC3c3cc(F)cc(F)c3)C2)n1] | 175 |
| 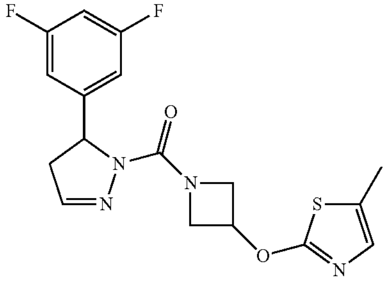 [SMILES: Cc1cnc(OC2CN(C(=O)N3N=CCC3c3cc(F)cc(F)c3)C2)s1] | 176 |
| 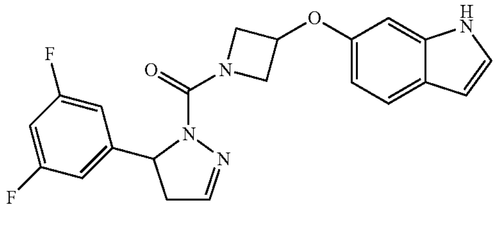 [SMILES: O=C(N1CC(Oc2ccc3cc[nH]c3c2)C1)N1N=CCC1c1cc(F)cc(F)c1] | 177 |
| 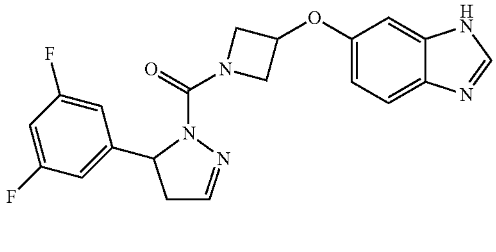 [SMILES: O=C(N1CC(Oc2ccc3nc[nH]c3c2)C1)N1N=CCC1c1cc(F)cc(F)c1] | 178 |

TABLE 1-continued
| Active Compounds | |
|---|---|
| 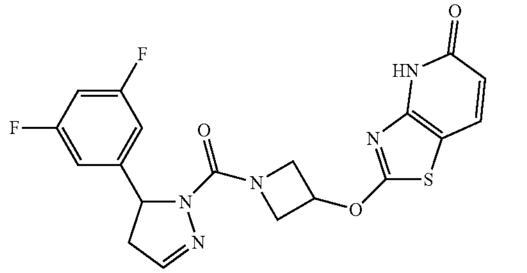 [SMILES: O=C(N1CC(Oc2nc3[nH]c(=O)ccc3s2)C1)N1N=CCC1c1cc(F)cc(F)c1] | 179 |
| 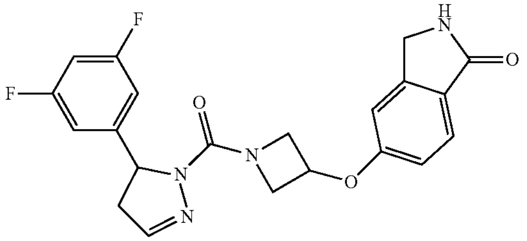 [SMILES: O=C1NCc2cc(OC3CN(C(=O)N4N=CCC4c4cc(F)cc(F)c4)C3)ccc21] | 180 |
| 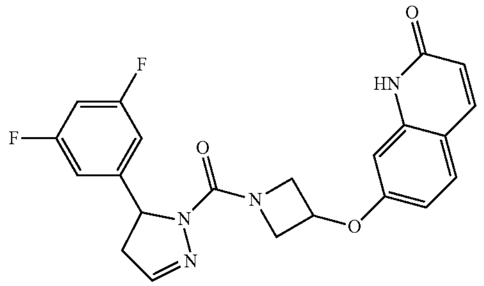 [SMILES: O=C(N1CC(Oc2ccc3ccc(=O)[nH]c3c2)C1)N1N=CCC1c1cc(F)cc(F)c1] | 181 |
| 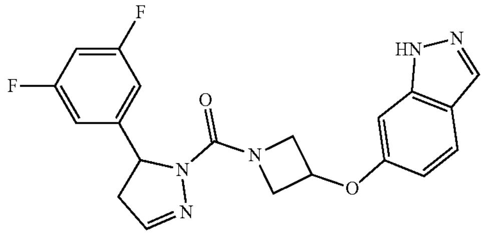 [SMILES: O=C(N1CC(Oc2ccc3cn[nH]c3c2)C1)N1N=CCC1c1cc(F)cc(F)c1] | 182 |
| 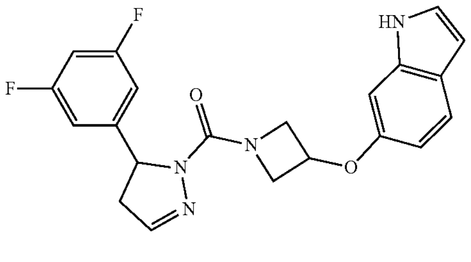 [SMILES: O=C(N1CC(Oc2ccc3cc[nH]c3c2)C1)N1N=CCC1c1cc(F)cc(F)c1] | 183 |
| 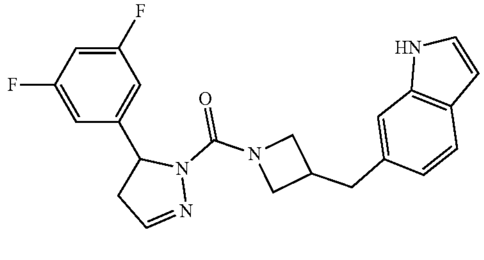 [SMILES: O=C(N1CC(Cc2ccc3cc[nH]c3c2)C1)N1N=CCC1c1cc(F)cc(F)c1] | 183 |

TABLE 1-continued
| Active Compounds | |
|---|---|
| 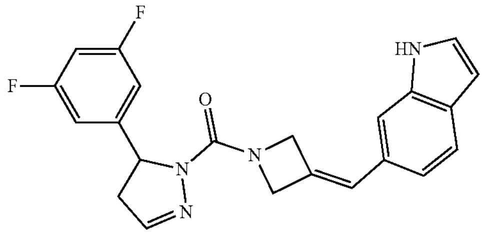 [SMILES: O=C(N1CC(=Cc2ccc3cc[nH]c3c2)C1)N1N=CCC1c1cc(F)cc(F)c1] | 184 |
| 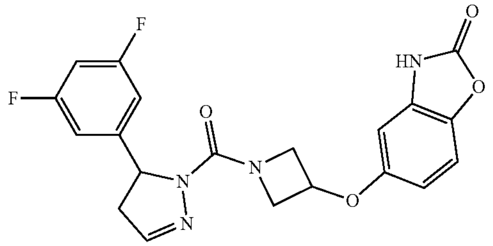 [SMILES: O=C(N1CC(Oc2ccc3oc(=O)[nH]c3c2)C1)N1N=CCC1c1cc(F)cc(F)c1] | 185 |
| 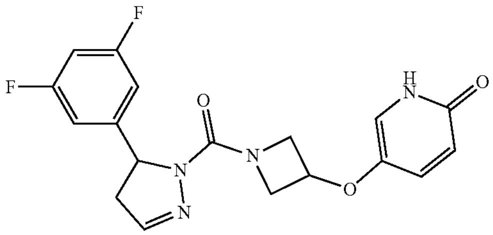 [SMILES: O=C(N1CC(Oc2ccc(=O)[nH]c2)C1)N1N=CCC1c1cc(F)cc(F)c1] | 186 |
| 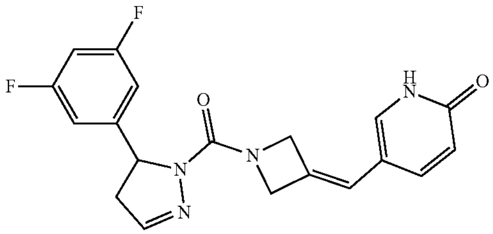 [SMILES: O=C(N1CC(=Cc2ccc(=O)[nH]c2)C1)N1N=CCC1c1cc(F)cc(F)c1] | 187 |
| 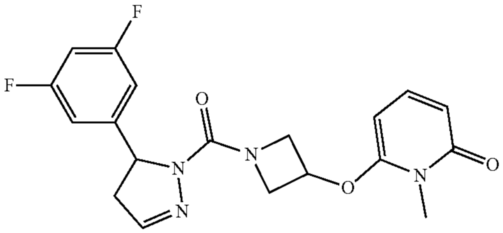 [SMILES: Cn1c(OC2CN(C(=O)N3N=CCC3c3cc(F)cc(F)c3)C2)cccc1=O] | 188 |
| 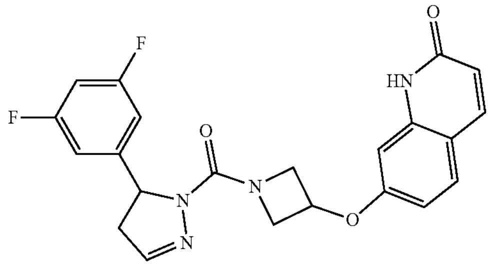 [SMILES: O=C(N1CC(Oc2ccc3ccc(=O)[nH]c3c2)C1)N1N=CCC1c1cc(F)cc(F)c1] | 189 |

TABLE 1-continued
| Active Compounds | |
|---|---|
| 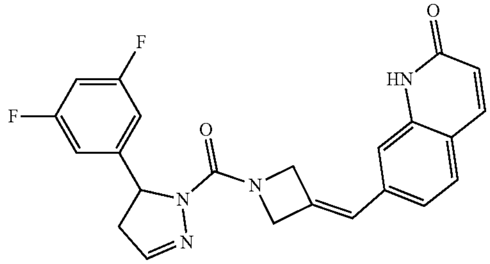 [SMILES: O=C(N1CC(=Cc2ccc3ccc(=O)[nH]c3c2)C1)N1N=CCC1c1cc(F)cc(F)c1] | 190 |
| 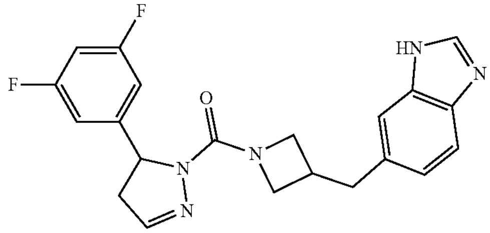 [SMILES: O=C(N1CC(Cc2ccc3nc[nH]c3c2)C1)N1N=CCC1c1cc(F)cc(F)c1] | 191 |
| 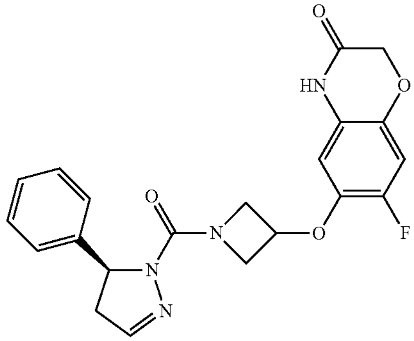 [SMILES: O=C1COc2cc(F)c(OC3CN(C(=O)N4N=CC[C@H]4c4ccccc4)C3)cc2N1] | 192 |
| 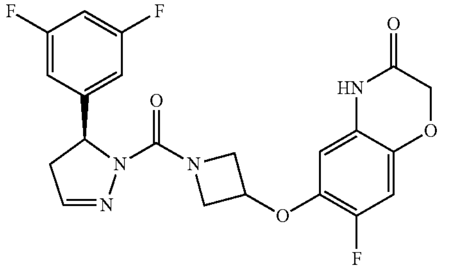 [SMILES: O=C1COc2cc(F)c(OC3CN(C(=O)N4N=CC[C@H]4c4cc(F)cc(F)c4)C3)cc2N1] | 193 |
| 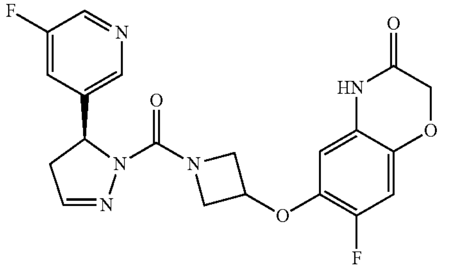 [SMILES: O=C1COc2cc(F)c(OC3CN(C(=O)N4N=CC[C@H]4c4cncc(F)c4)C3)cc2N1] | 194 |

TABLE 1-continued
| Active Compounds | |
|---|---|
| 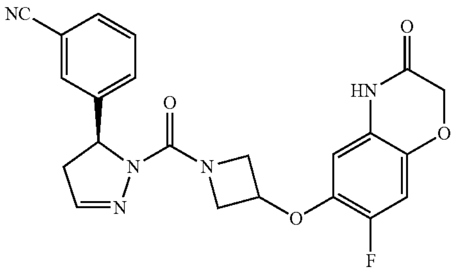 [SMILES: N#Cc1cccc([C@@H]2CC=NN2C(=O)N2CC(Oc3cc4c(cc3F)OCC(=O)N4)C2)c1] | 195 |
| 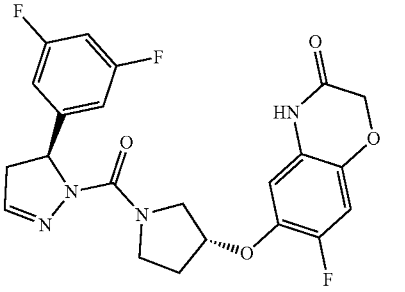 [SMILES: O=C1COc2cc(F)c(O[C@@H]3CCN(C(=O)N4N=CC[C@H]4c4cc(F)cc(F)c4)C3)cc2N1] | 196 |
| 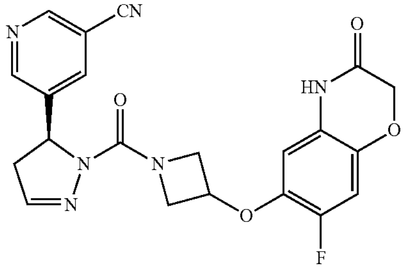 [SMILES: N#Cc1cncc([C@@H]2CC=NN2C(=O)N2CC(Oc3cc4c(cc3F)OCC(=O)N4)C2)c1] | 197 |
| 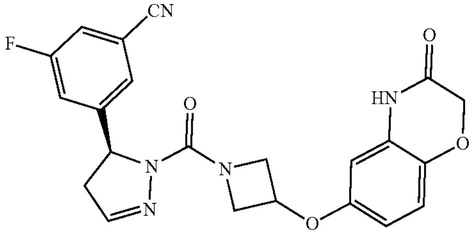 [SMILES: N#Cc1cc(F)cc([C@@H]2CC=NN2C(=O)N2CC(Oc3ccc4c(c3)NC(=O)CO4)C2)c1] | 198 |
| 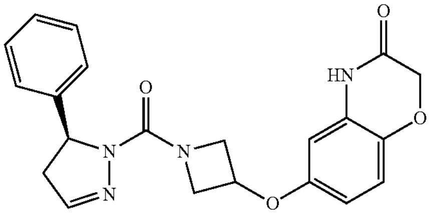 [SMILES: O=C1COc2ccc(OC3CN(C(=O)N4N=CC[C@H]4c4ccccc4)C3)cc2N1] | 199 |
| 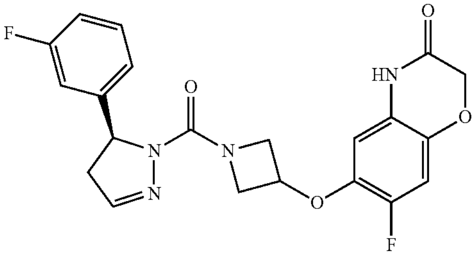 [SMILES: O=C1COc2cc(F)c(OC3CN(C(=O)N4N=CC[C@H]4c4cccc(F)c4)C3)cc2N1] | 200 |

TABLE 1-continued
| Active Compounds | |
|---|---|
| 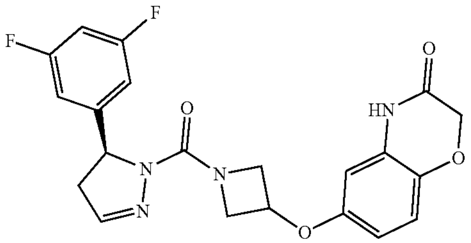 [SMILES: O=C1COc2ccc(OC3CN(C(=O)N4N=CC[C@H]4c4cc(F)cc(F)c4)C3)cc2N1] | 201 |
| 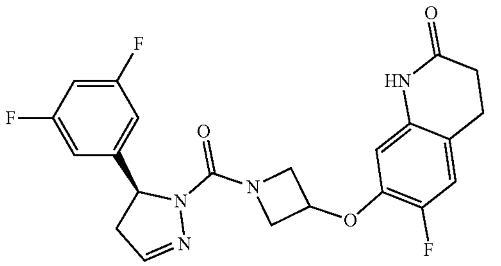 [SMILES: O=C1CCc2cc(F)c(OC3CN(C(=O)N4N=CC[C@H]4c4cc(F)cc(F)c4)C3)cc2N1] | 202 |
| 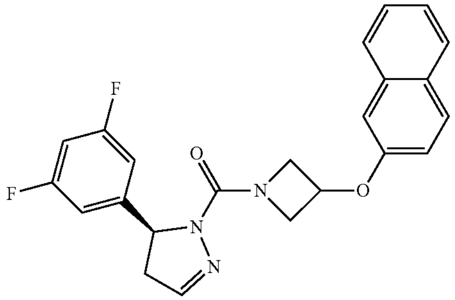 [SMILES: O=C(N1CC(Oc2ccc3ccccc3c2)C1)N1N=CC[C@H]1c1cc(F)cc(F)c1] | 203 |
| 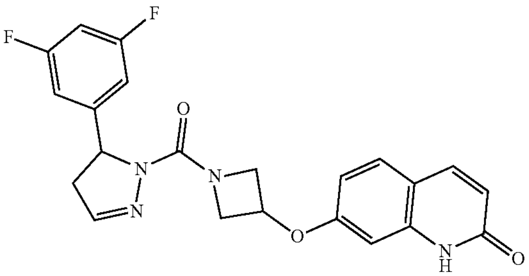 [SMILES: O=C(N1CC(Oc2ccc3ccc(=O)[nH]c3c2)C1)N1N=CCC1c1cc(F)cc(F)c1] | 204 |
| 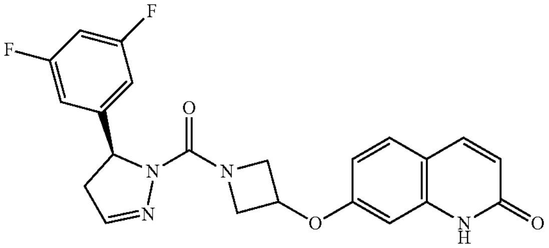 [SMILES: O=C(N1CC(Oc2ccc3ccc(=O)[nH]c3c2)C1)N1N=CC[C@H]1c1cc(F)cc(F)c1] | 205 |

TABLE 1-continued
| Active Compounds | |
|---|---|
| 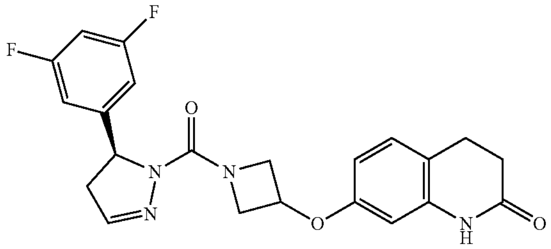 [SMILES: O=C1CCc2ccc(OC3CN(C(=O)N4N=CC[C@H]4c4cc(F)cc(F)c4)C3)cc2N1] | 206 |
| 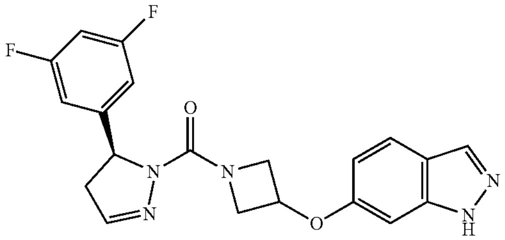 [SMILES: O=C(N1CC(Oc2ccc3cn[nH]c3c2)C1)N1N=CC[C@H]1c1cc(F)cc(F)c1] | 207 |
| 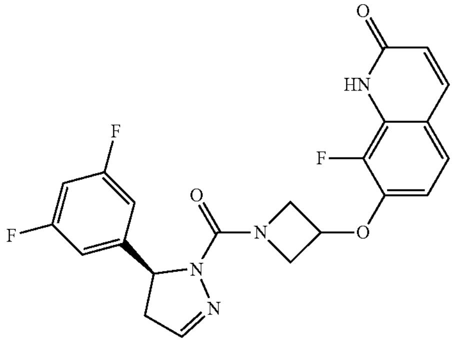 [SMILES: O=C(N1CC(Oc2ccc3ccc(=O)[nH]c3c2F)C1)N1N=CC[C@H]1c1cc(F)cc(F)c1] | 208 |
| 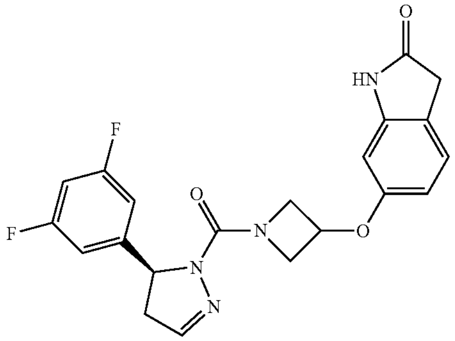 [SMILES: O=C1Cc2ccc(OC3CN(C(=O)N4N=CC[C@H]4c4cc(F)cc(F)c4)C3)cc2N1] | 209 |
| 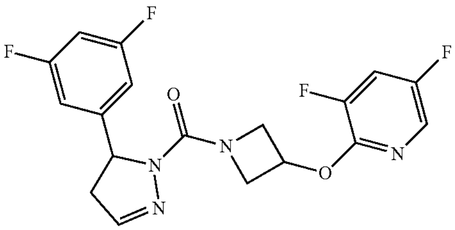 [SMILES: O=C(N1CC(Oc2ncc(F)cc2F)C1)N1N=CCC1c1cc(F)cc(F)c1] | 210 |

TABLE 1-continued
| Active Compounds | |
|---|---|
| 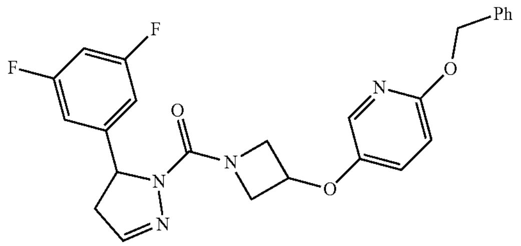 [SMILES: O=C(N1CC(Oc2ccc(OCc3ccccc3)nc2)C1)N1N=CCC1c1cc(F)cc(F)c1] | 211 |
| 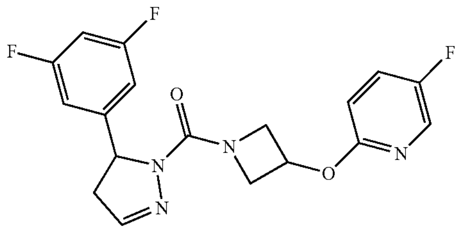 [SMILES: O=C(N1CC(Oc2ccc(F)cn2)C1)N1N=CCC1c1cc(F)cc(F)c1] | 212 |
| 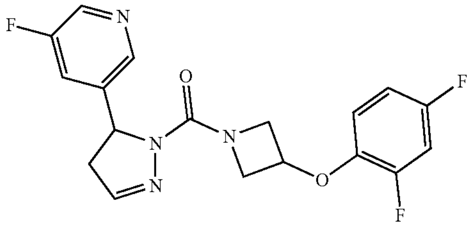 [SMILES: O=C(N1CC(Oc2ccc(F)cc2F)C1)N1N=CCC1c1cncc(F)c1] | 213 |
| 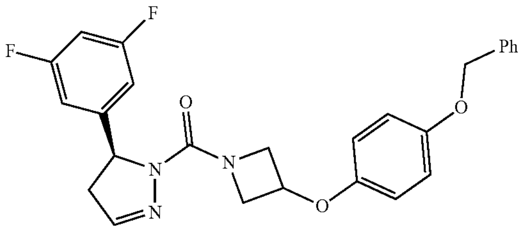 [SMILES: O=C(N1CC(Oc2ccc(OCc3ccccc3)cc2)C1)N1N=CC[C@H]1c1cc(F)cc(F)c1] | 214 |
| 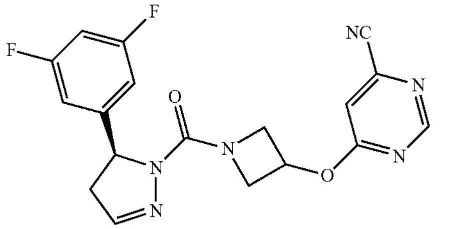 [SMILES: N#Cc1cc(OC2CN(C(=O)N3N=CC[C@H]3c3cc(F)cc(F)c3)C2)ncn1] | 215 |
| 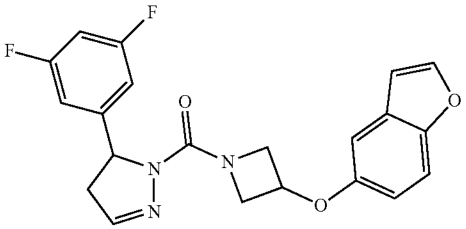 [SMILES: O=C(N1CC(Oc2ccc3occc3c2)C1)N1N=CCC1c1cc(F)cc(F)c1] | 216 |

TABLE 1-continued
| Active Compounds |
| --- |
| 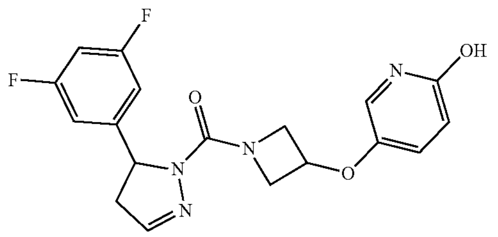 [SMILES: O=C(N1CC(Oc2ccc(O)nc2)C1)N1N=CCC1c1cc(F)cc(F)c1] 217 |
| 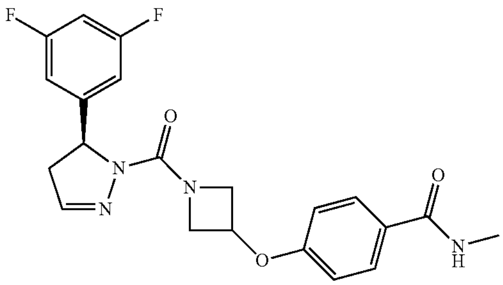 [SMILES: CNC(=O)c1ccc(OC2CN(C(=O)N3N=CC[C@H]3c3cc(F)cc(F)c3)C2)cc1] 218 |
| 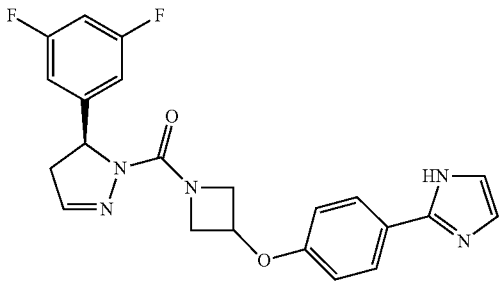 [SMILES: O=C(N1CC(Oc2ccc(-c3ncc[nH]3)cc2)C1)N1N=CC[C@H]1c1cc(F)cc(F)c1] 219 |
| 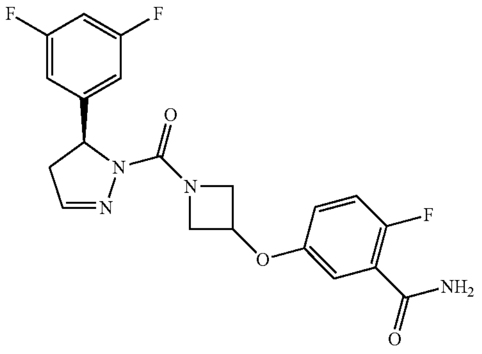 [SMILES: NC(=O)c1cc(OC2CN(C(=O)N3N=CC[C@H]3c3cc(F)cc(F)c3)C2)ccc1F] 220 |
| 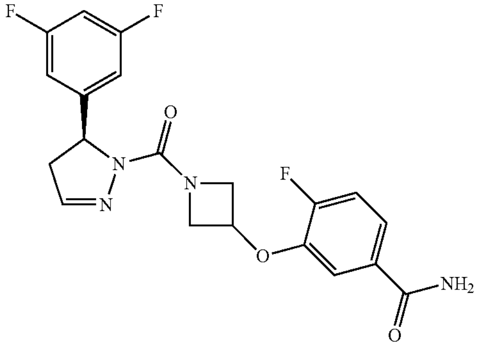 [SMILES: NC(=O)c1ccc(F)c(OC2CN(C(=O)N3N=CC[C@H]3c3cc(F)cc(F)c3)C2)c1] 221 |

TABLE 1-continued
| Active Compounds | |
|---|---|
| 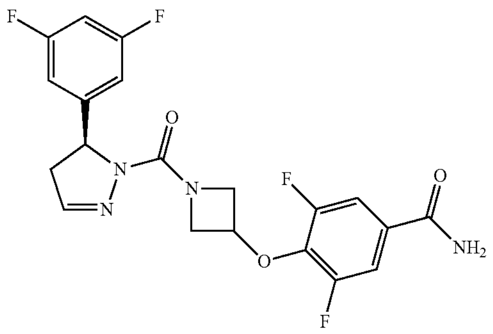 [SMILES: NC(=O)c1cc(F)c(OC2CN(C(=O)N3N=CC[C@H]3c3cc(F)cc(F)c3)C2)c(F)c1] | 222 |
| 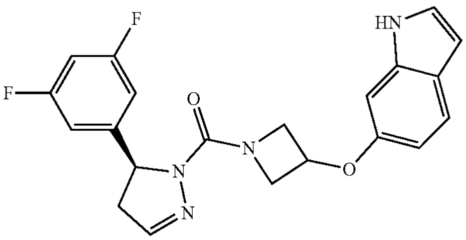 [SMILES: O=C(N1CC(Oc2ccc3cc[nH]c3c2)C1)N1N=CC[C@H]1c1cc(F)cc(F)c1] | 223 |
| 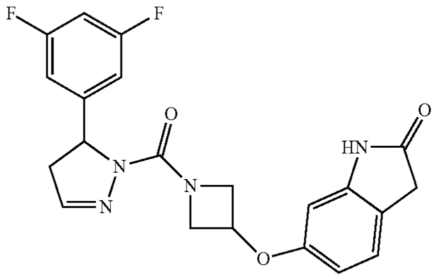 [SMILES: O=C1Cc2ccc(OC3CN(C(=O)N4N=CCC4c4cc(F)cc(F)c4)C3)cc2N1] | 224 |
| 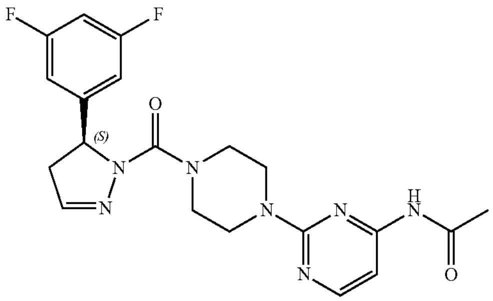 | 225 |
| 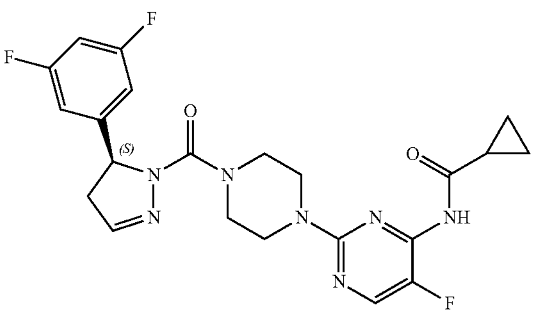 | 226 |

TABLE 1-continued
| Active Compounds | |
|---|---|
| 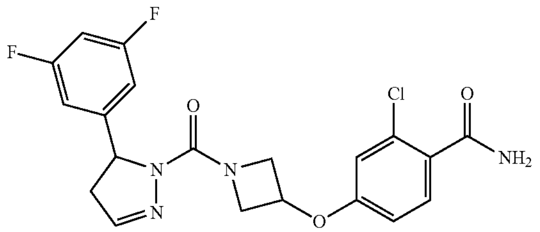 [SMILES: NC(=O)c1ccc(OC2CN(C(=O)N3N=CCC3c3cc(F)cc(F)c3)C2)cc1Cl] | 227 |
| 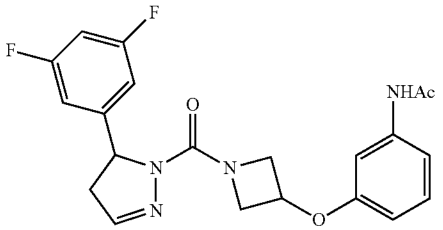 [SMILES: CC(=O)Nc1cccc(OC2CN(C(=O)N3N=CCC3c3cc(F)cc(F)c3)C2)c1] | 228 |
| 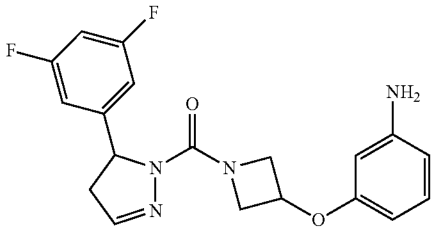 [SMILES: Nc1cccc(OC2CN(C(=O)N3N=CCC3c3cc(F)cc(F)c3)C2)c1] | 229 |
| 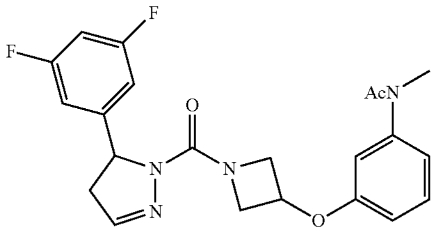 | 230 |
| 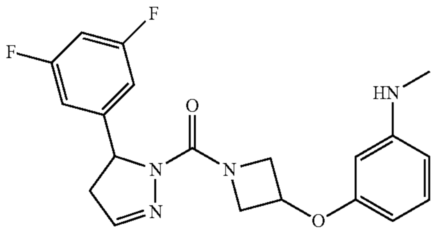 [SMILES: CNc1cccc(OC2CN(C(=O)N3N=CCC3c3cc(F)cc(F)c3)C2)c1] | 231 |
| 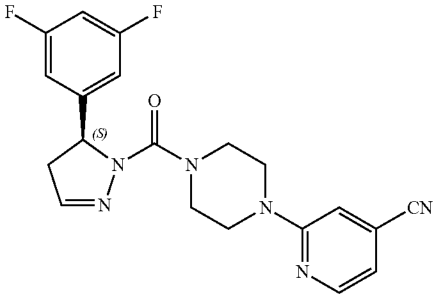 | 232 |

TABLE 1-continued
| Active Compounds |
|---|
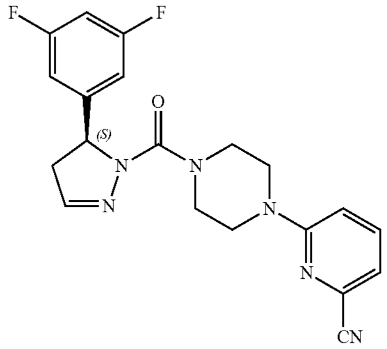
233
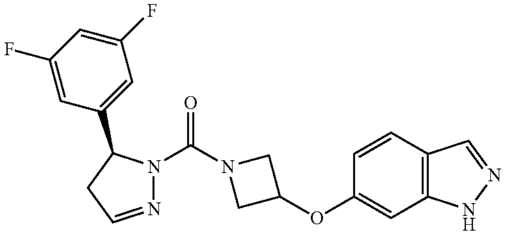 [SMILES: O=C(N1CC(Oc2ccc3cn[nH]c3c2)C1)N1N=CC[C@H]1c1cc(F)cc(F)c1]
234
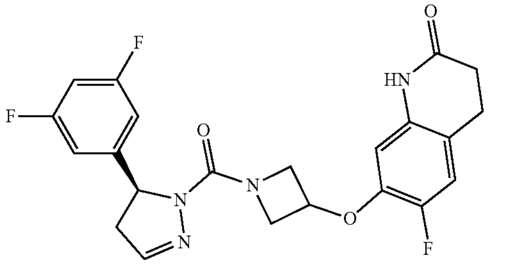 [SMILES: O=C1CCc2cc(F)c(OC3CN(C(=O)N4N=CC[C@H]4c4cc(F)cc(F)c4)C3)cc2N1]
235
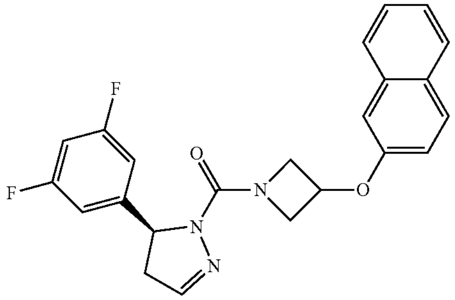 [SMILES: O=C(N1CC(Oc2ccc3ccccc3c2)C1)N1N=CC[C@H]1c1cc(F)cc(F)c1]
236
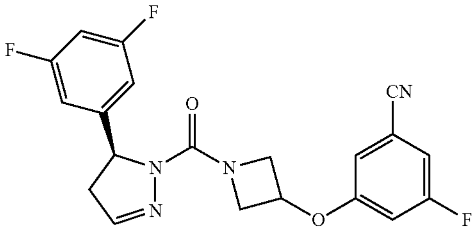 [SMILES: N#Cc1cc(F)cc(OC2CN(C(=O)N3N=CC[C@H]3c3cc(F)cc(F)c3)C2)c1]
237

TABLE 1-continued
| Active Compounds | |
|---|---|
| 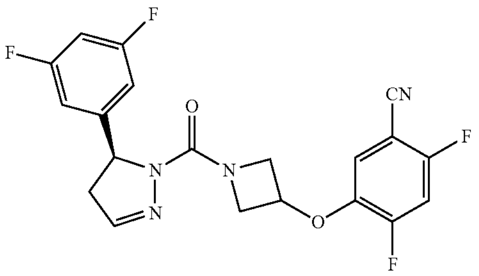 [SMILES: N#Cc1cc(OC2CN(C(=O)N3N=CC[C@H]3c3cc(F)cc(F)c3)C2)c(F)cc1F] | 238 |
| 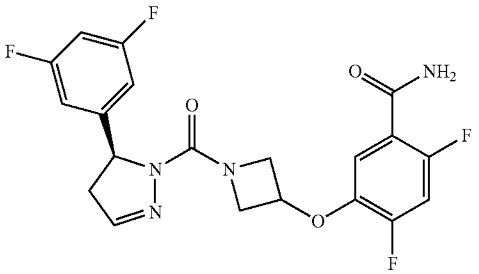 [SMILES: NC(=O)c1cc(OC2CN(C(=O)N3N=CC[C@H]3c3cc(F)cc(F)c3)C2)c(F)cc1F] | 239 |
| 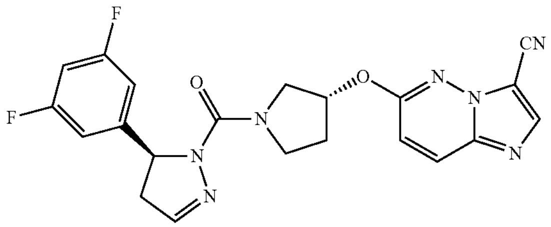 [SMILES: N#Cc1cnc2ccc(O[C@@H]3CCN(C(=O)N4N=CC[C@H]4c4cc(F)cc(F)c4)C3)nn12] | 240 |
| 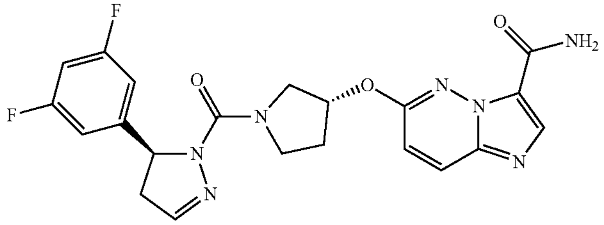 [SMILES: NC(=O)c1cnc2ccc(O[C@@H]3CCN(C(=O)N4N=CC[C@H]4c4cc(F)cc(F)c4)C3)nn12] | 241 |
| 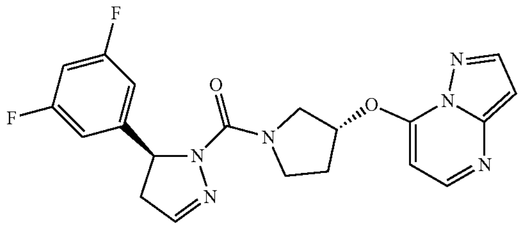 [SMILES: O=C(N1CC[C@@H](Oc2ccnc3ccnn23)C1)N1N=CC[C@H]1c1cc(F)cc(F)c1] | 242 |
| 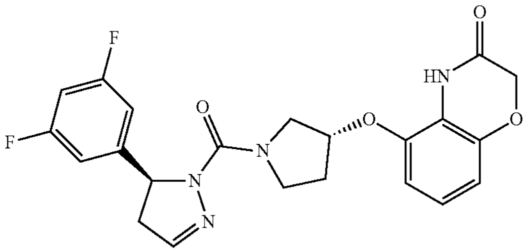 [SMILES: O=C1COc2cccc(O[C@@H]3CCN(C(=O)N4N=CC[C@H]4c4cc(F)cc(F)c4)C3)c2N1] | 243 |

TABLE 1-continued
| Active Compounds | |
|---|---|
| 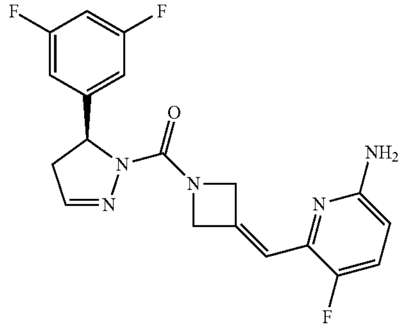 [SMILES: Nc1ccc(F)c(C=C2CN(C(=O)N3N=CC[C@H]3c3cc(F)cc(F)c3)C2)n1] | 244 |
| 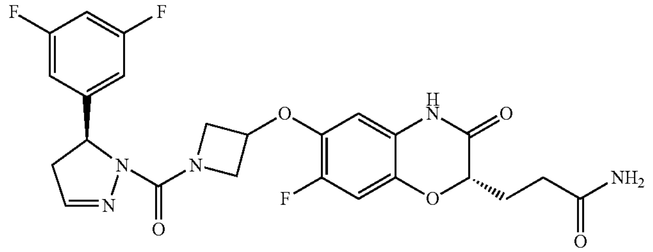 [SMILES: NC(=O)CC[C@@H]1Oc2cc(F)c(OC3CN(C(=O)N4N=CC[C@H]4c4cc(F)cc(F)c4)C3)cc2NC1=O] | 245 |
| 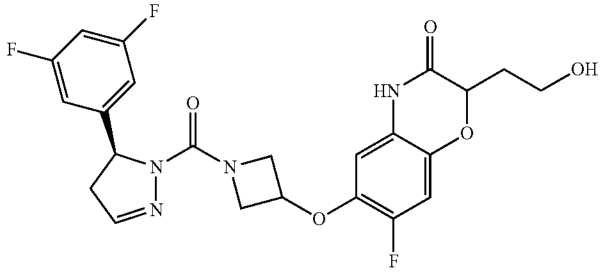 [SMILES: O=C1Nc2cc(OC3CN(C(=O)N4N=CC[C@H]4c4cc(F)cc(F)c4)C3)c(F)cc2OC1CCO] | 246 |
| 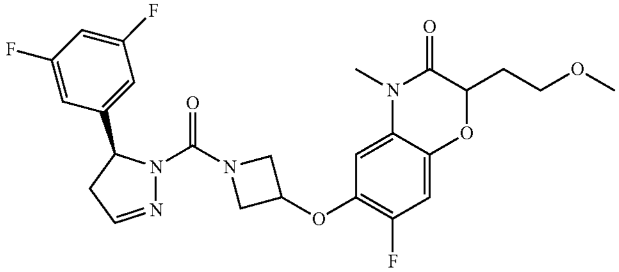 [SMILES: COCCC1Oc2cc(F)c(OC3CN(C(=O)N4N=CC[C@H]4c4cc(F)cc(F)c4)C3)cc2N(C)C1=O] | 247 |
| 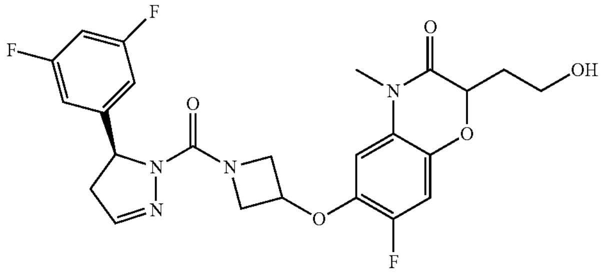 [SMILES: CN1C(=O)C(CCO)Oc2cc(F)c(OC3CN(C(=O)N4N=CC[C@H]4c4cc(F)cc(F)c4)C3)cc21] | 248 |

TABLE 1-continued
Active Compounds
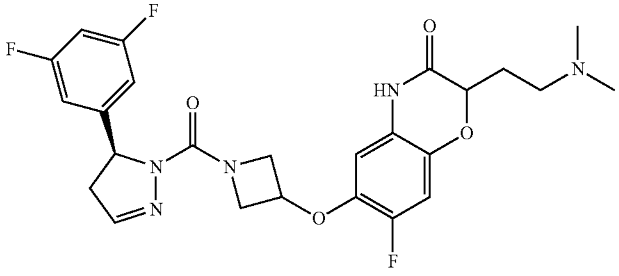 [SMILES: CN(C)CCC1Oc2cc(F)c(OC3CN(C(=O)N4N=CC[C@H]4c4cc(F)cc(F)c4)C3)cc2NC1=O]
249
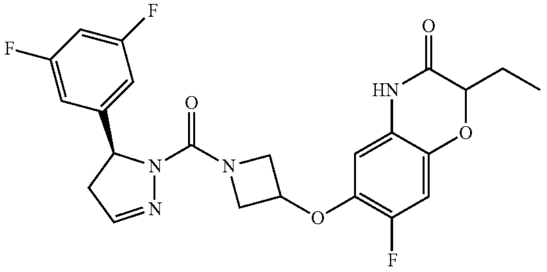 [SMILES: CCC1Oc2cc(F)c(OC3CN(C(=O)N4N=CC[C@H]4c4cc(F)cc(F)c4)C3)cc2NC1=O]
250
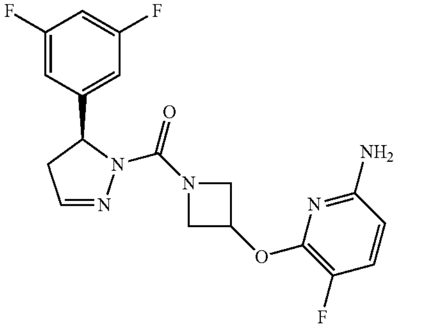 [SMILES: Nc1ccc(F)c(OC2CN(C(=O)N3N=CC[C@H]3c3cc(F)cc(F)c3)C2)n1]
251
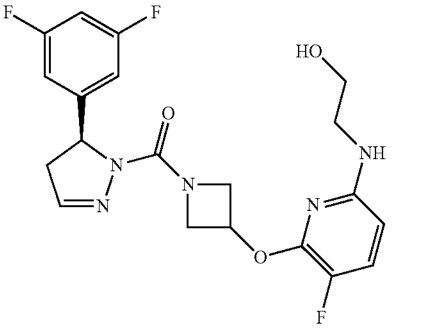 [SMILES: O=C(N1CC(Oc2nc(NCCO)ccc2F)C1)N1N=CC[C@H]1c1cc(F)cc(F)c1]
252
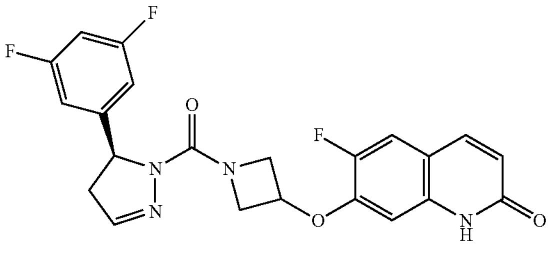 [SMILES: O=C(N1CC(Oc2cc3[nH]c(=O)ccc3cc2F)C1)N1N=CC[C@H]1c1cc(F)cc(F)c1]
253

TABLE 1-continued
| Active Compounds | |
|---|---|
| 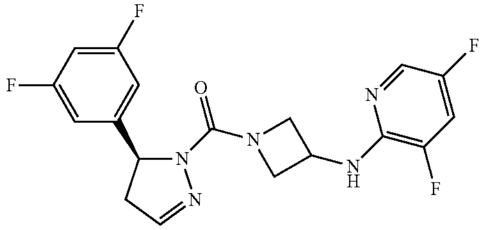 [SMILES: O=C(N1CC(Nc2ncc(F)cc2F)C1)N1N=CC[C@H]1c1cc(F)cc(F)c1] | 254 |
| 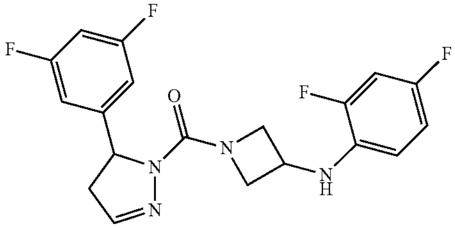 [SMILES: O=C(N1CC(Nc2ccc(F)cc2F)C1)N1N=CCC1c1cc(F)cc(F)c1] | 255 |
| 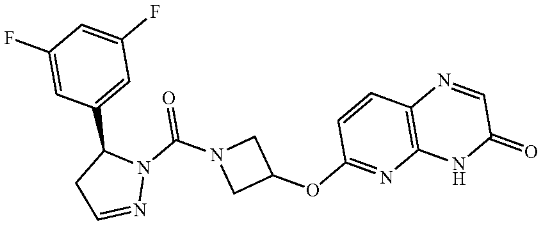 [SMILES: O=C(N1CC(Oc2ccc3ncc(=O)[nH]c3n2)C1)N1N=CC[C@H]1c1cc(F)cc(F)c1] | 256 |
| 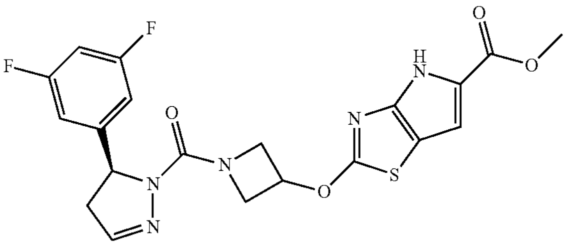 [SMILES: COC(=O)c1cc2sc(OC3CN(C(=O)N4N=CC[C@H]4c4cc(F)cc(F)c4)C3)nc2[nH]1] | 257 |
| 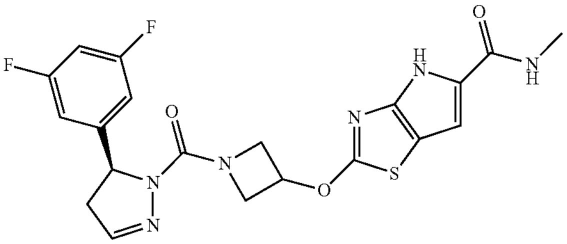 [SMILES: CNC(=O)c1cc2sc(OC3CN(C(=O)N4N=CC[C@H]4c4cc(F)cc(F)c4)C3)nc2[nH]1] | 258 |
| 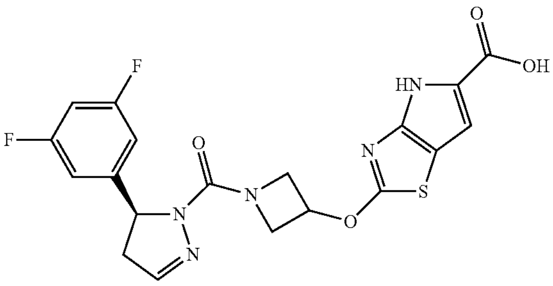 [SMILES: O=C(O)c1cc2sc(OC3CN(C(=O)N4N=CC[C@H]4c4cc(F)cc(F)c4)C3)nc2[nH]1] | 259 |

TABLE 1-continued
| Active Compounds | |
|---|---|
| 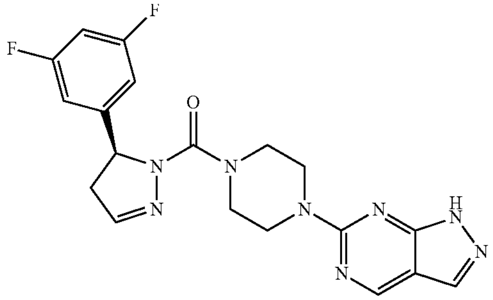 [SMILES: O=C(N1CCN(c2ncc3cn[nH]c3n2)CC1)N1N=CC[C@H]1c1cc(F)cc(F)c1] | 260 |
| 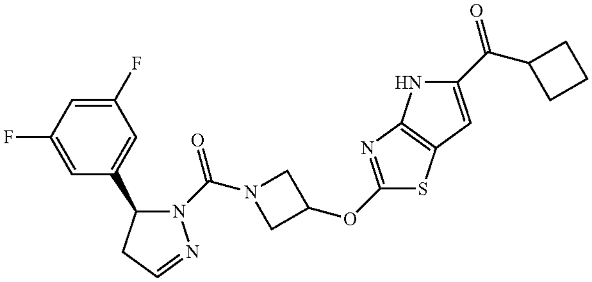 [SMILES: O=C(c1cc2sc(OC3CN(C(=O)N4N=CC[C@H]4c4cc(F)cc(F)c4)C3)nc2[nH]1)C1CCC1] | 261 |
| 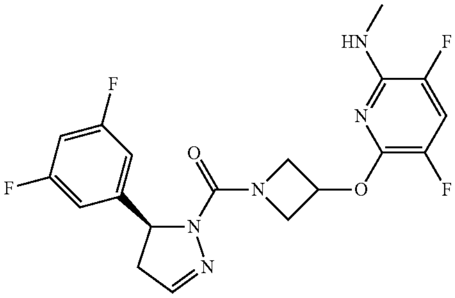 [SMILES: CNc1nc(OC2CN(C(=O)N3N=CC[C@H]3c3cc(F)cc(F)c3)C2)c(F)cc1F] | 262 |
| 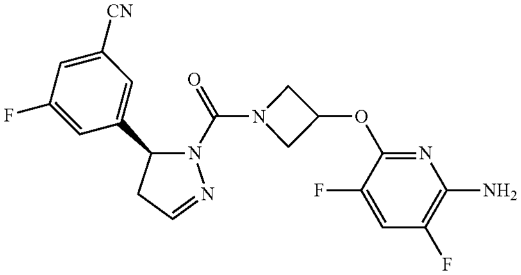 [SMILES: N#Cc1cc(F)cc([C@@H]2CC=NN2C(=O)N2CC(Oc3nc(N)c(F)cc3F)C2)c1] | 263 |
| 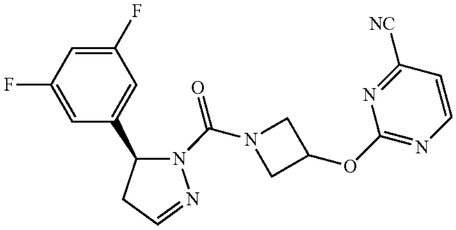 [SMILES: N#Cc1ccnc(OC2CN(C(=O)N3N=CC[C@H]3c3cc(F)cc(F)c3)C2)n1] | 264 |

TABLE 1-continued
| Active Compounds | |
|---|---|
| 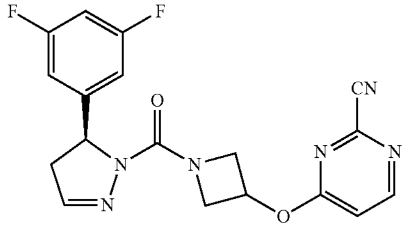 [SMILES: N#Cc1nccc(OC2CN(C(=O)N3N=CC[C@H]3c3cc(F)cc(F)c3)C2)n1] | 265 |
| 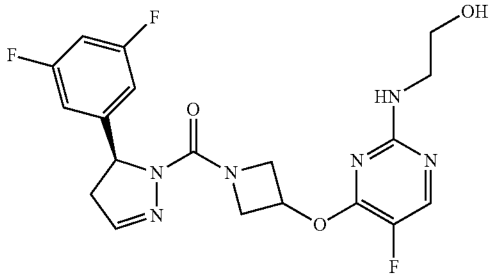 [SMILES: O=C(N1CC(Oc2nc(NCCO)ncc2F)C1)N1N=CC[C@H]1c1cc(F)cc(F)c1] | 266 |
| 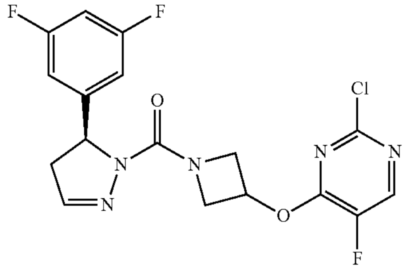 [SMILES: O=C(N1CC(Oc2nc(Cl)ncc2F)C1)N1N=CC[C@H]1c1cc(F)cc(F)c1] | 267 |
| 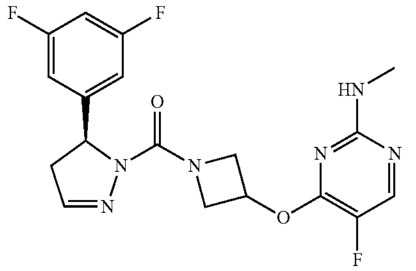 [SMILES: CNc1ncc(F)c(OC2CN(C(=O)N3N=CC[C@H]3c3cc(F)cc(F)c3)C2)n1] | 268 |
| 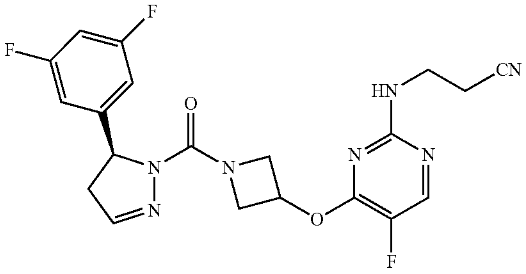 [SMILES: N#CCCNc1ncc(F)c(OC2CN(C(=O)N3N=CC[C@H]3c3cc(F)cc(F)c3)C2)n1] | 269 |

TABLE 1-continued
| Active Compounds | |
|---|---|
| 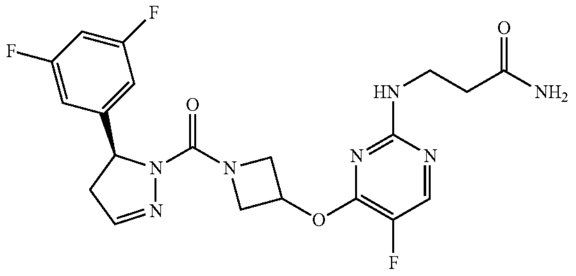 [SMILES: NC(=O)CCNc1ncc(F)c(OC2CN(C(=O)N3N=CC[C@H]3c3cc(F)cc(F)c3)C2)n1] | 270 |
| 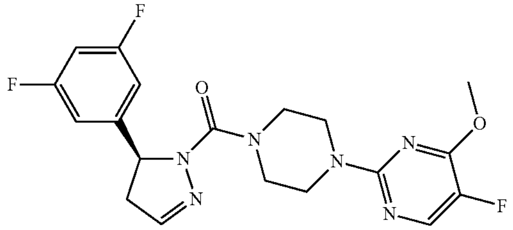 [SMILES: COc1nc(N2CCN(C(=O)N3N=CC[C@H]3c3cc(F)cc(F)c3)CC2)ncc1F] | 271 |
| 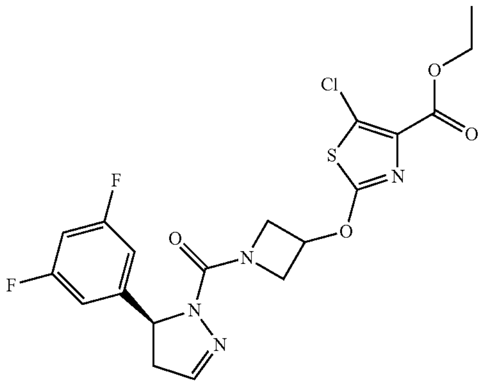 [SMILES: CCOC(=O)c1nc(OC2CN(C(=O)N3N=CC[C@H]3c3cc(F)cc(F)c3)C2)sc1Cl] | 272 |
| 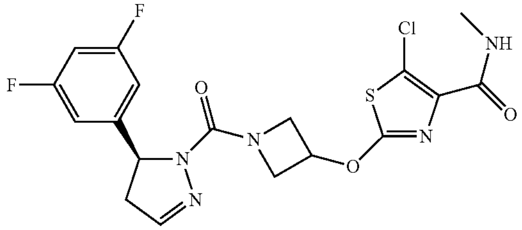 [SMILES: CNC(=O)c1nc(OC2CN(C(=O)N3N=CC[C@H]3c3cc(F)cc(F)c3)C2)sc1Cl] | 273 |
| 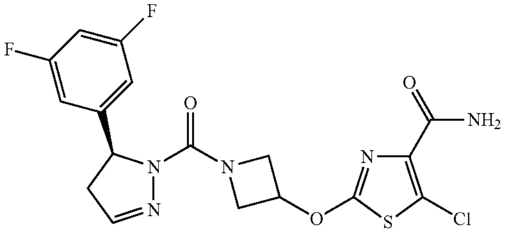 [SMILES: NC(=O)c1nc(OC2CN(C(=O)N3N=CC[C@H]3c3cc(F)cc(F)c3)C2)sc1Cl] | 274 |

TABLE 1-continued
| Active Compounds |
|---|
275
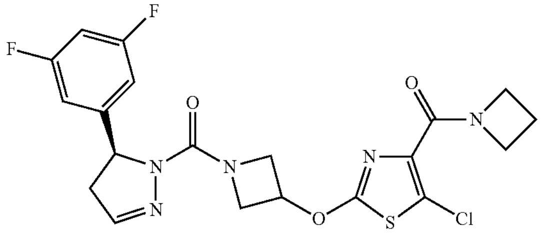 [SMILES: O=C(c1nc(OC2CN(C(=O)N3N=CC[C@H]3c3cc(F)cc(F)c3)C2)sc1Cl)N1CCC1]
276
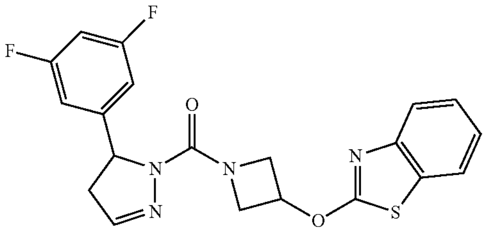 [SMILES: O=C(N1CC(Oc2nc3ccccc3s2)C1)N1N=CCC1c1cc(F)cc(F)c1]
277
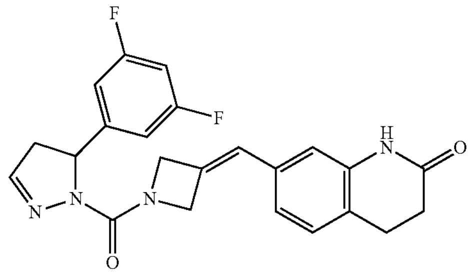 [SMILES: O=C1CCc2ccc(C=C3CN(C(=O)N4N=CCC4c4cc(F)cc(F)c4)C3)cc2N1]
278
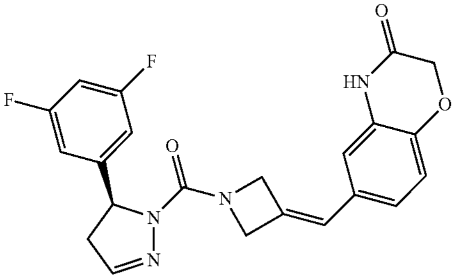 [SMILES: O=C1COc2ccc(C=C3CN(C(=O)N4N=CC[C@H]4c4cc(F)cc(F)c4)C3)cc2N1]
279
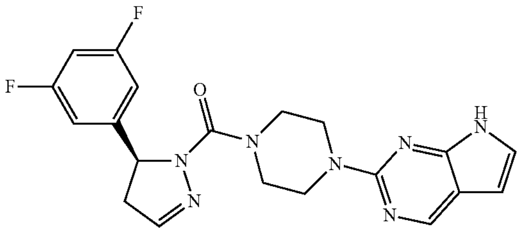 [SMILES: O=C(N1CCN(c2ncc3cc[nH]c3n2)CC1)N1N=CC[C@H]1c1cc(F)cc(F)c1]
280
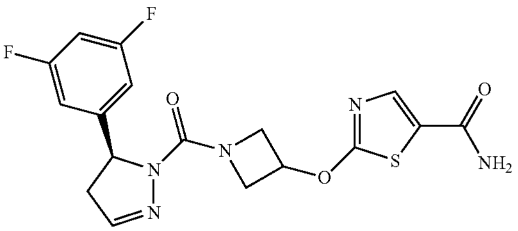 [SMILES: NC(=O)c1cnc(OC2CN(C(=O)N3N=CC[C@H]3c3cc(F)cc(F)c3)C2)s1]

TABLE 1-continued
| Active Compounds |
| --- |
| 281 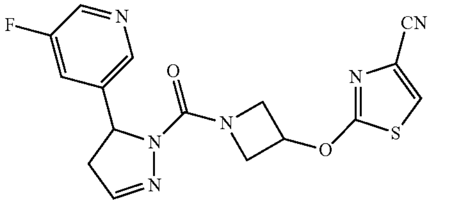 [SMILES: N#Cc1csc(OC2CN(C(=O)N3N=CCC3c3cncc(F)c3)C2)n1] |
| 282 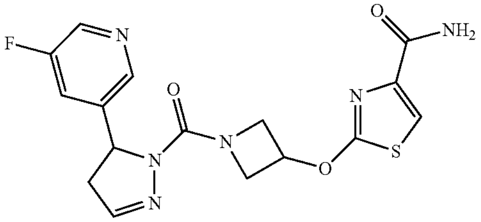 [SMILES: NC(=O)c1csc(OC2CN(C(=O)N3N=CCC3c3cncc(F)c3)C2)n1] |
| 283 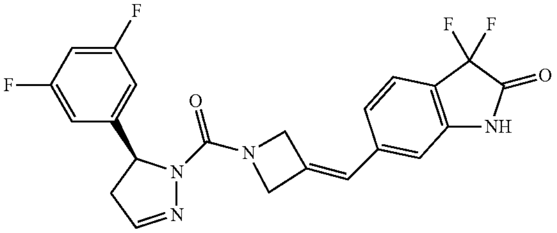 [SMILES: O=C(N1CC(=Cc2ccc3c(c2)NC(=O)C3(F)F)C1)N1N=CC[C@H]1c1cc(F)cc(F)c1] |
| 284 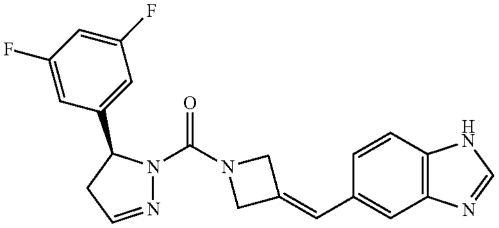 [SMILES: O=C(N1CC(=Cc2ccc3[nH]cnc3c2)C1)N1N=CC[C@H]1c1cc(F)cc(F)c1] |
| 285 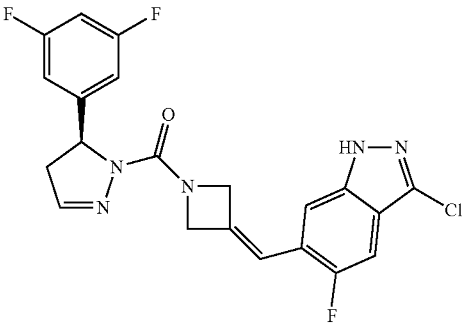 [SMILES: O=C(N1CC(=Cc2cc3[nH]nc(Cl)c3cc2F)C1)N1N=CC[C@H]1c1cc(F)cc(F)c1] |
| 286 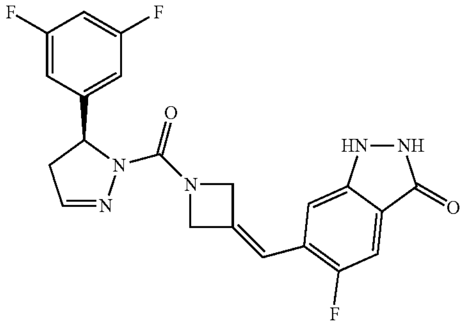 [SMILES: O=C(N1CC(=Cc2cc3[nH][nH]c(=O)c3cc2F)C1)N1N=CC[C@H]1c1cc(F)cc(F)c1] |

TABLE 1-continued
| Active Compounds | |
|---|---|
| 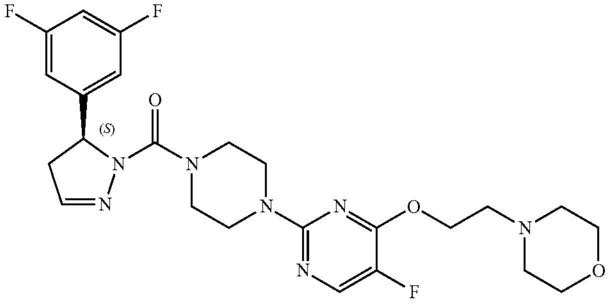 | 287 |
| 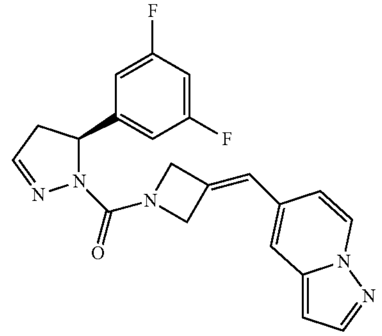 [SMILES: O=C(N1CC(=Cc2ccn3nccc3c2)C1)N1N=CC[C@H]1c1cc(F)cc(F)c1] | 288 |
| 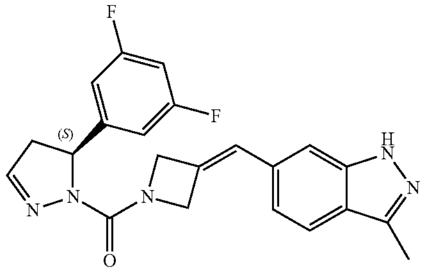 | 289 |
| 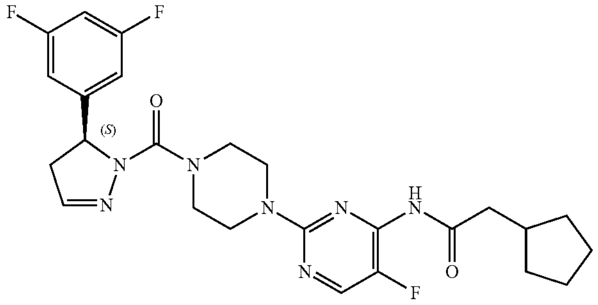 | 290 |
| 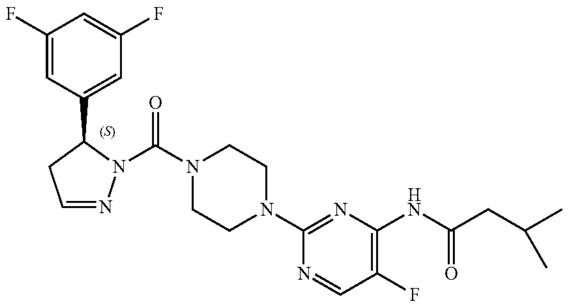 | 291 |

TABLE 1-continued
| Active Compounds | |
|---|---|
| 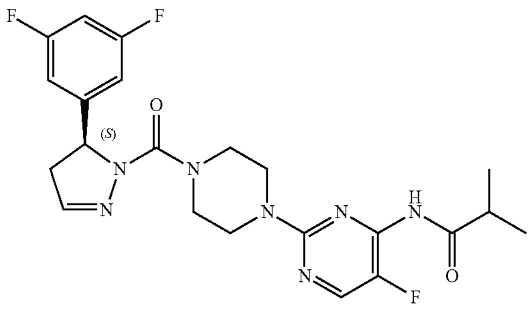 | 292 |
| 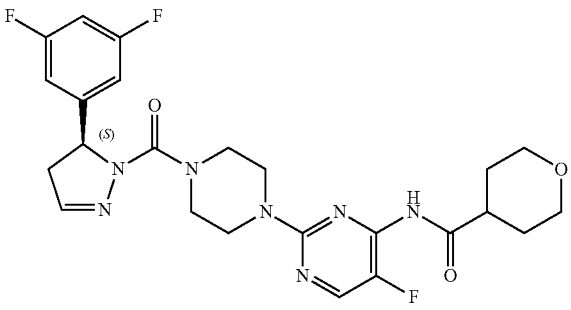 | 293 |
| 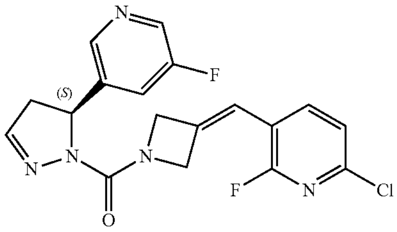 | 294 |
| 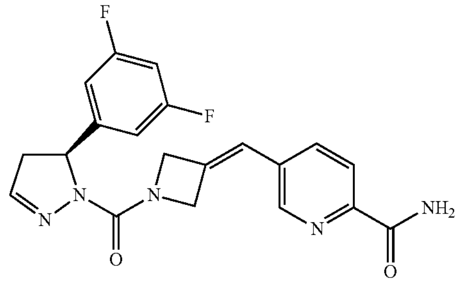 [SMILES: NC(=O)c1ccc(C=C2CN(C(=O)N3N=CC[C@H]3c3cc(F)cc(F)c3)C2)cn1] | 295 |
| 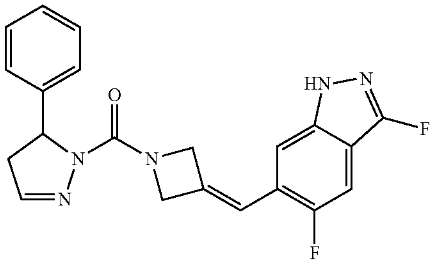 [SMILES: O=C(N1CC(=Cc2cc3[nH]nc(F)c3cc2F)C1)N1N=CCC1c1ccccc1] | 296 |

TABLE 1-continued
| Active Compounds | |
|---|---|
| 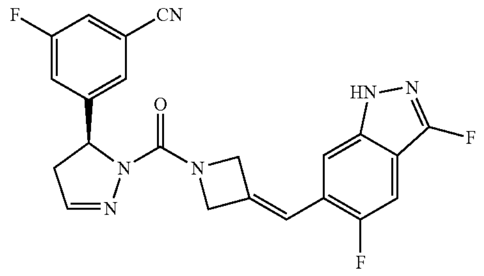 [SMILES: N#Cc1cc(F)cc([C@@H]2CC=NN2C(=O)N2CC(=Cc3cc4[nH]nc(F)c4cc3F)C2)c1] | 297 |
| 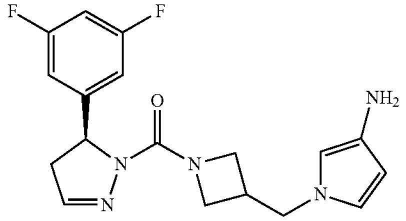 [SMILES: Nc1ccn(CC2CN(C(=O)N3N=CC[C@H]3c3cc(F)cc(F)c3)C2)c1] | 298 |
| 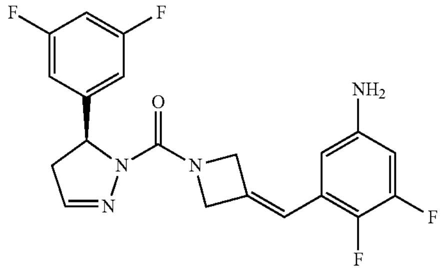 [SMILES: Nc1cc(F)c(F)c(C=C2CN(C(=O)N3N=CC[C@H]3c3cc(F)cc(F)c3)C2)c1] | 299 |
| 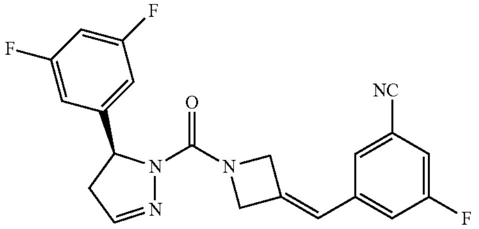 [SMILES: N#Cc1cc(F)cc(C=C2CN(C(=O)N3N=CC[C@H]3c3cc(F)cc(F)c3)C2)c1] | 300 |
| 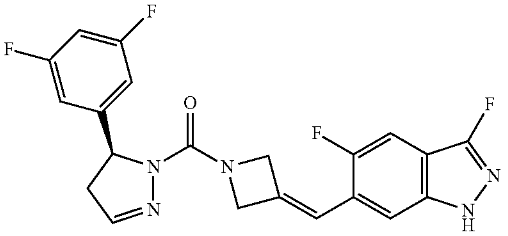 [SMILES: O=C(N1CC(=Cc2cc3[nH]nc(F)c3cc2F)C1)N1N=CC[C@H]1c1cc(F)cc(F)c1] | 301 |
| 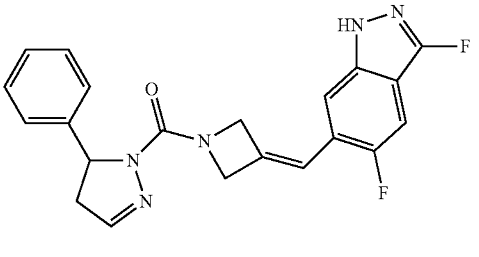 [SMILES: O=C(N1CC(=Cc2cc3[nH]nc(F)c3cc2F)C1)N1N=CCC1c1ccccc1] | 302 |

TABLE 1-continued
| Active Compounds | |
|---|---|
| 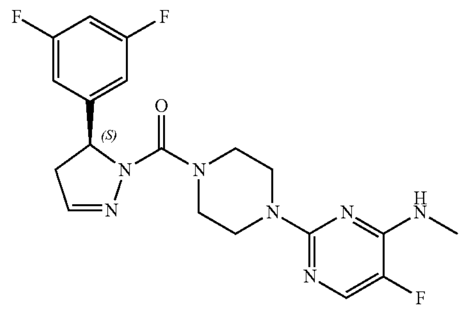 | 303 |
| 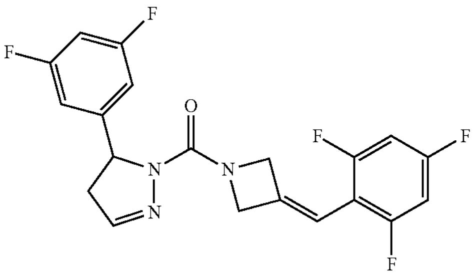 [SMILES: O=C(N1CC(=Cc2c(F)cc(F)cc2F)C1)N1N=CCC1c1cc(F)cc(F)c1] | 304 |
| 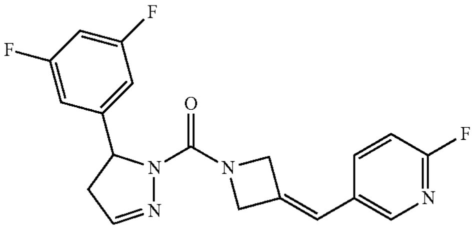 [SMILES: O=C(N1CC(=Cc2ccc(F)nc2)C1)N1N=CCC1c1cc(F)cc(F)c1] | 305 |
| 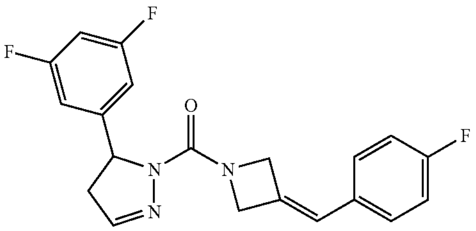 [SMILES: O=C(N1CC(=Cc2ccc(F)cc2)C1)N1N=CCC1c1cc(F)cc(F)c1] | 306 |
| 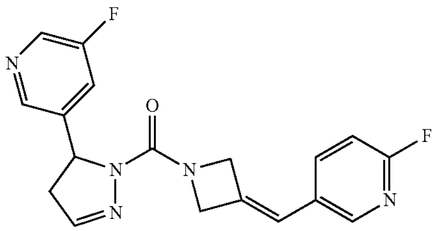 [SMILES: O=C(N1CC(=Cc2ccc(F)nc2)C1)N1N=CCC1c1cncc(F)c1] | 307 |
| 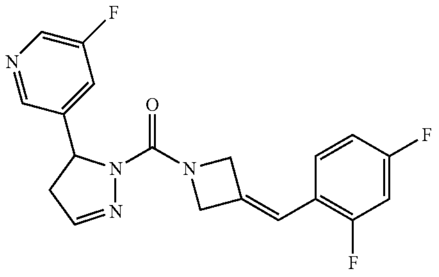 [SMILES: O=C(N1CC(=Cc2ccc(F)cc2F)C1)N1N=CCC1c1cncc(F)c1] | 308 |

TABLE 1-continued
| Active Compounds | |
|---|---|
| 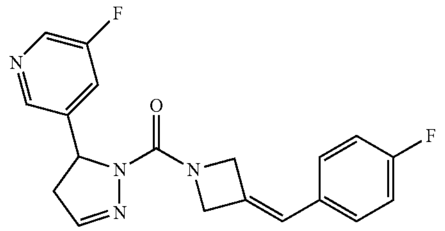 [SMILES: O=C(N1CC(=Cc2ccc(F)cc2)C1)N1N=CCC1c1cncc(F)c1] | 309 |
| 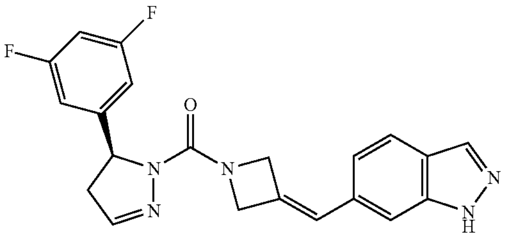 | 310 |
| 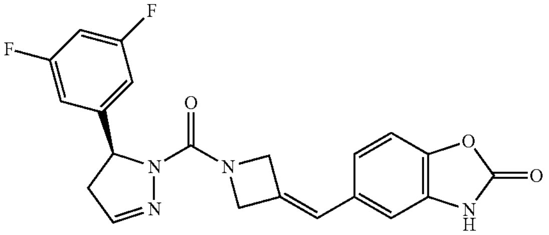 [SMILES: O=C(N1CC(=Cc2ccc3oc(=O)[nH]c3c2)C1)N1N=CC[C@H]1c1cc(F)cc(F)c1] | 311 |
| 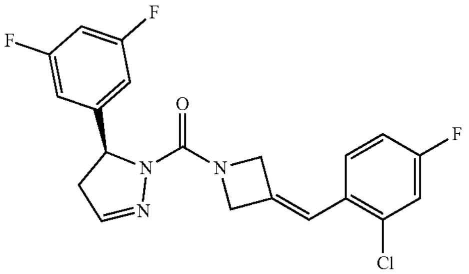 [SMILES: O=C(N1CC(=Cc2ccc(F)cc2Cl)C1)N1N=CC[C@H]1c1cc(F)cc(F)c1] | 312 |
| 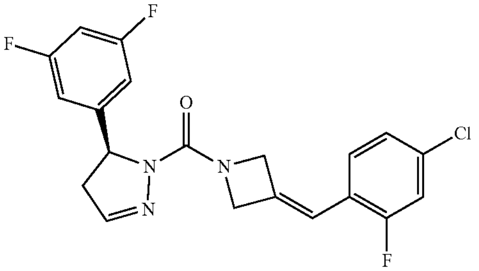 [SMILES: O=C(N1CC(=Cc2ccc(Cl)cc2F)C1)N1N=CC[C@H]1c1cc(F)cc(F)c1] | 313 |
| 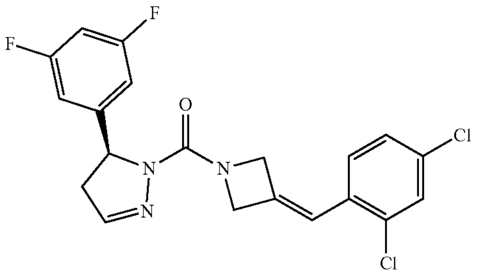 | 314 |

TABLE 1-continued
| Active Compounds | |
|---|---|
| 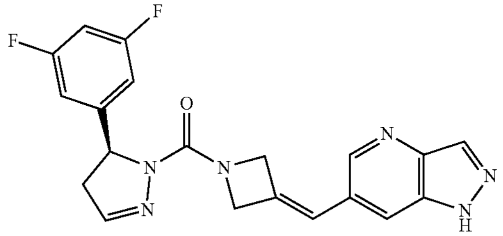 [SMILES: O=C(N1CC(=Cc2cnc3cn[nH]c3c2)C1)N1N=CC[C@H]1c1cc(F)cc(F)c1] | 315 |
| 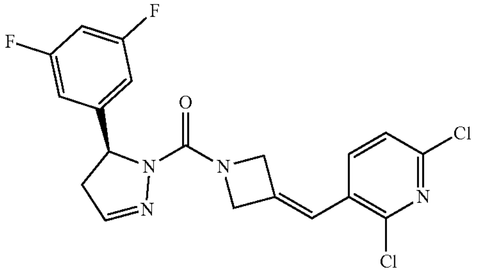 [SMILES: O=C(N1CC(=Cc2ccc(Cl)nc2Cl)C1)N1N=CC[C@H]1c1cc(F)cc(F)c1] | 316 |
| 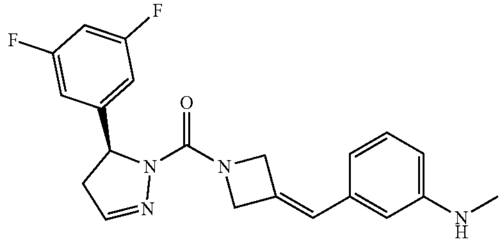 [SMILES: CNc1cccc(C=C2CN(C(=O)N3N=CC[C@H]3c3cc(F)cc(F)c3)C2)c1] | 317 |
| 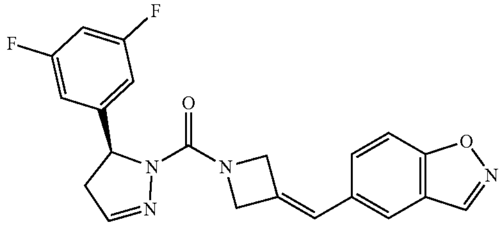 [SMILES: O=C(N1CC(=Cc2ccc3oncc3c2)C1)N1N=CC[C@H]1c1cc(F)cc(F)c1] | 318 |
| 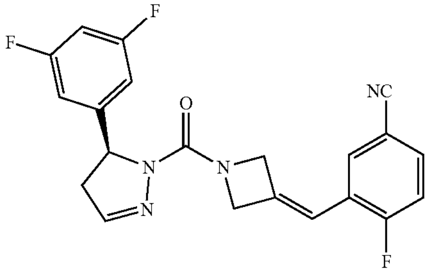 [SMILES: N#Cc1ccc(F)c(C=C2CN(C(=O)N3N=CC[C@H]3c3cc(F)cc(F)c3)C2)c1] | 319 |
| 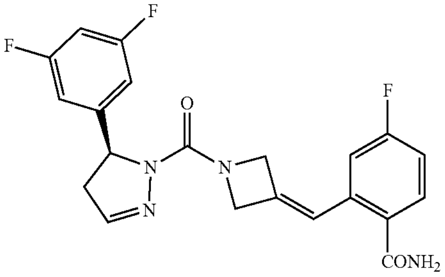 [SMILES: NC(=O)c1ccc(F)cc1C=C1CN(C(=O)N2N=CC[C@H]2c2cc(F)cc(F)c2)C1] | 320 |

TABLE 1-continued
| Active Compounds |
| --- |
| 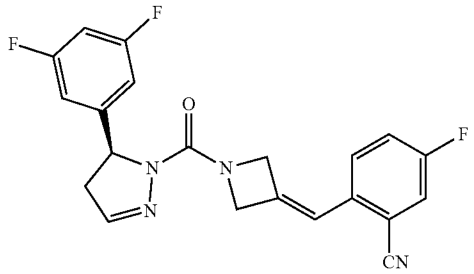 [SMILES: N#Cc1cc(F)ccc1C=C1CN(C(=O)N2N=CC[C@H]2c2cc(F)cc(F)c2)C1] 321 |
| 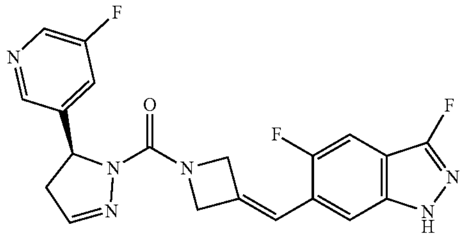 [SMILES: O=C(N1CC(=Cc2cc3[nH]nc(F)c3cc2F)C1)N1N=CC[C@H]1c1cncc(F)c1] 322 |
| 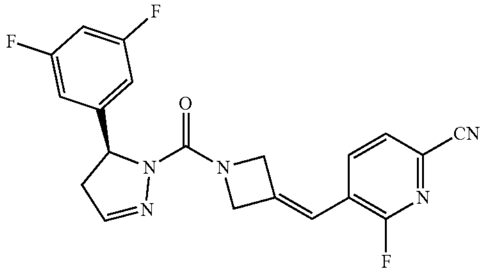 [SMILES: N#Cc1ccc(C=C2CN(C(=O)N3N=CC[C@H]3c3cc(F)cc(F)c3)C2)c(F)n1] 323 |
| 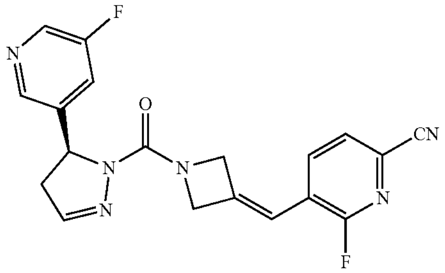 [SMILES: N#Cc1ccc(C=C2CN(C(=O)N3N=CC[C@H]3c3cncc(F)c3)C2)c(F)n1] 324 |
| 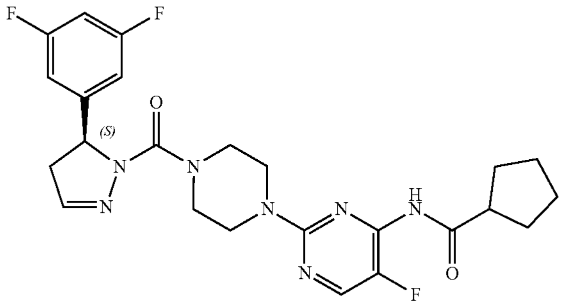 325 |

TABLE 1-continued
| Active Compounds |
|---|
| 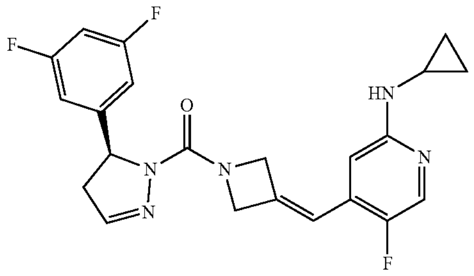 [SMILES: O=C(N1CC(=Cc2cc(NC3CC3)ncc2F)C1)N1N=CC[C@H]1c1cc(F)cc(F)c1] 326 |
| 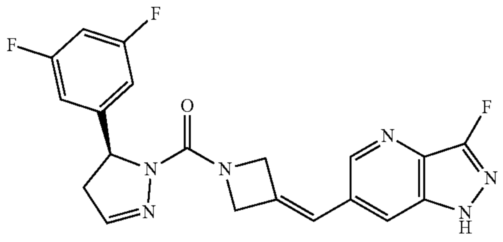 [SMILES: O=C(N1CC(=Cc2cnc3c(F)n[nH]c3c2)C1)N1N=CC[C@H]1c1cc(F)cc(F)c1] 327 |
| 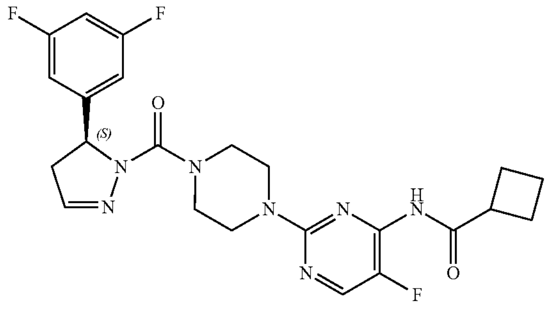 328 |
| 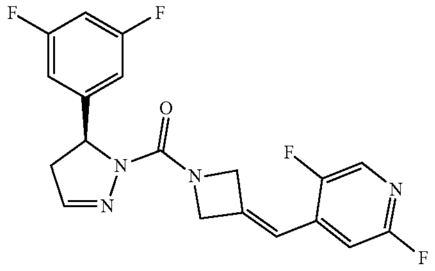 [SMILES: O=C(N1CC(=Cc2cc(F)ncc2F)C1)N1N=CC[C@H]1c1cc(F)cc(F)c1] 329 |
| 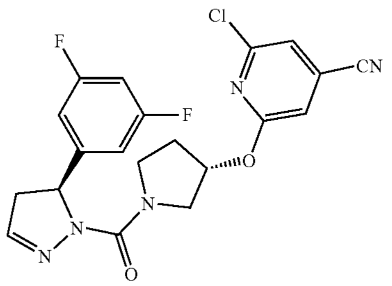 [SMILES: N#Cc1cc(Cl)nc(O[C@H]2CCN(C(=O)N3N=CC[C@H]3c3cc(F)cc(F)c3)C2)c1] 330 |

TABLE 1-continued
| Active Compounds |
| --- |
| 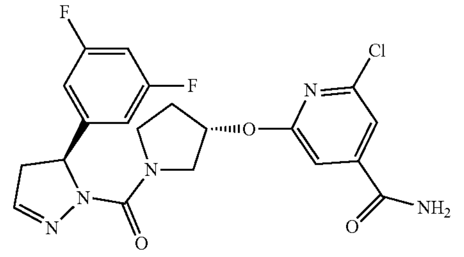 [SMILES: NC(=O)c1cc(Cl)nc(O[C@H]2CCN(C(=O)N3N=CC[C@H]3c3cc(F)cc(F)c3)C2)c1] 331 |
| 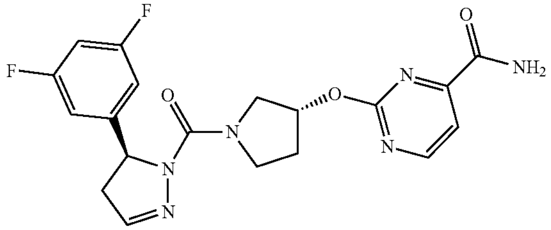 [SMILES: NC(=O)c1ccnc(O[C@@H]2CCN(C(=O)N3N=CC[C@H]3c3cc(F)cc(F)c3)C2)n1] 332 |
| 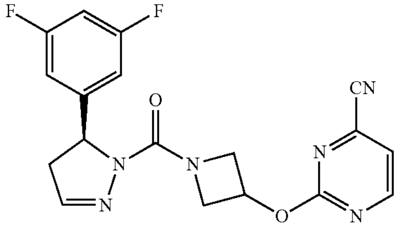 [SMILES: N#Cc1ccnc(OC2CN(C(=O)N3N=CC[C@H]3c3cc(F)cc(F)c3)C2)n1] 333 |
| 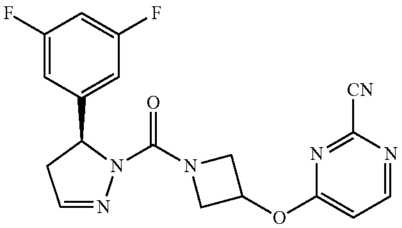 [SMILES: N#Cc1nccc(OC2CN(C(=O)N3N=CC[C@H]3c3cc(F)cc(F)c3)C2)n1] 334 |
| 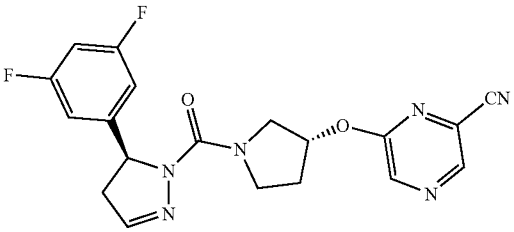 [SMILES: N#Cc1cncc(O[C@@H]2CCN(C(=O)N3N=CC[C@H]3c3cc(F)cc(F)c3)C2)n1] 335 |
| 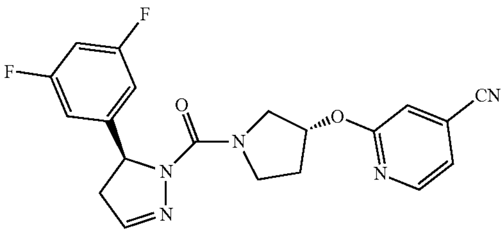 [SMILES: N#Cc1ccnc(O[C@@H]2CCN(C(=O)N3N=CC[C@H]3c3cc(F)cc(F)c3)C2)c1] 336 |

TABLE 1-continued
| Active Compounds | |
|---|---|
| 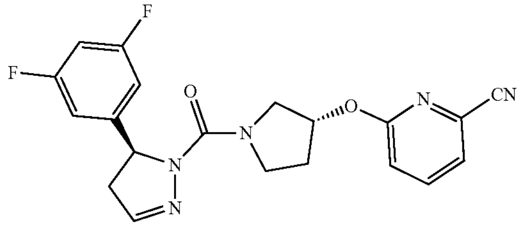 [SMILES: N#Cc1cccc(O[C@@H]2CCN(C(=O)N3N=CC[C@H]3c3cc(F)cc(F)c3)C2)n1] | 337 |
| 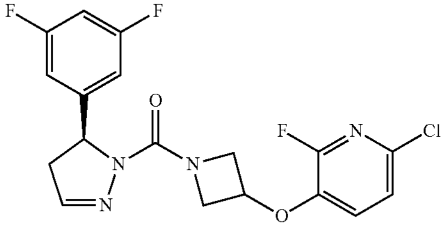 [SMILES: O=C(N1CC(Oc2ccc(Cl)nc2F)C1)N1N=CC[C@H]1c1cc(F)cc(F)c1] | 338 |
| 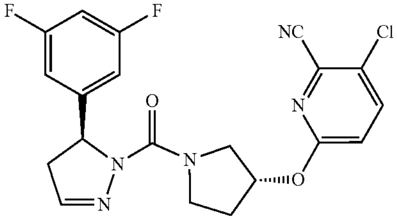 [SMILES: N#Cc1nc(O[C@@H]2CCN(C(=O)N3N=CC[C@H]3c3cc(F)cc(F)c3)C2)ccc1Cl] | 339 |
| 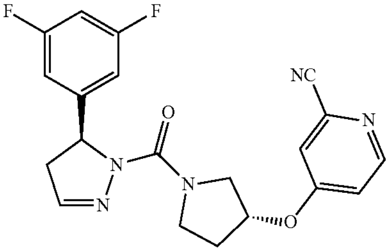 [SMILES: N#Cc1cc(O[C@@H]2CCN(C(=O)N3N=CC[C@H]3c3cc(F)cc(F)c3)C2)ccn1] | 340 |
| 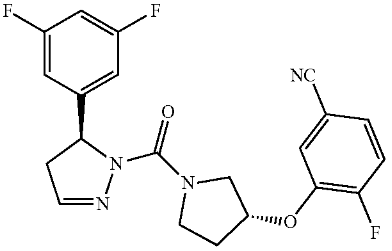 [SMILES: N#Cc1ccc(F)c(O[C@@H]2CCN(C(=O)N3N=CC[C@H]3c3cc(F)cc(F)c3)C2)c1] | 341 |
| 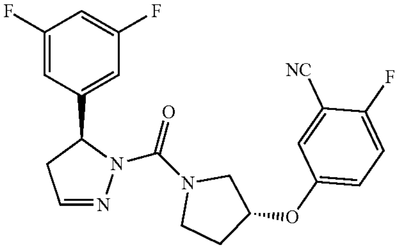 [SMILES: N#Cc1cc(O[C@@H]2CCN(C(=O)N3N=CC[C@H]3c3cc(F)cc(F)c3)C2)ccc1F] | 342 |

TABLE 1-continued
| Active Compounds | |
|---|---|
| 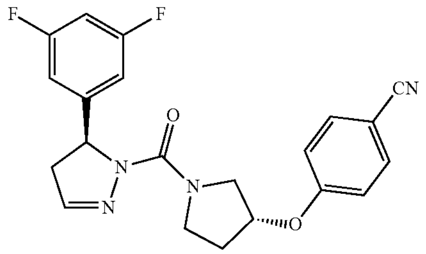 [SMILES: N#Cc1ccc(O[C@@H]2CCN(C(=O)N3N=CC[C@H]3c3cc(F)cc(F)c3)C2)cc1] | 343 |
| 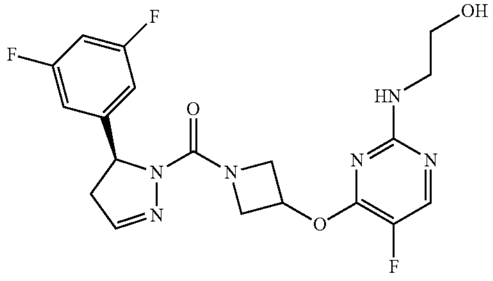 [SMILES: O=C(N1CC(Oc2nc(NCCO)ncc2F)C1)N1N=CC[C@H]1c1cc(F)cc(F)c1] | 344 |
| 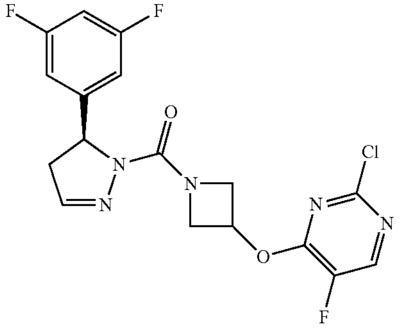 [SMILES: O=C(N1CC(Oc2nc(Cl)ncc2F)C1)N1N=CC[C@H]1c1cc(F)cc(F)c1] | 345 |
| 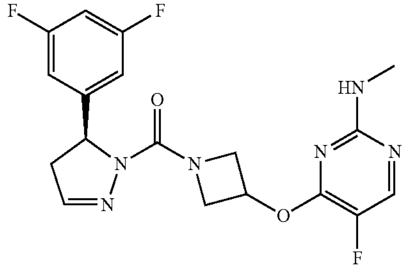 [SMILES: CNc1ncc(F)c(OC2CN(C(=O)N3N=CC[C@H]3c3cc(F)cc(F)c3)C2)n1] | 346 |
| 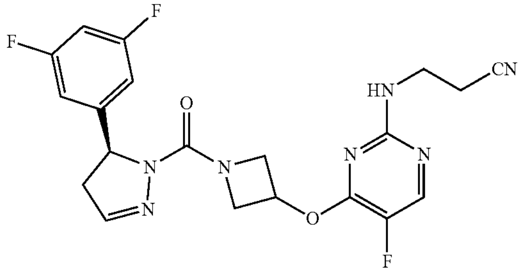 [SMILES: N#CCCNc1ncc(F)c(OC2CN(C(=O)N3N=CC[C@H]3c3cc(F)cc(F)c3)C2)n1] | 347 |

TABLE 1-continued
| Active Compounds | |
|---|---|
| 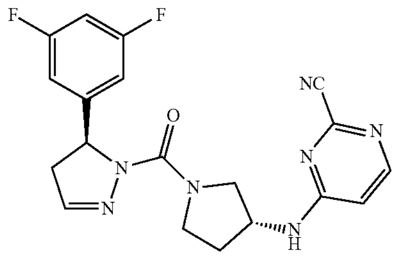 [SMILES: N#Cc1nccc(N[C@@H]2CCN(C(=O)N3N=CC[C@H]3c3cc(F)cc(F)c3)C2)n1] | 348 |
| 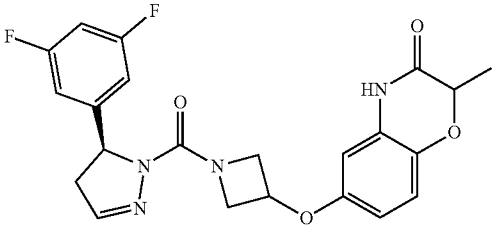 [SMILES: CC1Oc2ccc(OC3CN(C(=O)N4N=CC[C@H]4c4cc(F)cc(F)c4)C3)cc2NC1=O] | 349 |
| 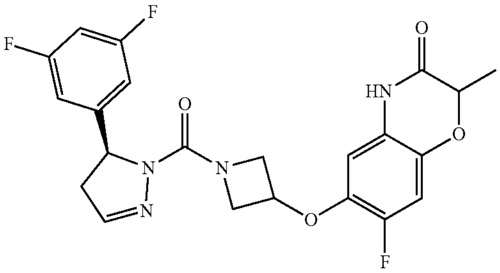 [SMILES: CC1Oc2cc(F)c(OC3CN(C(=O)N4N=CC[C@H]4c4cc(F)cc(F)c4)C3)cc2NC1=O] | 350 |
| 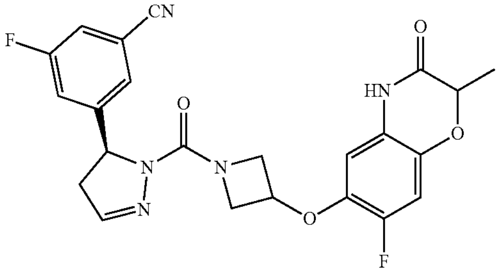 [SMILES: CC1Oc2cc(F)c(OC3CN(C(=O)N4N=CC[C@H]4c4cc(F)cc(C#N)c4)C3)cc2NC1=O] | 351 |
| 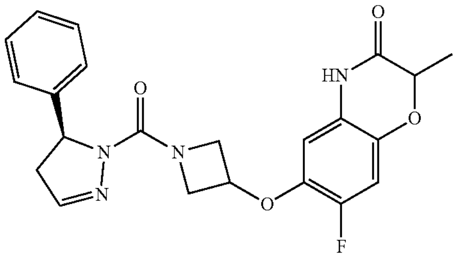 [SMILES: CC1Oc2cc(F)c(OC3CN(C(=O)N4N=CC[C@H]4c4ccccc4)C3)cc2NC1=O] | 352 |
| 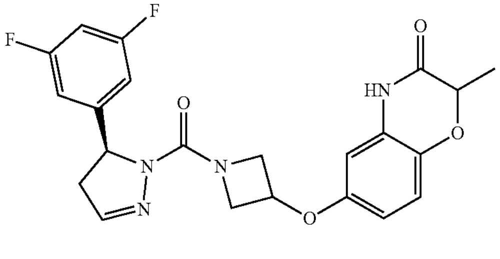 [SMILES: CC1Oc2ccc(OC3CN(C(=O)N4N=CC[C@H]4c4cc(F)cc(F)c4)C3)cc2NC1=O] | 353 |

TABLE 1-continued
| Active Compounds | |
|---|---|
| 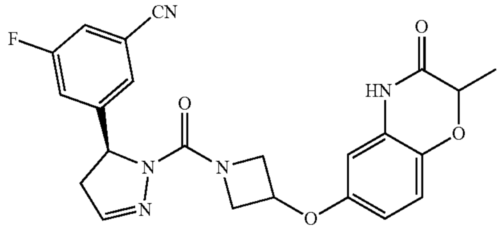 [SMILES: CC1Oc2ccc(OC3CN(C(=O)N4N=CC[C@H]4c4cc(F)cc(C#N)c4)C3)cc2NC1=O] | 354 |
| 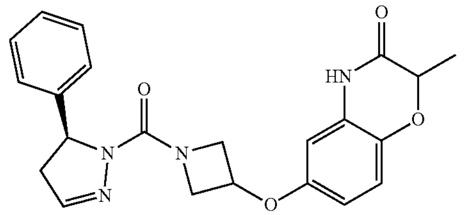 [SMILES: CC1Oc2ccc(OC3CN(C(=O)N4N=CC[C@H]4c4ccccc4)C3)cc2NC1=O] | 355 |
| 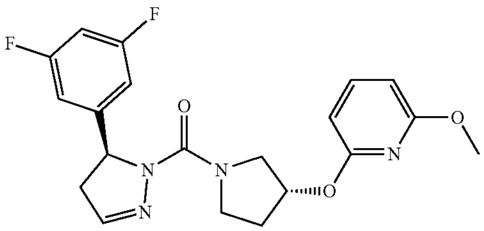 [SMILES: COc1cccc(O[C@@H]2CCN(C(=O)N3N=CC[C@H]3c3cc(F)cc(F)c3)C2)n1] | 356 |
| 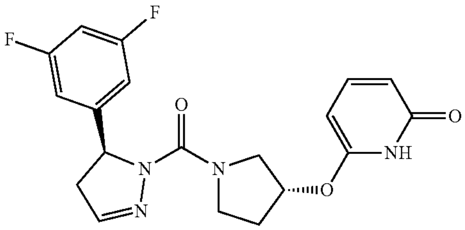 [SMILES: O=C(N1CC[C@@H](Oc2cccc(=O)[nH]2)C1)N1N=CC[C@H]1c1cc(F)cc(F)c1] | 357 |
| 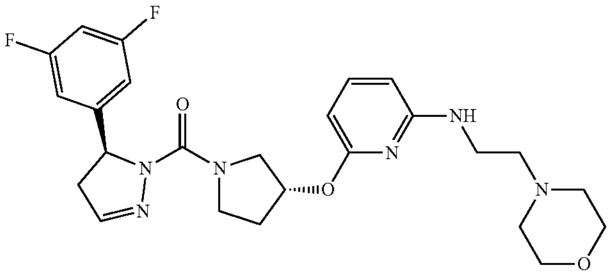 [SMILES: O=C(N1CC[C@@H](Oc2cccc(NCCN3CCOCC3)n2)C1)N1N=CC[C@H]1c1cc(F)cc(F)c1] | 358 |
| 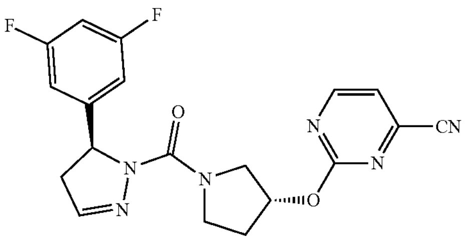 [SMILES: N#Cc1ccnc(O[C@@H]2CCN(C(=O)N3N=CC[C@H]3c3cc(F)cc(F)c3)C2)n1] | 359 |

TABLE 1-continued
Active Compounds
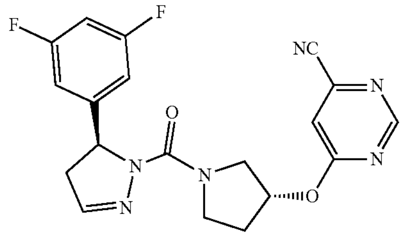 [SMILES: N#Cc1cc(O[C@@H]2CCN(C(=O)N3N=CC[C@H]3c3cc(F)cc(F)c3)C2)ncn1]
360
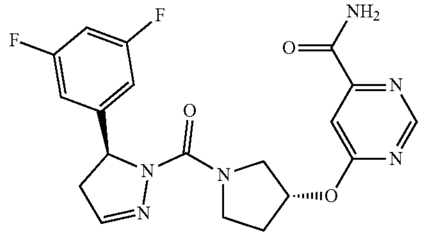 [SMILES: NC(=O)c1cc(O[C@@H]2CCN(C(=O)N3N=CC[C@H]3c3cc(F)cc(F)c3)C2)ncn1]
361
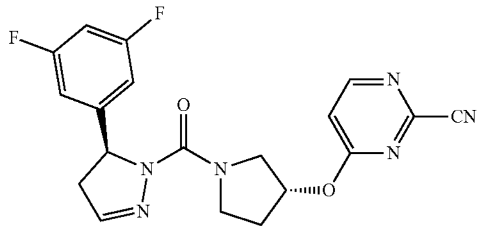 [SMILES: N#Cc1nccc(O[C@@H]2CCN(C(=O)N3N=CC[C@H]3c3cc(F)cc(F)c3)C2)n1]
362
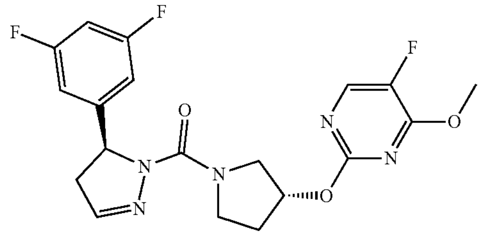 [SMILES: COc1nc(O[C@@H]2CCN(C(=O)N3N=CC[C@H]3c3cc(F)cc(F)c3)C2)ncc1F]
363
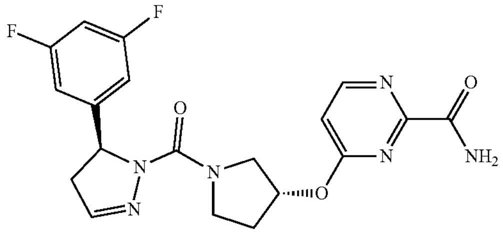 [SMILES: NC(=O)c1nccc(O[C@@H]2CCN(C(=O)N3N=CC[C@H]3c3cc(F)cc(F)c3)C2)n1]
364
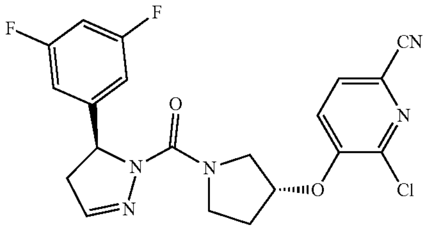 [SMILES: N#Cc1ccc(O[C@@H]2CCN(C(=O)N3N=CC[C@H]3c3cc(F)cc(F)c3)C2)c(Cl)n1]
365

TABLE 1-continued
| Active Compounds | |
|---|---|
| 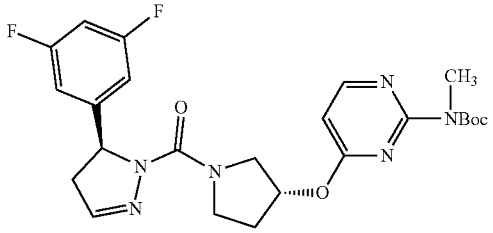 [SMILES: CN(C(=O)OC(C)(C)C)c1nccc(O[C@@H]2CCN(C(=O)N3N=CC[C@H]3c3cc(F)cc(F)c3)C2)n1] | 366 |
| 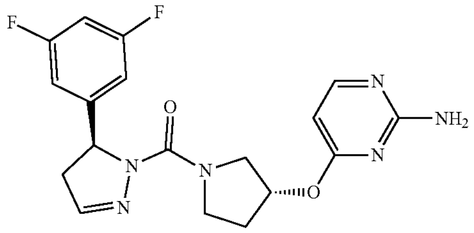 [SMILES: Nc1nccc(O[C@@H]2CCN(C(=O)N3N=CC[C@H]3c3cc(F)cc(F)c3)C2)n1] | 367 |
| 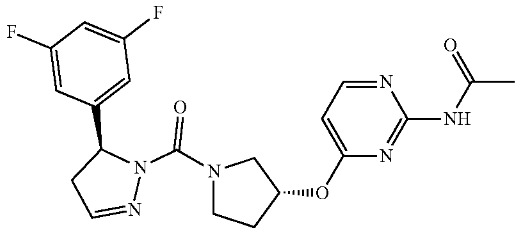 [SMILES: CC(=O)Nc1nccc(O[C@@H]2CCN(C(=O)N3N=CC[C@H]3c3cc(F)cc(F)c3)C2)n1] | 368 |
| 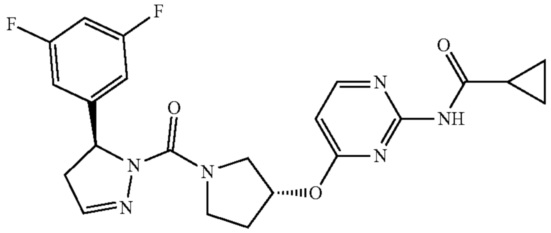 [SMILES: O=C(Nc1nccc(O[C@@H]2CCN(C(=O)N3N=CC[C@H]3c3cc(F)cc(F)c3)C2)n1)C1CC1] | 369 |
| 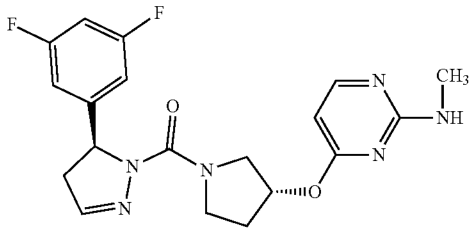 [SMILES: CNc1nccc(O[C@@H]2CCN(C(=O)N3N=CC[C@H]3c3cc(F)cc(F)c3)C2)n1] | 370 |
| 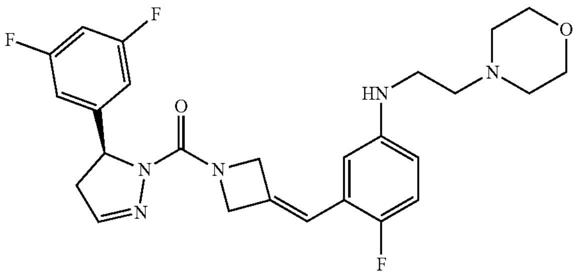 [SMILES: O=C(N1CC(=Cc2cc(NCCN3CCOCC3)ccc2F)C1)N1N=CC[C@H]1c1cc(F)cc(F)c1] | 371 |

TABLE 1-continued
| Active Compounds |
|---|
| 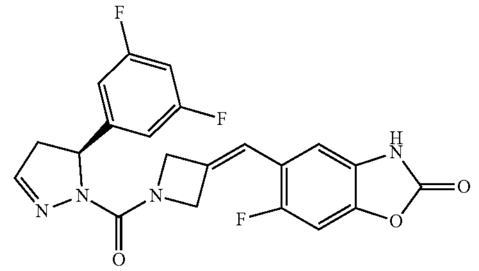 [SMILES: O=C(N1CC(=Cc2cc3[nH]c(=O)oc3cc2F)C1)N1N=CC[C@H]1c1cc(F)cc(F)c1] 372 |
| 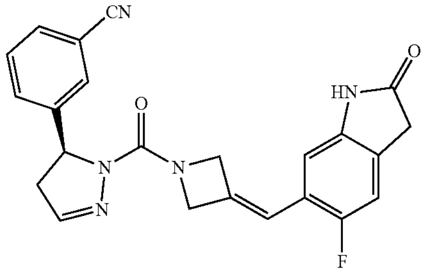 [SMILES: N#Cc1cccc([C@@H]2CC=NN2C(=O)N2CC(=Cc3cc4c(cc3F)CC(=O)N4)C2)c1] 373 |
| 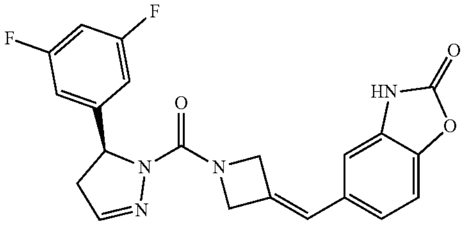 [SMILES: O=C(N1CC(=Cc2ccc3oc(=O)[nH]c3c2)C1)N1N=CC[C@H]1c1cc(F)cc(F)c1] 374 |
| 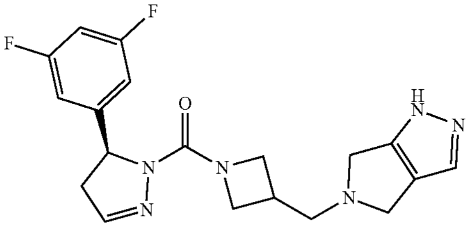 [SMILES: O=C(N1CC(CN2Cc3cn[nH]c3C2)C1)N1N=CC[C@H]1c1cc(F)cc(F)c1] 375 |
| 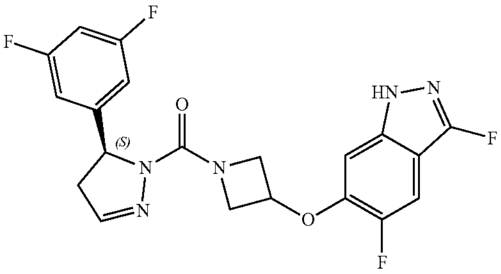 376 |
| 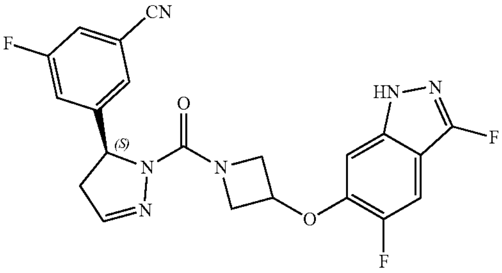 377 |

TABLE 1-continued
| Active Compounds | |
|---|---|
| 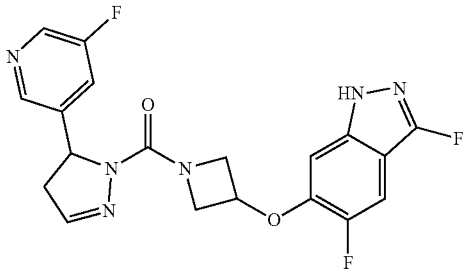 [SMILES: O=C(N1CC(Oc2cc3[nH]nc(F)c3cc2F)C1)N1N=CCC1c1cncc(F)c1] | 378 |
| 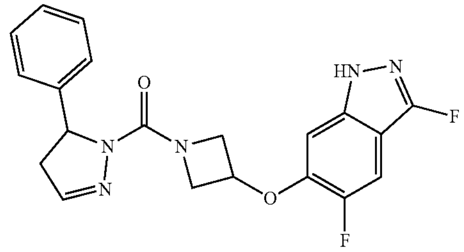 [SMILES: O=C(N1CC(Oc2cc3[nH]nc(F)c3cc2F)C1)N1N=CCC1c1ccccc1] | 379 |
| 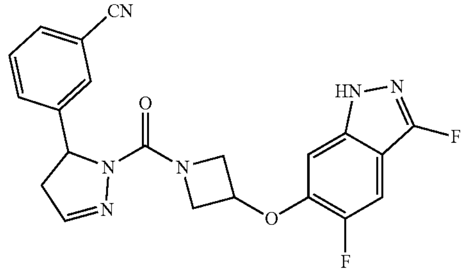 [SMILES: N#Cc1cccc(C2CC=NN2C(=O)N2CC(Oc3cc4[nH]nc(F)c4cc3F)C2)c1] | 380 |
| 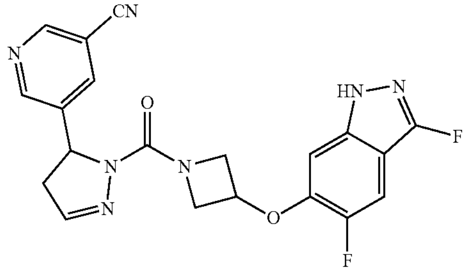 [SMILES: N#Cc1cncc(C2CC=NN2C(=O)N2CC(Oc3cc4[nH]nc(F)c4cc3F)C2)c1] | 381 |
| 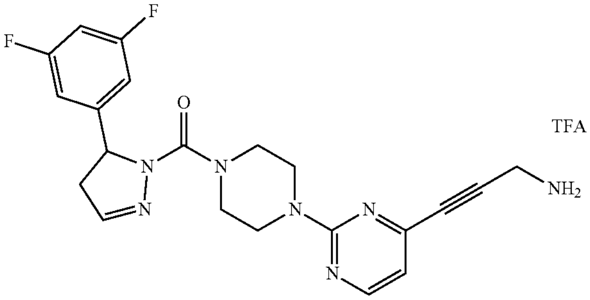 [SMILES: NCC#Cc1ccnc(N2CCN(C(=O)N3N=CCC3c3cc(F)cc(F)c3)CC2)n1] TFA | 382 |

TABLE 1-continued
| Active Compounds | |
|---|---|
| 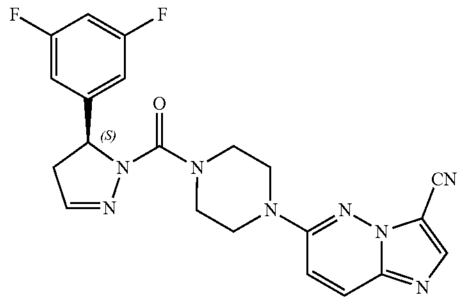 | 383 |
| 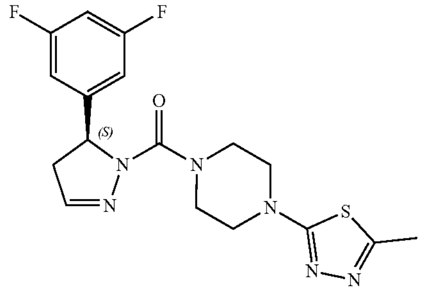 | 384 |
| 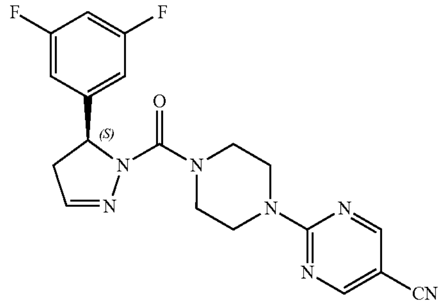 | 385 |
| 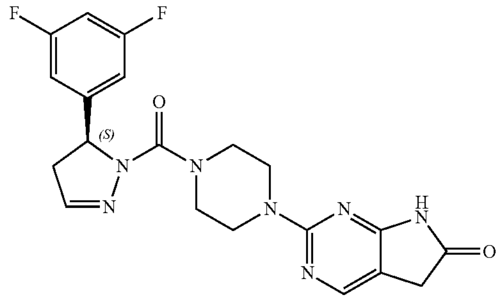 | 386 |
Active Compounds: Necrosis Inhibitor Activity; EC Data for 14-191 Extrapolated
| # | $EC_{50}$ |
|---|---|
| 1 | 1-10 uM |
| 2 | 1-1000 nM |
| 3 | 1-1000 nM |
| 4 | 1-1000 nM |
| 5 | 1-1000 nM |
| 6 | 1-1000 nM |
| 7 | 1-1000 nM |
| 8 | 1-10 uM |
| 9 | 1-1000 nM |
-continued
| # | $EC_{50}$ |
|---|---|
| 10 | 1-10 uM |
| 11 | 1-1000 nM |
| 12 | 1-10 uM |
| 13 | 1-1000 nM |
| 14 | 1-1000 nM |
| 15 | 1-10 uM |
| 16 | 1-1000 nM |
| 17 | 1-1000 nM |
| 18 | 1-1000 nM |
| 19 | 1-10 uM |
| 20 | 1-10 uM |
| 21 | 1-1000 nM |

-continued

| # | $EC_{50}$ |
|---|---|
| 22 | 1-10 uM |
| 23 | 1-1000 nM |
| 24 | 1-1000 nM |
| 25 | 1-10 uM |
| 26A | 1-1000 nM |
| 26B | 1-10 uM |
| 27A | 1-10 uM |
| 27B | 1-1000 nM |
| 28 | 1-1000 nM |
| 29 | 1-1000 nM |
| 30 | 1-1000 nM |
| 31 | 1-1000 nM |
| 32 | 1-1000 nM |
| 33 | 1-1000 nM |
| 34 | 1-10 uM |
| 35 | 1-10 uM |
| 36 | 1-1000 nM |
| 37 | 1-1000 nM |
| 38 | 1-1000 nM |
| 39 | 1-1000 nM |
| 40 | 1-1000 nM |
| 41 | 1-1000 nM |
| 42 | 1-1000 nM |
| 43 | 1-1000 nM |
| 44 | 1-10 uM |
| 45 | 1-1000 nM |
| 46 | 1-1000 nM |
| 47 | 1-1000 nM |
| 48 | 1-1000 nM |
| 49 | 1-1000 nM |
| 50 | 1-1000 nM |
| 51 | 1-1000 nM |
| 52 | 1-1000 nM |
| 53 | 1-1000 nM |
| 54 | 1-1000 nM |
| 55 | 1-1000 nM |
| 56 | 1-1000 nM |
| 57 | 1-1000 nM |
| 58 | 1-1000 nM |
| 59 | 1-1000 nM |
| 60 | 1-1000 nM |
| 61 | 1-1000 nM |
| 62 | 1-1000 nM |
| 63 | 1-1000 nM |
| 64 | 1-1000 nM |
| 65 | 1-1000 nM |
| 66 | 1-1000 nM |
| 67 | 1-1000 nM |
| 68 | 1-1000 nM |
| 69 | 1-1000 nM |
| 70 | 1-10 uM |
| 71 | 1-1000 nM |
| 72 | 1-1000 nM |
| 73 | 1-1000 nM |
| 74 | 1-1000 nM |
| 75 | 1-1000 nM |
| 76 | 1-1000 nM |
| 77 | 1-1000 nM |
| 78 | 1-1000 nM |
| 79 | 1-1000 nM |
| 80 | 1-1000 nM |
| 81 | 1-1000 nM |
| 82 | 1-1000 nM |
| 83 | 1-1000 nM |
| 84 | 1-1000 nM |
| 85 | 1-1000 nM |
| 86 | 1-1000 nM |
| 87 | 1-1000 nM |
| 88 | 1-1000 nM |
| 89 | 1-10 uM |
| 90 | 1-10 uM |
| 91 | 1-10 uM |
| 92 | 1-1000 nM |
| 93 | 1-10 uM |
| 94 | 1-10 uM |
| 95 | 1-10 uM |
| 96 | 1-10 uM |

-continued

| # | $EC_{50}$ |
|---|---|
| 97 | 1-10 uM |
| 98 | 1-10 uM |
| 99 | 1-10 uM |
| 100 | 1-1000 nM |
| 101 | 1-1000 nM |
| 102 | 1-10 uM |
| 103 | 1-10 uM |
| 104 | 1-1000 nM |
| 105 | 1-10 uM |
| 106 | 1-10 uM |
| 107 | 1-1000 nM |
| 108 | 1-1000 nM |
| 109 | 1-1000 nM |
| 110 | 1-1000 nM |
| 111A | 1-1000 nM |
| 111B | 1-10 uM |
| 112A | 1-1000 nM |
| 112B | 1-10 uM |
| 113A | 1-1000 nM |
| 113B | 1-10 uM |
| 114A | 1-1000 nM |
| 114B | 1-10 uM |
| 115A | 1-1000 nM |
| 116B | 1-10 uM |
| 117A | 1-1000 nM |
| 117B | 1-1000 nM |
| 118A | 1-1000 nM |
| 118B | 1-1000 nM |
| 119 | 1-1000 nM |
| 120 | 1-10 uM |
| 121 | 1-1000 nM |
| 122 | 1-10 uM |
| 123 | 1-1000 nM |
| 124 | 1-10 uM |
| 125 | 1-10 uM |
| 126 | 1-1000 nM |
| 127 | 1-1000 nM |
| 128 | 1-1000 nM |
| 129 | 1-1000 nM |
| 130 | 1-1000 nM |
| 131 | 1-1000 nM |
| 131 | 1-1000 nM |
| 132 | 1-1000 nM |
| 133 | 1-1000 nM |
| 134 | 1-1000 nM |
| 135 | 1-1000 nM |
| 136 | 1-1000 nM |
| 137 | 1-1000 nM |
| 138 | 1-1000 nM |
| 139 | 1-1000 nM |
| 140 | 1-1000 nM |
| 141 | 1-1000 nM |
| 142 | 1-1000 nM |
| 143 | 1-1000 nM |
| 144 | 1-1000 nM |
| 145 | 1-1000 nM |
| 155 | 1-1000 nM |
| 156 | 1-1000 nM |
| 157 | 1-1000 nM |
| 158 | 1-1000 nM |
| 159 | 1-1000 nM |
| 160 | 1-1000 nM |
| 161 | 1-1000 nM |
| 162 | 1-1000 nM |
| 163 | 1-1000 nM |
| 164 | 1-1000 nM |
| 165 | 1-1000 nM |
| 166 | 1-1000 nM |
| 167 | 1-1000 nM |
| 168 | 1-1000 nM |
| 169 | 1-1000 nM |
| 170 | 1-1000 nM |
| 171 | 1-1000 nM |
| 172 | 1-1000 nM |
| 173 | 1-1000 nM |
| 174 | 1-1000 nM |
| 175 | 1-1000 nM |

-continued

| # | $EC_{50}$ |
|---|---|
| 176 | 1-1000 nM |
| 177 | 1-1000 nM |
| 178 | 1-1000 nM |
| 179 | 1-1000 nM |
| 180 | 1-1000 nM |
| 181 | 1-1000 nM |
| 182 | 1-1000 nM |
| 183 | 1-1000 nM |
| 184 | 1-1000 nM |
| 185 | 1-1000 nM |
| 186 | 1-1000 nM |
| 187 | 1-1000 nM |
| 188 | 1-1000 nM |
| 189 | 1-1000 nM |
| 190 | 1-1000 nM |
| 191 | 1-1000 nM |
| 169 | 1-1000 nM |
| 170 | 1-1000 nM |
| 171 | 1-1000 nM |
| 172 | 1-1000 nM |
| 173 | 1-1000 nM |
| 174 | 1-1000 nM |
| 175 | 1-1000 nM |
| 176 | 1-1000 nM |
| 177 | 1-1000 nM |
| 178 | 1-1000 nM |
| 179 | 1-1000 nM |
| 180 | 1-1000 nM |
| 181 | 1-1000 nM |
| 182 | 1-1000 nM |
| 183 | 1-1000 nM |
| 184 | 1-1000 nM |
| 185 | 1-1000 nM |
| 186 | 1-1000 nM |
| 187 | 1-1000 nM |
| 188 | 1-1000 nM |
| 189 | 1-1000 nM |
| 190 | 1-1000 nM |
| 191 | 1-1000 nM |
| 192 | 1-1000 nM |
| 193 | 1-1000 nM |
| 194 | 1-1000 nM |
| 195 | 1-1000 nM |
| 196 | 1-1000 nM |
| 197 | 1-1000 nM |
| 198 | 1-1000 nM |
| 199 | 1-1000 nM |
| 200 | 1-1000 nM |
| 201 | 1-1000 nM |
| 202 | 1-1000 nM |
| 203 | 1-1000 nM |
| 204 | 1-1000 nM |
| 205 | 1-1000 nM |
| 206 | 1-1000 nM |
| 207 | 1-1000 nM |
| 208 | 1-1000 nM |
| 209 | 1-1000 nM |
| 210 | 1-1000 nM |
| 211 | 1-1000 nM |
| 212 | 1-1000 nM |
| 213 | 1-1000 nM |
| 214 | 1-1000 nM |
| 215 | 1-1000 nM |
| 216 | 1-1000 nM |
| 217 | 1-1000 nM |
| 218 | 1-1000 nM |
| 219 | 1-1000 nM |
| 220 | 1-1000 nM |
| 221 | 1-1000 nM |
| 222 | 1-1000 nM |
| 223 | 1-1000 nM |
| 224 | 1-1000 nM |
| 225 | 1-1000 nM |
| 226 | 1-1000 nM |
| 227 | 1-1000 nM |
| 228 | 1-1000 nM |
| 229 | 1-1000 nM |

-continued

| # | $EC_{50}$ |
|---|---|
| 230 | 1-1000 nM |
| 231 | 1-1000 nM |
| 232 | 1-1000 nM |
| 233 | 1-1000 nM |
| 234 | 1-1000 nM |
| 235 | 1-1000 nM |
| 236 | 1-1000 nM |
| 237 | 1-1000 nM |
| 238 | 1-1000 nM |
| 239 | 1-1000 nM |
| 240 | 1-1000 nM |
| 241 | 1-1000 nM |
| 242 | 1-1000 nM |
| 243 | 1-1000 nM |
| 244 | 1-1000 nM |
| 245 | 1-1000 nM |
| 246 | 1-1000 nM |
| 247 | 1-1000 nM |
| 248 | 1-1000 nM |
| 249 | 1-1000 nM |
| 250 | 1-1000 nM |
| 251 | 1-1000 nM |
| 252 | 1-1000 nM |
| 253 | 1-1000 nM |
| 254 | 1-1000 nM |
| 255 | 1-1000 nM |
| 256 | 1-1000 nM |
| 257 | 1-1000 nM |
| 258 | 1-1000 nM |
| 259 | 1-1000 nM |
| 260 | 1-1000 nM |
| 261 | 1-1000 nM |
| 262 | 1-1000 nM |
| 263 | 1-1000 nM |
| 264 | 1-1000 nM |
| 265 | 1-1000 nM |
| 266 | 1-1000 nM |
| 267 | 1-1000 nM |
| 268 | 1-1000 nM |
| 269 | 1-1000 nM |
| 270 | 1-1000 nM |
| 271 | 1-1000 nM |
| 272 | 1-1000 nM |
| 273 | 1-1000 nM |
| 274 | 1-1000 nM |
| 275 | 1-1000 nM |
| 276 | 1-1000 nM |
| 277 | 1-1000 nM |
| 278 | 1-1000 nM |
| 279 | 1-1000 nM |
| 280 | 1-1000 nM |
| 281 | 1-1000 nM |
| 282 | 1-1000 nM |
| 283 | 1-1000 nM |
| 284 | 1-1000 nM |
| 285 | 1-1000 nM |
| 286 | 1-1000 nM |
| 287 | 1-1000 nM |
| 288 | 1-1000 nM |
| 289 | 1-1000 nM |
| 290 | 1-1000 nM |
| 291 | 1-1000 nM |
| 292 | 1-1000 nM |
| 293 | 1-1000 nM |
| 294 | 1-1000 nM |
| 295 | 1-1000 nM |
| 296 | 1-1000 nM |
| 297 | 1-1000 nM |
| 298 | 1-1000 nM |
| 299 | 1-1000 nM |
| 300 | 1-1000 nM |
| 301 | 1-1000 nM |
| 302 | 1-1000 nM |
| 303 | 1-1000 nM |
| 304 | 1-1000 nM |
| 305 | 1-1000 nM |
| 306 | 1-1000 nM |

-continued

| # | $EC_{50}$ |
|---|---|
| 307 | 1-1000 nM |
| 308 | 1-1000 nM |
| 309 | 1-1000 nM |
| 310 | 1-1000 nM |
| 311 | 1-1000 nM |
| 312 | 1-1000 nM |
| 313 | 1-1000 nM |
| 314 | 1-1000 nM |
| 315 | 1-1000 nM |
| 316 | 1-1000 nM |
| 317 | 1-1000 nM |
| 318 | 1-1000 nM |
| 319 | 1-1000 nM |
| 320 | 1-1000 nM |
| 321 | 1-1000 nM |
| 322 | 1-1000 nM |
| 323 | 1-1000 nM |
| 324 | 1-1000 nM |
| 325 | 1-1000 nM |
| 326 | 1-1000 nM |
| 327 | 1-1000 nM |
| 328 | 1-1000 nM |
| 329 | 1-1000 nM |
| 330 | 1-1000 nM |
| 331 | 1-1000 nM |
| 332 | 1-1000 nM |
| 333 | 1-1000 nM |
| 334 | 1-1000 nM |
| 335 | 1-1000 nM |
| 336 | 1-1000 nM |
| 337 | 1-1000 nM |
| 338 | 1-1000 nM |
| 339 | 1-1000 nM |
| 340 | 1-1000 nM |
| 341 | 1-1000 nM |
| 342 | 1-1000 nM |
| 343 | 1-1000 nM |
| 344 | 1-1000 nM |
| 345 | 1-1000 nM |
| 346 | 1-1000 nM |
| 347 | 1-1000 nM |
| 348 | 1-1000 nM |
| 349 | 1-1000 nM |
| 350 | 1-1000 nM |
| 351 | 1-1000 nM |
| 352 | 1-1000 nM |
| 353 | 1-1000 nM |
| 354 | 1-1000 nM |
| 355 | 1-1000 nM |
| 356 | 1-1000 nM |
| 35 | 1-1000 nM |
| 358 | 1-1000 nM |
| 359 | 1-1000 nM |
| 360 | 1-1000 nM |
| 361 | 1-1000 nM |
| 362 | 1-1000 nM |
| 363 | 1-1000 nM |
| 364 | 1-1000 nM |
| 365 | 1-1000 nM |
| 366 | 1-1000 nM |
| 367 | 1-1000 nM |
| 368 | 1-1000 nM |
| 369 | 1-1000 nM |
| 370 | 1-1000 nM |
| 371 | 1-1000 nM |
| 372 | 1-1000 nM |
| 373 | 1-1000 nM |
| 374 | 1-1000 nM |
| 375 | 1-1000 nM |
| 376 | 1-1000 nM |
| 377 | 1-1000 nM |
| 378 | 1-1000 nM |
| 379 | 1-1000 nM |
| 380 | 1-1000 nM |
| 381 | 1-1000 nM |
| 382 | 1-1000 nM |
| 383 | 1-1000 nM |

-continued

| # | $EC_{50}$ |
|---|---|
| 384 | 1-1000 nM |
| 385 | 1-1000 nM |
| 386 | 1-1000 nM |

IC50 of hRIP1 Kinase Assay Correlated with Our IC50 of Cell Necrosis Assay; Representative, Exemplary Data:

| Compound No | Human RIP1 kinase assay IC50(nM) | Cell viability assay, EC50 (nM) |
|---|---|---|
| 14 | 100-1000 nM | 1-1000 nM |
| 1 | ~1000 nM | 1-10000 nM |
| 80 | <100 nM | 1-100 nM |
| 76 | <100 nM | 1-100 nM |
| 132 | <100 nM | 1-100 nM |
| 26A | <100 nM | 1-1000 nM |
| 26B | >1000 nM | >1000 nM |
| 41 | <100 nM | 1-100 nM |

Synthesis

Compound 1: azetidin-1-yl(5-phenyl-4,5-dihydro-1H-pyrazol-1-yl)methanone

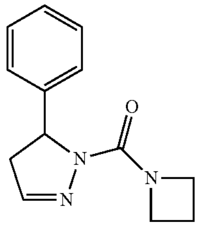 [SMILES: O=C(N1CCC1)N1N=CCC1c1ccccc1]

To a cooled solution of 5-phenyl-4,5-dihydro-1H-pyrazole (200 mg, 1.37 mmol) in dry DCM was added pyridine (216.7 mg, 2.74 mmol), followed by added triphosgene (162.6 mg, 0.548 mmol) in batches. The mixture was stirred at 0° C. for 3 h. Azetidine (150 mg, 2.7 mmol) and TEA (270 mg, 2.7 mmol) were dissolved in dry DCM (5 ml), and the above reaction mixture was added to the solution and stirred for overnight. The mixture was extracted with DCM, washed with brine, dried ($Na_2SO_4$), and concentrated in vacuo. Purification by silica gel chromatography to give compound 1. $^1H$ NMR (400 MHz, $CDCl_3$) δ 7.32-7.27 (m, 2H), 7.23-7.15 (m, 3H), 6.73 (t, J=1.7 Hz, 1H), 5.29 (dd, J=12.2, 6.5 Hz, 1H), 4.22-4.04 (m, 4H), 3.30 (ddd, J=18.5, 12.2, 1.7 Hz, 1H), 2.69 (ddd, J=18.5, 6.5, 1.7 Hz, 1H), 2.26-2.11 (m, 2H). LC-MS (m/z) 230.30 ($M+H^+$).

Compound 2: N-cyclobutyl-5-phenyl-4,5-dihydro-1H-pyrazole-1-carboxamide

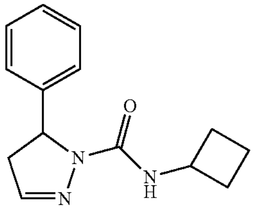 [SMILES: O=C(NC1CCC1)N1N=CCC1c1ccccc1]

The titled compound 2 was prepared in 35% yield from 5-phenyl-4,5-dihydro-1H-pyrazole (300 mg), cyclobutanamine (180 mg) and triphosgene (280 mg) according to the procedure outlined for compound 1. LC-MS (m/z) 244.3 ($M+H^+$)

Compound 3: (5-phenyl-4,5-dihydro-1H-pyrazol-1-yl)(2-azaspiro[3.3]heptan-2-yl)methanone

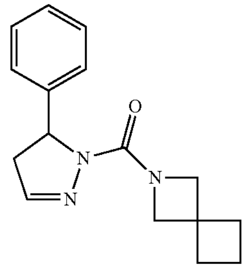 [SMILES: O=C(N1CC2(CCC2)C1)N1N=CCC1c1ccccc1]

The titled compound 3 was prepared in 40% yield from 5-phenyl-4,5-dihydro-1H-pyrazole (300 mg), 2-azaspiro[3.3]heptane (530 mg) and triphosgene (280 mg) according to the procedure outlined for compound 1. LC-MS (m/z) 270.4 ($M+H^+$)

Compound 4: (3-methylazetidin-1-yl)(5-phenyl-4,5-dihydro-1H-pyrazol-1-yl)methanone

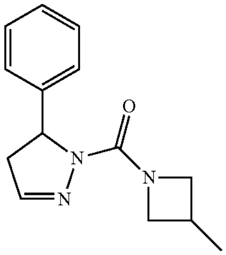 [SMILES: CC1CN(C(=O)N2N=CCC2c2ccccc2)C1]

The titled compound 4 was prepared in 16% yield from 5-phenyl-4,5-dihydro-1H-pyrazole (200 mg), 3-methylazetidine hydrochloride (290 mg) and triphosgene (162.5 mg) according to the procedure outlined for compound 1. $^1H$ NMR (400 MHz, $CDCl_3$) δ 7.32-7.26 (m, 2H), 7.23-7.19 (m, 3H), 6.73 (t, J=1.7 Hz, 1H), 5.29 (dd, J=12.2, 6.5 Hz, 1H), 4.23 (dt, J=21.5, 8.6 Hz, 2H), 3.69 (ddd, J=34.7, 8.8, 5.7 Hz, 2H), 3.30 (ddd, J=18.4, 12.2, 1.7 Hz, 1H), 2.69 (ddd, J=18.4, 6.5, 1.7 Hz, 1H), 2.66-2.58 (m, 1H), 1.20 (d, J=6.9 Hz, 3H). LC-MS (m/z) 244.3 ($M+H^+$)

Compound 5: N-cyclopentyl-5-phenyl-4,5-dihydro-1H-pyrazole-1-carboxamide

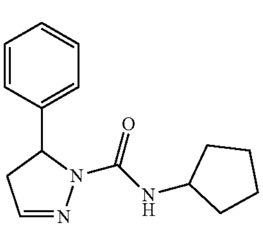 [SMILES: O=C(NC1CCCC1)N1N=CCC1c1ccccc1]

The titled compound 5 was prepared in 36% yield from 5-phenyl-4,5-dihydro-1H-pyrazole (200 mg), cyclopentanamine (230 mg) and triphosgene (162.5 mg) according to the procedure outlined for compound 1. $^1H$ NMR (400 MHz, $CDCl_3$) δ 7.32-7.27 (m, 2H), 7.26-7.17 (m, 3H), 6.74 (t, J=1.7 Hz, 1H), 5.27 (dd, J=12.2, 6.1 Hz, 2H), 4.12-4.02 (m, 1H), 3.40 (ddd, J=18.6, 12.2, 1.7 Hz, 1H), 2.78 (ddd, J=18.6, 6.2, 1.8 Hz, 1H), 1.99-1.88 (m, 2H), 1.71-1.50 (m, 4H), 1.45-1.34 (m, 2H). LC-MS (m/z) 258.34 ($M+H^+$)

Compound 6: (5-phenyl-4,5-dihydro-1H-pyrazol-1-yl)(pyrrolidin-1-yl)methanone

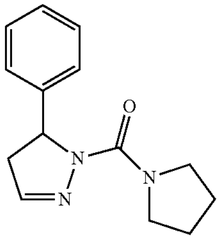 [SMILES: O=C(N1CCCC1)N1N=CCC1c1ccccc1]

The titled compound 6 was prepared in 35% yield from 5-phenyl-4,5-dihydro-1H-pyrazole (200 mg), pyrrolidine (190 mg) and triphosgene (162.5 mg) according to the procedure outlined for compound 1. $^1H$ NMR (400 MHz, $CDCl_3$) δ 7.33-7.26 (m, 3H), 7.26-7.19 (m, 2H), 6.74 (t, J=1.7 Hz, 1H), 5.34 (dd, J=12.0, 9.1 Hz, 1H), 3.64-3.55 (m, 2H), 3.51-3.44 (m, 2H), 3.28 (ddd, J=18.2, 12.0, 1.8 Hz, 1H), 2.70 (ddd, J=18.3, 9.1, 1.7 Hz, 1H), 1.93-1.72 (m, 4H). LC-MS (m/z) 244.31 ($M+H^+$)

Compound 7: (5-phenyl-4,5-dihydro-1H-pyrazol-1-yl)(piperidin-1-yl)methanone

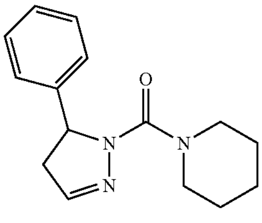 [SMILES: O=C(N1CCCCC1)N1N=CCC1c1ccccc1]

The titled compound 7 was prepared in 8.5% yield from 5-phenyl-4,5-dihydro-1H-pyrazole (200 mg), piperidine (235 mg) and triphosgene (250 mg) according to the procedure outlined for compound 1. $^1H$ NMR (400 MHz, $CDCl_3$) δ 7.34-7.25 (m, 4H), 7.24-7.19 (m, 1H), 6.78 (brs, 1H), 5.33 (dd, J=11.6, 10.4 Hz, 1H), 3.61-3.38 (m, 4H), 3.25 (ddd, J=18.1, 11.7, 1.6 Hz, 1H), 2.68 (ddd, J=18.2, 10.3, 1.5 Hz, 1H), 1.70-1.40 (m, 6H). LC-MS (m/z) 258.3 ($M+H^+$)

Compound 8: (2-methylpiperidin-1-yl)(5-phenyl-4,5-dihydro-1H-pyrazol-1-yl)methanone

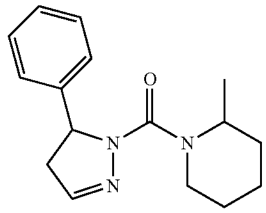 [SMILES: CC1CCCCN1C(=O)N1N=CCC1c1ccccc1]

The titled compound 8 was prepared in 17% yield from 5-phenyl-4,5-dihydro-1H-pyrazole (13 mg), 2-methylpiperidine (8.91 mg) and triphosgene (7.1 mg) according to the procedure outlined for compound 1. $^1$H NMR (400 MHz, $CDCl_3$) δ 7.32-7.27 (m, 3H), 7.26-7.18 (m, 2H), 6.79 (brs, 1H), 5.32 (t, J=11.1 Hz, 1H), 4.72-4.66 (m, 1H), 3.89 (dd, J=13.6, 3.2 Hz, 1H), 3.24 (ddd, J=18.0, 11.6, 1.2 Hz, 1H), 3.02 (td, J=13.4, 2.8 Hz, 1H), 2.73-2.61 (m, 1H), 1.81-1.69 (m, 1H), 1.62-1.35 (m, 5H), 1.11 (d, J=7.0 Hz, 3H). LC-MS (m/z) 272.4 ($M+H^+$)

Compound 9: (3-methylpiperidin-1-yl)(5-phenyl-4,5-dihydro-1H-pyrazol-1-yl)methanone

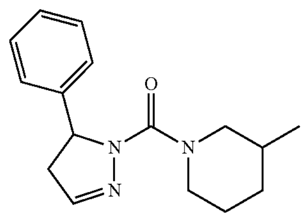 [SMILES: CC1CCCN(C(=O)N2N=CCC2c2ccccc2)C1]

To a cooled solution of triphosgene (320 mg, 1.08 mmol) in dry DCM (5 ml) was added dropwise a mixture solution of 5-phenyl-4,5-dihydro-1H-pyrazole (400 mg, 2.74 mmol) and TEA (550 mg, 5.44 mmol). The mixture was stirred at 0° C. for 3.

3-methylpiperidine (260 mg, 2.7 mmol) and TEA (270 mg, 2.7 mmol) were dissolved in dry DCM (5 ml), and the a volume of half above reaction mixture was added to the solution and stirred for overnight. The mixture was extracted with DCM, washed with brine, dried with ($Na_2SO_4$), and concentrated in vacuo. Purification by silica gel chromatography (EA/PE=1/3) to give compound 9 (180 mg, 48.2%) as a yellow oil. $^1$H NMR (400 MHz, $CDCl_3$) δ 7.34-7.25 (m, 3H), 7.24-7.22 (m, 2H), 6.78 (d, J=1.2 Hz, 1H), 5.39-5.24 (t, J=10.81H), 4.22 (ddd, J=11.1, 3.3, 1.7 Hz, 1H), 4.13-3.99 (m, 1H), 3.25 (ddd, J=18.1, 11.7, 1.7 Hz, 1H), 2.97-2.83 (m, 1H), 2.68 (ddd, J=12.1, 10.3, 1.4 Hz, 1H), 2.53-2.36 (m, 1H), 1.74 (dddd, J=25.1, 10.4, 7.7, 3.8 Hz, 1H), 1.70-1.50 (m, 2H), 1.16-1.00 (m, 2H), 0.89-0.78 (m, 3H). LC-MS (m/z) 272.40 ($M+H^+$).

Compound 10: N-cyclohexyl-5-phenyl-4,5-dihydro-1H-pyrazole-1-carboxamide

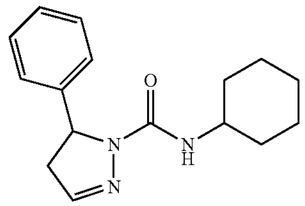 [SMILES: O=C(NC1CCCCC1)N1N=CCC1c1ccccc1]

The titled compound 10 was prepared in 8.5% yield from 5-phenyl-4,5-dihydro-1H-pyrazole (300 mg), cyclohexanamine (240 mg) and triphosgene (280 mg) according to the procedure outlined for compound 1. $^1$H NMR (400 MHz, $CDCl_3$) δ 7.32-7.27 (m, 2H), 7.24-7.13 (m, 3H), 6.74 (t, J=1.6 Hz, 1H), 5.79 (d, J=7.8 Hz, 1H), 5.30-5.22 (m, 1H), 3.60 (ddd, J=14.8, 10.6, 4.2 Hz, 1H), 3.39 (ddd, J=18.6, 12.2, 1.7 Hz, 1H), 2.79 (ddd, J=18.6, 6.2, 1.7 Hz, 1H), 1.90 (dd, J=18.0, 14.6 Hz, 2H), 1.73-1.61 (m, 2H), 1.39-1.05 (m, 6H). LC-MS (m/z) 272.4 ($M+H^+$).

Compound 11: N-(3-methylcyclohexyl)-5-phenyl-4,5-dihydro-1H-pyrazole-1-carboxamide

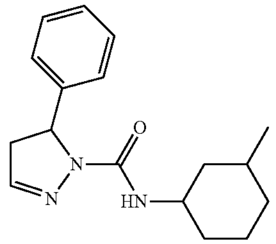 [SMILES: CC1CCCC(NC(=O)N2N=CCC2c2ccccc2)C1]

The titled compound 11 was prepared in 25.5% yield from 5-phenyl-4,5-dihydro-1H-pyrazole (200 mg), 3-methylcyclohexan-1-amine (233 mg) and triphosgene (162.3 mg) according to the procedure outlined for compound 9. $^1$H NMR (400 MHz, $CDCl_3$) δ 7.36-7.29 (m, 2H), 7.26-7.19 (m, 2H), 6.79-6.75 (m, 1H), 6.09 (s, 1H), 5.76 (d, J=8.2 Hz, 1H), 5.29 (ddd, J=12.3, 6.1, 3.3 Hz, 1H), 3.68-3.54 (m, 1H), 3.42 (dddd, J=18.5, 12.2, 3.1, 1.7 Hz, 1H), 3.25 (dt, J=14.3, 4.5 Hz, 2H), 2.86-2.77 (m, 1H), 2.05-1.91 (m, 3H), 1.73-1.61 (m, 2H), 0.92-0.87 (m, 3H). LC-MS (m/z) 286.4 ($M+H^+$)

Compound 12: N-cyclohexyl-N-methyl-5-phenyl-4,5-dihydro-1H-pyrazole-1-carboxamide

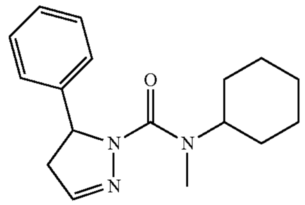 [SMILES: CN(C(=O)N1N=CCC1c1ccccc1)C1CCCCC1]

The titled compound 12 was prepared in 15% yield from 5-phenyl-4,5-dihydro-1H-pyrazole (200 mg), 3-methylcyclohexan-1-amine (305 mg) and triphosgene (162 mg) according to the procedure outlined for compound 1. $^1$H NMR (400 MHz, $CDCl_3$) δ 7.35-7.30 (m, 3H), 7.26-7.23 (m, 2H), 6.80 (s, 1H), 5.34 (t, J=11.1 Hz, 1H), 4.02 (t, J=11.6 Hz, 1H), 3.27 (dd, J=17.2, 12.4 Hz, 1H), 2.90 (s, 3H), 2.70 (dd, J=18.6, 11.3 Hz, 1H), 1.81-1.58 (m, 4H), 1.51-1.24 (m, 5H), 1.13-1.01 (m, 1H). LC-MS (m/z) 286.20 (M+H$^+$)

Compound 13: Isoindolin-2-yl(5-phenyl-4,5-dihydro-1H-pyrazol-1-yl)methanone

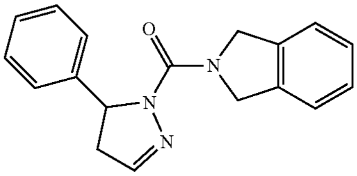 [SMILES: O=C(N1Cc2ccccc2C1)N1N=CCC1c1ccccc1]

The titled compound 13 was prepared in 23% yield from 5-phenyl-4,5-dihydro-1H-pyrazole (300 mg), isoindoline (320 mg) and triphosgene (162.5 mg) according to the procedure outlined for compound 1. $^1$H NMR (400 MHz, $CDCl_3$) δ 7.33-7.30 (m, 2H), 7.25-7.22 (m, 2H) 7.23-7.11 (m, 5H), 6.72 (t, J=1.7 Hz, 1H), 5.28 (dd, J=12.2, 6.1 Hz, 1H), 4.72-4.55 (m, 1H), 3.40 (ddd, J=18.6, 12.2, 1.7 Hz, 1H), 3.34-3.23 (m, 2H), 2.87-2.74 (m, 3H). LC-MS (m/z) 292.4 (M+H$^+$)

Compound 14: N-(2,3-dihydro-H-inden-2-yl)-5-phenyl-4,5-dihydro-1H-pyrazole-1-carboxamide

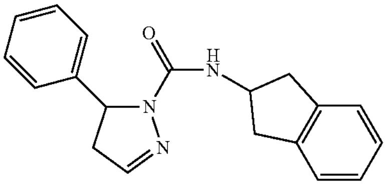 [SMILES: O=C(NC1Cc2ccccc2C1)N1N=CCC1c1ccccc1]

The titled compound 14 was prepared in 20% yield from 5-phenyl-4,5-dihydro-1H-pyrazole (300 mg), 2,3-dihydro-1H-inden-2-amine (450 mg) and triphosgene (162.5 mg) according to the procedure outlined for compound 1. $^1$H NMR (400 MHz, $CDCl_3$) δ 7.33-7.30 (m, 2H), 7.25-7.22 (m, 2H), 7.21-7.11 (m, 5H), 6.72 (t, J=1.7 Hz, 1H), 6.10 (d, J=7.9 Hz, 1H), 5.28 (dd, J=12.2, 6.1 Hz, 1H), 4.72-4.55 (m, 1H), 3.40 (ddd, J=18.6, 12.2, 1.7 Hz, 1H), 3.34-3.23 (m, 2H), 2.87-2.74 (m, 3H). LC-MS (m/z) 306.4 (M+H$^+$). LC-MS (m/z) 306.4 (M+H$^+$)

Compound 15: (3,4-dihydroisoquinolin-2(1H)-yl)(5-phenyl-4,5-dihydro-1H-pyrazol-1-yl)methanone

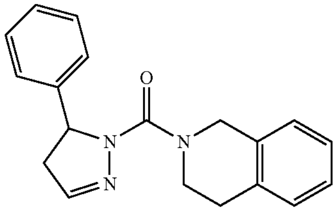 [SMILES: O=C(N1CCc2ccccc2C1)N1N=CCC1c1ccccc1]

The titled compound 15 was prepared in 30.6% yield from 5-phenyl-4,5-dihydro-1H-pyrazole (25 mg), 1,2,3,4-tetrahydroisoquinoline (50 mg) and triphosgene (12.7 mg) according to the procedure outlined for compound 1. LC-MS (m/z) 306.4 (M+H$^+$)

Compound 16: (3-benzylazetidin-1-yl)(5-phenyl-4,5-dihydro-1H-pyrazol-1-yl)methanone

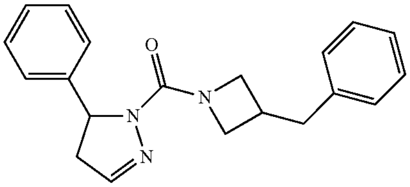 [SMILES: O=C(N1CC(Cc2ccccc2)C1)N1N=CCC1c1ccccc1]

The titled compound 16 was prepared in 64.6% yield from 5-phenyl-4,5-dihydro-1H-pyrazole (25 mg), 3-benzylazetidine and triphosgene according to the procedure outlined for compound 1. $^1$H NMR (400 MHz, $CDCl_3$) δ 7.36-7.26 (m, 4H), 7.26-7.12 (m, 6H), 6.75 (t, 1H, J=1.6 Hz), 5.31 (dd, 1H, J=12.4, 6.4 Hz), 4.25 (t, 1H, J=8.4 Hz), 4.18 (t, 1H, J=8.4 Hz), 3.92 (dd, 1H, J=8.8, 5.6 Hz), 3.83 (dd, 1H, J=8.8, 5.6 Hz), 3.32 (ddd, 1H, J=18.5, 12.0, 1.6 Hz), 2.95-2.90 (m, 2H), 2.89-2.84 (m, 1H), 2.72 (ddd, 1H, J=18.4, 6.4, 1.6 Hz). LC-MS (m/z): 320.35 [M+H]$^+$.

Compound 17: (3-benzylpyrrolidin-1-yl)(5-phenyl-4,5-dihydro-1H-pyrazol-1-yl)methanone

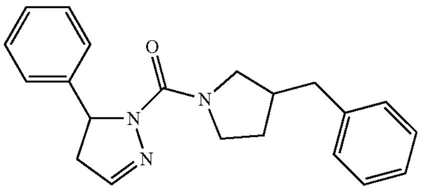 [SMILES: O=C(N1CCC(Cc2ccccc2)C1)N1N=CCC1c1ccccc1]

The titled compound 17 was prepared in 64.6% yield from 5-phenyl-4,5-dihydro-1H-pyrazole (25 mg), 3-benzylazetidine and triphosgene according to the procedure outlined for compound 1. $^1$H NMR (400 MHz, $CDCl_3$) δ 7.27-7.35 (m, 7H), 7.13-7.25 (m, 3H), 6.74-6.76 (m, 1H), 5.31-5.37 (m, 1H), 3.78-3.88 (m, 1H), 3.55-3.63 (m, 1H), 3.28-3.35 (m, 1H), 3.21-3.26 (m, 1H), 2.59-2.77 (m, 3H), 2.29-2.46 (m, 2H), 1.87-1.96 (m, 1H), 1.51-1.68 (m, 1H). LC-MS (m/z): 334.41 [M+H]$^+$.

Compound 18: (4-benzylpiperidin-1-yl)(5-phenyl-4,5-dihydro-1H-pyrazol-1-yl)methanone

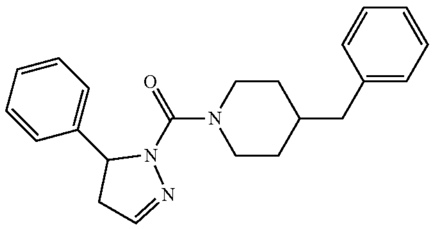 [SMILES: O=C(N1CCC(Cc2ccccc2)CC1)N1N=CCC1c1ccccc1]

The titled compound 18 was prepared in 14% yield from 5-phenyl-4,5-dihydro-1H-pyrazole, 4-benzylpiperidine and triphosgene according to the procedure outlined for compound 9. $^1$H NMR (400 MHz, $CDCl_3$) δ 7.36-7.28 (m, 5H), 7.27-7.23 (m, 2H), 7.21-7.17 (m, 1H), 7.15-7.13 (m, 2H), 6.80 (t, J=1.7 Hz, 1H), 5.35 (dd, J=11.7, 10.3 Hz, 1H), 4.33-4.25 (m, 1H), 4.19 (ddt, J=13.4, 4.4, 2.3 Hz, 1H), 3.28 (ddd, J=18.2, 11.8, 1.8 Hz, 1H), 2.86-2.77 (m, 1H), 2.77-2.65 (m, 2H), 2.54 (d, J=7.1 Hz, 2H), 1.80-1.58 (m, 1H), 1.40-1.29 (m, 2H), 1.24-1.08 (m, 2H). LC-MS (m/z) 348.5 $(M+H^+)$ Compound 19: (5-phenyl-4,5-dihydro-1H-pyrazol-1-yl)(3-(phenylamino)azetidin-1-yl)methanone

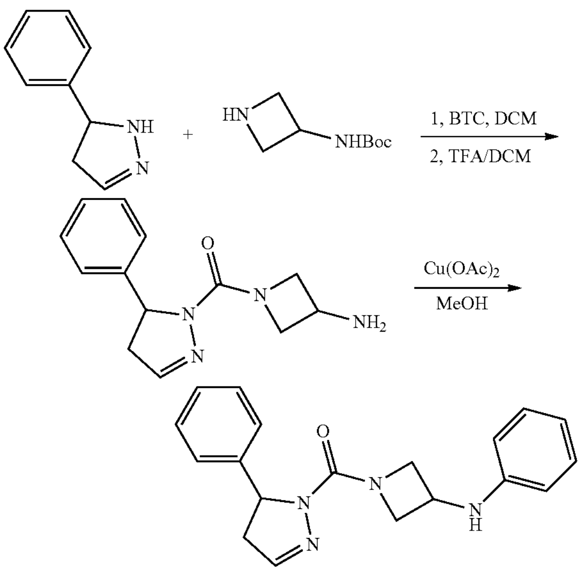

tert-butyl (1-(5-phenyl-4,5-dihydro-1H-pyrazole-1-carbonyl)azetidin-3-yl)carbamate (50 mg) was prepared by the method described for compound 1, which was dissolved in DCM (6 mL), 1 mL of TFA was added. The mixture was stirred at room temperature for 2 h, and concentrated to give the crude (3-aminoazetidin-1-yl)(5-phenyl-4,5-dihydro-1H-pyrazol-1-yl)methanone (30 mg). LC-MS (m/z) 244.4 $(M+H^+)$.

A mixture of (3-aminoazetidin-1-yl)(5-phenyl-4,5-dihydro-1H-pyrazol-1-yl)methanone (30 mg), phenylboronic acid (20 mg), $Cu(OAc)_2$ (3 mg), TEA (30 mg,) in DCM (10 mL) was stirred at 65° C. for 16 h. The mixture was extracted with DCM, washed with brine, dried ($Na_2SO_4$), and concentrated in vacuo. Purification by silica gel chromatography to give the titled compound 19 (14 mg, 32%). $^1$H NMR (400 MHz, $CDCl_3$) δ 7.50-7.22 (m, 9H), 6.74 (s, 1H), 6.51 (s, 1H), 4.84-4.10 (m, 5H), 3.33 (dd, J=18.6, 12.4 Hz, 1H), 2.97 (s, 3H), 2.72 (dd, J=18.8, 5.8 Hz, 1H) LC-MS (m/z) 321.40 $(M+H^+)$ Compound 20: (3-(methyl(phenyl)amino)azetidin-1-yl)(5-phenyl-4,5-dihydro-1H-pyrazol-1-yl)methanone

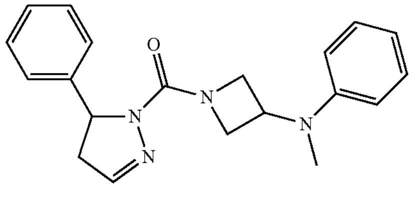

The titled compound 20 was prepared in 15% yield from 5-phenyl-4,5-dihydro-1H-pyrazole, N-methyl-N-phenylazetidin-3-amine and triphosgene according to the procedure outlined for compound 9. $^1$H NMR (400 MHz, $CDCl_3$) δ 7.41-7.26 (m, 3H), 7.24-6.98 (m, 7H), 6.77 (s, 1H), 5.30 (dd, J=11.9, 5.8 Hz, 1H), 4.34-4.28 (m, 5H), 3.33 (dd, J=18.6, 12.4 Hz, 1H), 2.97 (s, 3H), 2.72 (dd, J=18.8, 5.8 Hz, 1H). LC-MS (m/z) 335.5 $(M+H^+)$ Compound 21: 5-phenyl-N-(3-phenylcyclopentyl)-4,5-dihydro-1H-pyrazole-1-carboxamide

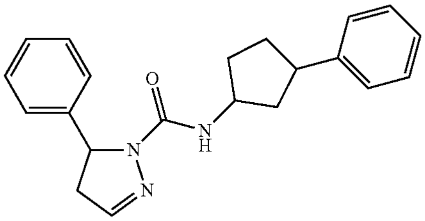 [SMILES: O=C(NC1CCC(c2ccccc2)C1)N1N=CCC1c1ccccc1]

The titled compound 21 was prepared in 14% yield from 5-phenyl-4,5-dihydro-1H-pyrazole (100 mg), 3-phenylcyclopentan-1-amine (100 mg) and triphosgene (81 mg) according to the procedure outlined for compound 1. $^1$H NMR (400 MHz, $CDCl_3$) δ 7.40-7.14 (m, 10H), 6.79 (d, J=5.1 Hz, 1H), 5.99 (d, J=7.2 Hz, 1H), 5.31 (dd, J=12.2, 6.0 Hz, 1H), 4.39-4.23 (m, 1H), 3.44 (dd, J=18.4, 12.4 Hz, 1H), 3.29-2.99 (m, 2H), 2.83 (d, J=18.7 Hz, 1H), 2.64-2.50 (m, 1H), 2.38-1.96 (m, 3H), 1.85-1.45 (m, 3H). LC-MS (m/z) 334.4 $(M+H^+)$ Compound 22: 5-phenyl-N-(pyrimidin-2-yl)pyrrolidin-3-yl)-4,5-dihydro-1H-pyrazole-1-carboxamide

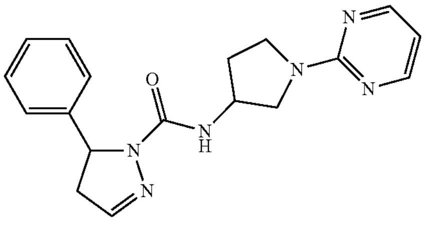 [SMILES: O=C(NC1CCN(c2ncccn2)C1)N1N=CCC1c1ccccc1]

To a solution of 2-bromopyrimidine (150 mg) in DMF (5 mL) was added tert-butyl pyrrolidin-3-ylcarbamate (200 mg) and $K_2CO_3$ (400 mg). The mixture was stirred at 95° C. for overnight under $N_2$. The mixture was diluted with $H_2O$ (10 mL), extracted with EA (15 mL*3). The combined organic layer were washed with brine, dried over ($Na_2SO_4$) and concentrated in vacuo.

Purification by Silica Gel Chromatography (EA/PE=1/1) to give tert-butyl (1-(pyrimidin-2-yl)pyrrolidin-3-yl)carbamate (170 mg, 68.5%) as a light yellow solid. LC-MS (m/z) 265.4 ($M+H^+$)

To a solution of tert-butyl (1-(pyrimidin-2-yl)pyrrolidin-3-yl)carbamate (170 mg) in DCM (5 mL) at 0° C. was added 1 ml of TFA. The mixture was stirred at room temperature for 3 hours. The mixture was concentrated to dryness and dissolved in DCM (5 mL), and TEA (270 mg) was added. A solution of 5-phenyl-4,5-dihydro-1H-pyrazole-1-carbonyl chloride (1.35 mmol, prepared by procedure outlined for compound 1) in 2.5 ml of DCM was added to the above mixture at 0° C. and stirred at room temperature for overnight. The mixture was extracted with DCM, washed with brine, dried ($Na_2SO_4$), and concentrated in vacuo. Purification by silica gel chromatography (EA/PE=1/1) to give compound 22 (74 mg, 16.2%) as a yellow oil. $^1$H NMR (400 MHz, $CDCl_3$) δ 8.35 (d, J=4.8 Hz, 1H), 7.37-7.26 (m, 2H), 7.26-7.13 (m, 3H), 6.78 (t, J=1.6 Hz, 1H), 6.54 (t, J=4.8 Hz, 1H), 6.06 (d, J=6.8 Hz, 1H), 5.29 (ddd, J=12.1, 6.0, 3.3 Hz, 1H), 4.53 (dd, J=11.9, 5.8 Hz, 1H), 3.87 (ddd, J=11.6, 6.2, 2.2 Hz, 1H), 3.72 (ddd, J=13.8, 7.6, 4.9 Hz, 2H), 3.59-3.37 (m, 2H), 2.82 (ddt, J=18.7, 6.0, 1.6 Hz, 1H), 2.28 (dd, J=13.6, 6.7 Hz, 1H), 2.04 (dd, J=14.8, 6.7 Hz, 1H). LC-MS (m/z) 337.40 ($M+H^+$)

Compound 23: N-(1-(5-fluoropyridin-2-yl)pyrrolidin-3-yl)-5-phenyl-4,5-dihydro-1H-pyrazole-1-carboxamide

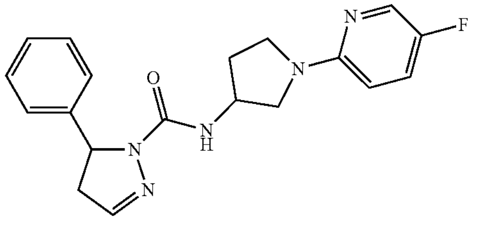 [SMILES: O=C(NC1CCN(c2ccc(F)cn2)C1)N1N=CCC1c1ccccc1]

The titled compound 23 was prepared in 34% yield from 5-phenyl-4,5-dihydro-1H-pyrazole, 1-(5-fluoropyridin-2-yl) pyrrolidin-3-amine and triphosgene according to the procedure outlined for compound 9. $^1$H NMR (400 MHz, $CDCl_3$) δ 8.02 (d, 1H, J=2.8 Hz), 7.34-7.31 (m, 2H), 7.25-7.19 (m, 3H), 6.78 (t, 1H, J=1.6 Hz), 6.29 (dd, 1H, J=9.2, 3.2 Hz), 6.06 (d, 1H, J=7.2 Hz), 5.29 (dd, 1H, J=12.4, 6.0 Hz), 4.55-4.48 (m, 1H), 3.70 (dd, 1H, J=10.4, 6.4 Hz), 3.63-3.56 (m, 1H), 3.54-3.48 (m, 1H), 3.43 (ddd, 1H, J=18.8, 12.4, 1.6 Hz), 3.34 (dd, 1H, J=10.4, 4.4 Hz), 2.82 (ddd, 1H, J=18.4, 6.0, 1.6 Hz), 2.32-2.24 (m, 1H), 2.08-1.92 (m, 1H). LC-MS (m/z): 354.39 $[M+H]^+$.

Compound 24: 5-phenyl-N-(1-phenylpyrrolidin-3-yl)-4,5-dihydro-1H-pyrazole-1-carboxamide

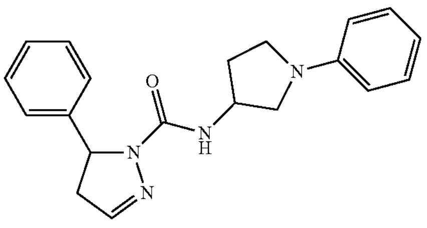 [SMILES: O=C(NC1CCN(c2ccccc2)C1)N1N=CCC1c1ccccc1]

The titled compound 24 was prepared in 8.1% yield from 5-phenyl-4,5-dihydro-1H-pyrazole, 1-phenylpyrrolidin-3-amine and triphosgene according to the procedure outlined for compound 9. $^1$H NMR (400 MHz, $CDCl_3$) δ 7.36-7.30 (m, 3H), 7.29-7.26 (m, 1H), 7.25-7.20 (m, 4H), 6.78 (t, 1H, J=1.6 Hz), 6.71-6.67 (m, 1H), 6.58-6.55 (m, 1H), 6.09 (d, 1H, J=7.6 Hz), 5.28 (dd, 1H, J=12.4, 6.0 Hz), 4.56-4.48 (m, 1H), 3.59 (dd, 1H, J=10.0, 6.4 Hz), 3.50-3.45 (m, 1H), 3.45-3.38 (m, 1H), 3.37-3.29 (m, 1H), 3.23 (dd, 1H, J=8.4, 4.0 Hz), 2.82 (ddd, 1H, J=18.8, 6.0, 1.6 Hz), 2.33-2.24 (m, 1H), 2.02-1.94 (m, 1H). LC-MS (m/z): 335.40 $[M+H]^+$ Compound 25: N-((1S,3S)-3-phenoxycyclopentyl)-5-phenyl-4,5-dihydro-1H-pyrazole-1-carboxamide

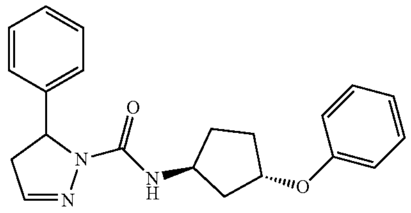 [SMILES: O=C(N[C@H]1CC[C@H](Oc2ccccc2)C1)N1N=CCC1c1ccccc1]

The titled compound 25 was prepared in 23% yield from 5-phenyl-4,5-dihydro-1H-pyrazole, (1S,3S)-3-phenoxycyclopentan-1-amine and triphosgene according to the procedure outlined for compound 9. LC-MS (m/z) 350.4 ($M+H^+$)

Compound 26: ((R)-3-phenoxypyrrolidin-1-yl)(5-phenyl-4,5-dihydro-1H-pyrazol-1-yl)methanone

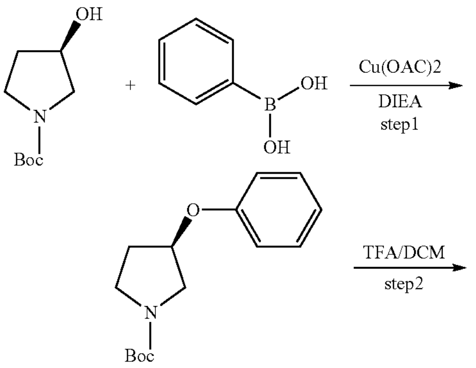

-continued

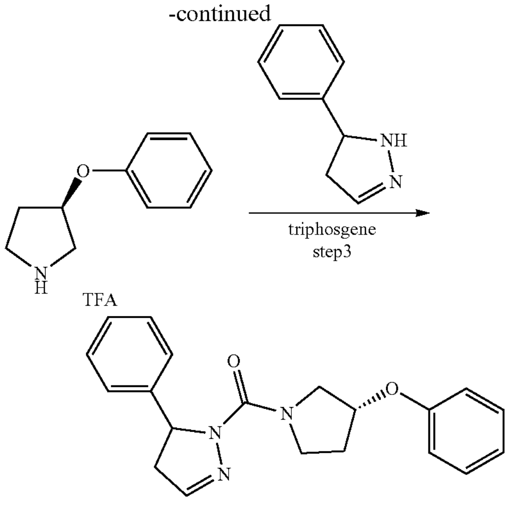

26A or 26B

Step1: Prepare of tert-butyl (R)-3-phenoxypyrrolidine-1-carboxylate

A mixture of tert-butyl (R)-3-hydroxypyrrolidine-1-carboxylate (500 mg, 2.67 mmol), phenylboronic acid (490 mg, 4 mmol), $Cu(OAc)_2$ (1.07 g, 5.34 mmol), pyridine (422 mg, 5.34 mmol) and DIEA (0.9 ml) in DCM (10 mL) was stirred at room temperature for 16 h. The mixture was extracted with DCM, washed with brine, dried ($Na_2SO_4$), and concentrated in vacuo. Purification by silica gel chromatography to give 200 mg of the desired product. LC-MS (m/z) 264.4 ($M+H^+$)

Step2: Prepare of (R)-3-phenoxypyrrolidine trifluoroacetic acid tert-butyl (R)-3-phenoxypyrrolidine-1-carboxylate (200 mg) was dissolved in DCM (3 ml) was added TFA (865 mg). The mixture was stirred at room temperature for 2 h. The mixture was concentrated in vacuo, and extracted with DCM, washed with saturated aqueous $NaHCO_3$, dried with ($Na_2SO_4$), and concentrated to give the crude product (200 mg), which used for next step without further purification. LC-MS (m/z) 164.2 ($M+H^+$)

Step3: Prepare of ((R)-3-phenoxypyrrolidin-1-yl)(5-phenyl-4,5-dihydro-1H-pyrazol-1-yl) methanone (26)

To a cooled solution of 5-phenyl-4,5-dihydro-1H-pyrazole (121 mg, 0.83 mmol) in dry DCM (2 ml) was added TEA (168 mg, 1.66 mmol), followed by added triphosgene (99 mg, 0.33 mmol) in three batches. The mixture was stirred at 0° C. for 30 min and at room temperature for 2 h. (R)-3-phenoxypyrrolidine trifluoroacetic acid (200 mg) and TEA (231 mg, 2.28 mmol) were dissolved in dry DCM (5 mL), and the above reaction mixture was added to the solution and stirred for overnight. The mixture was extracted with DCM, washed with brine, dried ($Na_2SO_4$), and concentrated in vacuo to give a mixture of racemate. Purification by silica gel chromatography to give compound 26A and 26B.

Compound 26A: $^1H$ NMR (400 MHz, $CDCl_3$) δ 7.32-7.25 (m, 5H), 7.24-7.20 (m, 2H), 6.94 (ddd, J=8.4, 2.1, 1.1 Hz, 1H), 6.87-6.85 (m, 1H), 6.84 (dd, J=2.0, 1.0 Hz, 1H), 6.75 (t, J=1.7 Hz, 1H), 5.35 (dd, J=12.0, 9.2 Hz, 1H), 4.88 (t, J=4.3 Hz, 1H), 3.94 (dd, J=12.8, 4.4 Hz, 1H), 3.84 (td, J=11.1, 6.6 Hz, 1H), 3.72 (d, J=12.8 Hz, 1H), 3.68-3.61 (m, 1H), 3.29 (ddd, J=18.4, 12.1, 1.8 Hz, 1H), 2.70 (ddd, J=18.4, 9.2, 1.6 Hz, 1H), 2.19 (ddd, J=13.4, 6.6, 1.7 Hz, 1H), 2.07-1.95 (m, 1H). LC-MS (m/z) 336.4 ($M+H^+$).

Compound 26B: $^1H$ NMR (400 MHz, $CDCl_3$) δ 7.34-7.20 (m, 7H), 6.94 (tt, J=7.5, 1.0 Hz, 1H), 6.89-6.83 (m, 2H), 6.75 (t, J=1.7 Hz, 1H), 5.35 (dd, J=13.6, 5.9 Hz, 1H), 4.89-4.85 (m, 1H), 3.96-3.80 (m, 3H), 3.67-3.60 (m, 1H), 3.28 (ddd, J=18.3, 11.9, 1.7 Hz, 1H), 2.69 (ddd, J=18.3, 7.7, 1.7 Hz, 1H), 2.12 (ddd, J=7.3, 6.3, 3.5 Hz, 2H). LC-MS (m/z) 336.4 ($M+H^+$).

Compound 27: ((S)-3-phenoxypyrrolidin-1-yl)(S-phenyl-4,5-dihydro-1H-pyrazol-1-yl)methanone

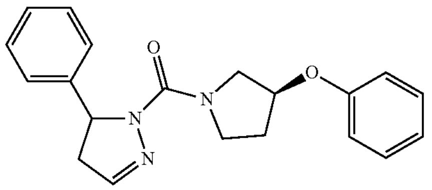 [SMILES: O=C(N1CC[C@H](Oc2ccccc2)C1)N1N=CCC1c1ccccc1]

Compound 27A and 27B were prepared from (S)-3-hydroxypyrrolidine-1-carboxylate (200 mg), TFA, triphosgene and 5-phenyl-4,5-dihydro-1H-pyrazole according to the procedure outlined for compound 26 and purified by silica gel chromatography.

Compound 27A: $^1H$ NMR (400 MHz, $CDCl_3$) δ 7.34-7.20 (m, 7H), 6.94 (t, J=7.4 Hz, 1H), 6.85 (d, J=7.8 Hz, 2H), 6.76 (brs, 1H), 5.37-5.32 (m, 1H), 4.88 (brs, 1H), 3.98-3.78 (m, 3H), 3.74-3.63 (m, 1H), 3.38-3.24 (m, 1H), 2.70 (dd, J=19.8, 9.2 Hz, 1H), 2.25-2.18 (m, 1H), 2.07-1.99 (m, 1H). LC-MS (m/z) 336.4 ($M+H^+$).

Compound 27B: $^1H$ NMR (400 MHz, $CDCl_3$) δ 7.35-7.18 (m, 7H), 6.93 (t, J=7.3 Hz, 1H), 6.85 (d, J=7.9 Hz, 2H), 6.76 (brs, 1H), 5.37-5.31 (m, 1H), 4.95-4.84 (m, 1H), 4.02-3.75 (m, 2H), 3.63 (dd, J=24.1, 13.1 Hz, 1H), 3.40-3.19 (m, 1H), 2.77-2.59 (m, 1H), 2.26-2.20 (m, 1H), 2.18-2.06 (m, 1H), 2.01-1.95 (m, 1H). LC-MS (m/z) 336.4 ($M+H^+$).

Compound 28: ((2R,6S)-4-(5-fluoropyrimidin-2-yl)-2,6-dimethylpiperazin-1-yl)(5-phenyl-4,5-dihydro-1H-pyrazol-1-yl)methanone

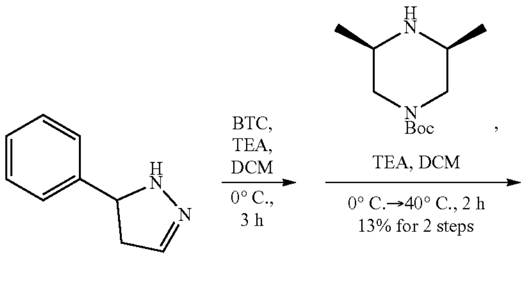

-continued

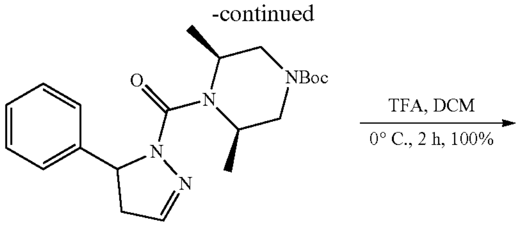

28-1

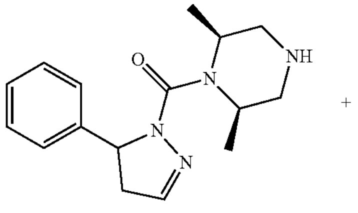

28-2

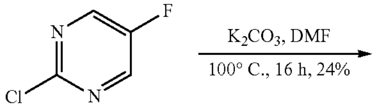

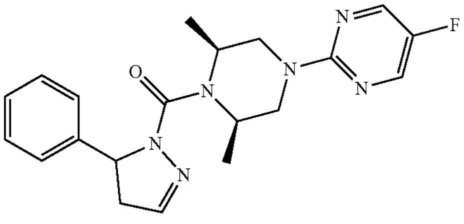

28

Step 1.

To a solution of 5-phenyl-4,5-dihydro-1H-pyrazole (73.5 mg, 0.5 mmol) in DCM was added BTC (148 mg, 0.25 mmol), and TEA (0.28 ml, 1.0 mmol) at 0° C. After 3 hours, a mixture of (3R,5S)-tert-butyl 3,5-dimethylpiperazine-1-carboxylate (107 mg, 0.5 mmol) and TEA (0.28 ml, 1.0 mmol) in DCM was added to the reaction in 0° C. Then the mixture was stirred at 40° C. for 2 hours. UPLC-MS monitored the completion of the reaction. The reaction mixture was poured into water and extracted with EA. The organic layer was separated, and the aqueous layer was repeatedly extracted with EA (2x5 mL). The combined extracts were dried with $Na_2SO_4$ and concentrated. The resulting residue was purified by silica gel chromatography (PE:EA=2:1) to give 24 mg of 28-1 as a yellow solid, yield: 13% (2 steps). LC-MS (ESI) m/z: 331.41 $[M+H]^+$.

Step 2.

28-1 (24 mg, 0.06 mmol) is dissolved in DCM and cooled to 0° C. TFA (0.09 ml, 1.2 mmol) was added dropwise and the mixture was stirred for 2 hours. UPLC-MS monitored the completion of the reaction. The reaction was quench with saturated $NaHCO_3$ and extracted with EA. The organic layer was separated, and the aqueous layer was repeatedly extracted with EA (2x5 mL). The combined extracts were dried with $Na_2SO_4$ and concentrated to give compound 28-2, which was used in the next reaction step without any further purification. For 28-2, LC-MS (ESI) m/z: 287.35, $[M+H]^+$.

Step 3.

To a solution of 28-2 (26 mg, 0.09 mmol) in DMF (5 mL) was added 2-chloro-5-fluoropyrimidine (24 mg, 0.18 mmol) and $K_2CO_3$ (25 mg, 0.18 mmol) at r.t., then the mixture was stirred at 100° C. for 16 hours. UPLC-MS monitored the completion of the reaction. The reaction mixture was poured into water and extracted with EA. The organic layer was separated, and the aqueous layer was repeatedly extracted with EA (2x5 mL). The combined extracts were dried with $Na_2SO_4$ and concentrated. The resulting residue was purified by silica gel chromatography (PE:EA=2:1) to give 6 mg of 28 as a yellow solid, yield: 24%. $^1$H-NMR (400 MHz, $CDCl_3$): δ 8.20 (s, 2H), 7.39-7.20 (m, 5H), 6.83 (s, 1H), 5.37 (dd, J=11.6, 9.6 Hz, 1H), 4.80 (m, 1H), 4.48-4.25 (m, 3H), 3.53-3.03 (m, 3H), 2.80-2.61 (m, 1H), 1.35 (d, J=6.8 Hz, 3H), 1.25 (d, J=6.8 Hz, 3H). LC-MS (ESI) m/z: 383.35, $[M+H]^+$.

Compound 29: (5-(3-fluorophenyl)-4,5-dihydro-1H-pyrazol-1-yl)((2R,6S)-4-(5-fluoropyrimidin-2-yl)-2,6-dimethylpiperazin-1-yl)methanone

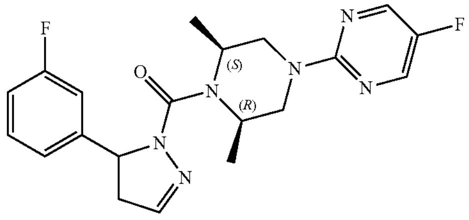

Compound 29 was synthesized according to the method of compound 28 while using ((2R,6S)-2,6-dimethylpiperazin-1-yl)(5-(3-fluorophenyl)-4,5-dihydro-1H-pyrazol-1-yl) methanone and 2-chloro-5-fluoropyrimidine. (5-(3-fluorophenyl)-4,5-dihydro-1H-pyrazol-1-yl)((2R,6S)-4-(5-fluoropyrimidin-2-yl)-2,6-dimethylpiperazin-1-yl) methanone was obtained as white powder (yield 31%). $^1$H NMR (400 MHz, Chloroform-d) δ 8.19 (t, J=0.6 Hz, 2H), 7.29 (m, 1H), 7.09 (dt, J=7.8, 1.2 Hz, 1H), 7.00 (ddd, J=9.8, 2.6, 1.6 Hz, 1H), 6.93 (tdd, J=8.4, 2.8, 1.0 Hz, 1H), 6.83 (t, J=1.8 Hz, 1H), 5.41-5.32 (m, 1H), 4.85-4.74 (m, 1H), 4.47-4.29 (m, 3H), 3.42-3.22 (m, 2H), 3.17 (dd, J=13.0, 4.2 Hz, 1H), 2.67 (ddd, J=18.2, 10.2, 1.6 Hz, 1H), 1.35 (d, J=6.8 Hz, 3H), 1.26 (d, J=6.9 Hz, 3H). LC-MS (m/z) 401.45 $[M+H]^+$.

Compound 30: (5-(3,5-difluorophenyl)-4,5-dihydro-1H-pyrazol-1-yl)((2R,6S)-4-(5-fluoropyrimidin-2-yl)-2,6-dimethylpiperazin-1-yl)methanone

30

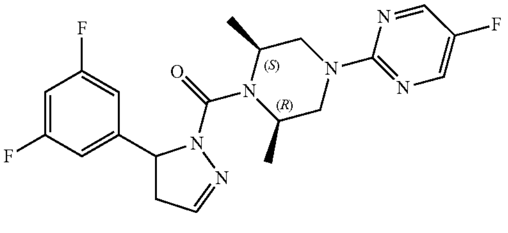

Compound 30 was synthesized according to the method of compound 28 while using (5-(3,5-difluorophenyl)-4,5-dihydro-1H-pyrazol-1-yl)((2R,6S)-2,6-dimethylpiperazin-1-yl)methanone and and 2-chloro-5-fluoropyrimidine. (5-(3,5-difluorophenyl)-4,5-dihydro-1H-pyrazol-1-yl)((2R,6S)-4-(5-fluoropyrimidin-2-yl)-2,6-dimethylpiperazin-1-yl)

methanone was obtained as white powder (yield 23%). $^{1}H$ NMR (400 MHz, Chloroform-d) δ 8.26 (s, 2H), 6.89-6.77 (m, 3H), 6.74-6.65 (m, 1H), 5.34 (t, J=10.9 Hz, 1H), 4.83 (s, 1H), 4.50 (d, J=13.1 Hz, 1H), 4.43 (d, J=12.0 Hz, 2H), 3.43 (dd, J=13.2, 4.5 Hz, 1H), 3.35-3.19 (m, 2H), 2.66 (dd, J=18.2, 10.2 Hz, 1H), 1.37 (d, J=6.8 Hz, 3H), 1.29 (d, J=6.8 Hz, 3H). LC-MS (m/z) 418.49 $[M+H]^{+}$.

Compound 31: ((R)-3-(2-fluorophenoxy)pyrrolidin-1-yl)(5-phenyl-4,5-dihydro-1H-pyrazol-1-yl)methanone

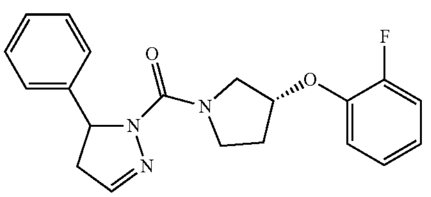 [SMILES: O=C(N1CC[C@@H](Oc2ccccc2F)C1)N1N=CCC1c1ccccc1]

(R)-3-(2-fluorophenoxy)pyrrolidine (304 mg) and (1H-imidazol-1-yl)(5-phenyl-4,5-dihydro-1H-pyrazol-1-yl) methanone (403 mg) and TEA (506 mg) were dissolved in THF (10 ml) and stirred at room temperature for 16 h. The mixture was extracted with DCM, washed with brine, dried ($Na_2SO_4$), and concentrated in vacuo. Purification by silica gel chromatography to give 31 (186 mg, 31.4%). $^{1}H$ NMR (400 MHz, $CDCl_3$) δ 7.35-7.27 (m, 3H), 7.26-7.19 (m, 2H), 7.11-7.00 (m, 2H), 6.98-6.89 (m, 2H), 6.77 (t, J=1.6 Hz, 1H), 5.40-5.32 (m, 1H), 4.94-4.87 (m, 1H), 4.05-3.66 (m, 4H), 3.38-3.26 (m, 1H), 2.78-2.66 (m, 1H), 2.26-2.05 (m, 2H). LC-MS (m/z) 354.4 ($M+H^{+}$)

Compound 32: ((R)-3-(3-fluorophenoxy)pyrrolidin-1-yl)(5-phenyl-4,5-dihydro-1H-pyrazol-1-yl)methanone

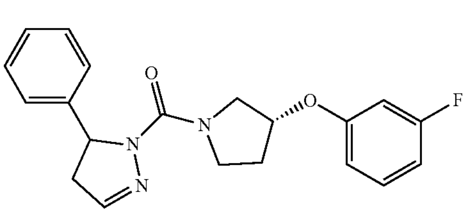 [SMILES: O=C(N1CC[C@@H](Oc2cccc(F)c2)C1)N1N=CCC1c1ccccc1]

(R)-3-(3-fluorophenoxy)pyrrolidine was prepared by procedure outlined for compound 26 (130 mg) and (1H-imidazol-1-yl)(5-phenyl-4,5-dihydro-1H-pyrazol-1-yl)methanone (172 mg) and TEA (513 mg) were dissolved in THF (5 ml) and stirred at room temperature for 16 h. The mixture was extracted with DCM, washed with brine, dried ($Na_2SO_4$), and concentrated in vacuo. Purification by silica gel chromatography to give 32 (95.8 mg, 38%). $^{1}H$ NMR (400 MHz, $CDCl_3$) δ 7.51-7.25 (m, 4H), 7.24-7.11 (m, 3H), 6.77-6.75 (m, 1H), 6.70-6.50 m, 2H), 5.38-5.29 (m, 1H), 4.84 (m, 1H), 3.99-3.78 (m, 2H), 3.75-3.50 (m, 2H), 3.36-3.21 (m, 1H), 2.70 (dd, J=18.4, 7.8 Hz, 1H), 2.21-2.08 (m, 1H), 2.08-1.96 (m, 1H). LC-MS (m/z) 354.4 ($M+H^{+}$)

Compound 33: ((R)-3-(4-fluorophenoxy)pyrrolidin-1-yl)(5-phenyl-4,5-dihydro-1H-pyrazol-1-yl)methanone

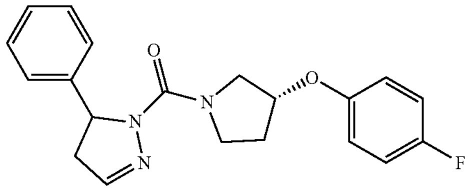 [SMILES: O=C(N1CC[C@@H](Oc2ccc(F)cc2)C1)N1N=CCC1c1ccccc1]

The titled compound 33 was prepared in 12% yield from (R)-3-(4-fluorophenoxy) pyrrolidine and (1H-imidazol-1-yl) (5-phenyl-4,5-dihydro-1H-pyrazol-1-yl) methanone according to the procedure outlined for compound 32. $^{1}H$ NMR (400 MHz, $CDCl_3$) δ 7.33-7.25 (m, 3H), 7.24-7.19 (m, 2H), 6.98-6.91 (m, 2H), 6.82-6.77 (m, 2H), 6.75 (t, J=1.6 Hz, 1H), 5.33 (ddd, J=12.0, 8.4, 4.0 Hz, 1H), 4.84-4.75 (m, 1H), 3.98-3.75 (m, 3H), 3.74-3.56 (m, 2H), 3.35-3.23 (m, 1H), 2.75-2.65 (m, 1H), 2.21-2.12 (m, 1H). LC-MS (m/z) 354.4 ($M+H^{+}$)

Compound 34: ((R)-3-((5-fluoropyrimidin-2-yl)oxy)pyrrolidin-1-yl)(5-phenyl-4,5-dihydro-1H-pyrazol-1-yl)methanone

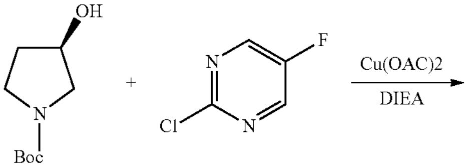

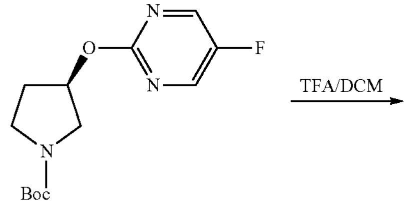

34-1

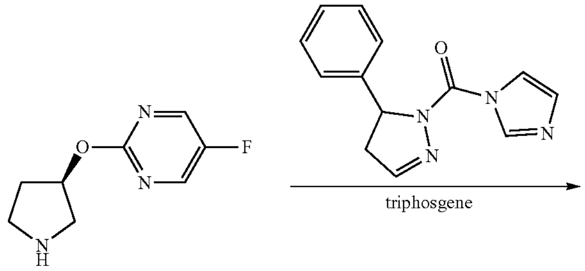

34-2

-continued

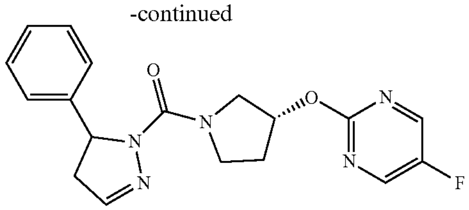

34

Step1: To a cold solution of NaH (128 mg) in 5 mL of DMF (5 mL) was added a solution of tert-butyl (R)-3-hydroxypyrrolidine-1-carboxylate (300 mg) in DMF (2 mL). The mixture was stirred at room temperature for 1 h, and than cooled to 0° C., 2-chloro-5-fluoropyrimidine (212 mg) was added. The mixture was stirred at room temperature for 16 h. The mixture was extracted with DCM, washed with brine, dried ($Na_2SO_4$), and concentrated in vacuo to give 34-1 (100 mg). LC-MS (m/z) 284.4 ($M+H^+$)

Step2: Compound 34-1 (100 mg) was dissolved in DCM (2 ml) was added TFA (401 mg). The mixture was stirred at room temperature for 2 h. The mixture was concentrated in vacuo, and extracted with DCM, washed with saturated aqueous $NaHCO_3$, dried with ($Na_2SO_4$), and concentrated to give the residue (34-2 (65 mg), which used for next step without purification.

Step3: (R)-5-fluoro-2-(pyrrolidin-3-yloxy)pyrimidine (64 mg) and (1H-imidazol-1-yl)(5-phenyl-4,5-dihydro-1H-pyrazol-1-yl)methanone (84 mg) and TEA (106 mg) were dissolved in THF (10 ml) and stirred at room temperature for 16 h. The mixture was extracted with DCM, washed with brine, dried ($Na_2SO_4$), and concentrated in vacuo. Purification by silica gel chromatography to give 34 (118 mg, 94.4%). $^1$H NMR (400 MHz, $CDCl_3$) δ 8.35 (d, J=2.9 Hz, 2H), 7.31-7.26 (m, 3H), 7.23-7.19 (m, 2H), 6.75-6.73 (m, 1H), 5.37-5.29 (m, 1H), 3.93-3.88 (m, 3H), 3.74-3.66 (m, 2H), 3.33-3.28 (m, 1H), 2.74-2.65 (m, 1H). 2.21-2.12 (m, 1H). LC-MS (m/z) 356.4 ($M+H^+$)

Compound 35: ((R)-3-(3-chlorophenoxy)pyrrolidin-1-yl)(5-phenyl-4,5-dihydro-1H-pyrazol-1-yl)methanone

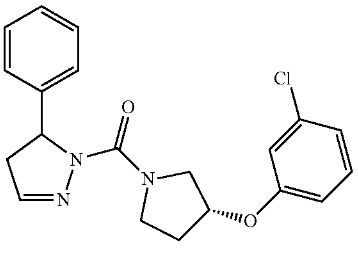 [SMILES: O=C(N1CC[C@@H](Oc2cccc(Cl)c2)C1)N1N=CCC1c1ccccc1]

The titled compound 35 was prepared in 19% yield from (R)-3-(3-chlorophenoxy) pyrrolidine and (1H-imidazol-1-yl)(5-phenyl-4,5-dihydro-1H-pyrazol-1-yl) methanone according to the procedure outlined for compound 32. $^1$H NMR (400 MHz, $CDCl_3$) δ 7.40-7.24 (m, 7H), 7.23-7.14 (m, 1H), 6.95-6.82 (m, 1H), 6.77-6.71 (m, 1H), 5.38-5.30 (m, 1H), 4.88-4.82 (m, 1H), 3.96-3.78 (m, 2H), 3.75-3.54 (m, 2H), 3.35-3.23 (m, 1H), 2.70 (dd, J=18.8, 8.4 Hz, 1H), 2.18-2.09 (m, 1H), 2.07-1.94 (m, 1H). LC-MS (m/z) 370.8 ($M+H^+$).

Compound 36: (3-benzylideneazetidin-1-yl)(5-phenyl-4,5-dihydro-1H-pyrazol-1-yl)methanone

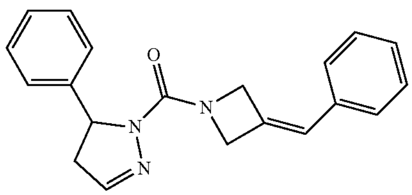 [SMILES: O=C(N1CC(=Cc2ccccc2)C1)N1N=CCC1c1ccccc1]

The titled compound 36 was prepared in 23% yield from 5-phenyl-4,5-dihydro-1H-pyrazole, 3-benzylideneazetidine and triphosgene according to the procedure outlined for compound 9. $^1$H NMR (400 MHz, $CDCl_3$) δ 7.34-7.28 (m, 4H), 7.26-7.17 (m, 7H), 7.11 (d, J=7.2 Hz, 2H), 6.81 (t, J=1.7 Hz, 1H), 6.25-6.21 (m, 1H), 5.34 (dd, J=12.1, 6.3 Hz, 1H), 5.04 (dd, J=34.9, 14.4 Hz, 2H), 4.82 (dd, J=31.0, 14.9 Hz, 2H), 3.35 (ddd, J=18.5, 12.2, 1.7 Hz, 1H), 2.75 (ddd, J=18.5, 6.3, 1.7 Hz, 1H). LC-MS (m/z) 318.4 ($M+H^+$)

Compound 37: (3-(2-methylbenzyl)azetidin-1-yl)(5-phenyl-4,5-dihydro-1H-pyrazol-1-yl) methanone

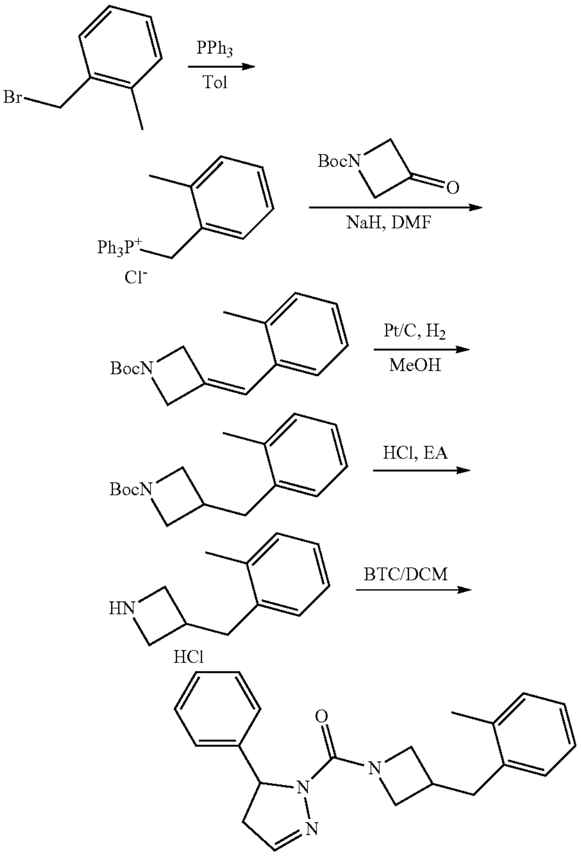

Step 1. Preparation of (2-methylbenzyl)triphenylphosphonium bromide

A mixture of 1-(bromomethyl)-2-methylbenzene (1.5 g, 8.15 mmol), PPh3 (2.14 g, 8.15 mmol) and Tol (20 mL) was stirred at 110° C. for 18 h. The mixture was filtrated and the solid was washed with $Et_2O$ for three times and dried to give the desired product as a white solid (1.8 g, 49.6%). LC-MS (m/z) 368.5 ($M+H^+$)

Step 2. Preparation of tert-butyl 3-(2-methylbenzylidene)azetidine-1-carboxylate To a suspension of (2-methylbenzyl)triphenylphosphonium bromide (236 mg, 0.528 mmol) in DMF (4 mL) was added NaH (13 mg) at 0° C., then the mixture was stirred at r.t. for 15 min before tert-butyl 3-oxoazetidine-1-carboxylate (86 mg, 0.503 mmol) was, added, then the mixture was stirred at room temperature for 2 days. Water was added and a large amount of white solid precipitated, the solid was collected by filtration, and dried to give the crude product (470 mg), which was used for the next step without further purification. LC-MS (m/z) 260.4 ($M+H^+$).

The following intermediates used for the preparation of titled example compounds were synthesized using the above methods analogous to give different substituted tert-butyl 3-benzylideneazetidine-1-carboxylate, and followed by removed Boc using TFA in DCM to give the desired intermediates.

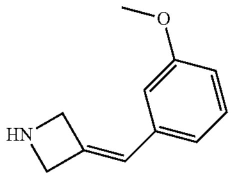
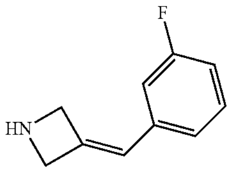
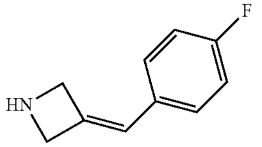
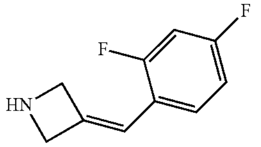
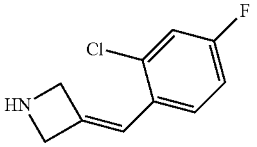
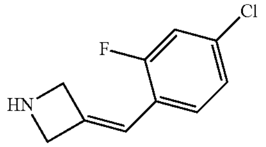
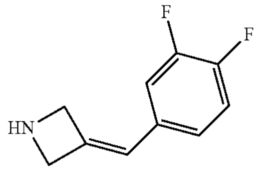
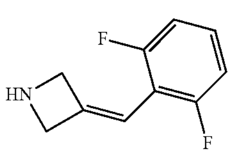
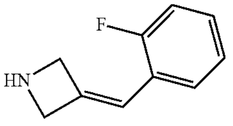

Step 3. Preparation of tert-butyl 3-(2-methylbenzyl)azetidine-1-carboxylate

To a solution of tert-butyl 3-(2-methylbenzylidene)azetidine-1-carboxylate (270 mg) in MeOH (5 mL) was added Pt/C (30 mg), the mixture was stirred at r.t. for 18 h under $H_2$ atmosphere. The mixture was filtrated and the filtrate was concentrated to give the desired product as a white solid (270 mg, 99.6%). LC-MS (m/z) 262.4 ($M+H^+$)

Step 4. Preparation of 3-(2-methylbenzyl)azetidine hydrochloride

A mixture of tert-butyl 3-(2-methylbenzyl)azetidine-1-carboxylate (270 mg) and HCl/EA (4 mL) was stirred at r.t. for 4 h. The mixture was concentrated to give the desired product, which was used for next step without further purification.

The following intermediates used for the preparation of titled example compounds were synthesized using the methods analogous to 3-(2-methylbenzyl)azetidine hydrochloride described above. TFA/DCM may be instead of HC/EA or basified by saturated $NaHCO_3$ to give free base.

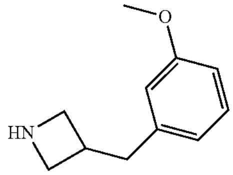
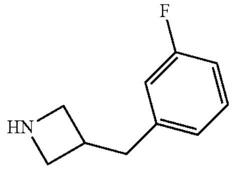
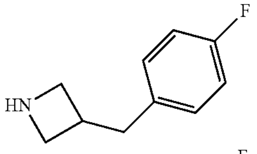
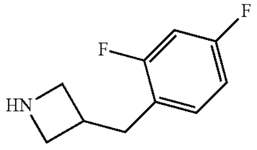
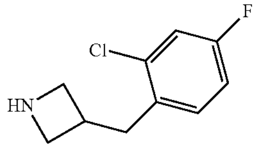
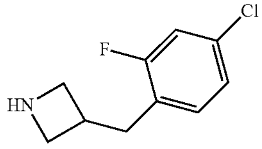
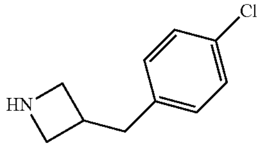
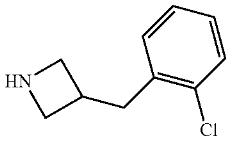
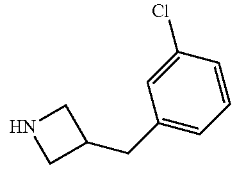
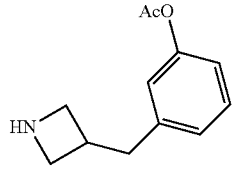
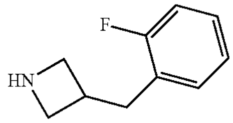

Step 5. Preparation of (3-(2-methylbenzyl)azetidin-1-yl)(5-phenyl-4,5-dihydro-1H-pyrazol-1-yl)methanone To a cooled solution of triphosgene (60 mg) in dry DCM (5 ml) was added dropwise a mixture solution of 5-phenyl-4,5-dihydro-1H-pyrazole (148 mg) and TEA (0.14 ml). The mixture was stirred at 0° C. for 3 h. 3-(2-methylbenzyl)azetidine hydrochloride (100 mg) and TEA (0.14 ml) were dissolved in dry DCM (2 ml), and the above reaction mixture was added to the solution and stirred for overnight. The mixture was extracted with DCM, washed with brine, dried with (Na2SO4), and concentrated in vacuo. Purification by silica gel chromatography (EA/PE=1/3) to give compound 37 (80 mg, 47.3%) as a yellow solid. $^1$H NMR (400 MHz, $CDCl_3$) δ 7.35-7.29 (m, 2H), 7.25-7.21 (m, 3H), 7.17-7.10 (m, 3H), 7.07-7.02 (m, 1H), 6.74 (t, 1H, J=1.6 Hz), 5.31 (dd, 1H, J=12.0, 1.6 Hz), 4.34-4.17 (m, 2H), 3.93 (dd, 1H, J=9.6, 4.4 Hz), 3.83 (dd, 1H, J=9.2, 4.4 Hz), 3.32 (ddd, 1H, J=18.4, 12.4, 2.0 Hz), 2.92-2.89 (m, 3H), 2.72 (ddd, 1H, J=18.4, 6.4, 1.6 Hz), 2.30 (s, 3H). LC-MS (m/z): 334.55 $[M+H]^+$.

Compound 38: (3-(2-methylbenzylidene)azetidin-1-yl)(5-phenyl-4,5-dihydro-1H-pyrazol-1-yl)methanone

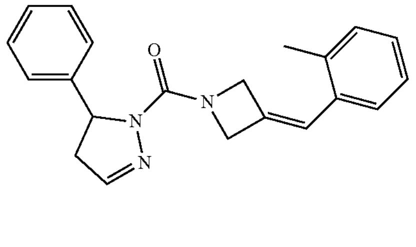 [SMILES: Cc1ccccc1C=C1CN(C(=O)N2N=CCC2c2ccccc2)C1]

The titled compound 38 was prepared in 51.6% yield from 3-benzylideneazetidine hydrochloride, 5-phenyl-4,5-dihydro-1H-pyrazole and triphosgene according to the procedure outlined for compound 37. $^1$H NMR (400 MHz, $CDCl_3$) δ 7.36-7.30 (m, 2H), 7.25-7.21 (m, 3H), 7.19-7.12 (m, 3H), 7.08-7.06 (m, 1H), 6.81 (t, 1H, J=1.6 Hz), 6.45-6.42 (m, 1H), 5.36 (dd, 1H, J=12.0, 6.4 Hz), 5.07-4.93 (m, 2H), 4.90-4.77 (m, 2H), 3.37 (ddd, 1H, J=18.4, 12.0, 1.6 Hz), 2.76 (ddd, 1H, J=18.4, 6.4, 2.0 Hz), 2.32 (s, 3H). LC-MS (m/z): 332.36 $[M+H]^+$.

Compound 39: (3-(3-methoxybenzyl)azetidin-1-yl)(5-phenyl-4,5-dihydro-1H-pyrazol-1-yl) methanone

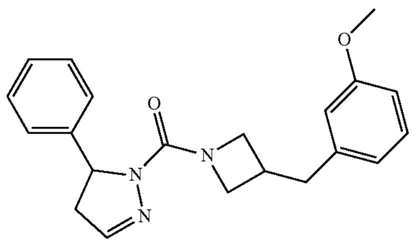 [SMILES: COc1cccc(CC2CN(C(=O)N3N=CCC3c3ccccc3)C2)c1]

The titled compound 39 was prepared in 36.6% yield from 3-(4-methoxybenzyl)azetidine hydrochloride, 5-phenyl-4,5-dihydro-1H-pyrazole and triphosgene according to the procedure outlined for compound 37. $^1$H-NMR (400 MHz, $CDCl_3$) δ 7.35-7.29 (m, 2H), 7.26-7.17 (m, 4H), 6.79-6.72 (m, 3H), 6.69 (t, J=2.4 Hz, 1H), 5.31 (dd, J=12.0, 6.4 Hz, 1H), 4.22 (dt, J=28.4, 8.4 Hz, 2H), 3.87 (ddd, J=32.8, 8.0, 4.8 Hz, 2H), 3.79 (s, 3H), 3.32 (ddd, J=18.4, 12.4, 1.6 Hz, 1H), 2.93-2.80 (m, 3H), 2.72 (ddd, J=18.4, 6.4, 1.6 Hz, 1H). LC-MS (m/z): 350.34$[M+H]^+$.

Compound 40: (3-(2-fluorobenzyl)azetidin-1-yl)(5-phenyl-4,5-dihydro-1H-pyrazol-1-yl)methanone

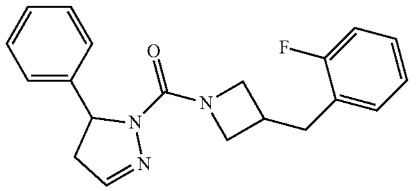 [SMILES: O=C(N1CC(Cc2ccccc2F)C1)N1N=CCC1c1ccccc1]

The titled compound 40 was prepared in 22.4% yield from 3-(2-fluorobenzyl) azetidine hydrochloride, 5-phenyl-4,5-dihydro-1H-pyrazole and triphosgene according to the procedure outlined for compound 37. $^1$H-NMR (400 MHz, $CDCl_3$) δ 7.37-7.29 (m, 2H), 7.25-7.12 (m, 5H), 7.09-6.98 (m, 2H), 6.77 (t, J=1.5 Hz, 1H), 5.32 (dd, J=12.0, 6.0 Hz, 1H), 4.26 (t, J=8.0 Hz, 1H), 4.20 (t, J=8.8 Hz, 1H), 3.93 (dd, J=8.4, 4.4 Hz, 1H), 3.86 (dd, J=9.2, 5.2 Hz, 1H), 3.33 (ddd, J=18.4, 12.0, 1.6 Hz, 1H), 2.96-2.84 (m, 3H), 2.73 (ddd, J=18.4, 6.4, 1.6 Hz, 1H). LC-MS (m/z): 338.36$[M+H]^+$.

Compound 41: (3-(3-fluorobenzyl)azetidin-1-yl)(5-phenyl-4,5-dihydro-1H-pyrazol-1-yl)methanone

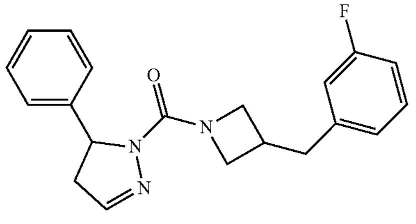 [SMILES: O=C(N1CC(Cc2cccc(F)c2)C1)N1N=CCC1c1ccccc1]

The titled compound 41 was prepared in 32.6% yield from 3-(3-fluorobenzyl) azetidine hydrochloride, 5-phenyl-4,5-dihydro-1H-pyrazole and triphosgene according to the procedure outlined for compound 37. $^1$H-NMR (400 MHz, $CDCl_3$) δ 7.35-7.29 (m, 2H), 7.26-7.19 (m, 4H), 6.95-6.80 (m, 3H), 6.75 (t, J=1.6 Hz, 1H), 5.31 (dd, J=12.0, 6.0 Hz, 1H), 4.22 (dt, J=28.2, 8.4 Hz, 2H), 3.86 (ddd, J=32.4, 8.8, 5.2 Hz, 2H), 3.32 (ddd, J=18.4, 12.4, 1.6 Hz, 1H), 2.92 (d, J=7.6 Hz, 2H), 2.90-2.80 (m, 1H), 2.72 (ddd, J=18.4, 6.4, 1.6 Hz, 1H). LC-MS (m/z): 338.34$[M+H]^+$.

Compound 42: (3-(4-fluorobenzyl)azetidin-1-yl)(5-phenyl-4,5-dihydro-1H-pyrazol-1-yl)methanone

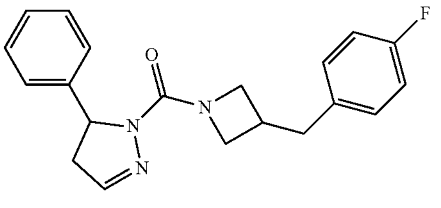 [SMILES: O=C(N1CC(Cc2ccc(F)cc2)C1)N1N=CCC1c1ccccc1]

The titled compound 42 was prepared in 22.4% yield from 3-(4-fluorobenzyl) azetidine hydrochloride, 5-phenyl-4,5-dihydro-1H-pyrazole and triphosgene according to the procedure outlined for compound 37. $^{1}$H-NMR (400 MHz, $CDCl_3$) δ 7.32 (t, J=7.6 Hz, 2H), 7.26-7.18 (m, 3H), 7.10 (dd, J=8.4, 5.6 Hz, 2H), 6.97 (t, J=8.4 Hz, 2H), 6.76-6.73 (m, 1H), 5.31 (dd, J=12.0, 6.4 Hz, 1H), 4.21 (dt, J=28.2, 8.4 Hz, 2H), 3.85 (ddd, J=32.4, 9.0, 5.2 Hz, 2H), 3.32 (dd, J=18.4, 12.0 Hz, 1H), 2.89 (d, J=7.6 Hz, 2H), 2.85-2.77 (m, 1H), 2.72 (dd, J=18.4, 6.4 Hz, 1H). LC-MS (m/z): 338.17[M+H]$^{+}$.

Compound 43: (3-(3-methoxybenzylidene)azetidin-1-yl)(5-phenyl-4,5-dihydro-1H-pyrazol-1-yl)methanone

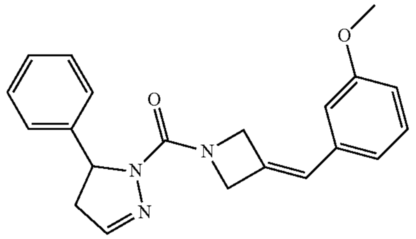 [SMILES: COc1cccc(C=C2CN(C(=O)N3N=CCC3c3ccccc3)C2)c1]

The titled compound 42 was prepared 3-(3-methoxybenzylidene)azetidine hydrochloride, 5-phenyl-4,5-dihydro-1H-pyrazole and triphosgene to give 43 in 36.6% yield, according to the procedure outlined for compound 37. 1H-NMR (400 MHz, $CDCl_3$) δ 7.36-7.30 (m, 2H), 7.27-7.22 (m, 4H), 6.82 (t, J=1.6 Hz, 1H), 6.77 (dd, J=8.0, 2.4 Hz, 1H), 6.73 (d, J=7.6 Hz, 1H), 6.67-6.64 (m, 1H), 6.22 (t, J=2.4 Hz, 1H), 5.36 (dd, J=12.4, 6.4 Hz, 1H), 5.05 (dd, J=37.6, 14.4 Hz, 2H), 4.83 (dd, J=32.4, 15.0 Hz, 2H), 3.80 (s, 3H), 3.37 (ddd, J=18.4, 12.0, 1.6 Hz, 1H), 2.77 (ddd, J=18.4, 6.4, 1.6 Hz, 1H). LC-MS (m/z): 348.32[M+H]$^{+}$.

Compound 44: (3-(3-hydroxybenzyl)azetidin-1-yl)(5-phenyl-4,5-dihydro-1H-pyrazol-1-yl)methanone

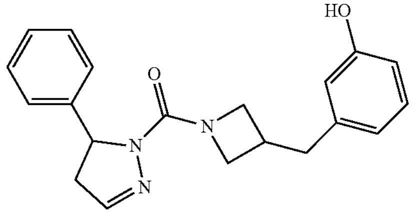 [SMILES: O=C(N1CC(Cc2cccc(O)c2)C1)N1N=CCC1c1ccccc1]

3-((1-(5-phenyl-4,5-dihydro-1H-pyrazole-1-carbonyl)azetidin-3-yl)methyl)phenyl acetate prepared by the procedure outlined for compound 37 (10 mg) was dissolved in MeOH (1 mL), and 1N LiOH (0.041 mmol) was added. The mixture was stirred at room temperature for 2 h. The mixture was adjusted to PH 2-3 with con. HCl, and extracted with EA, washed with brine, dried with ($Na_2SO_4$), and concentrated in vacuo. Purification by silica gel chromatography (EA/PE=1/1) to give compound 37 (7 mg, 77.8%). $^{1}$H-NMR (400 MHz, $CDCl_3$) δ 7.35-7.27 (m, 2H), 7.26-7.19 (m, 3H), 7.10 (t, J=7.8 Hz, 1H), 6.77-6.74 (m, 1H), 6.72-6.55 (m, 3H), 5.31 (dd, J=12.4, 6.4 Hz, 1H), 4.28-4.15 (m, 2H), 3.95-3.78 (m, 2H), 3.32 (ddd, J=18.8, 12.4, 1.6 Hz, 1H), 2.82 (s, 3H), 2.71 (ddd, J=18.4, 6.4, 1.6 Hz, 1H). LC-MS (m/z): 336.39[M+H]$^{+}$.

Compound 45: (3-(3-fluorobenzylidene)azetidin-1-yl)(5-phenyl-4,5-dihydro-1H-pyrazol-1-yl)methanone

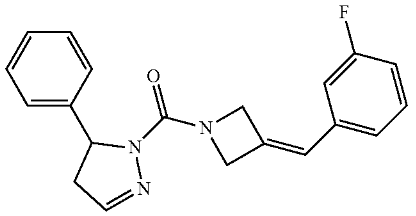 [SMILES: O=C(N1CC(=Cc2cccc(F)c2)C1)N1N=CCC1c1ccccc1]

The titled compound 45 was prepared in 36.3% yield form 3-(3-fluorobenzylidene) azetidine hydrochloride, 5-phenyl-4,5-dihydro-1H-pyrazole and triphosgene according to the procedure outlined for compound 37. $^{1}$H-NMR (400 MHz, $CDCl_3$) δ 7.36-7.31 (m, 2H), 7.28 (m, 2H), 7.26-7.23 (m, 2H), 6.95-6.87 (m, 2H), 6.86-6.76 (m, 2H), 6.22 (t, J=7.8 Hz, 1H), 5.36 (dd, J=12.0, 6.4 Hz, 1H), 5.14-4.96 (m, 2H), 4.90-4.74 (m, 2H), 3.38 (ddd, J=18.4, 12.0, 1.6 Hz, 1H), 2.77 (ddd, J=18.4, 6.4, 16 Hz, 1H). LC-MS (m/z): 336.38[M+H]$^{+}$.

Compound 46: (3-(4-fluorobenzylidene)azetidin-1-yl)(5-phenyl-4,5-dihydro-1H-pyrazol-1-yl)methanone

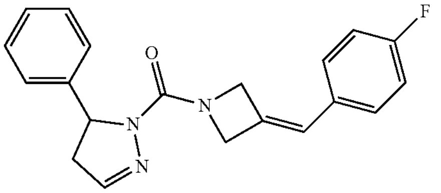 [SMILES: O=C(N1CC(=Cc2ccc(F)cc2)C1)N1N=CCC1c1ccccc1]

The titled compound 46 was prepared in 36.6% yield from 3-(4-fluorobenzylidene)azetidine hydrochloride, 5-phenyl-4,5-dihydro-1H-pyrazole and triphosgene according to the procedure outlined for compound 37. $^{1}$H-NMR (400 MHz, $CDCl_3$) δ 7.36-7.30 (m, 2H), 7.27-7.22 (m, 3H), 7.11-7.06 (m, 2H), 7.05-6.99 (m, 2H), 6.82 (t, J=1.6 Hz, 1H), 6.21 (t, J=2.4 Hz, 1H), 5.36 (dd, J=12.0, 6.4 Hz, 1H), 5.02 (dd, J=35.4, 14.6 Hz, 2H), 4.82 (dd, J=32.2, 14.4 Hz, 2H), 3.37 (ddd, J=18.4, 12.0, 1.6 Hz, 1H), 2.77 (ddd, J=18.4 6.4, 1.6 Hz, 1H). LC-MS (m/z): 336.29[M+H]$^{+}$.

Compound 47: (3-(2-chlorobenzyl)azetidin-1-yl)(5-phenyl-4,5-dihydro-1H-pyrazol-1-yl)methanone

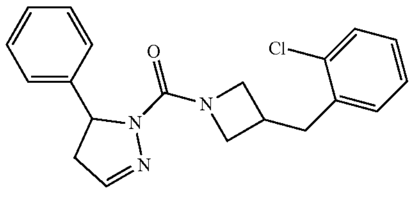 [SMILES: O=C(N1CC(Cc2ccccc2Cl)C1)N1N=CCC1c1ccccc1]

The titled compound 47 was prepared in 22.4% yield from 3-(2-chlorobenzyl) azetidine, 5-phenyl-4,5-dihydro-1H-pyrazole and triphosgene according to the procedure outlined for compound 37. $^1H$ NMR (400 MHz, $CDCl_3$) δ 7.36-7.27 (m, 3H), 7.26-7.18 (m, 3H), 7.18-6.94 (m, 3H), 6.74-6.71 (m, 1H), 5.29 (dd, J=12.2, 6.5 Hz, 1H), 4.20 (dt, J=25.9, 8.5 Hz, 2H), 3.87 (ddd, J=32.7, 8.9, 5.3 Hz, 2H), 3.31 (dd, J=18.5, 12.2 Hz, 1H), 3.14-2.82 (m, 3H), 2.70 (dd, J=18.5, 6.4 Hz, 1H).

LC-MS (m/z) 354.9 ($M+H^+$).

Compound 48: (3-(3-chlorobenzyl)azetidin-1-yl)(5-phenyl-4,5-dihydro-1H-pyrazol-1-yl)methanone

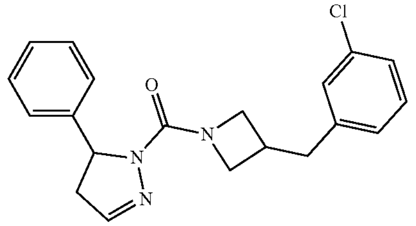

The titled compound 48 was prepared in 28.2% yield from 3-(3-chlorobenzyl) azetidine and (1H-imidazol-1-yl)(5-phenyl-4,5-dihydro-1H-pyrazol-1-yl)methanone according to the procedure outlined for compound 34. LC-MS (m/z) 354.9 ($M+H^+$). $^1H$ NMR (400 MHz, $CDCl_3$) δ 7.34-7.28 (m, 1H), 7.24-7.11 (m, 7H), 7.04-6.96 (m, 1H), 6.74 (s, 1H), 5.29 (dd, J=12.0, 6.4 Hz, 1H), 4.20 (dt, J=29.6, 8.0 Hz, 2H), 3.80 (ddd, J=31.8, 26.4, 5.2 Hz, 2H), 3.37-3.26 (m, 1H), 3.00-2.76 (m, 3H), 2.75-2.66 (m, 1H). LC-MS (m/z) 354.9 ($M+H^+$).

Compound 49: (3-(4-chlorobenzyl)azetidin-1-yl)(5-phenyl-4,5-dihydro-1H-pyrazol-1-yl)methanone

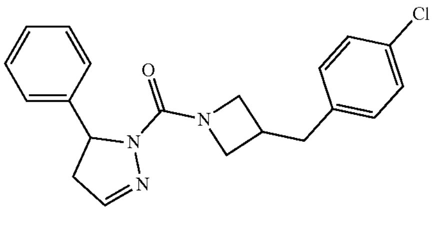 [SMILES: O=C(N1CC(Cc2ccc(Cl)cc2)C1)N1N=CCC1c1ccccc1]

The titled compound 49 was prepared in 11% yield from 3-(4-chlorobenzyl) azetidine, (1H-imidazol-1-yl)(5-phenyl-4,5-dihydro-1H-pyrazol-1-yl)methanone according to the procedure outlined for compound 34. LC-MS (m/z) 354.9 ($M+H^+$). $^1H$ NMR (400 MHz, $CDCl_3$) δ 7.34-7.28 (m, 1H), 7.24-7.11 (m, 7H), 7.04-6.96 (m, 1H), 6.74 (s, 1H), 5.29 (dd, J=12.0, 6.4 Hz, 1H), 4.20 (dt, J=29.6, 8.0 Hz, 2H), 3.80 (ddd, J=31.8, 26.4, 5.2 Hz, 2H), 3.37-3.26 (m, 1H), 3.00-2.76 (m, 3H), 2.75-2.66 (m, 1H). LC-MS (m/z) 338.4 ($M+H^+$).

Compound 50: (3-(2,4-difluorobenzyl)azetidin-1-yl)(5-phenyl-4,5-dihydro-1H-pyrazol-1-yl)methanone

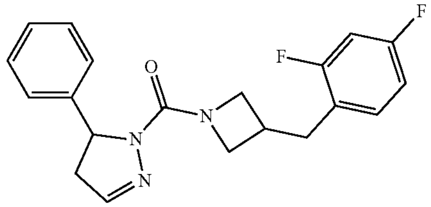 [SMILES: O=C(N1CC(Cc2ccc(F)cc2F)C1)N1N=CCC1c1ccccc1]

The titled compound 50 was prepared in 24.7% yield from 1-(bromomethyl)-2,4-difluorobenzene, $PPh_3$, NaH, 5-phenyl-4,5-dihydro-1H-pyrazole and triphosgene according to the procedure outlined for compound 37. $^1H$-NMR (400 MHz, $CDCl_3$) δ 7.35-7.29 (m, 2H), 7.25-7.19 (m, 3H), 7.14-7.06 (m, 1H), 6.84-6.77 (m, 2H), 6.76 (t, J=1.7 Hz, 1H), 5.31 (dd, J=12.0, 6.4 Hz, 1H), 4.24 (t J=8.4 Hz, 1H), 4.18 (t J=8.4 Hz, 1H), 389 (dd, J=9.2, 5.2 Hz, 1H), 381 (dd, J=9.2, 5.2 Hz, 1H), 3.33 (ddd, J=18.4, 12.0, 1.6 Hz, 1H), 2.93-2.79 (m, 3H), 2.72 (ddd, J=18.4, 6.4, 1.6 Hz, 1H). LC-MS (m/z): 356.56$[M+H]^+$.

Compound 51: (3-(4-chlor-2-fluorobenzyl)azetidin-1-yl)(5-phenyl-4,5-dihydro-1H-pyrazol-1-yl)methanone

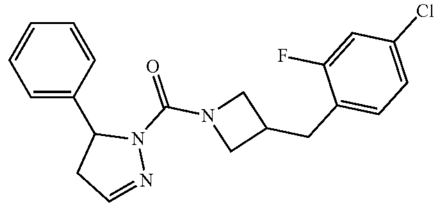 [SMILES: O=C(N1CC(Cc2ccc(Cl)cc2F)C1)N1N=CCC1c1ccccc1]

The titled compound 51 was prepared in 24.2% yield from 3-(4-chloro-2-fluorobenzyl)azetidine hydrochloride, 5-phenyl-4,5-dihydro-1H-pyrazole and triphosgene according to the procedure outlined for compound 37. $^1H$ NMR (400 MHz, $CDCl_3$) δ 7.35-7.30 (m, 2H), 7.24-7.21 (m, 3H), 7.11-7.02 (m, 3H), 6.75 (t, J=2.0 Hz, 1H), 5.30 (dd, J=12.0, 6.4 Hz, 1H), 4.24 (t, J=8.4 Hz, 1H), 4.17 (t, J=8.4 Hz, 1H), 3.89 (dd, J=9.2, 5.2 Hz, 1H), 3.80 (dd, J=9.2, 5.2 Hz, 1H), 3.32 (ddd, J=18.4, 12.0, 1.6 Hz, 1H), 2.92-2.89 (m, 2H), 2.88-2.80 (m, 1H), 2.72 (ddd, J=18.4, 6.4, 1.6 Hz, 1H). LC-MS (m/z): 372.29 $[M+H]^+$.

Compound 52: (3-(2-chloro-4-fluorobenzyl)azetidin-1-yl)(5-phenyl-4,5-dihydro-1H-pyrazol-1-yl)methanone

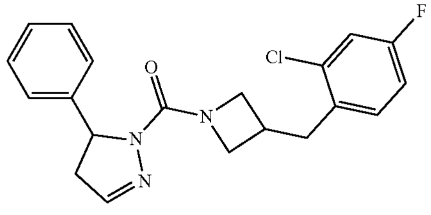 [SMILES: O=C(N1CC(Cc2ccc(F)cc2Cl)C1)N1N=CCC1c1ccccc1]

The titled compound 52 was prepared in 24.2% yield from 3-(2-chloro-4-fluorobenzyl)azetidine hydrochloride, 5-phenyl-4,5-dihydro-1H-pyrazole and triphosgene according to the procedure outlined for compound 37. $^1$H NMR (400 MHz, $CDCl_3$) δ 7.34-7.31 (m, 2H), 7.26-7.22 (m, 3H), 7.15-7.10 (m, 2H), 6.91 (td, J=8.0, 2.8 Hz, 1H), 6.77-6.74 (m, 1H), 5.31 (dd, J=12.8, 6.4 Hz, 1H), 4.25 (t, J=8.8 Hz, 1H), 4.18 (t, J=8.8 Hz, 1H), 3.91 (dd, J=9.2, 5.2 Hz, 1H), 3.81 (dd, J=9.2, 5.2 Hz, 1H), 3.33 (ddd, J=18.4, 6.4, 1.6 Hz, 1H), 3.00-2.99 (m, 2H), 2.96-2.87 (m, 1H), 2.73 (ddd, J=18.4, 6.4, 1.6 Hz, 1H). LC-MS (m/z): 372.49 $[M+H]^+$.

Compound 53: (3-(2,4-difluorobenzyl)azetidin-1-yl)(5-(3-fluorophenyl)-4,5-dihydro-1H-pyrazol-1-yl)methanone

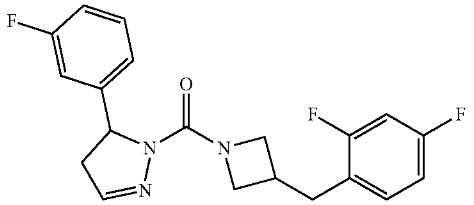 [SMILES: O=C(N1CC(Cc2ccc(F)cc2F)C1)N1N=CCC1c1cccc(F)c1]

The titled compound 53 was prepared in 23.5% yield from 3-(2,4-difluorobenzyl) azetidine hydrochloride, 5-(3,5-difluorophenyl)-4,5-dihydro-1H-pyrazole and triphosgene according to the procedure outlined for compound 37. $^1$H NMR (400 MHz, $CDCl_3$) δ 7.32-7.25 (m, 1H), 7.14-7.07 (m, 1H), 7.01 (dt, J=7.6, 1.2 Hz, 1H), 6.96-6.89 (m, 2H), 6.83-6.73 (m, 3H), 5.29 (dd, J=12.0, 6.4 Hz, 1H), 4.21 (dt, J=23.6, 8.2 Hz, 2H), 3.86 (ddd, J=29.6, 8.7, 4.9 Hz, 2H), 3.32 (ddd, J=18.4, 12.0, 1.6 Hz, 1H), 292-2.88 (m, 2H), 2.88-2.80 (m, 1H), 2.68 (ddd, J=18.4, 6.4, 1.6 Hz, 1H). LC-MS (m/z): 374.36 $[M+H]^+$.

Compound 54: (3-(2,4-difluorobenzyl)azetidin-1-yl)(5-(3,5-difluorophenyl)-4,5-dihydro-1H-pyrazol-1-yl)methanone

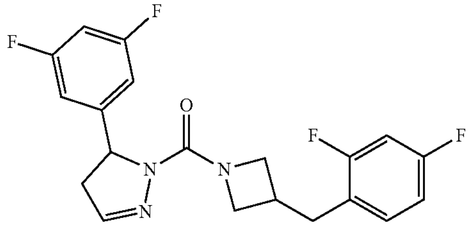 [SMILES: O=C(N1CC(Cc2ccc(F)cc2F)C1)N1N=CCC1c1cc(F)cc(F)c1]

The titled compound 54 was prepared in 22.3% yield from 3-(2,4-difluorobenzyl) azetidine hydrochloride, 5-(3,5-difluorophenyl)-4,5-dihydro-1H-pyrazole and triphosgene according to the procedure outlined for compound 37. $^1$H NMR (400 MHz, $CDCl_3$) δ 7.14-7.08 (m, 1H), 6.83-6.66 (m, 6H), 5.28 (dd, J=12.0, 6.4 Hz, 1H), 4.28-4.20 (m, 2H), 3.95-3.83 (m, 2H), 3.33 (ddd, J=18.4, 12.2, 1.6 Hz, 1H), 2.96-2.84 (m, 3H), 2.68 (ddd, J=18.4, 6.4, 1.6 Hz, 1H). LC-MS (m/z): 392.20 $[M+H]^+$.

Compound 55: (3-(2,4-difluorobenzylidene)azetidin-1-yl)(5-(3,5-difluorophenyl)-4,5-dihydro-1H-pyrazol-1-yl)methanone

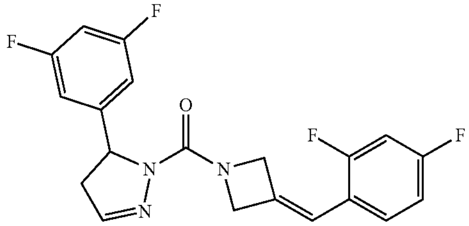 [SMILES: O=C(N1CC(=Cc2ccc(F)cc2F)C1)N1N=CCC1c1cc(F)cc(F)c1]

The titled compound 55 was prepared in 27.9% yield 3-(2,4-difluorobenzylidene) azetidine hydrochloride, 5-(3,5-difluorophenyl)-4,5-dihydro-1H-pyrazole and triphosgene according to the procedure outlined for compound 37. $^1$H NMR (400 MHz, $CDCl_3$) δ 7.11-7.03 (m, 1H), 6.89-6.73 (m, 5H), 6.69 (tt, J=8.0, 2.4 Hz, 1H), 6.39 (t J=2.0 Hz, 1H), 5.31 (dd, J=12.0, 6.4 Hz, 1H), 4.99 (q, J=14.4 Hz, 2H), 4.85 (q, J=14.4 Hz, 2H), 3.42-3.32 (m, 1H), 2.71 (ddd, J=18.4, 6.4, 1.6 Hz, 1H). LC-MS (m/z): 390.26 $[M+H]^+$.

Compound 56: (5-(3,5-difluorophenyl)-4,5-dihydro-1H-pyrazol-1-yl)(3-(2-fluorobenzylidene)azetidin-1-yl)methanone

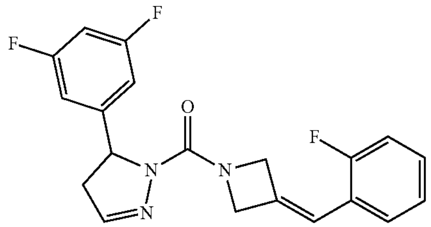 [SMILES: O=C(N1CC(=Cc2ccccc2F)C1)N1N=CCC1c1cc(F)cc(F)c1]

The titled compound 56 was prepared in 18.7% yield 3-(2-fluorobenzylidene) azetidine hydrochloride, 5-(3,5-difluorophenyl)-4,5-dihydro-1H-pyrazole and triphosgene according to the procedure outlined for compound 37. $^1$H NMR (400 MHz, $CDCl_3$) δ 7.23-7.17 (m, 1H), 7.13-7.00 (m, 3H), 6.83-6.74 (m, 3H), 6.69 (tt, J=8.8, 2.4 Hz, 1H), 6.47 (t J=2.4 Hz, 1H), 5.32 (dd, J=12.0, 6.4 Hz, 1H), 5.10-4.96 (m, 2H), 4.94-4.76 (m, 2H), 3.37 (ddd, J=18.4, 12.0, 1.6 Hz, 1H), 2.71 (ddd, J=18.4, 6.4, 1.6 Hz, 1H). LC-MS (m/z): 372.30 $[M+H]^+$.

Compound 57: (5-(3,5-difluorophenyl)-4,5-dihydro-1H-pyrazol-1-yl)(3-(4-fluorobenzylidene)azetidin-1-yl)methanone

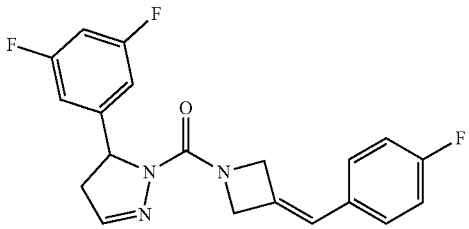 [SMILES: O=C(N1CC(=Cc2ccc(F)cc2)C1)N1N=CCC1c1cc(F)cc(F)c1]

The titled compound 57 was prepared in 25.5% yield 3-(4-fluorobenzylidene) azetidine hydrochloride, 5-(3,5-difluorophenyl)-4,5-dihydro-1H-pyrazole and triphosgene according to the procedure outlined for compound 37. $^1$H NMR (400 MHz, $CDCl_3$) δ 7.09-7.04 (m, 2H), 7.04-6.94 (m, 2H), 6.81-6.71 (m, 3H), 6.67 (tt, J=8.8, 2.4 Hz, 1H), 6.24-6.17 (m, 1H), 5.30 (dd, J=12.0, 6.4 Hz, 1H), 5.02 (q, J=13.6 Hz, 2H), 4.82 (q, J=13.6 Hz, 2H), 3.35 (ddd, J=18.4, 12.0, 1.6 Hz, 1H), 2.69 (ddd, J=18.4, 6.4, 1.6 Hz, 1H). LC-MS (m/z): 372.29 $[M+H]^+$.

Compound 58: (Z)-(3-benzylidenepyrrolidin-1-yl)(5-phenyl-4,5-dihydro-1H-pyrazol-1-yl)methanone

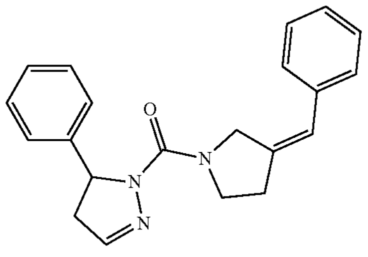 [SMILES: O=C(N1CC/C(=C/c2ccccc2)C1)N1N=CCC1c1ccccc1]

The titled compound 58 was prepared in 25% yield (Z)-3-benzylidenepyrrolidine, 5-(3,5-difluorophenyl)-4,5-dihydro-1H-pyrazole and triphosgene according to the procedure outlined for compound 37. $^1$H NMR (400 MHz, Chloroform-d) δ 7.48-7.12 (m, 10H), 6.80 (s, 1H), 6.42 (d, J=8.4 Hz, 1H), 5.37 (q, J=9.2 Hz, 1H), 4.65 (dd, J=26.4, 16.4 Hz, 1H), 4.29 (t, J=18.4 Hz, 1H), 3.84 (dq, J=35.2, 8.8 Hz, 1H), 3.67 (dq, J=25.6, 10.2, 8.4 Hz, 1H), 3.32 (ddd, J=18.2, 12.0, 4.6 Hz, 1H), 2.77 (td, J=22.2, 18.0, 7.8 Hz, 3H). LC-MS (m/z) 332.6 $[M+H]^+$.

Compound 59: (3-phenoxyazetidin-1-yl)(5-phenyl-4,5-dihydro-1H-pyrazol-1-methanone

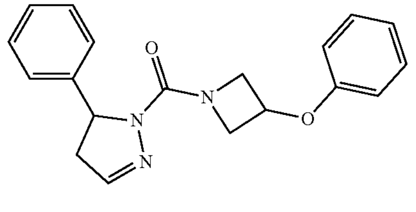 [SMILES: O=C(N1CC(Oc2ccccc2)C1)N1N=CCC1c1ccccc1]

The titled compound 59 was prepared in 18.7% yield from 3-(phenoxy)-azetidine hydrochloride, 5-phenyl-4,5-dihydro-1H-pyrazole and triphosgene according to the procedure outlined for compound 26. $^1$H NMR (400 MHz, $CDCl_3$) δ 7.36-7.26 (m, 4H), 7.25-7.20 (m, 3H), 6.98 (t, 1H, J=7.6 Hz), 6.80-6.70 (m, 3H), 5.32 (dd, 1H, J=12.0, 6.4 Hz), 4.94-4.88 (m, 1H), 4.55 (dd, 1H, J=10.0, 6.4 Hz), 4.48 (dd, 1H, J=10.0, 6.4 Hz), 4.24 (dd, 1H, J=10.0, 4.0 Hz), 4.17 (dd, 1H, J=10.0, 4.0 Hz), 3.34 (ddd, 1H, J=18.4, 12.4, 1.6 Hz), 2.74 (ddd, 1H, J=18.4, 6.4, 1.6 Hz). LC-MS (m/z): 322.21 $[M+H]^+$.

Compound 60: (3-(2-fluorophenoxy)azetidin-1-yl)(5-phenyl-4,5-dihydro-1H-pyrazol-1-yl)methanone

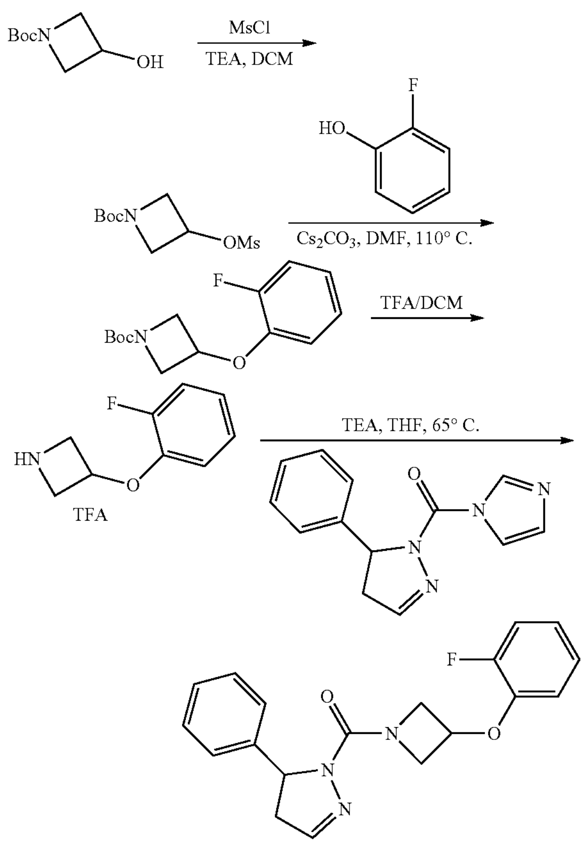

Step 1: Prepared of tert-butyl 3-((methylsulfonyl)oxy)azetidine-1-carboxylate tert-butyl 3-hydroxyazetidine-1-carboxylate (1 g, 5.35 mmol) was dissolved in 10 ml of dry DCM, TEA (1.08 g, 10.7 mmol) was added. MsCl (0.738 g, 6.42 mmol) was added slowly to the above solution at 0° C. The mixture was stirred for overnight. The mixture was extracted with DCM, washed with brine, dried ($Na_2SO_4$), and concentrated to dryness to give the desired product. LC-MS (m/z) 252.3 $(M+H^+)$.

Step 2: Prepared of tert-butyl 3-(2-fluorophenoxy)azetidine-1-carboxylate tert-butyl 3-((methylsulfonyl)oxy)azetidine-1-carboxylate (200 mg, 0.796 mmol), Cs2CO3 (518 mg, 1.6 mmol) and KI (3 mg) were placed in DMF (2 mL). The mixture was stirred 110° C. for overnight, water was added and extracted with EA, washed with brine, dried ($Na_2SO_4$), and concentrated to dryness to give the desired product. LC-MS (m/z) 268.3 $(M+H^+)$.

Step 3: Prepared of 3-(2-fluorophenoxy)azetidine trifluoroacetic acid tert-butyl 3-(2-fluorophenoxy)azetidine-1-carboxylate was dissolved in stirred at r.t. for 4 h. The mixture was concentrated to give the desired product, which was used for next step without further purification. LC-MS (m/z) 168.3 (M+H$^+$).

The following intermediates used for the preparation of titled example compounds were synthesized using the methods analogous to 3-(2-fluorophenoxy)azetidine trifluoroacetic acid described above, may be as TFA salt or free base was used in next step without further purification.

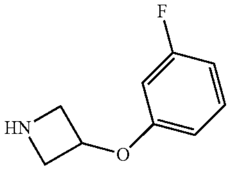
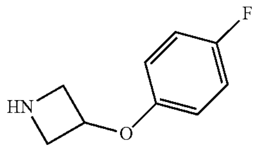
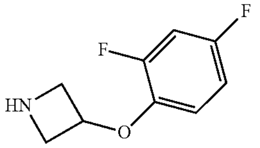
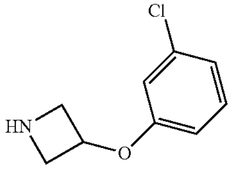
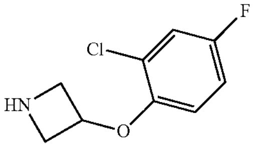
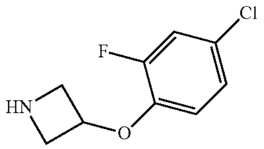
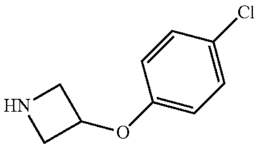
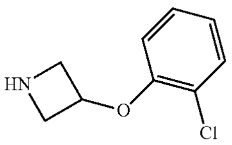
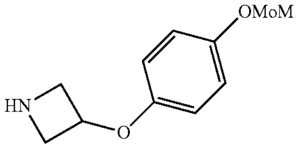
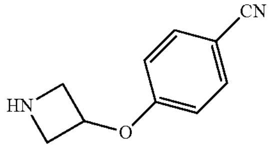
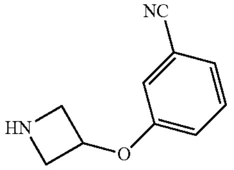
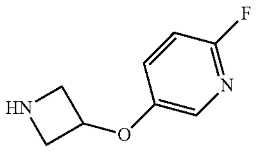
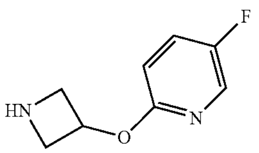
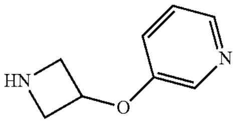
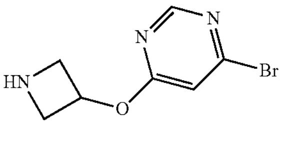
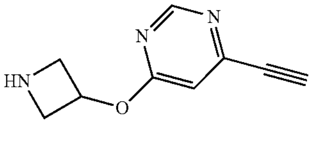
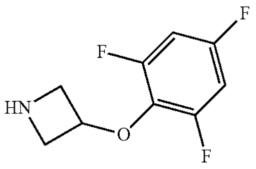

-continued

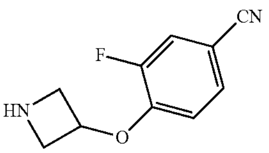
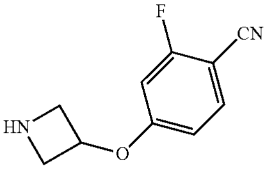
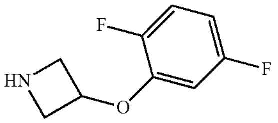
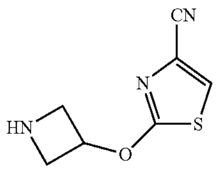
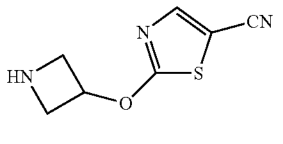

Step 4: Prepared of (3-(2-fluorophenoxy)azetidin-1-yl)(5-phenyl-4,5-dihydro-1H-pyrazol-1-yl)methanone 3-(2-fluorophenoxy)azetidine (100 mg) and (1H-imidazol-1-yl)(5-phenyl-4,5-dihydro-1H-pyrazol-1-yl)methanone (50 mg) and TEA (0.8 mL) were dissolved in THF (10 ml) and stirred at 65° C. for 16 h. The mixture was extracted with EA, washed with brine, dried ($Na_2SO_4$), and concentrated in vacuo. Purification by silica gel chromatography to give the titled compound 60 (53 mg, 74.4%). $^1$H NMR (400 MHz, $CDCl_3$) δ 7.31-7.35 (m, 2H), 7.21-7.27 (m, 3H), 7.01-7.12 (m, 2H), 6.90-6.96 (m, 1H), 6.78 (t, 1H, J=1.6 Hz), 6.70 (td, 1H, J=8.4, 1.6 Hz), 5.33 (dd, 1H, J=12.0, 6.4 Hz), 4.91-4.94 (m, 1H), 4.55 (dd, 1H, J=10.0, 6.8 Hz), 4.49 (dd, 1H, J=10.0, 6.8 Hz), 4.30 (dd, 1H, J=10.0, 4.0 Hz), 4.23 (dd, 1H, J=10.0, 4.0 Hz), 3.34 (ddd, 1H, J=18.8, 12.0, 1.6 Hz), 2.74 (ddd, 1H, J=18.4, 6.4, 1.6 Hz). LC-MS (m/z): 340.40 [M+H]$^+$.

Compound 61: (3-(3-fluorophenoxy)azetidin-1-yl)(5-phenyl-4,5-dihydro-1H-pyrazol-1-yl)methanone

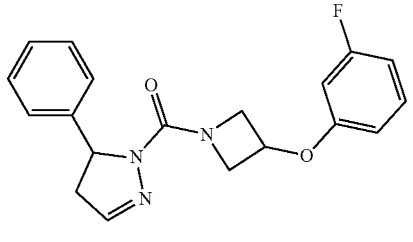 [SMILES: O=C(N1CC(Oc2cccc(F)c2)C1)N1N=CCC1c1ccccc1]

The titled compound 61 was prepared in 75.5% yield from 3-(3-fluorophenoxy) azetidine trifluoroacetic acid, (1H-imidazol-1-yl)(5-phenyl-4,5-dihydro-1H-pyrazol-1-yl)methanone according to the procedure outlined for compound 60. $^1$H NMR (400 MHz, $CDCl_3$) δ 7.29-7.35 (m, 2H), 7.15-7.26 (m, 4H), 6.75-6.79 (m, 1H), 6.62-6.72 (m, 1H), 6.40-6.55 (m, 2H), 5.32 (dd, 1H, J=12.0, 6.4 Hz), 4.85-4.91 (m, 1H), 4.46-4.57 (m, 2H), 4.09-4.25 (m, 2H), 3.30-3.39 (m, 1H), 2.71-2.78 (m, 1H). LC-MS (m/z): 340.32 [M+H]$^+$.

Compound 62: (3-(4-fluorophenoxy)azetidin-1-yl)(5-phenyl-4,5-dihydro-1H-pyrazol-1-yl)methanone

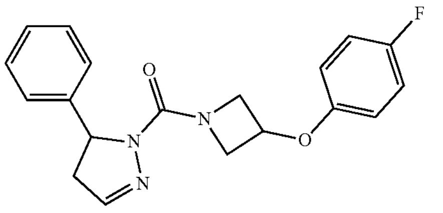 [SMILES: O=C(N1CC(Oc2ccc(F)cc2)C1)N1N=CCC1c1ccccc1]

The titled compound 62 was prepared in 70.2% yield from 3-(4-fluorophenoxy) azetidine trifluoroacetic acid, (1H-imidazol-1-yl)(5-phenyl-4,5-dihydro-1H-pyrazol-1-yl)methanone according to the procedure outlined for compound 60. $^{1}$H NMR (400 MHz, $CDCl_3$) δ 7.29-7.35 (m, 2H), 7.21-7.27 (m, 3H), 6.92-7.00 (m, 2H), 6.77 (t, 1H, J=1.6 Hz), 6.66-6.72 (m, 2H), 5.32 (dd, 1H, J=12.0, 6.4 Hz), 4.82-4.89 (m, 1H), 4.53 (dd, 1H, J=9.6, 6.4 Hz), 4.46 (dd, 1H, J=9.6, 6.4 Hz), 4.22 (dd, 1H, J=10.0, 4.0 Hz), 4.14 (dd, 1H, J=10.0, 4.0 Hz), 3.33 (ddd, 1H, J=18.4, 12.0, 1.6 Hz), 2.73 (ddd, 1H, J=18.4, 6.4, 1.6 Hz). LC-MS (m/z): 340.40 $[M+H]^+$.

Compound 63: (3-(2,4-difluorophenoxy)azetidin-1-yl)(5-phenyl-4,5-dihydro-1H-pyrazol-1-yl)methanone

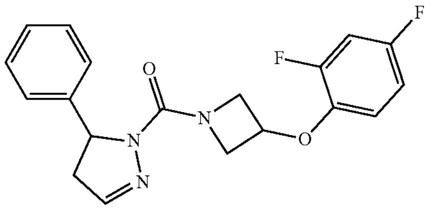

The titled compound 63 was prepared in 70.7% yield from 3-(2,4-difluorophenoxy) azetidine trifluoroacetic acid, (1H-imidazol-1-yl)(5-phenyl-4,5-dihydro-1H-pyrazol-1-yl)methanone according to the procedure outlined for compound 60. $^{1}$H NMR (400 MHz, $CDCl_3$) δ 7.30-7.34 (m, 2H), 7.20-7.25 (m, 3H), 6.84-6.90 (m, 1H), 6.78-6.79 (m, 1H), 6.74-6.77 (m, 1H), 6.67 (td, 1H, J=8.8, 6.4 Hz), 5.31 (dd, 1H, J=12.4, 6.4 Hz), 4.85-4.90 (m, 1H), 4.51 (dd, 1H, J=10.0, 6.4 Hz), 4.46 (dd, 1H, J=10.0, 6.4 Hz), 4.27 (dd, 1H, J=10.0, 4.0 Hz), 4.20 (dd, 1H, J=10.0, 4.0 Hz), 3.34 (ddd, 1H, J=18.8, 12.4, 2.0 Hz), 2.74 (ddd, 1H, J=18.4, 6.4, 1.6 Hz). LC-MS (m/z): 358.45 $[M+H]^+$.

Compound 64: (3-(2-chlorophenoxy)azetidin-1-yl)(5-phenyl-4,5-dihydro-1H-pyrazol-1-yl)methanone

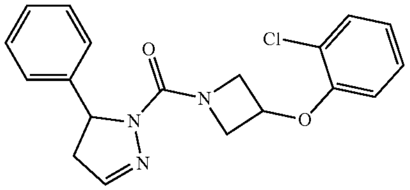 [SMILES: O=C(N1CC(Oc2ccccc2Cl)C1)N1N=CCC1c1ccccc1]

The titled compound 64 was prepared in 52% yield from 3-(2-chlorophenoxy) azetidine trifluoroacetic acid, (1H-imidazol-1-yl)(5-phenyl-4,5-dihydro-1H-pyrazol-1-yl)methanone according to the procedure outlined for compound 60. $^{1}$H NMR (400 MHz, $CDCl_3$) δ 7.43-7.27 (m, 3H), 7.26-7.14 (m, 4H), 6.93 (td, J=7.7, 1.4 Hz, 1H), 6.78 (t, J=1.7 Hz, 1H), 6.60 (dd, J=8.2, 1.3 Hz, 1H), 5.32 (dd, J=12.3, 6.5 Hz, 1H), 4.94 (ddd, J=10.7, 5.4, 3.2 Hz, 1H), 4.61-4.44 (m, 2H), 4.28 (ddd, J=31.8, 10.2, 4.0 Hz, 2H), 3.35 (ddd, J=18.5, 12.2, 1.7 Hz, 1H), 2.75 (ddd, J=18.5, 6.3, 1.7 Hz, 1H). LC-MS (m/z) 356.8 $(M+H^+)$ Compound 65: (3-(4-chlorophenoxy)azetidin-1-yl)(5-phenyl-4,5-dihydro-1H-pyrazol-1-yl)methanone

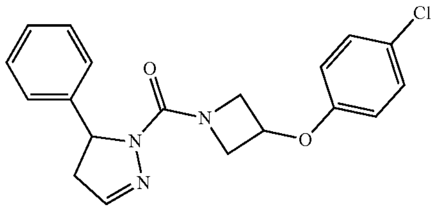 [SMILES: O=C(N1CC(Oc2ccc(Cl)cc2)C1)N1N=CCC1c1ccccc1]

The titled compound 65 was prepared in 40% yield from 3-(4-chlorophenoxy) azetidine trifluoroacetic acid, (1H-imidazol-1-yl(5-phenyl-4,5-dihydro-1H-pyrazol-1-yl)methanone according to the procedure outlined for compound 60. $^{1}$H NMR (400 MHz, $CDCl_3$) δ 7.36-7.26 (m, 3H), 7.25-7.18 (m, 4H), 6.78 (t, J=1.7 Hz, 1H), 6.71-6.65 (m, 2H), 5.35-5.28 (m, 1H), 4.86 (ddd, J=10.6, 5.3, 3.2 Hz, 1H), 4.59-4.43 (m, 2H), 4.18 (ddd, J=31.7, 10.1, 3.6 Hz, 2H), 3.35 (ddd, J=18.5, 12.2, 1.7 Hz, 1H), 2.75 (ddd, J=18.6, 6.4, 1.7 Hz, 1H). LC-MS (m/z) 356.8 $(M+H^+)$ Compound 66: (3-(3,4-difluorophenoxy)azetidin-1-yl)(5-phenyl-4,5-dihydro-1H-pyrazol-1-yl)methanone

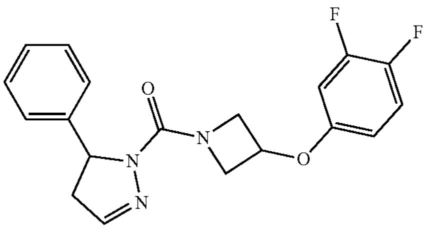 [SMILES: O=C(N1CC(Oc2ccc(F)c(F)c2)C1)N1N=CCC1c1ccccc1]

The titled compound 66 was prepared in 74.7% yield from 3-(3,4-difluorophenoxy) azetidine trifluoroacetic acid, (1H-imidazol-1-yl)(5-phenyl-4,5-dihydro-1H-pyrazol-1-yl)methanone according to the procedure outlined for compound 60. $^{1}$H NMR (400 MHz, $CDCl_3$) δ 7.30-7.35 (m, 2H), 7.21-7.27 (m, 3H), 7.06 (dd, 1H, J=18.8, 8.8 Hz), 6.78 (t, 1H, J=1.6 Hz), 6.58 (ddd, 1H, J=9.6, 6.8, 3.2 Hz), 6.41-6.45 (m, 1H), 5.31 (dd, 1H, J=12.0, 6.0 Hz), 4.80-4.85 (m, 1H), 4.53 (dd, 1H, J=10.0, 6.4 Hz), 4.46 (dd, 1H, J=10.0, 6.4 Hz), 4.21 (dd, 1H, J=10.0, 4.0 Hz), 4.13 (dd, 1H, J=10.0, 4.0 Hz), 3.34 (ddd, 1H, J=18.8, 12.0, 1.6 Hz), 2.74 (ddd, 1H, J=18.4, 6.4, 1.6 Hz). LC-MS (m/z): 358.42 $[M+H]^+$.

Compound 67: (3-(2-chloro-4-fluorophenoxy)azetidin-1-yl)(5-phenyl-4,5-dihydro-1H-pyrazol-1-yl) methanone

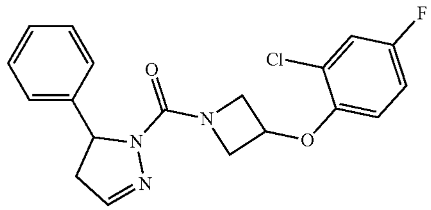 [SMILES: O=C(N1CC(Oc2ccc(F)cc2Cl)C1)N1N=CCC1c1ccccc1]

The titled compound 67 was prepared in 35% yield from 3-(2-chloro-4-fluorophenoxy)azetidine trifluoroacetic acid, (1H-imidazol-1-yl)(5-phenyl-4,5-dihydro-1H-pyrazol-1-yl) methanone according to the procedure outlined for compound 60. $^1$H NMR (400 MHz, $CDCl_3$) δ 7.36-7.30 (m, 2H), 7.26-7.20 (m, 3H), 7.15 (dd, J=8.0, 3.2 Hz, 1H), 6.90 (ddd, J=9.2, 7.6, 3.2 Hz, 1H), 6.79 (t, J=1.6 Hz, 1H), 6.56 (dd, J=9.0, 4.7 Hz, 1H), 5.32 (dd, J=12.0, 6.0 Hz, 1H), 4.92-4.86 (m, 1H), 4.58-4.52 (dd, J=9.6, 6.4 Hz, 1H), 4.51-4.45 (dd, J=9.6, 6.4 Hz, 1H), 4.30 (dd, J=10.4, 3.8 Hz, 1H), 4.22 (dd, J=10.0, 4.0 Hz, 1H), 3.35 (ddd, J=18.4, 12.0, 1.6 Hz, 1H), 2.75 (ddd, J=18.4, 6.4, 1.6 Hz, 1H). LC-MS (m/z) 374.8 $(M+H^+)$ Compound 68: 4-((1-(5-phenyl-4,5-dihydro-1H-pyrazole-1-carbonyl)azetidin-3-yl)oxy)benzonitrile

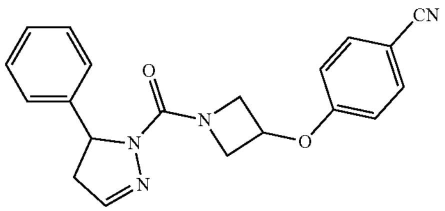 [SMILES: N#Cc1ccc(OC2CN(C(=O)N3N=CCC3c3ccccc3)C2)cc1]

The titled compound 67 was prepared in 70.7% yield from 4-(azetidin-3-yloxy) benzonitrile trifluoroacetic acid, (1H-imidazol-1-yl)(5-phenyl-4,5-dihydro-1H-pyrazol-1-yl) methanone according to the procedure outlined for compound 60. $^1$H NMR (400 MHz, $CDCl_3$) δ 7.57-7.61 (m, 2H), 7.30-7.35 (m, 2H), 7.25-7.27 (m, 1H), 7.21-7.23 (m, 2H), 6.81-6.82 (m, 1H), 6.79-6.80 (m, 2H), 5.31 ((dd, 1H, J=12.0, 6.0 Hz), 4.92-4.97 (m, 1H), 4.57 (dd, 1H, J=9.6, 6.0 Hz), 4.51 (dd, 1H, J=10.0, 6.4 Hz), 4.24 (dd, 1H, J=10.0, 4.0 Hz), 4.16 (dd, 1H, J=10.0, 4.0 Hz), 3.35 (ddd, 1H, J=18.8, 12.0, 2.0 Hz), 2.76 (ddd, 1H, J=18.4, 6.4, 2.0 Hz). LC-MS (m/z): 347.40 $[M+H]^+$.

Compound 69: (3-(4-chlor-2-fluorophenoxy)azetidin-1-yl)(5-phenyl-4,5-dihydro-1H-pyrazol-1-yl) methanone

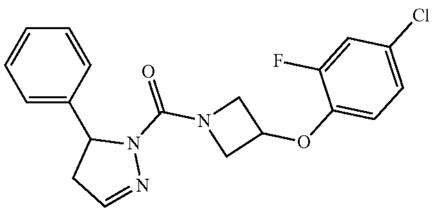 [SMILES: O=C(N1CC(Oc2ccc(Cl)cc2F)C1)N1N=CCC1c1ccccc1]

The titled compound 69 was prepared in 10.6% yield from 3-(2-chloro-4-fluorophenoxy)azetidine trifluoroacetic acid, (1H-imidazol-1-yl)(5-phenyl-4,5-dihydro-1H-pyrazol-1-yl) methanone according to the procedure outlined for compound 60. $^1$H NMR (400 MHz, $CDCl_3$) δ 7.34-7.28 (m, 2H), 7.23-7.17 (m, 3H), 7.10 (dd, J=10.8, 2.5 Hz, 1H), 7.03-6.97 (m, 1H), 6.76 (t, J=1.6 Hz, 1H), 6.61 (t, J=8.7 Hz, 1H), 5.30 (dd, J=12.4, 6.4 Hz, 1H), 4.94-4.83 (m, 1H), 4.48 (ddd, J=24.5, 9.6, 6.4 Hz, 2H), 4.23 (ddd, J=29.0, 10.0, 4.0 Hz, 2H), 3.33 (ddd, J=18.4, 12.4, 1.6 Hz, 1H), 2.73 (ddd, J=18.4, 6.4, 1.6 Hz, 1H). LC-MS (m/z) 374.8 $(M+H^+)$ Compound 70: (3-(4-hydroxyphenoxy)azetidin-1-yl)(5-phenyl-4,5-dihydro-1H-pyrazol-1-yl)methanone

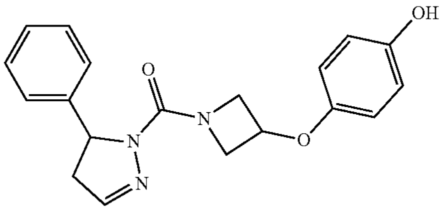 [SMILES: O=C(N1CC(Oc2ccc(O)cc2)C1)N1N=CCC1c1ccccc1]

(3-(4-(methoxymethoxy)phenoxy)azetidin-1-yl)(5-phenyl-4,5-dihydro-1H-pyrazol-1-yl)methanone was prepared in 16% yield from 3-(4-(methoxymethoxy) phenoxy)azetidine, (1H-imidazol-1-yl)(5-phenyl-4,5-dihydro-1H-pyrazol-1-yl)methanone according to the procedure outlined for compound 60, which was reacted with con.HCl (1 mL) in MeOH (3 mL) for 1 h. The mixture was concentrated and purified by Pre-TLC to give the titled compound 70 (18 mg, 41%). LC-MS (m/z) 338.4 $(M+H^+)$ $^1$H NMR (400 MHz, $CDCl_3$) δ 7.38-7.28 (m, 2H), 7.23-7.13 (m, 3H), 6.77 (brs, 1H), 6.66 (d, J=8.6 Hz, 2H), 6.55 (d, J=8.7 Hz, 2H), 5.30 (dd, J=12.0, 6.2 Hz, 1H), 4.78 (brs, 1H), 4.55-4.35 (m, 2H), 4.16 (dd, J=29.5, 6.6 Hz, 2H), 3.32 (dd, J=18.5, 12.2 Hz, 1H), 2.72 (dd, J=18.5, 6.2 Hz, 1H).

Compound 71: 3-((1-(5-(3,5-difluorophenyl)-4,5-dihydro-1H-pyrazole-1-carbonyl)azetidin-3-yl)oxy) benzonitrile

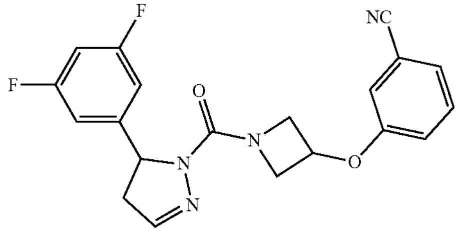 [SMILES: N#Cc1cccc(OC2CN(C(=O)N3N=CCC3c3cc(F)cc(F)c3)C2)c1]

The titled compound 71 was prepared in 22.3% yield from 3-(azetidin-3-yloxy)benzonitrile trifluoroacetic acid, (1H-imidazol-1-yl)(5-phenyl-4,5-dihydro-1H-pyrazol-1-yl) methanone according to the procedure outlined for compound 60. $^1$H NMR (400 MHz, $CDCl_3$) δ 7.39 (t, J=8.0 Hz, 1H), 7.33-7.26 (m, 1H), 7.05-6.94 (m, 2H), 6.82-6.62 (m, 4H), 5.28 (dd, J=12.2, 6.4 Hz, 1H), 4.93 (ddd, J=10.4, 5.2, 3.2 Hz, 1H), 4.67-4.48 (m, 2H), 4.29-4.03 (m, 2H), 3.35 (ddd, J=18.6, 12.2, 1.7 Hz, 1H), 2.70 (ddd, J=18.6, 6.5, 1.7 Hz, 1H). LC-MS (m/z) 383.4 $(M+H^+)$ Compound 72: (3-((5-fluoropyridin-2-yl)oxy)azetidin-1-yl)(5-phenyl-4,5-dihydro-1H-pyrazol-1-yl)methanone

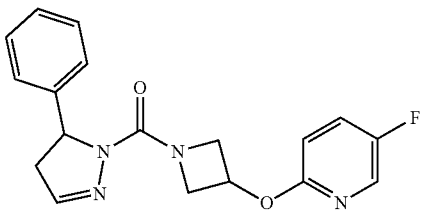 [SMILES: O=C(N1CC(Oc2ccc(F)cn2)C1)N1N=CCC1c1ccccc1]

The titled compound 72 was prepared in 32% yield from 2-(azetidin-3-yloxy)-5-fluoropyridine trifluoroacetic acid, (1H-imidazol-1-yl)(5-phenyl-4,5-dihydro-1H-pyrazol-1-yl)methanone according to the procedure outlined for compound 60. $^{1}$H NMR (400 MHz, $CDCl_3$) δ 7.91 (d, J=3.0 Hz, 1H), 7.37-7.27 (m, 4H), 7.24-7.21 (m, 1H), 7.20-7.18 (m, 1H), 6.76-6.69 (m, 2H), 5.33-5.24 (m, 2H), 4.57-4.44 (m, 2H), 4.13 (ddd, J=24.4, 10.5, 4.3 Hz, 2H), 3.32 (ddd, J=18.5, 12.2, 1.7 Hz, 1H), 2.71 (ddd, J=18.5, 6.4, 1.7 Hz, 1H). LC-MS (m/z) 341.4 ($M+H^+$)

Compound 73: (3-((6-fluoropyridin-3-yl)oxy)azetidin-1-yl)(5-phenyl-4,5-dihydro-1H-pyrazol-1-yl)methanone

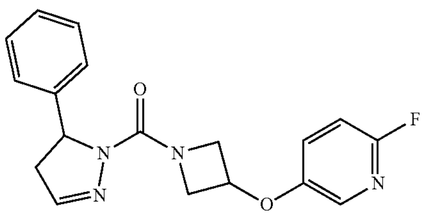 [SMILES: O=C(N1CC(Oc2ccc(F)nc2)C1)N1N=CCC1c1ccccc1]

The titled compound 73 was prepared in 9.3% yield from 5-(azetidin-3-yloxy)-2-fluoropyridine trifluoroacetic acid, (1H-imidazol-1-yl)(5-phenyl-4,5-dihydro-1H-pyrazol-1-yl)methanone according to the procedure outlined for compound 60. $^{1}$H NMR (400 MHz, $CDCl_3$) δ 7.66-7.62 (m, 1H), 7.33-7.28 (m, 2H), 7.24-7.16 (m, 4H), 6.85 (dd, J=8.9, 3.5 Hz, 1H), 6.77 (t, J=1.6 Hz, 1H), 5.34-5.26 (m, 1H), 4.89 (ddd, J=10.4, 6.3, 4.0 Hz, 1H), 4.58-4.41 (m, 2H), 4.22 (dd, J=10.2, 3.9 Hz, 1H), 4.14 (dd, J=10.2, 3.9 Hz, 1H), 3.34 (ddd, J=18.6, 12.1, 1.6 Hz, 1H), 2.74 (ddd, J=18.6, 6.3, 1.7 Hz, 1H). LC-MS (m/z) 341.4 ($M+H^+$)

Compound 74: (5-phenyl-4,5-dihydro-1H-pyrazol-1-yl)(3-(pyridin-3-yloxy)azetidin-1-yl)methanone

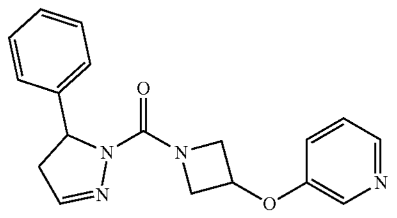 [SMILES: O=C(N1CC(Oc2cccnc2)C1)N1N=CCC1c1ccccc1]

The titled compound 74 was prepared in 3.1% yield from 3-(azetidin-3-yloxy) pyridine trifluoroacetic acid, (1H-imidazol-1-yl)(5-phenyl-4,5-dihydro-1H-pyrazol-1-yl)methanone according to the procedure outlined for compound 60. $^{1}$H NMR (400 MHz, $CDCl_3$) δ 7.35-7.31 (m, 2H), 7.27-7.20 (m, 7H), 6.79 (s, 1H), 5.31 (dd, J=12.0, 8.0 Hz, 1H), 4.99 (s, 1H), 4.61-4.51 (m, 2H), 4.22 (dd, J=32.0, 8.0 Hz, 2H), 3.39-3.32 (m, 1H), 2.79-2.73 (m, 1H). LC-MS (m/z) 323.43 $[M+H]^+$.

Compound 75: (3-(2,4-difluorophenoxy)azetidin-1-yl)(5-(3-fluorophenyl)-4,5-dihydro-1H-pyrazol-1-yl)methanone

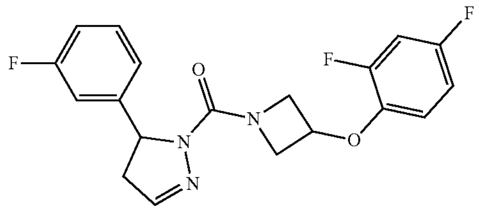 [SMILES: O=C(N1CC(Oc2ccc(F)cc2F)C1)N1N=CCC1c1cccc(F)c1]

The titled compound 75 was prepared in 16.8% yield from 3-(2,4-difluorophenoxy) azetidine trifluoroacetic acid, 5-(3-fluorophenyl)-4,5-dihydro-1H-pyrazole and triphosgene according to the procedure outlined for compound 37. $^{1}$H NMR (400 MHz, $CDCl_3$) δ 7.34-7.28 (m, 1H), 7.24-7.19 (m, 2H), 7.04-6.81 (m, 3H), 6.78-6.71 (m, 1H), 6.66 (td, J=9.0, 5.2 Hz, 1H), 5.29 (dd, J=12.2, 6.3 Hz, 1H), 4.92-4.85 (m, 1H), 4.54-4.42 (m, 2H), 4.34-4.16 (m, 2H), 3.33 (dd, J=18.5, 12.1 Hz, 1H), 2.77-2.58 (m, 1H). LC-MS (m/z) 376.4 ($M+H^+$)

Compound 76: (3-(2,4-difluorophenoxy)azetidin-1-yl)(5-(3,5-difluorophenyl)-4,5-dihydro-1H-pyrazol-1-yl)methanone

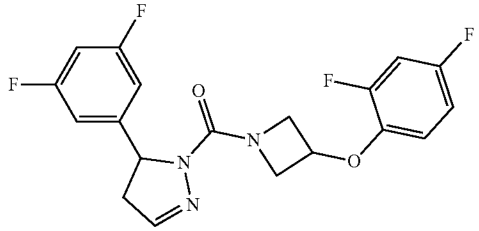 [SMILES: O=C(N1CC(Oc2ccc(F)cc2F)C1)N1N=CCC1c1cc(F)cc(F)c1]

The titled compound 76 was prepared in 22.6% yield from 3-(2,4-difluorophenoxy) azetidine trifluoroacetic acid, 5-(3,5-difluorophenyl)-4,5-dihydro-1H-pyrazole and triphosgene according to the procedure outlined for compound 37. $^{1}$H NMR (400 MHz, $CDCl_3$) δ 6.89 (ddd, J=11.3, 8.3, 2.9 Hz, 1H), 6.80-6.74 (m, 3H), 6.73-6.65 (m, 2H), 5.28 (dd, J=12.2, 6.5 Hz, 1H), 4.91 (ddd, J=10.5, 6.3, 4.0 Hz, 1H), 4.57-4.43 (m, 2H), 4.27 (ddd, J=14.4, 10.1, 3.3 Hz, 2H), 3.35 (ddd, J=18.5, 12.2, 1.5 Hz, 1H), 2.69 (ddd, J=18.6, 6.5, 1.5 Hz, 1H). LC-MS (m/z) 394.4 ($M+H^+$)

Compound 77: (S)-(3-(2-fluorophenoxy)azetidin-1-yl)(3-phenylisoxazolidin-2-yl)methanone

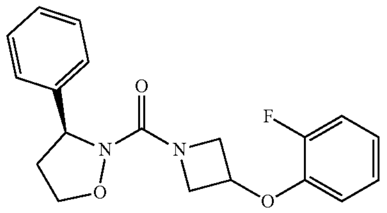 [SMILES: O=C(N1CC(Oc2ccccc2F)C1)N1OCC[C@H]1c1ccccc1]

The titled compound 77 was prepared in 13% yield from 3-(2-fluorophenoxy) azetidine trifluoroacetic acid, (S)-3-phenylisoxazolidine and triphosgene according to the procedure outlined for compound 26. $^1$H NMR (400 MHz, $CDCl_3$) δ 7.41-7.30 (m, 3H), 7.26-7.21 (m, 2H), 7.14-7.01 (m, 2H), 6.98-6.91 (m, 1H), 6.69 (t, J=8.2 Hz, 1H), 5.55 (dd, J=8.6, 5.3 Hz, 1H), 4.97 (ddd, J=10.6, 6.5, 4.2 Hz, 1H), 4.54 (dt, J=14.6, 7.4 Hz, 2H), 4.35 (dd, J=10.6, 3.9 Hz, 1H), 4.22 (dd, J=10.1, 3.4 Hz, 1H), 4.12 (td, J=8.0, 3.4 Hz, 1H), 3.82 (dd, J=16.3, 8.1 Hz, 1H), 2.82-2.71 (m, 1H), 2.37-2.25 (m, 1H). LC-MS (m/z) 343.4 ($M+H^+$)

Compound 78: (S)-(3-(4-fluorophenoxy)azetidin-1-yl)(3-phenylisoxazolidin-2-yl)methanone

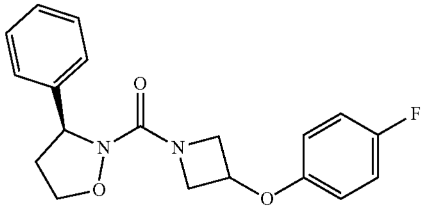 [SMILES: O=C(N1CC(Oc2ccc(F)cc2)C1)N1OCC[C@H]1c1ccccc1]

The titled compound 78 was prepared in 16% yield from 3-(4-fluorophenoxy) azetidine trifluoroacetic acid, (S)-3-phenylisoxazolidine and triphosgene according to the procedure outlined for compound 26. $^1$H NMR (400 MHz, $CDCl_3$) δ 7.40-7.30 (m, 3H), 7.26-7.22 (m, 1H), 7.02-6.94 (m, 2H), 6.72-6.66 (m, 2H), 5.54 (dd, J=8.8, 5.4 Hz, 1H), 4.94-4.84 (m, 1H), 4.58-4.48 (m, 2H), 4.25 (dd, J=10.4, 4.0 Hz, 1H), 4.12 (ddd, J=11.4, 7.6, 3.7 Hz, 2H), 3.82 (dd, J=16.1, 8.1 Hz, 1H), 2.82-2.68 (m, 1H), 2.42-2.28 (m, 1H). LC-MS (m/z) 343.4 ($M+H^+$)

Compound 79: (S)-(3-(4-fluorobenzyl)azetidin-1-yl)(3-phenylisoxazolidin-2-yl)methanone

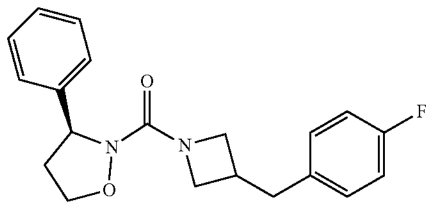 [SMILES: O=C(N1CC(Cc2ccc(F)cc2)C1)N1OCC[C@H]1c1ccccc1]

The titled compound 7 was prepared in 16% yield from 3-(4-fluorobenzyl)azetidine trifluoroacetic acid, (S)-3-phenylisoxazolidine and triphosgene according to the procedure outlined for compound 26. $^1$H NMR (400 MHz, $CDCl_3$) δ 7.41-7.29 (m, 4H), 7.26-7.22 (m, 1H), 7.10 (dd, J=8.1, 5.6 Hz, 2H), 6.98 (t, J=8.3 Hz, 2H), 5.54 (dd, J=8.7, 5.2 Hz, 1H), 4.26 (t, J=8.2 Hz, 1H), 4.17 (brs, 1H), 4.09 (td, J=8.0, 3.4 Hz, 1H), 3.89-3.80 (m, 3H), 3.78 (dd, J=16.2, 8.3 Hz, 1H), 2.93-2.80 (m, 3H), 2.78-2.69 (m, 1H), 2.29 (ddd, J=15.2, 7.8, 3.9 Hz, 1H). LC-MS (m/z) 341.4 ($M+H^+$)

Compound 80: (S)-(3-(2,4-difluorophenoxy)azetidin-1-yl)(3-phenylisoxazolidin-2-yl)methanone

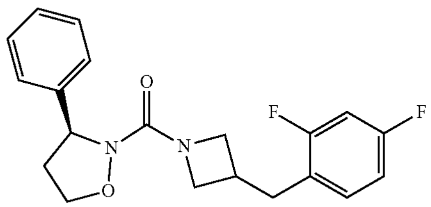 [SMILES: O=C(N1CC(Cc2ccc(F)cc2F)C1)N1OCC[C@H]1c1ccccc1]

The titled compound 80 was prepared in 12% yield from 3-(2,4-difluorophenoxy) azetidine trifluoroacetic acid, (S)-3-phenylisoxazolidine and triphosgene according to the procedure outlined for compound 26. $^1$H NMR (400 MHz, $CDCl_3$) δ 7.40-7.30 (m, 3H), 7.26-7.22 (m, 2H), 6.93-6.86 (m, 1H), 6.81-6.74 (m, 1H), 6.67 (td, J=9.0, 5.5 Hz, 1H), 5.54 (dd, J=8.7, 5.3 Hz, 1H), 4.96-4.88 (m, 1H), 4.57-4.46 (m, 2H), 4.32 (dd, J=10.5, 3.8 Hz, 1H), 4.20 (d, J=9.0 Hz, 1H), 4.12 (td, J=8.0, 3.3 Hz, 1H), 3.82 (dd, J=16.1, 8.2 Hz, 1H), 2.81-2.70 (m, 1H), 2.36-2.26 (m, 1H). LC-MS (m/z) 361.4 ($M+H^+$)

Compound 81: (S)-(4-(5-fluoropyrimidin-2-yl)piperazin-1-yl)(3-phenylisoxazolidin-2-yl)methanone

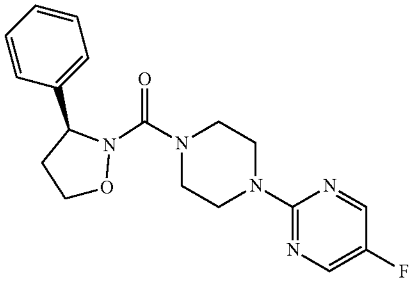 [SMILES: O=C(N1CCN(c2ncc(F)cn2)CC1)N1OCC[C@H]1c1ccccc1]

The titled compound 81 was prepared in 61.8% yield from 5-fluoro-2-(piperazin-1-yl)pyrimidine, (S)-3-phenylisoxazolidine and triphosgene according to the procedure outlined for compound 26. $^1$H NMR (400 MHz, $CDCl_3$) δ 8.21 (s, 2H), 7.42-7.30 (m, 4H), 7.26-7.23 (m, 1H), 5.46 (dd, J=8.5, 4.9 Hz, 1H), 4.13 (td, J=8.0, 4.1 Hz, 1H), 3.93 (q, J=7.9 Hz, 1H), 3.86-3.57 (m, 8H), 2.85-2.76 (m, 1H), 2.36-2.26 (m, 1H). LC-MS (m/z) 358.4 ($M+H^+$)

Compound 82: (S)-(3-(2,4-difluorobenzyl)azetidin-1-yl)(3-phenylisoxazolidin-2-yl)methanone

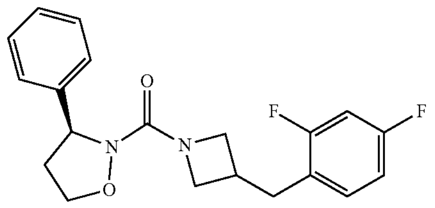 [SMILES: O=C(N1CC(Cc2ccc(F)cc2F)C1)N1OCC[C@H]1c1ccccc1]

The titled compound 82 was prepared in 11.6% yield from 3-(2,4-difluorobenzyl) azetidine, (S)-3-phenylisoxazolidine and triphosgene according to the procedure outlined for compound 26. $^1$H NMR (400 MHz, $CDCl_3$) δ 7.40-7.35 (m, 2H), 7.35-7.29 (m, 2H), 7.26-7.20 (m, 1H), 7.13-7.06 (m, 1H), 6.84-6.75 (m, 2H), 5.53 (dd, J=8.8, 5.2 Hz, 1H), 4.30-4.14 (m, 2H), 4.14-4.05 (m, 1H), 3.92-3.82 (m, 2H), 3.81-3.74 (m, 1H), 2.95-2.83 (m, 3H), 2.78-2.67 (m, 1H), 2.33-2.23 (m, 1H). LC-MS (m/z): 359.51 $[M+H]^+$.

Compound 83: (4-(5-fluoropyrimidin-2-yl)piperazin-1-yl)(5-phenyl-4,5-dihydro-1H-pyrazol-1-yl) methanone

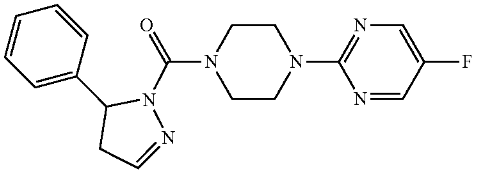 [SMILES: O=C(N1CCN(c2ncc(F)cn2)CC1)N1N=CCC1c1ccccc1]

The titled compound 81 was prepared in 61.8% yield from 5-fluoro-2-(piperazin-1-yl)pyrimidine, 5-phenyl-4,5-dihydro-1H-pyrazole and triphosgene according to the procedure outlined for compound 26. $^1$H NMR (400 Hz, $CDCl_3$): δ 8.21 (s, 2H), 7.36-7.23 (m, 5H), 6.85 (s, 1H), 5.37 (dd, J=11.6, 9.6 Hz, 1H), 3.95-3.56 (m, 8H), 3.36-3.28 (m, 1H), 2.79-2.71 (m, 1H). LC-MS (m/z) 355.4 $(M+H^+)$ Compound 84: (5-phenyl-4,5-dihydro-1H-pyrazol-1-yl)(4-(pyrimidin-2-yl)piperazin-1-yl)methanone

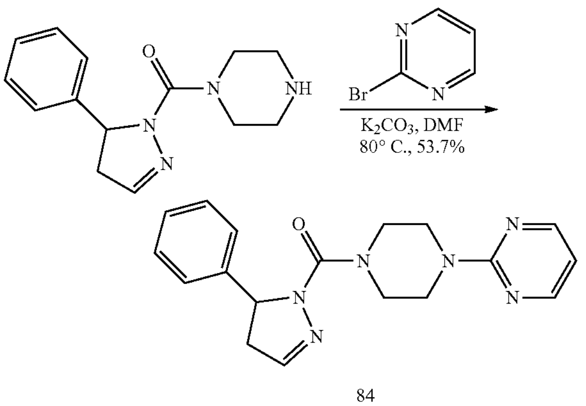

84

Step 1.

To a solution of (5-phenyl-4,5-dihydro-1H-pyrazol-1-yl) (piperazin-1-yl)methanone (50 mg, 0.19 mmol) and $K_2CO_3$ (67 mg, 0.48 mmol) in DMF (5 mL), (5-phenyl-4,5-dihydro-1H-pyrazol-1-yl)(4-(pyrimidin-2-yl)piperazin-1-yl)methanone (31 mg, 0.19 mmol) were added. The mixture was heated to 80° C. for 2.5 hrs. And then 30 mL $H_2O$ was added, extracted with EA (20 ml×3). The solvent was evaporated under reduced pressure to provide crude product 84 and further purified by silica gel column chromatography (PE/EA=1/1) to give 35 mg of 84 as a light yellow solid. For 84, $^1$H NMR (400 MHz, $CDCl_3$) δ 8.31 (d, J=4.0 Hz, 2H), 7.35-7.22 (m, 5H), 6.84 (t, J=4.0 Hz, 1H), 6.50 (t, J=4.0 Hz, 1H), 5.37-5.31 (m, 1H), 3.93-3.86 (m, 2H), 3.81-3.72 (m, 4H), 3.64-3.57 (m, 2H), 3.35-3.27 (m, 1H), 2.78-2.70 (m, 1H). LC-MS (m/z) 337.31 $[M+H]^+$.

Compound 85: (4-(5-fluoropyridin-2-yl)piperazin-1-yl)(5-phenyl-4,5-dihydro-1H-pyrazol-1-yl)methanone

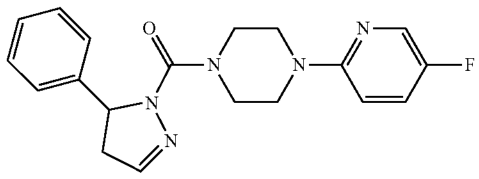 [SMILES: O=C(N1CCN(c2ccc(F)cn2)CC1)N1N=CCC1c1ccccc1]

The titled compound 84 was prepared in 62.3% yield from 1-(5-fluoropyridin-2-yl)piperazine, 5-phenyl-4,5-dihydro-1H-pyrazole and triphosgene according to the procedure outlined for compound 26. $^1$H NMR (400 MHz, $CDCl_3$) δ 8.07 (d, 1H, J=3.0 Hz), 7.35-728 (m, 5H), 7.25-7.21 (m, 1H), 6.84 (t, 1H, J=1.6 Hz), 6.64 (dd, 1H, J=9.6, 3.6 Hz), 5.36 (dd, 1H, J=9.6, 11.6 Hz), 3.86-3.76 (m, 2H), 3.73-3.63 (m, 2H), 3.62-3.54 (m, 2H), 3.50-3.42 (m, 2H), 3.32 (ddd, 1H, J=18.4, 12.0, 1.6 Hz), 2.75 (ddd, 1H, J=18.4, 9.6, 1.6 Hz). LC-MS (m/z): 354.40 $[M+H]^+$.

Compound 86: (5-phenyl-4,5-dihydro-1H-pyrazol-1-yl)(4-(pyrazin-2-yl)piperazin-1-yl)methanone

86

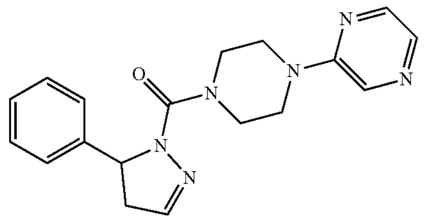

The titled compound 86 was prepared in a yield of 22% (15 mg) as a yellow solid according to the procedure for compound 28. $^1$H NMR (400 Hz, $CDCl_3$): δ 8.20-8.03 (m, 2H), 7.87 (s, 1H), 7.38-7.22 (m, 5H), 6.86 (s, 1H), 5.37 (dd, J=11.6, 9.6 Hz, 1H), 3.90-3.50 (m, 8H), 3.40-3.21 (m, 1H), 2.79-2.72 (m, 1H). LC-MS (ESI) m/z: 337.41, $[M+H]^+$.

Compound 87: (4-(5-methylpyrimidin-2-yl)piperazin-1-yl)(5-phenyl-4,5-dihydro-1H-pyrazol-1-yl) methanone

87

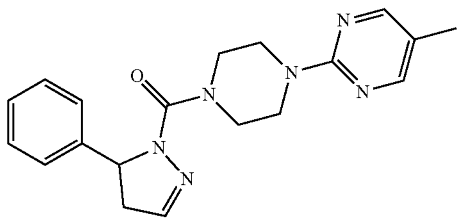

The titled compound 87 was prepared in a yield of 36% (25 mg) as a yellow solid according to the procedure for compound 28. $^1$H NMR (400 Hz, $CDCl_3$): δ 8.16 (s, 2H), 7.40-7.20 (m, 5H), 6.84 (s, 1H), 5.37 (dd, J=11.6, 9.6 Hz, 1H), 4.06-3.46 (m, 8H), 3.31 (m, 1H), 2.77-2.63 (m, 1H), 2.12 (s, 3H). LC-MS (ESI) m/z: 351.40, $[M+H]^+$.

Compound 88: (4-(5-chloropyrimidin-2-yl)piperazin-1-yl)(5-phenyl-4,5-dihydro-1H-pyrazol-1-yl) methanone

88

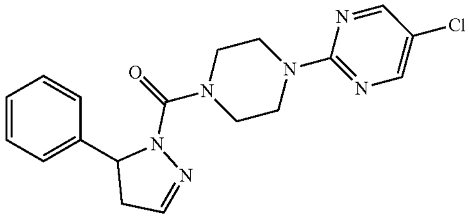

The titled compound 88 was prepared in a yield of 24% (18 mg) as a yellow solid according to the procedure for compound 28. $^1$H NMR (400 Hz, $CDCl_3$): δ 8.23 (s, 2H), 7.36-7.23 (m, 5H), 6.85 (s, 1H), 5.37 (dd, J=11.6, 9.6 Hz, 1H), 3.95-3.56 (m, 8H), 3.36-3.28 (m, 1H), 2.79-2.71 (m, 1H). LC-MS (ESI) m/z: 371.37, $[M+H]^+$.

Compound 89: (5-phenyl-4,5-dihydro-1H-pyrazol-1-yl)(4-(pyridazin-3-yl)piperazin-1-yl)methanone

89

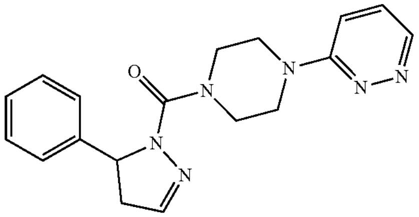

The titled compound 89 was prepared in a yield of 13% (9 mg) as a yellow solid according to the procedure for compound 28. $^1$H NMR (400 Hz, $CDCl_3$): δ 8.86 (s, 1H), 7.44-7.25 (m, 7H), 6.90 (s, 1H), 5.36 (dd, J=11.6, 9.6 Hz, 1H), 3.88-3.69 (m, 8H), 3.35 (m, 1H), 2.79 (m, 1H). LC-MS (ESI) m/z: 337.37, $[M+H]^+$.

Compound 90: (5-phenyl-4,5-dihydro-1H-pyrazol-1-yl)(4-(pyrimidin-4-yl)piperazin-1-yl)methanone

90

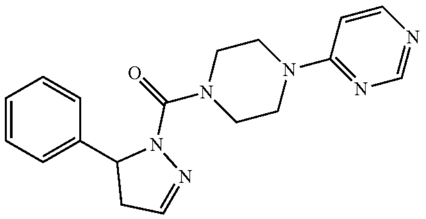

The titled compound 90 was prepared in a yield of 44% (29 mg) as a white solid according to the procedure for compound 28. $^1$H NMR (400 Hz, $CDCl_3$): δ 8.62 (s, 1H), 8.28 (d, J=6.8 Hz, 1H), 7.36-7.24 (m, 5H), 6.87 (s, 1H), 6.56 (d, J=6.8 Hz, 1H), 5.35 (dd, J=11.6, 9.6 Hz, 1H), 3.86-3.59 (m, 8H), 3.34 (m, 1H), 2.77 (m, 1H). LC-MS (ESI) m/z: 337.41, $[M+H]^+$.

Compound 91: (5-phenyl-4,5-dihydro-1H-pyrazol-1-yl)(4-phenylpiperazin-1-yl)methanone

91

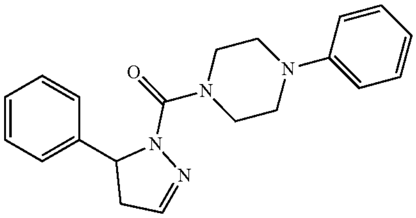

The titled compound 91 was prepared in a yield of 23% (15 mg) as a white solid according to the procedure for compound 28. $^1$H NMR (400 Hz, $CDCl_3$): δ 7.38-7.25 (m, 7H), 7.18 (d, J=8.4 Hz, 2H), 7.11 (t, J=7.2 Hz, 1H), 6.87 (s, 1H), 5.37 (dd, J=11.6, 9.6 Hz, 1H), 3.97-3.81 (m, 4H), 3.41-3.24 (m, 5H), 2.76 (m, 1H). LC-MS (ESI) m/z: 335.39, $[M+H]^+$.

Compound 92: (5-phenyl-4,5-dihydro-1H-pyrazol-1-yl)(4-(thiazol-2-yl)piperazin-1-yl)methanone

92

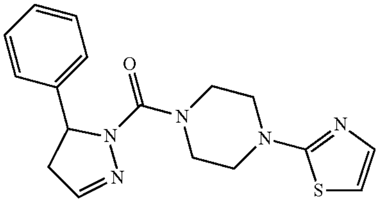

The titled compound 92 was prepared in a yield of 19.7% (13.0 mg) as a light yellow solid according to the procedure for 84. $^1$H NMR (400 MHz, $CDCl_3$) δ 7.39-7.25 (m, 6H), 6.89 (s, 1H), 6.63 (d, J=4.0 Hz, 1H), 5.34 (dd, J=12.0, 12.0

Hz, 1H), 3.88-3.82 (m, 2H), 3.78-3.70 (m, 4H), 3.66-3.61 (m, 2H), 3.38-3.30 (m, 1H), 2.81-2.74 (m, 1H). LC-MS (m/z) 342.41 $[M+H]^+$.

Compound 93: (4-(cyclopropanecarbonyl)piperazin-1-yl)(5-phenyl-4,5-dihydro-1H-pyrazol-1-yl)methanone

91

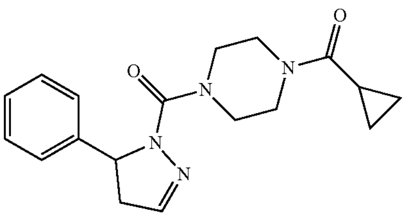

The titled compound 93 was prepared in a yield of 76% (49 mg) as a white solid according to the procedure for compound 28. $^1H$ NMR (400 Hz, $CDCl_3$): δ 7.36-7.26 (m, 5H), 6.85 (s, 1H), 5.35 (dd, J=11.6, 9.6 Hz, 1H), 3.77-3.52 (m, 8H), 3.31 (m, 1H), 2.75 (m, 1H), 1.14 (m, 1H), 1.02-0.98 (m, 2H), 0.80-0.75 (m, 2H) LC-MS (ESI) m/z: 327.35, $[M+H]^+$.

Compound 94: (4-(furan-2-carbonyl)piperazin-1-yl)(5-phenyl-4,5-dihydro-1H-pyrazol-1-yl)methanone

94

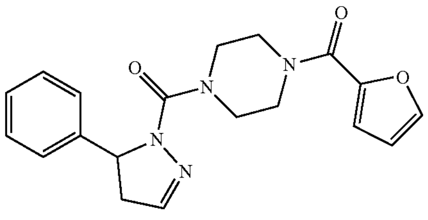

The titled compound 94 was prepared in a yield of 77% (54 mg) as a white solid according to the procedure for compound 28. $^1H$ NMR (400 Hz, $CDCl_3$): δ 7.48 (m, 1H), 7.36-7.25 (m, 5H), 7.02 (m, 1H), 6.85 (s, 1H), 6.49 (m, 1H), 5.36 (dd, J=11.6, 9.6 Hz, 1H), 3.91-3.55 (m, 8H), 3.31 (m, 1H), 2.75 (m, 1H). LC-MS (ESI) m/z: 353.35, $[M+H]^+$.

Compound 95: (4-benzoylpiperazin-1-yl)(5-phenyl-4,5-dihydro-1H-pyrazol-1-yl)methanone

95

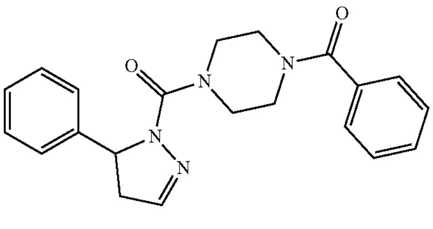

The titled compound 95 was prepared in a yield of 71% (51 mg) as a yellow solid according to the procedure for compound 28. $^1H$ NMR (400 Hz, $CDCl_3$): δ 7.43-7.25 (m, 10H), 6.83 (s, 1H), 5.34 (dd, J=11.6, 9.6 Hz, 1H), 3.91-3.17 (m, 9H), 2.72 (m, 1H). LC-MS (ESI) m/z: 363.42, $[M+H]^+$.

Compound 96: (4-(5-fluoropyrimidin-2-yl)-1,4-diazepan-1-yl)(5-phenyl-4,5-dihydro-1H-pyrazol-1-yl)methanone

96

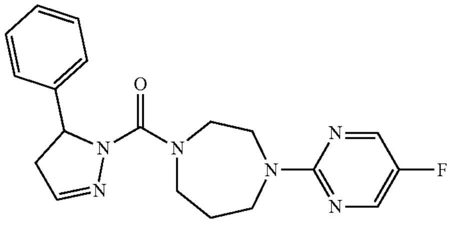

The titled compound 96 was prepared in a yield of 13.1% (13.0 mg) as a light yellow solid according to the procedure for 84. $^1H$ NMR (400 MHz, $CDCl_3$) δ 8.14 (s, 2H), 7.28-7.18 (m, 5H), 6.77 (t, J=4.0 Hz, 1H), 5.36-5.30 (m, 1H), 4.02-3.89 (m, 2H), 3.81-3.73 (m, 2H), 3.70-3.62 (m, 2H), 3.47-3.33 (m, 2H), 3.28-3.20 (m, 1H), 2.71-2.64 (m, 1H), 2.11-2.01 (m, 1H), 1.90-1.81 (m, 1H). LC-MS (m/z) 369.42 $[M+H]^+$.

Compound 97: (4-benzylpiperazin-1-yl)(5-phenyl-4,5-dihydro-1H-pyrazol-1-yl)methanone

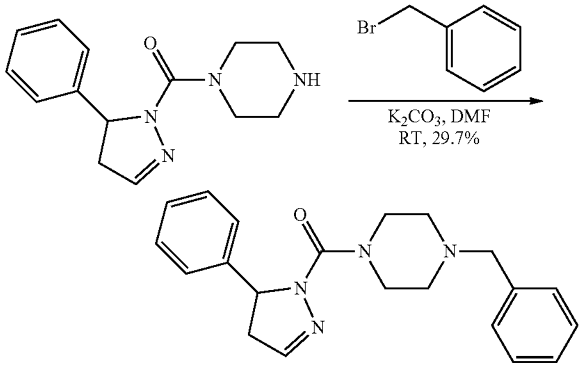

97

To a solution of (5-phenyl-4,5-dihydro-1H-pyrazol-1-yl)(piperazin-1-yl)methanone (50 mg, 0.19 mmol) and $K_2CO_3$ (66.7 mg, 0.48 mmol) in DMF (5 mL), (bromomethyl)benzene (33 mg, 0.19 mmol) were added. The mixture was stirred at RT for 2 hrs. And then 30 ml $H_2O$ was added, extracted with EA (20 ml×3). The solvent was evaporated under reduced pressure to provide crude product 97 and further purified by silica gel column chromatography (PE/EA=1/1) to give 20 mg of 97 as a light yellow solid. For 97, $^1H$ NMR (400 MHz, $CDCl_3$) δ 7.35-7.23 (m, 10H), 6.80 (t, J=4.0 Hz, 1H), 5.37-5.31 (m, 1H), 3.73-3.67 (m, 2H), 3.56-3.50 (m, 4H), 3.32-3.24 (m, 1H), 2.74-2.66 (m, 1H), 2.52-2.47 (m, 2H), 2.44-2.39 (m, 2H). LC-MS (m/z) 349.43 $[M+H]^+$.

Compound 98: 4-((4-(5-phenyl-4,5-dihydro-1H-pyrazole-1-carbonyl)piperazin-1-yl)methyl)benzonitrile

98

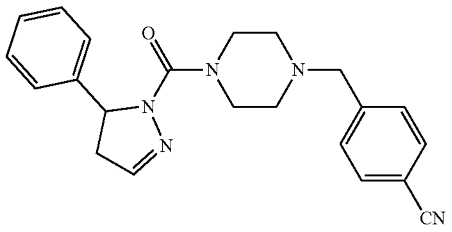

The titled compound 98 was prepared in a yield of 47% (34.0 mg) as a light yellow solid according to the procedure for 97. $^1$H NMR (400 MHz, $CDCl_3$) δ 7.61 (d, J=8.0 Hz, 2H), 7.45 (d, J=8.0 Hz, 2H), 7.34-7.23 (m, 5H), 6.81 (t, J=4.0 Hz, 1H), 5.34-5.29 (m, 1H), 3.73-3.67 (m, 2H), 3.56-3.50 (m, 4H), 3.33-3.25 (m, 1H), 2.74-2.67 (m, 1H), 2.51-2.45 (m, 2H), 2.42-2.37 (m, 2H). LC-MS (m/z) 374.51 $[M+H]^+$.

Compound 99: (5-phenyl-4,5-dihydro-1H-pyrazol-1-yl)(4-(pyrimidin-5-yl)piperazin-1-yl)methanone

99

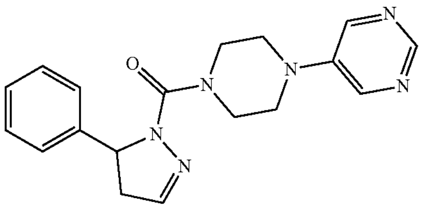

The titled compound 99 was prepared in a yield of 15% (19 mg) as a yellow solid according to the procedure for compound 28. $^1$H NMR (400 Hz, $CDCl_3$): δ 8.71 (s, 1H), 8.38 (s, 2H), 7.36-7.24 (m, 5H), 6.86 (s, 1H), 5.37 (dd, J=11.6, 9.6 Hz, 1H), 3.89-3.69 (m, 4H), 3.37-3.19 (m, 5H), 2.76 (m, 1H). LC-MS (ESI) m/z: 337.32, $[M+H]^+$.

Compound 100: (5-(3-fluorophenyl)-4,5-dihydro-1H-pyrazol-1-yl)(4-(5-fluoropyrimidin-2-yl)piperazin-1-yl)methanone

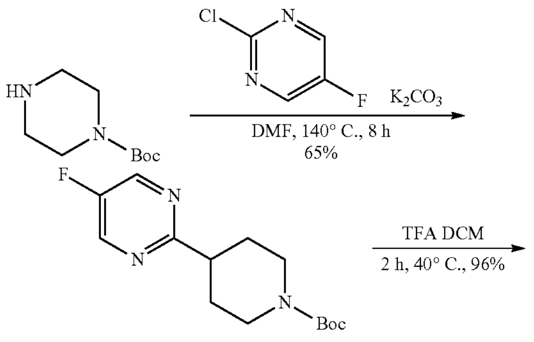

100-1

-continued

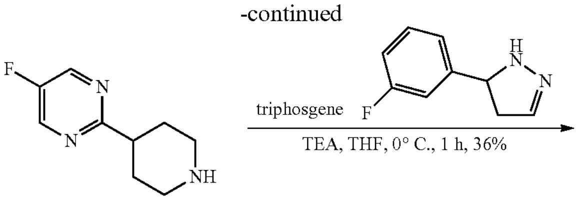

100-2

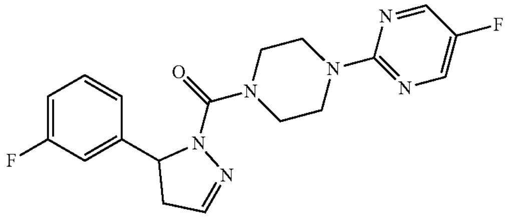

100

Step1: Compound 100-1 was synthesized according to the method of compound 28 while using tert-butyl piperazine-1-carboxylate (1.0 g, 5.37 mmol) and 2-chloro-5-fluoropyrimidine (782 mg, 5.91 mmol). tert-butyl 4-(5-fluoropyrimidin-2-yl)piperazine-1-carboxylate was obtained as pale yellow powder (980 mg, yield 65%). LC-MS (m/z) 283.34 $[M+H]^+$.

Step2: To a solution of tert-butyl 4-(5-fluoropyrimidin-2-yl)piperazine-1-carboxylate (980 mg, 3.47 mmol) in dichloromethane (10 mL), trifluoroacetic was added dropwise at 0° C. then the mixture was refluxed for 2 hours. The volatiles was removed in vacuo and the residue was suspension in dichloromethane, sat The organic layer was washed with water, sat.$NaHCO_3$(aq) and brine respectively. Then dried over $MgSO_4$, filtered, and concentrated under reduced pressure. 5-fluoro-2-(piperazin-1-yl)pyrimidine was obtained as light pink solid (610 mg, yield 96%). The crude product was used in next step directly without further purification. LC-MS (m/z) 183.44 $[M+H]^+$.

Step3: To a solution of 5-(3-fluorophenyl)-4,5-dihydro-1H-pyrazole (50 mg, 0.3 mmol) and triethylamine (93 mg, 0.94 mmol) in super dry dichloromethane (8 mL), triphosgene (36 mg, 0.12 mmol) was added at 0° C. under argon protection. the mixture was stirred for 30 mins before a solution of 5-fluoro-2-(piperazin-1-yl)pyrimidine (73 mg, 0.4 mmol) and triethylamine (61 mg, 0.61 mmol) in super dry dichloromethane (2 mL) was added dropwise. The mixture was stirred for other 30 mins. The reaction was quenched by sat.$NaHCO_3$(aq), the volatiles was removed in vacuo and the residue was suspension in dichloromethane, sat The organic layer was washed with water, and brine respectively. The residue was purified by silica gel column chromatography (petroleum ether/AcOEt, 1/1) to give (5-(3-fluorophenyl)-4,5-dihydro-1H-pyrazol-1-yl)(4-(5-fluoropyrimidin-2-yl)piperazin-1-yl)methanone 100 (40.5 mg, yield 36%) as a white powder after lyophilization. $^1$H NMR (400 MHz, Chloroform-d) δ 8.22-8.19 (s, 2H), 7.33-7.27 (m, 1H), 7.08 (dt, J=7.6, 1.4 Hz, 1H), 7.03-6.91 (m, 2H), 6.84 (q, J=1.8 Hz, 1H), 5.36 (dd, J=11.8, 9.8 Hz, 1H), 3.90-3.79 (m, 2H), 3.79-3.70 (m, 4H), 3.67-3.54 (m, 2H), 3.32 (ddt, J=18.2, 11.8, 1.8 Hz, 1H), 2.71 (ddt, J=18.4, 9.8, 1.6 Hz, 1H). LC-MS (m/z) 373.42 $[M+H]^+$.

Compound 101: (5-(3,5-difluorophenyl)-4,5-dihydro-1H-pyrazol-1-yl)(4-(5-fluoropyrimidin-2-yl)piperazin-1-yl)methanone

101

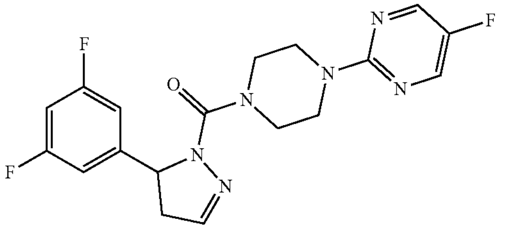

Compound 101 was synthesized according to the method of compound 100 while using 5-(3,5-difluorophenyl)-4,5-dihydro-1H-pyrazole. (5-(3,5-difluorophenyl)-4,5-dihydro-1H-pyrazol-1-yl)(4-(5-fluoropyrimidin-2-yl)piperazin-1-yl)methanone was obtained as white powder (yield 39%). $^1$H NMR (400 MHz, Chloroform-d) δ 8.21 (d, J=0.6 Hz, 2H), 6.87-6.78 (m, 3H), 6.69 (tt, J=8.8, 2.4 Hz, 1H), 5.33 (dd, J=11.6, 9.8 Hz, 1H), 3.92-3.81 (m, 2H), 3.81-3.70 (m, 4H), 3.69-3.57 (m, 2H), 3.32 (ddd, J=18.2, 11.8, 1.8 Hz, 1H), 2.68 (ddd, J=18.2, 9.8, 1.6 Hz, 1H). LC-MS (m/z) 391.76 $[M+H]^+$.

Compound 102: (4-(4-aminopyrimidin-2-yl)piperazin-1-yl)(5-phenyl-4,5-dihydro-1H-pyrazol-1-yl)methanone

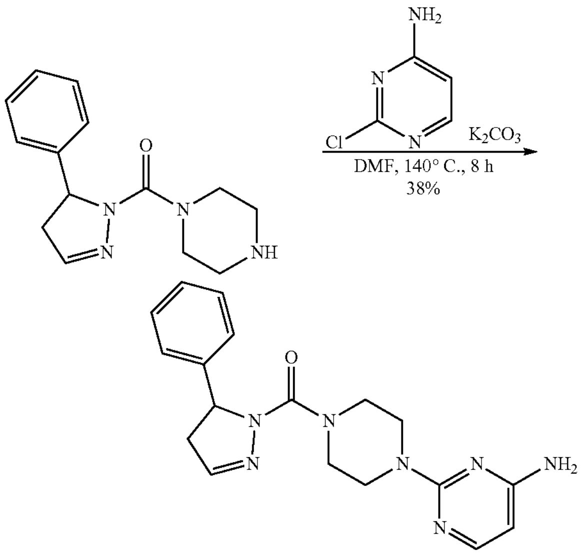

102

To a solution of (5-phenyl-4,5-dihydro-1H-pyrazol-1-yl)(piperazin-1-yl)methanone (50.0 mg, 0.19 mmol) and 2-chloropyrimidin-4-amine (30.1 mg, 0.23 mmol) in super dry DMF (3.0 mL), $K_2CO_3$ (80.3 mg, 0.58 mmol) was added under argon protection. The mixture was stirred at 140° C. for 8 h. The solvent was removed in vacuo and the residue was purified by column chromatography (silica gel, ethyl acetate/methanol=1:0 to 10:1) to afford (4-(4-aminopyrimidin-2-yl)piperazin-1-yl)(5-phenyl-4,5-dihydro-1H-pyrazol-1-yl)methanone (compound 102) as pale yellow powder (26 mg, yield 38%). $^1$H NMR (400 MHz, Chloroform-d) δ 7.88 (d, J=5.8 Hz, 1H), 7.40-7.19 (m, 5H), 6.83 (t, J=2.8 Hz, 1H), 5.82 (d, J=5.8 Hz, 1H), 5.35 (t, J=11.7 Hz, 1H), 4.97 (br, 2H), 3.91-3.78 (m, 2H), 3.77-3.65 (m, 4H), 3.57 (m, 2H), 3.36-3.24 (m, 1H), 2.73 (m, 1H). LC-MS (m/z) 352.63 $[M+H]^+$.

Compound 103: (4-(4-hydroxypyrimidin-2-yl)piperazin-1-yl)(5-phenyl-4,5-dihydro-1H-pyrazol-1-yl)methanone

103

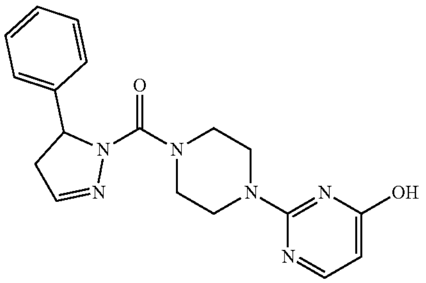

Compound 103 was synthesized according to the method of compound 102 while using 2-chloropyrimidin-4-ol. (4-(4-hydroxypyrimidin-2-yl)piperazin-1-yl)(5-phenyl-4,5-dihydro-1H-pyrazol-1-yl)methanone was obtained as a white powder (yield 46%). $^1$H NMR (400 MHz, Chloroform-d) δ 8.07 (s, 1H), 7.42-7.15 (m, 5H), 6.85 (d, J=2.8 Hz, 1H), 5.33 (d, J=9.8 Hz, 1H), 3.74-3.45 (m, 6H), 3.46-3.24 (m, 4H), 2.75 (d, J=8.6 Hz, 2H). LC-MS (m/z) 353.36 $[M+H]^+$.

Compound 104: (4-(5-chlorothiazol-2-yl)piperazin-1-yl)(5-phenyl-4,5-dihydro-1H-pyrazol-1-yl)methanone

104

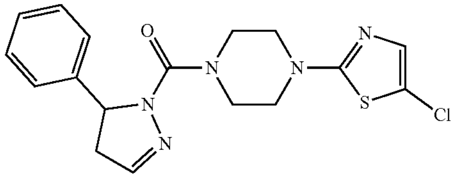

The titled compound 104 was prepared in a yield of 2.8% (2.0 mg) as a light yellow solid according to the procedure for 84. $^1$H NMR (400 MHz, $CDCl_3$) δ 7.35-7.24 (m, 5H), 6.99 (s, 1H), 6.85 (s, 1H), 5.38-5.33 (m, 1H), 3.81-3.75 (m, 2H), 3.69-3.63 (m, 2H), 3.53-3.48 (m, 2H), 3.41-3.35 (m, 2H), 3.34-3.29 (m, 1H), 2.79-2.72 (m, 1H). LC-MS (m/z) 376.94 $[M+H]^+$.

Compound 105: (4-(4-methylthiazol-2-yl)piperazin-1-yl)(5-phenyl-4,5-dihydro-1H-pyrazol-1-yl)methanone

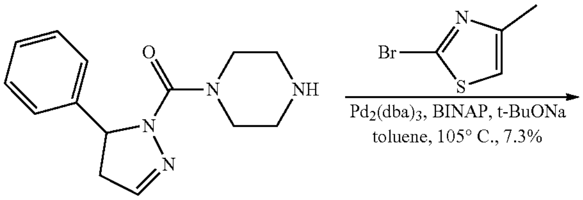

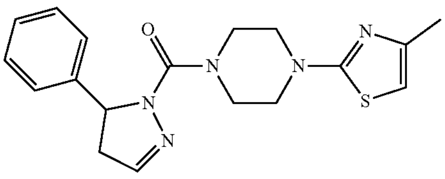

105

To a solution of (5-phenyl-4,5-dihydro-1H-pyrazol-1-yl)(piperazin-1-yl)methanone (50 mg, 0.19 mmol), 2-bromo-4-methylthiazole (35 mg, 0.19 mmol), $Pd_2(dba)_3$ (30 mg, 0.033 mmol), BINAP (36 mg, 0.058 mmol) and t-BuONa (22.3 mg, 0.23 mmol) in toluene (5 mL). The mixture was heated to 105° C. overnight. The solvent was evaporated under reduced pressure to provide crude product 105 and further purified by silica gel column chromatography (PE/EA=1/1) to give 5 mg of 105 as a light yellow solid. For 105, 1H NMR (400 MHz, $CDCl_3$) δ 7.36-7.32 (m, 2H), 7.28-726 (m, 3H), 6.90 (s, 1H), 6.20 (s, 1H), 5.35-5.30 (m, 1H), 3.88-3.82 (m, 2H), 3.77-3.74 (m, 4H), 3.69-3.65 (m, 2H), 3.38-3.31 (m, 1H), 2.82-2.75 (m, 1H), 2.32 (s, 3H). LC-MS (m/z) 356.51 $[M+H]^+$.

Compound 106: (4-(5-methylthiazol-2-yl)piperazin-1-yl)(5-phenyl-4,5-dihydro-1H-pyrazol-1-yl)methanone

106

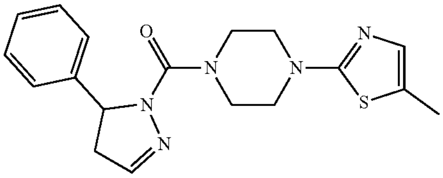

The titled compound 106 was prepared in a yield of 10.2% (7.0 mg) as a light yellow solid according to the procedure for 105. $^1H$ NMR (400 MHz, $CDCl_3$) δ 7.36-7.32 (m, 2H), 7.28-7.25 (m, 3H), 7.06 (s, 1H), 6.90 (s, 1H), 5.35-5.30 (m, 1H), 3.88-3.82 (m, 2H), 3.78-3.70 (m, 4H), 3.67-3.61 (m, 2H), 3.39-3.31 (m, 1H), 2.82-2.75 (m, 1H), 2.32 (s, 3H). LC-MS (m/z) 356.51 $[M+H]^+$.

Compound 107: 2-(4-(5-phenyl-4,5-dihydro-1H-pyrazole-1-carbonyl)piperazin-1-yl)thiazole-4-carbonitrile

107

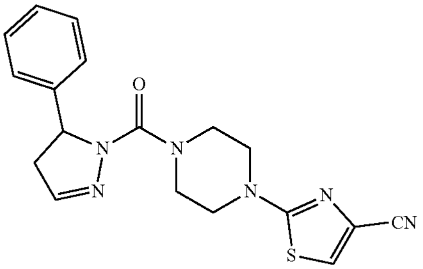

Compound 107 was synthesized according to the method of compound 102 while using 2-bromothiazole-4-carbonitrile. 2-(4-(5-phenyl-4,5-dihydro-1H-pyrazole-1-carbonyl)piperazin-1-yl)thiazole-4-carbonitrile was obtained as white powder (yield 42%). $^1H$ NMR (400 MHz, Chloroform-d) δ 7.38-7.22 (m, 6H), 6.86 (t, J=1.8 Hz, 1H), 5.35 (dd, J=11.8, 9.6 Hz, 1H), 3.79 (m, 2H), 3.67 (m, 2H), 3.59 (m, 2H), 3.47 (m, 2H), 3.33 (m, 1H), 2.76 (m, 1H). LC-MS (m/z) 367.45 $[M+H]^+$.

Compound 108: 2-(4-(5-phenyl-4,5-dihydro-H-pyrazole-1-carbonyl)piperazin-1-yl)thiazole-5-carbonitrile

108

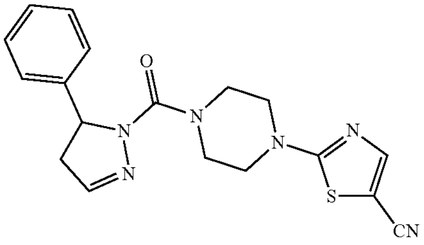

Compound 108 was synthesized according to the method of compound 102 while using 2-chlorothiazole-5-carbonitrile. 2-(4-(5-phenyl-4,5-dihydro-1H-pyrazole-1-carbonyl)piperazin-1-yl)thiazole-5-carbonitrile was obtained as white powder (yield 45%). $^1H$ NMR (400 MHz, Chloroform-d) δ 7.69 (s, 1H), 7.37-7.23 (m, 5H), 6.86 (t, J=1.8 Hz, 1H), 5.35 (dd, J=11.8, 9.4 Hz, 1H), 3.86-3.75 (m, 2H), 3.73-3.62 (m, 4H), 3.60-3.48 (m, 2H), 3.34 (m, 1H), 2.77 (m, 1H). LC-MS (m/z) 367.63 $[M+H]^+$.

Compound 109: ((S)-4-(5-fluoropyrimidin-2-yl)-2-methylpiperazin-1-yl)((S)-3-phenylisoxazolidin-2-yl)methanone

109

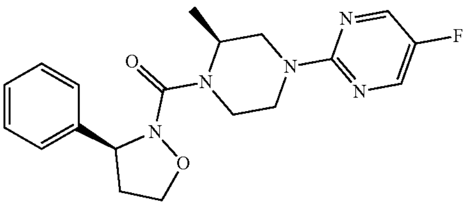

The titled compound 109 was prepared in a yield of 65% (24 mg) as a white solid according to the procedure for compound 28. 1H NMR (400 Hz, CDCl3): δ 8.19 (s, 2H), 7.42-7.24 (m, 5H), 5.48 (dd, J=8.4, 4.4 Hz, 1H), 4.54-4.40 (m, 3H), 4.20-4.10 (m, 2H), 3.91 (m, 1H), 3.25-3.02 (m, 3H), 2.80 (m, 1H), 2.31 (m, 1H), 1.26 (d, J=6.8 Hz, 3H). LC-MS (ESI) m/z: 372.39, [M+H]+.

Compound 110: ((2R,6S)-4-(5-fluoropyrimidin-2-yl)-2,6-dimethylpiperazin-1-yl)((S)-3-phenylisoxazolidin-2-yl)methanone

110

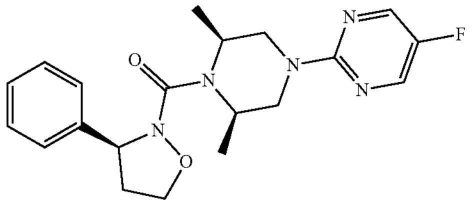

The titled compound 110 was prepared in a yield of 37% (14 mg) as a white solid according to the procedure for compound 28. 1H NMR (400 Hz, CDCl3): δ 8.19 (s, 2H), 7.42-7.25 (m, 5H), 5.46 (dd, J=8.4, 4.8 Hz, 1H), 4.67 (m, 1H), 4.43-4.34 (m, 3H), 4.13 (m, 1H), 3.92 (m, 1H), 3.32-3.09 (m, 2H), 2.82 (m, 1H), 2.32 (m, 1H), 1.36 (d, J=6.8 Hz, 3H), 1.28 (d, J=6.8 Hz, 3H). LC-MS (ESI) m/z: 386.39, $[M+H]^+$.

Compound 111A: (S)-(4-(5-fluoropyrimidin-2-yl)-2-methylpiperazin-1-yl)(5-phenyl-4,5-dihydro-1H-pyrazol-1-yl)methanone

111A

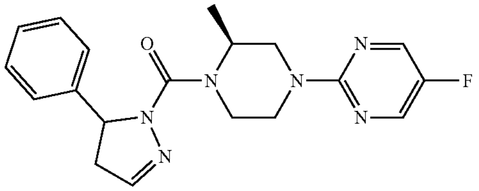

The titled compound 111A was prepared in a yield of 16% (23.0 mg) as a light yellow solid according to the procedure for 84. $^1H$ NMR (400 MHz, $CDCl_3$) δ 8.18 (s, 2H), 7.35-7.22 (m, 5H), 6.82 (t, J=4.0 Hz, 1H), 5.41-5.35 (m, 1H), 4.50-4.47 (m, 2H), 4.44-4.40 (m, 1H), 4.28-4.24 (m, 1H), 3.34-3.07 (m, 4H), 2.75-2.68 (m, 1H), 1.26 (d, J=8.0 Hz, 3H). LC-MS (m/z) 369.42 $[M+H]^+$.

111B: (S)-(4-(5-fluoropyrimidin-2-yl)-2-methylpiperazin-1-yl)(5-phenyl-4,5-dihydro-1H-pyrazol-1-yl)methanone

111B

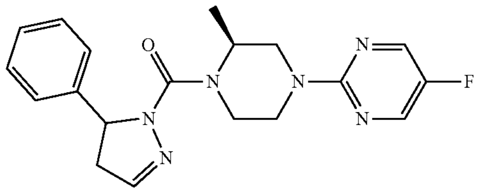

The titled compound 111B was prepared in a yield of 22.3% (32.0 mg) as a light yellow solid according to the procedure for 84. $^1H$ NMR (400 MHz, $CDCl_3$) δ 8.18 (s, 2H), 7.36-7.22 (m, 5H), 6.85 (t, J=4.0 Hz, 1H), 5.38-5.33 (m, 1H), 4.79-4.73 (m, 1H), 4.55-4.51 (m, 1H), 4.40-4.36 (m, 1H), 3.96-3.93 (m, 1H), 3.39-3.27 (m, 3H), 3.01-2.94 (m, 1H), 2.77-2.70 (m, 1H), 1.15 (d, J=8.0 Hz, 3H). LC-MS (m/z) 369.41 $[M+H]^+$.

Compound 112A: (S)-(2-methyl-4-(pyrimidin-2-yl)piperazin-1-yl)(5-phenyl-4,5-dihydro-1H-pyrazol-1-yl)methanone

112A

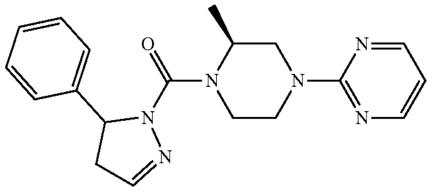

The titled compound 112A was prepared in a yield of 49.7% (32.0 mg) as a light yellow solid according to the procedure for 84. $^1H$ NMR (400 MHz, $CDCl_3$) δ 8.30 (d, J=4.0 Hz, 2H), 7.35-7.22 (m, 5H), 6.83-6.82 (m, 1H), 6.49-4.47 (m, 1H), 5.41-5.35 (m, 1H), 4.60-4.47 (m, 3H), 4.29-4.25 (m, 1H), 3.33-3.11 (m, 4H), 2.75-2.67 (m, 1H), 1.26 (d, J=4.0 Hz, 3H). LC-MS (m/z) 351.41 $[M+H]^+$.

Compound 112B (S)-(2-methyl-4-(pyrimidin-2-yl)piperazin-1-yl)(5-phenyl-4,5-dihydro-1H-pyrazol-1-yl)methanone

112B

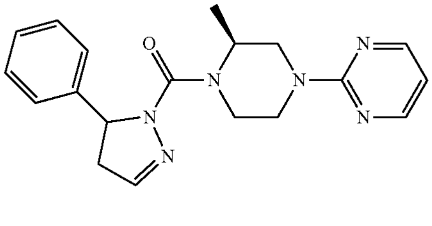

The titled compound 112B was prepared in a yield of 45.1% (29.0 mg) as a light yellow solid according to the procedure for 84. $^1H$ NMR (400 MHz, $CDCl_3$) δ 8.29 (d, J=4.0 Hz, 2H), 7.35-7.22 (m, 5H), 6.86-6.85 (m, 1H), 6.49-6.47 (m, 1H), 5.39-5.33 (m, 1H), 4.80-4.73 (m, 1H), 4.65-4.61 (m, 1H), 4.49-4.45 (m, 1H), 3.98-3.93 (m, 1H), 3.40-3.26 (m, 3H), 3.00-2.95 (m, 1H), 2.77-2.70 (m, 1H), 1.15 (d, J=8.0 Hz, 3H). LC-MS (m/z) 351.42 [M+H]$^+$.

Compound 113A: ((S)-4-(5-chloropyrimidin-2-yl)-2-methylpiperazin-1-yl)(5-phenyl-4,5-dihydro-1H-pyrazol-1-yl)methanone

113A

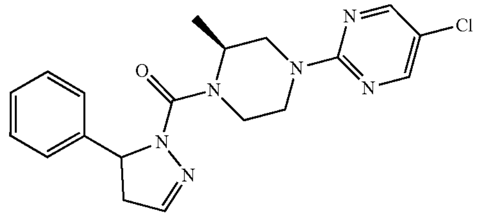

The titled compound 113A was prepared in a yield of 41% (32 mg) as a yellow solid according to the procedure for compound 28. 1H NMR (400 Hz, CDCl3): δ 8.21 (s, 2H), 7.35-7.22 (m, 5H), 6.82 (s, 1H), 5.38 (dd, J=11.6, 10.0 Hz, 1H), 4.56-4.41 (m, 3H), 4.25 (m, 1H), 3.34-3.07 (m, 4H), 2.71 (m, 1H), 1.24 (d, J=6.8 Hz, 3H). LC-MS (ESI) m/z: 385.34, [M+H]$^+$.

Compound 113B ((S)-4-(5-chloropyrimidin-2-yl)-2-methylpiperazin-1-yl)(5-phenyl-4,5-dihydro-1H-pyrazol-1-yl)methanone

113B

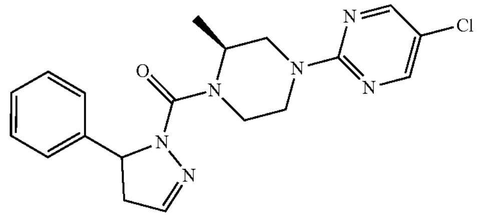

The titled compound 113B was prepared in a yield of 91% (70 mg) as a yellow solid according to the procedure for compound 28. 1H NMR (400 Hz, CDCl3): δ 8.21 (s, 2H), 7.36-7.21 (m, 5H), 6.85 (s, 1H), 5.35 (dd, J=11.6, 10.0 Hz, 1H), 4.79-4.39 (m, 3H), 3.95 (m, 1H), 3.38-3.25 (m, 3H), 3.03-2.94 (m, 1H), 2.72 (m, 1H), 1.13 (d, J=7.2 Hz, 3H). LC-MS (ESI) m/z: 385.34, [M+H]$^+$.

Compound 114A: ((R)-4-(5-fluoropyrimidin-2-yl)-2-methylpiperazin-1-yl)(5-phenyl-4,5-dihydro-1H-pyrazol-1-yl)methanone

114A

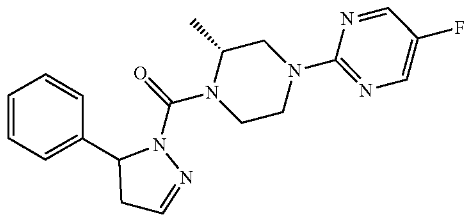

The titled compound 114A was prepared in a yield of 15% (11.2 mg) as a yellow solid according to the procedure for compound 28. 1H NMR (400 Hz, CDCl3): δ 8.18 (s, 2H), 7.35-7.23 (m, 5H), 6.83 (s, 1H), 5.38 (dd, J=12.0, 10.0 Hz, 1H), 4.52-4.23 (m, 4H), 3.35-3.07 (m, 4H), 2.72 (m, 1H), 1.26 (d, J=6.8 Hz, 3H). LC-MS (ESI) m/z: 369.36, [M+H]$^+$.

Compound 114B: ((R)-4-(5-fluoropyrimidin-2-yl)-2-methylpiperazin-1-yl)(5-phenyl-4,5-dihydro-1H-pyrazol-1-yl)methanone

114B

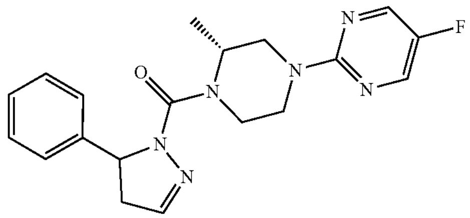

The titled compound 114B was prepared in a yield of 38% (28 mg) as a yellow solid according to the procedure for compound 28. $^1$H NMR (400 Hz, $CDCl_3$): δ 8.18 (s, 2H), 7.35-7.23 (m, 5H), 6.86 (s, 1H), 5.36 (dd, J=12.0, 10.0 Hz, 1H), 4.78-4.36 (m, 3H), 3.95 (m, 1H), 3.40-3.24 (m, 3H), 2.97 (m, 1H), 2.72 (m, 1H), 1.15 (d, J=6.8 Hz, 3H). LC-MS (ESI) m/z: 369.37, [M+H]$^+$.

Compound 115A: ((S)-4-(5-fluoropyridin-2-yl)-2-methylpiperazin-1-yl)(5-phenyl-4,5-dihydro-1H-pyrazol-1-yl)methanone

115A

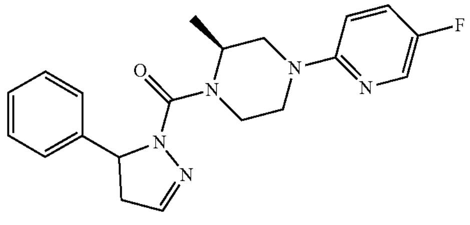

The titled compound 115A was prepared in a yield of 14% (10 mg) as a yellow solid according to the procedure for compound 28. $^1$H NMR (400 Hz, $CDCl_3$): δ 8.07 (d, J=2.8

Hz, 1H), 7.35-7.21 (m, 6H), 6.83 (s, 1H), 6.65 (d, J=9.2, 2.8 Hz, 1H), 5.37 (dd, J=11.6, 9.6 Hz, 1H), 4.53 (m, 1H), 4.30 (m, 1H), 4.04-3.92 (m, 2H), 3.37-3.09 (m, 4H), 2.72 (m, 1H), 1.34 (d, J=6.8 Hz, 3H). LC-MS (ESI) m/z: 368.34, [M+H]$^+$.

Compound 115B ((S)-4-(5-fluoropyridin-2-yl)-2-methylpiperazin-1-yl)(5-phenyl-4,5-dihydro-1H-pyrazol-1-yl)methanone

115B

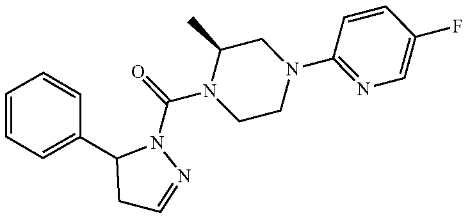

The titled compound 115B was prepared in a yield of 12% (9 mg) as a yellow solid according to the procedure for compound 28. $^1$H NMR (400 Hz, $CDCl_3$): δ 8.05 (d, J=3.2 Hz, 1H), 7.34-7.23 (m, 6H), 6.85 (s, 1H), 6.63 (d, J=9.2, 3.2 Hz, 1H), 5.35 (dd, J=11.6, 9.6 Hz, 1H), 4.80 (m, 1H), 4.09-3.89 (m, 3H), 3.48-3.07 (m, 4H), 2.72 (m, 1H), 1.23 (d, J=6.8 Hz, 3H). LC-MS (ESI) m/z: 368.35, [M+H]$^+$.

Compound 116A: 2-((3S)-3-methyl-4-(5-phenyl-4,5-dihydro-1H-pyrazole-1-carbonyl)piperazin-1-yl)pyrimidine-5-carbonitrile

116A

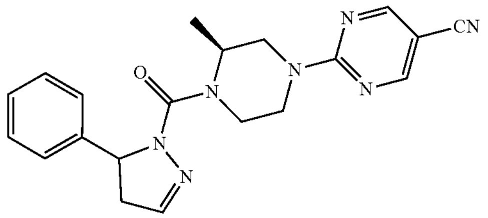

The titled compound 116A was prepared in a yield of 32% (12 mg) as a white solid according to the procedure for compound 28. $^1$H NMR (400 Hz, $CDCl_3$): δ 8.48 (s, 2H), 7.36-7.24 (m, 5H), 6.84 (s, 1H), 5.37 (dd, J=11.6, 9.6 Hz, 1H), 4.69-4.51 (m, 3H), 4.29 (m, 1H), 3.36-3.18 (m, 4H), 2.74 (m, 1H), 1.22 (d, J=6.8 Hz, 3H). LC-MS (ESI) m/z: 376.44, [M+H]$^+$.

Compound 116B: 2-((3S)-3-methyl-4-(5-phenyl-4,5-dihydro-1H-pyrazole-1-carbonyl)piperazin-1-yl)pyrimidine-5-carbonitrile

116B

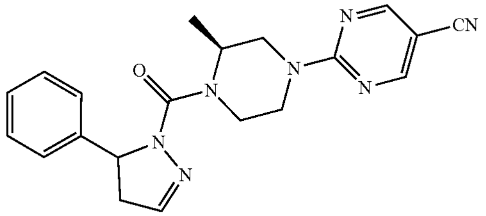

The titled compound 116B was prepared in a yield of 48% (18 mg) as a white solid according to the procedure for compound 28. $^1$H NMR (400 Hz, $CDCl_3$): δ 8.48 (s, 2H), 7.35-7.25 (m, 5H), 6.87 (s, 1H), 5.35 (dd, J=11.6, 9.6 Hz, 1H), 4.82-4.54 (m, 3H), 3.99 (m, 1H), 3.41-3.28 (m, 3H), 3.06 (m, 1H), 2.75 (m, 1H), 1.11 (d, J=6.8 Hz, 3H). LC-MS (ESI) m/z: 376.41, [M+H]$^+$.

Compound 117A: ((S)-5-(3-fluorophenyl)-4,5-dihydro-H-pyrazol-1-yl)((S)-4-(5-fluoropyrimidin-2-yl)-2-methylpiperazin-1-yl)methanone

117A

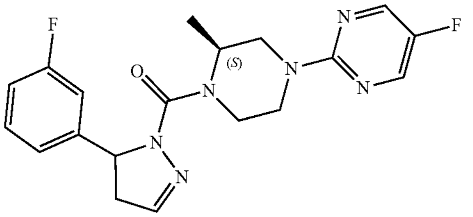

Compound 117A was synthesized according to the method of compound 102 while using (5-(3-fluorophenyl)-4,5-dihydro-1H-pyrazol-1-yl)((S)-2-methylpiperazin-1-yl)methanone and 2-chloro-5-fluoropyrimidine. ((S)-5-(3-fluorophenyl)-4,5-dihydro-1H-pyrazol-1-yl)((S)-4-(5-fluoropyrimidin-2-yl)-2-methylpiperazin-1-yl)methanone was obtained as white powder (yield 26%). $^1$H NMR (400 MHz, Chloroform-d) δ 8.19 (s, 2H), 7.08 (s, 1H), 7.02-6.91 (m, 3H), 6.83 (s, 1H), 5.37 (s, 1H), 4.37-4.56 (m, 3H), 4.26 (m, 1H), 3.04-3.40 (m, 4H), 2.70 (m, 1H), 1.26 (s, 3H). LC-MS (m/z) 387.56 [M+H]$^+$.

Compound 117B: ((R)-5-(3-fluorophenyl)-4,5-dihydro-1H-pyrazol-1-yl)((S)-4-(5-fluoropyrimidin-2-yl)-2-methylpiperazin-1-yl)methanone

117B

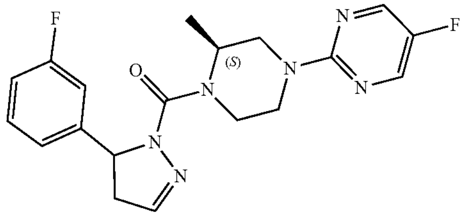

Compound 117B was synthesized according to the method of compound 102 while using (5-(3-fluorophenyl)-4,5-dihydro-1H-pyrazol-1-yl)((S)-2-methylpiperazin-1-yl) methanone and 2-chloro-5-fluoropyrimidine. ((S)-5-(3-fluorophenyl)-4,5-dihydro-1H-pyrazol-1-yl)((S)-4-(5-fluoropyrimidin-2-yl)-2-methylpiperazin-1-yl)methanone was obtained as white powder (yield 22%). $^1$H NMR (400 MHz, Chloroform-d) δ 8.20 (s, 2H), 7.08 (s, 1H), 7.02-6.91 (m, 3H), 6.83 (s, 1H), 5.32 (s, 1H), 4.36-4.52 (m, 3H), 4.26 (m, 1H), 3.05-3.36 (m, 4H), 2.71 (m, 1H), 1.24 (s, 3H). LC-MS (m/z) 387.69 [M+H]$^+$.

Compound 118A: ((S)-5-(3,5-difluorophenyl)-4,5-dihydro-1H-pyrazol-1-yl)((S)-4-(5-fluoropyrimidin-2-yl)-2-methylpiperazin-1-yl)methanone

118A

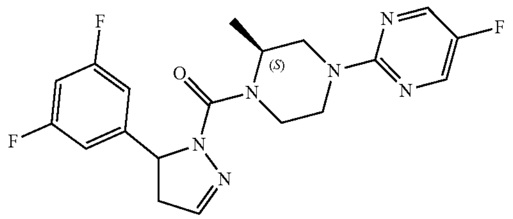

Compound 118A was synthesized according to the method of compound 102 while using (5-(3,5-difluorophenyl)-4,5-dihydro-1H-pyrazol-1-yl)((S)-2-methylpiperazin-1-yl)methanone and 2-chloro-5-fluoropyrimidine. ((S)-5-(3,5-difluorophenyl)-4,5-dihydro-1H-pyrazol-1-yl)((S)-4-(5-fluoropyrimidin-2-yl)-2-methylpiperazin-1-yl)methanone was obtained as white powder (yield 14%). $^1$H NMR (400 MHz, Chloroform-d) δ 8.22 (s, 2H), 6.86-6.76 (m, 3H), 6.74-6.64 (m, 1H), 5.34 (t, J=10.8 Hz, 1H), 4.60-4.40 (m, 3H), 4.28 (d, J=13.0 Hz, 1H), 3.24 (ddd, J=43.0, 16.2, 11.2 Hz, 4H), 2.66 (dd, J=18.2, 10.0 Hz, 1H), 1.28 (d, J=6.7 Hz, 3H). LC-MS (m/z) 405.82 [M+H]$^+$.

Compound 118B: ((R)-5-(3,5-difluorophenyl)-4,5-dihydro-1H-pyrazol-1-yl)((S)-4-(5-fluoropyrimidin-2-yl)-2-methylpiperazin-1-yl)methanone

118B

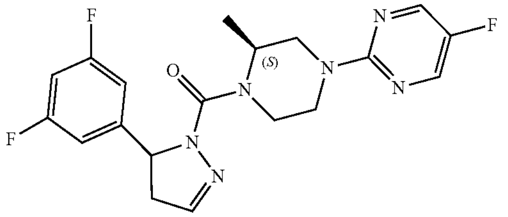

Compound 118B was synthesized according to the method of compound 102 while using (5-(3,5-difluorophenyl)-4,5-dihydro-1H-pyrazol-1-yl)((S)-2-methylpiperazin-1-yl)methanone and 2-chloro-5-fluoropyrimidine. ((R)-5-(3,5-difluorophenyl)-4,5-dihydro-1H-pyrazol-1-yl)((S)-4-(5-fluoropyrimidin-2-yl)-2-methylpiperazin-1-yl)methanone was obtained as white powder (yield 16%). $^1$H NMR (400 MHz, Chloroform-d) δ 8.22 (s, 2H), 6.84-6.73 (m, 3H), 6.74-6.65 (m, 1H), 5.30 (t, J=10.9 Hz, 1H), 4.60-4.41 (m, 3H), 4.28 (d, J=13.0 Hz, 1H), 3.24 (ddd, J=43.0, 16.2, 11.1 Hz, 4H), 2.66 (dd, J=18.2, 10.0 Hz, 1H), 1.29 (d, J=6.8 Hz, 3H). LC-MS (m/z) 405.76 [M+H]$^+$.

Compound 119: (5-phenyl-4,5-dihydro-1H-pyrazol-1-yl)(3-(pyrazin-2-yloxy)azetidin-1-yl)methanone

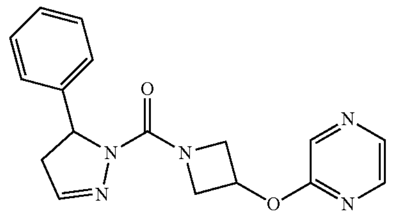 [SMILES: O=C(N1CC(Oc2cnccn2)C1)N1N=CCC1c1ccccc1]

The titled compound 119 was prepared in 40% yield from 2-(azetidin-3-yloxy) pyrazine trifluoroacetic acid, (1H-imidazol-1-yl)(5-phenyl-4,5-dihydro-1H-pyrazol-1-yl)methanone according to the procedure outlined for compound 60. $^1$H NMR (400 MHz, $CDCl_3$) δ 8.26 (s, 1H), 8.14 (d, J=2.7 Hz, 1H), 8.06-8.00 (m, 1H), 7.34-7.27 (m, 2H), 7.24-7.18 (m, 3H), 6.81-6.72 (m, 1H), 5.36-5.26 (m, 2H), 4.62-4.44 (m, 2H), 4.17 (dd, J=26.0, 6.5 Hz, 2H), 3.33 (dd, J=18.5, 12.1 Hz, 1H), 2.73 (dd, J=18.6, 6.3 Hz, 1H). LC-MS (m/z) 324.4 (M+H$^+$)

Compound 120: 2-((1-(5-phenyl-4,5-dihydro-1H-pyrazole-1-carbonyl)azetidin-3-yl)oxy)thiazole-5-carbonitrile

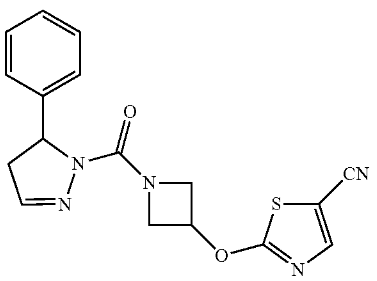 [SMILES: N#Cc1cnc(OC2CN(C(=O)N3N=CCC3c3ccccc3)C2)s1]

The titled compound 120 was prepared in 30% yield from 2-(azetidin-3-yloxy) thiazole-5-carbonitrile trifluoroacetic acid, (1H-imidazol-1-yl)(5-phenyl-4,5-dihydro-1H-pyrazol-1-yl)methanone according to the procedure outlined for compound 60. $^1$H NMR (400 MHz, $CDCl_3$) δ 7.63 (s, 1H), 7.35-7.25 (m, 2H), 7.23-7.13 (m, 3H), 6.77 (t, J=1.7 Hz, 1H), 5.47-5.39 (m, 1H), 5.29 (dd, J=12.1, 6.3 Hz, 1H), 4.61-4.43 (m, 2H), 4.22 (dd, J=31.0, 9.3 Hz, 2H), 3.40-3.27 (m, 1H), 2.74 (ddd, J=18.6, 6.3, 1.7 Hz, 1H). LC-MS (m/z) 354.4 (M+H$^+$)

Compound 121: 2-((1-(5-phenyl-4,5-dihydro-1H-pyrazole-1-carbonyl)azetidin-3-yl)oxy)thiazole-4-carbonitrile

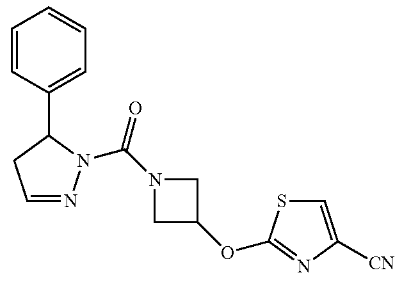 [SMILES: N#Cc1csc(OC2CN(C(=O)N3N=CCC3c3ccccc3)C2)n1]

The titled compound 121 was prepared in 28% yield from 2-(azetidin-3-yloxy) thiazole-4-carbonitrile trifluoroacetic acid, (1H-imidazol-1-yl)(5-phenyl-4,5-dihydro-1H-pyrazol-1-yl)methanone according to the procedure outlined for compound 60. LC-MS (m/z) 354.4 $(M+H^+)$ Compound 122: ((2R,6R)-4-(5-fluoropyrimidin-2-yl)-2,6-dimethylpiperazin-1-yl)(5-phenyl-4,5-dihydro-1H-pyrazol-1-yl)methanone ( )

122

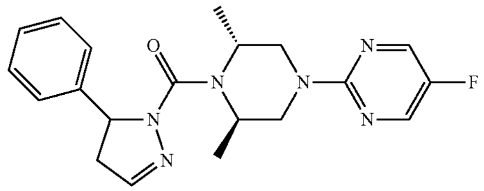

The titled compound 122 was prepared in a yield of 40.5% (6.0 mg) as a light yellow solid according to the procedure for 84. $^1H$ NMR (400 MHz, $CDCl_3$) δ 8.23 (s, 2H), 7.35-7.29 (m, 4H), 7.27-7.23 (m, 1H), 6.89 (s, 1H), 5.37 (dd, J=12.0, 8.0 Hz, 1H), 4.53-4.46 (m, 2H), 3.85-3.84 (m, 4H), 3.38-3.30 (m, 1H), 2.82-2.75 (m, 1H), 1.17 (d, J=4.0 Hz, 6H). LC-MS (m/z) 383.43 $[M+H]^+$.

Compound 123: (5-phenyl-4,5-dihydro-1H-pyrazol-1-yl)(3-(1-phenylethylidene)azetidin-1-yl)methanone

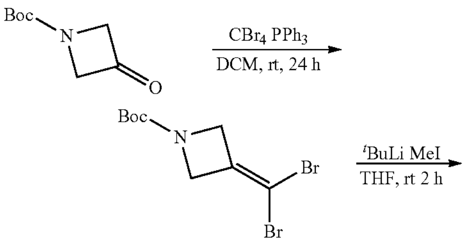

123-1

-continued

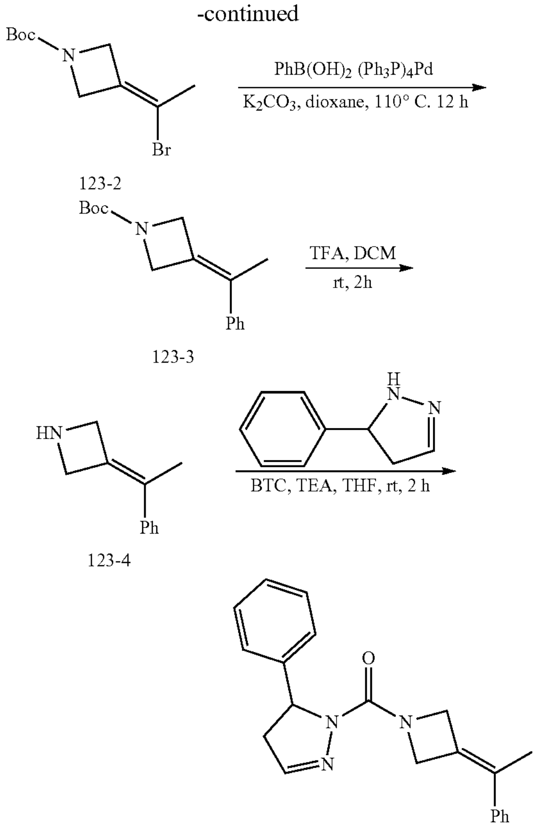

123-2

123-3

123-4

123

Step1: To a solution of triphenylphosphine (6.13 g, 23.37 mmol) in anhydrous dichloromethane (15 mL), Carbon tetrabromide (3.87 g, 11.68 mmol) was added at 0° C. under argon protection. The solution was stirred for 5 mins at the same temperature before a solution of tert-butyl 3-oxoazetidine-1-carboxylate (1 g, 5.84 mmol) in anhydrous dichloromethane (5 mL) was added dropwise. After stirring for 20 mins. The reaction was allowed to stirred for 24 h at room temperature. Hexane was added and the resulting precipitate removed by filtration. The filtrate was concentrated to give off-white solid. This solid was stirred in hexane with sonication, and then residual solids removed by suction filtration. The filtrate was concentrated to give tert-butyl 3-(dibromomethylene)azetidine-1-carboxylate (1.57 g, 82%). LC-MS (m/z) 325.87 $[M+H]^+$.

Step2: To a solution of tert-butyl 3-(dibromomethylene) azetidine-1-carboxylate (1.57 g, 4.80 mmol) in anhydrous tetrahydrofuran (20 mL) at −78° C. n-butyllithium (4.43 mL, 1.3M) was added dropwise under argon protection. After 10 mins iodomethane was added dropwise, the reaction was stirred for 2 h at same temperature. The reaction was quenched with sat.$NH_4Cl$(aq) and extracted with ether for two times, the organic layer were combine and washed by water, brine respectively, dry over $MgSO_4$, filtered, and concentrated under reduced pressure. Subject to purified by silica gel column chromatography (petroleum ether/AcOEt, 30/1) give tert-butyl 3-(1-bromoethylidene)azetidine-1-carboxylate (720 mg, 57%) as colorless oil. LC-MS (m/z) 263.45 $[M+H]^+$.

Step3: To a solution of tert-butyl 3-(1-bromoethylidene) azetidine-1-carboxylate (100 mg, 0.38 mmol) and phenylboronic acid (56 mg, 0.46 mmol) in anhydrous 1,4-dioxane (10 mL), Tetrakis(triphenylphosphine)palladium (88 mg, 0.76 mmol) and potassium carbonate (158 mg, 1.14 mmol) were added under argon protection. The reaction mixture was stirred at 110° C. for 12 h. the volatiles was removed in vacuo and the residue was suspension in dichloromethane, sat The organic layer was washed with water, and brine respectively. The residue was purified by silica gel column chromatography (petroleum ether/AcOEt, 1/1) give tert-butyl 3-(1-phenylethylidene)azetidine-1-carboxylate (76 mg, 77%) as pale yellow oil. LC-MS (m/z) 260.68 [M+H]$^+$.

Step4: Intermediate 123-4 was synthesized according to the method of intermediate 100-2 while using tert-butyl 3-(1-phenylethylidene)azetidine-1-carboxylate. 3-(1-phenylethylidene)azetidine was obtained as pale yellow oil (yield 95%). LC-MS (m/z) 160.46 [M+H]$^+$.

Step5: Compound 123 was synthesized according to the method of compound 100 while using 5-phenyl-4,5-dihydro-1H-pyrazole and 3-(1-phenylethylidene)azetidine. (5-phenyl-4,5-dihydro-1H-pyrazol-1-yl)(3-(1-phenylethylidene)azetidin-1-yl) methanone was obtained (22 mg, yield 17%) as pale white powder. $^1$H NMR (400 MHz, Chloroform-d) δ 7.49-7.07 (m, 10H), 6.81 (d, J=8.2 Hz, 1H), 5.50-5.27 (m, 1H), 5.03-4.66 (m, 4H), 3.36 (dd, J=17.6, 10.8 Hz, 1H), 2.76 (d, J=18.8 Hz, 1H), 1.94 (s, 3H). LC-MS (m/z) 332.57 [M+H]$^+$.

Compound 124: (5-phenyl-4,5-dihydro-1H-pyrazol-1-yl)(3-(1-phenylethyl)azetidin-1-yl)methanone

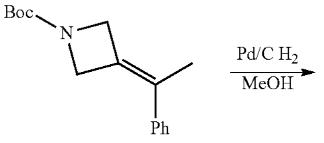

123-3

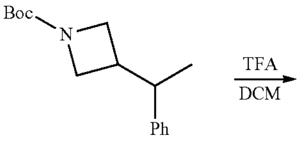

124-1

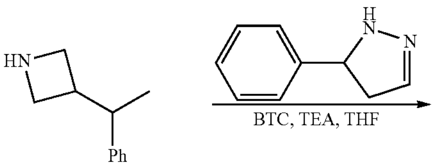

124-2

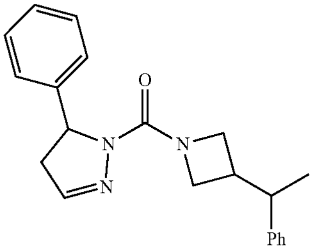

124

Step1: To a solution of tert-butyl 3-(1-phenylethylidene) azetidine-1-carboxylate (217 mg, 836.71 mmol) in methanol (10 mL), Palladium 10% on Carbon was added under argon protection. Hydrogen was bubbled with balloon. The reaction mixture was stirred at r,t for 12 h. the mixture was filtered with celite and the filtrate was concentrated. The crude product (123 mg, 56%) was used directly in next step without further purification. LC-MS (m/z) 262.83 [M+H]$^+$.

Step2: Intermediate 124-2 was synthesized according to the method of intermediate 100-2 while using tert-butyl 3-(1-phenylethyl)azetidine-1-carboxylate. 3-(1-phenylethyl) azetidine was obtained (72 mg, 94%) as pale yellow oil. The crude product was used directly in next step without further purification. LC-MS (m/z) 162.67 [M+H]$^+$.

Step3: Compound 124 was synthesized according to the method of compound 100 while using 5-phenyl-4,5-dihydro-1H-pyrazole and 3-(1-phenylethyl)azetidine. (5-phenyl-4,5-dihydro-1H-pyrazol-1-yl)(3-(1-phenylethyl)azetidin-1-yl)methanone was obtained (41 mg, yield 27%) as pale white powder. $^1$H NMR (400 MHz, Chloroform-d) δ 7.39-7.09 (m, 10H), 6.74 (s, 1H), 5.31 (s, 1H), 4.29 (d, J=28.8 Hz, 1H), 3.92 (d, J=31.2 Hz, 2H), 3.71 (d, J=29.8 Hz, 1H), 3.30 (d, J=16.8 Hz, 1H), 2.89 (s, 1H), 2.74 (s, 2H), 1.20 (d, J=5.6 Hz, 3H). LC-MS (m/z) 334.84 [M+H]$^+$.

Compound 125: (3-((6-ethynylpyrimidin-4-yl)oxy) azetidin-1-yl)(5-phenyl-4,5-dihydro-1H-pyrazol-1-yl)methanone

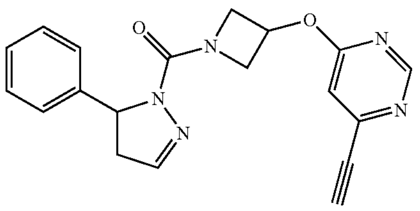 [SMILES: C#Cc1cc(OC2CN(C(=O)N3N=CCC3c3ccccc3)C2)ncn1]

The titled compound 125 was prepared in 18% yield from (5-phenyl-4,5-dihydro-1H-pyrazol-1-yl)(3-((6-((trimethylsilyl)ethynyl)pyrimidin-4-yl)oxy)azetidin-1-yl) methanone removed TMS group, which was prepared from 4-(azetidin-3-yloxy)-6-((trimethylsilyl)ethynyl)pyrimidine trifluoroacetic acid, (1H-imidazol-1-yl)(5-phenyl-4,5-dihydro-1H-pyrazol-1-yl)methanone according to the procedure outlined for compound 60. LC-MS (m/z) 348.4 (M+H$^+$)

Compound 126: (5-(3,5-difluorophenyl)-4,5-dihydro-1H-pyrazol-1-yl)(3-(2,4,6-trifluorophenoxy) azetidin-1-yl)methanone

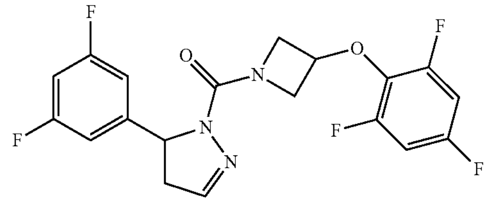 [SMILES: O=C(N1CC(Oc2c(F)cc(F)cc2F)C1)N1N=CCC1c1cc(F)cc(F)c1]

The titled compound 126 was prepared in 21% yield from 3-(2,4,6-trifluorophenoxy) azetidine, (5-(3,5-difluorophenyl)-4,5-dihydro-1H-pyrazol-1-yl)(1H-imidazol-1-yl) methanone according to the procedure outlined for compound 60. $^1$H NMR (400 MHz, $CDCl_3$) δ 6.80-6.63 (m, 6H), 5.28 (dd, J=12.2, 6.4 Hz, 1H), 4.93-4.80 (m, 1H), 4.49-4.40

(m, 2H), 4.38-4.24 (m, 2H), 3.22 (dd, J=14.0, 7.0 Hz, 1H), 2.69 (ddd, 6.5 Hz, 1H). LC-MS (m/z) 412.33 (M+H$^+$)

Compound 127: (3-((6-bromopyrimidin-4-yl)oxy)azetidin-1-yl)(5-phenyl-4,5-dihydro-1H-pyrazol-1-yl)methanone

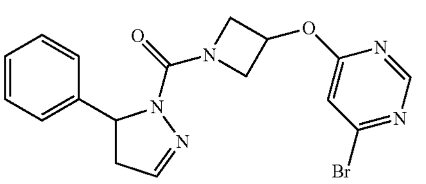 [SMILES: O=C(N1CC(Oc2cc(Br)ncn2)C1)N1N=CCC1c1ccccc1]

The titled compound 127 was prepared in 18% yield from 4-(azetidin-3-yloxy)-6-bromopyrimidine trifluoroacetic acid, (1H-imidazol-1-yl)(5-phenyl-4,5-dihydro-1H-pyrazol-1-yl)methanone according to the procedure outlined for compound 60. LC-MS (m/z) 402.35 (M+H$^+$)

Compound 128: (3-(2,5-difluorophenoxy)azetidin-1-yl)(5-phenyl-4,5-dihydro-1H-pyrazol-1-yl)methanone

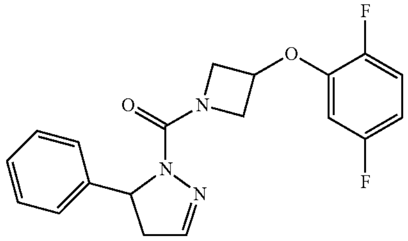 [SMILES: O=C(N1CC(Oc2cc(F)ccc2F)C1)N1N=CCC1c1ccccc1]

The titled compound 128 was prepared in 37.7% yield from 3-(2,5-difluorophenoxy) azetidine trifluoroacetic acid, (1H-imidazol-1-yl)(5-phenyl-4,5-dihydro-1H-pyrazol-1-yl) methanone according to the procedure outlined for compound 60. $^1$H NMR (400 MHz, $CDCl_3$) δ 7.34-7.27 (m, 2H), 7.24-7.18 (m, 3H), 7.06-6.97 (m, 1H), 6.77 (brs, 1H), 6.60 (ddt, J=9.0, 7.8, 3.1 Hz, 1H), 6.40 (ddd, J=9.5, 6.6, 3.0 Hz, 1H), 5.30 (dd, J=12.2, 6.2 Hz, 1H), 4.92-4.86 (m, J=10.6, 6.4, 4.2 Hz, 1H), 4.58-4.45 (m, J=25.1, 10.1, 6.5 Hz, 2H), 4.28 (dd, J=10.3, 3.8 Hz, 1H), 4.21 (dd, J=10.3, 4.1 Hz, 1H), 3.33 (dd, J=18.7, 12.4 Hz, 1H), 2.73 (ddd, J=18.6, 6.3, 1.6 Hz, 1H). LC-MS (m/z) 358.4 (M+H$^+$)

Compound 129: 3-((1-(5-(3,5-difluorophenyl)-4,5-dihydro-1H-pyrazole-1-carbonyl)azetidin-3-yl)oxy)benzamide

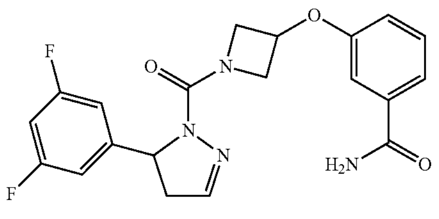 [SMILES: NC(=O)c1cccc(OC2CN(C(=O)N3N=CCC3c3cc(F)cc(F)c3)C2)c1]

To a solution of tert-butyl 3-(3-cyanophenoxy)azetidine-1-carboxylate prepared by the mothed described for tert-butyl 3-(2-fluorophenoxy)azetidine-1-carboxylate (200 mg) in MeOH (3 mL) was added DMSO (0.1 mL), 30% $H_2O_2$ (0.4 mL) and 1NNaOH (0.9 mL)

at 0° C. The mixture was stirred at 50° C. for 3 h. The mixture was extracted with DCM, washed with brine, dried ($Na_2SO_4$), and concentrated in vacuo to give the crude desired product (250 mg). LC-MS (m/z) 293.43 (M+H$^+$). tert-butyl 3-(3-carbamoylphenoxy)azetidine-1-carboxylate was removed Boc group and coupling with 5-(3,5-difluorophenyl)-4,5-dihydro-1H-pyrazole using triphosgene to give the titled product 129 (46 mg, 32%). $^1$H NMR (400 MHz, $CDCl_3$) δ 7.45-7.31 (m, 2H), 7.29-7.25 (m, 1H), 7.24-7.20 (m, 1H), 6.95 (ddd, J=7.9, 6.5, 2.8 Hz, 1H), 6.82-6.63 (m, 3H), 6.16 (brs, 2H), 5.26 (dd, J=12.1, 6.4 Hz, 1H), 4.96 (ddd, J=10.4, 6.3, 4.0 Hz, 1H), 4.67-4.46 (m, 2H), 4.21 (dd, J=24.1, 7.2 Hz, 2H), 3.33 (ddd, J=18.6, 12.2, 1.5 Hz, 1H), 2.67 (ddd, J=18.6, 6.4, 1.6 Hz, 1H). LC-MS (m/z) 401.4 (M+H$^+$).

Compound 130: 4-((1-(5-(3,5-difluorophenyl)-4,5-dihydro-1H-pyrazole-1-carbonyl)azetidin-3-yl)oxy)benzamide

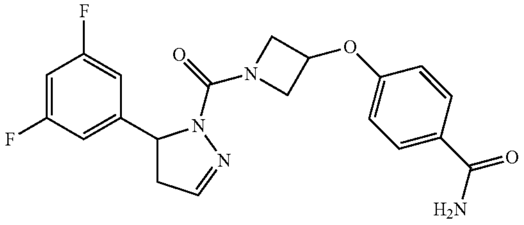 [SMILES: NC(=O)c1ccc(OC2CN(C(=O)N3N=CCC3c3cc(F)cc(F)c3)C2)cc1]

The titled compound 130 was prepared in 37% yield from 4-(azetidin-3-yloxy) benzamide trifluoroacetic acid, 5-(3,5-difluorophenyl)-4,5-dihydro-1H-pyrazole using triphosgene, according to the procedure outlined for compound 129. LC-MS (m/z) 401.40 (M+H$^+$)

Compound 131: 2-((1-(5-(3,5-difluorophenyl)-4,5-dihydro-1H-pyrazole-1-carbonyl)azetidin-3-yl)oxy)thiazole-4-carbonitrile

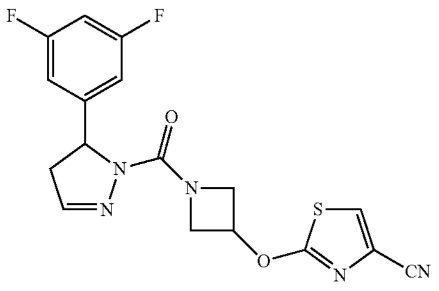 [SMILES: N#Cc1csc(OC2CN(C(=O)N3N=CCC3c3cc(F)cc(F)c3)C2)n1]

The titled compound 128 was prepared in 37.7% yield from 2-(azetidin-3-yloxy)thiazole-4-carbonitrile trifluoroacetic acid, (5-(3,5-difluorophenyl)-4,5-dihydro-1H-pyrazol-1-yl)(1H-imidazol-1-yl)methanone according to the procedure outlined for compound 60. $^1$H NMR (400 MHz, $CDCl_3$) δ 7.42 (s, 1H), 6.81-6.60 (m, 4H), 5.45-5.35 (m, 1H), 5.25 (dd, J=11.9, 6.1 Hz, 1H), 4.64-4.48 (m, 2H), 4.23 (dd, J=17.2, 11.1 Hz, 2H), 3.34 (dd, J=18.3, 11.9 Hz, 1H), 2.68 (dd, J=18.2, 5.2 Hz, 1H).

LC-MS (m/z) 390.4 (M+H+)

Compound 132: 2-((1-(5-(3,5-difluorophenyl)-4,5-dihydro-1H-pyrazole-1-carbonyl)azetidin-3-yl)oxy) thiazole-4-carboxamide

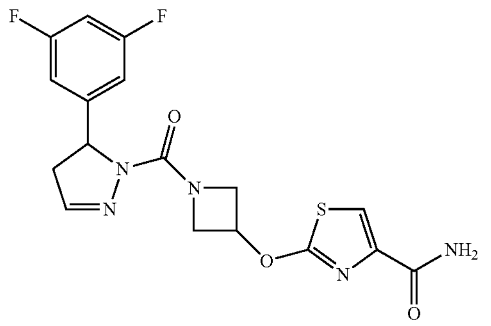 [SMILES: NC(=O)c1csc(OC2CN(C(=O)N3N=CCC3c3cc(F)cc(F)c3)C2)n1]

The titled compound 132 was prepared in 27.7% yield from 2-(azetidin-3-yloxy) thiazole-4-carboxamide trifluoroacetic acid, (5-(3,5-difluorophenyl)-4,5-dihydro-1H-pyrazol-1-yl)(1H-imidazol-1-yl)methanone according to the procedure outlined for compound 129. $^{1}H$ NMR (400 MHz, $CDCl_3$) δ 7.59 (s, 1H), 6.86-6.59 (m, 5H), 5.61 (s, 1H), 5.44-5.36 (m, 1H), 5.26 (dd, J=12.2, 6.5 Hz, 1H), 4.65-4.45 (m, 2H), 4.27 (ddd, J=30.4, 10.6, 3.3 Hz, 2H), 3.34 (ddd, J=18.6, 12.2, 1.6 Hz, 1H), 2.68 (ddd, J=18.6, 6.5, 1.7 Hz, 1H). LC-MS (m/z) 408.4 (M+H+)

Compound 133: (3-(2,6-difluorobenzylidene)azetidin-1-yl)(5-(3,5-difluorophenyl)-4,5-dihydro-1H-pyrazol-1-yl)methanone

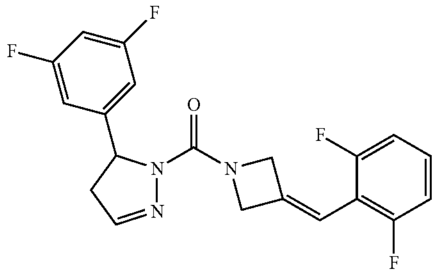 [SMILES: O=C(N1CC(=Cc2c(F)cccc2F)C1)N1N=CCC1c1cc(F)cc(F)c1]

The titled compound 133 was prepared in 37% yield form 3-(2,6-difluorobenzylidene)azetidine hydrochloride, 5-(3,5-difluorophenyl)-4,5-dihydro-1H-pyrazole and triphosgene according to the procedure outlined for compound 37. $^{1}H$ NMR (400 MHz, $CDCl_3$) δ 7.23-7.13 (m, 1H), 6.87 (t, J=8.4 Hz, 2H), 6.81-6.73 (m, 3H), 6.72-6.65 (m, 1H), 6.34-6.27 (m, 1H), 5.31 (dd, J=12.0, 6.4 Hz, 1H), 4.95-4.75 (m, 4H), 3.36 (ddd, J=18.4, 12.0, 1.6 Hz, 1H), 2.70 (ddd, J=18.4, 6.0, 1.6 Hz, 1H). LC-MS (m/z): 390.31 [M+H]+.

Compound 134: (5-(3,5-difluorophenyl)-4,5-dihydro-1H-pyrazol-1-yl)(3-((2,4-difluorophenyl)fluoromethyl)azetidin-1-yl)methanone

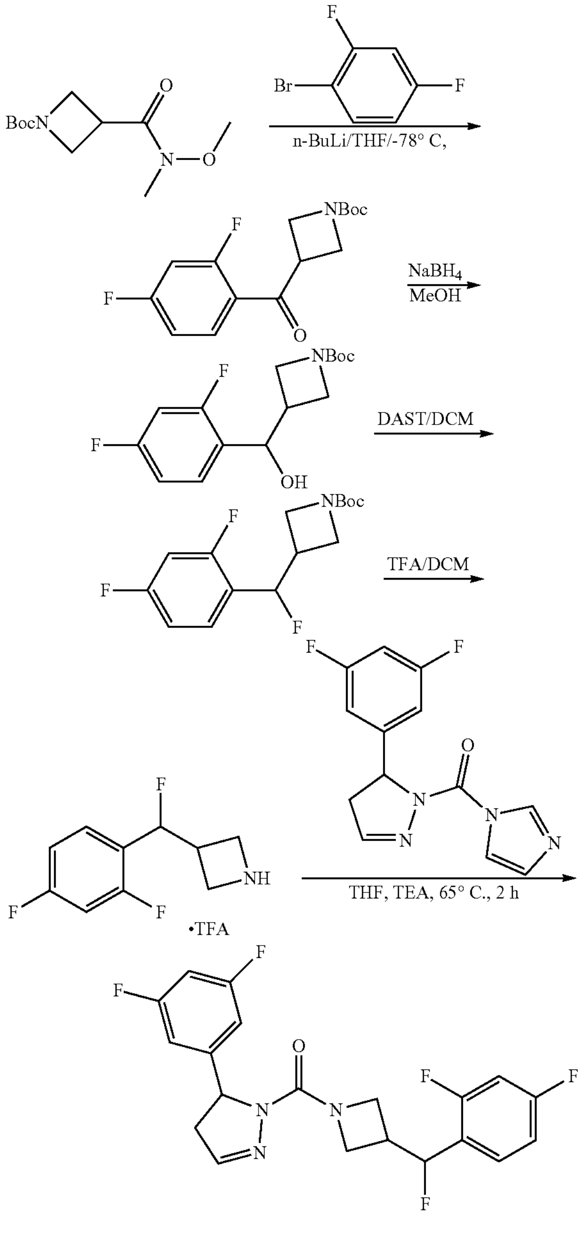

Step1:1-bromo-2,4-difluorobenzene (474 mg, 2.46 mmol) was dissolved in 5 mL dry THF. Let it cool to −78° C. n-BuLi (1.28 mL, 2.4 M, 3.07 mmol) was added dropwise at −78° C. Let it stir at −78° C. for 1 h. Then tert-butyl 3-(methoxy(methyl)carbamoyl)azetidine-1-carboxylate (0.5 g, 2.05 mmol) in 2 ml THF was added slowly to the solution at −78° C. Let it stir at −78° C. for 1 h. The starting material was consumed completely by TLC. Sat. $NH_4Cl$ solution was added to quench the reaction and extracted with EtOAc (20 ml×3). The organic layer was evaporated to dryness and purified by column chromatography (PE/EA=3/1) to give 360 mg tert-butyl 3-(2,4-difluorobenzoyl)azetidine-1-carboxylate as light-yellow-oil. Yield: 74.4%. LC-MS (m/z): 298.40 [M+H]+.

Step2: Tert-butyl 3-(2,4-difluorobenzoyl)azetidine-1-carboxylate (160 mg, 0.537 mmol) was dissolved in 5 ml MeOH. $NaBH_4$ (128.3 mg, 3.29 mmol) was added in portions at 0° C. Let it stir at r.t. for 16 hrs. Water was added to quench the reaction. The solvent was evaporated to dryness and extracted with DCM (15 ml×3). Dried with $Na_2SO_4$ and filtered. Evaporated to dryness and purified by Prep-TLC (PE/EA=2/1) to give 160 mg tert-butyl 3-((2,4-difluorophenyl)(hydroxy)methyl)azetidine-1-carboxylate as brown oil. Yield: 99.3%. LC-MS (m/z): 300.45 $[M+H]^+$.

Step3: Tert-butyl 3-((2,4-difluorophenyl)(hydroxy)methyl)azetidine-1-carboxylate (160 mg, 0.533 mmol) was dissolved in 7.5 ml dry DCM. Diethylaminosulfur trifluoride (174 mg, 1.07 mmol) in 1 mL DCM was added slowly to the solution at 0° C. Let it stir at 0° C. for 0.5 h. Then stir at r.t. for 0.5 h. It was washed with $H_2O$ and the organic layer was evaporated to dryness and purified by column chromatography (PE/EA=4/1) to give 115 mg tert-butyl 3-((2,4-difluorophenyl)fluoromethyl)azetidine-1-carboxylate as light-yellow oil. Yield: 71.7%. LC-MS (m/z): 302.40 $[M+H]^+$.

Step4: Tert-butyl 3-((2,4-difluorophenyl)fluoromethyl)azetidine-1-carboxylate (40 mg, 0.133 mmol) was dissolved in 2 mL dry DCM. 5 ml TFA/DCM (3/1) solution was added to the solution at 0° C. Let it stir at r.t. for 1.5 hrs. The solvent was evaporated to dryness to give 3-((2,4-difluorophenyl)fluoromethyl)azetidine as brown oil and it was used for next step without further purification. Yield: quantitative. LC-MS (m/z): 203.30 $[M+H]^+$.

Step5: The obtained above product 3-((2,4-difluorophenyl)fluoromethyl)azetidine was dissolved in 2 ml THF. (5-(3,5-difluorophenyl)-4,5-dihydro-1H-pyrazol-1-yl)(1H-imidazol-1-yl)methanone (36.8 mg, 0.133 mmol) was added. 0.2 ml TEA was added to the solution. Let it stir at 65° C. for 16 hrs. The solvent was evaporated to dryness and purified by Prep-TLC (PE/EA=2/1) to give 40 mg (5-(3,5-difluorophenyl)-4,5-dihydro-1H-pyrazol-1-yl)(3-((2,4-difluorophenyl)fluoromethyl)azetidin-1-yl) methanone as light-yellow oil. Yield: 73.7%. $^1H$ NMR (400 MHz, $CDCl_3$) δ 7.29-7.58 (m 1H), 6.83-6.94 (m, 2H), 6.73-6.77 (m, 3H), 6.65-6.70 (m, 1H), 5.91-6.05 (m, 1H), 5.26 (dd, 1H, J=12.0, 6.4 Hz), 4.09-4.41 (m, 3H), 3.71-3.82 (m, 1H), 3.38-3.47 (m, 1H), 3.28-3.37 (m 1H), 2.66 (ddd, 1H, J=18.4, 6.4, 1.6 Hz). LC-MS (m/z): 410.40 $[M+H]^+$.

Compound 135: (5-(3,5-difluorophenyl)-4,5-dihydro-1H-pyrazol-1-yl)(3-((2,4-difluorophenyl)difluoromethyl)azetidin-1-yl)methanone

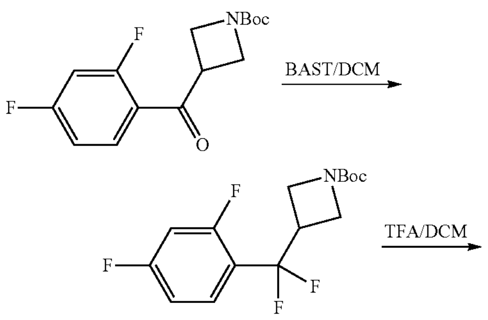

-continued

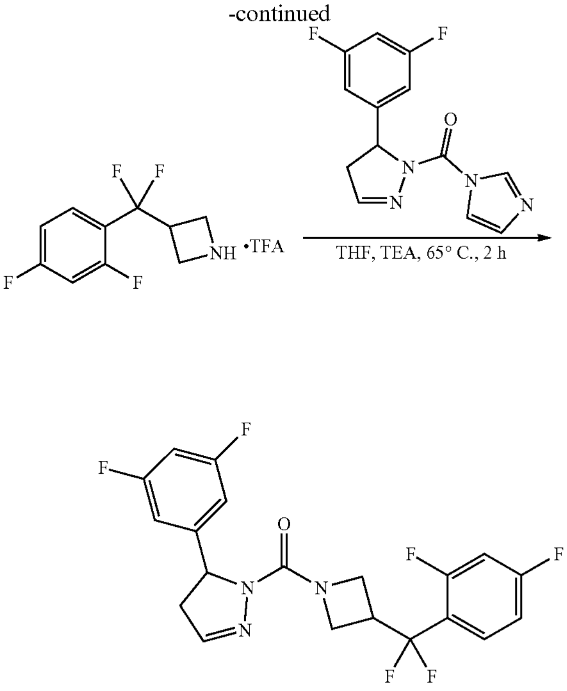

Step1: Tert-butyl 3-(2,4-difluorobenzoyl)azetidine-1-carboxylate (205 mg, 0.688 mmol) was dissolved in 4 ml dry DCM. Bis(2-methoxyethyl)aminosulfur trifluoride (1.272 ml, 6.89 mmol) was added slowly to the solution at r.t. Let it stir at r.t for 5 d. The solvent was poured into ice and extracted with DCM (15 ml×3). The organic layers were combined and washed with sat. $NaHCO_3$. The solvent was evaporated to dryness and purified by Prep-TLC (PE/EA=2/1) to give 122 mg tert-butyl 3-((2,4-difluorophenyl)difluoromethyl)azetidine-1-carboxylate as yellow-light oil. Yield: 61.6%. LC-MS (m/z): 320.3 $[M+H]^+$.

Step2: 3-((2,4-difluorophenyl)difluoromethyl)azetidine-1-carboxylate (60 mg, 0.188 mmol) was dissolved in in 2 mL dry DCM. 5 ml TFA/DCM (3/1) solution was added to the solution at 0° C. Let it stir at r.t. for 1.5 hrs. The solvent was evaporated to dryness to give 3-((2,4-difluorophenyl)difluoromethyl)azetidine as brown oil and it was used for next step without further purification. Yield: quantitative. LC-MS (m/z): 221.30 $[M+H]^+$.

Step3: The obtained above product 3-((2,4-difluorophenyl)difluoromethyl)azetidine was dissolved in 3 ml THF. (5-(3,5-difluorophenyl)-4,5-dihydro-1H-pyrazol-1-yl)(1H-imidazol-1-yl)methanone (51.9 mg, 0.187 mmol) was added. 0.4 ml TEA was added to the solution. Let it stir at 65° C. for 16 hrs. The solvent was evaporated to dryness and purified by Prep-TLC (PE/EA=2/1) to give 40 mg (5-(3,5-difluorophenyl)-4,5-dihydro-1H-pyrazol-1-yl)(3-((2,4-difluorophenyl)difluoromethyl)azetidin-1-yl)methanone as light-yellow oil. Yield: 50.1%. $^1H$ NMR (400 MHz, $CDCl_3$) δ 7.37-7.67 (m, 1H), 6.88-6.99 (m, 2H), 6.62-6.77 (m, 3H), 6.65-6.71 (m, 1H), 5.27 (dd, 1H, J=12.0, 6.4 Hz), 4.35-4.39 (m, 1H), 4.19-4.32 (m, 3H), 3.47-3.60 (m, 1H), 3.34 (ddd, 1H, J=18.4, 12.4, 1.6 Hz), 2.68 (ddd, 1H, J=18.4, 6.4, 1.6 Hz). LC-MS (m/z): 428.35 $[M+H]^+$.

Compound 136: 4-((1-(5-(3,5-difluorophenyl)-4,5-dihydro-1H-pyrazole-1-carbonyl)azetidin-3-yl)oxy)-3-fluorobenzonitrile

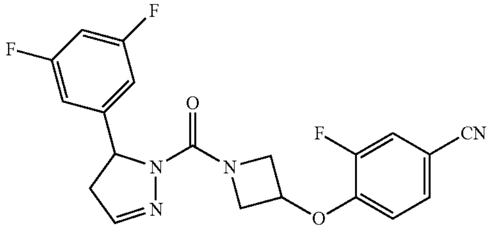 [SMILES: N#Cc1ccc(OC2CN(C(=O)N3N=CCC3c3cc(F)cc(F)c3)C2)c(F)c1]

The titled compound 136 was prepared in 74.7% yield from 4-(azetidin-3-yloxy)-3-fluorobenzonitrile trifluoroacetic acid, (5-(3,5-difluorophenyl)-4,5-dihydro-1H-pyrazol-1-yl)(1H-imidazol-1-yl)methanone according to the procedure outlined for compound 60. $^1$H NMR (400 MHz, $CDCl_3$) δ 7.41-7.39 (m, 1H), 7.38-7.36 (m, 1H), 6.81-6.62 (m, 5H), 5.25 (dd, J=12.2, 6.4 Hz, 1H), 5.05-4.96 (m, 1H), 4.55 (dd, J=17.1, 10.8 Hz, 2H), 4.40-4.20 (m, 2H), 3.34 (ddd, J=18.6, 12.2, 1.7 Hz, 1H), 2.77-2.63 (m, 1H). LC-MS (m/z) 301.4 ($M+H^+$)

Compound 137: 4-((1-(5-(3,5-difluorophenyl)-4,5-dihydro-1H-pyrazole-1-carbonyl)azetidin-3-yl)oxy)-2-fluorobenzonitrile

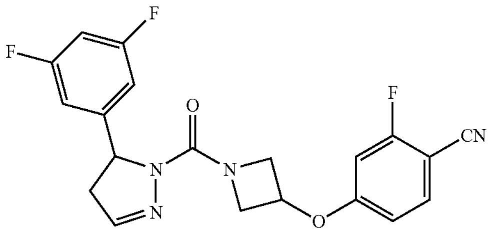 [SMILES: N#Cc1ccc(OC2CN(C(=O)N3N=CCC3c3cc(F)cc(F)c3)C2)cc1F]

The titled compound 137 was prepared in 74.7% yield from 4-(azetidin-3-yloxy)-2-fluorobenzonitrile trifluoroacetic acid, (5-(3,5-difluorophenyl)-4,5-dihydro-1H-pyrazol-1-yl)(1H-imidazol-1-yl)methanone according to the procedure outlined for compound 60. $^1$H NMR (400 MHz, $CDCl_3$) δ 7.55-7.50 (m, 1H), 6.78 (t, J=1.7 Hz, 1H), 6.74-6.52 (m, 5H), 5.25 (dd, J=12.2, 6.4 Hz, 1H), 4.93 (tt, J=6.4, 4.0 Hz, 1H), 4.63-4.45 (m, 2H), 4.28-4.12 (m, 2H), 3.34 (ddd, J=18.6, 12.2, 1.7 Hz, 1H), 2.69 (ddd, J=18.6, 6.4, 1.7 Hz, 1H). LC-MS (m/z) 301.4 ($M+H^+$)

Compound 138: (3-(4-chloro-2-fluorobenzylidene)azetidin-1-yl)(5-(3,5-difluorophenyl)-4,5-dihydro-1H-pyrazol-1-yl)methanone

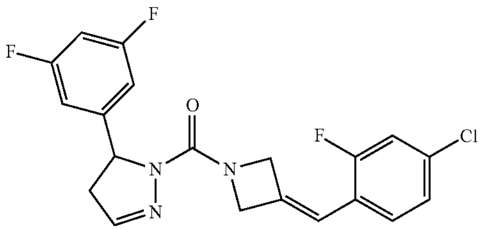 [SMILES: O=C(N1CC(=Cc2ccc(Cl)cc2F)C1)N1N=CCC1c1cc(F)cc(F)c1]

The titled compound 138 was prepared in 36.3% yield form 3-(4-chloro-2-fluorobenzylidene)azetidine hydrochloride, 5-(3,5-difluorophenyl)-4,5-dihydro-1H-pyrazole and triphosgene according to the procedure outlined for compound 37. $^1$H NMR (400 MHz, $CDCl_3$) δ 7.13-7.06 (m, 2H), 7.05-6.99 (m, 1H), 6.83-6.74 (m, 3H), 6.72-6.66 (m, 1H), 6.40 (t, J=2.0 Hz, 1H), 5.31 (dd, J=12.0, 6.4 Hz, 1H), 4.99 (dd, J=30.6, 15.4 Hz, 2H), 4.85 (dd, J=28.0, 14.4 Hz, 2H), 3.37 (ddd, J=18.4, 12.0, 1.6 Hz, 1H), 2.72 (ddd, J=18.4, 6.4, 1.6 Hz, 1H). LC-MS (m/z): 406.29 $[M+H]^+$.

Compound 139: (3-(2-chloro-4-fluorobenzylidene)azetidin-1-yl)(5-(3,5-difluorophenyl)-4,5-dihydro-1H-pyrazol-1-yl)methanone

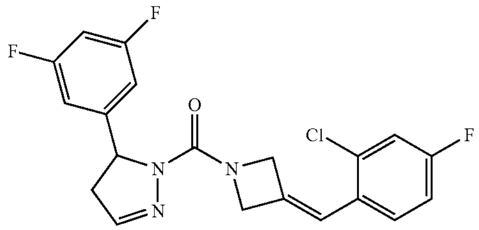

The titled compound 139 was prepared in 36.3% yield form 3-(2-chloro-4-fluorobenzylidene)azetidine hydrochloride, 5-(3,5-difluorophenyl)-4,5-dihydro-1H-pyrazole and triphosgene according to the procedure outlined for compound 37. $^1$H NMR (400 MHz, $CDCl_3$) δ 7.18-7.04 (m, 2H), 6.97 (td, J=8.4, 2.8 Hz, 1H), 6.84-6.73 (m, 3H), 6.73-6.66 (m, 1H), 6.60 (t, J=2.4 Hz, 1H), 5.31 (dd, J=12.0, 6.4 Hz, 1H), 5.08-4.77 (m, 4H), 3.37 (ddd, J=18.4, 12.0, 1.6 Hz, 1H), 2.72 (ddd, J=184, 6.4, 1.6 Hz, 1H). LC-MS (m/z): 406.33 $[M+H]^+$.

Compound 140: (3-(3,4-difluorobenzylidene)azetidin-1-yl)(5-(3,5-difluorophenyl)-4,5-dihydro-1H-pyrazol-1-yl)methanone

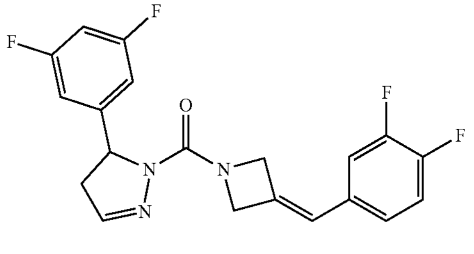 [SMILES: O=C(N1CC(=Cc2ccc(F)c(F)c2)C1)N1N=CCC1c1cc(F)cc(F)c1]

The titled compound 140 was prepared in 36.3% yield form 3-(3,4-difluorobenzylidene)azetidine hydrochloride, 5-(3,5-difluorophenyl)-4,5-dihydro-1H-pyrazole and triphosgene according to the procedure outlined for compound 37. $^1$H NMR (400 MHz, $CDCl_3$) δ 7.17-7.07 (m, 1H), 6.94-6.88 (m, 1H), 6.87-6.81 (m, 2H), 6.81-6.66 (m, 3H), 6.19 (t, J=2.0 Hz, 1H), 5.31 (dd, J=12.0, 6.4 Hz, 1H), 5.03 (dd, J=30.0, 14.8 Hz, 2H), 4.83 (dd, J=28.0, 14.4 Hz, 2H), 3.38 (ddd, J=18.4, 12.0, 1.6 Hz, 1H), 2.72 (ddd, J=18.5, 6.5, 1.7 Hz, 1H). LC-MS (m/z): 390.29 $[M+H]^+$.

Compound 141: (5-(3,5-difluorophenyl)-4,5-dihydro-1H-pyrazol-1-yl)(3-((6-fluoropyridin-3-yl)oxy)azetidin-1-yl)methanone

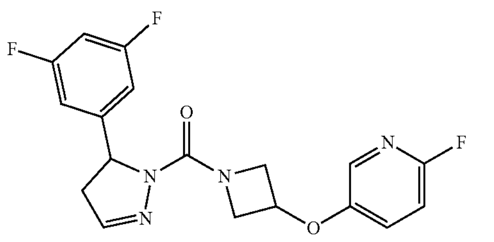 [SMILES: O=C(N1CC(Oc2ccc(F)nc2)C1)N1N=CCC1c1cc(F)cc(F)c1]

The titled compound 141 was prepared in 34.7% yield from 5-(azetidin-3-yloxy)-2-fluoropyridine trifluoroacetic acid, (5-(3,5-difluorophenyl)-4,5-dihydro-1H-pyrazol-1-yl)(1H-imidazol-1-yl)methanone according to the procedure outlined for compound 60. $^{1}H$ NMR (400 MHz, $CDCl_3$) δ 7.65 (s, 1H), 7.23-7.11 (m, 2H), 6.86 (brs, 1H), 6.78-6.62 (m, 3H), 5.30-5.25 (m, 1H), 4.98-4.86 (m, 1H), 4.64-4.45 (m, 2H), 4.30-4.12 (m, 2H), 3.41-3.26 (m, 1H), 2.75-2.60 (m, 1H). LC-MS (m/z) 377.4 ($M+H^+$)

Compound 142-147: Preparation of 142-47 According to the Following Route

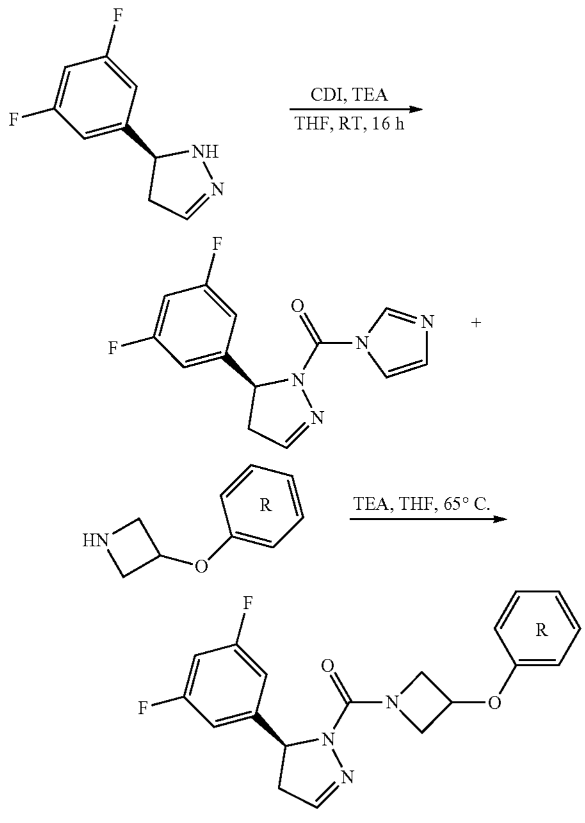

141-147

Compound 148-150: Preparation of 148-150 According to the Following Route

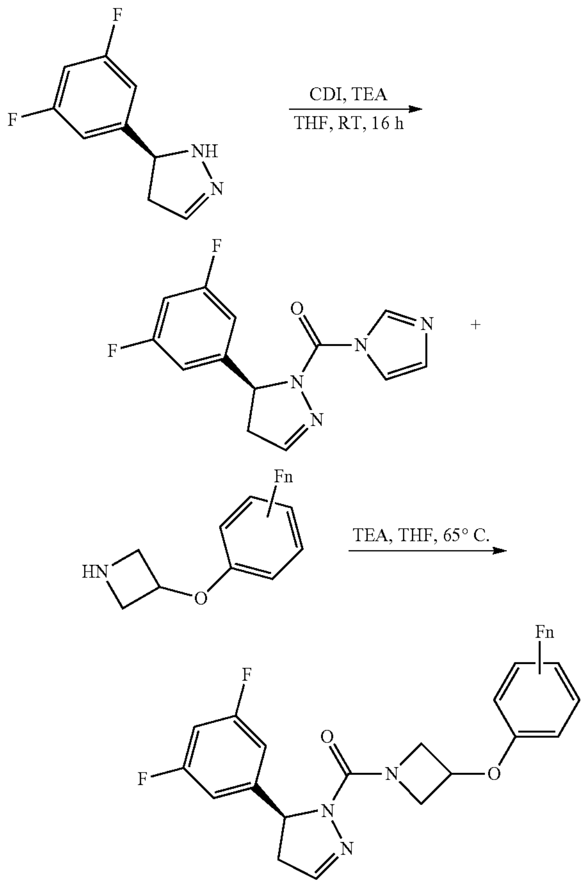

148-150

Compound 151-154: Preparation of 151-154 According to the Following Route

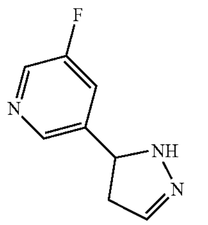

or

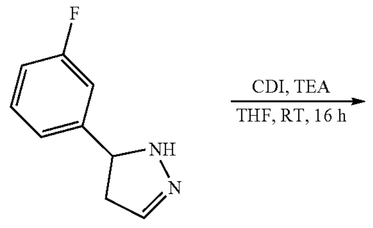

-continued

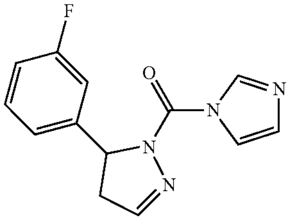

or

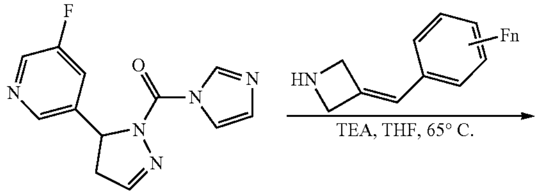

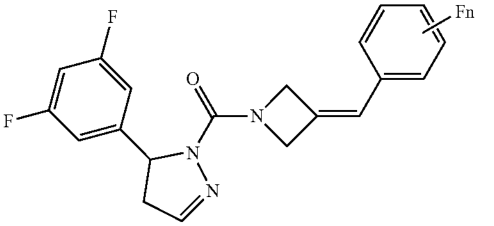

or

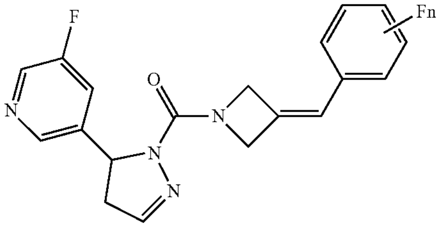

151-154

Compound 155-191: Preparation of 155-191 According to the Following Route

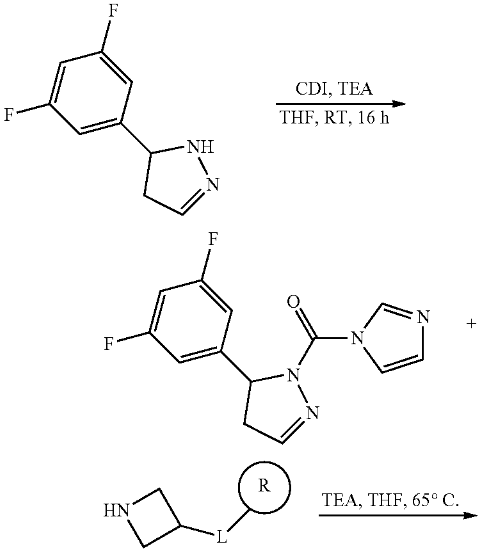

-continued

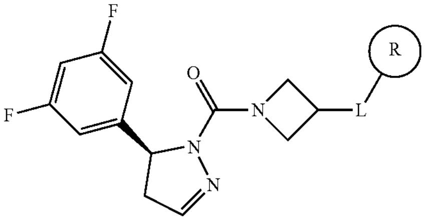

155-191

L = O, CH2, OH
R = substituted or unsubstituted phenyl or heterocyclic ring, benzoheterecyclic ring

Preparation of Intermediate 1: (5-(3,5-difluorophenyl)-4,5-dihydro-1H-pyrazol-1-yl)(1H-Imidazol-1-yl)methanone

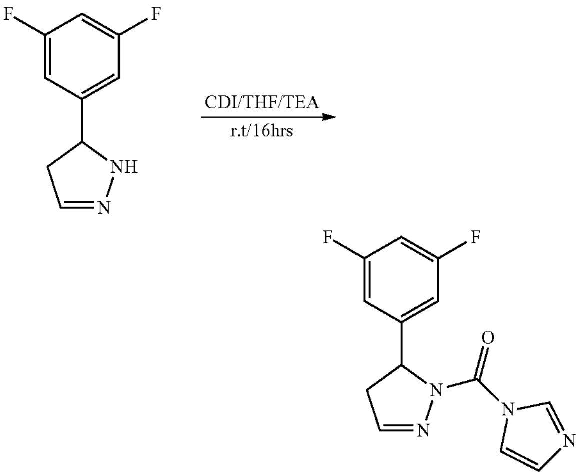

CDI (44.5 g, 274.7 mmol) was dissolved in 450 mL THF and added TEA (38.00 g, 375.00 mmol). Compound A2 (45.50 g, 249.75 mmol) was dissolved in 460 mL THF and added to the mixture. Let it stir at r.t over night. The mixture was evaporated to dryness and purified by column chromatography (PE/EA=3/1-1/1) to give the titled compound as a light-yellow solid (40.7 g, 59%). LCMS (m/z): 277, $[M+H]^+$. H-NMR The following intermediates used for the preparation of the titled example compounds were synthesized using the methods analogous to the ones described above.

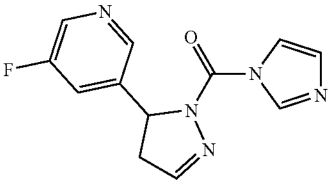

-continued

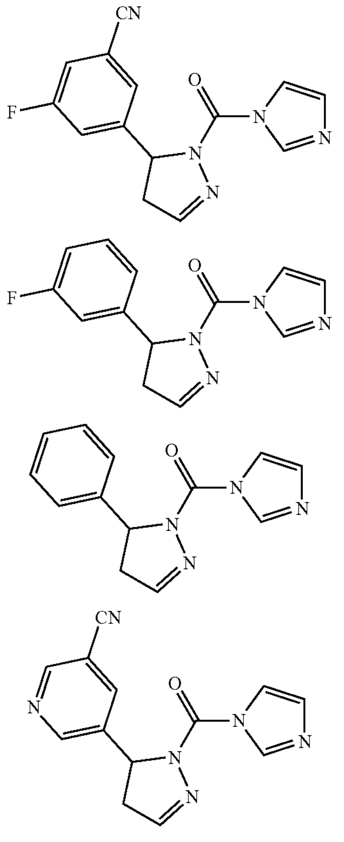

The above intermediates were isolated as racemates. Chiral HPLC separation to yield two single-enantiomer, The absolute configuration of the active enantiomer was assigned as (S) in each case, based on the assignment of XXX as described in example, and the S configuration enantiomer was carried on selected examples, as indicated by the structure.

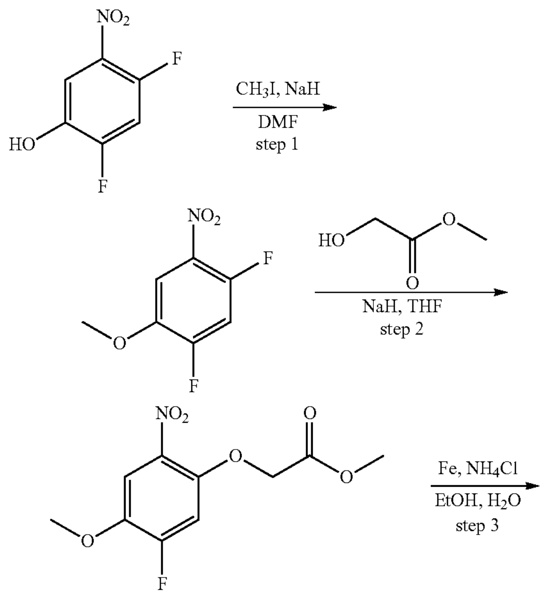

-continued

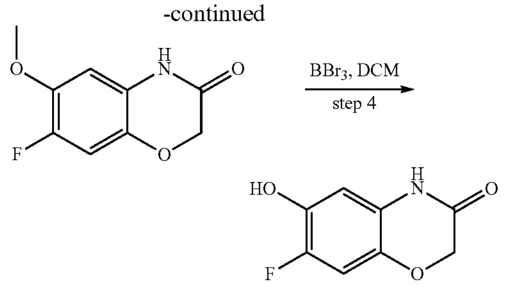

Step1: 2,4-difluoro-5-nitrophenol (10 g,) in DMF 150 ml was added NaH (4.57 g, 60% in oil) at 0° C. under nitrogen protection, 30 min later, $CH_3I$ (12.17 g) was added. The mixture was stirred at room temperature for 12 h. The solution was added $H_2O$ and extracted by EA. The combined organic layers were washed with brine, dried over $Na_2SO_4$, filtered and concentrated under reduced pressure. Purification by column chromatography to afford 10 g of 1,5-difluoro-2-methoxy-4-nitrobenzene as a yellow solid. LC-MS (m/z) 199.2 ($M+H^+$)

Step2: 3.44 g of methyl 2-hydroxyacetate was dissolved in 150 ml of THF, NaH (1.8 g, 60% in oil) was added at 0° C. under nitrogen protection, 30 min later, 6.56 g of 1,5-difluoro-2-methoxy-4-nitrobenzene was added. The mixture was stirred for 3 h at room temperature. The reaction mixture was added EA and $H_2O$. After separation, the combined organic layers were dried over $Na_2SO_4$, filtered and concentrated under reduced pressure. 8 g of crude methyl 2-(5-fluoro-4-methoxy-2-nitrophenoxy)acetate was obtained and used for the next step without further purification. LC-MS (m/z) 260.2 ($M+H^+$)

Step3: Fe (11.63 g), $NH_4Cl$ (9.3 g) were added to a suspension of methyl 2-(5-fluoro-4-methoxy-2-nitrophenoxy)acetate (8 g) in $C_2H_5OH$ and $H_2O$ (v/v=10:1, 110 ml) at rt. The mixture was stirred at 70° C. for 2 h. The resultant precipitate was filtered. The filtrate was concentrated in vacuo and added DCM. The mixture was filtered once more and concentrated in vacuo. Purification by column chromatography to afford 2.8 g of 7-fluoro-6-methoxy-2H-benzo[b][1,4]oxazin-3(4H)-one as brown solid (purity 80%, UPLC). LC-MS (m/z) 198.2 ($M+H^+$)

Step4: 2.8 g of 7-fluoro-6-methoxy-2H-benzo[b][1,4]oxazin-3(4H)-one was dissolved in 60 ml of DCM, $BBr_3$ (20 ml) was added slowly at −78° C. under nitrogen protection. The mixture was allowed to warm to rt and stirred for 12 h. The resulting solution was quenched by $H_2O$ and extracted by EA. The organic layers were dried by $Na_2SO_4$ and concentrated in vacuo. Purification by column chromatography to afford 0.29 g of 7-fluoro-6-hydroxy-2H-benzo[b][1,4]oxazin-3(4H)-one as yellow solid. LC-MS (m/z) 184.2 ($M+H^+$).

Compound 192: (S)-7-fluoro-6-((1-(5-phenyl-4,5-dihydro-1H-pyrazole-1-carbonyl)azetidin-3-yl)oxy)-2H-benzo[b][1,4]oxazin-3(4H)-one

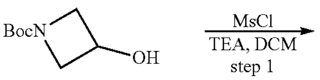

-continued

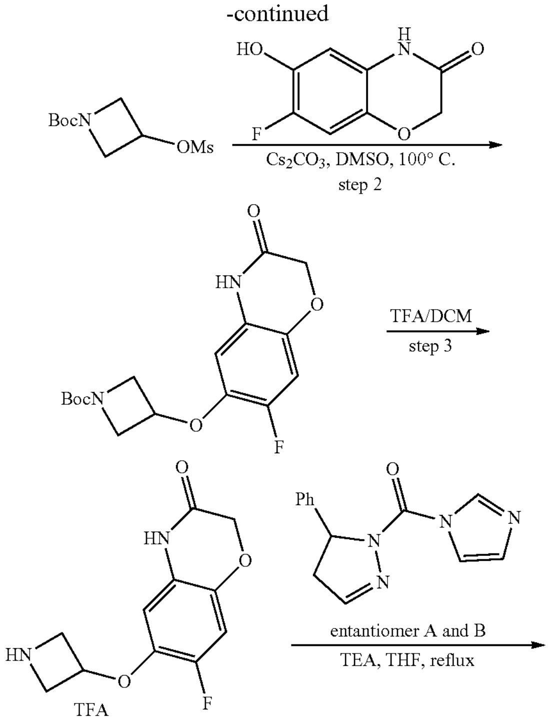

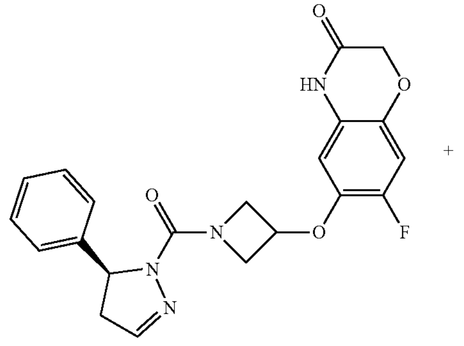

192

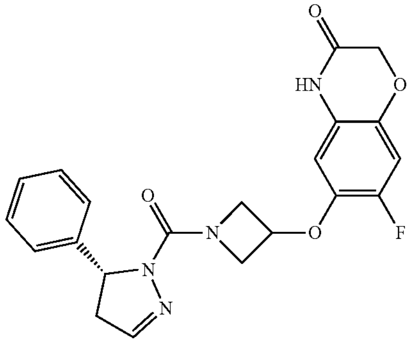

Step 1: tert-butyl 3-hydroxyazetidine-1-carboxylate (15 g, 86.6 mmol) was dissolved in 150 ml of dry DCM, TEA (26.2 g, 259.8 mmol) was added. MsCl (1.2 g, 103.92 mmol) was added slowly to the above solution at 0° C. The mixture was stirred for overnight. The mixture was extracted with DCM, washed with brine, dried (Na2SO4), and concentrated. The crude product was crystalized with EtOH/petroleum to yield tert-butyl 3-((methylsulfonyl)oxy)azetidine-1-carboxylate (13 g, 59.8%). LCMS (m/z) 252.3 ($M+H^+$).

Step 2: To a solution of tert-butyl 3-((methylsulfonyl)oxy) azetidine-1-carboxylate (26.5 g, 144.7 mmo), 7-fluoro-6-hydroxy-2H-benzo[b][1,4]oxazin-3(4H)-one (40 g, 159.17 mmol) in DMSO (270 ml) was added $Cs_2CO_3$ (94.3 g, 289.4 mmol) at r.t, then the temperature was allowed to rise to 100° C. and stir for another 3 h, Upon completion, the reaction was diluted with ethyl acetate (500 ml), washed with $H_2O$ (700 ml), brine (250 ml), dried over $Na_2SO_4$, and concentrated to give the crude product. The crude product was then purified by added EA/PE=1:3 (300 ml) to afford tert-butyl 3-((7-fluoro-3-oxo-3,4-dihydro-2H-benzo[b][1,4]oxazin-6-yl)oxy)azetidine-1-carboxylate (35.1 g, 71.8%). MS (m/z) 338.4 ($M+H^+$).

Step 3: tert-butyl 3-((7-fluoro-3-oxo-3,4-dihydro-2H-benzo[b][1,4]oxazin-6-yl)oxy)azetidine-1-carboxylate (100 mg, 0.3 mmol) was dissolved in DCM (5 mL), and TFA (350 mg, 10 mmol) was added. The mixture was stirred at r.t. for 4 h. The mixture was concentrated to give 6-(azetidin-3-yloxy)-7-fluoro-2H-benzo[b][1,4]oxazin-3(4H)-one as TFA salt, which was used for next step without further purification. LC-MS (m/z) 238.4 ($M+H^+$).

Step 4: half part of the above crude 6-(azetidin-3-yloxy)-7-fluoro-2H-benzo[b][1,4]oxazin-3(4H)-one trifluoroacetic acid salt and (S)-(1H-imidazol-1-yl)(5-phenyl-4,5-dihydro-1H-pyrazol-1-yl)methanone (65 mg, enantiomer B) and TEA (0.2 ml) were dissolved in THF (5 ml) and stirred at room temperature for 16 h. The mixture was extracted with EA, washed with brine, dried (Na2SO4), and concentrated in vacuo. Purification by Pre-HPLC to give the titled compound 192 (36 mg) as a white solid with potent activity based on the cell activity assay. LC-MS (m/z) 411.2 ($M+H^+$). $^1H$ NMR (400 MHz, Chloroform-d) δ 9.30 (s, 1H), 7.30-7.24 (m, 2H), 7.23-7.17 (m, 3H), 6.81 (t, J=1.7 Hz, 1H), 6.73 (d, J=11.2 Hz, 1H), 6.20 (d, J=8.0 Hz, 1H), 5.48 (dd, J=12.1, 5.9 Hz, 1H), 4.77-4.69 (m, 1H), 4.54-4.46 (m, 3H), 4.46-4.39 (m, 1H), 4.38-4.31 (m, 1H), 4.14-4.06 (m, 1H), 3.38 (ddd, J=18.5, 12.1, 1.7 Hz, 1H), 2.72 (ddd, J=18.5, 5.9, 1.8 Hz, 1H). while another part of 6-(azetidin-3-yloxy)-7-fluoro-2H-benzo[b][1,4]oxazin-3(4H)-one trifluoroacetic acid salt was reacted with (R)-(1H-imidazol-1-yl)(5-phenyl-4,5-dihydro-1H-pyrazol-1-yl)methanone to give (R)-7-fluoro-6-((1-(5-phenyl-4,5-dihydro-1H-pyrazole-1-carbonyl)azetidin-3-yl)oxy)-2H-benzo[b][1,4]oxazin-3(4H)-one with weak activity based on the cell activity assay Compound 193; (S)-6-((1-(5-(3,5-difluorophenyl)-4,5-dihydro-1H-pyrazole-1-carbonyl)azetidin-3-yl)oxy)-7-fluoro-2H-benzo[b][1,4]oxazin-3(4H)-one

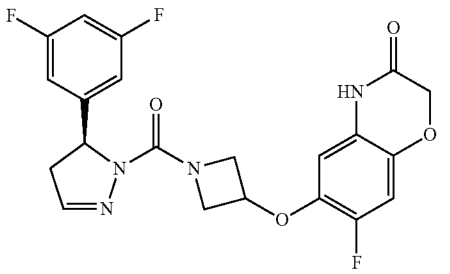 [SMILES: O=C1COc2cc(F)c(OC3CN(C(=O)N4N=CC[C@H]4c4cc(F)cc(F)c4)C3)cc2N1]

The titled compound 193 was synthesized in an analogous manner to the preparation of compound 192. LC-MS (m/z): 447.2 $[M+H]^+$. $^1H$ NMR (400 MHz, Chloroform-d) δ 8.93 (s, 1H), 6.83-6.80 (m, 1H), 6.78 (s, 1H), 6.77-6.73 (m, 2H), 6.66 (tt, J=9.0, 2.4 Hz, 1H), 6.22 (d, J=7.8 Hz, 1H), 5.46 (dd, J=12.1, 6.1 Hz, 1H), 4.88-4.79 (m, 1H), 4.60-4.45 (m, 4H), 4.43-4.34 (m, 1H), 4.19-4.08 (m, 1H), 3.44-3.33 (m, 1H), 2.75-2.64 (m, 1H).

Compound 194: (S)-7-fluoro-6-((1-(5-(5-fluoropyridin-3-yl)-4,5-dihydro-1H-pyrazole-1-carbonyl)azetidin-3-yl)oxy)-2H-benzo[b][1,4]oxazin-3(4H)-one

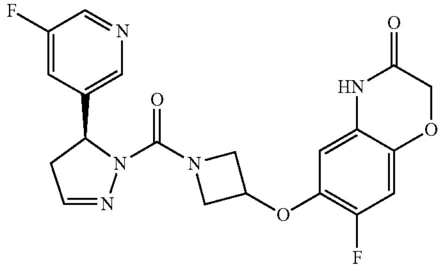 [SMILES: O=C1COc2cc(F)c(OC3CN(C(=O)N4N=CC[C@H]4c4cncc(F)c4)C3)cc2N1]

The titled compound 194 were synthesized in an analogous manner to the preparation of compound 1. LC-MS (m/z): 430.2 $[M+H]^+$. $^1H$ NMR (400 MHz, Chloroform-d) δ 8.43-8.36 (m, 2H), 7.38 (d, J=8.8 Hz, 1H), 6.87-6.84 (m, 1H), 6.78 (dd, J=11.2, 2.3 Hz, 1H), 6.27-6.21 (m, 1H), 5.58-5.45 (m, 1H), 4.91-4.81 (m, 1H), 4.57-4.54 (m, 2H), 4.53-4.44 (m, 2H), 4.39-4.28 (m, 1H), 4.23-4.10 (m, 1H), 3.50-3.40 (m, 1H), 2.75 (dd, J=18.5, 6.4 Hz, 1H).

Compound 195: (S)-3-(1-(3-(7-fluoro-3-oxo-3,4-dihydro-2H-benzo[b][1,4]oxazin-6-yl)oxy)azetidine-1-carbonyl)-4,5-dihydro-1H-pyrazol-5-yl)benzonitrile

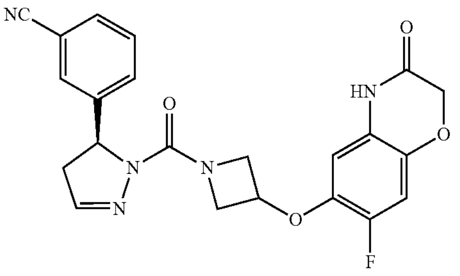 [SMILES: N#Cc1cccc([C@@H]2CC=NN2C(=O)N2CC(Oc3cc4c(cc3F)OCC(=O)N4)C2)c1]

The titled compound 195 were synthesized in an analogous manner to the preparation of compound 192. LC-MS (m/z): 436.2 $[M+H]^+$. $^1H$ NMR (400 MHz, Chloroform-d) δ 9.11 (s, 1H), 7.54-7.39 (m, 4H), 6.83 (t, J=1.7 Hz, 1H), 6.76 (d, J=11.2 Hz, 1H), 6.25 (d, J=7.8 Hz, 1H), 5.47 (dd, J=12.2, 6.3 Hz, 1H), 4.87-4.80 (m, 1H), 4.54 (s, 2H), 4.53-4.45 (m, 2H), 4.39-4.30 (m, 1H), 4.21-4.11 (m, 1H), 3.41 (ddd, J=18.6, 12.2, 1.7 Hz, 1H), 2.69 (ddd, J=18.6, 6.3, 1.8 Hz, 1H).

Compound 196: 7-(((R)-1-((S)-5-(3,5-difluorophenyl)-4,5-dihydro-1H-pyrazole-1-carbonyl)pyrrolidin-3-yl)oxy)-6-fluoro-3,4-dihydroquinolin-2(1H)-one

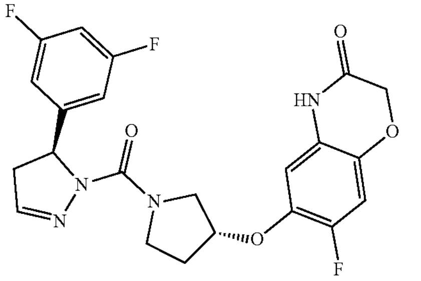 [SMILES: O=C1COc2cc(F)c(O[C@@H]3CCN(C(=O)N4N=CC[C@H]4c4cc(F)cc(F)c4)C3)cc2N1]

The titled compound 196 were synthesized in an analogous manner to the preparation of compound 192. LC-MS (m/z): 461.2 $[M+H]^+$. $^1H$ NMR (400 MHz, Chloroform-d) δ 6.83-6.73 (m, 4H), 6.72-6.65 (m, 1H), 6.42 (d, J=7.7 Hz, 1H), 5.33 (dd, J=12.0, 7.7 Hz, 1H), 4.84-4.78 (m, 1H), 4.56 (s, 2H), 4.07-4.00 (m, 1H), 3.99-3.90 (m, 1H), 3.77-3.67 (m, 2H), 3.36-3.26 (m, 1H), 2.71-2.62 (m, 1H), 2.25-2.15 (m, 1H), 2.14-2.04 (m, 1H).

Compound 197: (S)-5-(1(3-((7-fluoro-3-oxo-3,4-dihydro-2H-benzo[b][1,4]oxazin-6-yl)oxy)azetidine-1-carbonyl)-4,5-dihydro-1H-pyrazol-5-yl)nicotinonitrile

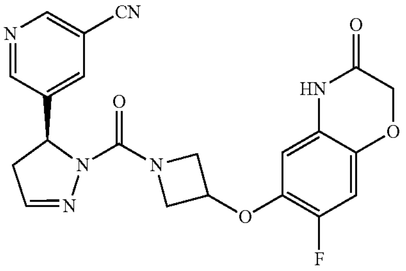 [SMILES: N#Cc1cncc([C@@H]2CC=NN2C(=O)N2CC(Oc3cc4c(cc3F)OCC(=O)N4)C2)c1]

The titled compound 197 were synthesized in an analogous manner to the preparation of compound 192. LC-MS (m/z): 437.2 $[M+H]^+$. $^1H$ NMR (400 MHz, Chloroform-d) δ 8.96-8.82 (br, 1H), 8.80-8.71 (m, 2H), 7.84 (t, J=2.1 Hz, 1H), 6.91-6.84 (m, 1H), 6.77 (d, J=11.1 Hz, 1H), 6.22 (d, J=7.8 Hz, 1H), 5.65-5.54 (m, 1H), 4.88-4.81 (m, 1H), 4.54 (s, 2H), 4.52-4.43 (m, 2H), 4.42-4.33 (m, 1H), 4.19-4.07 (m, 1H), 3.48 (ddd, J=18.7, 12.2, 1.7 Hz, 1H), 2.73 (ddd, J=18.6, 6.7, 1.7 Hz, 1H).

Compound 198: (S)-3-fluoro-5-(1-(3-((3-oxo-3,4-dihydro-2H-benzo[b][1,4]oxazin-6-yl)oxy)azetidine-1-carbonyl)-4,5-dihydro-1H-pyrazol-5-yl)benzonitrile

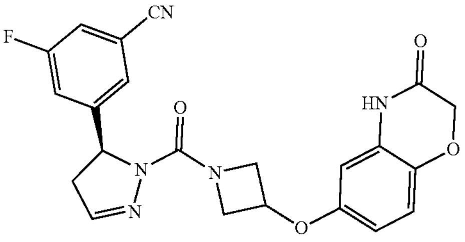 [SMILES: N#Cc1cc(F)cc([C@@H]2CC=NN2C(=O)N2CC(Oc3ccc4c(c3)NC(=O)CO4)C2)c1]

The titled compound 198 were synthesized in an analogous manner to the preparation of compound 192. Yield 92.9% $^1$H NMR (400 MHz, Chloroform-d) δ 8.86 (s, 1H), 7.33 (t, J=1.6 Hz, 1H), 7.24-7.17 (m, 2H), 6.87 (d, J=8.8 Hz, 1H), 6.81 (t, J=1.6 Hz, 1H), 6.34 (dd, J=8.8, 2.8 Hz, 1H), 6.25 (d, J=2.8 Hz, 1H), 5.47-5.37 (m, 1H), 4.88-4.80 (m, 1H), 4.64-4.40 (m, 4H) 4.32-4.04 (m, 2H), 3.46-3.35 (m 1H), 2.73-2.63 (m, 1). LC-MS (m/z) 436.2 (M+H$^+$)

Compound 199: (S)-6-((1-(5-phenyl-4,5-dihydro-1H-pyrazole-1-carbonyl)azetidin-3-yl)oxy)-2H-benzo[b][1,4]oxazin-3(4H)-one

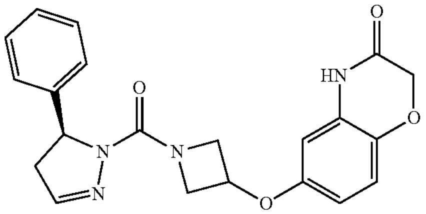 [SMILES: O=C1COc2ccc(OC3CN(C(=O)N4N=CC[C@H]4c4ccccc4)C3)cc2N1]

The titled compound 199 were synthesized in an analogous manner to the preparation of compound 192. Yield 90.9% $^1$H NMR (400 MHz, Chloroform-d) δ 8.82 (s, 1H), 7.36-7.27 (m, 2H), 7.26-7.17 (m, 3H), 6.85 (d, J=8.8 Hz, 1H), 6.78 (t, J=1.6 Hz, 1H), 6.32 (dd, J=8.8, 2.8 Hz, 1H), 6.23 (d, J=2.8 Hz, 1H), 5.39 (dd, J=12.0, 6.2 Hz, 1H), 4.82-4.74 (m, 1H), 4.53 (s, 2H), 4.51-4.41 (m, 2H), 4.26-4.04 (m, 2H), 3.42-3.30 (m, 1H), 2.78-2.68 (m, 1H). LC-MS (m/z) 393.2 (M+H$^+$)

Compound 200: (S)-7-fluoro-6-((1-(5-(3-fluorophenyl)-4,5-dihydro-1H-pyrazole-1-carbonyl)azetidin-3-yl)oxy)-2H-benzo[b][1,4]oxazin-3(4H)-one

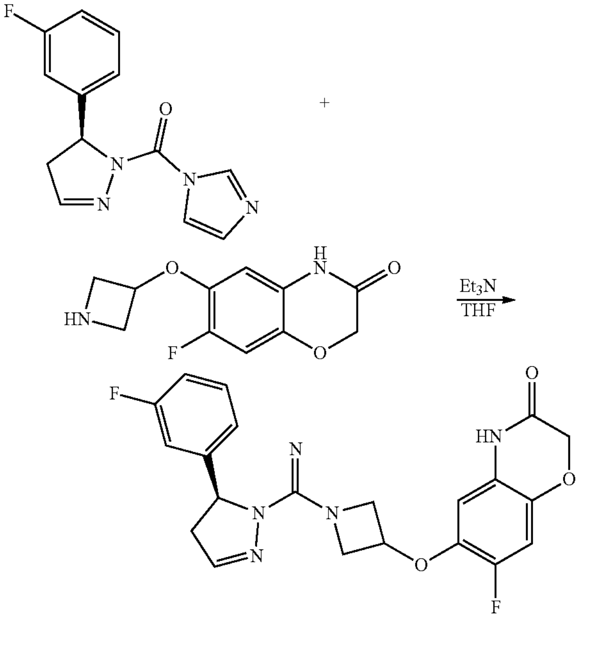

(S)-(5-(3-fluorophenyl)-4,5-dihydro-1H-pyrazol-1-yl)(1H-imidazol-1-yl)methanone (64 mg, 0.25 mmol) was added to a solution of $Et_3N$ (303 mg, 3.0 mmol) in MeOH and e 6-(azetidin-3-yloxy)-7-fluoro-2H-benzo[b][1,4]oxazin-3(4H)-one (71 mg, 0.25 mmol) was added in portions, and the whole reaction mixture was stirred and refluxed at 25° C. overnight. After the organic solvent was concentrated and further purified by silica gel column chromatography (PE/EA=2/1), to give 30 mg of (S)-7-fluoro-6-((1-(5-(3-fluorophenyl)-4,5-dihydro-1H-pyrazole-1-carbonyl)azetidin-3-yl)oxy)-2H-benzo[b][1,4]oxazin-3(4H)-one in a yield of 28% (30 mg) as a white solid. $^1$H NMR (400 MHz, Chloroform-d) δ 9.04 (s, 1H), 7.26-7.21 (m, 1H), 7.03-6.98 (m, 1H), 6.94-6.87 (m, 2H), 6.81 (t, J=1.6 Hz, 1H), 6.74 (d, J=11.2 Hz, 1H), 6.20 (d, J=7.9 Hz, 1H), 5.49 (dd, J=12.1, 6.0 Hz, 1H), 4.82-4.75 (m, 1H), 4.59-4.50 (m, 3H), 4.48-4.33 (m, 2H), 4.10 (d, J=10.1 Hz, 1H), 3.39 (ddd, J=18.5, 12.2, 1.7 Hz, 1H), 2.70 (ddd, J=18.5, 6.1, 1.8 Hz, 1H). LC-MS (ESI, m/z): M+H]$^+$=429.2.

Compound 201: (S)-6-((1-(5-(3,5-difluorophenyl)-4,5-dihydro-1H-pyrazole-1-carbonyl)azetidin-3-yl)oxy)-2H-benzo[b][1,4]oxazin-3(4H)-one

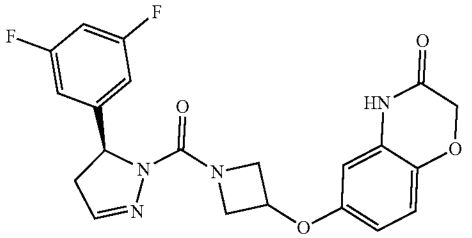 [SMILES: O=C1COc2ccc(OC3CN(C(=O)N4N=CC[C@H]4c4cc(F)cc(F)c4)C3)cc2N1]

The titled compound 201 were synthesized in an analogous manner to the preparation of compound 192. yield 41.0%. $^1$H NMR (400 MHz, Chloroform-d) δ 8.50 (brs, 1H), 6.87 (d, J=8.8 Hz, 1H), 6.81-6.71 (m, 3H), 6.70-6.60 (m, 1H), 6.34 (dd, J=8.8, 2.8 Hz, 1H), 6.24 (d, J=2.8 Hz, 1H), 5.36 (dd, J=12.0, 6.4 Hz, 1H), 4.87-4.80 (m, 1H), 4.55 (s, 2H), 4.53-4.45 (m, 2H), 4.31-4.21 (m, 1H), 4.16-4.06 (m, 1H), 3.42-3.30 (m, 1H), 2.74-2.64 (m, 1H). LC-MS (m/z) 429.2 (M+H$^+$).

Compound 202: (S)-7-((1-(5-(3,5-difluorophenyl)-4,5-dihydro-1H-pyrazole-1-carbonyl)azetidin-3-yl)oxy)-6-fluoro-3,4-dihydroquinolin-2(1H)-one

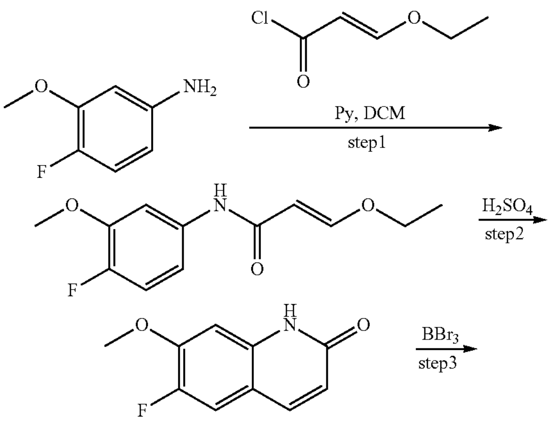

-continued

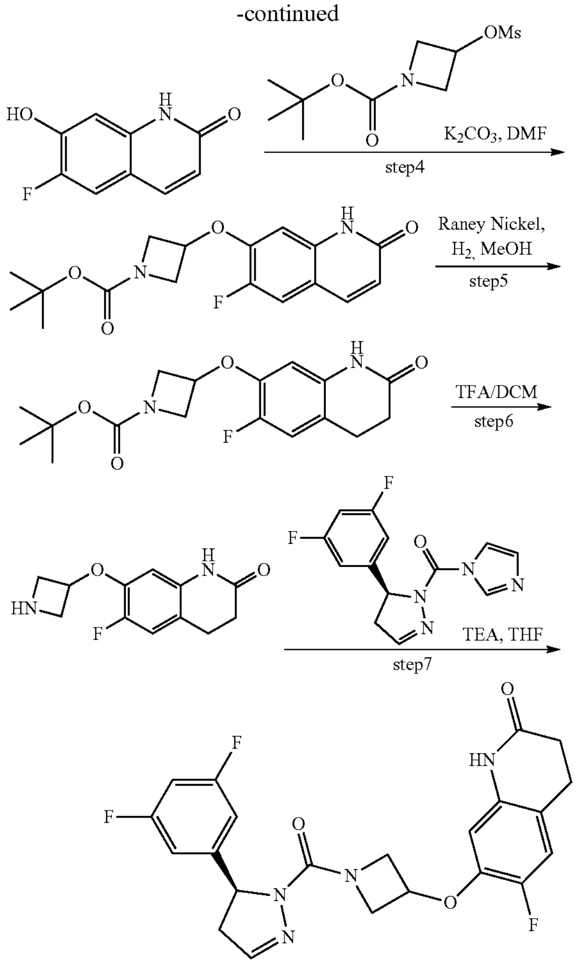

Step 1: 4-fluoro-3-methoxyaniline (3 g, 21.26 mmol) was dissolved in dry DCM (80 mL), pyridine (2.02 g, 25.51 mmol) was added, (E)-3-ethoxy-N-(4-fluoro-3-methoxyphenyl)acrylamide (3.43 g, 25.506 mmol) in 5 mL dry DCM was added to the mixture at 0° C. The mixture was stirred at room temperature for 16 hour, and then evaporated to dryness and the residue was purified by flash chromatography (PE/EA=3/2) to give (E)-N-(4-fluoro-3-methoxyphenyl)-3-methoxyacrylamide as an orange solid (5.1 g, 99%). LC-MS(ESI) m/z=240.2 [M+H$^+$]

Step 2: (E)-N-(4-fluoro-3-methoxyphenyl)-3-methoxyacrylamide (5.1 g, 21.32 mmol) was added to 57 mL of con. $H_2SO_4$ at 0° C., and the mixture was stirred at room temperature for 1.5 h. The reaction mixture was slowly added to the ice with strong stirring and the resulting solid was filtered and washed with water, evaporated to dryness to give 6-fluoro-7-methoxyquinolin-2(1H)-one as pale pink solid (3.21 g, 77.6%). $^1$H NMR (DMSO, 400 MHz) δ 11.68 (s, 1H), 7.78 (d, 1H, J=9.6 Hz), 7.54 (d, 1H, J=11.6 Hz), 6.96 (d, 1H, J=7.6 Hz), 6.38 (d, 1H, J=9.6 Hz), 3.88 (s, 3H). LC-MS(ESI) m/z=194.2 [M+H$^+$]

Step 3: 6-fluoro-7-methoxyquinolin-2(1H)-one (3.41 g, 17.57 mmol) was suspension in DCM (100 mL), and $BBr_3$ (1 M in DCM, 30 mL) was added to the mixture at 0° C. The mixture was stirred at room temperature for 16 hour, and was quenched by added MeOH and water, the resulting solid was filtered and washed with water, evaporated to dryness to give 6-fluoro-7-hydroxyquinolin-2(1H)-one as pale pink solid (3.06 g, 97%) as a light yellow solid. $^1$H NMR (DMSO, 400 MHz) δ 11.59 (s, 1H), 10.67 (brs, 1H), 7.72 (d, 1H, J=9.6 Hz), 7.45 (d, 1H, J=11.6 Hz), 6.88 (d, 1H, J=7.6 Hz), 6.30 (d, 1H, J=9.6 Hz). LC-MS(ESI) m/z=180.2 [M+H$^+$].

Step 4: A mixture of 6-fluoro-7-hydroxyquinolin-2(1H)-one (300 mg, 1.676 mmol), tert-butyl 3-((methylsulfonyl)oxy)azetidine-1-carboxylate (420 mg, 1.676 mmol) and $K_2CO_3$ (275 mg, 2.01 mmol) in dry DMF (5 mL) were stirred at 120° C. for 60 h. The mixture was evaporated to dryness and purified by flash chromatography (MeOH/DCM=1/20) to give tert-butyl 3-((6-fluoro-2-oxo-1,2-dihydroquinolin-7-yl)oxy)azetidine-1-carboxylate as a yellow solid (258 mg, 46%). LC-MS(ESI) m/z=335.4 [M+H$^+$].

Step 5: tert-butyl 3-((6-fluoro-2-oxo-1,2-dihydroquinolin-7-yl)oxy)azetidine-1-carboxylate (200 mg) was dissolved in MeOH (20 mL), Raney Nickel (50% in water, 20 mg) and AcOH (2-3 drops) was added. The mixture was stirred under $H_2$ at 1 atm for 16 h. the mixture was filter and evaporated to dryness to give tert-butyl 3-((6-fluoro-2-oxo-1,2,3,4-tetrahydroquinolin-7-yl)oxy)azetidine-1-carboxylate (200 mg, crude) was used for next step without purification. LC-MS(ESI) m/z=337.4[M+H$^+$]

Step 6: tert-butyl 3-((6-fluoro-2-oxo-1,2,3,4-tetrahydroquinolin-7-yl)oxy)azetidine-1-carboxylate (200 mg, crude) was dissolved in DCM (5 mL), TFA (1 mL) was added. The mixture was stirred at room temperature for 2 h, and then evaporated to dryness to give 7-(azetidin-3-yloxy)-6-fluoro-3,4-dihydroquinolin-2(1H)-one (180 mg, crude), which was used for next step without purification. LC-MS(ESI) m/z=237.3 [M+H$^+$]

Step 7: A mixture of (S)-(5-(3,5-difluorophenyl)-4,5-dihydro-1H-pyrazol-1-yl)(1H-imidazol-1-yl)methanone (149 mg) and 7-(azetidin-3-yloxy)-6-fluoro-3,4-dihydroquinolin-2(1H)-one (180 mg) in dry THF (5 mL) was added TEA (0.1 mL). The mixture was stirred at room temperature for 2 h, and evaporated to dryness and the residue was purified by pre-HPLC to give the titled compound 202 (40 mg, 15% in three steps) as a white solid. LC-MS(ESI) m/z=445.2 [M+H$^+$] 1H NMR (400 MHz, CDCl3) δ 8.44 (s, 1H), 6.88 (d, J=11.0 Hz, 1H), 6.77-6.76 (m, 1H), 6.73 (dd, J=8.0, 2.2 Hz, 2H), 6.64 (tt, J=8.9, 2.3 Hz, 1H), 6.13 (d, J=7.2 Hz, 1H), 5.37 (dd, J=12.2, 6.3 Hz, 1H), 4.92-4.84 (m, 1H), 4.51 (d, J=6.7 Hz, 2H), 4.23 (dd, J=75.9, 9.8 Hz, 3H), 3.35 (ddd, J=18.5, 12.2, 1.5 Hz, 1H), 2.85 (t, J=7.5 Hz, 2H), 2.67 (ddd, J=18.6, 6.3, 1.7 Hz, 1H), 2.56 (t, J=7.5 Hz, 2H).

Compound 203: (S)(5-(3,5-difluorophenyl)-4,5-dihydro-1H-pyrazol-1-yl)(3-(naphthalen-2-yloxy)azetidin-1-yl)methanone

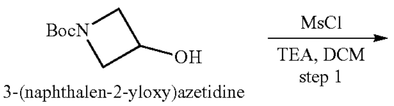

3-(naphthalen-2-yloxy)azetidine

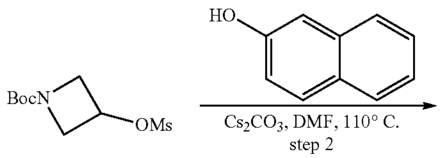

-continued

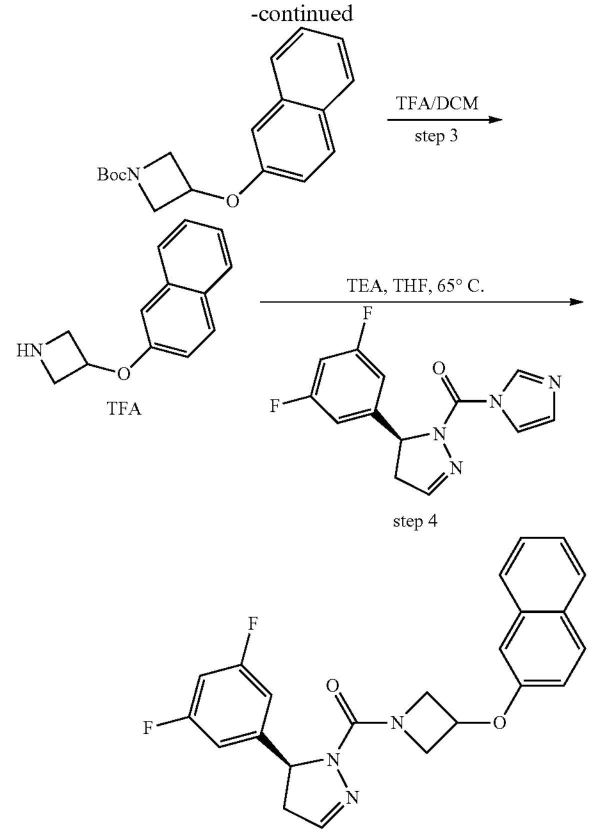

Step 1: tert-butyl 3-hydroxyazetidine-1-carboxylate (15 g, 86.6 mmol) was dissolved in 150 ml of dry DCM, TEA (26.2 g, 259.8 mmol) was added. MsCl (1.2 g, 103.92 mmol) was added slowly to the above solution at 0° C. The mixture was stirred for overnight. The mixture was extracted with DCM, washed with brine, dried (Na2SO4), and concentrated. The crude product was crystalized with EtOH/petroleum to yield tert-butyl 3-((methylsulfonyl)oxy)azetidine-1-carboxylate (13 g, 59.8%). LCMS (m/z) 252.3 (M+H$^+$).

Step 2: A mixture of tert-butyl 3-((methylsulfonyl)oxy)azetidine-1-carboxylate (1.0 g, 6.94 mmol), naphthalen-2-ol (1 g, 6.94 mmol) $Cs_2CO_3$ (4.52 g, 13.88 mmol) were placed in DMF (20 mL). The mixture was stirred 110° C. for overnight, water was added and extracted with EA, washed with brine, dried (Na2SO4), and concentrated. The crude product was purified by column chromatography on silica gel eluted with (EA/PE=1:5) to give tert-butyl 3-(naphthalen-2-yloxy)azetidine-1-carboxylate (880 mg, 48%) as a yellow oil. LC-MS (m/z) 300.4 (M+H$^+$).

Step 3: tert-butyl 3-(naphthalen-2-yloxy)azetidine-1-carboxylate (300 mg, 1 mmol) was dissolved in DCM (5 mL), and TFA (1.14 g, 10 mmol) was added. The mixture was stirred at r.t. for 4 h. The mixture was concentrated to give the desired product: 3-(naphthalen-2-yloxy)azetidine trifluoroacetic acid as TFA salt, which was used for next step without further purification. LC-MS (m/z) 200.3 (M+H$^+$).

Step 4: 3-(naphthalen-2-yloxy)azetidine trifluoroacetic acid (43 mg, 0.22 mmol) and (S)-(5-(3,5-difluorophenyl)-4,5-dihydro-1H-pyrazol-1-yl)(1H-imidazol-1-yl)methanone (50 mg, 0.18 mmol) and TEA (55 mg, 0.54 mmol) were dissolved in THF (5 ml) and stirred at room temperature for 16 h. The mixture was extracted with EA, washed with brine, dried (Na2SO4), and concentrated in vacuo. Purification by Pre-TLC (EA/PE=1:1) to give the titled compound 204 (71 mg, 97%) as a yellow solid. LC-MS (m/z) 408.4 (M+H$^+$). $^1$H NMR (400 MHz, Chloroform-d) δ 7.77 (d, J=9.0 Hz, 2H), 7.71 (d, J=8.2 Hz, 1H), 7.47-7.43 (m, 1H), 7.38-7.33 (m, 1H), 7.13 (dd, J=8.9, 2.5 Hz, 1H), 6.86 (d, J=2.5 Hz, 1H), 6.78-6.75 (m, 3H), 6.69 (tt, J=8.8, 2.3 Hz, 1H), 5.35-5.22 (m, 1H), 5.10-5.05 (m, 1H), 4.70-4.55 (m, 2H), 4.39-4.21 (m, 2H), 3.35 (dd, J=18.6, 12.0 Hz, 1H), 2.69 (dd, J=18.5, 6.2 Hz, 1H).

Compound 204: 7-((1-(5-(3,5-difluorophenyl)-4,5-dihydro-1H-pyrazole-1-carbonyl)azetidin-3-yl)oxy)quinolin-2(1H)-one

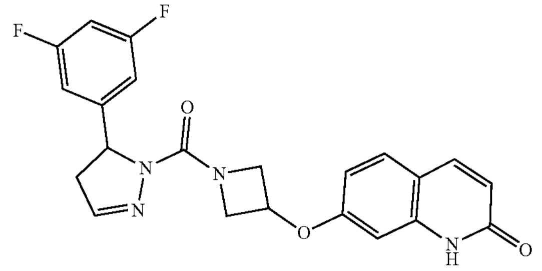 [SMILES: O=C(N1CC(Oc2ccc3ccc(=O)[nH]c3c2)C1)N1N=CCC1c1cc(F)cc(F)c1]

The titled compound 204 was synthesized in an analogous manner to the preparation of compound 203 yield: 40.9%. $^1$H NMR (400 MHz, DMSO-d$_6$) δ 11.55 (s, 1H), 7.82 (d, J=9.6 Hz, 1H), 7.59 (d, J=8.4 Hz, 1H), 7.16-7.08 (m, 1H), 7.04-6.98 (m, 1H), 6.96-6.87 (m, 2H), 6.74 (dd, J=8.8, 2.4 Hz, 1H), 6.67 (d, J=2.4 Hz, 1H), 6.32 (dd, J=9.6, 2.0 Hz, 1H), 5.24 (dd, J=12.0, 6.4 Hz, 1H), 5.08-4.99 (m, 1H), 4.49 (s, 2H), 4.00 (s, 2H), 3.44-3.34 (m, 1H), 2.69-2.60 (m, 1H). LC-MS (m/z) 425.3 (M+H$^+$).

Compound 205: (S)-7-((1-(5-(3,5-difluorophenyl)-4,5-dihydro-1H-pyrazole-1-carbonyl)azetidin-3-yl)oxy)quinolin-2(1H)-one

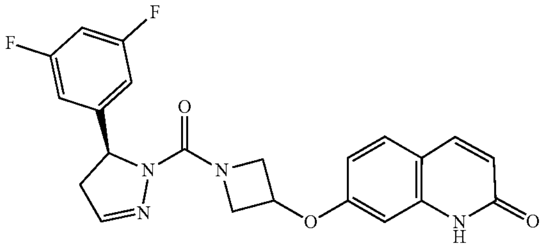 [SMILES: O=C(N1CC(Oc2ccc3ccc(=O)[nH]c3c2)C1)N1N=CC[C@H]1c1cc(F)cc(F)c1]

The titled compound 205 was synthesized in an analogous manner to the preparation of compound 203 yield: 56.9%. $^1$H NMR (400 MHz, Chloroform-d) δ 11.71 (s, 1H), 7.77 (d, J=9.4 Hz, 1H), 7.49 (d, J=8.7 Hz, 1H), 6.81-6.71 (m, 4H), 6.70-6.58 (m, 3H), 5.36 (dd, J=12.2, 6.4 Hz, 1H), 5.08-4.98 (m, 1H), 4.69-4.52 (m, 2H), 4.31 (d, J=5.3 Hz, 1H), 4.19 (d, J=10.2 Hz, 1H), 3.36 (m, 1H), 2.72-2.61 (m, 1H).

LC-MS (m/z) 425.3 (M+H$^+$).

Compound 206: (S)-7-((1-(5-(3,5-difluorophenyl)-4,5-dihydro-1H-pyrazole-1-carbonyl)azetidin-3-yl)oxy)-3,4-dihydroquinolin-2(1H)-one

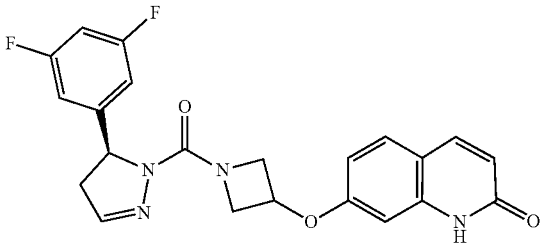 [SMILES: O=C(N1CC(Oc2ccc3ccc(=O)[nH]c3c2)C1)N1N=CC[C@H]1c1cc(F)cc(F)c1]

The titled compound 206 was synthesized in an analogous manner to the preparation of compound 203. yield: 65.2%. $^1$H NMR (400 MHz, Chloroform-d) δ 8.05 (s, 1H), 7.06-7.02 (m, 1H), 6.81-6.71 (m, 3H), 6.71-6.63 (m, 1H), 6.34 (dd, J=8.4, 2.4 Hz, 1H), 6.21 (d, J=2.4 Hz, 1H), 5.36-5.22 (m, 1H), 4.94-4.81 (m, 1H), 4.60-4.42 (m, 2H), 4.24 (d, J=10.1 Hz, 1H), 4.14 (d, J=8.8 Hz, 1H), 3.35 (m, 1H), 2.89 (dd, J=8.4, 6.4 Hz, 2H), 2.68 (m, 1H), 2.61 (dd, J=8.4, 6.4 Hz, 2H). LC-MS (m/z) 427.3 (M+H$^+$).

Compound 207: (S)-(3-((1H-indazol-6-yl)oxy)azetidin-1-yl(5-(3,5-difluorophenyl)-4,5-dihydro-1H-pyrazol-1-yl)methanone

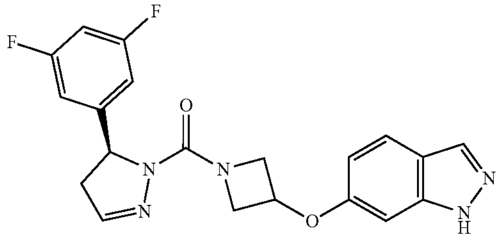 [SMILES: O=C(N1CC(Oc2ccc3cn[nH]c3c2)C1)N1N=CC[C@H]1c1cc(F)cc(F)c1]

The titled compound 207 was synthesized in an analogous manner to the preparation of compound 203. yield: 11.4% $^1$H NMR (400 MHz, Chloroform-d) δ 7.99 (s, 1H), 7.64 (d, J=8.8 Hz, 1H), 6.86-6.54 (m, 5H), 5.29 (dd, J=12.0, 6.4 Hz, 1H), 5.06-4.91 (m, 1H), 4.70-4.52 (m, 2H), 4.35-4.14 (m, 2H), 3.78-3.68 (m, 1H), 3.40-3.30 (m, 1H), 2.73-2.64 (m, 1H). LC-MS (m/z) 398.2 (M+H$^+$).

Compound 208: (S)-7-((1(5-(3,5-difluorophenyl)-4,5-dihydro-1H-pyrazole-1-carbonyl)azetidin-3-yl)oxy)-8-fluoroquinolin-2(1H)-one

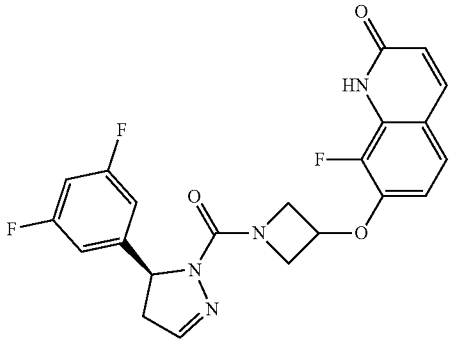 [SMILES: O=C(N1CC(Oc2ccc3ccc(=O)[nH]c3c2F)C1)N1N=CC[C@H]1c1cc(F)cc(F)c1]

The titled compound 208 was prepared in 36% yield from (S)-(5-(3,5-difluorophenyl)-4,5-dihydro-1H-pyrazol-1-yl)(1H-pyrrol-1-yl)methanone and 7-(azetidin-3-yloxy)-8-fluoroquinolin-2(1H)-one according to the procedure outlined for compound 203. LC-MS (m/z) 443.4 (M+H$^+$). $^1$H NMR (400 MHz, DMSO-d$_6$) δ 11.68 (s, 1H), 7.86 (dd, J=9.6, 1.5 Hz, 1H), 7.43 (dd, J=8.8, 1.7 Hz, 1H), 7.14-7.06 (m, 1H), 7.04-7.00 (m, 1H), 6.95-6.87 (m, 2H), 6.82 (dd, J=8.8, 7.5 Hz, 1H), 6.39 (d, J=9.6 Hz, 1H), 5.24 (dd, J=12.1, 6.6 Hz, 1H), 5.18-5.13 (m, 1H), 4.51 (s, 2H), 4.10-3.91 (m, 2H), 3.39 (ddd, J=18.7, 12.1, 1.7 Hz, 1H), 2.65 (ddd, J=18.7, 6.6, 1.7 Hz, 1H).

Compound 209: (S)-6-((1-(5-(3,5-difluorophenyl)-4,5-dihydro-1H-pyrazole-1-carbonyl)azetidin-3-yl)oxy)indolin-2-one

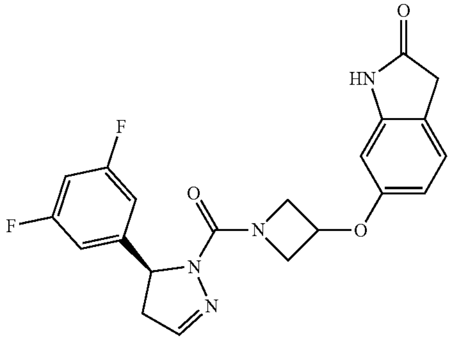 [SMILES: O=C1Cc2ccc(OC3CN(C(=O)N4N=CC[C@H]4c4cc(F)cc(F)c4)C3)cc2N1]

The titled compound 209 was prepared in 90% yield from (S)-(5-(3,5-difluorophenyl)-4,5-dihydro-1H-pyrazol-1-yl)(1H-pyrrol-1-yl)methanone and 6-(azetidin-3-yloxy)indolin-2-one according to the procedure outlined for compound 203. LC-MS (m/z) 413.4 (M+H$^+$). $^1$H NMR (400 MHz, Chloroform-d) δ 7.47 (brs, 1H), 7.10-7.06 (m, 1H), 6.77-6.71 (m, 2H), 6.71-6.63 (m, 1H), 6.35-6.30 (m, 2H), 5.26 (dd, J=12.3, 6.4 Hz, 1H), 4.92-4.85 (m, 1H), 4.55-4.45 (m, 2H), 4.26-4.12 (m, 2H), 3.45 (s, 2H), 3.33 (dd, J=18.6, 12.3 Hz, 1H), 2.67 (ddd, J=18.5, 6.5, 1.6 Hz, 1H).

Compound 210: (5-(3,5-difluorophenyl)-4,5-dihydro-1H-pyrazol-1-yl)(3-((3,5-difluoropyridin-2-yl)oxy)azetidin-1-)methanone

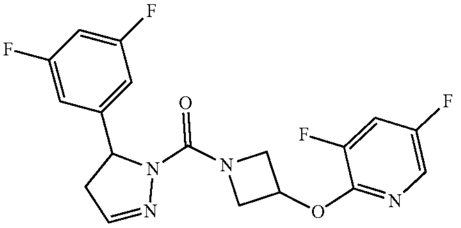 [SMILES: O=C(N1CC(Oc2ncc(F)cc2F)C1)N1N=CCC1c1cc(F)cc(F)c1]

The titled compound 210 was synthesized in an analogous manner to the preparation of compound 203. $^1$H NMR (400 MHz, Chloroform-d) δ 7.79 (d, J=2.6 Hz, 1H), 7.25-7.20 (m, 1H), 6.78-6.74 (m, 3H), 6.68 (tt, J=8.9, 2.3 Hz, 1H), 5.40-5.34 (m, 1H), 5.28 (dd, J=12.2, 6.5 Hz, 1H), 4.61-4.53 (m, 2H), 4.32-4.14 (m, 2H), 3.34 (ddd, J=18.6, 12.2, 1.7 Hz, 1H), 2.69 (ddd, J=18.5, 6.5, 1.7 Hz, 1H).

Compound 211: (3-((6-(benzyloxy)pyridin-3-yl)oxy)azetidin-1-yl)(5-(3,5-difluorophenyl)-4,5-dihydro-1H-pyrazol-1-yl)methanone

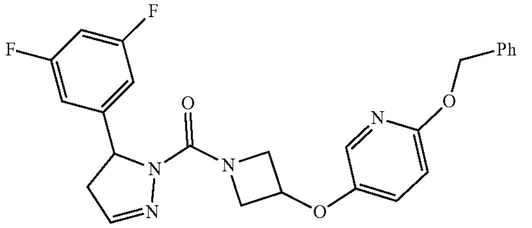 [SMILES: O=C(N1CC(Oc2ccc(OCc3ccccc3)nc2)C1)N1N=CCC1c1cc(F)cc(F)c1]

The titled compound 211 was synthesized in an analogous manner to the preparation of compound 203. $^1$H NMR (400 MHz, Chloroform-d) δ 7.63-7.59 (m, 1H), 7.47-7.25 (m, 5H), 7.15 (dd, J=8.9, 3.0 Hz, 1H), 6.78-6.71 (m, 4H), 6.67 (tt, J=8.9, 2.3 Hz, 1H), 5.30 (s, 2H), 5.25 (dd, J=12.2, 6.5 Hz, 1H), 4.90-4.85 (m, 1H), 4.57-4.38 (m, 2H), 4.28-4.11 (m, 2H), 3.33 (ddd, J=18.6, 12.2, 1.7 Hz, 1H), 2.68 (ddd, J=18.6, 6.5, 1.7 Hz, 1H).

Compound 212: (5-(3,5-difluorophenyl)-4,5-dihydro-1H-pyrazol-1-yl)(3-((5-fluoropyridin-2-yl)oxy)azetidin-1-yl)methanone SN-038-91

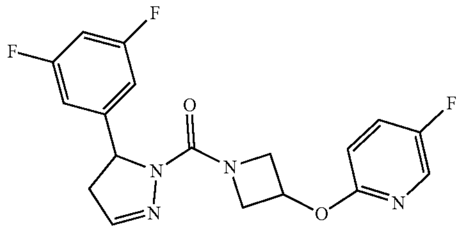 [SMILES: O=C(N1CC(Oc2ccc(F)cn2)C1)N1N=CCC1c1cc(F)cc(F)c1]

The titled compound 212 was synthesized in an analogous manner to the preparation of compound 203. $^1$H NMR (400 MHz, Chloroform-d) δ 7.94 (d, J=3.1 Hz, 1H), 7.36 (ddd, J=9.0, 7.5, 3.1 Hz, 1H), 6.79-6.72 (m, 3H), 6.68 (tt, J=8.9, 2.3 Hz, 1H), 5.33-5.24 (m, 2H), 4.55 (dd, J=21.6, 11.6 Hz, 2H), 4.17 (ddd, J=20.8, 10.6, 4.3 Hz, 2H), 3.34 (ddd, J=18.6, 12.2, 1.7 Hz, 1H), 2.68 (ddd, J=18.5, 6.6, 1.7 Hz, 1H).

Compound 213: (3-(2,4-difluorophenoxy)114zetidine-1-yl)(5-(5-fluoropyridin-3-yl)-4,5-dihydro-1H-pyrazol-1-yl)methanone

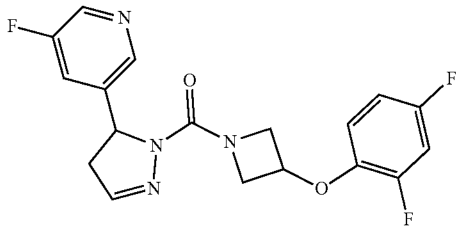 [SMILES: O=C(N1CC(Oc2ccc(F)cc2F)C1)N1N=CCC1c1cncc(F)c1]

The titled compound 213 was prepared from 3-(2,4-difluorophenoxy)azetidine trifluoroacetic acid salt and (5-(5-fluoropyridin-3-yl)-4,5-dihydro-1H-pyrazol-1-yl)(1H-imidazol-1-yl)methanone according the produce outlined for compound 203. LC-MS (m/z) 377.5 (M+H$^+$). $^1$H NMR (400 MHz, Chloroform-d) δ 8.47 (brs, 2H), 7.48 (d, J=8.2 Hz, 1H), 6.93-6.83 (m, 2H), 6.78 (dddd, J=9.3, 7.8, 3.0, 1.6 Hz, 1H), 6.69 (td, J=9.0, 5.2 Hz, 1H), 5.40 (dd, J=12.1, 6.2 Hz, 1H), 4.99-4.87 (m, 2H), 4.37-4.17 (m, 2H), 3.45 (dd, J=18.5, 12.0 Hz, 1H), 2.77 (dd, J=18.6, 6.4 Hz, 1H).

Compound 214: (S)-(3-(4-(benzyloxy)phenoxy)zetidine-1-yl)(5-(3,5-difluorophenyl)-4,5-dihydro-1H-pyrazol-1-yl)methanone

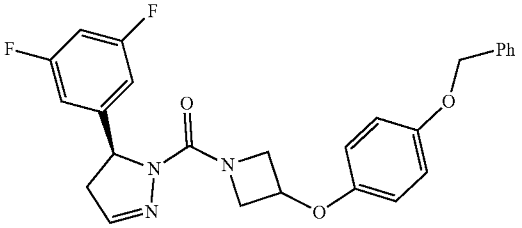 [SMILES: O=C(N1CC(Oc2ccc(OCc3ccccc3)cc2)C1)N1N=CC[C@H]1c1cc(F)cc(F)c1]

The titled compound 214 was synthesized in an analogous manner to the preparation of compound 203. $^1$H NMR (400 MHz, Chloroform-d) δ 7.43-7.27 (m, 5H), 6.92-6.86 (m, 2H), 6.78-6.63 (m, 6H), 5.26 (dd, J=12.6, 6.9 Hz, 1H), 4.99 (s, 2H), 4.87-4.82 (m, 1H), 4.56-4.40 (m, 2H), 4.26-4.10 (m, 2H), 3.32 (dd, J=18.6, 12.1 Hz, 1H), 2.72-2.62 (m, 1H).

Compound 215: (S)-6-((1-(5-(3,5-difluorophenyl)-4,5-dihydro-1H-pyrazole-1-carbonyl)115zetidine-3-yl)oxy)pyrimidine-4-carbonitrile

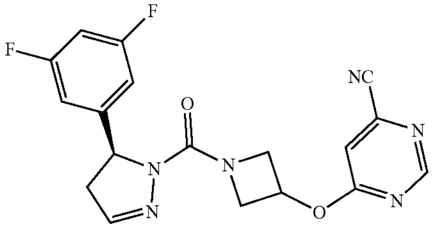 [SMILES: N#Cc1cc(OC2CN(C(=O)N3N=CC[C@H]3c3cc(F)cc(F)c3)C2)ncn1]

The titled compound 215 was synthesized in an analogous manner to the preparation of compound 203. $^1$H NMR (400 MHz, Chloroform-d) δ 8.83 (d, J=1.2 Hz, 1H), 7.17 (d, J=1.1 Hz, 1H), 6.79 (s, 1H), 6.77-6.73 (m, 2H), 6.70 (tt, J=8.8, 2.3 Hz, 1H), 5.49-5.44 (m, 1H), 5.27 (dd, J=12.2, 6.5 Hz, 1H), 4.63-4.55 (m, 2H), 4.29-4.13 (m, 2H), 3.36 (dd, J=18.7, 11.9 Hz, 1H), 2.70 (dd, J=18.6, 6.1 Hz, 1H).

Compound 216: (3-(benzofuran-5-yloxy)115zetidine-1-yl)(5-(3,5-difluorophenyl)-4,5-dihydro-1H-pyrazol-1-yl)methanone

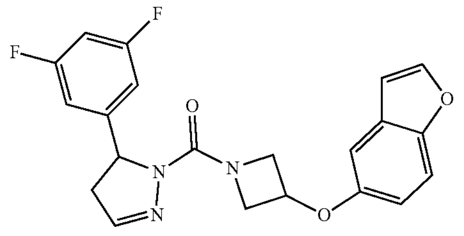 [SMILES: O=C(N1CC(Oc2ccc3occc3c2)C1)N1N=CCC1c1cc(F)cc(F)c1]

The titled compound 216 was synthesized in an analogous manner to the preparation of compound 203. $^1$H NMR (400 MHz, Chloroform-d) δ 7.54 (d, J=2.2 Hz, 1H), 7.47 (d, J=8.5 Hz, 1H), 6.85-6.73 (m, 5H), 6.71-6.65 (m, 2H), 5.28 (dd, J=12.1, 6.4 Hz, 1H), 4.98-4.95 (m, 1H), 4.64-4.48 (m, 2H), 4.26 (dd, J=31.3, 9.6 Hz, 2H), 3.34 (dd, J=18.6, 12.0 Hz, 1H), 2.69 (dd, J=18.5, 6.2 Hz, 1H).

Compound 217: (5-(3,5-difluorophenyl)-4,5-dihydro-1H-pyrazol-1-yl)(3-((6-hydroxypyridin-3-yl)oxy)115zetidine-1-yl)methanone

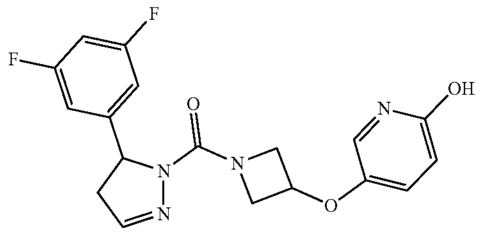 [SMILES: O=C(N1CC(Oc2ccc(O)nc2)C1)N1N=CCC1c1cc(F)cc(F)c1]

The titled compound 217 was prepared from 5-(116zetidine-3-yloxy)116zetidin-2-ol trifluoroacetic acid salt and (5-(3,5-difluorophenyl)-4,5-dihydro-1H-pyrazol-1-yl)(1H-imidazol-1-yl)methanone according the produce outlined for compound 203. LC-MS (m/z) 375.5 (M+H$^+$) $^1$H NMR (400 MHz, Chloroform-d) δ 7.32-7.28 (m, 1H), 6.78 (t, J=1.7 Hz, 1H), 6.76-6.74 (m, 3H), 6.73-6.66 (m, 1H), 6.60 (d, J=9.8 Hz, 1H), 5.26 (dd, J=12.2, 6.5 Hz, 1H), 4.72-4.65 (m, 1H), 4.51-4.42 (m, 2H), 4.22-4.18 (m, 2H), 3.35 (ddd, J=18.6, 12.2, 1.7 Hz, 1H), 2.69 (ddd, J=18.6, 6.5, 1.8 Hz, 1H).

Compound 218: (S)-4-((1-(5-(3,5-difluorophenyl)-4,5-dihydro-1H-pyrazole-1-carbonyl)azetidin-3-yl)oxy)-N-methylbenzamide

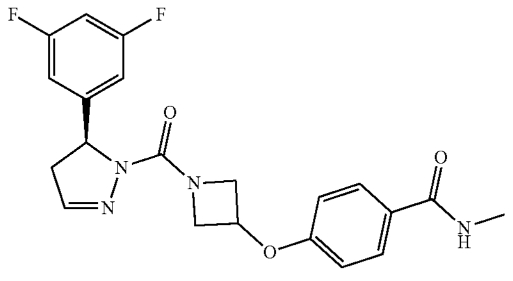 [SMILES: CNC(=O)c1ccc(OC2CN(C(=O)N3N=CC[C@H]3c3cc(F)cc(F)c3)C2)cc1]

The titled compound 218 was synthesized in an analogous manner to the preparation of compound 203. $^1$H NMR (400 MHz, Chloroform-d) δ 7.72-7.69 (m, 2H), 6.77-6.64 (m, 5H), 6.05 (s, 1H), 5.25 (dd, J=12.0, 8.0 Hz, 1H), 4.97-4.92 (m, 1H), 4.57-4.53 (m, 2H), 4.25-4.15 (m, 2H), 3.37-3.29 (m, 1H), 2.98 (d, J=4.0 Hz, 3H), 2.71-2.64 (m, 1H).

Compound 219: (S)-(3-(4-(1H-imidazol-2-yl)phenoxy)azetidin-1-yl)(5-(3,5-difluorophenyl)-4,5-dihydro-1H-pyrazol-1-yl)methanone

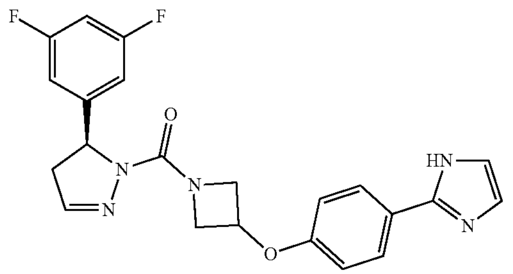 [SMILES: O=C(N1CC(Oc2ccc(-c3ncc[nH]3)cc2)C1)N1N=CC[C@H]1c1cc(F)cc(F)c1]

The titled compound 219 was synthesized in an analogous manner to the preparation of compound 203. $^1$H NMR (400 MHz, Chloroform-d) δ 7.89 (d, J=8.0 Hz, 2H), 7.08 (s, 2H), 6.80 (s, 1H), 6.71-6.61 (m, 5H), 5.23 (s, 1H), 4.86 (s, 1H), 4.49 (s, 2H), 4.11 (s, 2H), 3.34 (dd, J=20.0, 12.0 Hz, 1H), 2.67 (dd, J=16.0, 4.0 Hz, 1H).

Compound 220: (S)-4-((1-(5-(3,5-difluorophenyl-4,5-dihydro-1H-pyrazole-1-carbonyl)azetidin-3-yl)oxy)-2-fluorobenzamide

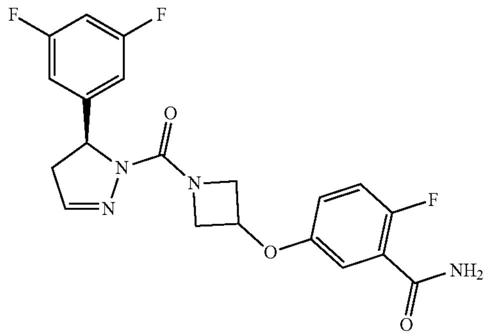 [SMILES: NC(=O)c1cc(OC2CN(C(=O)N3N=CC[C@H]3c3cc(F)cc(F)c3)C2)ccc1F]

The titled compound 220 was synthesized in an analogous manner to the preparation of compound 203. $^1$H NMR (400 MHz, Chloroform-d) δ 7.39-7.36 (m, 1H), 7.10-7.05 (m, 1H), 6.99-6.94 (m, 1H), 6.76-6.65 (m, 4H), 5.93 (s, 1H), 5.26 (dd, J=12.0, 8.0, 1H), 4.96-4.91 (m, 1H), 4.56 (dd, J=16.0, 8.0 Hz, 2H), 4.18 (dd, J=24.0, 8.0 Hz, 2H), 3.33 (dd, J=20.0, 12.0 Hz, 1H), 2.70-2.64 (m, 1H), 2.08 (s, 2H). LC-MS (m/z) 419.4 (M+H$^+$)

Compound 221: (S)-4-((1-(5-(3,5-difluorophenyl)-4,5-dihydro-1H-pyrazole-1-carbonyl)azetidin-3-yl)oxy)-3-fluorobenzamide

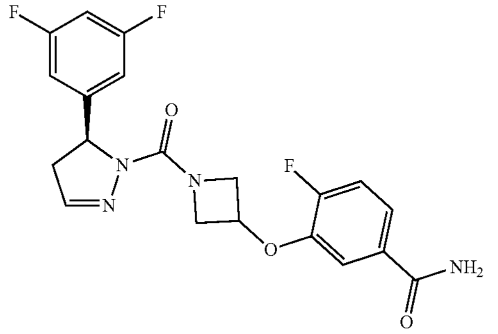 [SMILES: NC(=O)c1ccc(F)c(OC2CN(C(=O)N3N=CC[C@H]3c3cc(F)cc(F)c3)C2)c1]

The titled compound 221 was synthesized in an analogous manner to the preparation of compound 203 $^1$H NMR (400 MHz, DMSO-$d_6$) δ 8.00 (s, 1H), 7.53-7.49 (m, 1H), 7.43 (s, 1H), 7.34-7.29 (m, 2H), 7.11-7.05 (m, 1H), 6.99 (s, 1H), 6.91-6.86 (m, 2H), 5.21 (dd, J=12.0, 4.0 Hz, 1H), 5.09 (s, 1H), 4.48 (s, 2H), 3.98 (s, 2H), 3.40-3.34 (m, 1H), 2.64-2.57 (m, 1H). LC-MS (m/z) 419.4 (M+H$^+$)

Compound 222: (S)-4-((1-(5-(3,5-difluorophenyl)-4,5-dihydro-1H-pyrazole-1-carbonyl)azetidin-3-yl)oxy)-3,5-difluorobenzamide

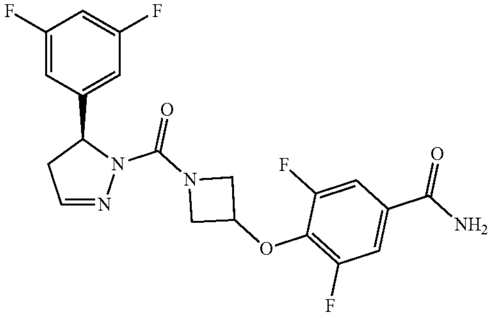 [SMILES: NC(=O)c1cc(F)c(OC2CN(C(=O)N3N=CC[C@H]3c3cc(F)cc(F)c3)C2)c(F)c1]

The titled compound 222 was synthesized in an analogous manner to the preparation of compound 203 $^1$H NMR (400 MHz, Chloroform-d) δ 7.38 (d, J=8.0 Hz, 2H), 6.77-6.65 (m, 4H), 5.26 (dd, J=12.0, 8.0 Hz, 1H), 5.07 (s, 1H), 4.48-4.44 (m, 2H), 4.37-4.26 (m, 2H), 3.34 (dd, J=16.0, 12.0 Hz, 1H), 2.68 (dd, J=20.0, 8.0 Hz, 1H), 1.79 (s, 2H).

Compound 223: (S)-(3-((1H-indol-6-yl)oxy)azetidin-1-yl)(5-(3,5-difluorophenyl)-4,5-dihydro-1H-pyrazol-1-yl)methanone

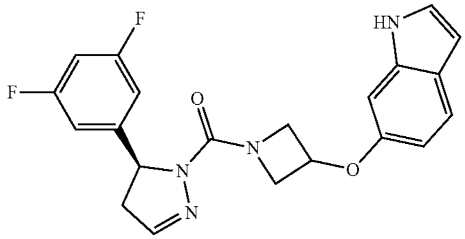 [SMILES: O=C(N1CC(Oc2ccc3cc[nH]c3c2)C1)N1N=CC[C@H]1c1cc(F)cc(F)c1]

The titled compound 223 was synthesized in an analogous manner to the preparation of compound 203 $^1$H NMR (400 MHz, Methanol-$d_4$) δ 7.40 (d, J=8.0 Hz, 1H), 7.09 (d, J=4.0 Hz, 1H), 6.91 (s, 1H), 6.83-6.78 (m, 3H), 6.72 (d, J=2.4 Hz, 1H), 6.61 (dd, J=12.0, 4.0 Hz, 1H), 6.33 (dd, J=3.2, 1.2 Hz, 1H), 5.26 (dd, J=12.0, 8.0 Hz, 1H), 5.01-4.96 (m, 1H), 4.56 (s, 2H), 4.14 (dd, J=28.0, 12.0 Hz, 2H), 3.44-3.36 (m, 1H), 2.71-2.64 (m, 1H).

Compound 224: 6-((1-(5-(3,5-difluorophenyl)-4,5-dihydro-1H-pyrazole-1-carbonyl)azetidin-3-yl)oxy)indolin-2-one

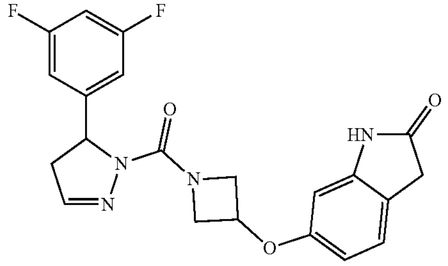 [SMILES: O=C1Cc2ccc(OC3CN(C(=O)N4N=CCC4c4cc(F)cc(F)c4)C3)cc2N1]

The titled compound 224 was synthesized in an analogous manner to the preparation of compound 203. $^1$H NMR (400 MHz, DMSO-$d_6$) δ 10.28 (s, 1H), 7.11-7.05 (m, 2H), 6.98 (s, 1H), 6.90-6.85 (m, 2H), 6.33 (dd, J=8.0, 4.0 Hz, 1H), 6.26 (d, J=4.0 Hz, 1H), 5.20 (dd, J=12.0, 8.0 Hz, 1H), 4.93 (s, 1H), 4.40 (s, 2H), 3.90 (s, 2H), 3.36-3.29 (m, 3H), 2.64-2.57 (m, 1H).

Compound 225: (S)—N-(2-(4-(5-(3,5-difluorophenyl-4,5-dihydro-1H-pyrazole-1-carbonyl)piperazin-1-yl)pyrimidin-4-yl)acetamide

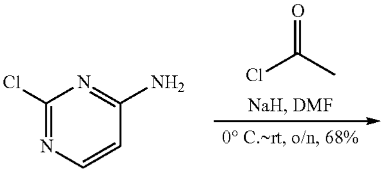

-continued

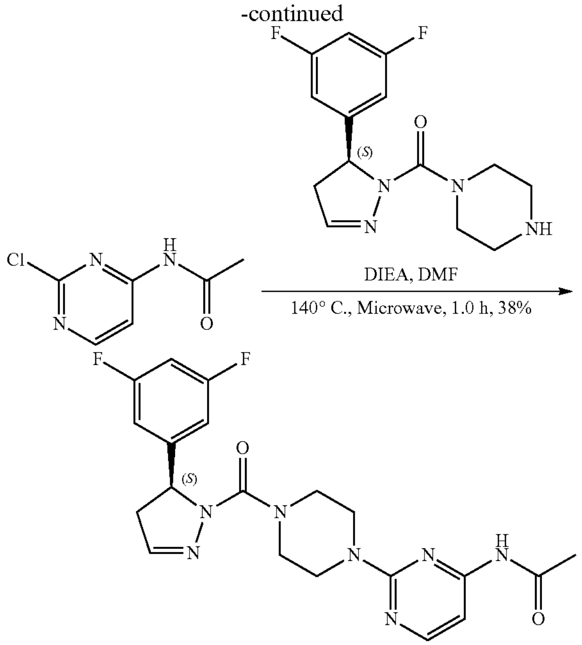

Step 1: 2-chloropyrimidin-4-amine (3.0 g, 23.16 mmol) was dissolved in 30 ml of dry DMF. NaH (1.38 g, 34.80 mmol) was added to the above solution under nitrogen at 0 degrees C. The mixture was stirred for 0.5 hour at 0 degrees C. To this was added acetyl chloride (2.16 g, 27.69 mmol), the mixture was stirred for another 1 overnight at room temperature. The mixture was extracted with EA, washed with brine, dried ($Na_2SO_4$), and concentrated in vacuo. Purification by silica gel chromatography to give N-(2-chloropyrimidin-4-yl)acetamide (2.7 g, 68%) as a white solid. (ES, m/s): 172.1[M+H]$^+$ Step 2: (S)-(5-(3,5-difluorophenyl)-4,5-dihydro-1H-pyrazol-1-yl)(piperazin-1-yl)methanone (1.0 g, 3.39 mmol) was dissolved in 15 ml of dry DMF. N-(2-chloropyrimidin-4-yl) acetamide (1.2 g, 6.97 mmol) and DIEA (870 mg, 6.74 mmol) were added to the above solution under nitrogen at room temperature. The mixture was stirred for 1.0 hour at 140 degrees C. under microwave. The mixture was extracted with EA, washed with brine, dried ($Na_2SO_4$), and concentrated in vacuo. Purification by silica gel chromatography to give the titled compound 225 (950 mg, 38%) as a white solid. (ES, m/s): 430.4[M+H]$^+$ $^1$H NMR (400 MHz, DMSO-$d_6$) δ 10.35 (s, 1H), 8.22 (d, J=5.6 Hz, 1H), 7.25 (d, J=5.6 Hz, 1H), 7.14-7.05 (m, 2H), 7.01-6.94 (m, 2H), 5.28-5.20 (m, 1H), 3.79-3.45 (m, 8H), 3.39-3.33 (m, 1H), 2.67-2.58 (m, 1H), 2.08 (s, 3H).

Compound 226: (S)—N-(2-(4-(5-(3,5-difluorophenyl)-4,5-dihydro-1H-pyrazole-1-carbonyl)piperazin-1-yl)-5-fluoropyrimidin-4-yl)cyclopropanecarboxamide

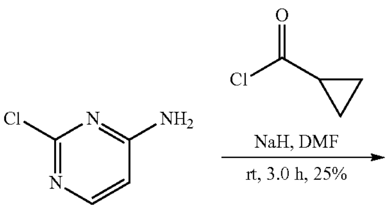

-continued

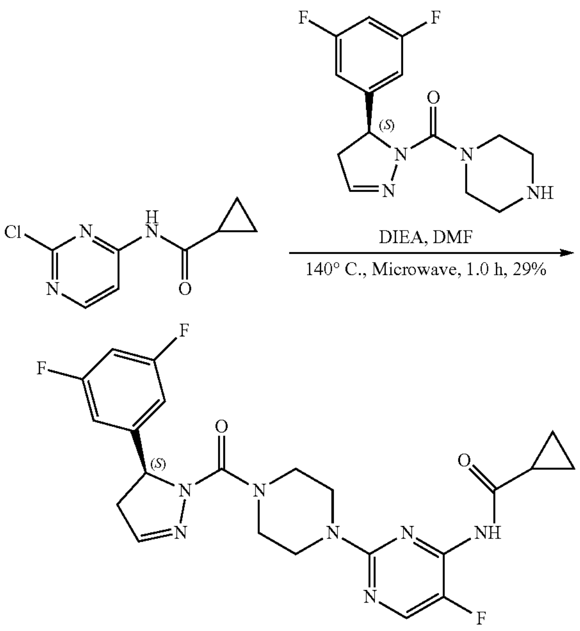

The titled compound 226 as a white solid (62 mg, 29%) was prepare from (S)-(5-(3,5-difluorophenyl)-4,5-dihydro-1H-pyrazol-1-yl)(piperazin-1-yl)methanone and N-(2-chloropyrimidin-4-yl)cyclopropanecarboxamide according to the procedure outlined for compound 225 (ES, m/s): 474.4 [M+H]$^+$ $^1$H NMR (400 MHz, DMSO-$d_6$) δ 10.59 (brs, 1H), 8.32 (d, J=2.8 Hz, 1H), 7.13-7.05 (m, 2H), 6.99-6.96 (m, 2H), 5.24 (dd, J=11.6, 10.0 Hz, 1H), 3.73-3.66 (m, 2H), 3.65-3.57 (m, 4H), 3.54-3.46 (m, 2H), 3.38-3.32 (m, 1H), 2.65-2.59 (m, 1H), 2.03-1.94 (m, 1H), 0.87-0.77 (m, 4H).

Compound 227: 2-chloro-4-((1-(5-(3,5-difluorophenyl)-4,5-dihydro-1H-pyrazole-1-carbonyl)azetidin-3-yl)oxy)benzamide

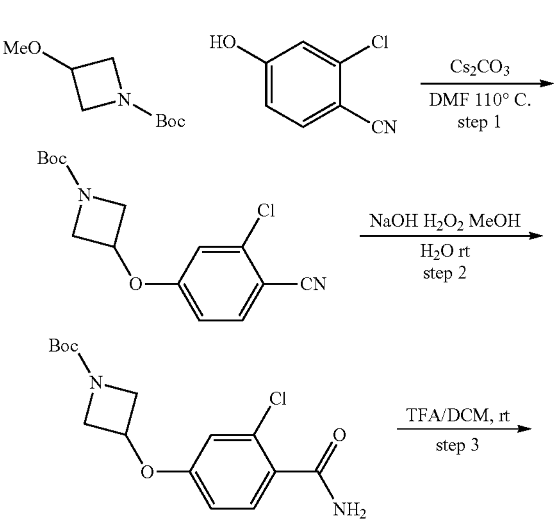

-continued

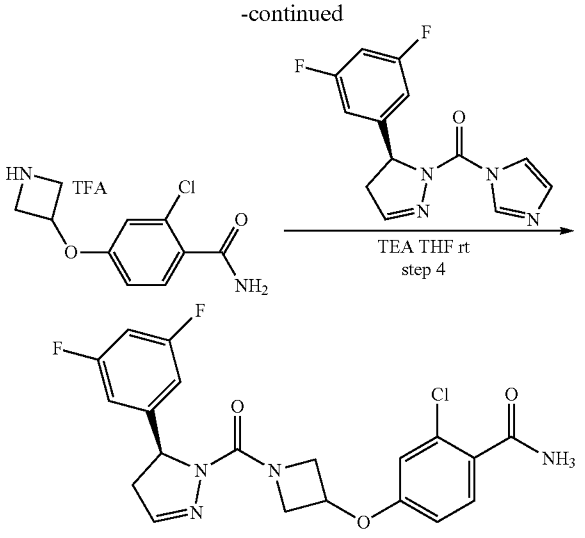

Step1: Synthesis of tert-butyl 3-(4-chloro-3-cyanophenoxy)azetidine-1-carboxylate To a solution of tert-butyl 3-((methylsulfonyl)oxy)azetidine-1-carboxylate (200 mg, 0.80 mmol, 1.0 equivs) and 2-chloro-4-hydroxybenzonitrile (134 mg, 0.88 mmol, 1.1 equivs) in anhydrous N,N-dimethylformamide (10 mL), Caesium carbonate (777.9 mg, 3.0 equivs) was added at room temperature. The reaction mixture was heated to 110° C. and stirred for 4 hours. The volatiles was removed in vacuo and the residue was suspension in dichloromethane, sat The organic layer was washed with water and brine respectively. Then dried over $MgSO_4$, filtered, and concentrated under reduced pressure. The residue was purified by silica gel column chromatography (petroleum ether/AcOEt, 4/1) to give tert-butyl 3-(3-chloro-4-cyanophenoxy)azetidine-1-carboxylate (190 mg, yield 77.3%) as a pale yellow solid. LC-MS (m/z) 254.4, 252.5 $[M-tBu]^+$.

Step2: Synthesis of tert-butyl 3-(3-carbamoyl-4-chlorophenoxy)azetidine-1-carboxylate A solution of tert-butyl 3-(3-chloro-4-cyanophenoxy)azetidine-1-carboxylate (190 mg, 0.615 mmol, 1.0 equivs) in methanol (6 mL) was treated with 30 percent hydrogen peroxide aqueous (75 mmL) and 1M aqueous sodium hydroxide solution (3 mL), the reaction mixture was stirred for overnight at 40° C. quenched with sat.$NaHCO_3$(aq) and the volatiles was removed in vacuo and the residue was suspension in dichloromethane, filtered and the filtrate was concentrated and used in next step directly without further purification. LC-MS (m/z) 327.5 $[M+H]^+$ Step3: Synthesis of 5-(azetidin-3-yloxy)-2-chlorobenzamide-2,2,2-trifluoroacetaldehyde. To a solution of tert-butyl 3-(3-carbamoyl-4-chlorophenoxy)azetidine-1-carboxylate in dichloromethane, trifluoroacetic was added dropwise at 0° C. then the mixture was refluxed for 2 hours. The volatiles was removed in vacuo and the residue was used in next step directly without further purification. LC-MS (m/z) 227.6 $[M+H]^+$.

Step4: Synthesis of (S)-2-chloro-5-((1-(5-(3,5-difluorophenyl)-4,5-dihydro-1H-pyrazole-1-carbonyl)azetidin-3-yl)oxy)benzamide (intermediate 4). To a solution of 4-(azetidin-3-yloxy)-2-chlorobenzamide-2,2,2-trifluoroacetaldehyde (1/1) in tetrahydrofuran (10 mL), triethylamine was added dropwise slowly at 0° C. afterwards, (S)-(5-(3,5-difluorophenyl)-4,5-dihydro-1H-pyrazol-1-yl)(1H-imidazol-1-yl)methanone (50 mg, 0.18 mmol, 1.0 equivs) was added at room temperature. The reaction mixture was stirred for overnight at the same temperature. The reaction was quenched with sat.$NH_4Cl$(aq), extracted with dichloromethane 3 times. The organic layer was combined and washed with water, sat.$NaHCO_3$(aq), and brine respectively. Then dried over $MgSO_4$, filtered, and concentrated under reduced pressure. The residue was purified by silica gel column chromatography (AcOEt/methanol, 20/1) to give 28.6 mg of 2-chloro-4-((1-(5-(3,5-difluorophenyl)-4,5-dihydro-1H-pyrazole-1-carbonyl)azetidin-3-yl)oxy)benzamide 227 as white powder. yield: 36.3%. 1H NMR (400 MHz, Chloroform-d) δ 7.48-7.06 (m, 2H), 7.04-6.43 (m, 5H), 5.31 (s, 1H), 4.97 (s, 1H), 4.62 (s, 2H), 4.18 (s, 2H), 3.31-3.42 (m, 1H), 2.81-2.62 (m, 1H). LC-MS (m/z) 435.5, 437.4 $[M+H]^+$. $^1$H NMR (400 MHz, Chloroform-d) δ 7.48-7.06 (m, 2H), 7.04-6.43 (m, 5H), 5.31 (s, 1H), 4.97 (s, 1H), 4.62 (s, 2H), 4.18 (s, 2H), 3.31-3.42 (m, 1H), 2.81-2.62 (m, 1H). LC-MS (m/z) 435.3 $[M+H]^+$.

Compound 228: N-(3-((1-(5-(3,5-difluorophenyl)-4,5-dihydro-1H-pyrazole-1-carbonyl)azetidin-3-yl)oxy)phenyl)acetamide

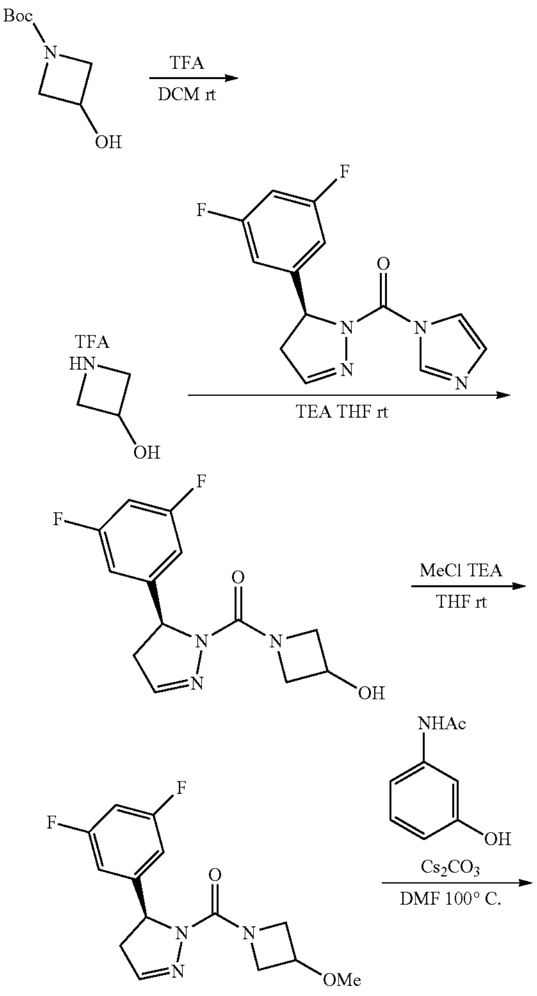

-continued

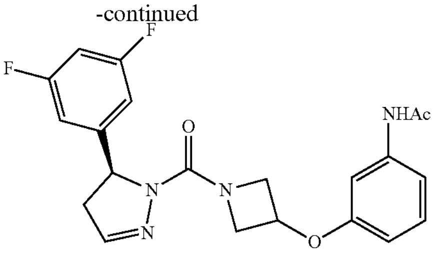

Step1: Synthesis of 2,2,2-trifluoroacetaldehyde-azetidin-3-ol (1/1) (intermediate 1) To a solution of tert-butyl 3-hydroxyazetidine-1-carboxylate (4.0 g, 23.09 mmol) in dichloromethane, trifluoroacetic was added dropwise at 0° C. then the mixture was refluxed for 2 hours. The volatiles was removed in vacuo and the residue was used in next step directly without further purification. LC-MS (m/z) 74.2 $[M+H]^+$.

Step2: Synthesis of (S)-(5-(3,5-difluorophenyl)-4,5-dihydro-1H-pyrazol-1-yl)(3-hydroxyazetidin-1-yl)methanone. To a solution of 2,2,2-trifluoroacetaldehyde-1-azetidin-3-ol (1/1) in tetrahydrofuran (100 mL), triethylamine was added dropwise slowly at 0° C. afterwards, (S)-(5-(3,5-difluorophenyl)-4,5-dihydro-1H-pyrazol-1-yl)(1H-imidazol-1-yl)methanone (1.05 g, 0.18 mmol, 1.3 equivs) was added at room temperature. The reaction mixture was stirred for overnight at the same temperature. The reaction was quenched with sat.$NH_4Cl$(aq), extracted with dichloromethane 3 times. The organic layer was combined and washed with water, sat.$NaHCO_3$(aq), and brine respectively. Then dried over $MgSO_4$, filtered, and concentrated under reduced pressure. The residue was purified by silica gel column chromatography (petroleum ether/AcOEt, 1/1) to give 2.05 g of (S)-(5-(3,5-difluorophenyl)-4,5-dihydro-1H-pyrazol-1-yl)(3-hydroxyazetidin-1-yl)methanone as pale yellow solid in a yield of 71.9% b. LC-MS (m/z) 283.6 $[M+H]^+$.

Step3: Synthesis of (S)-1-(5-(3,5-difluorophenyl)-4,5-dihydro-1H-pyrazole-1-carbonyl)azetidin-3-yl methanesulfonate (intermediate 3). To a solution of (S)-(5-(3,5-difluorophenyl)-4,5-dihydro-1H-pyrazol-1-yl)(3-hydroxyazetidin-1-yl)methanone (1.55 g, 5.51 mmol, 1.0 equivs) in tetrahydrofuran (60 mL), triethylamine was added dropwise slowly at room temperature. afterwards, methanesulfonyl chloride (469 mmL, 6.06 mmol, 1.1 equivs) was added dropwise at 0° C. The reaction mixture was stirred for overnight at the same temperature. The reaction was quenched with sat.$NaHCO_3$(aq), extracted with dichloromethane 2 times. The organic layer was combined and washed with water, sat.$NH_4Cl$(aq), and brine respectively. Then dried over $MgSO_4$, filtered, and concentrated under reduced pressure. The residue was purified by silica gel column chromatography (petroleum ether/AcOEt, 1/1) to give 1.9 g of (S)-1-(5-(3,5-difluorophenyl)-4,5-dihydro-1H-pyrazole-1-carbonyl)azetidin-3-yl methanesulfonate as pale yellow solid in a yield of 95.9%. LC-MS (m/z) 360.6 $[M+H]^+$.

Step 4: Synthesis of (S)—N-(3-((1-(5-(3,5-difluorophenyl)-4,5-dihydro-1H-pyrazole-1<carbonyl)azetidin-3-yl)oxy)phenyl)acetamide (37). To a solution of (S)-1-(5-(3,5-difluorophenyl)-4,5-dihydro-1H-pyrazole-1-carbonyl)azetidin-3-yl methanesulfonate (200 mg, 0.56 mmol, 1.0 equivs) and N-(3-hydroxyphenyl)acetamide (92.6 mg, 0.61 mmol, 1.1 equivs) in anhydrous N,N-dimethylformamide (5 mL), Caesium carbonate (544 mg, 1.67 mmol, 3.0 equivs) was added at room temperature. The reaction mixture was heated to 100° C. and stirred for 4 hours. The volatiles was removed in vacuo and the residue was suspension in dichloromethane, sat The organic layer was washed with water and brine respectively. Then dried over $MgSO_4$, filtered, and concentrated under reduced pressure. The residue was purified by silica gel column chromatography (petroleum ether/AcOEt, 1/1) to give 48 mg of N-(3-((1-(5-(3,5-difluorophenyl)-4,5-dihydro-1H-pyrazole-1-carbonyl)azetidin-3-yl)oxy)phenyl)acetamide 228 as pale yellow powder, in a yield of 20.8%. $^1H$ NMR (400 MHz, Chloroform-d) δ 7.23-7.17 (m, 2H), 6.95 (d, J=8.1 Hz, 1H), 6.75 (d, J=9.3 Hz, 3H), 6.68 (t, J=8.8 Hz, 1H), 6.51 (d, J=8.1 Hz, 1H), 5.26 (d, J=9.6 Hz, 1H), 4.93 (s, 1H), 4.54 (s, 2H), 4.21 (dd, J=27.9, 9.4 Hz, 2H), 3.34 (d, J=6.6 Hz, 1H), 2.69 (d, J=18.7 Hz, 1H), 2.18 (s, 3H). LC-MS (m/z) 415.5 $[M+H]^+$.

Compound 229: (3-(3-aminophenoxy)azetidin-1-yl)(5-(3,5-difluorophenyl)-4,5-dihydro-1H-pyrazol-1-yl)methanone

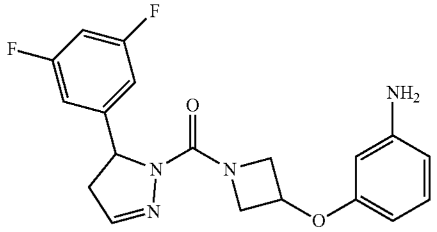 [SMILES: Nc1cccc(OC2CN(C(=O)N3N=CCC3c3cc(F)cc(F)c3)C2)c1]

To a solution of N-(3-((1-(5-(3,5-difluorophenyl)-4,5-dihydro-1H-pyrazole-1-carbonyl)azetidin-3-yl)oxy)phenyl)acetamide (16 mg, 0.038 mmol, 1.0 equivs) in methanol (2 mL), a solution of hydrochloric acid in ethyl acetate was added at room temperature. The reaction mixture was heated to 69° C. and stirred for 2 hours. The reaction was quenched with sat.$NaHCO_3$(aq), The volatiles was removed in vacuo and the residue was suspension in dichloromethane, The organic layer was washed with water and brine respectively. Then dried over $MgSO_4$, filtered, and concentrated under reduced pressure. The residue was purified by silica gel column chromatography (petroleum ether/AcOEt, 1/5) to give 2.7 mg of (3-(3-aminophenoxy)azetidin-1-yl)(5-(3,5-difluorophenyl)-4,5-dihydro-1H-pyrazol-1-yl)methanone 229 as pale white solid. In a yield of 18.8%. $^1H$ NMR (400 MHz, Chloroform-d) δ 7.06 (s, 1H), 6.93-6.61 (m, 4H), 6.38 (s, 1H), 6.28-6.09 (m, 2H), 5.27 (s, 1H), 4.88 (s, 1H), 4.51 (s, 2H), 4.20 (d, J=28.6 Hz, 2H), 3.51 (d, J=22.0 Hz, 1H), 2.68 (d, J=18.9 Hz, 1H). LC-MS (m/z) 373.1 $[M+H]^+$.

Compound 230: N-(3-((1-(5-(3,5-difluorophenyl)-4,5-dihydro-1H-pyrazole-1-carbonyl)azetidin-3-yl)oxy)phenyl)-N-methylacetamide

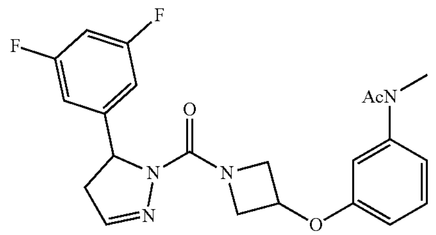

To a solution of N-(3-((1-(5-(3,5-difluorophenyl)-4,5-dihydro-H-pyrazole-1-carbonyl)azetidin-3-yl)oxy)phenyl)acetamide (20 mg, 0.048 mmol, 1.0 equivs) in super dry tetrahydrofuran (5 mL), sodium hydride (60% in mineral oil) was added as several portions at 0° C. with ice-water bath. Then iodomethane was added dropwise at room temperature. The mixture was stirred for overnight at the same temperature. The reaction was quenched with sat.$NH_4Cl$ (aq), extracted with dichloromethane 3 times. The organic layer was combined and washed with water, sat.$NaHCO_3$ (aq), and brine respectively. Then dried over $MgSO_4$, filtered, and concentrated under reduced pressure. The residue was purified by silica gel column chromatography (petroleum ether/AcOEt, 1/3) to give 16 mg of N-(3-((1-(5-(3,5-difluorophenyl)-4,5-dihydro-1H-pyrazole-1-carbonyl)azetidin-3-yl)oxy)phenyl)-N-methylacetamide as yellow oil in a yield of 77.4%. $^1$H NMR (400 MHz, Chloroform-d) δ 7.32 (t, J=8.0 Hz, 2H), 6.74 (m, 6H), 5.28 (dd, J=12.2, 6.5 Hz, 1H), 4.92 (dd, J=7.6, 3.2 Hz, 1H), 4.56 (s, 2H), 4.35-4.11 (m, 2H), 3.35 (ddd, J=18.5, 12.2, 1.8 Hz, 1H), 3.26 (s, 3H), 2.79-2.65 (m, 1H), 1.90 (s, 3H). LC-MS (m/z) 429.3 $[M+H]^+$.

Compound 231: (5-(3,5-difluorophenyl)-4,5-dihydro-1H-pyrazol-1-yl)(3-(3-(methylamino)phenoxy)azetidin-1-yl)methanone

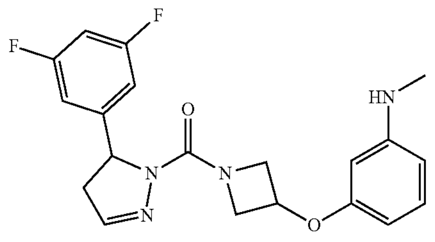 [SMILES: CNc1cccc(OC2CN(C(=O)N3N=CCC3c3cc(F)cc(F)c3)C2)c1]

To a solution of N-(3-((1-(5-(3,5-difluorophenyl)-4,5-dihydro-1H-pyrazole-1-carbonyl)azetidin-3-yl)oxy)phenyl)-N-methylacetamide (10 mg, 0.023 mmol) in methanol (5 mL), a solution of 1M aqueous sodium hydroxide (15 mL) was added at room temperature. The reaction mixture was heated to 100° C. and stirred for 4 hours. The mixture was cooled to room temperature and extracted with dichloromethane 3 times. The organic layer was combined and washed with water, sat.$NaHCO_3$(aq), and brine respectively. Then dried over $MgSO_4$, filtered, and concentrated under reduced pressure. The residue was purified by preparation thin liquid chromatography (development by ethyl acetate) to give 3.5 mg of (5-(3,5-difluorophenyl)-4,5-dihydro-1H-pyrazol-1-yl)(3-(3-(methylamino)phenoxy)azetidin-1-yl) methanone as pale yellow powder in a yield of 38.88%. $^1$H NMR (400 MHz, Chloroform-d) δ 7.09 (t, J=8.0 Hz, 1H), 6.75 (dd, J=8.3, 2.1 Hz, 3H), 6.72-6.64 (m, 1H), 6.33 (d, J=8.0 Hz, 1H), 6.13 (m, 2H), 5.27 (dd, J=12.2, 6.5 Hz, 1H), 5.00-4.86 (m, 1H), 4.52 (s, 2H), 4.22 (d, J=30.9 Hz, 2H), 3.41-3.26 (m, 1H), 2.84 (s, 3H), 2.68 (ddd, J=18.4, 6.5, 1.7 Hz, 1H). LC-MS (m/z) 387.4 $[M+H]^+$.

Compound 232: (S)-2-(4-(5-(3,5-difluorophenyl)-4,5-dihydro-1H-pyrazole-1-carbonyl)piperazin-1-yl) isonicotinonitrile

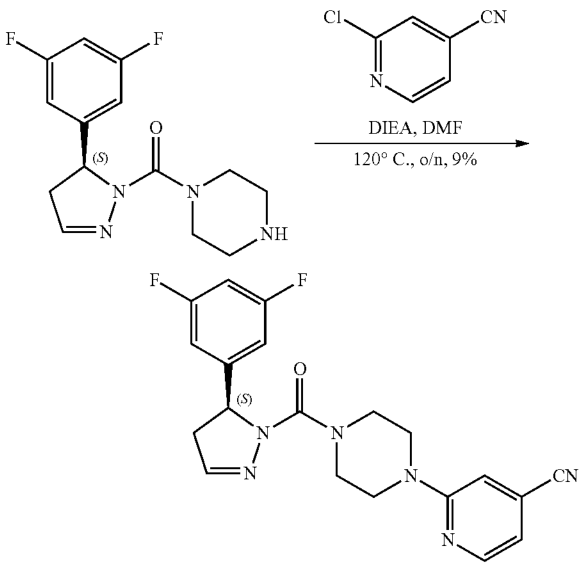

(S)-(5-(3,5-difluorophenyl)-4,5-dihydro-1H-pyrazol-1-yl)(piperazin-1-yl)methanone (213 mg, 0.72 mmol) was dissolved in 5 ml of dry DMF. 2-chloroisonicotinonitrile (100 mg, 0.72 mmol) and DIEA (188 mg, 1.45 mmol) were added to the above solution under nitrogen at room temperature. The mixture was stirred for 1 overnight at 120 degrees C. The mixture was extracted with EA, washed with brine, dried ($Na_2SO_4$), and concentrated in vacuo. Purification by silica gel chromatography to give the titled compound 232 (26 mg, 9%) as a yellow solid. (ES, m/s): 397.4$[M+H]^+$ $^1$H NMR (400 MHz, DMSO-$d_6$) δ 8.46-8.40 (m, 1H), 7.47-7.41 (m, 2H), 7.28-7.19 (m, 2H), 7.17-7.08 (m, 2H), 5.43-5.33 (m, 1H), 3.84-3.63 (m, 8H), 3.52-3.47 (m, 1H), 2.83-2.71 (m, 1H).

Compound 233: (S)-6-(4-(5-(3,5-difluorophenyl)-4,5-dihydro-1H-pyrazol-1-carbonyl)piperazin-1-yl) picolinonitrile

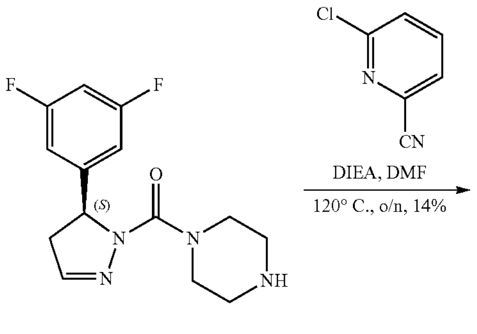

-continued

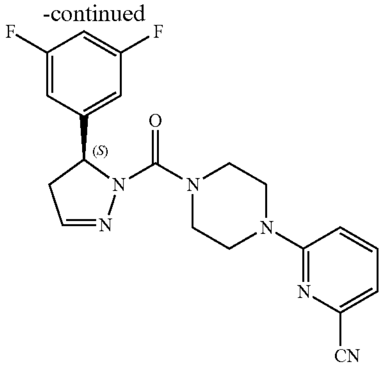

(S)-(5-(3,5-difluorophenyl)-4,5-dihydro-1H-pyrazol-1-yl)(piperazin-1-yl)methanone (213 mg, 0.72 mmol) was dissolved in 5 ml of dry DMF. 6-chloropicolinonitrile (100 mg, 0.72 mmol) and DIEA (188 mg, 1.45 mmol) were added to the above solution under nitrogen at room temperature. The mixture was stirred for 1 overnight at 120 degrees C. The mixture was extracted with EA, washed with brine, dried ($Na_2SO_4$), and concentrated in vacuo. Purification by silica gel chromatography to give the titled compound 233 (40 mg, 14%) as a yellow solid. (ES, m/s): 397.4[M+H]$^+$ $^1$H NMR (400 MHz, DMSO-$d_6$) δ 7.73-7.68 (m, 1H), 7.23-7.15 (m, 2H), 7.13-7.06 (m, 2H), 7.02-6.95 (m, 2H), 5.32-5.16 (m, 1H), 3.70-3.45 (m, 8H), 3.39-3.33 (m, 1H), 2.68-2.59 (m, 1H).

Compound 234: (S)(3-((1H-indazol-6-yl)oxy)azetidin-1-yl)(5-(3,5-difluorophenyl)-4,5-dihydro-1H-pyrazol-1-yl)methanone

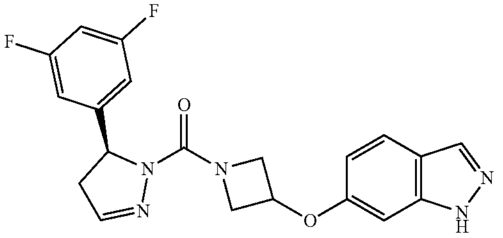 [SMILES: O=C(N1CC(Oc2ccc3cn[nH]c3c2)C1)N1N=CC[C@H]1c1cc(F)cc(F)c1]

The titled compound 234 was synthesized in an analogous manner to the preparation of compound 203. yield: 11.4% $^1$H NMR (400 MHz, Chloroform-d) δ 7.99 (s, 1H), 7.64 (d, J=8.8 Hz, 1H), 6.86-6.54 (m, 5H), 5.29 (dd, J=12.0, 6.4 Hz, 1H), 5.06-4.91 (m, 1H), 4.70-4.52 (m, 2H), 4.35-4.14 (m, 2H), 3.78-3.68 (m, 1H), 3.40-3.30 (m, 1H), 2.73-2.64 (m, 1H). LC-MS (m/z) 398.2 (M+H$^+$).

Compound 235: (S)-3-((1-(5-(3,5-difluorophenyl)-4,5-dihydro-1H-pyrazole-1-carbonyl)azetidin-3-yl)oxy)-4-fluorobenzonitrile

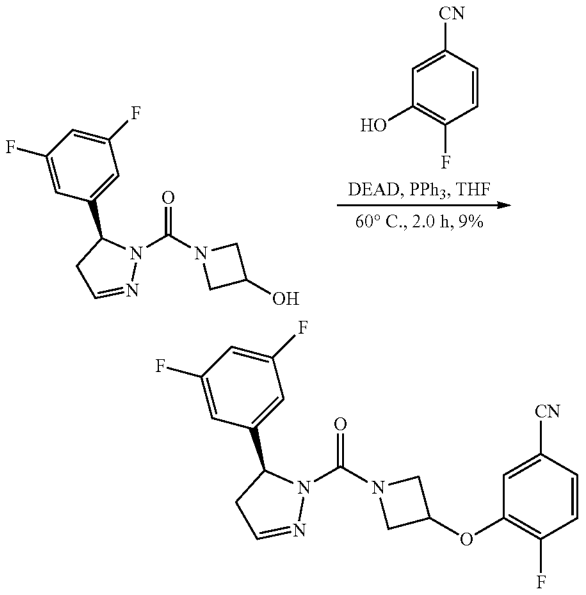

(S)-(5-(3,5-difluorophenyl)-4,5-dihydro-1H-pyrazol-1-yl)(3-hydroxyazetidin-1-yl)methanone (187 mg, 0.66 mmol) was dissolved in 10 ml of dry THF. DEAD (160 mg, 0.92 mmol), 4-fluoro-3-hydroxybenzonitrile (100 mg, 0.72 mmol), $PPh_3$ (240 mg, 0.92 mmol) was added to the above solution at room temperature. The mixture was stirred for 2.0 hour at 60 degrees C. under nitrogen. The mixture was extracted with EA, washed with brine, dried ($Na_2SO_4$), and concentrated in vacuo. Purification by silica gel chromatography to give the titled compound 235 (25 mg, 9%) as a white solid. (ES, m/s): 401.2 [M+H]$^+$ $^1$H NMR (400 MHz, DMSO-$d_6$) δ 7.56-7.51 (m, 2H), 7.50-7.46 (m, 1H), 7.10 (tt, J=9.4, 2.4 Hz, 1H), 7.01 (t, J=1.6 Hz, 1H), 6.93-6.87 (m, 2H), 5.23 (dd, J=12.2, 6.6 Hz, 1H), 5.13 (tt, J=6.6, 3.6 Hz, 1H), 4.52 (brs, 2H), 4.00 (brs, 2H), 3.42-3.36 (m, 1H), 2.68-2.55 (m, 1H).

Compound 236: (S)-5-((1-(5-(3,5-difluorophenyl)-4,5-dihydro-1H-pyrazole-1-carbonyl)azetidin-3-yl)oxy)-2-fluorobenzonitrile

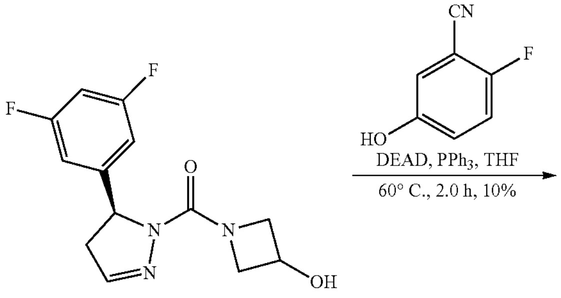

-continued

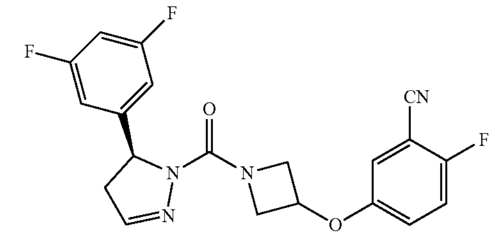

(S)-(5-(3,5-difluorophenyl)-4,5-dihydro-1H-pyrazol-1-yl)(3-hydroxyazetidin-1-yl)methanone (187 mg, 0.66 mmol) was dissolved in 10 ml of dry THF. DEAD (160 mg, 0.92 mmol), 2-fluoro-5-hydroxybenzonitrile (100 mg, 0.72 mmol), $PPh_3$ (240 mg, 0.92 mmol) was added to the above solution at room temperature. The mixture was stirred for 2 hours at 60° C. under nitrogen. The mixture was extracted with EA, washed with brine, dried ($Na_2SO_4$), and concentrated in vacuo. Purification by silica gel chromatography to give the titled compound 236 (30 mg, 10%) as a white solid. (ES, m/s): 401.2 $[M+H]^+$ $^1H$ NMR (400 MHz, DMSO-$d_6$) δ 7.73-7.61 (m, 2H), 7.56-7.48 (m, 1H), 7.37-7.28 (m, 1H), 7.23 (d, J=3.2 Hz, 1H), 7.16-7.08 (m, 2H), 5.49-5.39 (m, 1H), 5.26 (brs, 1H), 4.72 (brs, 2H), 4.17 (brs, 2H), 3.66-3.57 (m, 1H), 2.91-2.81 (m, 1H).

Compound 237: (S)-3-((1-(5-(3,5-difluorophenyl)-4,5-dihydro-1H-pyrazole-1-carbonyl)azetidin-3-yl)oxy)-5-fluorobenzonitrile

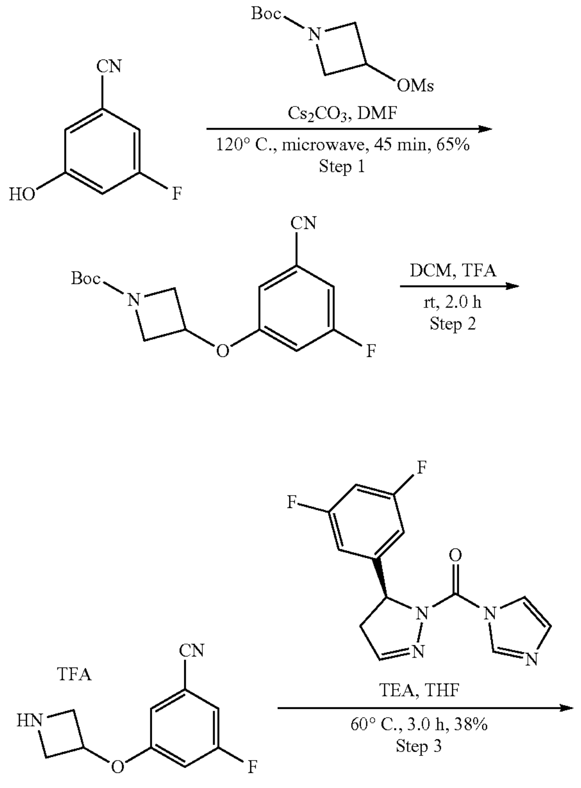

-continued

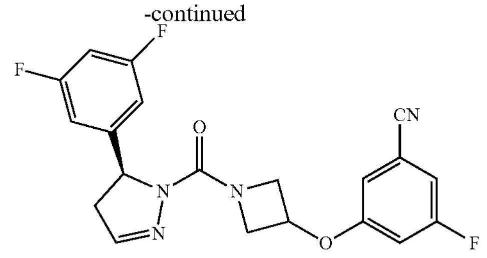

Step 1: 3-fluoro-5-hydroxybenzonitrile (200 mg, 1.46 mmol) was dissolved in 10 ml of dry DMF. $Cs_2CO_3$ (958 mg, 2.92 mmol) and tert-butyl 3-((methylsulfonyl)oxy)azetidine-1-carboxylate (439 mg, 1.75 mmol) were added to the above solution under nitrogen at room temperature. The mixture was stirred for 45 minutes at 120 degrees C. under Microwave. The mixture was extracted with EA, washed with brine, dried ($Na_2SO_4$), and concentrated in vacuo. Purification by silica gel chromatography to give tert-butyl 3-(3-cyano-5-fluorophenoxy)azetidine-1-carboxylate (280 mg, 655%) as a white solid. (ES, m/s): 293.3 $[M+H]^+$ Step 2: tert-butyl 3-(3-cyano-5-fluorophenoxy)azetidine-1-carboxylate (280 mg, 0.96 mmol) was dissolved in 6 ml of dry DCM. TFA (2 mL) was added to the above solution at room temperature. The mixture was stirred for 2.0 hours at room temperature. The mixture was concentrated in vacuo to give 3-(azetidin-3-yloxy)-5-fluorobenzonitrile trifluoroacetate (300 mg, crude) as brown oil which was used for next step without further purification. (ES, m/s): 191.3$[M-H]^-$ Step 3: (S)-(5-(3,5-difluorophenyl)-4,5-dihydro-1H-pyrazol-1-yl)(1H-imidazol-1-yl)methanone (200 mg, 0.72 mmol) was dissolved in 10 ml of dry THF and TEA (3 mL). 3-(azetidin-3-yloxy)-5-fluorobenzonitrile trifluoroacetate (300 mg, crude) in 5 mL of THF was added to the above solution at room temperature. The mixture was stirred for 3.0 hours at at 60° C. The mixture was extracted with EA, washed with brine, dried ($Na_2SO_4$), and concentrated in vacuo. Purification by silica gel chromatography to give the titled compound 237 (146 mg, 38%) as a white solid. (ES, m/s): 401.0 $[M+H]^+$ $^1H$ NMR (400 MHz, DMSO-$d_6$) δ 7.46 (ddd, J=8.4, 2.2, 1.2 Hz, 1H), 7.25 (t, J=2.0 Hz, 1H), 7.19 (dt, J=10.8, 2.4 Hz, 1H), 7.10 (tt, J=9.4, 2.4 Hz, 1H), 7.01-6.98 (m, 1H), 6.92-6.85 (m, 2H), 5.22 (dd, J=12.2, 6.6 Hz, 1H), 5.11-5.05 (m, 1H), 4.51 (brs, 2H), 3.94 (brs, 2H), 3.42-3.33 (m, 1H), 2.63 (ddd, J=18.6, 6.6, 1.8 Hz, 1H).

Compound 238: (S)-5-((1(5-(3,5-difluorophenyl)-4,5-dihydro-1H-pyrazole-1-carbonyl)azetidin-3-yl)oxy)-2,4-difluorobenzonitrile

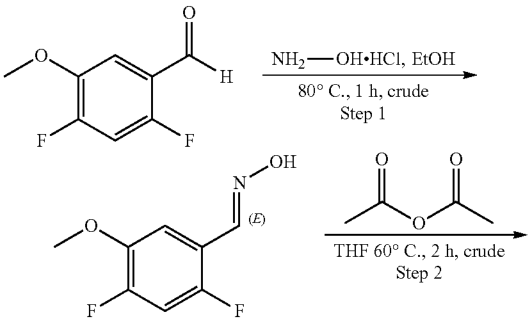

-continued

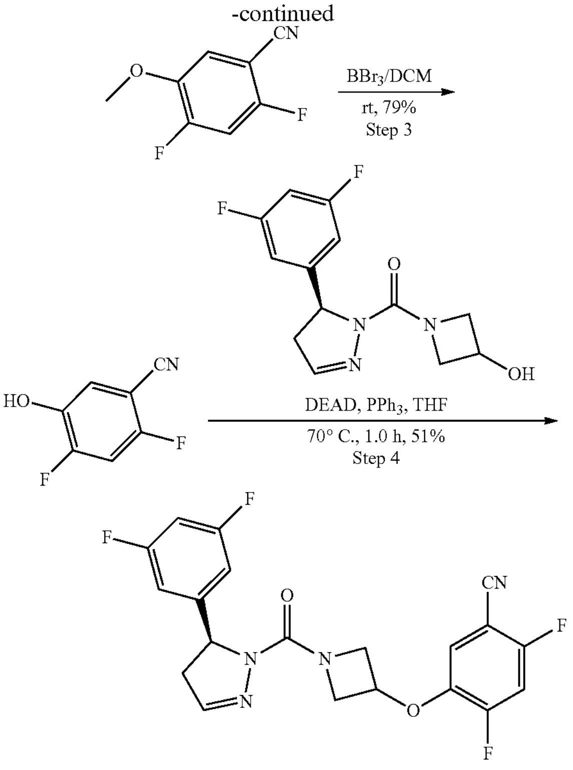

Step 1: 2,4-difluoro-5-methoxybenzaldehyde (3 g, 17.44 mmol) was dissolved in 100 ml of dry EtOH. Hydroxylamine hydrochloride (2.4 g, 34.78 mmol) was added to the above solution under at room temperature. The mixture was stirred for 1.0 hour at 80° C. The mixture was concentrated in vacuo to (E)-2,4-difluoro-5-methoxybenzaldehyde oxime (4.5 g, crude) as yellow solids, which was used for next step without further purification. (ES, m/s): 188.1 $[M+H]^+$ Step 2: (E)-2,4-difluoro-5-methoxybenzaldehyde oxime (4.5 g, crude) was dissolved in 60 ml of dry THF. acetic anhydride (15 mL) was added to the above solution under at room temperature. The mixture was stirred for 2.0 hours at 60° C. The mixture was concentrated in vacuo to give 2,4-difluoro-5-methoxybenzonitrile (5.0 g, crude) as yellow solids, which was used for next step without further purification. (ES, m/s): 170.1 $[M+H]^+$ Step 3: 2,4-difluoro-5-methoxybenzonitrile (1.3 g, crude) was dissolved in 20 ml of dry DCM. $BBr_3$ (35 mL, 1 N in DCM) was added to the above solution under at room temperature. The mixture was stirred for room temperature. The mixture was extracted with EA, washed with brine, dried ($Na_2SO_4$), and concentrated in vacuo. Purification by silica gel chromatography to give 2,4-difluoro-5-hydroxybenzonitrile (950 mg, 79%) as a white solid. (ES, m/s): 156.1 $[M+H]^+$ Step 4: (S)-(5-(3,5-difluorophenyl)-4,5-dihydro-1H-pyrazol-1-yl)(3-hydroxyazetidin-1-yl)methanone (1.73 g, 6.13 mmol) was dissolved in 10 ml of dry THF. DEAD (1.56 g, 9.17 mmol), 2,4-difluoro-5-hydroxybenzonitrile (950 mg, 6.13 mmol), $PPh_3$ (2.4 g, 9.16 mmol) was added to the above solution at room temperature. The mixture was stirred for 1.0 hour at 70° C. under nitrogen. The mixture was extracted with EA, washed with brine, dried ($Na_2SO_4$), and concentrated in vacuo. Purification by silica gel chromatography to give the titled compound 238 (1.3 g, 51%) as a white solid. (ES, m/s): 419.4 $[M+H]^+$ $^1H$ NMR (400 MHz, DMSO-$d_6$) δ 7.76 (t, J=10.2 Hz, 1H), 7.62-7.55 (m, 1H), 7.10 (t, J=9.4 Hz, 1H), 7.01 (s, 1H), 6.89 (d, J=7.6 Hz, 2H), 5.22 (dd, J=12.2, 6.6 Hz, 1H), 5.08 (brs, 1H), 4.50 (brs, 2H), 3.98 (brs, 2H), 3.37 (dd, J=18.6, 12.2 Hz, 1H), 2.63 (dd, J=18.6, 6.6 Hz, 1H).

Compound 239: (S)-5-((1-(5-(3,5-difluorophenyl)-4,5-dihydro-1H-pyrazole-1-carbonyl)azetidin-3-yl)oxy)-2,4-difluorobenzamide

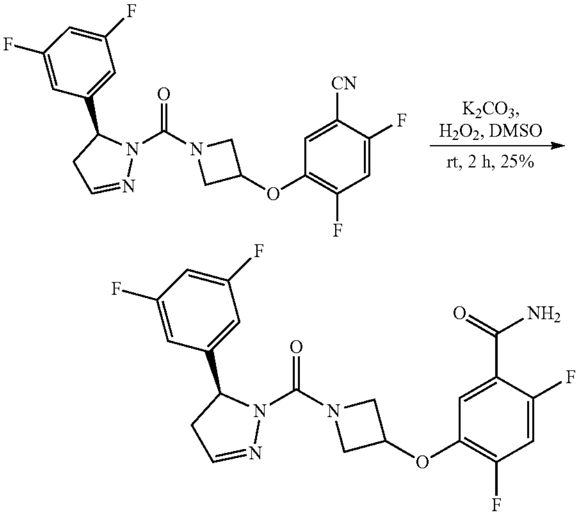

(S)-5-((1-(5-(3,5-difluorophenyl)-4,5-dihydro-1H-pyrazole-1-carbonyl)azetidin-3-yl)oxy)-2,4-difluorobenzonitrile (150 mg, 0.36 mmol) was dissolved in 6 ml of dry DMSO and $H_2O_2$ (1.5 mL). $K_2CO_3$ (10 mg, 0.07 mmol) was added to the above solution at room temperature. The mixture was stirred for 2.0 hours at room temperature. The mixture was extracted with EA, washed with brine, dried ($Na_2SO_4$), and concentrated in vacuo. Purification by silica gel chromatography to give the titled compound 48 (38 mg, 25%) as a white solid. (ES, m/s): 437.4 $[M+H]^+$ $^1H$ NMR (400 MHz, DMSO-$d_6$) δ 7.67 (brs, 21H), 7.42 (t, J=10.6 Hz, 1N), 7.14-7.02 (m, 2H), 7.00-6.96 (m, 1H), 6.88 (d, J=7.8 Hz, 2H), 5.20 (dd, J=12.2, 6.6 Hz, 1H), 5.07 (brs, 1H), 4.43 (brs, 2H), 3.97 (brs, 2H), 3.40-3.33 (m, 1H), 2.60 (dd, J=18.6, 6.6 Hz, 1H).

Compound 240: 6-(((R)-1-((S)-5-(3,5-difluorophenyl)-4,5-dihydro-1H-pyrazole-1-carbonyl) pyrrolidin-3-yl)oxy)imidazo[1,2-b]pyridazine-3-carbonitrile

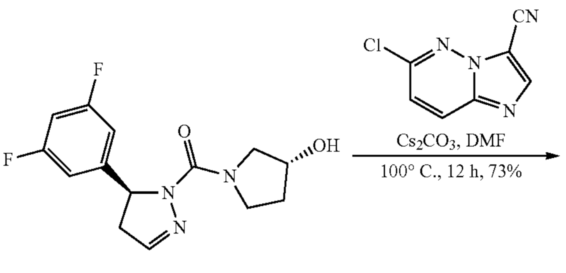

-continued

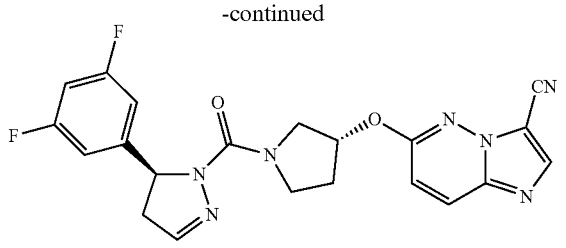

((S)-5-(3,5-difluorophenyl)-4,5-dihydro-1H-pyrazol-1-yl) ((R)-3-hydroxypyrrolidin-1-yl)methanone (180 mg, 1.2 mmol) was dissolved in 6 ml of dry DMF. $CS_2CO_3$ (652 mg, 2.0 mmol) and 6-chloroimidazo[1,2-b]pyridazine-3-carbonitrile (300 mg, 1 mmol) were added to the above solution at room temperature. The mixture was stirred for 12 hour at 100 degrees C. The mixture was extracted with EA, washed with brine, dried ($Na_2SO_4$), and concentrated in vacuo. Purification by silica gel chromatography to give the titled compound 240 (320 mg, 73%) as a white solid. (ES, m/s): 438.4 $[M+H]^+$ $^1H$ NMR (400 MHz, Chloroform-d) δ 8.10 (s, 1H), 7.94 (d, J=9.7 Hz, 1H), 6.91 (d, J=9.6 Hz, 1H), 6.84-6.76 (m, 3H), 6.68 (m, 1H), 5.67 (t, J=4.2 Hz, 1H), 5.32 (dd, J=12.0, 9.1 Hz, 1H), 4.08 (dd, J=13.6, 4.3 Hz, 1H), 3.91-3.80 (m, 2H), 3.73 (t, J=9.9 Hz, 1H), 3.33 (m, 1H), 2.68 (m, 1H), 2.39-2.17 (m, 2H).

Compound 241: 6-(((R)-1-((S)-5-(3,5-difluorophenyl)-4,5-dihydro-1H-pyrazole-1-carbonyl)pyrrolidin-3-yl)oxy)imidazo[1,2-b]pyridazine-3-carboxamide

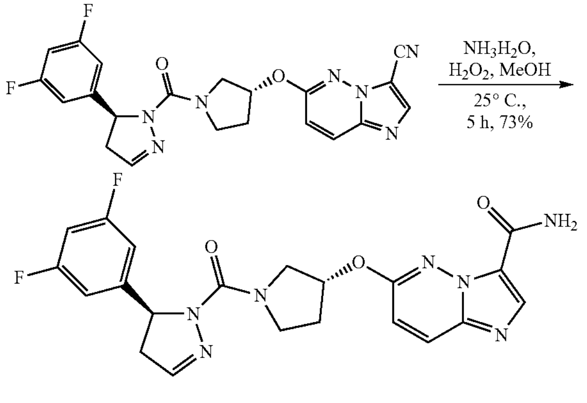

6-(((R)-1-((S)-5-(3,5-difluorophenyl)-4,5-dihydro-1H-pyrazole-1-carbonyl)pyrrolidin-3-yl)oxy)imidazo[1,2-b] pyridazine-3-carbonitrile (40 mg, 0.092 mmol) was dissolved in 6 ml of dry MeOH. aqueous ammonia (25 ul) and hydrogen peroxide (25 ul) were added to the above solution at room temperature. The mixture was stirred for 5 hour at 25 degrees C. The mixture was extracted with EA, washed with brine, dried ($Na_2SO_4$), and concentrated in vacuo. Purification by silica gel chromatography to give the titled compound 241 (10 mg, 24%) as a white solid. (ES, m/s): 438.4$[M+H]^+$ $^1H$ NMR (400 MHz, Chloroform-d) δ 8.37 (s, 1H), 8.01 (d, J=9.7 Hz, 1H), 6.86 (d, J=9.7 Hz, 1H), 6.82-6.78 (m, 3H), 6.69 (tt, J=8.8, 2.3 Hz, 1H), 5.97 (s, 1H), 5.46 (t, J=4.4 Hz, 1H), 5.31 (dd, J=12.0, 9.2 Hz, 1H), 4.08 (dd, J=13.4, 4.3 Hz, 1H), 3.96-3.85 (m, 2H), 3.78 (t, J=10.0 Hz, 1H), 3.34 (ddd, J=18.5, 12.0, 1.8 Hz, 1H), 2.69 (ddd, J=18.4, 9.2, 1.6 Hz, 1H), 2.45-2.35 (m, 1H), 2.30-2.16 (m, 1H).

Compound 242: ((S)-5-(3,5-difluorophenyl)-4,5-dihydro-1H-pyrazol-1-yl)((R)-3-(pyrazolo[1,5-a] pyrimidin-7-yloxy)pyrrolidin-1-yl)methanone

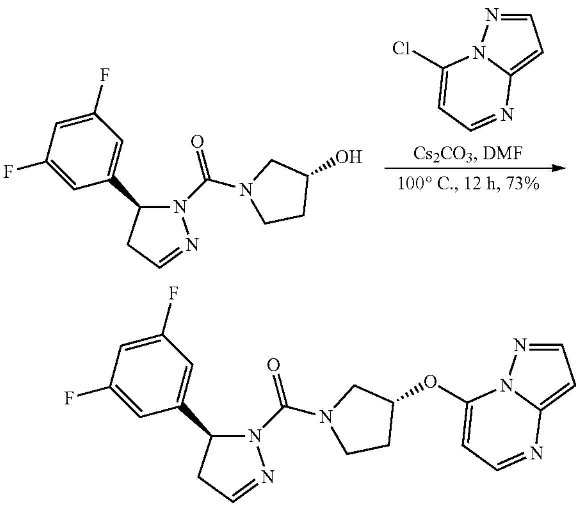

((S)-5-(3,5-difluorophenyl)-4,5-dihydro-1H-pyrazol-1-yl)((R)-3-hydroxypyrrolidin-1-yl)methanone (100 mg, 0.339 mmol) was dissolved in 6 ml of dry DMF. $CS_2CO_3$ (260 mg, 0.68 mmol) and 7-chloropyrazolo[1,5-a]pyrimidine (62.24 mg, 0.4068 mmol) were added to the above solution at room temperature. The mixture was stirred for 12 hour at 100 degrees C. The mixture was extracted with EA, washed with brine, dried ($Na_2SO_4$), and concentrated in vacuo. Purification by silica gel chromatography to give the titled compound 242 (8.6 mg, 6.1%) as a white solid. (ES, m/s): 413.4$[M+H]^+$ $^1H$ NMR (400 MHz, Chloroform-d) δ 8.46 (s, 1H), 8.17 (d, J=2.3 Hz, 1H), 6.83-6.65 (m, 5H), 6.22 (d, J=4.7 Hz, 1H), 5.39-5.22 (m, 2H), 4.22-3.83 (m, 4H), 3.33 (dd, J=18.5, 11.9 Hz, 1H), 2.68 (dd, J=18.4, 8.6 Hz, 1H), 2.58-2.44 (m, 2H), 2.33 (m, 1H).

Compound 243: 5-(((R)-1-((S)-5-(3,5-difluorophenyl)-4,5-dihydro-1H-pyrazole-1-carbonyl) pyrrolidin-3-yl)oxy)-2H-benzo[b][1,4]oxazin-3(4H)-one

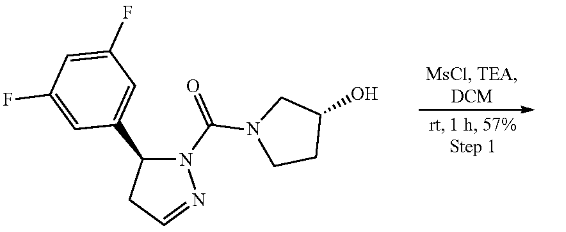

-continued

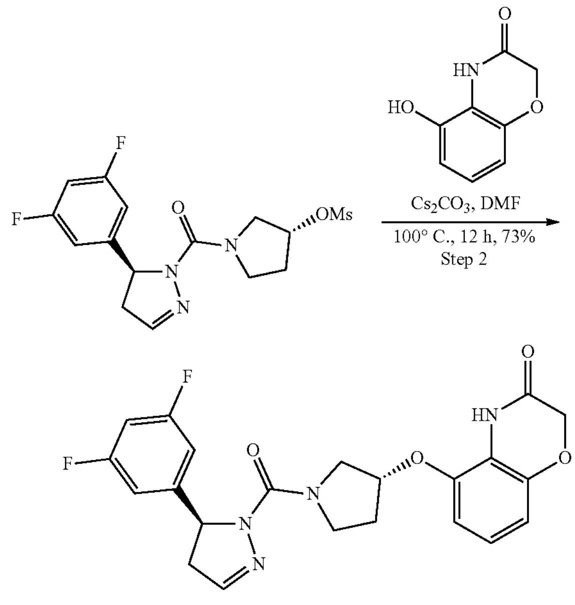

Step 1: ((S)-5-(3,5-difluorophenyl)-4,5-dihydro-1H-pyrazol-1-yl)((R)-3-hydroxypyrrolidin-1-yl)methanone (200 mg, 0.68 mmol) was dissolved in 4 ml of dry DCM. TEA (150 mg, 1.10 mmol) and MsCl (386 mg, 1.36 mmol) were added to the above solution at room temperature. The mixture was stirred for 1.0 hour at room temperature. The mixture was extracted with EA, washed with brine, dried ($Na_2SO_4$), and concentrated in vacuo to give (R)-1-((S)-5-(3,5-difluorophenyl)-4,5-dihydro-1H-pyrazole-1-carbonyl) pyrrolidin-3-yl methanesulfonate (260 mg, crude) as a yellow solid. (ES, m/s): 374.4 $[M+H]^+$ Step 2: (R)-1-((S)-5-(3,5-difluorophenyl)-4,5-dihydro-1H-pyrazole-1-carbonyl)pyrrolidin-3-yl methanesulfonate (100 mg, 0.27 mmol) was dissolved in 4 ml of dry DMF. $CS_2CO_3$ (260 mg, 0.68 mmol) and 5-hydroxy-2H-benzo[b][1,4]oxazin-3(4H)-one (36.9 mg, 0.23 mmol) were added to the above solution at room temperature. The mixture was stirred for 12 hour at 100 degrees C. The mixture was extracted with EA, washed with brine, dried ($Na_2SO_4$), and concentrated in vacuo. Purification by silica gel chromatography to give the titled compound 243 (8.6 mg, 6.1%) as a white solid. (ES, m/s): 443.1 $[M+H]^+$ $^1H$ NMR (400 MHz, Chloroform-d) δ 8.03 (s, 1H), 6.98-6.44 (m, 7H), 5.30 (ddd, J=11.3, 7.6, 3.0 Hz, 1H), 4.94 (s, 1H), 4.58 (d, J=3.1 Hz, 2H), 4.09-3.80 (m, 3H), 3.67 (q, J=8.3 Hz, 1H), 3.31 (m, 1H), 2.66 (dd, J=18.3, 7.8 Hz, 1H), 2.19 (s, 2H).

Compound 244: tert-butyl (S)-(6-((1-(5-(3,5-difluorophenyl)-4,5-dihydro-1H-pyrazole-1-carbonyl)azetidin-3-ylidene)methyl)-5-fluoropyridin-2-yl)carbamate

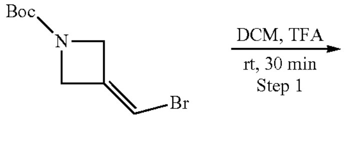

-continued

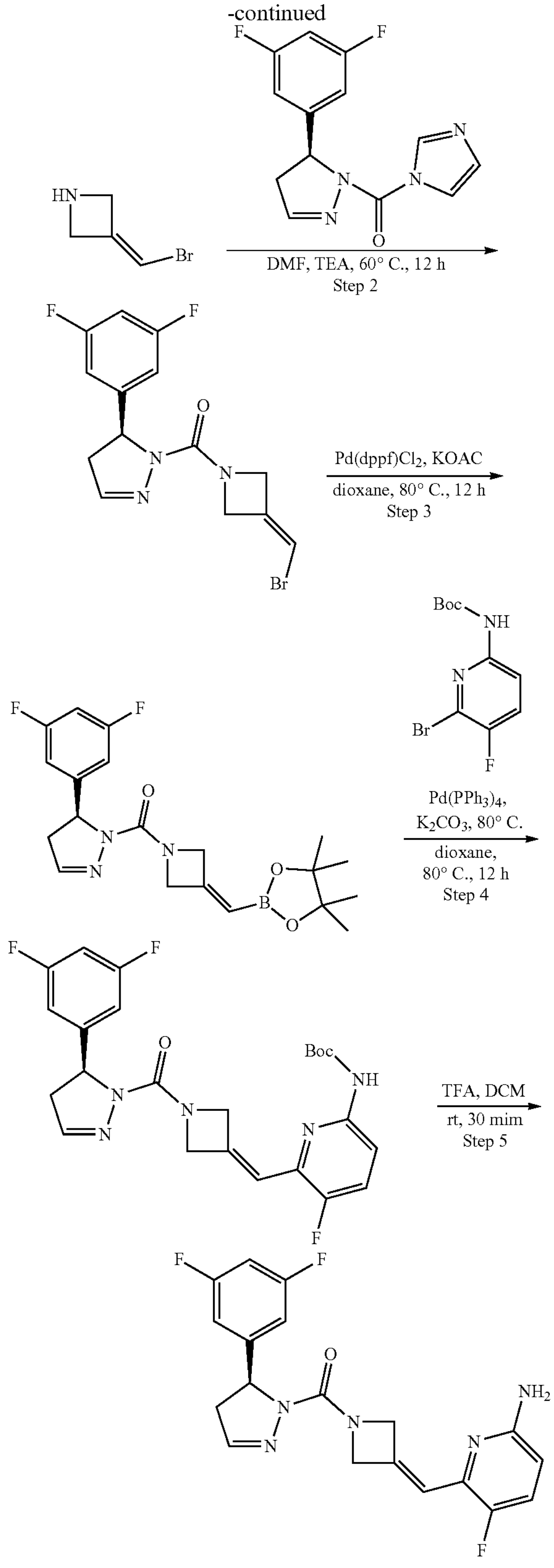

Step 1: tert-butyl 3-(bromomethylene)azetidine-1-carboxylate (3 g, 12.1 mmol) was dissolved in 40 ml of dry DCM, TFA (12 ml) were added to the above solution at room temperature. The mixture was stirred for 30 min at room temperature. The mixture was concentrated in vacuo to give 3-(bromomethylene)azetidine (2.8 g, crude) as a yellow oil. (ES, m/s): 148.0 [M+H]$^+$ Step 2: 3-(bromomethylene)azetidine (2.8 g, crude, 12.1 mmol) was dissolved in 30 ml of dry THF. TEA (5 ml) and (S)-(5-(3,5-difluorophenyl)-4,5-dihydro-1H-pyrazol-1-yl)(1H-imidazol-1-yl)methanone (3.7 g, 13.3 mmol) were added to the above solution at room temperature. The mixture was stirred for 12 hour at 60 degrees C. The mixture was extracted with EA, washed with brine, dried ($Na_2SO_4$), and concentrated in vacuo. Purification by silica gel chromatography to give (S)-(3-(bromomethylene) azetidin-1-yl)(5-(3,5-difluorophenyl)-4,5-dihydro-1H-pyrazol-1-yl) methanone (2.1 mg, 49%) as a white solid. (ES, m/s): 356.4 [M+H]$^+$ Step 3: (S)-(3-(bromomethylene)azetidin-1-yl)(5-(3,5-difluorophenyl)-4,5-dihydro-1H-pyrazol-1-yl)methanone (200 mg, 0.56 mmol) was dissolved in 3 ml of dry dioxane. (Pd(dppf)$Cl_2$ (40 mg, 0.17 mmol), KOAc (166 mg, 1.68 mmol) and 4,4,4',4',5,5,5',5'-octamethyl-2,2'-bi(1,3,2-dioxaborolane) (215 mg, 1.12 mmol) were added to the above solution under nitrogen at room temperature. The mixture was stirred for 12.0 hour at 80 degrees C. The mixture was extracted with EA, washed with brine, dried ($Na_2SO_4$), and concentrated in vacuo. Purification by silica gel chromatography to give (S)-(5-(3,5-difluorophenyl)-4,5-dihydro-1H-pyrazol-1-yl)(3-((4,4,5,5-tetramethyl-1,3,2-dioxaborolan-2-yl)methylene)azetidin-1-yl)methanone (2.1 mg, 49%) as a white solid. (ES, m/s): 404.2 [M+H]$^+$ Step 4: (S)-(5-(3,5-difluorophenyl)-4,5-dihydro-1H-pyrazol-1-yl)(3-((4,4,5,5-tetramethyl-1,3,2-dioxaborolan-2-yl) methylene)azetidin-1-yl)methanone (200 mg, 0.50 mmol) was dissolved in 3 ml of dry dioxane. (Pd($PPh_3$)$_4$ (72 mg, 0.07 mmol), $K_2CO_3$ (170 mg, 1.5 mmol) and(S)-(3-(bromomethylene)azetidin-1-yl)(5-(3,5-difluorophenyl)-4,5-dihydro-1H-pyrazol-1-yl)methanone (120 mg, 0.41 mmol) were added to the above solution under nitrogen at room temperature. The mixture was stirred for 12.0 hour at 80 degrees C. The mixture was extracted with EA, washed with brine, dried ($Na_2SO_4$), and concentrated in vacuo. Purification by silica gel chromatography to give (S)-(3-((6-amino-3-fluoropyridin-2-yl)methylene)azetidin-1-yl)(5-(3,5-difluorophenyl)-4,5-dihydro-1H-pyrazol-1-yl)methanone (80 mg, 40%) as a white solid. (ES, m/s): 488.2 [M+H]$^+$ Step 5: (S)-(3-((6-amino-3-fluoropyridin-2-yl)methylene) azetidin-1-yl)(5-(3,5-difluorophenyl)-4,5-dihydro-1H-pyrazol-1-yl)methanone (80 mg, 0.16 mmol) was dissolved in 2 ml of dry DCM. TFA (0.6 ml) were added to the above solution at room temperature. The mixture was stirred for 30 min at room temperature. The mixture was extracted with EA, washed with brine, dried ($Na_2SO_4$), and concentrated in vacuo. Purification by silica gel chromatography to give the titled compound 244 (17 mg, 20.7%) as a white solid. (ES, m/s): 391.1 [M+H]$^+$ $^1$H NMR (400 MHz, Chloroform-d) δ 8.31 (s, 1H), 7.61 (t, J=8.7 Hz, 1H), 6.96 (d, J=9.5 Hz, 1H), 6.86 (d, J=1.7 Hz, 1H), 6.79 (s, 1H), 6.77-6.62 (m, 2H), 5.25 (dd, J=12.1, 6.0 Hz, 1H), 5.08 (s, 2H), 4.49 (dd, J=17.6, 5.5 Hz, 1H), 4.32 (d, J=17.3 Hz, 1H), 3.48 (dd, J=18.7, 12.1 Hz, 1H), 2.83-2.73 (m, 1H).

Compound 245: 3-((S)-6-((1-((S)-5-(3,5-difluorophenyl)-4,5-dihydro-1H-pyrazole-1-carbonyl)azetidin-3-yl)oxy)-7-fluoro-3-oxo-3,4-dihydro-2H-benzo[b][1,4]oxazin-2-yl)propanamide

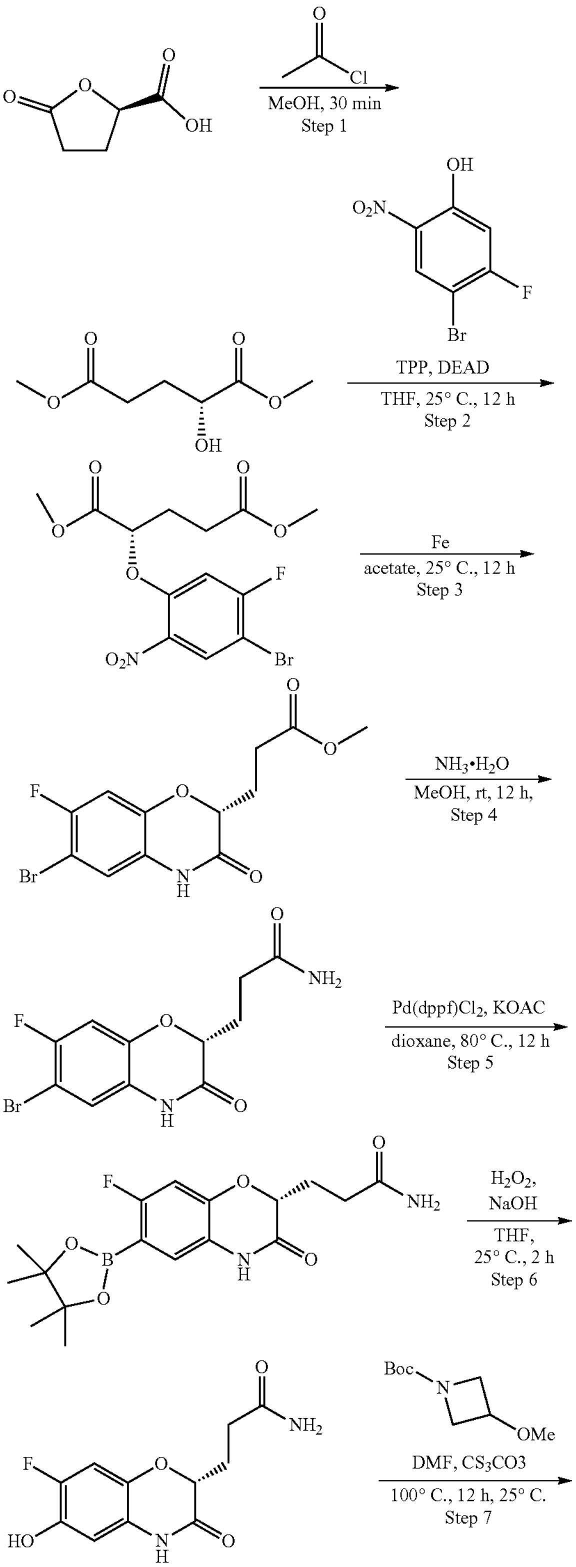

-continued

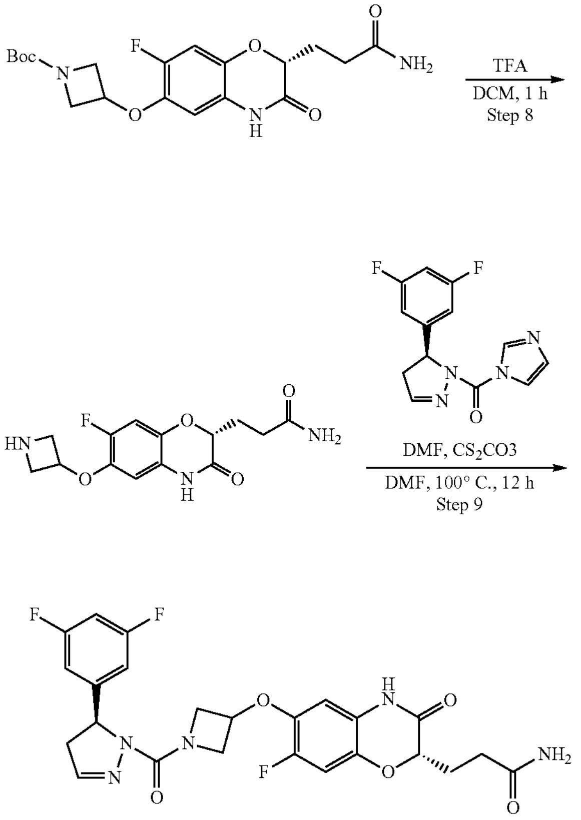

Step 1: (R)-5-oxotetrahydrofuran-2-carboxylic acid (5 g, 3.84 mmol) was dissolved in 40 ml of dry MeOH. acetyl chloride (1 ml) were added to the above solution at room temperature. The mixture was stirred for 12.0 hour at 60 degrees C. The mixture was concentrated in vacuo to give dimethyl (R)-2-hydroxypentanedioate (2.8 g, crude) as a colorless oil. (ES, m/s): 177.2 $[M+H]^+$ Step 2: dimethyl (R)-2-hydroxypentanedioate (1.38 g, 7.83 mmol) was dissolved in 10 ml of dry THF. DEAD (1.82 ml, 9.4 mmol), 4-bromo-5-fluoro-2-nitrophenol (2.22 g, 9.4 mmol), $PPh_3$ (3.15 g, 12.03 mmol) was added to the above solution at room temperature. The mixture was stirred for 12.0 hour at 25 degrees C. The mixture was extracted with EA, washed with brine, dried ($Na_2SO_4$), and concentrated in vacuo. Purification by silica gel chromatography to (R)-3-(7-fluoro-6-hydroxy-3-oxo-3,4-dihydro-2H-benzo[b][1,4]oxazin-2-yl)propanamide (2.1 g, 57%) as a white solid. (ES, m/s): 395.2 $[M+H]^+$ Step 3: (R)-3-(7-fluoro-6-hydroxy-3-oxo-3,4-dihydro-2H-benzo[b][1,4]oxazin-2-yl) propanamide (500 mg, 1.27 mmol) was dissolved in 10 ml of dry acetate. Fe (71 m g, 12.6 mmol) was added to the above solution at room temperature. The mixture was stirred for 12.0 hour at 25 degrees C. The mixture was extracted with EA, washed with brine, dried ($Na_2SO_4$), and concentrated in vacuo. Purification by silica gel chromatography to give methyl (R)-3-(6-bromo-7-fluoro-3-oxo-3,4-dihydro-2H-benzo[b][1,4]oxazin-2-yl)propanoate (360 mg, 86%) as a white solid. (ES, m/s): 333.2 $[M+H]^+$ Step 4: methyl (R)-3-(6-bromo-7-fluoro-3-oxo-3,4-dihydro-2H-benzo[b][1,4]oxazin-2-yl)propanoate (300 mg, 0.9 mmol) was dissolved in 2 ml of MeOH and Ammonia (2 mL, 15%) were added to the above solution at room temperature. The mixture was stirred for 12.0 hour at 60 degrees C. The mixture was concentrated in vacuo to give (R)-3-(6-bromo-7-fluoro-3-oxo-3,4-dihydro-2H-benzo[b][1,4]oxazin-2-yl) propanamide (100 mg, 35%) as a white solid. (ES, m/s): 318.1 [M+H]+

Step 5: (R)-3-(6-bromo-7-fluoro-3-oxo-3,4-dihydro-2H-benzo[b][1,4]oxazin-2-yl)propanamide (50 mg, 0.157 mmol) was dissolved in 1 ml of dry dioxane. (Pd(dppf)$Cl_2$ (11 mg, 0.015 mmol), KOAc (46 mg, 0.48 mmol) and 4,4,4',4',5,5,5',5'-octamethyl-2,2'-bi(1,3,2-dioxaborolane) (80 mg, 0.31 mmol) were added to the above solution under nitrogen at room temperature. The mixture was stirred for 12.0 hour at 100 degrees C. The mixture was extracted with EA, washed with brine, dried ($Na_2SO_4$), and concentrated in vacuo to give (R)-3-(7-fluoro-3-oxo-6-(4,4,5,5-tetramethyl-1,3,2-dioxaborolan-2-yl)-3,4-dihydro-2H-benzo[b][1,4]oxazin-2-yl)propanamide (52 mg, crude) as a white solid. (ES, m/s): 365.2 $[M+H]^+$ Step 6: (R)-3-(7-fluoro-3-oxo-6-(4,4,5,5-tetramethyl-1,3,2-dioxaborolan-2-yl)-3,4-dihydro-2H-benzo[b][1,4]oxazin-2-yl)propanamide (52 mg, crude) was dissolved in 1 ml of THF and NaOH(aq) (0.2 mL, 1 N). $H_2O_2$ (0.1 mL, 30% in $H_2O$) was added to the above solution at room temperature. The mixture was stirred for 1.0 hours at 0 degrees C. slowly warned to room temperature. The pH of resulting mixture was adjusted to 3-4 with HCl (aq, 1N). The mixture was extracted with EA, washed with brine, dried ($Na_2SO_4$), and concentrated in vacuo to give (R)-3-(7-fluoro-6-hydroxy-3-oxo-3,4-dihydro-2H-benzo[b][1,4]oxazin-2-yl) propanamide (30 mg, crude) as a white solid. (ES, m/s): 255.2 $[M+H]^+$ Step 7: (R)-3-(7-fluoro-6-hydroxy-3-oxo-3,4-dihydro-2H-benzo[b][1,4]oxazin-2-yl)propanamide (30 mg, crude) was dissolved in 1 ml of dry DMF. $CS_2CO_3$ (60 mg, 0.24 mmol) and tert-butyl 3-((methylsulfonyl)oxy)azetidine-1-carboxylate (65 mg, 0.2 mmol) were added to the above solution at room temperature. The mixture was stirred for 12 hour at 100 degrees C. The mixture was extracted with EA, washed with brine, dried ($Na_2SO_4$), and concentrated in vacuo to give tert-butyl (R)-3-((2-(3-amino-3-oxopropyl)-7-fluoro-3-oxo-3,4-dihydro-2H-benzo[b][1,4]oxazin-6-yl)oxy)azetidine-1-carboxylate (39 mg, crude) as a oil.

Step 8: tert-butyl (R)-3-((2-(3-amino-3-oxopropyl)-7-fluoro-3-oxo-3,4-dihydro-2H-benzo[b][1,4]oxazin-6-yl)oxy)azetidine-1-carboxylate (39 mg, crude) was dissolved in 1 ml of dry DCM. TFA (0.3 ml) were added to the above solution at room temperature. The mixture was stirred for 1.0 hour at room temperature. The mixture was extracted with EA, washed with brine, dried ($Na_2SO_4$), and concentrated in vacuo to give (R)-3-(6-(azetidin-3-yloxy)-7-fluoro-3-oxo-3,4-dihydro-2H-benzo[b][1,4]oxazin-2-yl)propanamide (45 mg, crude) as a brown solid. (ES, m/s): 410.2 $[M+H]^+$ Step 9: (R)-3-(6-(azetidin-3-yloxy)-7-fluoro-3-oxo-3,4-dihydro-2H-benzo[b][1,4]oxazin-2-yl)propanamide (39 mg, crude) was dissolved in 1 ml of dry THF and 0.1 mL of TEA. (S)-(5-(3,5-difluorophenyl)-4,5-dihydro-1H-pyrazol-1-yl)(1H-imidazol-1-yl)methanone (32.2 mg, 0.12) in 5 mL of THF was added to the above solution at room temperature. The mixture was stirred for 1 overnight at 60 degrees C. The mixture was extracted with EA, washed with brine, dried ($Na_2SO_4$), and concentrated in vacuo. Purification by silica gel chromatography to give the titled compound 245 (2.4 mg) as a white solid. (ES, m/s): 518.2 $[M+H]^+$ Compound 246: 6-((1-((S)-5-(3,5-difluorophenyl)-4,5-dihydro-1H-pyrazole-1-carbonyl)azetidin-3-yl)oxy)-7-fluoro-2-(2-hydroxyethyl)-2H-benzo[b][1,4]oxazin-3(4H)-one

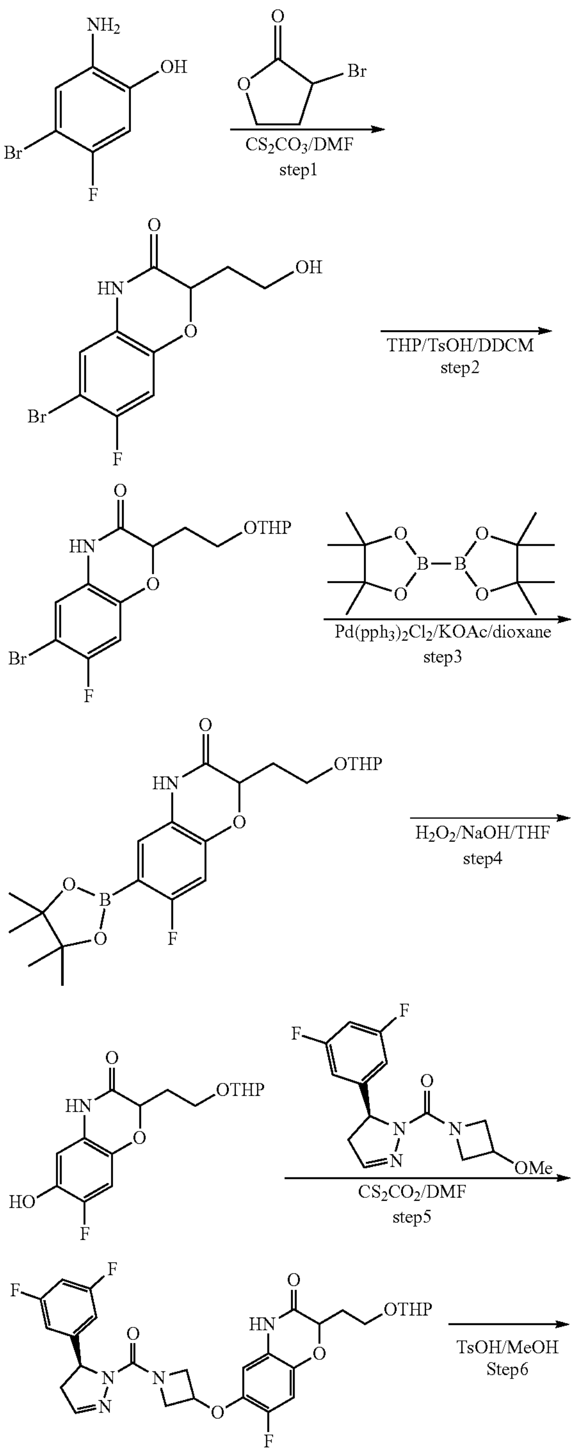

-continued

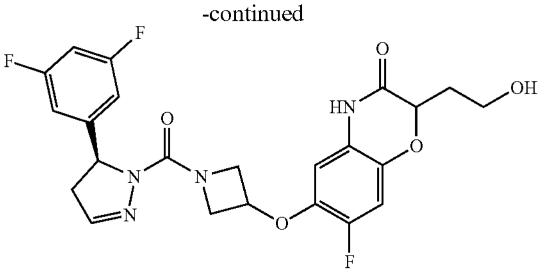

Step 1:2-amino-4-bromo-5-fluorophenol (4.4 g, 21.4 mmol), 3-bromodihydrofuran-2(3H)-one (3.9 g, 23.5 mmol) and $CS_2CO_3$ (40.5 g, 32.1 mmol) were dissolved in DMF (70 mL). The mixture was stirred at 80° C. for 15 hrs. The solvent was evaporated to dryness and purified by flash chromatography (PE/EA=2/1) to give the product as a yellow solid (4.5 g). Yield 72.6% LC-MS (m/z) 291.2 ($M+H^+$)

Step 2: THP (2.67 g, 31 mmol) was added to the solution of 6-bromo-7-fluoro-2-(2-hydroxyethyl)-2H-benzo[b][1,4]oxazin-3(4H)-one (4.5 g, 15.5 mmol) and TsOH (1.33 g, 7.75 mmol) in DCM (80 mL). The mixture was stirred at r.t. overnight. The solvent was evaporated to dryness and purified by flash chromatography (PE/EA=8/1) to give the product as a yellow oil (8.0 g). Yield 100% LC-MS (m/z) 374.2 ($M+H^+$)

Step 3: 6-bromo-7-fluoro-2-(2-((tetrahydro-2H-pyran-2-yl)oxy)ethyl)-2H-benzo[b][1,4]oxazin-3(4H)-one (8.0 g, 21.4 mmol), 4,4,4',4',5,5,5',5'-octamethyl-2,2'-bi(1,3,2-dioxaborolane) (10.9 g, 42.9 mmol), $Pd(pph_3)_2Cl_2$ (1.5 g, 2.14 mmol) and KOAc (6.3 g, 64.3 mmol) were added to dioxane (100 mL) under $N_2$ atmosphere. The mixture was stirred at 100° C. for 3 hrs. The solvent was evaporated to dryness and used for next step directly. LC-MS (m/z) 422.2 ($M+H^+$).

Step 4: H2O2 (4 mL) was added to the solution of 7-fluoro-2-(2-((tetrahydro-2H-pyran-2-yl)oxy)ethyl)-6-(4,4,5,5-tetramethyl-1,3,2-dioxaborolan-2-yl)-2H-benzo[b][1,4]oxazin-3(4H)-one (4.5 g, 10.7 mmol) and 1N NaOH (4 mL) in THF (60 mL) at 0° C. The mixture was stirred at r.t. for 2 hrs. Then 1N HCl was added to adjust PH=6 and EA added to extracted. The solvent was evaporated to dryness and purified by flash chromatography (PE/EA=5/1) to give the product as a yellow solid (1.7 g). Yield 51.5% LC-MS (m/z) 334.2 ($M+Na^+$).

Step 5: 7-fluoro-6-hydroxy-2-(2-((tetrahydro-2H-pyran-2-yl)oxy)ethyl)-2H-benzo[b][1,4]oxazin-3(4H)-one (710 mg, 2.28 mmol), (S)-1-(5-(3,5-difluorophenyl)-4,5-dihydro-1H-pyrazole-1-carbonyl)azetidin-3-yl methanesulfonate (820 mg, 2.28 mmol) and $CS_2CO_3$ (829 mg, 2.74 mmol) were dissolved in DMF (10 mL). The mixture was stirred at 100° C. for 15 hrs. The solvent was evaporated to dryness and purified by HPLC to give the product as yellow solid (190 mg). Yield 17.3% LC-MS (m/z) 575.3 ($M+H^+$).

Step 6: TsOH (2 mg, 0.009 mmol) was added to the solution of 6-((1-((S)-5-(3,5-difluorophenyl)-4,5-dihydro-1H-pyrazole-1-carbonyl)azetidin-3-yl)oxy)-7-fluoro-2-(2-((tetrahydro-2H-pyran-2-yl)oxy)ethyl)-2H-benzo[b][1,4]oxazin-3(4H)-one (50 mg, 0.087 mmol) in MeOH (2 mL). The mixture was stirred at r.t. for 1 hrs. The solvent was evaporated to dryness and purified by flash chromatography (PE/EA=1/1) to give the titled compound 246 as a white solid (40 mg). Yield 93.7% $^1H$ NMR (400 MHz, Chloroform-d) δ 8.91 (d, J=10.8 Hz, 1H), 6.81 (t, J=7.6 Hz, 1H), 6.79-6.72 (m, 2H), 6.69-6.62 (m, 1H), 6.23 (d, J=7.8 Hz, 1H), 5.49-5.39 (m, 1H), 4.86-4.79 (m, 1H), 4.71-4.61 (m, 1H), 4.61-4.43 (m, 2H), 4.41-4.33 (m, 1H), 4.20-4.08 (m, 1H), 3.91-3.80 (m, 2H), 3.38 (dd, J=18.4, 12.0 Hz, 1H), 2.74-2.64 (m, 1H), 2.30-2.05 (m, 2H). LC-MS (m/z) 491.4 ($M+H^+$)

Compound 247: 6-((1-((S)-5-(3,5-difluorophenyl)-4,5-dihydro-1H-pyrazole-1-carbonyl)azetidin-3-yl)oxy-7-fluoro-2-(2-met oxyethyl)-4-meth-2H-benzo[b][1,4]oxazin-3(4H)-one

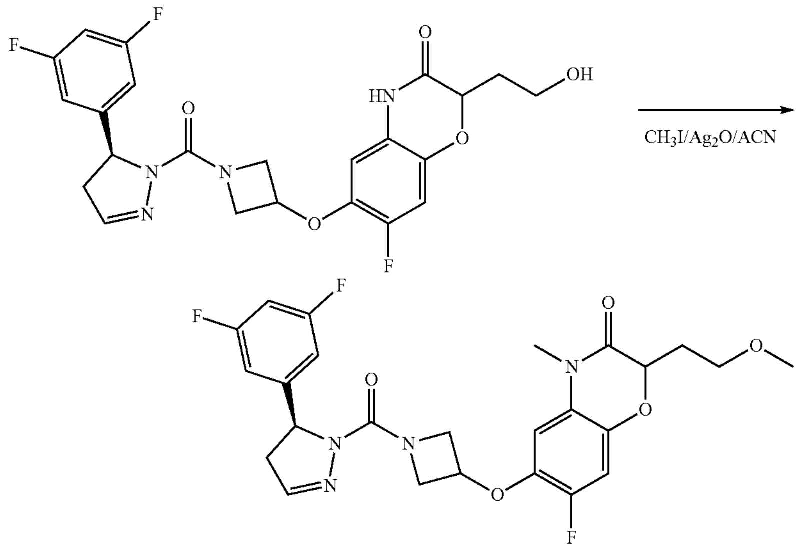

$CH_3I$ (28 mg, 0.2 mmol) and $Ag_2O$ (24 mg, 0.1 mmol) were added to the solution of 6-((1-((S)-5-(3,5-difluorophenyl)-4,5-dihydro-1H-pyrazole-1-carbonyl)azetidin-3-yl)oxy)-7-fluoro-2-(2-hydroxyethyl)-2H-benzo[b][1,4]oxazin-3(4H)-one (10 mg, 0.02 mmol) in CAN (2 mL). The mixture was stirred at r,t, for 24 hrs. The solvent was evaporated to dryness and purified by TLC (DCM/MeOH=25/1) to give the titled compound 247 as a white solid 2.5 mg. Yield 25.0%. $^1$H NMR (400 MHz, Chloroform-d) δ 6.91-6.61 (m, 5H), 6.44 (dd, J=7.6, 1.2 Hz, 1H), 5.31-5.23 (m, 1H), 4.94 (t, J=5.2 Hz, 1H), 4.66 (dd, J=9.0, 4.2 Hz, 1H), 4.49 (d, J=6.8 Hz, 2H), 4.33-4.28 (m, 1H), 4.24 (d, J=10.4 Hz, 1H), 3.68-3.47 (m, 2H), 3.41-3.33 (m, 4H), 3.30 (s, 3H), 2.75-2.65 (m, 1H), 2.06-1.94 (m, 2H). LC-MS (m/z) 519.5 $(M+H^+)$ Compound 248: 6-((1-((S)-5-(3,5-difluorophenyl)-4,5-dihydro-1H-pyrazole-1-carbonyl)azetidin-3-yl)oxy)-7-fluoro-2-(2-hydroxyethyl)-4-methyl-2H-benzo[b][1,4]oxazin-3(4H)-one

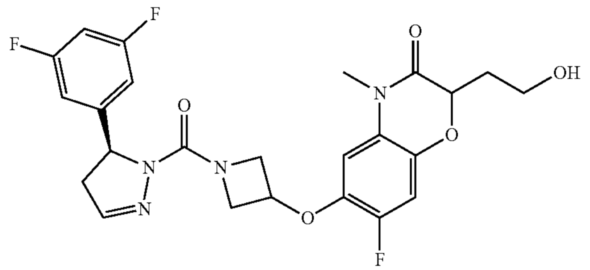 [SMILES: CN1C(=O)C(CCO)Oc2cc(F)c(OC3CN(C(=O)N4N=CC[C@H]4c4cc(F)cc(F)c4)C3)cc21]

The titled compound 248 was synthesized in an analogous manner to the preparation of compound 246. Yield 25.0% $^1$H NMR (400 MHz, Chloroform-d) δ 6.86-6.77 (m, 2H), 6.78-6.58 (m, 3H), 6.46 (d, J=7.6 Hz, 1H), 5.30-5.24 (m, 1H), 4.98-4.91 (m, 1H), 4.68 (dd, J=7.6, 5.6 Hz, 1H), 4.49 (dd, J=18.0, 10.4 Hz, 2H), 4.30 (t, J=6.8 Hz, 1H), 4.23 (d, J=9.2 Hz, 1H), 3.86 (dd, J=6.8, 4.8 Hz, 2H), 3.42-3.24 (m, 4H), 2.74-2.66 (m 1H), 2.26-2.13 (m, 2H). LC-MS (m/z) 505.5 $(M+H^+)$ Compound 249: 6-((1-((S)-5-(3,5-difluorophenyl)-4,5-dihydro-1H-pyrazole-1-carbonyl)azetidin-3-yl)oxy)-2-(2-(dimethylamino)ethyl)-7-fluoro-2H-benzo[b][1,4]oxazin-3(4H)-one

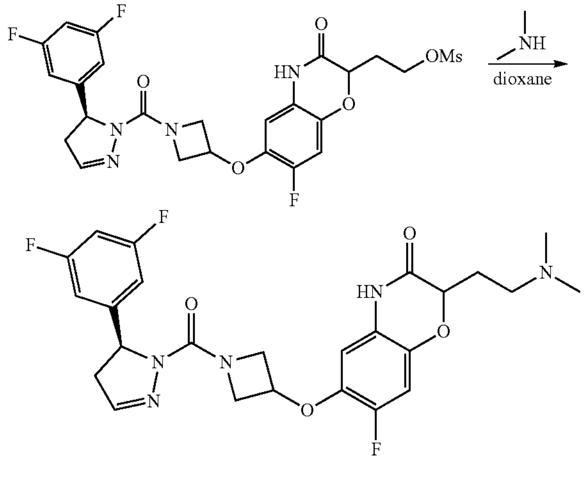

2-(6-((1-((S)-5-(3,5-difluorophenyl)-4,5-dihydro-1H-pyrazole-1-carbonyl)azetidin-3-yl)oxy)-7-fluoro-3-oxo-3,4-dihydro-2H-benzo[b][1,4]oxazin-2-yl)ethyl methanesulfonate (10 mg, 0.018 mmol) and dimethylamine (4 mg, 0.09 mmol) were dissolved in dioxane (2 mL). The mixture was stirred at 900 C for 2 hrs. The solvent was evaporated to dryness and purified by HPLC to give the titled compound 249 as a white solid (2.5 mg). Yield 27.8% $^{1}$H NMR (400 MHz, Chloroform-d) δ 12.17 (s, 1H), 9.24 (s, 1H), 6.95-6.57 (m, 3H), 6.40-6.28 (m, 1H), 5.68-5.50 (m, 1H), 5.40-5.21 (m, 1H), 4.92-4.80 (m, 1H), 4.63-4.42 (m, 2H), 4.35-4.12 m, 2H), 3.89-3.66 (m, 1H), 3.43-3.27 (m, 2H), 3.04-2.63 (m, 7H), 2.25 (t, J=7.6 Hz, 1H), 2.05-1.98 (m, 1H), 1.69-1.60 (m, 1H). LC-MS (m/z) 518.5 (M+H$^{+}$)

Compound 250: 6-((1-((S)-5-(3,5-difluorophenyl)-4,5-dihydro-1H-pyrazole-1-carbonyl)azetidin-3-yl)oxy)-2-ethyl-7-fluoro-2H-benzo[b][1,4]oxazin-3(4H)-one

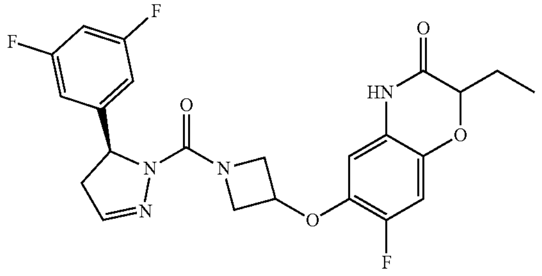 [SMILES: CCC1Oc2cc(F)c(OC3CN(C(=O)N4N=CC[C@H]4c4cc(F)cc(F)c4)C3)cc2NC1=O]

The titled compound 250 was synthesized in an analogous manner to the preparation of compound 246. Yield 16.3%. $^{1}$H NMR (400 MHz, Chloroform-d) δ 9.12 (d, J=20.0 Hz, 1H), 6.81 (t, J=1.7 Hz, 1H), 6.79-6.69 (m, 3H), 6.69-6.59 (m, 1H), 6.21 (d, J=8.0 Hz, 1H), 5.52-5.43 (m, 1H), 4.87-4.77 (m, 1H), 4.63-4.25 (m, 4H), 4.20-4.05 (m, 1H), 3.45-3.32 (m, 1H), 2.68 (m, 1H), 1.98-1.72 (m, 2H), 1.08 (t, J=7.2 Hz, 3H). LC-MS (m/z) 475.4 (M+H$^{+}$)

Compound 251: (S)-(3-((6-amino-3-fluoropyridin-2-yl)oxy)azetidin-1-yl)(5-(3,5-difluorophenyl)-4,5-dihydro-1H-pyrazol-1-yl)methanone

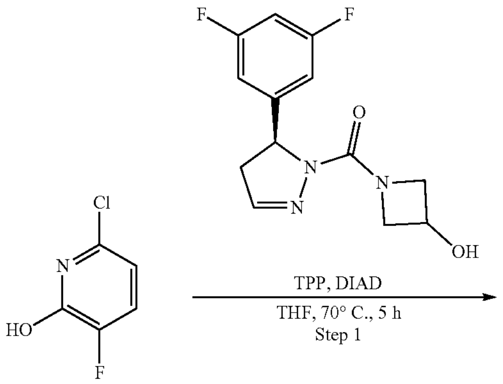

-continued

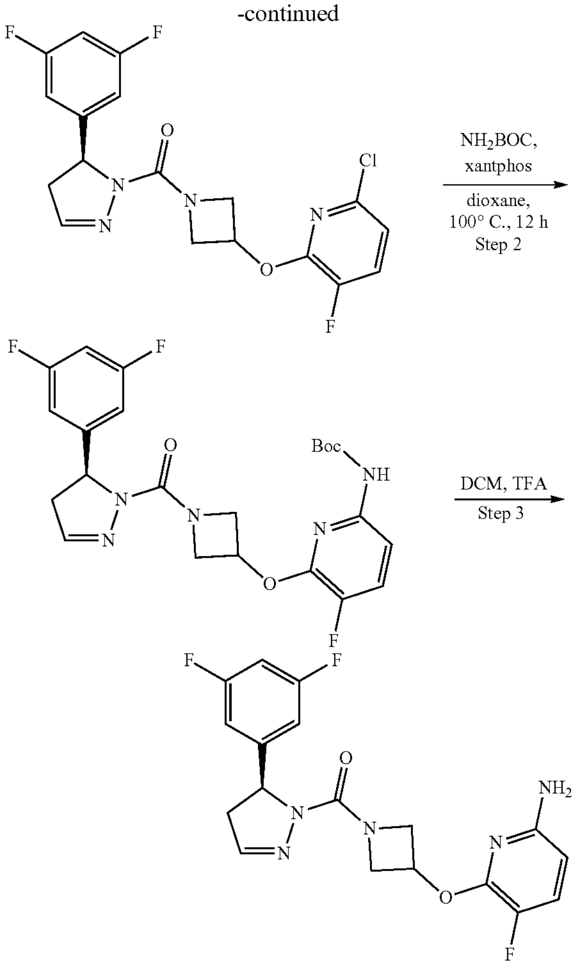

Step 1: 6-chloro-3-fluoropyridin-2-ol (200 mg, 1.36 mmol) was dissolved in 3 ml of dry THF. DEAD (328 mg ml, 1.63 mmol), (S)-(5-(3,5-difluorophenyl)-4,5-dihydro-1H-pyrazol-1-yl)(3-hydroxyazetidin-1-yl)methanone (400 mg, 1.423 mmol), $PPh_3$ (540 mg, 2.04 mmol) was added to the above solution at room temperature. The mixture was stirred for 12.0 hour at 25 degrees C. The mixture was extracted with EA, washed with brine, dried ($Na_2SO_4$), and concentrated in vacuo. Purification by silica gel chromatography to give (S)-(3-((6-chloro-3-fluoropyridin-2-yl)oxy)azetidin-1-yl)(5-(3,5-difluorophenyl)-4,5-dihydro-1H-pyrazol-1-yl)methanone (300 mg, 51%) as a white solid. (ES, m/s): 411.2 [M+H]$^{+}$.

Step 2: (S)-(3-((6-amino-3-fluoropyridin-2-yl)oxy)azetidin-1-yl)(5-(3,5-difluorophenyl)-4,5-dihydro-1H-pyrazol-1-yl)methanone (300 mg, 0.72 mmol) was dissolved in 2 ml of dry dioxane. $Pd_2(dba)_3$ (33.6 mg ml, 0.036 mmol), 2-(Dicyclohexylphosphino)-2',4',6'-tri-i-propyl-1,1'-biphenyl (51.4 mg, 0.108 mmol), $Cs_2CO_3$ (240 mg, 0.74 mmol) was added to the above solution at room temperature. The mixture was stirred for 3 hour at 100 degrees C. The mixture was extracted with EA, washed with brine, dried ($Na_2SO_4$), and concentrated in vacuo. Purification by silica gel chromatography to give tert-butyl (S)-(6-((1-(5-(3,5-difluorophenyl)-4,5-dihydro-1H-pyrazole-1-carbonyl)azetidin-3-yl)oxy)-5-fluoropyridin-2-yl)carbamate (300 mg, 84%) as a white solid. (ES, m/s): 411.2 [M+H]$^{+}$ Step 3: tert-butyl (S)-(6-((1-(5-(3,5-difluorophenyl)-4,5-dihydro-1H-pyrazole-1-carbonyl)azetidin-3-yl)oxy)-5-fluoropyridin-2-yl)carbamate (100 mg, 0.2 mml) was dissolved in 1 ml of dry DCM. TFA (0.3 ml) were added to the above solution at room temperature. The mixture was stirred for 1.0 hour at room temperature. The mixture was extracted with EA, washed with brine, dried ($Na_2SO_4$), and concentrated in vacuo to give the titled compound 251 (30 mg) as a white solid. (ES, m/s): 388.2 $[M+H]^+$. $^1H$ NMR (400 MHz, Chloroform-d) δ 8.69 (d, J=8.6 Hz, 2H), 7.51 (t, J=9.2 Hz, 1H), 6.82 (m, 1H), 6.66 (m, 4H), 5.37 (m, 1H), 5.22 (m, 1H), 4.86-4.65 (m, 2H), 3.81 (m, 4.9 Hz, 1H), 3.66 (m, 1H), 3.45 (dd, J=18.7, 12.2 Hz, 1H), 2.74 (m, 1H).

Compound 252: (S)(5-(3,5-difluorophenyl)-4,5-dihydro-1H-pyrazol-1-yl)(3-((3-fluoro-6-((2-hydroxyethyl)amino)pyridin-2-yl)oxy)azetidin-1-yl) methanone

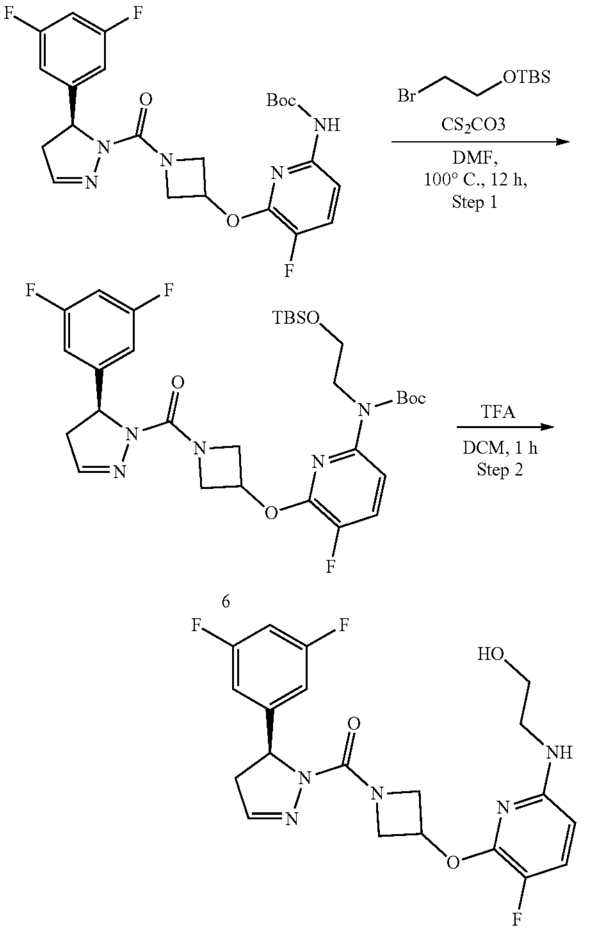

6

Step 1: tert-butyl (S)-(6-((1-(5-(3,5-difluorophenyl)-4,5-dihydro-1H-pyrazole-1-carbonyl) azetidin-3-yl)oxy)-5-fluoropyridin-2-yl)carbamate (200 mg, 0.4 mml) and (2-bromoethoxy)(tert-butyl)dimethylsilane (140 mg, 0.6 mmol) $Pd_2(dba)_3$ (33.6 mg ml, 0.036 mmol) was dissolved in 2 ml of dry DMF. $Cs_2CO_3$ (240 mg, 0.74 mmol) was added to the above solution at room temperature. The mixture was stirred for 12 hour at 100 degrees C. The mixture was extracted with EA, washed with brine, dried ($Na_2SO_4$), and concentrated in vacuo. Purification by silica gel chromatography to give (S)-(3-((6-amino-3-fluoropyridin-2-yl)oxy)azetidin-1-yl)(5-(3,5-difluorophenyl)-4,5-dihydro-1H-pyrazol-1-yl) methanone (300 mg, 84%) as a white solid. LC-MS (ES, m/s): 650.8 [M+H].

Step 2: (S)-(3-((6-amino-3-fluoropyridin-2-yl)oxy)azetidin-1-yl)(5-(3,5-difluorophenyl)-4,5-dihydro-1H-pyrazol-1-yl)methanone (300 mg) was dissolved in 1 ml of dry DCM. TFA (0.3 ml) were added to the above solution at room temperature. The mixture was stirred for 1.0 hour at room temperature. The mixture was extracted with EA, washed with brine, dried ($Na_2SO_4$), and concentrated in vacuo to give the titled compound 252 (30 mg) as a white solid. (ES, m/s): 436.4 $[M+H]^+$ $^1H$ NMR (400 MHz, DMSO-$d_6$) δ 8.09 (td, J=9.7, 7.7 Hz, 1H), 7.15-7.00 (m, 2H), 6.81 (tdd, J=6.4, 4.4, 2.1 Hz, 2H), 6.60 (dt, J=9.7, 2.9 Hz, 1H), 5.46 (m, 1H), 5.19 (ddd, J=12.2, 8.9, 6.1 Hz, 1H), 4.52 (dd, J=11.5, 9.1 Hz, 1H), 4.28 (ddd, J=20.5, 11.5, 7.3 Hz, 1H), 3.66-3.50 (m, 4H), 3.40-3.30 (m, 2H), 2.69 (ddd, J=18.8, 6.1, 1.8 Hz, 1H).

Compound 253: (S)-7-((1-(5-(3,5-difluorophenyl)-4,5-dihydro-1H-pyrazole-1-carbonyl)140zetidine-3-yl) oxy)-6-fluoroquinolin-2(1H)-one

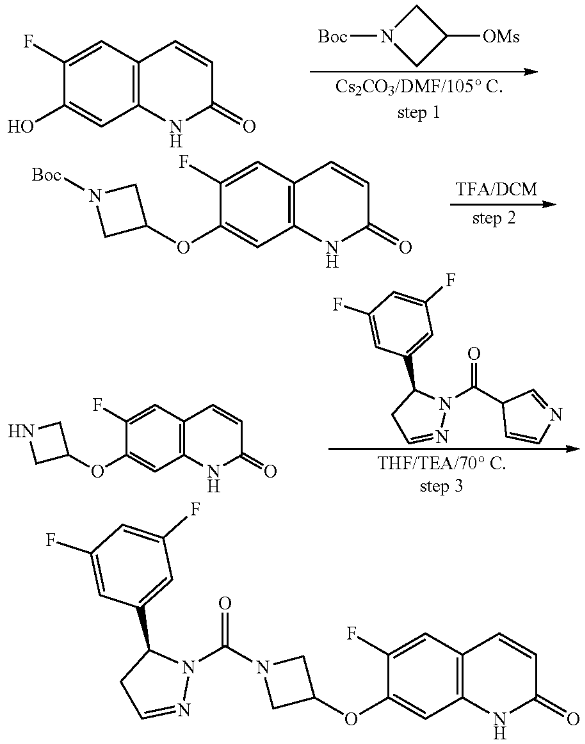

Step 1. 6-fluoro-7-hydroxyquinolin-2(1H)-one (1.2 g, 6.7 mmoL) and tert-butyl 3-((methylsulfonyl)oxy)azetidine-1-carboxylate (1.85 g, 17.37 mmoL) were dissolved in 15 mL DMF. $Cs_2CO_3$ (3.28 g, 10.067 mmoL) was added. Let it stir at 105° C. for 3 days. The solvent was evaporated to dryness and purified by column chromatography (100% EA) to give 1.7 g of tert-butyl 3-((6-fluoro-2-oxo-1,2-dihydroquinolin-7-yl)oxy)azetidine-1-carboxylate as yellow solid mg of white solid. Yield: 76%. LC-MS (m/z) 335.3 $[M+H]^+$.

Step 2. 3-((6-fluoro-2-oxo-1,2-dihydroquinolin-7-yl)oxy) azetidine-1-carboxylate (24 mg, 0.072 mmoL) was dissolved in 2 mL DCM. 2 mL DCM/TFA (1/1) was added slowly to the solution at 0° C. Let it stir r.t for 1 h. The solvent was evaporated to dryness 7-(azetidin-3-yloxy)-6-fluoroquinolin-2(1H)-one as TFA salt, which was used for next step without further purification. LC-MS (m/z) 235.4 $[M+H]^+$.

Step 3. The above residue was dissolved in 2 mL THF. 0.2 mL of TEA and (S)-(5-(3,5-difluorophenyl)-4,5-dihydro-1H-pyrazol-1-yl)(1H-imidazol-1-yl)methanone (20 mg, 0.072 mmoL) were added. The mixture was stirred at 70° C. for 36 his. The solvent was evaporated to dryness and purified by Prep-TLC (DCM/MeOH=15/1) to give the titled compound 253 as light-brown solid. (9 mg, 28.3%. yield in two steps) $^1$H NMR (400 M Hz, $CDCl_3$) δ (ppm): δ 12.25 (brs, 1H), 7.67 (d, J=9.6 Hz, 1H), 7.23-7.25 (m, 1H), 6.71-6.79 (m, 4H), 6.59-6.67 (m, 2H), 5.40-5.44 (m, 1H), 5.01-5.12 (m, 1H), 4.58-4.74 (m, 2H), 4.32-4.45 (m, 1H), 4.15-4.26 (m 1H), 3.37 (dd, J=12.0, 18.8 Hz, 1H), 2.68 (dd, J=6.0, 18.4 Hz, 1H). LC-MS (ESI): m/z calcd for $C_{22}H_{17}F_3N_4O_3$ 442.4, found 443.5 $[M+H]^+$.

Compound 254: (S)-(5-(3,5-difluorophenyl)-4,5-dihydro-1H-pyrazol-1-yl)(3-((3,5-difluoropyridin-2-yl)amino)azetidin-1-yl)methanone

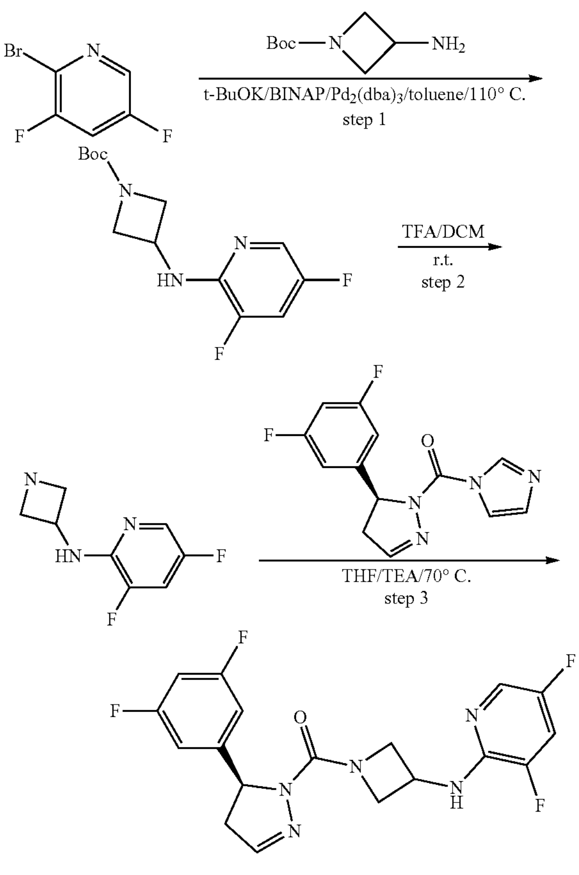

Step 1. 2-bromo-3,5-difluoropyridine (150 mg, 0.77 mmoL), tert-butyl 3-aminoazetidine-1-carboxylate (146.5 mg, 0.85 mmoL) and t-BuOK (111 mg, 1 mmoL) were mixed in 2 mL of toluene. BINAP (70.8 mg, 0.114 mmoL) an $Pd_2(dba)_3$ (96.3 mg, 0.105 mmoL) were added. Let it stir at 110° C. under nitrogen for 16 hrs. The solvent was evaporated to dryness and purified by column chromatography (PE/EA=2/1) to give 90 mg tert-butyl 3-((3,5-difluoropyridin-2-yl)amino)azetidine-1-carboxylate as brown oil. Yield: 41%. LC-MS (m/z) 286.3 $[M+H]^+$.

Step 2. Tert-butyl 3-((3,5-difluoropyridin-2-yl)amino)azetidine-1-carboxylate (35 mg, 0.123 mmoL) was dissolved in 2 mL DCM. 2 mL DCM/TFA (1/1) was added slowly to the solution at 0° C. Let it stir r.t for 1 h. The solvent was evaporated to dryness and used for next step without further purification. LC-MS (m/z) 186.2 $[M+H]^+$.

Step 3. The above residue was dissolved in 2 mL THF. 0.2 mL of TEA was added. (S)-(5-(3,5-difluorophenyl)-4,5-dihydro-1H-pyrazol-1-yl)(1H-imidazol-1-yl)methanone (25 mg, 0.09 mmoL) was added. Let it stir at 70° C. for 16 hrs. The solvent was evaporated to dryness and purified by Prep-TLC (PE/EA=1/1) to give 12 mg of the titled compound 254 as brown oil. Yield: 33.8%. $^1$H NMR (400 MHz, $CDCl_3$) δ (ppm): 7.81 (dd, J=0.8, 2.4 Hz, 1H), 7.06-7.11 (m, 1H), 6.73-6.78 (m, 3H), 6.66-6.71 (m, 1H), 5.27 (dd, J=6.4, 12.0 Hz, 1H), 4.79-4.88 (m, 1H), 4.66-4.75 (m, 1H), 4.58 (t, J=7.6 Hz, 1H), 4.51 (t, J=8.0 Hz, 1H), 3.95-3.98 (m, 1H), 3.34 (dd, J=12.4, 18.8 Hz, 1H), 2.68 (dd, J=6.8, 18.8 Hz, 1H). LC-MS (ESI): m/z calcd for $C_{18}H_{15}F_4N_5O$, 393.4, found 394.3 $[M+H]^+$.

Compound 255: (5-(3,5-difluorophenyl)-4,5-dihydro-1H-pyrazol-1-yl)(3-((2,4-difluorophenyl)amino)azetidin-1-yl)methanone

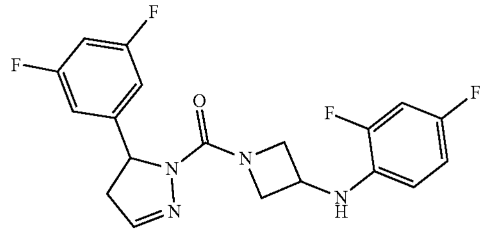 [SMILES: O=C(N1CC(Nc2ccc(F)cc2F)C1)N1N=CCC1c1cc(F)cc(F)c1]

The titled compound 255 was synthesized in an analogous manner to the preparation of compound 254. $^1$H NMR (400 MHz, Chloroform-d) δ 7.63-7.55 (m, 1H), 6.85-6.81 (m, 2H), 6.80-6.73 (m, 2H), 6.70 (tt, J=8.9, 2.3 Hz, 1H), 6.37-6.33 (m, 1H), 5.31 (dd, J=12.2, 6.5 Hz, 1H), 5.05-4.81 (m, 4H), 3.38 (ddd, J=18.6, 12.2, 1.7 Hz, 1H), 2.72 (ddd, J=18.6, 6.5, 1.7 Hz, 1H). LC-MS (m/z) 393.4 $[M+H]^+$.

Compound 256: (S)-6-((1-(5-(3,5-difluorophenyl)-4,5-dihydro-1H-pyrazole-1-carbonyl)azetidin-3-yl)oxy)pyrido[2,3-b]pyrazin-3(4H)-one

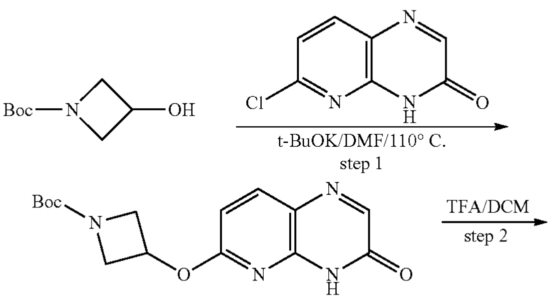

-continued

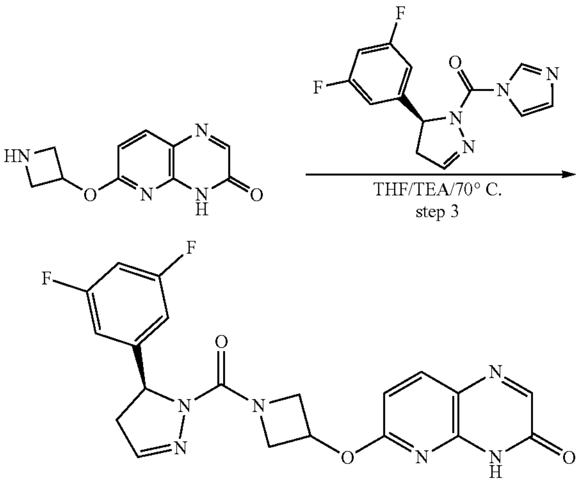

Step 1. 6-chloropyrido[2,3-b]pyrazin-3(4H)-one (80 mg, 0.44 mmoL) and tert-butyl 3-hydroxyazetidine-1-carboxylate (76.3 mg, 0.44 mmoL) were dissolved in 2 mL DMF. t-BuOK (74 mg, 0.66 mmoL) was added. Let it stir at 110° C. for 16 hrs. The solvent was evaporated to dryness and purified by Prep-TLC (EA) to give 100 mg light-yellow solid. Yield: 71.5%. LC-MS (m/z): 319.2 $[M+H]^+$.

Step 2 and 3. The titled compound 256 was prepared in 12.9% yield from 6-(azetidin-3-yloxy)pyrido[2,3-b]pyrazin-3(4H)-one and (s)-(5-(3,5-difluorophenyl)-4,5-dihydro-1H-pyrazol-1-yl)(1H-imidazol-1-yl)methanone according to the procedure outlined for compound 62. $^1$H NMR (400 MHz, $CDCl_3$) δ (ppm): δ 9.63 (brs, 1H), 8.17 (s, 1H), 8.07 (d, J=8.8 Hz, 1H), 6.75-6.80 (m, 4H), 6.66 (t, J=8.8 Hz, 1H), 5.38-5.44 (m, 1H), 5.32 (dd, J=6.4, 12.8 Hz, 1H), 4.59-4.68 (m, 2H), 4.26-4.29 (m, 1H), 4.17-4.20 (m, 1H), 3.36 (dd, J=12.0, 18.4 Hz, 1H), 2.69 (dd, J=6.4, 18.8 Hz, 1H). LC-MS (ESI): m/z calcd for $C_{20}H_{16}F_2N_6O_3$ 426.4, found 427.5 $[M+H]^+$.

Compound 257: methyl (S)-2-((1-(5-(3,5-difluorophenyl)-4,5-dihydro-1H-pyrazole-1-carbonyl)azetidin-3-yl)oxy)-4H-pyrrolo[2,3-d]thiazole-5-carboxylate

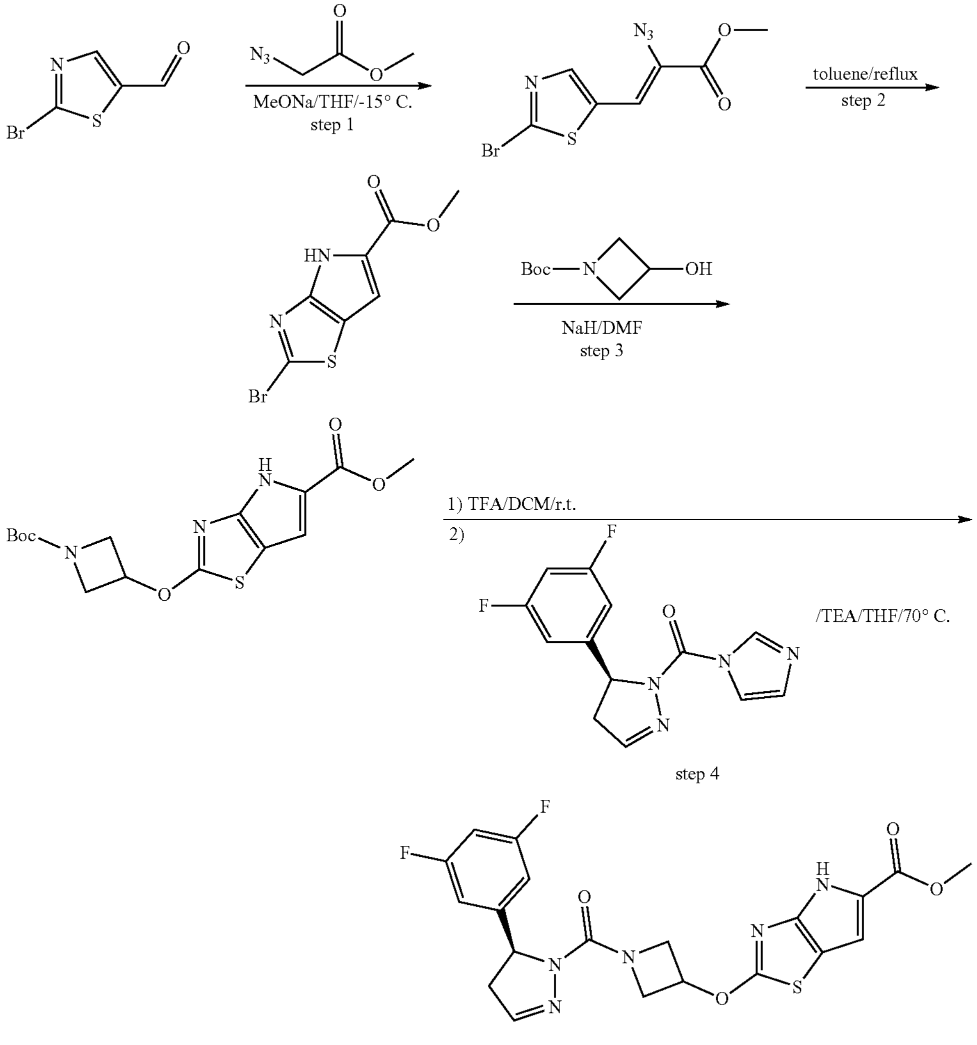

Step 1. 11.57 mL of MeONa in MeOH solution (5.4 M, 62.5 mmoL) was added slowly to the mixture of 2-bromothiazole-5-carbaldehyde (3 g, 15.625 mmoL) and methyl 2-azidoacetate (7.2 g, 62.61 mmoL) in 80 mL THF at −15° C. Let it stir at −15° C. for 2 hrs. Sat. $NH_4Cl$ solution was added to quench the reaction and extracted with EtOAc (100 mL×3). Dried with $Na_2SO_4$ and filtered. The solvent was evaporated to dryness and purified by column chromotography (PE/EA=3/1) to give 680 mg of methyl (Z)-2-azido-3-(2-bromothiazol-5-yl)acrylate as light-yellow solid. Yield: 15%. LC-MS (m/z) 289.2 $[M+H]^+$.

Step 2. methyl (Z)-2-azido-3-(2-bromothiazol-5-yl)acrylate (680 mg, 2.28 mmoL) in 3 ml toluene was added slowly to the refluxed toluene solution. Let it stir at reflux for another 2 hrs. The solvent was evaporated to dryness and purified by column chromotography (PE/EA=4/1) to give 585 mg methyl 2-bromo-4H-pyrrolo[2,3-d]thiazole-5-carboxylate as light-yellow solid. Yield: 98.2%. LC-MS (m/z) 261.1 $[M+H]^+$.

Step 3. Tert-butyl 3-hydroxyazetidine-1-carboxylate (199.6 mg, 1.156 mmoL) was dissolved in 5 mL DMF. NaH (97.1 mg, 2.43 mmoL) was added in portions at r.t. Let it stir at r.t for 1 h. Then methyl 2-bromo-4H-pyrrolo[2,3-d]thiazole-5-carboxylate (150 mg, 0.577 mmoL) in 3 mL DMF was added to the solution. Let it stir at 80° C. for 3 h. Water was added to quench the reaction and extracted with EtOAc (20 mL×3). The solvent was evaporated to dryness and purified by column chromotography (PE/EA=3/1) to give 140 mg methyl 2-((1-(tert-butoxycarbonyl)azetidin-3-yl)oxy)-4H-pyrrolo[2,3-d]thiazole-5-carboxylate as light-yellow solid. Yield: 68.7%. LC-MS (m/z) 298.2 $[M+H-56]^+$.

Step 4. Methyl 2-((1-(tert-butoxycarbonyl)azetidin-3-yl)oxy)-4H-pyrrolo[2,3-d]thiazole-5-carboxylate (80 mg, 0.227 mmoL) was dissolved in 2 mL DCM. 2 mL DCM/TFA (1/1) was added slowly to the solution at 0° C. Let it stir r.t for 1 h. The solvent was evaporated to dryness and used for next step without further purification. LC-MS (m/z) 254.1 $[M+H]^+$. The above residue was dissolved in 3 mL THF. (S)-(5-(3,5-difluorophenyl)-4,5-dihydro-1H-pyrazol-1-yl)(1H-imidazol-1-yl)methanone (65 mg, 0.235 mmoL) and 0.2 mL TEA were added. Let it stir at 70° C. for 32 hrs. The solvent was evaporated to dryness and purified by Prep-HPLC to give 47 mg of the titled compound 257 as a white solid. Yield: 44.9%. $^1H$ NMR (400 MHz, $CDCl_3$) δ (ppm): δ 9.19 (s, 1H), 6.98 (d, J=2.0 Hz, 1H), 6.66-6.79 (m, 4H), 5.43-5.48 (m, 1H), 5.27 (dd, J=6.4, 12.4 Hz, 1H), 4.55-4.62 (m, 2H), 4.33 (dd, J=2.0, 10.4 Hz, 1H), 4.26 (dd, J=2.4, 10.8 Hz, 1H), 3.88 (s, 3H), 3.35 (ddd, J=1.6, 12.0, 13.6 Hz, 1H), 2.69 (ddd, J=1.6, 6.4, 8.4 Hz, 1H). LC-MS (ESI): m/z calcd for $C_{20}H_{17}F_2N_5O_4S$, 461.4, found 462.5 $[M+H]^+$.

Compound 258: (S)-2-((1-(5-(3,5-difluorophenyl)-4,5-dihydro-1H-pyrazole-1-carbonyl)azetidin-3-yl)oxy)-N-methyl-4H-pyrrolo[2,3-d]thiazole-5-carboxamide

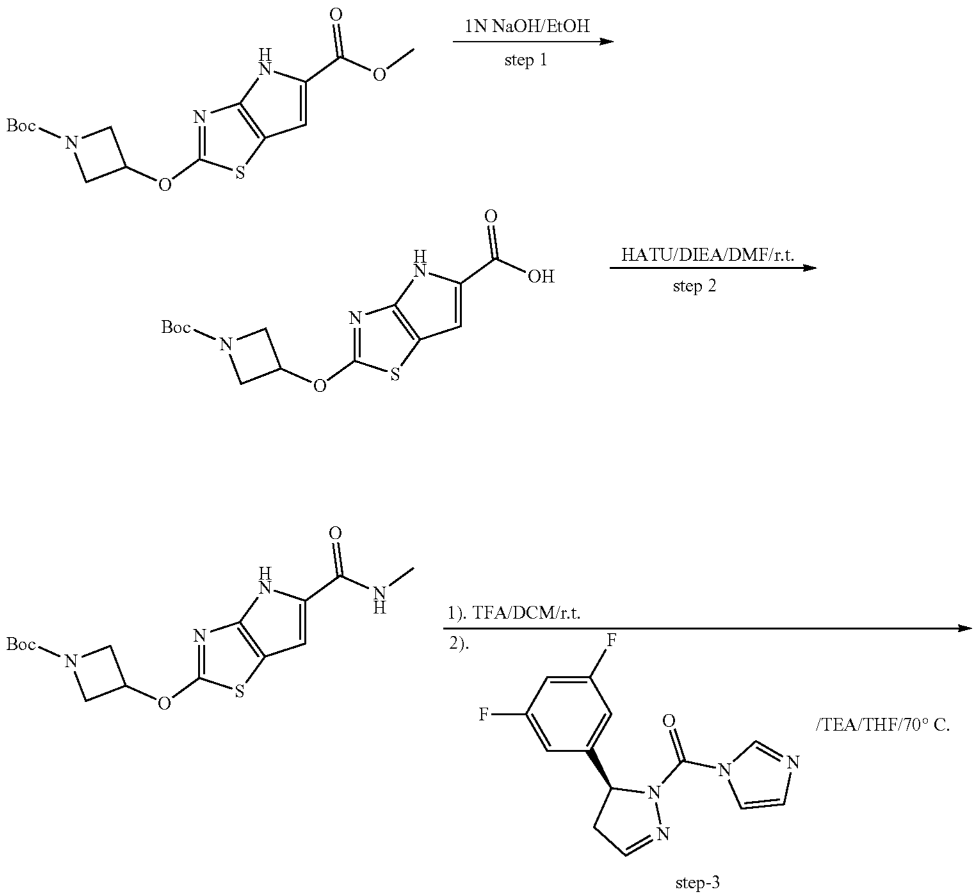

-continued

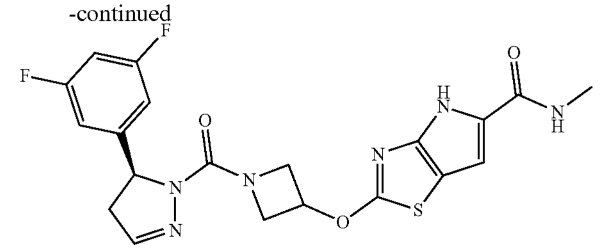

Step 1. Methyl 2-((1-(tert-butoxycarbonyl)azetidin-3-yl)oxy)-4H-pyrrolo[2,3-d]thiazole-5-carboxylate (300 mg, 0.85 mmoL) was suspended in 8 mL EtOH. 6 mL 1N NaOH was added. Let it stir at 60° C. under nitrogen for 7 hrs. The solvent was evaporated to dryness and adjusted to PH=5 with 1N HCl. The amaranth solid was filtered and used for next step without further purification. Amount: 100 mg. Yield: 34.7%. LC-MS (m/z) 339.9 $[M+H]^+$.

Step 2: the product was prepared in 60% field from 2-((1-(tert-butoxycarbonyl)azetidin-3-yl)oxy)-4H-pyrrolo[2,3-d]thiazole-5-carboxylic acid and methylamine hydrochloride by coupling reaction using HATU.

Step 3 The titled compound 67 was prepared in 25.6% yield from 2-(azetidin-3-yloxy)-N-methyl-4H-pyrrolo[2,3-d]thiazole-5-carboxamide and (S)-(5-(3,5-difluorophenyl)-4,5-dihydro-1H-pyrazol-1-yl)(1H-imidazol-1-yl)methanone according to the procedure outlined for compound 258. $^1$H NMR (400 MHz, CDCl3) δ (ppm): δ 9.49 (brs, 1H), 6.67-6.78 (m, 4H), 6.58 (s, 1H), 5.41-5.52 (m, 1H), 5.27 (dd, J=5.6, 12.0 Hz, 1H), 4.51-4.64 (m, 2H), 4.22-4.36 (m, 2H), 3.34 (dd, J=12.0, 17.6 Hz, 1H), 2.99 (s, 3H), 2.69 (dd, J=6.8, 18.4 Hz, 1H). LC-MS (ESI): m/z calcd for $C_{20}H_{18}F_2N_6O_3S$, 460.5, found 461.4 $[M+H]^+$.

Compound 259: (S)-2-((1(5-(3,5-difluorophenyl)-4,5-dihydro-1H-pyrazole-1-carbonyl)azetidin-3-yl)oxy)-4H-pyrrolo[2,3-d]thiazole-5-carboxylic acid

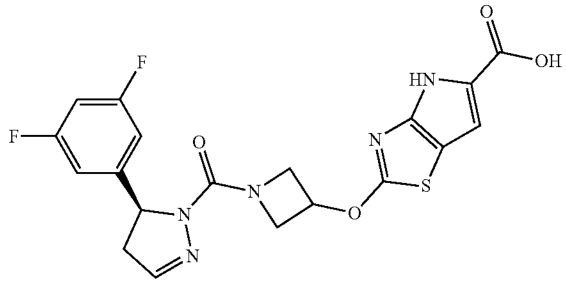 [SMILES: O=C(O)c1cc2sc(OC3CN(C(=O)N4N=CC[C@H]4c4cc(F)cc(F)c4)C3)nc2[nH]1]

Methyl(S)-2-((1-(5-(3,5-difluorophenyl)-4,5-dihydro-1H-pyrazole-1-carbonyl) azetidin-3-yl)oxy)-4H-pyrrolo[2,3-d]thiazole-5-carboxylate (28 mg, 0.06 mmoL) was dissolved in 2 mL MeOH. 1N NaOH (1 mL) was added. Let it stir at 60° C. for 10 hrs. The solvent was evaporated to dryness and dissolved with $H_2O$. It was adjusted to PH=5 with 1N HCl. The brown solid was filtered and without further purification to give the titled compound 259. Amount: 10 mg, yield: 37%. $^1$H NMR (400 MHz, $CDCl_3$) δ (ppm): δ 6.97 (s, 1H), 6.74-6.77 (m, 1H), 6.63-6.72 (m, 3H), 5.39-5.44 (m, 1H), 5.19-5.25 (m, 1H), 4.45-4.65 (m, 2H), 4.20-4.33 (m, 2H), 3.25-3.35 (m, 1H), 2.62-2.70 (m, 1H). LC-MS (ESI): m/z calcd for $C_{19}H_{15}F_2N_5O_4S$ 447.2, found 448.3 $[M+H]^+$.

Compound 260: (S)-(4-(1H-pyrazolo[3,4-d]pyrimidin-6-yl)piperazin-1-yl)(5-(3,5-difluorophenyl)-4,5-dihydro-1H-pyrazol-1-yl)methanone

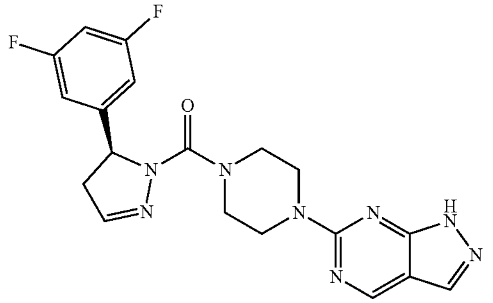 [SMILES: O=C(N1CCN(c2ncc3cn[nH]c3n2)CC1)N1N=CC[C@H]1c1cc(F)cc(F)c1]

(S)-(5-(3,5-difluorophenyl)-4,5-dihydro-1H-pyrazol-1-yl)(piperazin-1-yl)methanone (100 mg, 0.34 mmoL) and 6-chloro-1H-pyrazolo[3,4-d]pyrimidine (57.8 mg, 0.37 mmoL) were dissolved in 2 mL DMF. 0.5 mL DIEA was added. Let it stir at 150° C. under microwave for 40 mins. The solvent was evaporated to dryness and purified by prep-TLC (PE/EA=1/2) to give 56 mg of the titled compound 260 as a white solid. Yield: 39.9%. $^1$H NMR (400 MHz, $CDCl_3$) δ (ppm): 11.41 (brs, 1H), 8.82 (s, 1H), 7.92 (s, 1H), 6.75-6.96 (m, 3H), 6.60-6.72 (m, 1H), 5.36 (t, J=9.6 Hz, 1H), 3.99-4.10 (m, 2H), 3.87-3.97 (m, 2H), 3.76-3.86 (m, 2H), 3.60-3.75 (m, 2H), 3.32 (dd, J=8.4, 17.2 Hz, 1H), 2.68 (dd, J=8.8, 17.2 Hz, 1H). Mass (ESI): m/z calcd for $C_{19}H_{18}F_2N_8O$ 412.4, found 413.3 $[M+H]^+$.

Compound 261: (S)-azetidin-1-yl(2-((1-(5-(3,5-difluorophenyl)-4,5-dihydro-1H-pyrazole-1-carbonyl)azetidin-3-yl)oxy)-4H-pyrrolo[2,3-d]thiazol-5-yl)methanone

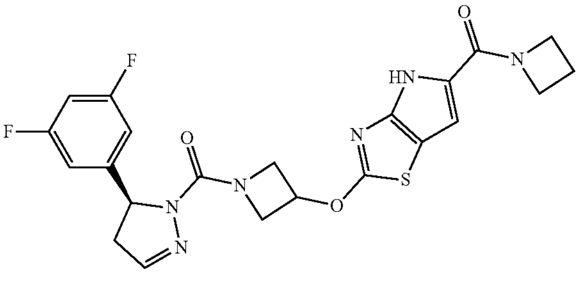 [SMILES: O=C(c1cc2sc(OC3CN(C(=O)N4N=CC[C@H]4c4cc(F)cc(F)c4)C3)nc2[nH]1)N1CCC1]

The titled compound 261 was prepared in 46% yield from azetidine and (S)-2-((1-(5-(3,5-difluorophenyl)-4,5-dihydro-1H-pyrazole-1-carbonyl)azetidin-3-yl)oxy)-4H-pyrrolo[2,3-d]thiazole-5-carbonyl chloride according to the procedure outlined for compound 67. $^1$H NMR (400 MHz, $CDCl_3$) δ (ppm): δ 9.47 (brs, 1H), 6.74-6.78 (m, 3H), 6.67-6.72 (m, 1H), 6.48 (d, J=2.0 Hz, 1H), 5.43-5.48 (m, 1H), 5.27 (dd, J=6.4, 12.0 Hz, 1H), 4.52-4.65 (m, 2H), 4.35-4.46 (m, 2H), 4.17-4.34 (m, 4H), 3.34 (ddd, J=1.6, 12.4, 14.0 Hz, 1H), 2.69 (ddd, J=1.6, 6.4, 8.4 Hz, 1H), 2.38-2.47 (m, 2H). LC-MS (ESI): m/z calcd for $C_{22}H_{20}F_2N_6O_3S$ 486.5, found 487.3 $[M+H]^+$.

Compound 262: (S)-(3-((3,5-difluoro-6-(methylamino)pyridin-2-yl)oxy)azetidin-1-yl)(5-(3,5-difluorophenyl)-4,5-dihydro-1H-pyrazol-1-yl)methanone

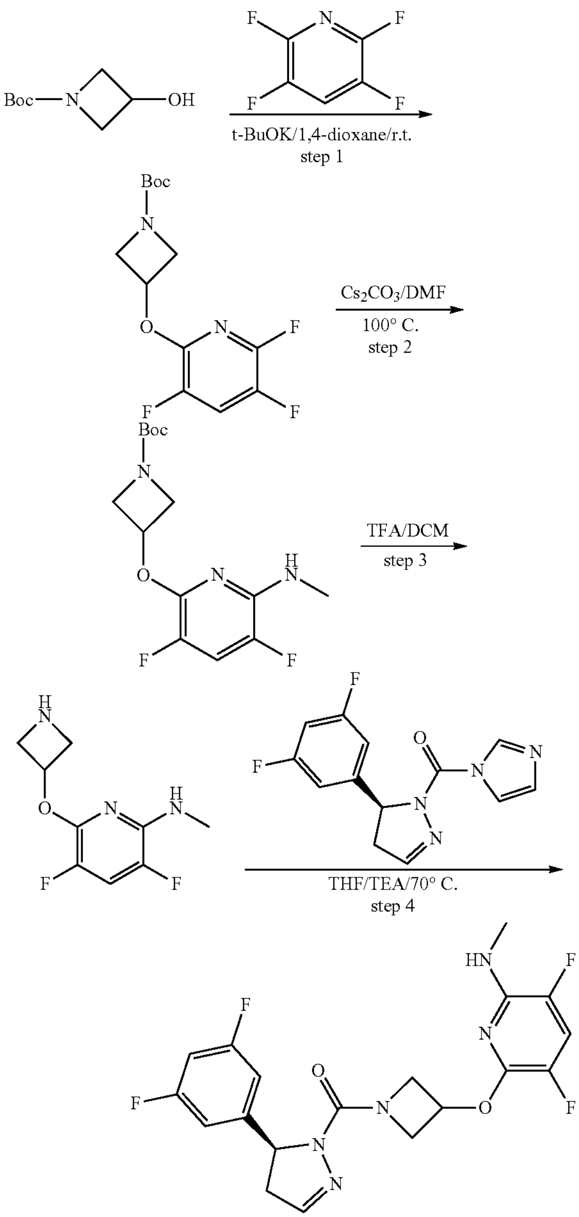

Step 1. 2,3,5,6-tetrafluoropyridine (350 mg, 2.32 mmoL) and tert-butyl 3-hydroxyazetidine-1-carboxylate (441 mg, 2.55 mmol) and t-BuOK (415.6 mg, 3.70 mmoL) were mixed in 10 mL 1,4-dioxane. Let it stir at r.t for 16 hrs. Water was added and extracted with EtOAc (30 mL×3). The solvent was evaporated to dryness and purified by column chromatography (PE/EA=85/15) to give 460 mg tert-butyl 3-((3,5,6-trifluoropyridin-2-yl)oxy)azetidine-1-carboxylate as light-yellow solid. Yield: 63.9%. LC-MS (m/z) 305.2 $[M+H]^+$.

Step 2. Tert-butyl 3-((3,5,6-trifluoropyridin-2-yl)oxy)azetidine-1-carboxylate (200 mg, 0.66 mmoL), methylamine hydrochloride (48.8 mg, 0.73 mmoL) and $Cs_2CO_3$ (427.6 mg, 1.316 mmoL) were mixed in 5 mL DMF. Let it stir at 100° C. for 16 hrs. Water was added and extracted with EtOAc (30 mL×3). The solvent was evaporated to dryness and purified by Prep-TLC (PE/EA=4/1) to give 170 mg tert-butyl 3-((3,5-difluoro-6-(methylamino)pyridin-2-yl)oxy)azetidine-1-carboxylate as light-yellow solid. Yield: 81.8%. LC-MS (m/z) 317.1 $[M+H]^+$.

Step 3. Tert-butyl 3-((3,5-difluoro-6-(methylamino)pyridin-2-yl)oxy)azetidine-1-carboxylate (100 mg, 0.316 mmoL) was dissolved in 2 mL DCM. 2 mL DCM/TFA (1/1) was added slowly to the solution at 0° C. Let it stir r.t for 1 h. The solvent was evaporated to dryness and used for next step without further purification. LC-MS (m/z) 217.2 $[M+H]^+$.

Step 4. The above residue was dissolved in 2 mL THF. 0.2 mL of TEA was added. (S)-(5-(3,5-difluorophenyl)-4,5-dihydro-1H-pyrazol-1-yl)(1H-imidazol-1-yl)methanone (87 mg, 0.315 mmoL) was added. Let it stir at 70° C. for 16 hrs. The solvent was evaporated to dryness and purified by Prep-TLC (PE/EA=1/1) to give 80 mg of the titled compound 262 as light-yellow solid. Yield: 59.8%. $^1$H NMR (400 MHz, $CDCl_3$) δ (ppm): δ 7.11 (t, J=8.8 Hz, 1H), 6.74-6.79 (m, 3H), 6.66-6.71 (m, 1H), 5.32-5.37 (m, 1H), 5.28 (dd, J=6.4, 12.0 Hz, 1H), 4.51-4.59 (m, 2H), 4.31 (dd, J=4.8, 10.4 Hz, 1H), 4.22 (dd, J=4.0, 10.4 Hz, 1H), 3.34 (ddd, J=2.0, 12.4, 14.0 Hz, 1H), 2.94 (s, 3H), 2.69 (ddd, J=2.0, 6.8, 8.4 Hz, 1H). LC-MS (ESI): m/z calcd for $C_{19}H_{17}F_4N_5O_2$ 423.4, found 424.3 $[M+H]^+$.

Compound 263: (S)-(3-((6-amino-3,5-difluoropyridin-2-yl)oxy)azetidin-1-yl)(5-(3,5-difluorophenyl)-4,5-dihydro-1H-pyrazol-1-yl)methanone

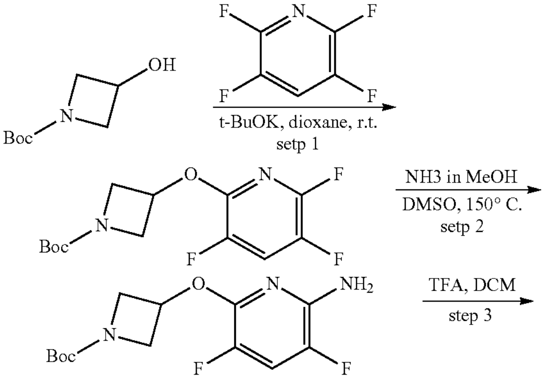

-continued

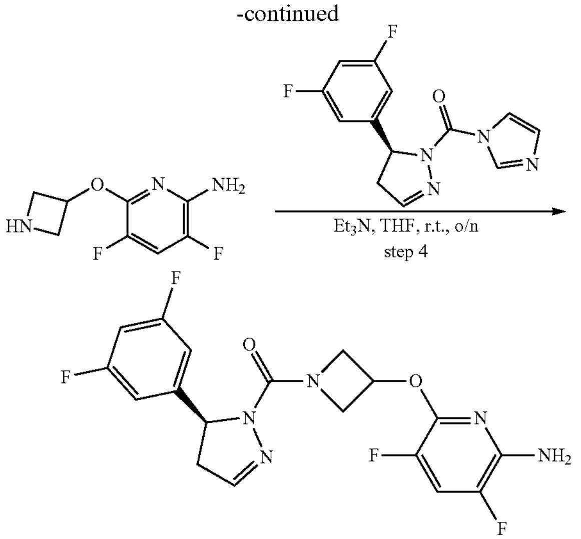

Step 1: tert-butyl 3-((3,5,6-trifluoropyridin-2-yl)oxy)azetidine-1-carboxylate To a solution of 2,3,5-trifluoropyridine (795 mg, 5.2 mmol) and tert-butyl 3-hydroxyazetidine-1-carboxylate (1.0 g, 5.8 mmol) in 1,4-dioxane (200 mL) was added t-BuOK (882 mg, 7.8 mmol). The mixture was stirred to at room temperature for overnight. The reaction mixture was concentrated in vacuo to a residue. The crude product was purified by silica gel chromatography (petrol ether/EtOAc=5/1) to give the titled compound (1.1 g, 45% yield) as a white solid. LCMS (ES, m/z): 305.3[M+H]+.

Step 2: tert-butyl 3-((6-amino-3,5-difluoropyridin-2-yl)oxy)azetidine-1-carboxylate To a solution of tert-butyl 3-((3,5,6-trifluoropyridin-2-yl)oxy)azetidine-1-carboxylate (3.4 g, 11.2 mmol) in DMSO (30 mL) was added NH3 in MeOH (20 mL, 7M). The mixture was stirred to 150° C. for overnight. The mixture was extracted with DCM, washed with brine, dried (Na2SO4), and concentrated in vacuo to give the titled compound (2.0 g, 62%) as a yellow Solid. (ES, m/s): 302.1 [M+H]+.

Step 3 and 4: The titled compound 72 was prepared in 5% yield (two steps) from 6-(azetidin-3-yloxy)-3,5-difluoropyridin-2-amine TFA salt and (S)-(5-(3,5-difluorophenyl)-4,5-dihydro-1H-pyrazol-1-yl)(1H-imidazol-1-yl)methanone according the produce outlined for compound 62. $^1$H NMR (400 MHz, Chloroform-d) δ 7.15 (t, J=8.8 Hz, 1H), 6.80-6.62 (m, 4H), 5.31-5.23 (m, 2H), 4.56-4.49 (m, 2H), 4.27-4.17 (m, 2H), 3.76 (brs, 2H), 3.34 (ddd, J=18.6, 12.2, 1.5 Hz, 1H), 2.68 (ddd, J=18.5, 6.5, 1.6 Hz, 1H). Yield: 5% (5 mg), LCMS (ES, m/z): 410.1[M+H]+

Compound 264: (S)-2-((1-(5-(3,5-difluorophenyl)-4,5-dihydro-1H-pyrazole-1-carbonyl)azetidin-3-yd)oxy)pyrimidine-4-carbonitrile

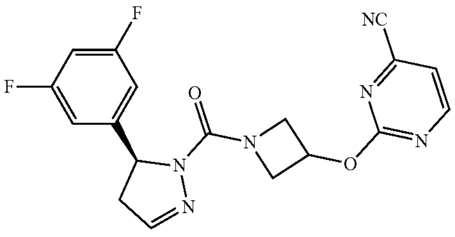 [SMILES: N#Cc1ccnc(OC2CN(C(=O)N3N=CC[C@H]3c3cc(F)cc(F)c3)C2)n1]

The titled compound 264 was synthesized in an analogous manner to the preparation of compound 256. $^1$H NMR (400 MHz, Chloroform-d) δ 8.77 (d, J=4.7 Hz, 1H), 7.33 (d, J=4.8 Hz, 1H), 6.79 (t, J=1.7 Hz, 1H), 6.77-6.73 (m, 2H), 6.69 (tt, J=8.9, 2.3 Hz, 1H), 5.39 (tt, J=6.6, 4.2 Hz, 1H), 5.28 (dd, J=12.2, 6.5 Hz, 1H), 4.66-4.52 (m, 2H), 4.34-4.19 (m, 2H), 3.35 (ddd, J=18.6, 12.2, 1.7 Hz, 1H), 2.69 (ddd, J=18.6, 6.5, 1.7 Hz, 1H). LC-MS (m/z): 385.2 $[M+H]^+$.

Compound 265: (S)-4-((1-(5-(3,5-difluorophenyl)-4,5-dihydro-1H-pyrazole-1-carbonyl)azetidin-3-yl)oxy)pyrimidine-2-carbonitrile

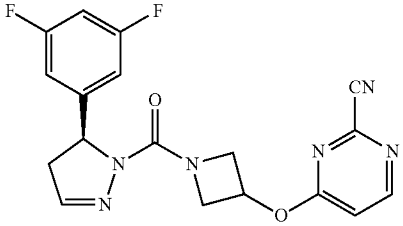 [SMILES: N#Cc1nccc(OC2CN(C(=O)N3N=CC[C@H]3c3cc(F)cc(F)c3)C2)n1]

The titled compound 265 was synthesized in an analogous manner to the preparation of compound 256. $^1$H NMR (400 MHz, Chloroform-d) δ 8.57 (d, J=5.8 Hz, 1H), 7.00 (d, J=5.8 Hz, 1H), 6.82 (t, J=1.7 Hz, 1H), 6.76-6.73 (m, 2H), 6.70 (tt, J=8.9, 2.3 Hz, 1H), 5.45 (tt, J=6.6, 4.1 Hz, 1H), 5.28 (dd, J=12.2, 6.3 Hz, 1H), 4.71-4.55 (m, 2H), 4.28-4.17 (m, 2H), 3.36 (ddd, J=18.7, 12.2, 1.7 Hz, 1H), 2.71 (ddd, J=18.6, 6.4, 1.7 Hz, 1H). LC-MS (m/z): 385.2 $[M+H]^+$.

Compound 266: (S)-(5-(3,5-difluorophenyl)-4,5-dihydro-H-pyrazol-1-yl)(3-((5-fluoro-2-((2-hydroxyethyl)amino)pyrimidin-4-yl)oxy)azetidin-1-yl)methanone

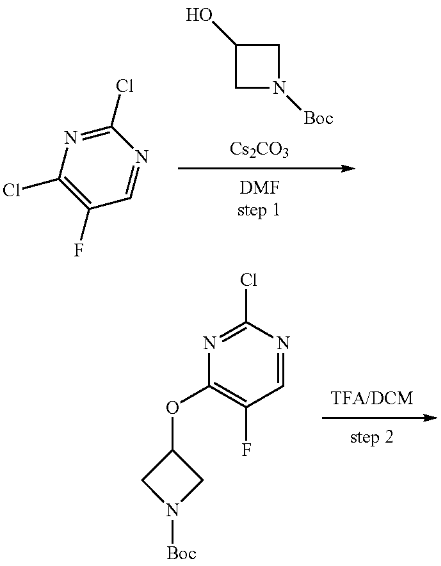

-continued

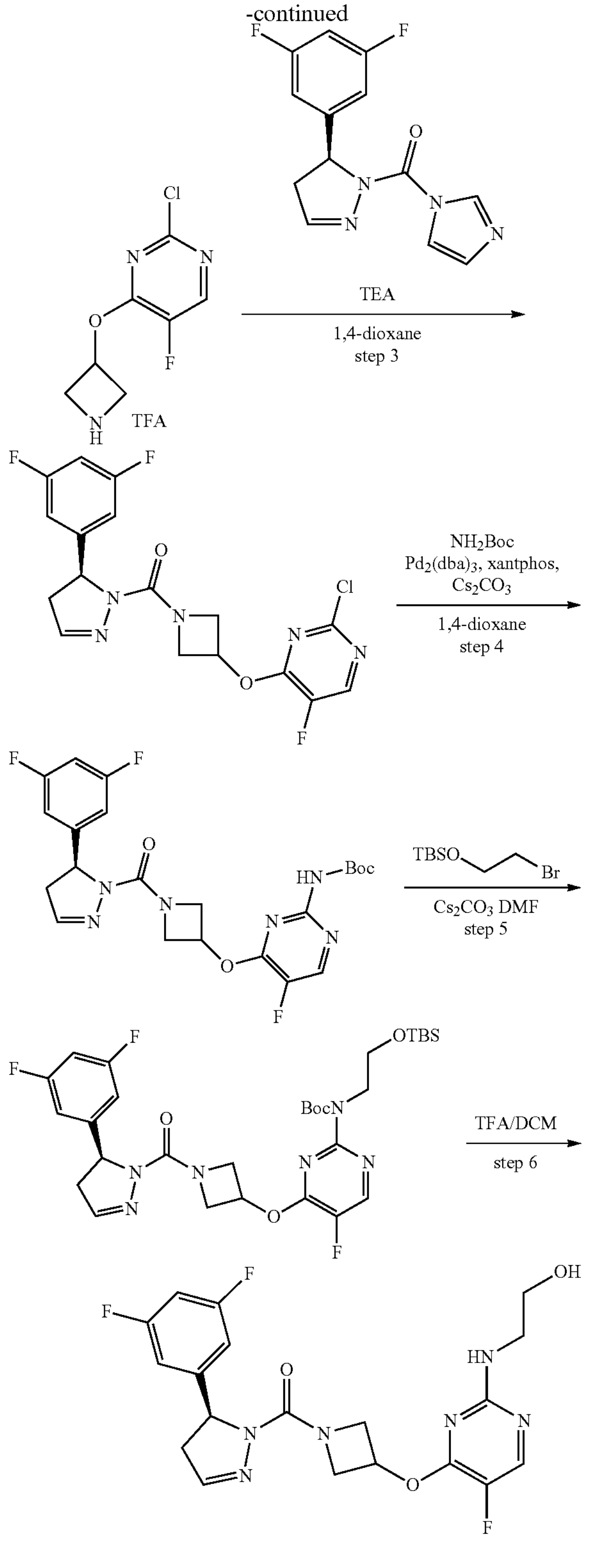

Step 1. Preparation of tert-butyl 3-((2-chloro-5-fluoropyrimidin-4-yl)oxy)azetidine-1-carboxylate. 2,4-dichloro-5-fluoropyrimidine (5 g, 29.9 mmol) was added to a solution of $Cs_2CO_3$ (19.5 g, 59.9 mmol) in DMF (100 mL), and tert-butyl 3-hydroxyazetidine-1-carboxylate (5.7 g, 32.9 mmol) was added. The mixture was stirred at 100° C. for 2 hrs. The reaction mixture was then extracted by EtOAc/$H_2O$ (50 mL/50 mL) 3 times. The organic layer was combined, washed with brine, dried over $Na_2SO_4$, concentrated and further purified by silica gel column chromatography (PE/EA=5/1) to give tert-butyl 3-((2-chloro-5-fluoropyrimidin-4-yl)oxy)azetidine-1-carboxylate (3.9 g) as a colorless oil (43%). LC-MS (ESI) m/z $[M+H]^+$: 304.1.

Step 2. Preparation of 4-(azetidin-3-yloxy)-2-chloro-5-fluoropyrimidine. TFA (5 mL) was added to a solution of tert-butyl 3-((2-chloro-5-fluoropyrimidin-4-yl)oxy)azetidine-1-carboxylate (3.9 g, 12.9 mmol) in DCM (10 mL). the reaction mixture was stirred at room temperature for 0.5 hr. then the solvent was evaporated in vacuo to give 5.2 g of 4-(azetidin-3-yloxy)-2-chloro-5-fluoropyrimidine as a colorless oil (crude). LC-MS (ESI) m/z $[M+H]^+$: 204.1.

Step 3. Preparation of (S)-(3-((2-chloro-5-fluoropyrimidin-4-yl)oxy)azetidin-1-yl)(5-(3,5-difluorophenyl)-4,5-dihydro-1H-pyrazol-1-yl)methanone. (S)-(5-(3,5-difluorophenyl)-4,5-dihydro-1H-pyrazol-1-yl)(1H-imidazol-1-yl)methanone (3.23 g, 11.7 mmol) was added to a solution of 4-(azetidin-3-yloxy)-2-chloro-5-fluoropyrimidine and TEA (3.55 g, 35.1 mmol) in 1,4-dioxane (30 mL). The reaction mixture was stirred at room temperature overnight. Then the solvent was evaporated in vacuo. The oil residue was purified by silica gel column chromatography (PE/EA=1/1) to give 4.35 g of (S)-(3-((2-chloro-5-fluoropyrimidin-4-yl)oxy)azetidin-1-yl)(5-(3,5-difluorophenyl)-4,5-dihydro-1H-pyrazol-1-yl)methanone as a yellow oil (90%). LC-MS (ESI) m/z $[M+H]^+$: 412.1.

Step 4. Preparation of tert-butyl (S)-(2-((tert-butyldimethylsilyl)oxy)ethyl)(4-((1-(5-(3,5-difluorophenyl)-4,5-dihydro-1H-pyrazole-1-carbonyl)azetidin-3-yl)oxy)-5-fluoropyrimidin-2-yl)carbamate. (2-bromoethoxy)(tert-butyl)dimethylsilane (29.1 mg, 0.122 mmol) was added to a solution of $Cs_2CO_3$ (66.5 mg, 0.204 mmol) in DMF (1 mL), and (3-01) (50 mg, 0.102 mmol) was added. The mixture was stirred at 100° C. for 1 hr. The reaction mixture was then extracted by EtOAc/$H_2O$ (50 mL/50 mL) 3 times. The organic layer was combined, washed with brine, dried over $Na_2SO_4$, concentrated to give tert-butyl (S)-(2-((tert-butyldimethylsilyl)oxy)ethyl)(4-((1-(5-(3,5-difluorophenyl)-4,5-dihydro-1H-pyrazole-1-carbonyl)azetidin-3-yl)oxy)-5-fluoropyrimidin-2-yl)carbamate (60 mg) as a yellow oil.

Step 5. Preparation of (S)-(5-(3,5-difluorophenyl)-4,5-dihydro-1H-pyrazol-1-yl)(3-((5-fluoro-2-((2-hydroxyethyl)amino)pyrimidin-4-yl)oxy)azetidin-1-yl)methanone. TFA (5 mL) was added to a solution of tert-butyl (S)-(2-((tert-butyldimethylsilyl)oxy)ethyl)(4-((1-(5-(3,5-difluorophenyl)-4,5-dihydro-1H-pyrazole-1-carbonyl)azetidin-3-yl)oxy)-5-fluoropyrimidin-2-yl)carbamate (60 mg, 0.092 mmol) in DCM (10 mL). the reaction mixture was stirred at room temperature for 0.5 hr. The reaction mixture was concentrated and purified by pre-HPLC to give 16 mg of the titled compound 266: (S)-(5-(3,5-difluorophenyl)-4,5-dihydro-1H-pyrazol-1-yl)(3-((5-fluoro-2-((2-hydroxyethyl)amino)pyrimidin-4-yl)oxy)azetidin-1-yl)methanone (40%). LC-MS (ESI) m/z $[M+H]^+$:437.2 $^1H$ NMR (400 MHz, $CDCl_3$): δ 7.82 (d, J=3.4 Hz, 1H), 6.85-6.64 (m, 4H), 5.50 (s, 1H), 5.27 (dd, J=12.1, 6.4 Hz, 1H), 4.60 (br, 2H), 4.38-4.26 ((m, 2H), 3.85 (s, 2H), 3.55 (s, 2H), 3.41-3.33 (m, 1H), 2.77-2.66 (m, 1H).

Compound 267: (S)-(3-((2-chloropyrimidin-4-yl)oxy)azetidin-1-yl)(5-(3,5-difluorophenyl)-4,5-dihydro-1H-pyrazol-1-yl)methanone

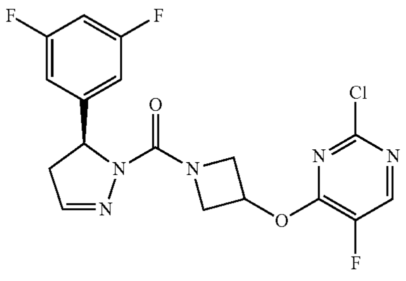 [SMILES: O=C(N1CC(Oc2nc(Cl)ncc2F)C1)N1N=CC[C@H]1c1cc(F)cc(F)c1]

The titled compound 267 was synthesized in the manner to the preparation of compound 75. $^1$H NMR (400 MHz, Chloroform-d) δ 8.25 (d, J=2.1 Hz, 1H), 6.79 (t, J=1.7 Hz, 1H), 6.78-6.73 (m, 2H), 6.69 (tt, J=8.9, 2.3 Hz, 1H), 5.50 (tt, J=6.7, 4.1 Hz, 1H), 5.27 (dd, J=12.2, 6.5 Hz, 1H), 4.69-4.54 (m, 2H), 4.34-4.22 (m, 2H), 3.36 (ddd, J=18.6, 12.2, 1.7 Hz, 1H), 2.70 (ddd, J=18.6, 6.5, 1.7 Hz, 1H). LC-MS (m/z): 412.1[M+H]$^+$.

Compound 268: (S)-(5-(3,5-difluorophenyl)-4,5-dihydro-1H-pyrazol-1-yl)(3-((5-fluoro-2-(methylamino)pyrimidin-4-yl)oxy)azetidin-1-yl)methanone The titled compound 268 was synthesized in 68% yield from compound 267 and methylamine according to the similar manner to the preparation of compound 266

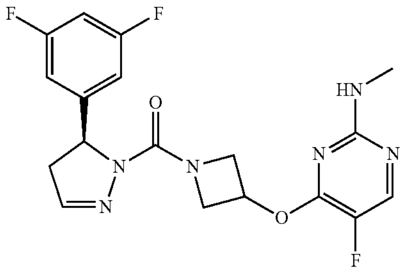 [SMILES: CNc1ncc(F)c(OC2CN(C(=O)N3N=CC[C@H]3c3cc(F)cc(F)c3)C2)n1]

$^1$H NMR (400 MHz, Chloroform-d) δ 10.25-10.01 (br, 1H), 7.80 (d, J=3.7 Hz, 1H), 6.82 (t, J=1.7 Hz, 1H), 6.78-6.73 (m, 2H), 6.70 (tt, J=8.8, 2.3 Hz, 1H), 5.54 (tt, J=6.7, 4.1 Hz, 1H), 5.28 (dd, J=12.2, 6.4 Hz, 1H), 4.68-4.55 (m, 2H), 4.42-4.33 (m, 1H), 4.33-4.25 (m, 1H), 3.37 (ddd, J=18.6, 12.2, 1.7 Hz, 1H), 3.00 (s, 3H), 2.72 (ddd, J=18.7, 6.4, 1.7 Hz, 1H). LC-MS (m/z): 407.2 [M+H]$^+$.

Compound 269: (S)-3-((4-((1-(5-(3,5-fluorophenyl)-4,5-dihydro-1H-pyrazole-1-carbonyl)azetidin-3-yl)oxy)-5-fluoropyrimidin-2-yl)amino)propanenitrile

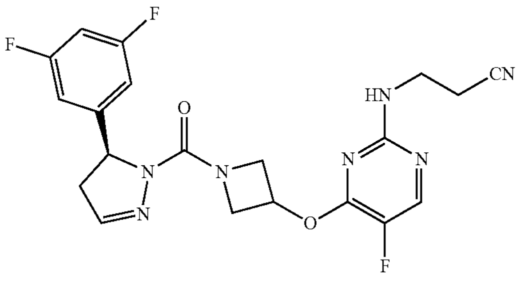

The titled compound 269 was prepared in an analogous manner to the preparation of 266 $^1$H NMR (400 MHz, Chloroform-d) δ 10.29 (s, 1H), 8.00 (s, 1H), 6.88 (s, 1H), 6.80-6.61 (m, 3H), 5.68-5.57 (m, 1H), 5.30 (dd, J=12.4, 6.0 Hz, 1H), 4.76-4.62 (m, 2H), 4.51-4.30 (m, 2H), 3.84-3.77 (m, 2H), 3.45-3.30 (m, 1H), 2.81-2.64 (m, 3H).

LC-MS (m/z) 446.3 (M+H$^+$), Yield 12.4%

Compound 270: (S)-3-((4-((1-(5-(3,5-difluorophenyl)-4,5-dihydro-1H-pyrazole-1-carbonyl)azetidin-3-yl)oxy)-5-fluoropyrimidin-2-yl)amino)propanamide

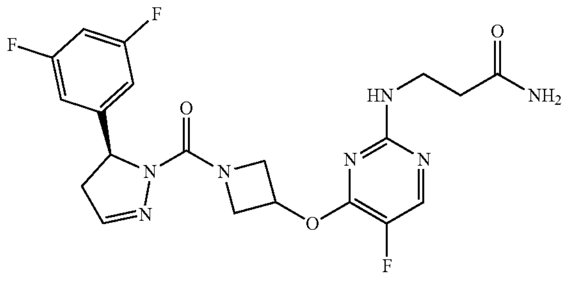

The titled compound 270 was prepared from compound 269 by hydrolysis reaction using 1 N NaOH solution. Yield 48.2%. $^1$H NMR (400 MHz, Chloroform-d) δ 7.95 (s, 1H), 6.78 (t, J=1.6 Hz, 1H), 6.77-6.71 (m, 2H), 6.71-6.65 (m, 1H), 5.74 (s, 1H), 5.60 (s, 2H), 5.39-5.32 (m, 1H), 5.27 (dd, J=12.4, 6.4 Hz, 1H), 4.61-4.47 (m, 2H), 4.36-4.09 (m, 2H), 3.64 (q, J=6.0 Hz, 2H), 3.40-3.29 (m, 1H), 2.73-2.64 (m, 1H), 2.50 (t, J=6.0 Hz, 2H). LC-MS (m/z) 464.3 (M+H$^+$).

Compound 271: (S)-(5-(3,5-difluorophenyl)-4,5-dihydro-1H-pyrazol-1-yl)(4-(5-fluoro-4-methoxypyrimidin-2-yl)piperazin-1-yl)methanone

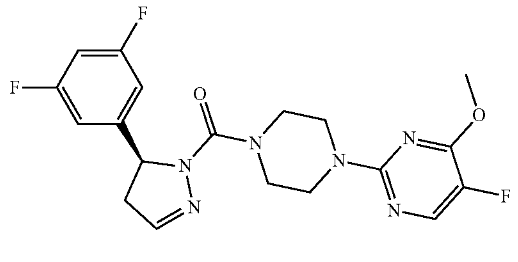 [SMILES: COc1nc(N2CCN(C(=O)N3N=CC[C@H]3c3cc(F)cc(F)c3)CC2)ncc1F]

(S)-(5-(3,5-difluorophenyl)-4,5-dihydro-1H-pyrazol-1-yl)(piperazin-1-yl)methanone (100 mg, 0.34 mmoL) and 2-chloro-5-fluoro-4-methoxypyrimidine (60.8 mg, 0.37 mmoL) were dissolved in 2 mL 1,4-dioxane. p-Toluenesulfonic acid (11.7 mg, 0.068 mmoL) was added. Let it stir at 100° C. under sealed tube for 16 hrs. The solvent was evaporated to dryness and purified by prep-TLC (PE/EA=1/2) to give 35 mg of the titled compound as a white solid. Yield: 24.5%. $^1$H NMR (400 MHz, $CDCl_3$) δ (ppm): δ 7.96 (s, 1H), 6.81-6.85 (m, 3H), 6.69 (t, J=8.8 Hz, 1H), 5.33 (t, J=10.8 Hz, 1H), 3.98 (s, 3H), 3.70-3.87 (m, 6H), 3.58-3.64 (m, 2H), 3.32 (dd, J=12.0, 18.4 Hz, 1H), 2.68 (dd, J=10.4, 18.4 Hz, 1H). Mass (ESI): m/z calcd for $C_{19}H_{19}F_3N_6O_2$ 420.4, found 421.5 [M+H]$^+$.

Compound 272: ethyl (S)-5-chloro-2-((1-(5-(3,5-difluorophenyl)-4,5-dihydro-1H-pyrazole-1-carbonyl)azetidin-3-yl)oxy)thiazol-4-carboxylate

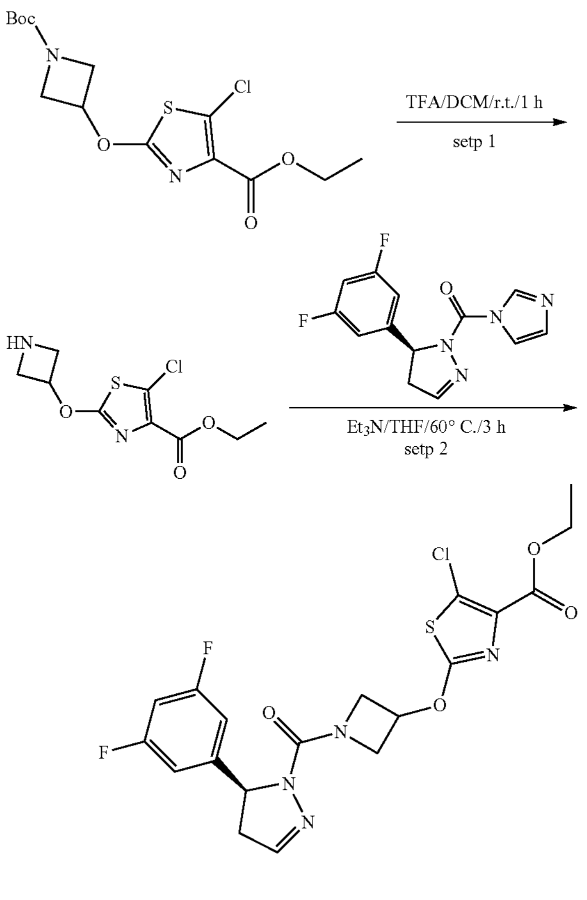

Step1: A solution of ethyl 2-((1-(tert-butoxycarbonyl) azetidin-3-yl)oxy)-5-chlorothiazole-4-carboxylate (240 mg, 0.7 mmol) in DCM (5 mL) was added TFA (1 mL). The resulting mixture was stirred at room temperature for 2 h, then concentrated in vacuo to give ethyl 2-(azetidin-3-yloxy)-5-chlorothiazole-4-carboxylate (174 mg crude) as TFA salt. which was used for next step directly.

Step 2: To a solution of (S)-(5-(3,5-difluorophenyl)-4,5-dihydro-1H-pyrazol-1-yl)(1H-imidazol-1-yl)methanone (183 mg, 0.7 mmol) and ethyl 2-(azetidin-3-yloxy)-5-chlorothiazole-4-carboxylate (174 g crude, 0.7 mmol) in THF (5 mL) was added Et3N (0.5 mL, 2.0 mmol). The mixture was stirred at 70° C. for 3 h. When the reaction was completed, the reaction mixture was concentrated in vacuo to a residue. The crude product was purified by pre-TLC (petrol ether/EtOAc=1/1) to give the titled compound (220 mg, 74% yield) as a white solid. LCMS (ES, m/z): 471.1[M+H]$^+$. $^1$H NMR (400 MHz, Chloroform-d) δ 6.84-6.55 (m, 4H), 5.53-5.51 (m, 1H), 5.33 (dd, J=5.2, 16.4 Hz, 1H), 4.63-4.47 (m, 2H), 4.37 (q, J=7.2 Hz, 2H), 4.33-4.06 (m, 2H), 3.34 (ddd, J=18.6, 12.2, 1.7 Hz, 1H), 2.69 (ddd, J=18.6, 6.5, 1.7 Hz, 1H), 1.39 (t, J=7.2 Hz, 3H).

Compound 273: (S)-5-chloro-2-((1-(5-(3,5-difluorophenyl)-4,5-dihydro-1H-pyrazole-1-carbonyl)azetidin-3-yl)oxy)-N-methylthiazole-4-carboxamide

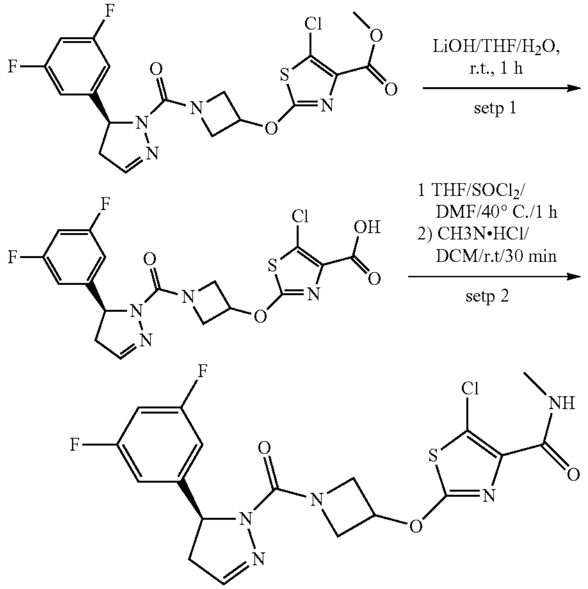

Step1: To a solution of ethyl (S)-5-chloro-2-((1-(5-(3,5-difluorophenyl)-4,5-dihydro-1H-pyrazole-1-carbonyl)azetidin-3-yl)oxy)thiazole-4-carboxylate (180 mg, 0.4 mmol) in THF (3 mL) was added a solution of LiOH (17 g, 0.4 mmol) in water (3 mL). The resulting mixture was stirred at room temperature for 2 h. TLC analysis showed the reaction was completed. THF was evaporated in vacuo and 1N HCl was added to adjust pH<5, The mixture was poured into water (20 ml) and then extracted with DCM (3×10 ml). The organic layers were combined, dried over anhydrous sodium sulfate, filtered and concentrated under vacuum to give (S)-5-chloro-2-((1-(5-(3,5-difluorophenyl)-4,5-dihydro-1H-pyrazole-1-carbonyl)azetidin-3-yl)oxy)thiazole-4-carboxylic acid as a white solid (170 mg, crude).

Step 2: To a solution of (S)-5-chloro-2-((1-(5-(3,5-difluorophenyl)-4,5-dihydro-1H-pyrazole-1-carbonyl)azetidin-3-yl)oxy)thiazole-4-carboxylic acid (50 mg, 0.11 mmol) was dissolved in 10 ml of dry THF and DMF (cat.) was added. $SO_2Cl_2$ (0.738 g, 6.42 mmol) and added slowly to the above solution at 0° C. The mixture was stirred for 1 h, then concentrated in vacuo give crude as a residue. The residue was dissolved in DCM (100 mL), methylamine hydrochloride (13.5 mg, 0.2 mmol) was added and the mixture was stirred at room temperature for 1 h. then concentrated in vacuo to give crude product. The crude product was purified by pre-TLC (petrol ether/EtOAc=1/1) to give the titled compound 273 (12 mg, 24%). $^1$H NMR (400 MHz, Chloroform-d) δ 6.90 (brs, 1H), 6.80 (t, J=1.6 Hz, 1H), 6.78-6.66 (m, 3H), 5.42-5.36 (m, 1H), 5.28 (dd, J=6.4, 12.4 Hz, 1H), 4.57-4.52 (m, 2H), 4.32-4.20 (m, 2H), 3.36 (ddd, J=18.4, 12.2, 1.6 Hz, 1H), 2.94 (d, J=3.6 Hz, 3H), 2.71 (ddd, J=18.4, 6.4, 1.6 Hz, 1H). LCMS (ES, m/z): 456.9[M+H]+.

Compound 274: (S)-5-chloro-2-((1-(5-(3,5-difluorophenyl)-4,5-dihydro-1H-pyrazole-1-carbonyl)azetidin-3-yl)oxy)thiazole-4-carboxamide

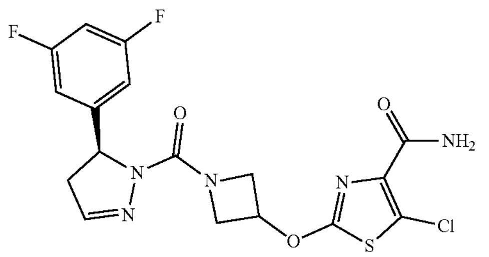 [SMILES: NC(=O)c1nc(OC2CN(C(=O)N3N=CC[C@H]3c3cc(F)cc(F)c3)C2)sc1Cl]

The titled compound 274 was prepared in an analogous manner to the preparation of compound 273. Yield: 30%. 1H NMR (400 MHz, Chloroform-d) δ 6.83-6.63 (m, 4H), 5.68 (brs, 1H), 5.42-5.36 (m, 1H), 5.33 (dd, J=6.4, 12.4 Hz, 1H), 4.68-4.45 (m, 2H), 4.39-4.11 (m, 2H), 3.36 (ddd, J=18.4, 12.4, 1.6 Hz, 1H), 2.70 (ddd, J=18.4, 6.4, 1.6 Hz, 1H). LCMS (ES, m/z): 442.8 [M+H]+.

Compound 275

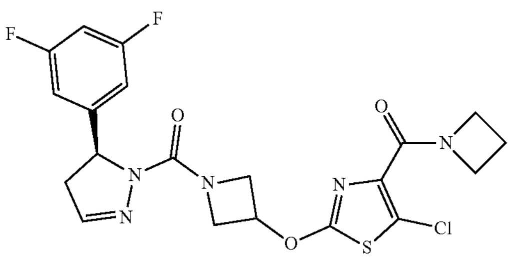 [SMILES: O=C(c1nc(OC2CN(C(=O)N3N=CC[C@H]3c3cc(F)cc(F)c3)C2)sc1Cl)N1CCC1]

The titled compound 275 was prepared in an analogous manner to the preparation of compound 273. $^1$H NMR (400 MHz, cdcl3) δ 6.87-6.65 (m, 4H), 5.38-5.33 (m, 1H), 5.27 (dd, J=6.4, 12.0 Hz, 1H), 4.61-4.47 (m, 2H), 4.47-4.36 (m, 2H), 4.31-4.27 (m, 1H), 4.25-4.10 (m, 3H), 3.36 (dd, J=17.3, 12.3 Hz, 1H), 2.71 (ddd, J=18.6, 6.5, 1.7 Hz, 1H)., 2.35-2.27 (m, 2H). Yield: 45% (12.1 mg). LCMS (ES, m/z): 482.1 [M+H]+.

Compound 276: (3-(benzo[d]thiazol-2-yloxy)azetidin-1-yl)(5-(3,5-difluorophenyl)-4,5-dihydro-1H-pyrazol-1-yl)methanone

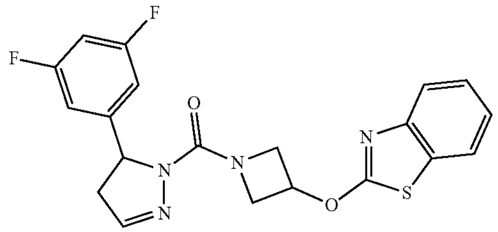 [SMILES: O=C(N1CC(Oc2nc3ccccc3s2)C1)N1N=CCC1c1cc(F)cc(F)c1]

The titled compound 276 was synthesized in an analogous manner to the preparation of compound 203. $^1$H NMR (400 MHz, Chloroform-d) δ 7.67 (dddd, J=7.9, 7.4, 1.2, 0.6 Hz, 2H), 7.40-7.34 (m, 1H), 7.24-7.28 (m, 1H), 6.80-6.73 (m, 3H), 6.73-6.65 (m, 1H), 5.59 (dt, J=6.6, 2.8 Hz, 1H), 5.37-5.19 (m, 1H), 4.62 (s, 2H), 4.46-4.23 (m, 2H), 3.43-3.25 (m, 1H), 2.70 (dd, J=18.5, 6.1 Hz, 1H). LC-MS (m/z) 414.6 [M+H]+.

Compound 277: 7-((1-(5-(3,5-difluorophenyl)-4,5-dihydro-1H-pyrazole-1-carbonyl)azetidin-3-yildene)methyl)-3,4-dihydroquinolin-2(1H)-one

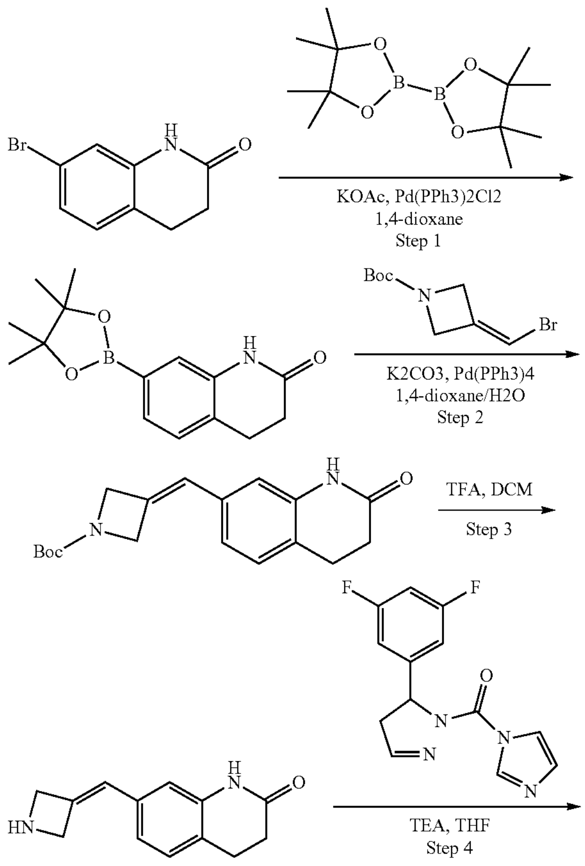

-continued

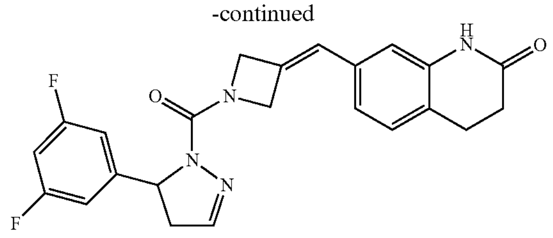

Step 1: 7-bromo-3,4-dihydroquinolin-2(1H)-one (100 mg, 0.44 mmol) was dissolved in 5 ml of dry 1,4-dioxane, 4,4,4',4',5,5,5',5'-octamethyl-2,2'-bi(1,3,2-dioxaborolane) (223 mg, 0.88 mmol) KOAc (130 mg, 1.32 mmol) $Pd(PPh_3)2Cl_2$ (32 mg, 0.04 mmol) was added, The mixture was stirred at 80° C. for overnight. The mixture was filtered, the filtrate was concentrated to give 7-(4,4,5,5-tetramethyl-1,3,2-dioxaborolan-2-yl)-3,4-dihydroquinolin-2(1H)-one, which was used for next step without further purification. LC-MS (m/z) 274.15 $(M+H^+)$.

Step 2: 7-(4,4,5,5-tetramethyl-1,3,2-dioxaborolan-2-yl)-3,4-dihydroquinolin-2(1H)-one (120 mg) was dissolved in 5 ml of 1,4-dioxane/$H_2O$, tert-butyl 3-(bromomethylene)azetidine-1-carboxylate (90 mg, 0.36 mmol) $K_2CO_3$ (150 mg, 1.08 mmol) $Pd(PPh_3)_4$ (83 mg, 0.072 mmol) was added, The mixture was stirred at 80° C. for 2 h, The mixture was filtered, the filtrate was concentrated in vacuo. Purification by silica gel chromatography (EA/PE=1:1) to give tert-butyl 3-((2-oxo-1,2,3,4-tetrahydroquinolin-7-yl)methylene)azetidine-1-carboxylate (58 mg) as a yellow solid. LC-MS (m/z) 315.16 $(M+H^+)$ Step 3: tert-butyl 3-((2-oxo-1,2,3,4-tetrahydroquinolin-7-yl)methylene)azetidine-1-carboxylate (58 mg, 0.18 mmol) was dissolved in 3 ml of DCM, trifluoroacetic acid (210 mg, 1.8 mmol) was added, The mixture was stirred at r.t. for 4 h. The mixture was concentrated to give 7-(azetidin-3-ylidenemethyl)-3,4-dihydroquinolin-2(1H)-one trifluoroacetic acid salt, which was used for next step without further purification. LC-MS (m/z) 215.15 $(M+H^+)$.

Step 4: 7-(azetidin-3-ylidenemethyl)-3,4-dihydroquinolin-2(1H)-one and (1H-imidazol-1-yl)(5-phenyl-4,5-dihydro-1H-pyrazol-1-yl)methanone (45 mg, 0.16 mmol) and TEA (0.4 ml) were dissolved in THF (5 mL) and stirred at 65° C. for 6 h. The mixture was extracted with EA, washed with brine, dried ($Na_2SO_4$), and concentrated in vacuo. Purification by Pre-HPLC to give the titled compound 277 (0.6 mg, 0.8% yield in two steps). LC-MS (m/z) 423.16 $(M+H^+)$. $^1H$ NMR (400 MHz, Chloroform-d) δ 8.05 (s, 1H), 7.14 (d, J=7.4 Hz, 1H), 6.84 (s, 1H), 6.80-6.64 (m, 3H), 6.50 (s, 1H), 6.21 (s, 1H), 5.37-5.30 (m, 1H), 5.11-5.10 (m, 2H), 4.90-4.80 (m, 2H), 3.38 (dd, J=18.6, 11.7 Hz, 1H), 2.96 (t, J=7.5 Hz, 2H), 2.72 (dd, J=18.6, 5.8 Hz, 1H), 2.65 (m, J=7.5 Hz, 2H).

Compound 278: 6-((1-(5-(3,5-difluorophenyl)-4,5-dihydro-1H-pyrazole-1-carbonyl)azetidin-3-ylidene)methyl)-2H-benzo[b][1,4]oxazin-3(4H)-one

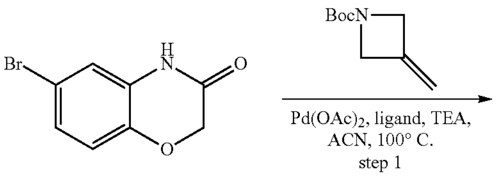

-continued

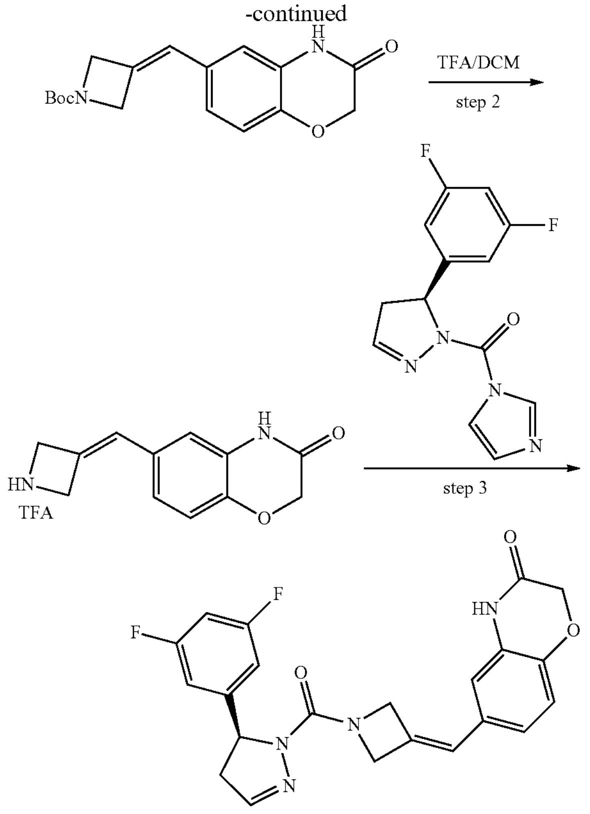

Step 1: 6-bromo-2H-benzo[b][1,4]oxazin-3(4H)-one (100 mg, 0.44 mmol) was dissolved in 5 ml of ACN, tert-butyl 3-methyleneazetidine-1-carboxylate (149 mg, 0.88 mmol) $Pd(OAc)_2$ (10 mg, 0.044 mmol), tris(2-methylphenyl)phosphine (27 mg, 0.08 mmol) and TEA (133 mg, 1.32 mmol) were added, The mixture was stirred at 100° C. for 3 h. The mixture was extracted with EA, washed with brine, dried with ($Na_2SO_4$), and concentrated in vacuo. Purification by silica gel chromatography (EA/PE=1:1) to give tert-butyl 3-((3-oxo-3,4-dihydro-2H-benzo[b][1,4]oxazin-6-yl)methylene)azetidine-1-carboxylate (100 mg). LC-MS (m/z) 316.14 $(M+H^+)$ Step 2: tert-butyl3-((3-oxo-3,4-dihydro-2H-benzo[b][1,4]oxazin-6-yl)methylene)azetidine-1-carboxylate (100 mg, 0.32 mmol) was dissolved in 6 ml of DCM, trifluoroacetic acid (1.5 ml) was added, The mixture was stirred at r.t. for 4 h. The mixture was concentrated to give 6-(azetidin-3-ylidenemethyl)-2H-benzo[b][1,4]oxazin-3(4H)-one trifluoroacetic acid, which was used for next step without further purification. LC-MS (m/z) 216.15 $(M+H^+)$ Step 3: 6-(azetidin-3-ylidenemethyl)-2H-benzo[b][1,4]oxazin-3(4H)-one and (1H-imidazol-1-yl)(5-phenyl-4,5-dihydro-1H-pyrazol-1-yl)methanone (73 mg) and TEA (0.4 mL) were dissolved in THF (10 ml) and stirred at 65° C. for 6 h. The mixture was extracted with EA, washed with brine, dried ($Na_2SO_4$), and concentrated in vacuo. Purification by silica gel chromatography to give the titled compound 278 (15 mg, 8% yield in three steps). LC-MS (m/z) 425.13 $(M+H^+)$. $^1H$ NMR (400 MHz, DMSO-$d_6$) δ 10.68 (s, 1H), 7.11 (tt, J=9.4, 2.4 Hz, 1H), 7.05 (brs, 1H), 6.97-6.90 (m, 3H), 6.76-6.74 (m, 2H), 6.25 (brs, 1H), 5.28 (dd, J=12.2, 6.6 Hz, 1H), 4.90 (bs, 2H), 4.73 (brs, 2H), 4.56 (s, 2H), 3.46-3.36 (m, 1H), 2.66-2.60 (m, 1H).

Compound 279: (S)-(4-(7H-pyrrolo[2,3-d]pyrimidin-2-yl)piperazin-1-yl)(5-(3,5-difluorophenyl)-4,5-dihydro-1H-pyrazol-1-yl)methanone

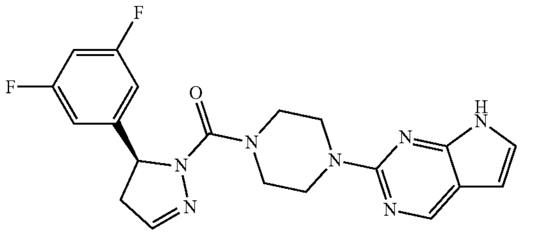 [SMILES: O=C(N1CCN(c2ncc3cc[nH]c3n2)CC1)N1N=CC[C@H]1c1cc(F)cc(F)c1]

The titled compound 279 was prepared in 3.9% yield from 2-chloro-7H-pyrrolo[2,3-d]pyrimidine and (S)-(5-(3,5-difluorophenyl)-4,5-dihydro-1H-pyrazol-1-yl)(piperazin-1-yl)methanone according to the procedure outlined for compound 271. $^1$H NMR (400 MHz, $CDCl_3$) δ (ppm): 8.93 (brs, 1H), 8.62 (s, 1H), 6.91 (dd, J=2.0, 3.6 Hz, 1H), 6.80-6.86 (m, 3H), 6.66-6.72 (m, 1H), 6.37 (dd, J=1.6, 4.0 Hz, 1H), 5.35 (dd, J=10.0, 11.6 Hz, 1H), 3.90-3.96 (m, 2H), 3.78-3.86 (m, 4H), 3.65-3.71 (m, 2H), 3.31 (ddd, J=2, 11.6, 13.6 Hz, 1H), 2.68 (ddd, J=1.6, 10.0, 11.6 Hz, 1H). Mass (ESI): m/z calcd for $C_{20}H_{19}F_2N_7O$ 411.4, found 412.3 $[M+H]^+$.

Compound 280: (S)-2-((1-(5-(3,5-difluorophenyl)-4,5-dihydro-1H-pyrazole-1-carbonyl)azetidin-3-yl)oxy)thiazole-5-carboxamide

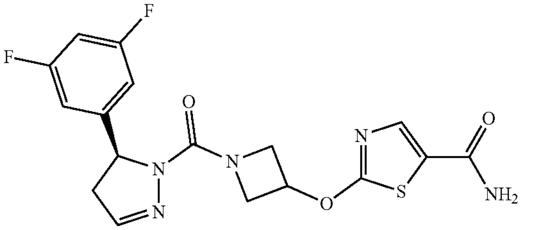 [SMILES: NC(=O)c1cnc(OC2CN(C(=O)N3N=CC[C@H]3c3cc(F)cc(F)c3)C2)s1]

The titled compound 280 was prepared from 2-(azetidin-3-yloxy)thiazole-5-carboxamide trifluoroacetic acid salt and (S)-(5-(3,5-difluorophenyl)-4,5-dihydro-1H-pyrazol-1-yl)(1H-imidazol-1-yl)methanone according the produce outlined for compound 203. LC-MS (m/z) 408.4 $(M+H^+)$ $^1$H NMR (400 MHz, Chloroform-d) δ 7.54 (s, 1H), 6.78 (t, J=1.7 Hz, 1H), 6.77-6.73 (m, 2H), 6.72-6.66 (m, 1H), 5.45-5.40 (m, 1H), 5.27 (dd, J=12.1, 6.4 Hz, 1H), 4.62-4.49 (m, 2H), 4.31-4.22 (m, 2H), 3.35 (ddd, J=18.6, 12.2, 1.7 Hz, 1H), 2.70 (ddd, J=18.6, 6.5, 1.8 Hz, 1H).

Compound 281: 2-((1-(5-(5-fluoropyridin-3-yl)-4,5-dihydro-1H-pyrazole-1-carbonyl)azetidin-3-yl)oxy)thiazole-4-carbonitrile

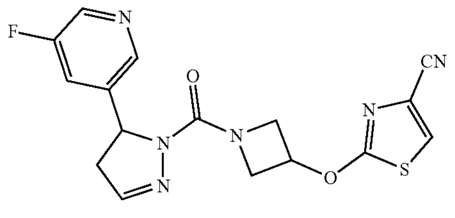 [SMILES: N#Cc1csc(OC2CN(C(=O)N3N=CCC3c3cncc(F)c3)C2)n1]

The titled compound 90 was prepared from 2-(azetidin-3-yloxy)thiazole-4-carbonitrile trifluoroacetic acid salt and (5-(5-fluoropyridin-3-yl)-4,5-dihydro-1H-pyrazol-1-yl)(1H-imidazol-1-yl)methanone according the produce outlined for compound 203. LC-MS (m/z) 373.4 (M+H+) LC-MS (m/z) 395.5 $(M+H^+)$ $^1$H NMR (400 MHz, Chloroform-d) δ 8.43 (d, J=8.0 Hz, 2H), 7.50-7.45 (m, 1H), 7.43 (brs, 1H), 6.86-6.84 (m, 1H), 5.45-5.40 (m, 1H), 5.40-5.35 (m, 1H), 4.57 (brs, 2H), 4.27-4.22 (m, 2H), 3.44 (ddd, J=18.7, 12.3, 1.7 Hz, 1H), 2.76 (ddd, J=18.7, 6.8, 1.7 Hz, 1H).

Compound 282: (S)-2-((1-(5-(3,5-difluorophenyl)-4,5-dihydro-H-pyrazole-1-carbonyl)azetidin-3-yl)oxy)thiazole-4-carboxamide

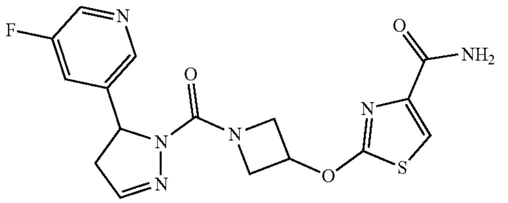 [SMILES: NC(=O)c1csc(OC2CN(C(=O)N3N=CCC3c3cncc(F)c3)C2)n1]

The titled compound 282 was prepared from compound 281 by hydrolysis reaction using 1N NaOH. 2 LC-LC-MS (m/z) 391.4 $(M+H^+)$. $^1$H NMR (400 MHz, Chloroform-d) δ 7.65 (s, 1H), 6.81 (t, J=1.7 Hz, 1H), 6.77-6.73 (m, 2H), 6.70 (tt, J=8.8, 2.3 Hz, 1H), 5.46-5.39 (m, 1H), 5.29 (dd, J=12.2, 6.3 Hz, 1H), 4.62-4.54 (m, 2H), 4.37-4.23 (m, 2H), 3.37 (ddd, J=18.7, 12.2, 1.7 Hz, 1H), 2.71 (ddd, J=18.6, 6.4, 1.7 Hz, 1H).

Compound 283: (S)-6-((1-(5-(3,5-difluorophenyl)-4,5-dihydro-1H-pyrazole-1-carbonyl)azetidin-3-ylidene)methyl)-3,3-difluoroindolin-2-one

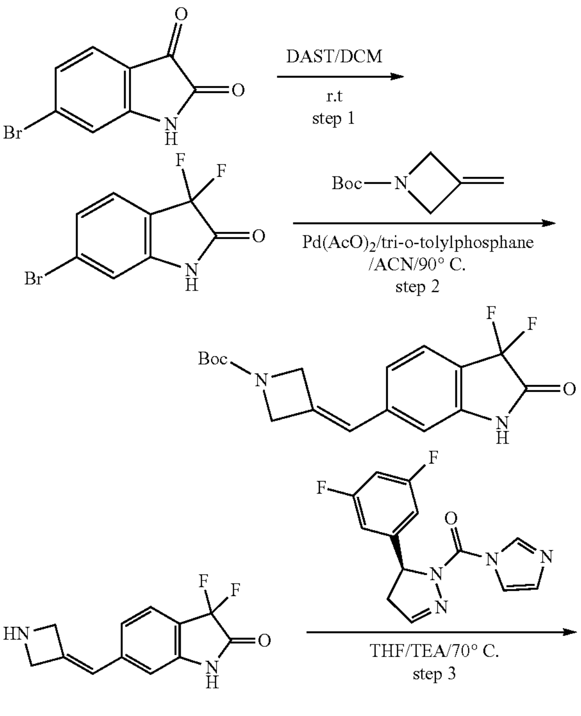

-continued

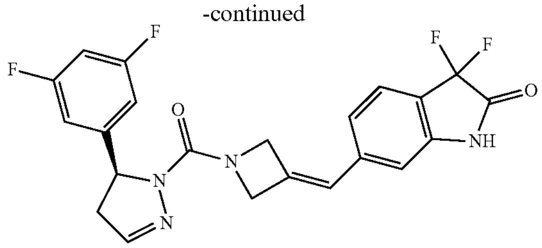

Step 1. 6-bromoindoline-2,3-dione (1 g, 4.44 mmoL) was dissolved in 2 mL DCM. DAST (1.78 g, 11.04 mmoL) was added slowly to the suspension at 0° C. Let it stir at r.t under nitrogen for 16 hrs. Water was added to quench the reaction and extracted with DCM (50 mL×3). The organic layers were combined and evaporated to dryness and purified by column chromatography (PE/EA=4/1) to give 0.5 g of 6-bromo-3,3-difluoroindolin-2-one as red solid. Yield: 45.6%. LC-MS (m/z) 249.1 $[M+H]^+$.

Step 2. 6-bromo-3,3-difluoroindolin-2-one (140 mg, 0.57 mmoL) and tert-butyl 3-methyleneazetidine-1-carboxylate (115 mg, 0.68 mmoL) and DIEA (0.19 mL) were dissolved in 5 mL $CH_3CN$. $Pd(AcO)_2$ (12.8 mg, 0.057 mmoL) and tri-o-tolylphosphane (35 mg, 0.115 mmoL) were added. Let it stir at 100° C. under nitrogen for 16 hrs. The solvent was evaporated to dryness and purified by column chromatography (PE/EA=7/1) to give 100 mg tert-butyl 3-((3,3-difluoro-2-oxoindolin-6-yl)methylene)azetidine-1-carboxylate as light-yellow solid. Yield: 43.8%. LC-MS (m/z) 337.2 $[M+H]^+$.

Step 3. tert-butyl 3-((3,3-difluoro-2-oxoindolin-6-yl) methylene)azetidine-1-carboxylate (35 mg, 0.104 mmoL) was dissolved in 2 mL DCM. 2 mL DCM/TFA (1/1) was added slowly to the solution at 0° C. Let it stir r.t for 1 h. The solvent was evaporated to dryness and used for next step without further purification. LC-MS (m/z) 237.1 $[M+H]^+$.

Step 4. The above residue was dissolved in 2 mL THF. 0.2 mL of TEA was added. (S)-(5-(3,5-difluorophenyl)-4,5-dihydro-1H-pyrazol-1-yl)(1H-imidazol-1-yl)methanone (28.7 mg, 0.104 mmoL) was added. Let it stir at 70° C. for 16 hrs. The solvent was evaporated to dryness and purified by Prep-TLC (PE/EA=1/1) to give 25 mg of the titled compound 283 as a white solid. Yield: 53%. $^1H$ NMR (400 MHz, $CDCl_3$) δ (ppm): δ 8.86 (brs, 1H), 7.46 (d, J=7.6 Hz, 1H), 6.83-6.88 (m, 2H), 6.73-6.79 (m, 2H), 6.61-6.67 (m, 2H), 6.25 (s, 1H), 5.43 (dd, J=6.0, 12.0 Hz, 1H), 4.94-5.09 (m, 4H), 3.41 (ddd, J=1.6, 12.4, 13.6 Hz, 1H), 2.70 (ddd, J=1.6, 6.4, 7.6 Hz, 1H). LC-MS (ESI): m/z calcd for $C_{22}H_{16}F_4N_4O_2$ 444.4, found 445.3 $[M+H]^+$.

Compound 284: (S)-(3-((1H-benzo[d]imidazol-5-yl) methylene)azetidin-1-yl)(5%3,5-difluorophenyl)-4, 5-dihydro-1H-pyrazol-1-yl)methanone

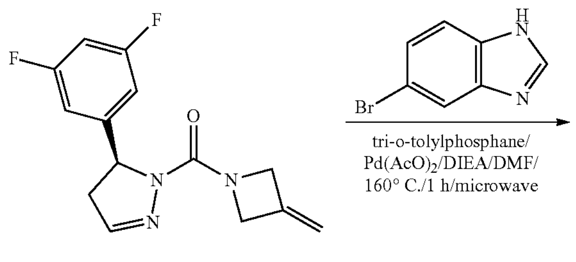

-continued

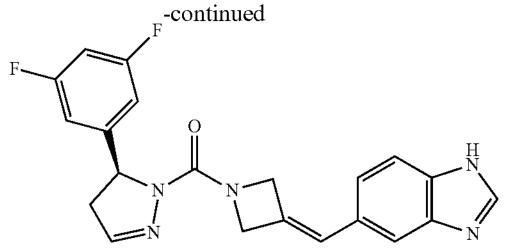

6-bromo-1H-benzo[d]imidazole (8.5 mg, 0.043 mmoL) and (S)-(5-(3,5-difluorophenyl)-4,5-dihydro-1H-pyrazol-1-yl)(3-methyleneazetidin-1-yl)methanone (10 mg, 0.036 mmoL). $Pd(AcO)_2$ (5 mg) and tri-o-tolylphosphane (1.8 mg, 0.006 mmoL) were added. 0.2 mL DIEA was added. Let it stir at 160° C. under microwave for 1 h. The solvent was evaporated to dryness and purified by column chromatography (DCM/MeOH=92/8) to give the titled compound 284 as orange solid (6 mg, 42.4%). $^1H$ NMR (400 MHz, $CDCl_3$) δ (ppm): δ 8.64 (s, 1H), 7.61 (d, J=7.6 Hz, 1H), 7.45 (s, 1H), 7.10 (d, J=7.6 Hz, 1H), 6.84 (s, 1H), 6.78 (d, J=5.6 Hz, 2H), 6.64-6.70 (m, 1H), 6.34 (s, 1H), 5.35 (dd, J=6.4, 8.4 Hz, 1H), 5.09 (s, 2H), 4.90 (s, 2H), 3.39 (dd, J=12.8, 18.0 Hz, 1H), 2.71 (dd, J=6.8, 18.0 Hz, 1H). LC-MS (ESI): m/z calcd for $C_{21}H_{17}F_2N_3O$ 393.4, found 394.3 $[M+H]^+$.

Compound 285: (S)-(3-((3-chloro-5-fluoro-1H-indazol-6-yl)methylene)azetidin-1-yl)(5-(3,5-difluorophenyl)-4,5-dihydro-1H-pyrazol-1-yl)methanone

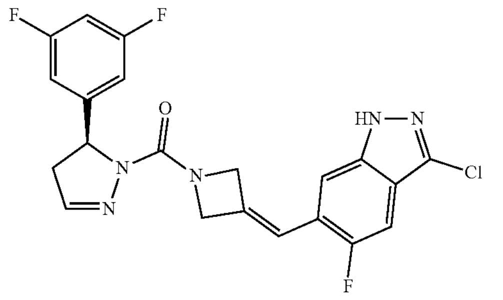 [SMILES: O=C(N1CC(=Cc2cc3[nH]nc(Cl)c3cc2F)C1)N1N=CC[C@H]1c1cc(F)cc(F)c1]

The titled compound 285 was synthesized in an analogous manner to the preparation of compound 284. $^1H$ NMR (400 MHz, Methanol-$d_4$) δ 7.71-7.68 (m, 1H), 7.61-7.58 (m, 1H), 7.33-7.26 (m, 1H), 6.96 (s, 1H), 6.85-6.79 (m, 2H), 6.59 (s, 1H), 5.30 (dd, J=12.0, 8.0 Hz, 1H), 5.07 (s, 2H), 4.89 (s, 2H), 3.48-3.40 (m, 1H), 2.74-2.68 (m, 1H).

Compound 286: (S)-6-((1-(5-(3,5-difluorophenyl)-4,5-dihydro-1H-pyrazole-1-carbonyl)azetidin-3-ylidene)methyl)-5-fluoro-1H-315-indazol-3-one

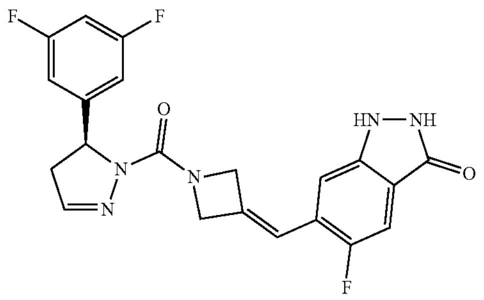 [SMILES: O=C(N1CC(=Cc2cc3[nH][nH]c(=O)c3cc2F)C1)N1N=CC[C@H]1c1cc(F)cc(F)c1]

The titled compound 286 was synthesized in an analogous manner to the preparation of compound 284 $^1$H NMR (400 MHz, Methanol-$d_4$) δ 7.37 (d, J=12.0 Hz, 1H), 7.06 (d, J=4.0 Hz, 1H), 6.96 (d, J=4.0 Hz, 1H), 6.85-6.79 (m, 3H), 6.58 (s, 1H), 5.30 (dd, J=12.0, 4.0 Hz, 1H), 5.06 (s, 2H), 4.89 (s, 2H), 3.48-3.40 (m, 1H), 2.74-2.67 (m, 1H).

Compound 287: (S)-(5-(3,5-difluorophenyl)-4,5-dihydro-H-pyrazol-1-yl)(4-(5-fluoro-4-(2-morpholinoethoxy)pyrimidin-2-yl)piperazin-1-yl)methanone

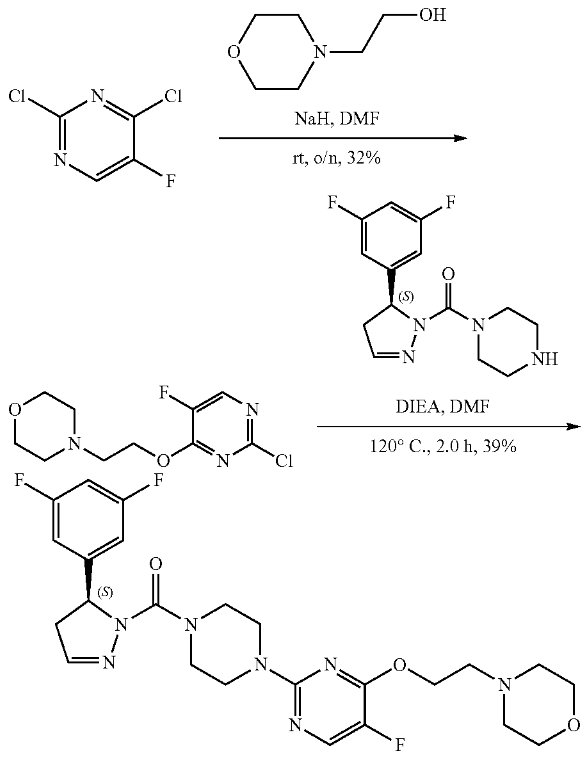

Step 1: 4-(2-((2-chloro-5-fluoropyrimidin-4-yl)oxy)ethyl) morpholine. 2-morpholinoethan-1-ol (863 mg, 7.13 mmol) was dissolved in 20 ml of dry DMF. NaH (263 mg, 6.57 mmol) was added to the above solution under nitrogen at 0 degrees C. The mixture was stirred for 0.5 hour at 0 degrees C. To this was added 2,4-dichloro-5-fluoropyrimidine (1.0 g, 5.98 mmol), the mixture was stirred for another 1 overnight at room temperature. The mixture was extracted with EA, washed with brine, dried ($Na_2SO_4$), and concentrated in vacuo. Purification by silica gel chromatography to give the titled compound (500 mg, 32%) as a yellow oil. (ES, m/s): 262.1 $[M+H]^+$ Step 2: (S)-(5-(3,5-difluorophenyl)-4,5-dihydro-1H-pyrazol-1-yl)(4-(5-fluoro-4-(2-morpholinoethoxy)pyrimidin-2-yl)piperazin-1-yl)methanone. (S)-(5-(3,5-difluorophenyl)-4,5-dihydro-1H-pyrazol-1-yl)(piperazin-1-yl)methanone (295 mg, 1.00 mmol) was dissolved in 5 ml of dry DMF. 4-(2-((2-chloro-5-fluoropyrimidin-4-yl)oxy)ethyl)morpholine (261 mg, 1.00 mmol) and DIEA (260 mg, 2.00 mmol) were added to the above solution under nitrogen at room temperature. The mixture was stirred for 2.0 hours at 120 degrees C. The mixture was extracted with EA, washed with brine, dried ($Na_2SO_4$), and concentrated in vacuo. Purification by silica gel chromatography to give the titled compound 287 (200 mg, 39%) as a white solid. (ES, m/s): 520.2 $[M+H]^+$ $^1$H NMR (400 MHz, DMSO-$d_6$) δ 8.17 (d, J=3.2 Hz, 1H), 7.13-7.05 (m, 2H), 7.01-6.94 (m, 2H), 5.28-5.18 (m, 1H), 4.47 (t, J=5.8 Hz, 2H), 3.73-3.65 (m, 2H), 3.64-3.56 (m, 4H), 3.55-3.46 (m, 6H), 3.39-3.32 (m, 1H), 2.68 (t, J=5.8 Hz, 2H), 2.65-2.56 (m, 1H), 2.45-2.41 (m, 4H).

Compound 288: (S)-(5-(3,5-difluorophenyl)-4,5-dihydro-1H-pyrazol-1-yl)(3-(pyrazolo[1,5-a]pyridin-5-ylmethylene)azetidin-1-yl)methanone

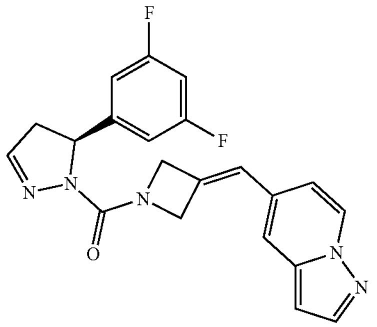 [SMILES: O=C(N1CC(=Cc2ccn3nccc3c2)C1)N1N=CC[C@H]1c1cc(F)cc(F)c1]

The titled compound 288 was prepared in 50% yield from 5-bromopyrazolo[1,5-a]pyridine and (S)-(5-(3,5-difluorophenyl)-4,5-dihydro-1H-pyrazol-1-yl)(3-methyleneazetidin-1-yl)methanone according to the procedure outlined for compound 284. 1H NMR (400 MHz, CDCl3) δ (ppm): δ 8.39 (d, J=7.2 Hz, 1H), 7.92 (d, J=2.4 Hz, 1H), 7.25 (s, 1H), 6.83 (t, J=1.6 Hz, 1H), 6.75-6.80 (m, 2H), 6.66-6.72 (m, 1H), 6.53 (dd, J=1.6, 7.2 Hz, 1H), 6.49 (d, J=2.0 Hz, 1H), 6.25 (t, J=2.0 Hz, 1H), 5.31 (dd, J=6.4, 12.0 Hz, 1H), 5.12 (q, J=14.0 Hz, 2H), 4.86 (q, J=14.0 Hz, 2H), 3.37 (ddd, J=1.6, 12.0, 13.6 Hz, 1H), 2.71 (ddd, J=1.6, 6.8, 8.0 Hz, 1H). LC-MS (ESI): m/z calcd for C21H17F2N5O 393.4, found 394.3 $[M+H]^+$.

Compound 289: (S)-(5-(3,5-difluorophenyl)-4,5-dihydro-1H-pyrazol-1-yl)(3-((3-methyl-1H-indazol-6-yl)methylene)azetidin-1-yl)methanone

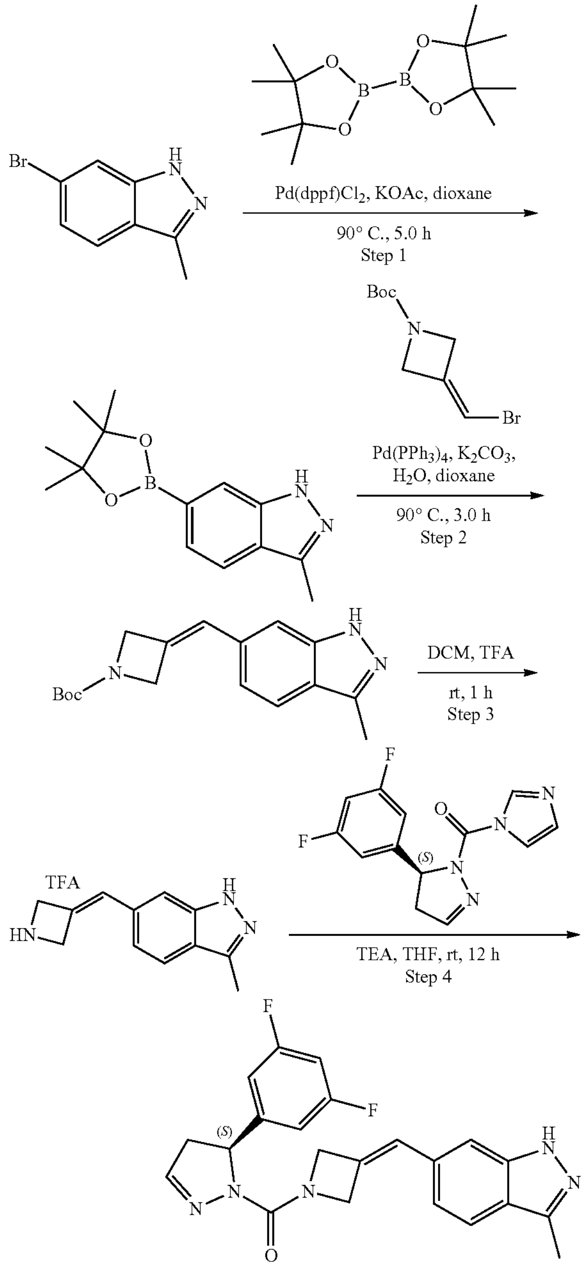

Step 1: 6-bromo-3-methyl-1H-indazole (100 mg, 0.47 mmol) was dissolved in 10 ml of dry dioxane. 4,4,4',4',5,5,5',5'-octamethyl-2,2'-bi(1,3,2-dioxaborolane) (241 mg, 0.95 mmol), Pd(dppf)$Cl_2$ (52 mg, 0.07 mmol), AcOK (140 mg, 1.01 mmol) were added to the above solution under nitrogen at room temperature. The mixture was stirred for 5.0 hour at 90° C. The mixture was filtered and concentrated in vacuo to give 3-methyl-6-(4,4,5,5-tetramethyl-1,3,2-dioxaborolan-2-yl)-1H-indazole (400 mg, crude) as brown oil which was used for next step without further purification. LC-MS (m/z): 259.2 $[M+H]^+$.

Step 2: 3-methyl-6-(4,4,5,5-tetramethyl-1,3,2-dioxaborolan-2-yl)-1H-indazole (400 mg, crude) was dissolved in 15 ml dioxane and 4 ml $H_2O$. $Pd(PPh_3)_4$ (82 mg, 0.07 mmol), $K_2CO_3$ (197 mg, 1.43 mmol) were added to the above solution under nitrogen at room temperature. The mixture was stirred for 3.0 hour at 90° C. The resulting solution was added $H_2O$ and extracted with EA. The organic layers were washed with brine, dried over $Na_2SO_4$ and concentrated under vacuum. The crude product was purified by silica gel chromatography to afford 20 mg of tert-butyl 3-((3-methyl-1H-indazol-6-yl)methylene)azetidine-1-carboxylate as a yellow solid. (Two-step yield: 14%) LC-MS (m/z): 300.2 $[M+H]^+$.

Step 3: tert-butyl 3-((3-methyl-1H-indazol-6-yl)methylene)azetidine-1-carboxylate (20 mg, 0.07 mmol) was dissolved in 10 ml dry DCM. TFA (1 mL) was added to the above solution at room temperature. The mixture was stirred for 1 hour at room temperature. The mixture was concentrated in vacuo to give 6-(azetidin-3-ylidenemethyl)-3-methyl-1H-indazole as TFA salt (30 mg, crude) as brown oil which was used for next step without further purification. LC-MS (m/z): 200.2 $[M+H]^+$.

Step 4: 6-(azetidin-3-ylidenemethyl)-3-methyl-1H-indazole (20 mg, crude) was dissolved in 10 ml dry THF. TEA (0.5 mL), 3-methyl-6-(4,4,5,5-tetramethyl-1,3,2-dioxaborolan-2-yl)-1H-indazole (22 mg, 0.08 mmol) was added to the above solution at room temperature. The mixture was stirred for 12 h at room temperature. The resulting solution was concentrated in vacuo. Purification by Prep-HPLC to give 1 mg of the titled compound 289 (yield: 4%) as a white solid. LC-MS (m/z): 408.2 $[M+H]^+$. $^1$H NMR (400 MHz, Chloroform-d) δ 8.13 (s, 1H), 7.18 (d, J=7.7 Hz, 1H), 6.85-6.72 (m, 4H), 6.61 (s, 1H), 6.26-6.18 (m, 1H), 5.34 (dd, J=12.2, 6.5 Hz, 1H), 5.13-4.95 (m, 2H), 4.94-4.76 (m, 2H), 3.52 (s, 3H), 3.44-3.30 (m, 1H), 2.78-2.64 (m, 1H).

Compound 290: (S)-2-cyclopentyl-N-(2-(4-(5-(3,5-difluorophenyl)-4,5-dihydro-1H-pyrazole-1-carbonylpiperazin-1-ye-5-fluoropyrimidin-4-yl)acetamide

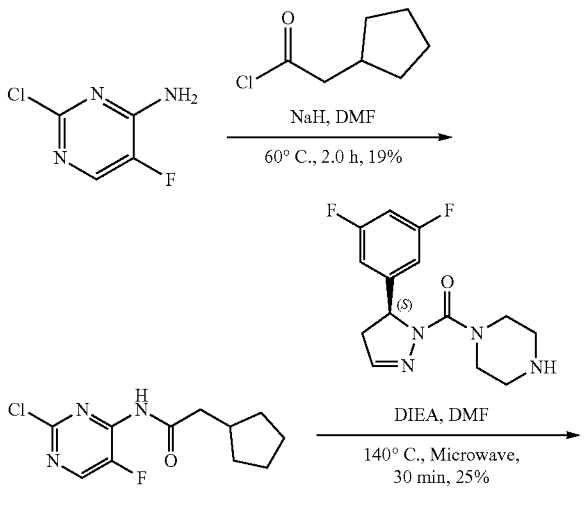

-continued

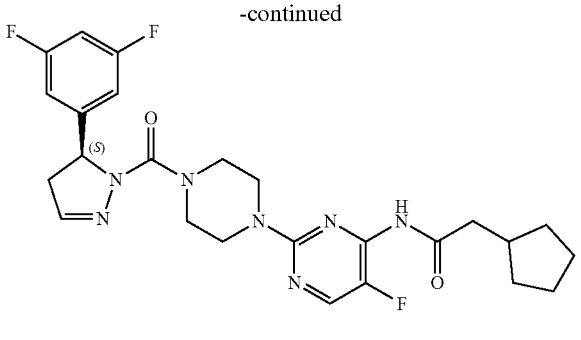

The titled compound 290 as a gray solid (21.8 mg, 25%) was prepare from (S)-2-cyclopentyl-N-(2-(4-(5-(3,5-difluorophenyl)-4,5-dihydro-1H-pyrazole-1-carbonyl)piperazin-1-yl)-5-fluoropyrimidin-4-yl)acetamide and N-(2-chloro-5-fluoropyrimidin-4-yl)-2-cyclopentylacetamide according to the procedure outlined for compound 225 (ES, m/s): 416.2 $[M+H]^+$ $^1H$ NMR (400 MHz, DMSO-$d_6$) δ 10.27 (brs, 1H), 8.30 (d, J=3.0 Hz, 1H), 7.12-7.04 (m, 2H), 7.00-6.93 (m, 2H), 5.23 (m, 1H), 3.72-3.64 (m, 2H), 3.62-3.58 (m, 4H), 3.54-3.44 (m, 2H), 3.38-3.34 (m, 1H), 2.66-2.57 (m, 1H), 2.41 (d, J=7.6 Hz, 2H), 2.21-2.12 (m, 1H), 1.76-1.67 (m, 2H), 1.60-1.52 (m, 1H), 1.51-1.43 (m, 1H), 1.23-1.19 (m, 2H), 1.17-1.10 (m, 2H).

Compound 291: (S)—N-(2-(4-(5-(3,5-difluorophenyl)-4,5-dihydro-1H-pyrazole-1-carbonyl)piperazin-1-yl)-5-fluoropyrimidin-4-yl)-3-methylbutanamide

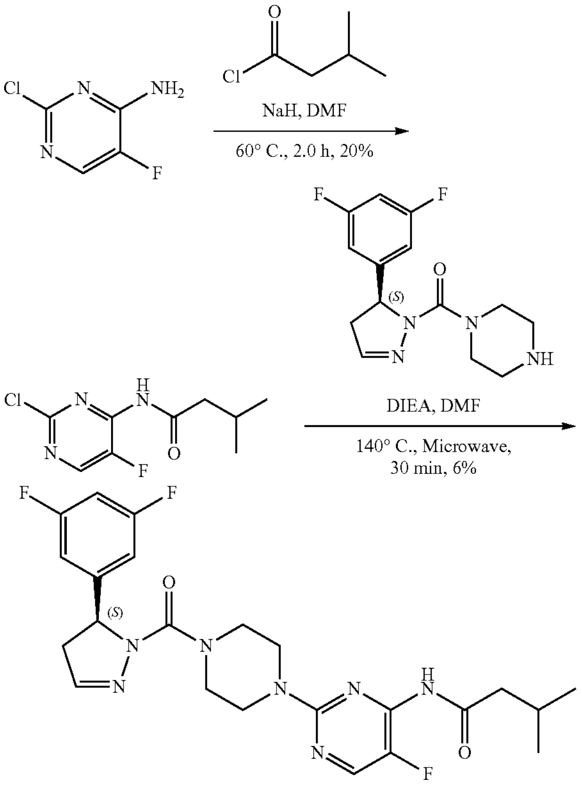

The titled compound 291 as a gray solid (5.4 mg, 6%) was prepare from (S)-(5-(3,5-difluorophenyl)-4,5-dihydro-1H-pyrazol-1-yl)(piperazin-1-yl)methanone and N-(2-chloro-5-fluoropyrimidin-4-yl)-3-methylbutanamide according to the procedure outlined for compound 225 (ES, m/s): 490.2 $[M+H]^+$ $^1H$ NMR (400 MHz, DMSO-$d_6$) δ 10.46 (brs, 1H), 8.48 (d, J=3.0 Hz, 1H), 7.28-7.20 (m, 2H), 7.18-7.10 (m, 2H), 5.43-5.39 (m, 1H), 3.90-3.59 (m, 8H), 3.38-3.34 (m, 1H), 2.84-2.72 (m, 1H), 2.47-2.41 (m, 2H), 2.16-2.07 (m, 1H), 1.40-1.34 (m, 3H), 1.10-1.03 (m, 3H)

Compound 292: (S)—N-(2-(4-(5-(3,5-difluorophenyl)-4,5-dihydro-1H-pyrazole-1-carbonyl)piperazin-1-yl)-5-fluoropyrimidin-4-yl)isobutyramide

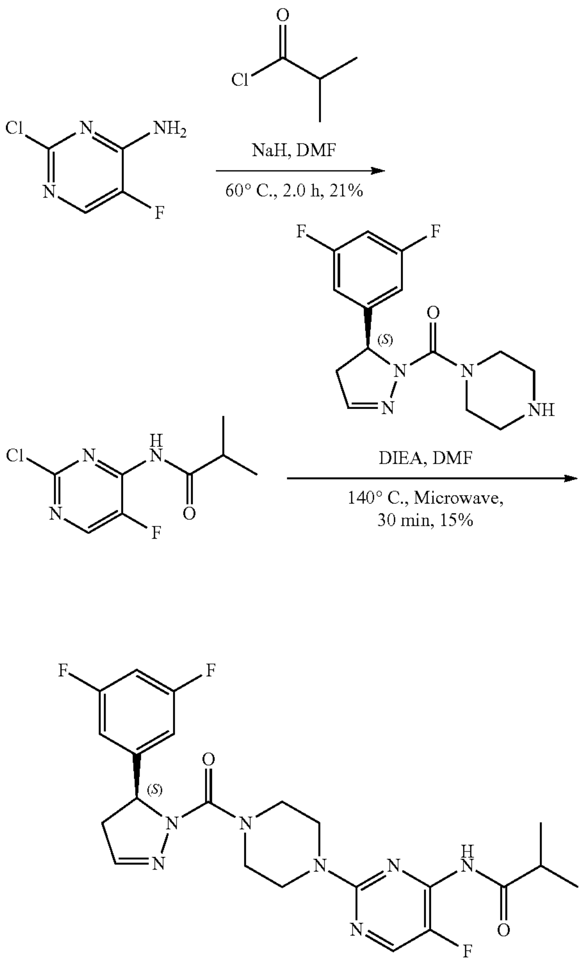

The titled compound 205 as a white solid (13.0 mg, 15%) was prepare from (S)-(5-(3,5-difluorophenyl)-4,5-dihydro-1H-pyrazol-1-yl)(piperazin-1-yl)methanone and N-(2-chloro-5-fluoropyrimidin-4-yl)isobutyramide according to the procedure outlined for compound 199 (ES, m/s): 476.2 $[M+H]^+$ $^1H$ NMR (400 MHz, DMSO-$d_6$) δ 10.26 (brs, 1H), 8.31 (d, J=3.0 Hz, 1H), 7.13-7.05 (m, 2H), 7.00-6.93 (m, 2H), 5.28-5.18 (m, 1H), 3.73-3.65 (m, 2H), 3.64-3.56 (m, 4H), 3.53-3.45 (m, 2H), 3.38-3.34 (m, 1H), 2.77-2.70 (m, 1H), 2.66-2.57 (m, 1H), 1.06 (d, J=6.8 Hz, 6H).

Compound 293: (S)—N-(2-(4-(5-(3,5-difluorophenyl)-4,5-dihydro-1H-pyrazole-1-carbonyl)piperazin-1-yl)-5-fluoropyrimidin-4-yl)tetrahydro-2H-pyran-4-carboxamide

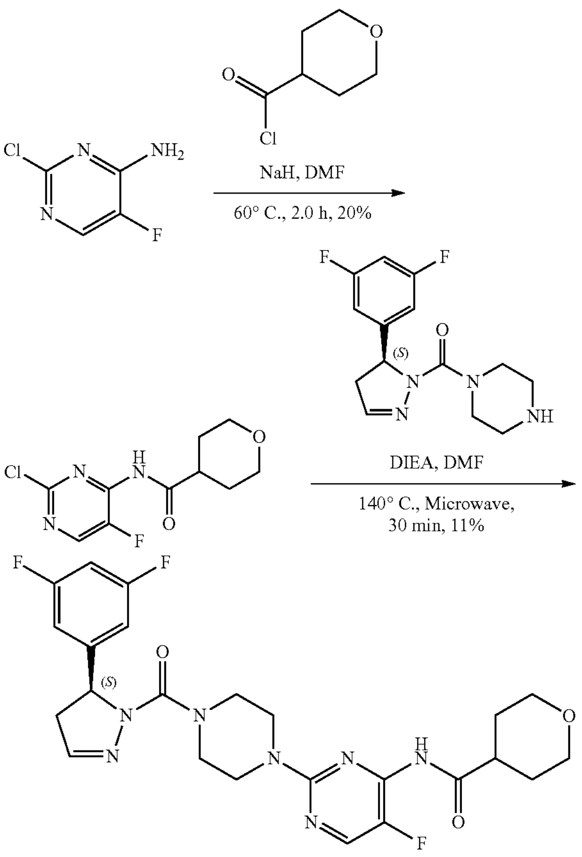

The titled compound 293 as a white solid (10.0 mg, 11%) was prepare from (S)-(5-(3,5-difluorophenyl)-4,5-dihydro-1H-pyrazol-1-yl)(piperazin-1-yl)methanone and N-(2-chloro-5-fluoropyrimidin-4-yl)tetrahydro-2H-pyran-4-carboxamide according to the procedure outlined for compound 225 (ES, m/s): 518.2 $[M+H]^+$ $^1H$ NMR (400 MHz, DMSO-$d_6$) δ 10.31 (brs, 1H), 8.32 (d, J=3.0 Hz, 1H), 7.12-7.05 (m, 2H), 7.00-6.94 (m, 2H), 5.26-5.19 (m, 1H), 3.90-3.82 (m, 2H), 3.73-3.65 (m, 2H), 3.64-3.56 (m, 2H), 3.53-3.44 (m, 2H), 3.39-3.34 (m, 1H), 2.81-2.73 (m, 1H), 2.66-2.57 (m, 1H), 1.74-1.65 (m, 4H), 1.64-1.52 (m, 4H), Compound 294: (S)-(3-((6-chloro-2-fluoropyridin-3-yl)methylene)azetidin-1-yl)(5-(5-fluoropyridin-3-yl)-4,5-dihydro-1H-pyrazol-1-yl)methanone

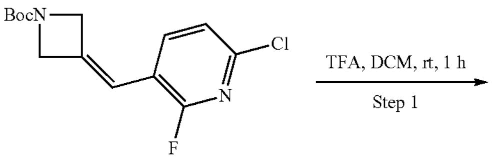

-continued

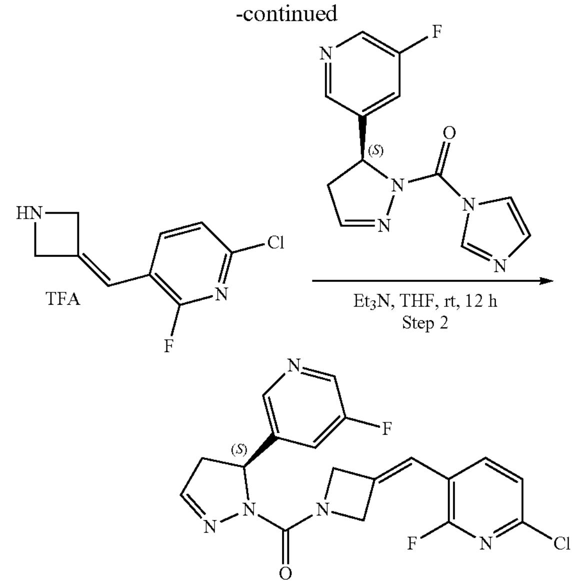

Step 1: tert-butyl 3-((6-chloro-2-fluoropyridin-3-yl)methylene)azetidine-1-carboxylate (135 mg, 0.45 mmol) was dissolved in 10 ml dry DCM. TFA (2 mL) was added to the above solution at room temperature. The mixture was stirred for 1 hour at room temperature. The mixture was concentrated in vacuo to give 3-(azetidin-3-ylidenemethyl)-6-chloro-2-fluoropyridine (200 mg, crude) as TFA salt, which was used for next step without further purification.

Step 2: 3-(azetidin-3-ylidenemethyl)-6-chloro-2-fluoropyridine (200 mg, crude) was dissolved in 10 ml dry THF. TEA (1 mL), SM2 (98 mg, 0.38 mmol) was added to the above solution at room temperature. The mixture was stirred for 12 h at room temperature. The resulting solution was concentrated in vacuo. Purification by silica gel chromatography to afford 85 mg of 294: (S)-(3-((6-chloro-2-fluoropyridin-3-yl)methylene)azetidin-1-yl)(5-(5-fluoropyridin-3-yl)-4,5-dihydro-1H-pyrazol-1-yl)methanone (yield: 58%) as a white solid. LC-MS (m/z): 390.2 $[M+H]^+$. $^1H$ NMR (400 MHz, Chloroform-d) δ 8.44-8.35 (m, 2H), 7.49-7.39 (m, 1H), 7.34-7.28 (m, 1H), 7.24-7.18 (m, 1H), 6.89-6.85 (m, 1H), 6.37-6.31 (m, 1H), 5.39 (dd, J=12.3, 6.7 Hz, 1H), 5.10-4.76 (m, 4H), 3.44 (ddd, J=18.6, 12.2, 1.8 Hz, 1H), 2.78 (ddd, J=18.5, 6.7, 1.8 Hz, 1H).

Compound 295: (S)-5-((1-(5-(3,5-difluorophenyl)-4,5-dihydro-1H-pyrazole-1-carbonyl)azetidin-3-ylidene)methyl)picolinamide

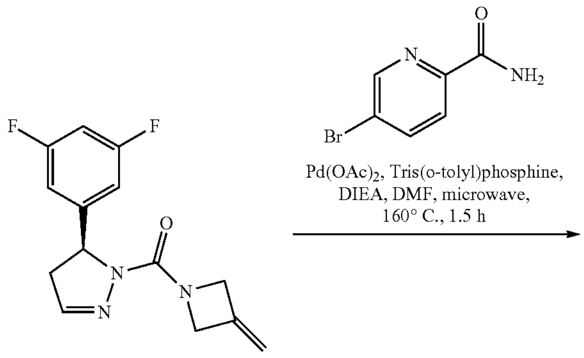

-continued

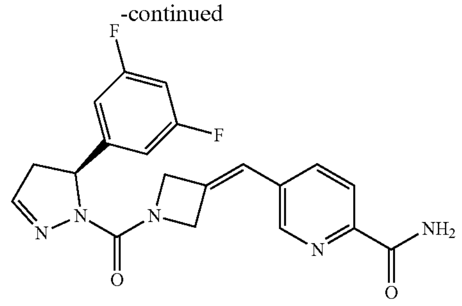

(S)-(5-(3,5-difluorophenyl)-4,5-dihydro-1H-pyrazol-1-yl)(3-methyleneazetidin-1-yl)methanone (45 mg, 0.16 mmol) was dissolved in 2.5 ml DMF. 5-bromopicolinamide (30 mg, 0.15 mmol), $Pd(OAc)_2$ (7 mg, 0.03 mmol), DIEA (38 mg, 0.29 mmol), Tris(o-tolyl)phosphine (18 mg, 0.06 mmol) were added to the above solution under nitrogen at room temperature. The mixture was stirred for 1.5 hour at 160° C. under Microwave. The resulting solution was added $H_2O$ and extracted with EA. The organic layers were washed with brine, dried over $Na_2SO_4$ and concentrated under vacuum. The crude product was purified by prep-HPLC to afford the titled compound (3.6 mg, 6%) as an yellow solid. LC-MS (m/z): 398.2 $[M+H]^+$. $^1H$ NMR (400 MHz, Chloroform-d) δ 8.40 (s, 1H), 8.17 (d, J=8.1 Hz, 1H), 8.02 (s, 1H), 7.63-7.54 (m, 1H), 6.92-6.86 (m, 1H), 6.82-6.66 (m, 2H), 6.37 (s, 1H), 5.33 (dd, J=12.0, 6.2 Hz, 1H), 5.23-5.06 (m, 2H), 5.02-4.84 (m, 2H), 3.40 (ddd, J=18.5, 12.2, 1.8 Hz, 1H), 2.75 (ddd, J=18.6, 6.2, 1.8 Hz, 1H).

Compound 296: (3-((3,5-difluoro-1H-indazol-6-yl)methylene)azetidin-1-yl)(5-phenyl-4,5-dihydro-1H-pyrazol-1-yl)methanone

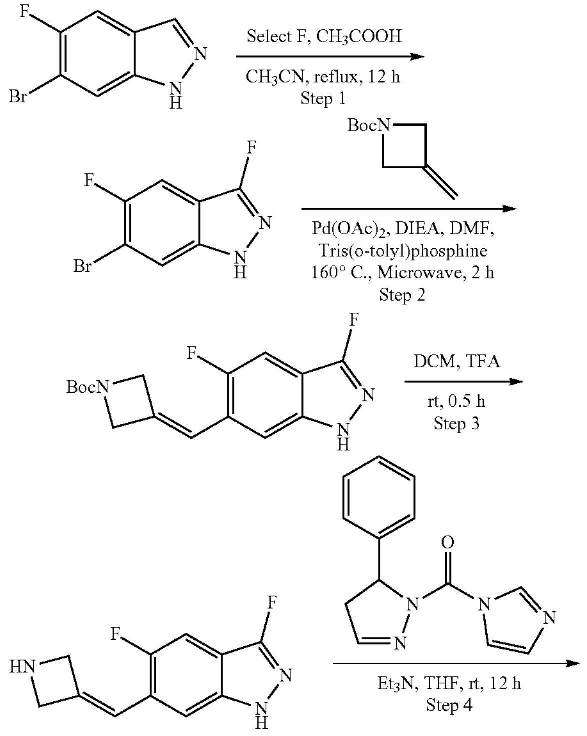

-continued

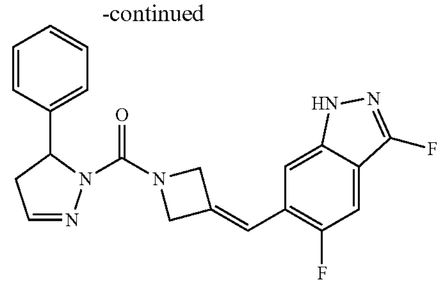

Step 1: 6-bromo-5-fluoro-1H-indazole (6.5 g, 30 mmol) was dissolved in 130 ml dry $CH_3CN$. Select F (16 g, 45 mmol), CH3COOH (6.5 ml) was added to the above solution at room temperature under nitrogen protection. The mixture was heated to reflux for 12 h. The resulting solution was concentrated in vacuo, added $H_2O$ and extracted with EA. The organic layers were washed with brine, dried over Na2SO4 and concentrated under vacuum. The crude product was purified by silica gel chromatography to afford 2.67 g of 6-bromo-3,5-difluoro-1H-indazole (yield: 38%) as a yellow solid. LC-MS (m/z): 234.2 $[M+H]^+$.

Step 2: 6-bromo-3,5-difluoro-1H-indazole (300 mg, 1.29 mmol) was dissolved in 20 ml DMF. tert-butyl 3-methyleneazetidine-1-carboxylate (436 mg, 2.58 mmol), $Pd(OAc)_2$ (58 mg, 0.26 mmol), DIEA (332 mg, 2.57 mmol), Tris(o-tolyl)phosphine (158 mg, 0.51 mmol) were added to the above solution under nitrogen at room temperature. The mixture was stirred for 2 hour at 160° C. under Microwave. The resulting solution was added $H_2O$ and extracted with EA. The organic layers were washed with brine, dried over Na2SO4 and concentrated under vacuum. The crude product was purified by silica gel chromatography to afford 200 mg of tert-butyl 3-((3,5-difluoro-1H-indazol-6-yl)methylene)azetidine-1-carboxylate (yield: 48%) as a light yellow solid. LC-MS (m/z): 322.3$[M+H]^+$ Step 3 and 4: The title compound 105 was prepared in a yield of 19.5% as white solid from tert-butyl 3-((3,5-difluoro-1H-indazol-6-yl)methylene)azetidine-1-carboxylate and (1H-imidazol-1-yl)(5-phenyl-4,5-dihydro-1H-pyrazol-1-yl)methanone according to the procedure outlined for 203. LC-MS (m/z): 394.2 $[M+H]^+$. $^1H$ NMR (400 MHz, Methanol-$d_4$) δ 7.36-7.28 (m, 3H), 7.25-7.16 (m, 4H), 6.95 (t, J=1.7 Hz, 1H), 6.60-6.56 (m, 1H), 5.30 (dd, J=12.0, 5.8 Hz, 1H), 5.08-5.02 (m, 2H), 4.93-4.81 (m, 2H), 3.43 (ddd, J=18.6, 12.1, 1.7 Hz, 1H), 2.70 (ddd, J=18.7, 5.8, 1.8 Hz, 1H).

Compound 297: (S)-3-(1-(3-((3,5-difluoro-1H-indazol-6-yl)methylene)azetidine-1-carbonyl)-4,5-dihydro-1H-pyrazol-5-yl)-5-fluorobenzonitrile

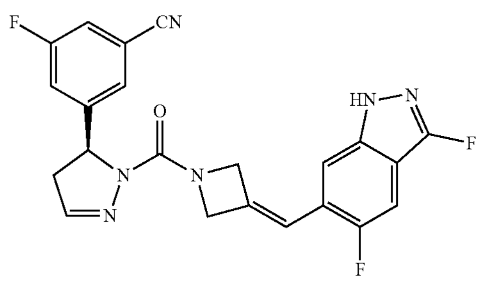 [SMILES: N#Cc1cc(F)cc([C@@H]2CC=NN2C(=O)N2CC(=Cc3cc4[nH]nc(F)c4cc3F)C2)c1]

The titled compound 297 was prepared in 55% yield as white solid from tert-butyl 3-((3,5-difluoro-1H-indazol-6-yl)methylene)azetidine-1-carboxylate and (S)-3-(1-(1H-imidazole-1-carbonyl)-4,5-dihydro-1H-pyrazol-5-yl)-5-fluorobenzonitrile according to the procedure for 296. LC-MS (m/z): 437.2 $[M+H]^+$. $^1H$ NMR (400 MHz, Methanol-$d_4$) δ 7.51-7.43 (m, 2H), 7.39-7.32 (m, 2H), 7.23-7.18 (m, 1H), 7.01-6.97 (m, 1H), 6.62-6.57 (m, 1H), 5.39-5.31 (m, 1H), 5.14-5.04 (m, 2H), 4.95-4.81 (m, 2H), 3.53-3.43 (m, 1H), 2.80-2.70 (m, 1H).

Compound 298: (S)-(3-((3-amino-H-pyrrol-1-yl)methyl)azetidin-1-yl)(5-(3,5-difluorophenyl)-4,5-dihydro-1H-pyrazol-1-yl)methanone

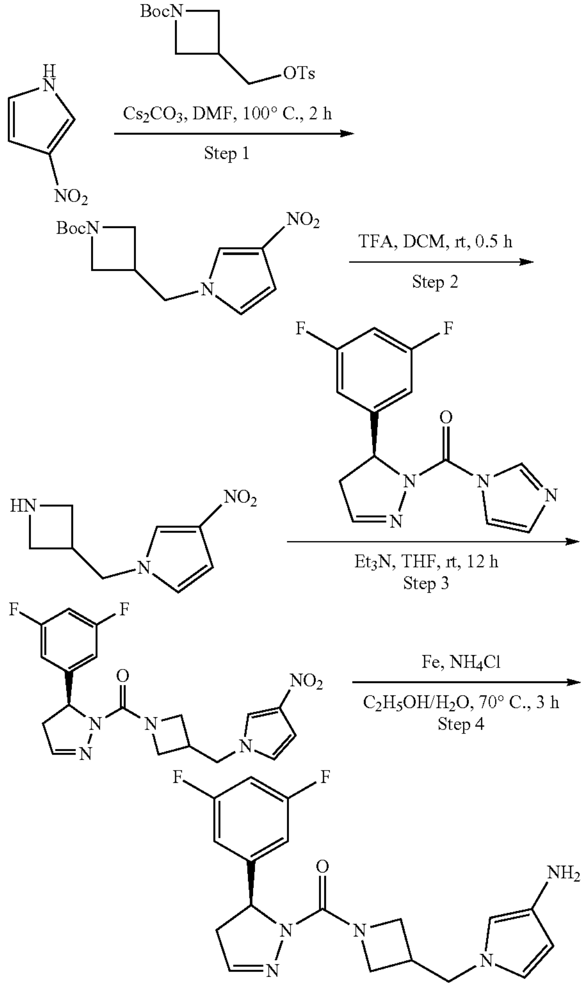

Step 1: 3-nitro-1H-pyrrole (270 mg, 0.79 mmol) was dissolved in 13 ml dry DMF. tert-butyl 3-((tosyloxy)methyl)azetidine-1-carboxylate (108 g, 0.96 mmol), $Cs_2CO_3$ (515 mg, 1.58 mmol) was added to the above solution at room temperature under nitrogen protection. The mixture was heated to 100° C. for 2 h. The resulting solution was added $H_2O$ and extracted with EA. The organic layers were washed with brine, dried over $Na_2SO_4$ and concentrated under vacuum. The crude product was purified by silica gel chromatography to afford 203 mg of tert-butyl 3-((3-nitro-1H-pyrrol-1-yl)methyl)azetidine-1-carboxylate (yield: 91%) as a white solid. LC-MS (m/z): 282.2 $[M+H]^+$.

Step 2 and Step 3: (S)-(5-(3,5-difluorophenyl)-4,5-dihydro-1H-pyrazol-1-yl)(3-((3-nitro-1H-pyrrol-1-yl)methyl)azetidin-1-yl)methanone (218 mg) was prepared in 78% yield as white solid from tert-butyl 3-((3-nitro-1H-pyrrol-1-yl)methyl)azetidine-1-carboxylate and (S)-(5-(3,5-difluorophenyl)-4,5-dihydro-1H-pyrazol-1-yl)(1H-imidazol-1-yl)methanone according to the procedure outlined for 203.

Step 4: (S)-(5-(3,5-difluorophenyl)-4,5-dihydro-1H-pyrazol-1-yl)(3-((3-nitro-1H-pyrrol-1-yl)methyl)azetidin-1-yl)methanone (30 mg, 0.08 mmol) in $EtOH/H_2O$ (12 ml v:v=5:1) was added Fe (52 mg, 0.93 mmol), $NH_4Cl$ (42 mg, 0.79 mmol) under nitrogen protection at rt. The mixture was stirred at 70° C. for 3 h, the resulting solution was filtrated and evaporated to give 100 mg crude product. The crude product was purified by pre-HPLC to afford the titled compound 298 (6.2 mg, 22%) as an yellow solid. LC-MS (m/z): 360.2 $[M+H]^+$. $^1H$ NMR (400 MHz, Chloroform-d) δ 6.84-6.58 (m, 5H), 6.56-6.42 (m, 1H), 6.09-5.94 (m, 1H), 5.31-5.13 (m, 1H), 4.34-4.10 (m, 2H), 4.06-3.92 (m, 2H), 3.91-3.70 (m, 2H), 3.40-3.24 (m, 1H), 2.88 (s, 1H), 2.75-2.56 (m, 1H).

Compound 299: (S)-(3-(5-amino-2,3-difluorobenzylidene)azetidin-1-yl)(5-(3,5-difluorophenyl)-4,5-dihydro-1H-pyrazol-1-yl)methanone

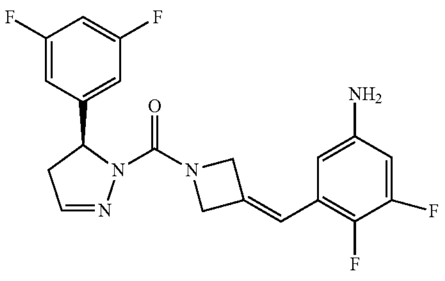 [SMILES: Nc1cc(F)c(F)c(C=C2CN(C(=O)N3N=CC[C@H]3c3cc(F)cc(F)c3)C2)c1]

The title compound 299 was prepared in a yield of 4.5% as gray solid from (S)-(5-(3,5-difluorophenyl)-4,5-dihydro-1H-pyrazol-1-yl)(3-methyleneazetidin-1-yl)methanone and 3-bromo-4,5-difluoroaniline according to the procedure outlined for 294. LC-MS (m/z): 405.2 $[M+H]^+$. $^1H$ NMR (400 MHz, Chloroform-d) δ 6.81 (t, J=1.7 Hz, 1H), 6.80-6.73 (m, 2H), 6.69 (tt, J=8.9, 2.3 Hz, 1H), 6.41-6.33 (m, 2H), 6.12-6.08 (m, 1H), 5.31 (dd, J=12.1, 6.5 Hz, 1H), 5.06-4.93 (m, 2H), 4.89-4.77 (m, 2H), 3.37 (ddd, J=18.5, 12.2, 1.7 Hz, 1H), 2.71 (ddd, J=18.5, 6.5, 1.7 Hz, 1H).

Compound 300: (S)-(5-(3,5-difluorophenyl)-4,5-dihydro-1H-pyrazol-1-yl)(3-(3-fluoro-5-isocyano-benzylidene)azetidin-1-yl)methanone

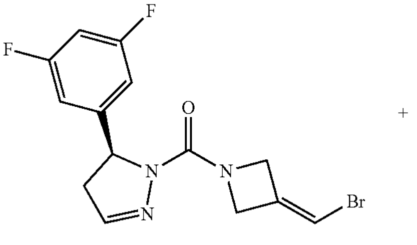

-continued

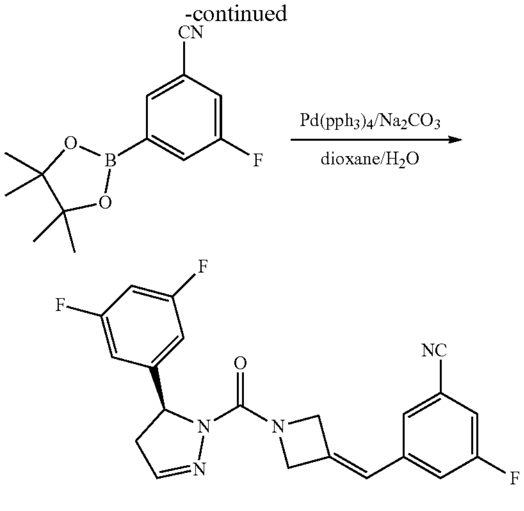

The titled compound 300 was prepared in an analogous manner to the preparation of compound 244 yield: 54.5% $^{1}H$ NMR (400 MHz, Chloroform-d) δ 7.39 (dd, J=9.0, 1.6 Hz, 2H), 7.18 (t, J=7.6 Hz, 1H), 6.91-6.58 (m, 4H), 6.49 (s, 1H), 5.31 (dd, J=12.0, 6.4 Hz, 1H), 5.13-4.65 (m, 4H), 3.45-3.32 (m, 1H), 2.738-2.68 (m, 1H). LC-MS (m/z) 397.2 ($M+H^+$).

Compound 301: (S)-(3-((3,5-difluoro-1H-indazol-6-yl)methylene)azetidin-1-yl)(5-(3,5-difluorophenyl)-4,5-dihydro-1H-pyrazol-1-yl)methanone

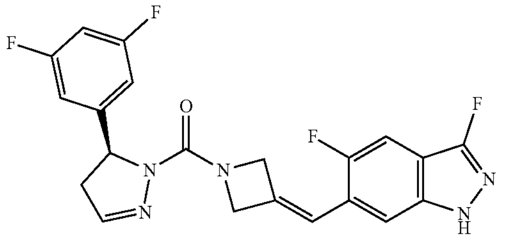 [SMILES: O=C(N1CC(=Cc2cc3[nH]nc(F)c3cc2F)C1)N1N=CC[C@H]1c1cc(F)cc(F)c1]

The titled compound 301 was prepared in an analogous manner to the preparation of compound 2%. yield: 38.7%. $^{1}H$ NMR (400 MHz, Chloroform-d) δ 9.37 (s, 1H), 7.34-7.29 (m, 1H), 7.04 (d, J=5.6 Hz, 1H), 6.83 (d, J=1.7 Hz, 1H), 6.81-6.73 (m, 2H), 6.72-6.63 (m, 1H), 6.57 (s, 1H), 5.41-5.30 (m, 1H), 5.13-4.85 (m 4H), 3.44-3.34 (m, 1H), 2.79-2.66 (m, 1H). LC-MS (m/z) 430.2 ($M+H^+$).

Compound 302: (3-((3,5-difluoro-1H-indazol-6-yl)methylene)azetidin-1-yl)(5-phenyl-4,5-dihydro-1H-pyrazol-1-yl)methanone

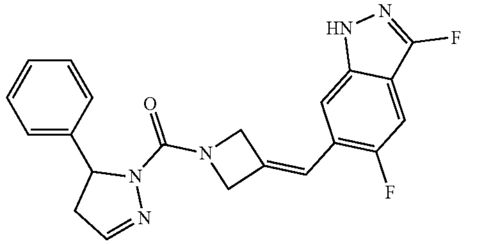 [SMILES: O=C(N1CC(=Cc2cc3[nH]nc(F)c3cc2F)C1)N1N=CCC1c1ccccc1]

The titled compound 302 was prepared in an analogous manner to the preparation of 296 LC-MS (m/z): 394.2 $[M+H]^+$. $^{1}H$ NMR (400 MHz, Methanol-$d_4$) δ 7.36-7.28 (m, 3H), 7.25-7.16 (m, 4H), 6.95 (t, J=1.7 Hz, 1H), 6.60-6.56 (m, 1H), 5.30 (dd, J=12.0, 5.8 Hz, 1H), 5.08-5.02 (m, 2H), 4.93-4.81 (m, 2H), 3.43 (ddd, J=18.6, 12.1, 1.7 Hz, 1H), 2.70 (ddd, J=18.7, 5.8, 1.8 Hz, 1H).

Compound 303: (S)-(5-(3,5-difluorophenyl)-4,5-dihydro-1H-pyrazol-1-yl)(4-(5-fluoro-4-(methylamino)pyrimidin-2-yl)piperazin-1-yl)methanone

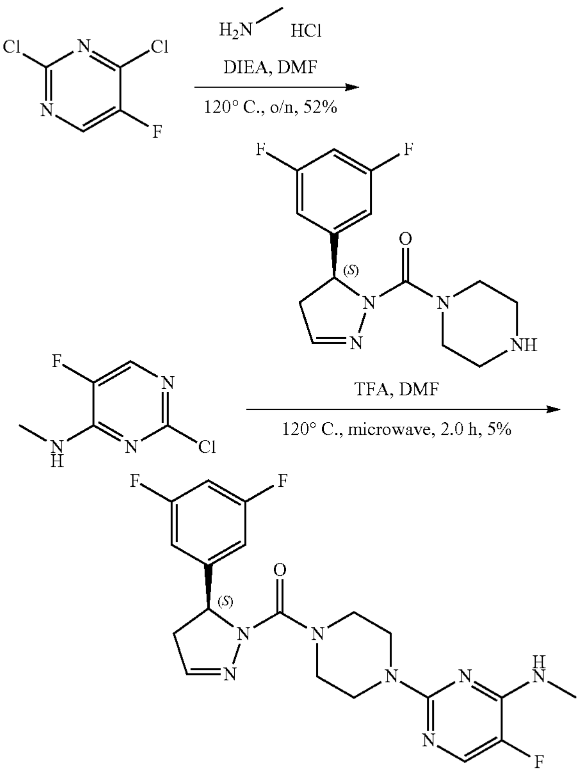

Step 1: 2-chloro-5-fluoro-N-methylpyrimidin-4-amine. 2,4-dichloro-5-fluoropyrimidine (1.0 g, 5.98 mmol) was dissolved in 20 ml of dry DMF. DIEA (1.8 g, 13.95 mmol) and Methylamine hydrochloride (474 mg, 7.18 mmol) were added to the above solution under nitrogen at room temperature. The mixture was stirred for 1 overnight at 120 degrees C. The mixture was extracted with EA, washed with brine, dried ($Na_2SO_4$), and concentrated in vacuo. Purification by silica gel chromatography to give the titled compound (500 mg, 52%) as a white solid. (ES, m/s): 162.1 $[M+H]^+$ Step 2: (S)-(5-(3,5-difluorophenyl)-4,5-dihydro-1H-pyrazol-1-yl)(4-(5-fluoro-4-(methylamino)pyrimidin-2-yl)piperazin-1-yl)methanone. (S)-(5-(3,5-difluorophenyl)-4,5-dihydro-1H-pyrazol-1-yl)(piperazin-1-yl)methanone (295 mg, 1.00 mmol) was dissolved in 5 ml of dry DMF. 2-chloro-5-fluoro-N-methylpyrimidin-4-amine (161 mg, 1.00 mmol) and TFA (1 mL) were added to the above solution under nitrogen at room temperature. The mixture was stirred for 1.0 hours at 120 degrees C. under microwave. The mixture was extracted with EA, washed with brine, dried ($Na_2SO_4$), and concentrated in vacuo. Purification by silica gel chromatography to give the titled compound 303 (21.8 mg, 5%) as a white solid. (ES, m/s): 420.4[M+H]$^+$ $^1$H NMR (400 MHz, DMSO-$d_6$) δ 7.74 (d, J=4.0 Hz, 1H), 7.25 (d, J=5.2 Hz, 1H), 7.13-7.05 (m, 2H), 6.99-6.96 (m, 2H), 5.27-5.18 (m, 1H), 3.70-3.62 (m, 2H), 3.61-3.52 (m, 4H), 3.51-3.41 (m, 2H), 3.37-3.32 (m, 1H), 2.81 (d, J=4.6 Hz, 3H), 2.66-2.58 (m, 1H).

Compound 304: (5-(3,5-difluorophenyl)-4,5-dihydro-1H-pyrazol-1-yl)(3-(2,4,6-trifluorobenzylidene) azetidin-1-yl)methanone

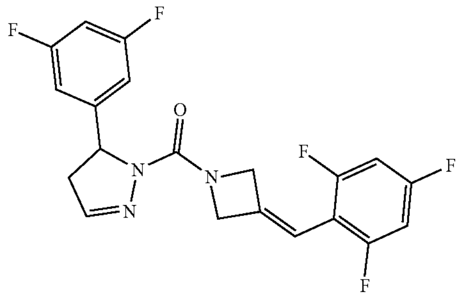 [SMILES: O=C(N1CC(=Cc2c(F)cc(F)cc2F)C1)N1N=CCC1c1cc(F)cc(F)c1]

The titled compound 304 was prepared in an analogous manner to the preparation of 296 yield: 14.8%. $^1$H NMR (400 MHz, Chloroform-d) δ 6.86-6.73 (m, 3H), 6.72-6.54 (m, 3H), 6.24-6.19 (m, 1H), 5.30 (dd, J=12.0, 6.4 Hz, 1H), 4.95-4.68 (m, 4H), 344-3.30 (m, 1H), 2.77-2.63 (m, 1H). LC-MS (m/z) 408.3 (M+H$^+$).

Compound 305: (5-(3,5-difluorophenyl)-4,5-dihydro-1H-pyrazol-1-yl)(3-((6-fluoropyridin-3-yl) methylene)azetidin-1-yl)methanone

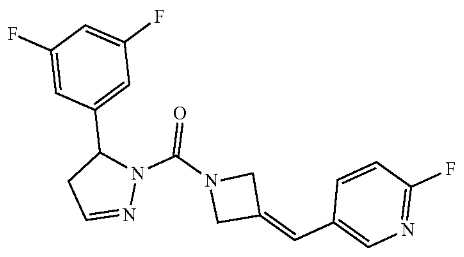 [SMILES: O=C(N1CC(=Cc2ccc(F)nc2)C1)N1N=CCC1c1cc(F)cc(F)c1]

The titled compound 305 was prepared in an analogous manner to the preparation of 296 yield: 97.0%. 1H NMR (400 MHz, DMSO-d6) δ 8.11 (d, J=2.4 Hz, 1H), 7.81-7.7 (m, 1H), 7.19 (dd, J=8.4, 2.8 Hz, 1H), 7.14-7.07 (m, 1H), 7.08-7.02 (m, 1H), 6.99-6.88 (m, 2H), 6.42 (t, J=2.4 Hz, 1H), 5.27 (dd, J=12.0, 6.4 Hz, 1H), 5.09-4.90 (m, 2H), 4.83-7.66 (m, 2H), 3.47-3.35 (m, 1H), 2.70-2.60 (m, 1H). LC-MS (m/z) 373.3 (M+H+).

Compound 306: (5-(3,5-difluorophenyl)-4,5-dihydro-1H-pyrazol-1-yl)(3-(4-fluorobenzylidene) azetidin-1-yl)methanone

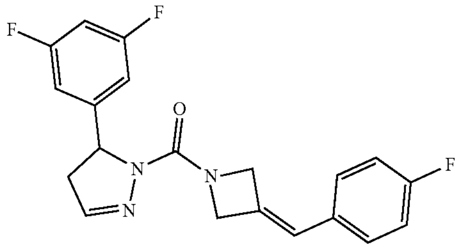 [SMILES: O=C(N1CC(=Cc2ccc(F)cc2)C1)N1N=CCC1c1cc(F)cc(F)c1]

The titled compound 306 was prepared in an analogous manner to the preparation of 296. yield: 22.8%. $^1$H NMR (400 MHz, Chloroform-d) δ 7.15-6.91 (m, 4H), 6.85-6.72 (m, 3H), 6.72-6.63 (m, 1H), 6.24 (s, 1H), 5.32 (dd, J=12.4, 6.4 Hz, 1H), 5.13-4.98 (m, 2H), 4.90-4.75 (m, 2H), 3.37 (dd, J=18.4, 11.6 Hz, 1H), 2.72 (dd, J=18.4, 5.8 Hz, 1H). LC-MS (m/z) 372.3 (M+H$^+$).

Compound 307: (5(5-fluoropyridin-3-yl)-4,5-dihydro-H-pyrazol-1-yl)(3-((6-fluoropyridin-3-yl) methylene)azetidin-1-yl)methanone

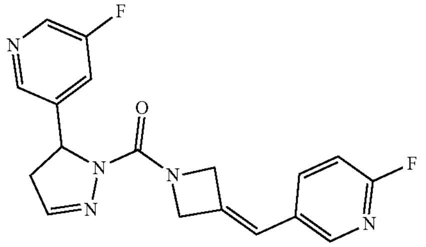 [SMILES: O=C(N1CC(=Cc2ccc(F)nc2)C1)N1N=CCC1c1cncc(F)c1]

The titled compound 307 was prepared in an analogous manner to the preparation of 296 yield: 25.5%. $^1$H NMR (400 MHz, Chloroform-d) δ 8.60-8.33 (m, 2H), 8.03 (d, J=2.4 Hz, 1H), 7.63-7.46 (m, 2H), 6.97-6.85 (m, 2H), 6.28 (t, J=2.3 Hz, 1H), 5.45 (dd, J=12.0, 6.0 Hz, 1H), 5.15-4.99 (m, 2H), 4.93-4.77 (m, 2H), 3.56-3.41 (m, 1H), 2.87-2.73 (m, 1H). LC-MS (m/z) 3563 (M+H$^+$).

Compound 308: (3-(2,4-difluorobenzylidene)azetidin-1-yl)(5-(5-fluoropyridin-3-yl)-4,5-dihydro-1H-pyrazol-1-yl)methanone

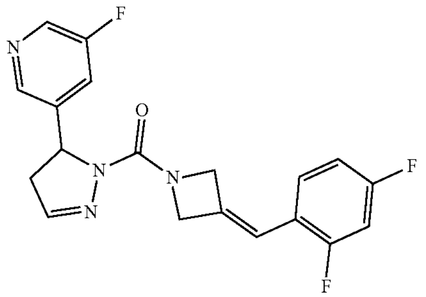 [SMILES: O=C(N1CC(=Cc2ccc(F)cc2F)C1)N1N=CCC1c1cncc(F)c1]

The titled compound 308 was prepared in an analogous manner to the preparation of 296 yield: 30.8%. $^1$H NMR (400 MHz, Chloroform-d) δ 8.59-8.31 (m, 2H), 7.53 (d, J=8.4 Hz, 1H), 7.05 (q, J=8.4 Hz, 1H), 6.92-6.68 (m, 3H), 6.40 (s, 1H), 5.50-5.39 (m, 1H), 5.12-4.72 (m, 4H), 3.47 (dd, J=18.4, 12.0 Hz, 1H), 2.80 (dd, J=18.0, 6.4 Hz, 1H). LC-MS (m/z) 373.3 (M+H$^+$).

Compound 309: (3-(4-fluorobenzylidene)azetidin-1-yl)(5-(5-fluoropyridin-3-yl)-4,5-dihydro-1H-pyrazol-1-yl)methanone

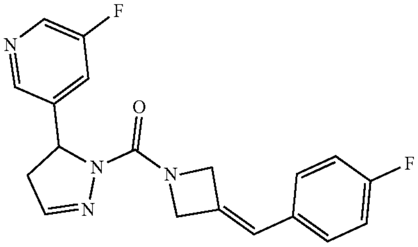 [SMILES: O=C(N1CC(=Cc2ccc(F)cc2)C1)N1N=CCC1c1cncc(F)c1]

The titled compound 309 was prepared in an analogous manner to the preparation of 2%. yield: 23.1%. $^1$H NMR (400 MHz, Chloroform-d) δ 8.59-8.30 (m, 2H), 7.38 (d, J=8.4 Hz, 1H), 7.09 (dd, J=8.8, 5.6 Hz, 2H), 7.06-6.96 (m, 2H), 6.87 (s, 1H), 6.24 (t, J=2.4 Hz, 1H), 5.41 (dd, J=12.0, 6.4 Hz, 1H), 5.09-4.94 (m, 2H), 4.90-4.74 (m, 2H), 3.51-3.35 (m, 1H), 2.82-2.73 (m, 1H). LC-MS (m/z) 355.2 (M+H$^+$).

Compound 310: (S)-(3-((1H-indazol-6-yl)methylene)azetidin-1-yl)(5-(3,5-difluorophenyl)-4,5-dihydro-1H-pyrazol-1-yl)methanone

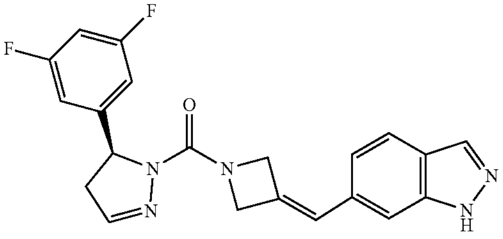 [SMILES: O=C(N1CC(=Cc2ccc3cn[nH]c3c2)C1)N1N=CC[C@H]1c1cc(F)cc(F)c1]

The titled compound 310 was prepared in an analogous manner to the preparation of 296. yield: 32.1%. $^1$H NMR (400 MHz, Chloroform-d) δ 7.87 (s, 1H), 7.58 (dd, J=8.4, 3.1 Hz, 1H), 7.30-7.27 (m, 1H), 7.17-7.09 (m, 1H), 6.92-6.71 (m, 2H), 6.70-6.54 (m, 2H), 6.35-6.21 (m, 1H), 5.18 (dd, J=12.0, 6.0 Hz, 1H), 5.08-4.90 (m, 2H), 4.87-4.70 (m, 2H), 3.37-3.14 (m, 2H), 2.70-2.52 (m, 1H). LC-MS [M+H]$^+$: 394.2

Compound 311: (S)-5-((1(5-(3,5-difluorophenyl)-4,5-dihydro-1H-pyrazole-1-carbonyl)azetidin-3-ylidene)methyl)benzo[d]oxazol-2(3H)-one

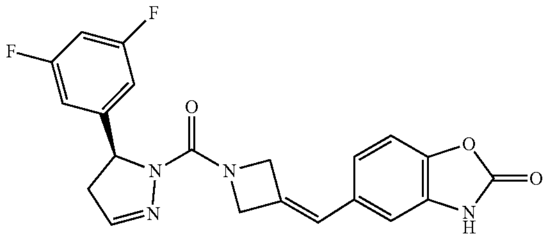 [SMILES: O=C(N1CC(=Cc2ccc3oc(=O)[nH]c3c2)C1)N1N=CC[C@H]1c1cc(F)cc(F)c1]

The titled compound 311 was prepared in an analogous manner to the preparation of 296. yield: 54.2%. $^1$H NMR (400 MHz, Chloroform-d) δ 7.05 (d, J=8.3 Hz, 1H), 6.81-6.75 (m, 2H), 6.74-6.66 (m, 3H), 6.66-6.56 (m, 1H), 6.19 (t, J=2.4 Hz, 1H), 5.26-5.18 (m, 1H), 5.02-4.70 (m, 4H), 3.38-3.26 (m, 1H), 2.70-2.60 (m, 1H). LC-MS (m/z) 411.2 (M+H$^+$).

Compound 312: (S)-(3-(2-chloro-4-fluorobenzylidene)azetidin-1-yl)(5-(3,5-difluorophenyl)-4,5-dihydro-1H-pyrazol-1-yl)methanone

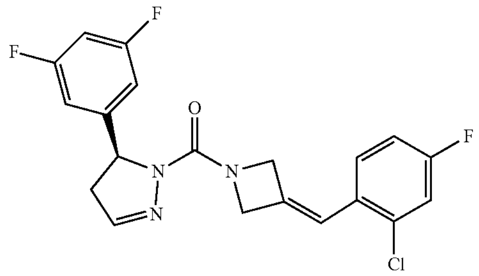 [SMILES: O=C(N1CC(=Cc2ccc(F)cc2Cl)C1)N1N=CC[C@H]1c1cc(F)cc(F)c1]

The titled compound 312 was prepared in an analogous manner to the preparation of 2%. yield: 31.3%. $^1$H NMR (400 MHz, Chloroform-d) δ 7.14 (dd, J=8.4, 2.4 Hz, 1H), 7.10 (dd, J=8.8, 6.0 Hz, 1H), 7.00-6.92 (m, 1H), 6.81 (t, J=1.7 Hz, 1H), 6.77 (dt, J=6.5, 2.1 Hz, 2H), 6.72-6.65 (m, 1H), 6.62-6.56 (m, 1H), 5.31 (q, J=6.4 Hz, 1H), 5.09-4.67 (m, 4H), 3.44-3.30 (m, 1H), 2.76-2.65 (m, 1H). LC-MS (m/z) 406.2 (M+H$^+$).

Compound 313: (S)-(3-(2,4-dichlorobenzylidene) azetidin-1-yl)(5-(3,5-difluorophenyl)-4,5-dihydro-1H-pyrazol-1-yl)methanone

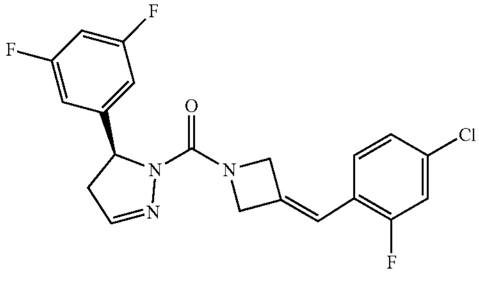 [SMILES: O=C(N1CC(=Cc2ccc(Cl)cc2F)C1)N1N=CC[C@H]1c1cc(F)cc(F)c1]

The titled compound 313 was prepared in an analogous manner to the preparation of 2% yield: 25.1%. $^1$H NMR (400 MHz, Chloroform-d) δ 7.13-7.06 (m, 2H), 7.05-6.97 (m, 1H), 6.82 (t, J=1.7 Hz, 1H), 6.80-6.73 (m, 2H), 6.73-6.63 (m, 1H), 6.40 (t, J=2.4 Hz, 1H), 5.31 (q, J=6.0 Hz, 1H), 5.10-4.76 (m, 4H), 3.42-3.32 (m, 1H), 2.75-2.67 (m, 1H). LC-MS (m/z) 406.2 (M+H$^+$).

Compound 314: (S)-(3-(2,4-dichlorobenzylidene)azetidin-1-yl)(5-(3,5-difluorophenyl)-4,5-dihydro-1H-pyrazol-1-yl)methanone

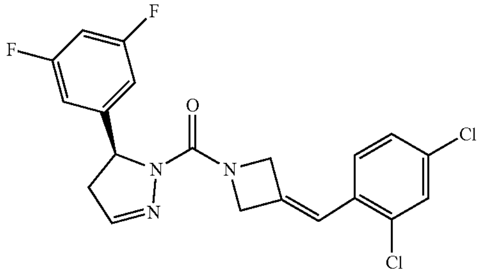 [SMILES: O=C(N1CC(=Cc2ccc(Cl)cc2Cl)C1)N1N=CC[C@H]1c1cc(F)cc(F)c1]

The titled compound 314 was prepared in an analogous manner to the preparation of 2% yield: 65.6%. $^1$H NMR (400 MHz, Chloroform-d) δ 7.40 (d, J=2.2 Hz, 1H), 7.24-7.19 (m, 1H), 7.05 (d, J=8.4 Hz, 1H), 6.82 (t, J=1.6 Hz, 1H), 6.79-6.73 (m, 2H), 6.72-6.65 (m, 1H), 6.61 (t, J=2.4 Hz, 1H), 5.34-5.26 (q, J=6.0 Hz, 1H, 1H), 5.10-4.78 (m, 4H), 3.42-3.32 (m, 1H), 2.76-2.67 (m, 1H). LC-MS [M+H]$^+$: 422.1

Compound 315: (S)-(3-((1H-pyrazolo[4,3-b]pyridin-6-yl)methylene)azetidin-1-yl)(5-(3,5-difluorophenyl)-4,5-dihydro-1H-pyrazol-1-yl)methanone

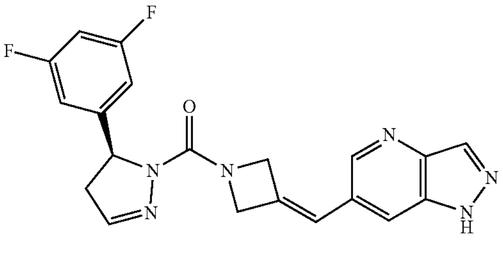 [SMILES: O=C(N1CC(=Cc2cnc3cn[nH]c3c2)C1)N1N=CC[C@H]1c1cc(F)cc(F)c1]

The titled compound 315 was prepared in an analogous manner to the preparation of 2%. yield: 27.9%. $^1$H NMR (400 MHz, Chloroform-d) δ 8.34 (s, 2H), 7.53 (s 1H), 6.84 (t, J=1.6 Hz, 1H), 6.80-6.71 (m, 2H), 6.71-6.63 (m, 1H), 6.46-6.40 (m, 1H), 5.30 (q J=6.0 Hz, 1H), 5.21-4.73 (m, 4H), 3.46-3.32 (m, 1H), 2.76-2.67 (m, 1H). LC-MS (m/z) 395.2 (M+H$^+$).

Compound 316: (S)-(3-((2,6-dichloropyridin-3-yl)methylene)azetidin-1-yl)(5-(3,5-difluorophenyl)-4,5-dihydro-1H-pyrazol-1-yl)methanone

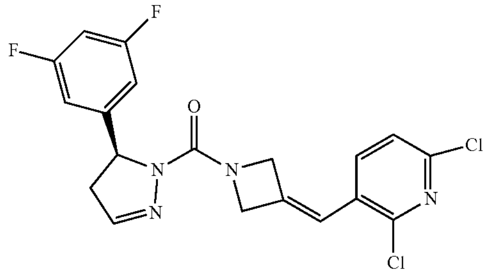 [SMILES: O=C(N1CC(=Cc2ccc(Cl)nc2Cl)C1)N1N=CC[C@H]1c1cc(F)cc(F)c1]

The titled compound 316 was prepared in an analogous manner to the preparation of 2% yield: 30.4%. $^1$H NMR (400 MHz, Chloroform-d) δ 7.39 (d, J=8.0 Hz, 1H), 7.27-7.25 (m, 1H), 6.83 (t, J=1.6 Hz, 1H), 6.80-6.72 (m, 2H), 6.72-6.67 (m, 1H), 6.57 (p, J=2.4 Hz, 1H), 5.30 (dd, J=12.0, 6.4 Hz, 1H), 5.05-4.82 (m, 4H), 3.43-3.34 (m, 1H), 2.77-2.68 (m, 1H). LC-MS (m/z) 423.2 (M+H$^+$).

Compound 317: (S)-(5-(3,5-difluorophenyl)-4,5-dihydro-1H-pyrazol-1-yl)(3-(3-(methylamino)benzylidene)azetidin-1-yl)methanone

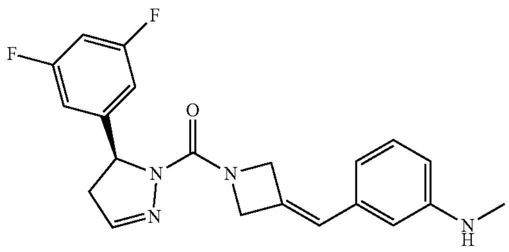 [SMILES: CNc1cccc(C=C2CN(C(=O)N3N=CC[C@H]3c3cc(F)cc(F)c3)C2)c1]

The titled compound 317 was prepared in an analogous manner to the preparation of 296. yield: 12.7%. $^1$H NMR (400 MHz, Chloroform-d) δ 8.05 (s, 1H), 7.35 (t, J=7.8 Hz, 1H), 7.13 (d, J=8.0 Hz, 1H), 7.06-6.99 (m, 2H), 6.87-6.72 (m, 3H), 6.68 (t, J=8.8 Hz, 1H), 6.23 (s, 1H), 5.36-5.31 (m, 1H), 5.05-4.79 (m, 4H), 3.43-3.31 (m, 1H), 2.99 (s, 3H), 2.76-2.67 (m, 1H). LC-MS (m/z) 383.2 (M+H$^+$).

Compound 318: (S)-(3-(benzo[d]isoxazol-5-ylmethylene)azetidin-1-yl)(5-(3,5-difluorophenyl)-4,5-dihydro-1H-pyrazol-1-yl)methanone

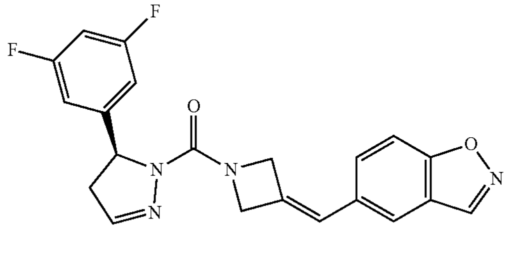 [SMILES: O=C(N1CC(=Cc2ccc3oncc3c2)C1)N1N=CC[C@H]1c1cc(F)cc(F)c1]

The titled compound 313 was prepared in an analogous manner to the preparation of 2% yield: 27.3%. $^{1}H$ NMR (400 MHz, DMSO-$d_6$) δ 11.18 (s, 1H), 7.40 (d, J=2.4 Hz, 1H), 7.31 (dd, J=8.8, 2.4 Hz, 1H), 7.15-7.07 (m, 1H), 7.07-7.04 (m, 1H), 7.01 (d, J=8.8 Hz, 1H), 6.98-6.89 (m, 2H), 6.29-6.22 (m, 1H), 5.27 (dd, J=12.0, 6.8 Hz, 1H), 4.95 (s, 2H), 4.71 (s, 2H), 3.45-3.36 (m, 1H), 2.69-2.61 (m, 1H). LC-MS (m/z) 395.3 (M+$H^+$).

Compound 319: (S)-3-((1-(5-(3,5-difluorophenyl)-4,5-dihydro-1H-pyrazole-1-carbonyl)azetidin-3-ylidene)methyl)-4-fluorobenzonitrile

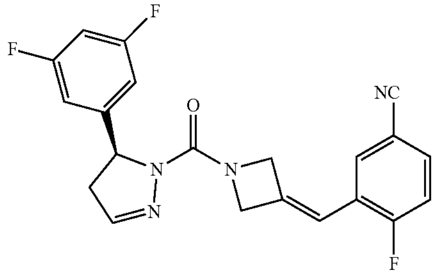 [SMILES: N#Cc1ccc(F)c(C=C2CN(C(=O)N3N=CC[C@H]3c3cc(F)cc(F)c3)C2)c1]

The titled compound 319 was prepared in an analogous manner to the preparation of 2% yield: 77.3%. $^{1}H$ NMR (400 MHz, Chloroform-d) δ 7.55-7.50 (m, 1H), 7.39 (dd, J=6.8, 2.0 Hz, 1H), 7.17 (dd, J=9.6, 8.4 Hz, 1H), 6.86 (t, J=1.6 Hz, 1H), 6.82-6.74 (m, 2H), 6.73-6.66 (m, 1H), 6.44 (q, J=2.4 Hz, 1H), 5.38-5.26 (m, 1H), 5.05 (q, J=15.6, 15.1 Hz, 2H), 4.84 (q, J=15.2 Hz, 2H), 3.44-3.33 (m, 1H), 2.78-2.69m, 1H).

LC-MS (m/z) 397.3 (M+$H^+$).

Compound 320 (S)-2-((1-(5-(3,5-difluorophenyl)-4,5-dihydro-1H-pyrazole-1-carbonyl)azetidin-3-ylidene)methyl)-4-fluorobenzamide

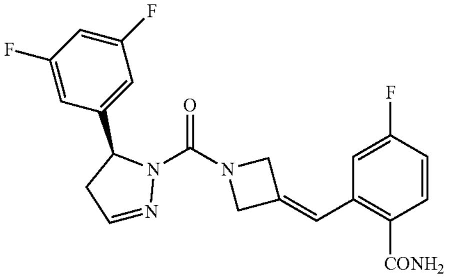 [SMILES: NC(=O)c1ccc(F)cc1C=C1CN(C(=O)N2N=CC[C@H]2c2cc(F)cc(F)c2)C1]

The titled compound 320 was prepared in an analogous manner to the preparation of 296. yield: 34.5%. $^{1}H$ NMR (400 MHz, Chloroform-d) δ 7.26-7.22 (m, 1H), 7.18-7.10 (, 2H), 6.81 (t, J=1.6 Hz, 1H), 6.79-6.73 (m, 2H), 6.73-6.64 (m, 2H), 5.86 (brs, 2H), 5.38-5.22 (m, 1H), 5.05-4.95 (m, 4H), 3.45-3.26 (m, 1H), 2.76-2.66 (m, 1H).

LC-MS (m/z) 415.2 (M+$H^+$).

Compound 321: (S)-2-((1-(5-(3,5-difluorophenyl)-4,5-dihydro-1H-pyrazole-1-carbonyl)azetidin-3-ylidene)methyl)-5-fluorobenzonitrile

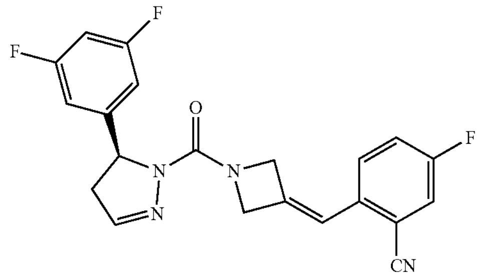 [SMILES: N#Cc1cc(F)ccc1C=C1CN(C(=O)N2N=CC[C@H]2c2cc(F)cc(F)c2)C1]

The titled compound 321 was prepared in an analogous manner to the preparation of 2% yield: 9.0%. $^{1}H$ NMR (400 MHz, Chloroform-d) δ 7.35 (dd, J=8.0, 2.8 Hz, 1H), 7.32-7.27 (m, 1H), 7.18 (dd, J=8.8, 5.2 Hz, 1H), 6.83 (t, J=1.6 Hz, 1H), 6.80-6.74 (m, 2H), 6.73-6.61 (m, 2H), 5.34-5.28 (m, 1H), 5.11-4.78 (m, 4H), 3.44-3.33 (m, 1H), 2.77-2.67 (m, 1H). LC-MS (m/z) 397.2 (M+$H^+$).

Compound 322: (S)-(3-((3,5-difluoro-1H-indazol-6-yl)methylene)azetidin-1-yl)(5-(5-fluoropyridin-3-yl)-4,5-dihydro-1H-pyrazol-1-yl)methanone

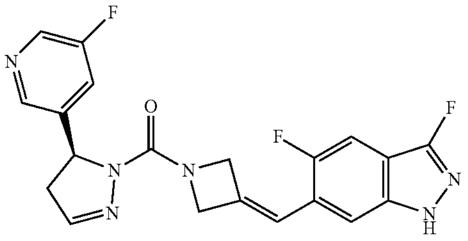 [SMILES: O=C(N1CC(=Cc2cc3[nH]nc(F)c3cc2F)C1)N1N=CC[C@H]1c1cncc(F)c1]

The titled compound 322 was prepared in an analogous manner to the preparation of 2% yield: 19.0%. $^{1}H$ NMR (400 MHz, Chloroform-d) δ 9.45 (brs, 1H), 8.47-8.33 (m, 2H), 7.39 (d, J=8.8 Hz, 1H), 7.42-7.36 (m 1H), 7.03 (dd, J=5.6, 2.4 Hz, 1H), 6.91-6.85 (m, 1H), 6.60-6.55 (m, 1H), 5.45 (dd, J=12.4, 6.4 Hz, 1H), 5.15-4.79 (m, 4H), 3.53-3.41 (m, 1H), 2.85-2.74 (m, 1H). LC-MS (m/z) 413.2 (M+$H^+$).

Compound 323: (S)-5-((1-(5-(3,5-difluorophenyl)-4,5-dihydro-1H-pyrazole-1-carbonyl)azetidin-3-ylidene)methyl)-6-fluoropicolinonitrile

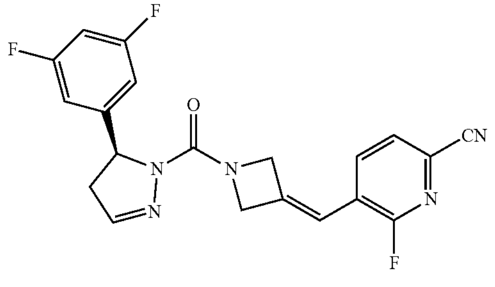 [SMILES: N#Cc1ccc(C=C2CN(C(=O)N3N=CC[C@H]3c3cc(F)cc(F)c3)C2)c(F)n1]

The titled compound 323 was prepared in an analogous manner to the preparation of 2% yield: 27.3%. $^{1}$H NMR (400 MHz, Chloroform-d) δ 7.62-7.55 (m, 2H), 6.84 (t, J=1.6 Hz, 1H), 6.80-6.64 (m, 3H), 6.44 (p, J=2.4 Hz, 1H), 5.36-5.28 (m, 1H), 5.18-4.71 (m, 4H), 3.45-3.34 (m, 1H), 2.79-2.69 (m, 1H). LC-MS (m/z) 389.2 (M+H$^{+}$).

Compound 324: (S)-6-fluoro-5-((1-(5-(5-fluoropyridin-3-yl)-4,5-dihydro-1H-pyrazole-1-carbonyl)azetidin-3-ylidene)methyl)picolinonitrile

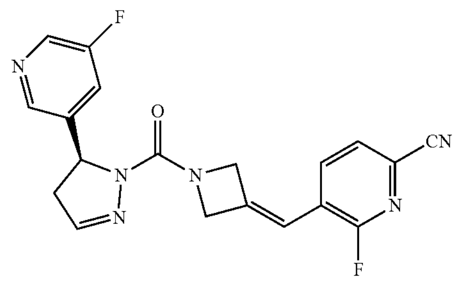 [SMILES: N#Cc1ccc(C=C2CN(C(=O)N3N=CC[C@H]3c3cncc(F)c3)C2)c(F)n1]

The titled compound 324 was prepared in an analogous manner to the preparation of 296 yield: 21.4%. $^{1}$H NMR (400 MHz, Chloroform-d) δ 8.89-8.24 (m, 2H), 7.72-7.53 (m, 3H), 6.95 (d, J=1.6 Hz, 1H), 6.46 (t, J=2.4 Hz, 1H), 5.48 (dd, J=12.4, 6.8 Hz, 1H), 5.54-5.43 (m, 4H), 3.60-3.43 (m, 1H), 2.95-2.80 (m, 1H). LC-MS (m/z) 381.2 (M+H$^{+}$).

Compound 325: (S)—N-(2-(4-(5-(3,5-difluorophenyl)-4,5-dihydro-1H-pyrazole-1-carbonyl)piperazin-1-yl)-5-fluoropyrimidin-4-yl)cyclopentanecarboxamide

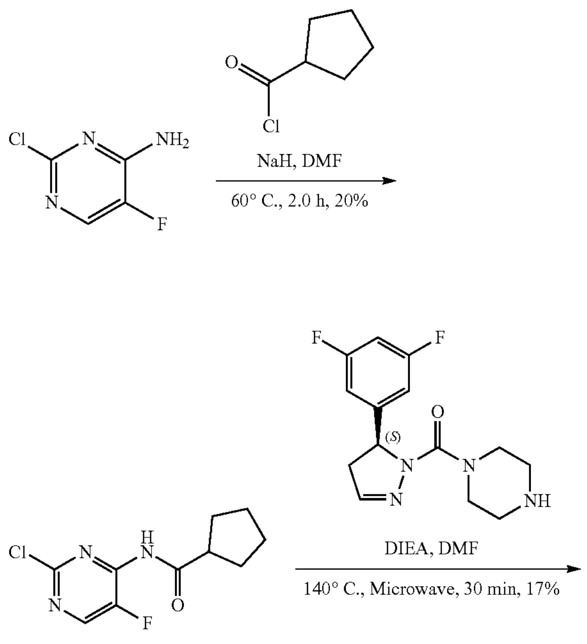

-continued

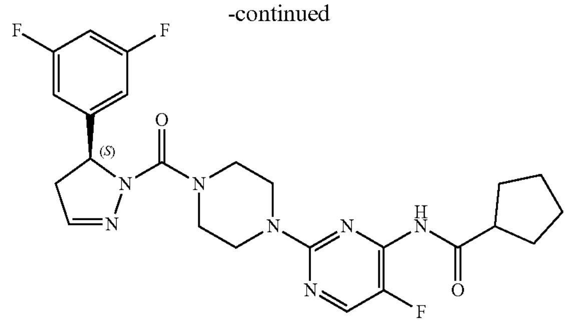

The titled compound 325 as a white solid (14.4 mg, 17%) was prepare from (S)-(5-(3,5-difluorophenyl)-4,5-dihydro-1H-pyrazol-1-yl)(piperazin-1-yl)methanone and N-(2-chloro-5-fluoropyrimidin-4-yl)cyclopentanecarboxamide according to the procedure outlined for compound 225 (ES, m/s): 502.2 [M+H]$^{+}$ $^{1}$H NMR (400 MHz, DMSO-$d_6$) δ 10.27 (brs, 1H), 8.31 (d, J=3.0 Hz, 1H), 7.12-7.02 (m, 2H), 7.02-6.91 (m, 2H), 5.24 (m, 1H), 3.73-3.65 (m, 2H), 3.64-3.56 (m, 4H), 3.54-3.43 (m, 2H), 3.39-3.33 (m, 1H), 2.87-2.95 (m, 1H), 2.65-2.58 (m, 1H), 1.88-1.74 (m, 2H), 1.71-1.57 (m, 4H), 1.55-1.47 (m, 2H).

Compound 326: (S)-(3-((2-(cyclopropylamino)-5-fluoropyridin-4-yl)methylene)azetidin-1-yl)(5-(3,5-difluorophenyl)-4,5-dihydro-1H-pyrazol-1-yl)methanone

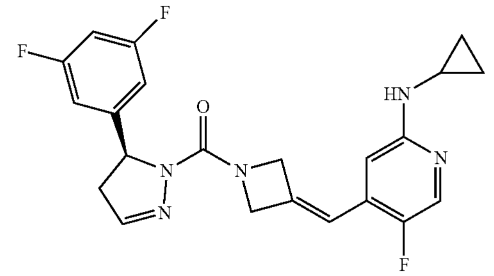 [SMILES: O=C(N1CC(=Cc2cc(NC3CC3)ncc2F)C1)N1N=CC[C@H]1c1cc(F)cc(F)c1]

The titled compound 326 was prepared in an analogous manner to the preparation of 105. yield: 23.4%. $^{1}$H NMR (400 MHz, Chloroform-d) δ 7.69 (s, 1H), 7.24-7.16 (m, 1H), 6.85 (s, 1H), 6.81-6.62 (m, 3H), 6.11 (s, 1H), 5.31 (dd, J=12.0, 6.4 Hz, 1H), 5.14-4.70 (m, 4H), 3.47-3.32 (m, 1H), 3.01-2.93 (m, 1H), 2.79-2.68 (m, 1H), 0.99-0.90 (m, 2H), 0.78-0.68 (m, 2H). LC-MS (m/z) 428.4 (M+H$^{+}$).

Compound 327: (S)-5-(3,5-difluorophenyl)-4,5-dihydro-1H-pyrazol-1-yl)(3-((3-fluoro-1H-pyrazolo[4,3-b]pyridin-6-yl)methylene)azetidin-1-yl)methanone

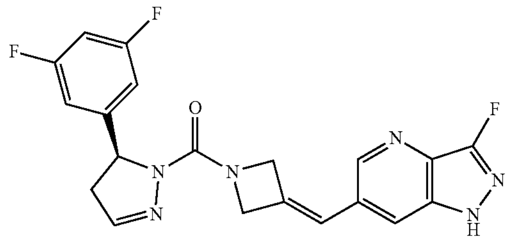 [SMILES: O=C(N1CC(=Cc2cnc3c(F)n[nH]c3c2)C1)N1N=CC[C@H]1c1cc(F)cc(F)c1]

The titled compound 327 was prepared in an analogous manner to the preparation of 296 yield: 6.8%. $^1$H NMR (400 MHz, Chloroform-d) δ 10.09 (brs, 1H), 8.45 (s, 1H), 7.39 (s, 1H), 6.86 (s, 1H), 6.82-6.72 (m, 2H), 6.72-6.62 (m, 1H), 6.44 (s, 1H), 5.37 (dd, J=12.4, 6.4 Hz, 1H), 5.21-4.78 (m, 4H), 3.47-3.35 (dd, J=18.4, 12.0 Hz, 1H), 2.74 (dd, J=18.4, 6.0 Hz, 1H). LC-MS (m/z) 413.3 (M+H$^+$).

Compound 328: (S)—N-(2-(4-(5-(3,5-difluorophenyl)-4,5-dihydro-1H-pyrazole-1-carbonyl)piperazin-1-yl)-5-fluoropyrimidin-4-yl)cyclobutanecarboxamide

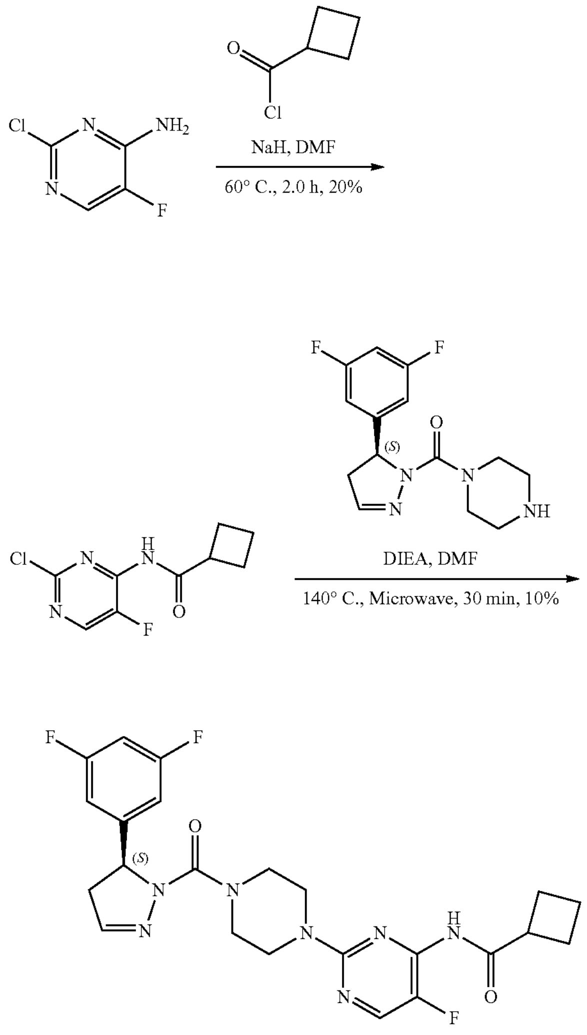

The titled compound 328 as a white solid (9.8 mg, 10%) was prepare from (S)-(5-(3,5-difluorophenyl)-4,5-dihydro-1H-pyrazol-1-yl)(piperazin-1-yl)methanone and N-(2-chloro-5-fluoropyrimidin-4-yl)cyclobutanecarboxamide according to the procedure outlined for compound 225 (ES, m/s): 488.2 [M+H]$^+$ $^1$H NMR (400 MHz, DMSO-$d_6$) δ 10.17 (brs, 1H), 8.31 (d, J=3.0 Hz, 1H), 7.13-7.05 (m, 2H), 7.01-6.93 (m, 2H), 5.27-5.17 (m, 1H), 3.73-3.45 (m, 8H), 3.42-3.36 (m, 1H), 3.35-3.33 (m, 1H), 2.66-2.57 (m, 1H), 2.20-2.04 (m, 2H), 2.00-1.86 (m, 2H), 1.82-1.71 (m, 2H).

Compound 329: (S)-(5-(3,5-difluorophenyl)-4,5-dihydro-1H-pyrazol-1-yl(3-((2,5-difluoropyridin-4-yl)methylene)azetidin-1-yl)methanone

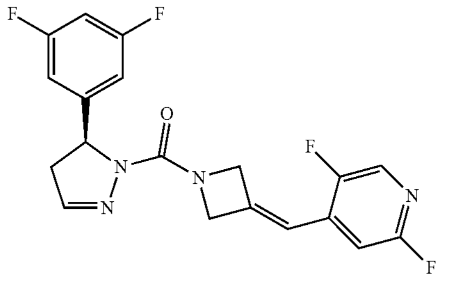 [SMILES: O=C(N1CC(=Cc2cc(F)ncc2F)C1)N1N=CC[C@H]1c1cc(F)cc(F)c1]

The titled compound 329 was prepared in an analogous manner to the preparation of 296 $^1$H NMR (400 MHz, Chloroform-d) δ 6.95-6.91 (m, 1H), 6.84-6.66 (m, 4H), 6.58-6.56 (m, 1H), 6.43 (s, 1H), 5.29 (dd, J=16.0, 8.0 Hz, 1H), 5.07-5.06 (m, 2H), 4.88-4.84 (m, 2H), 3.42-3.33 (m, 1H), 2.76-2.69 (m, 1H).

Compound 330: 2-chloro-6-(((S)-1-((S)-5-(3,5-difluorophenyl)-4,5-dihydro-1H-pyrazole-1-carbonyl)pyrrolidin-3-yl)oxy)isonicotinonitrile

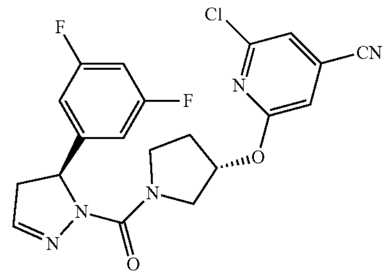 [SMILES: N#Cc1cc(Cl)nc(O[C@H]2CCN(C(=O)N3N=CC[C@H]3c3cc(F)cc(F)c3)C2)c1]

The titled compound 330 was prepared in an analogous manner to the preparation of compound 203. LC-MS (m/z): 432.2 [M+H]$^+$. $^1$H NMR (400 MHz, Chloroform-d) δ 7.14-7.11 (m, 1H), 6.92-6.88 (m, 1H), 6.84-6.76 (m, 3H), 6.74-6.65 (m, 1H), 5.61 (s, 1H), 5.36-5.27 (m, 1H), 4.03-3.94 (m, 1H), 3.91-3.80 (m, 1H), 3.73 (d, J=12.7 Hz, 2H), 3.38-3.27 (m, 1H), 2.73-2.62 (m, 1H), 2.26-2.11 (m, 2H).

Compound 331: 2-chloro-6-(((S)-1-((S)-5-(3,5-difluorophenyl)-4,5-dihydro-1H-pyrazole-1-carbonyl)pyrrolidin-3-yl)oxy)isonicotinamide

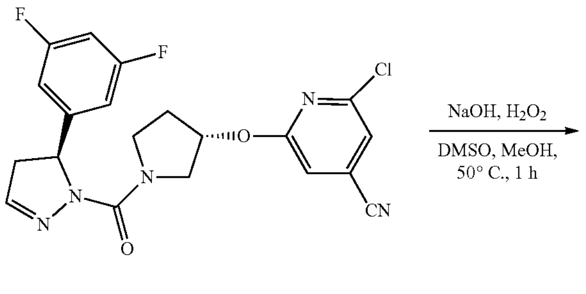

-continued

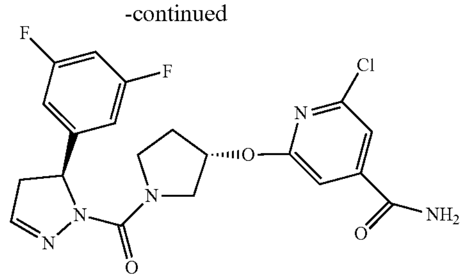

The titled compound 331 was prepared from 2-chloro-6-(((S)-1-((S)-5-(3,5-difluorophenyl)-4,5-dihydro-1H-pyrazole-1-carbonyl)pyrrolidin-3yl)oxy) isonicotinonitrile by hydrolysis reaction using NaOH and $H_2O_2$ LC-MS (m/z): 450.1[M+H]$^+$. $^1$H NMR (400 MHz, Chloroform-d) δ 7.30-7.28 (m, 1H), 6.93 (d, J=1.2 Hz, 1H), 6.83-6.76 (m, 3H), 6.68 (tt, J=8.9, 2.3 Hz, 1H), 5.65-5.61 (m, 1H), 5.32 (dd, J=11.9, 9.1 Hz, 1H), 4.02-3.94 (m, 1H), 3.91-3.81 (m, 1H), 3.79-3.65 (m, 2H), 3.33 (ddd, J=18.4, 12.1, 1.8 Hz, 1H), 2.67 (ddd, J=18.3, 9.3, 1.7 Hz, 1H), 2.28-2.09 (m, 2H).

Compound 332: 2-(((R)-1-((S)-5-(3,5-difluorophenyl)-4,5-dihydro-1H-pyrazole-1-carbonyl)pyrrolidin-3-yl)oxy)pyrimidine-4-carboxamide

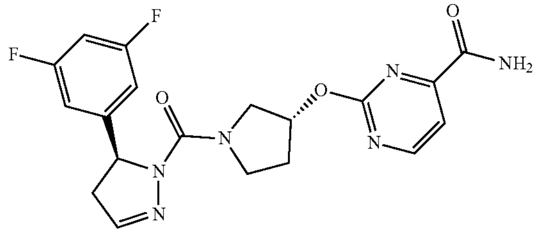 [SMILES: NC(=O)c1ccnc(O[C@@H]2CCN(C(=O)N3N=CC[C@H]3c3cc(F)cc(F)c3)C2)n1]

The titled compound 332 was prepared in an analogous manner to the preparation of 256 LC-MS (m/z): 417.2 [M+H]$^+$. $^1$H NMR (400 MHz, Chloroform-d) δ 8.58 (s, 1H), 7.80 (s, 1H), 6.91-6.85 (m, 1H), 6.84-6.75 (m, 3H), 6.69 (tt, J=8.9, 2.2 Hz, 1H), 6.30 (s, 1H), 5.86 (s, 1H), 5.33 (dd, J=12.0, 9.0 Hz, 1H), 4.09-3.99 (m, 1H), 3.93-3.70 (m, 3H), 3.40-3.27 (m, 1H), 2.73-2.64 (m, 1H), 2.38-2.17 (m, 2H).

Compound 333: (S)-2-((1-(5-(3,5-difluorophenyl)-4,5-dihydro-1H-pyrazole-1-carbonyl)azetidin-3-yl)oxy)pyrimidine-4-carbonitrile

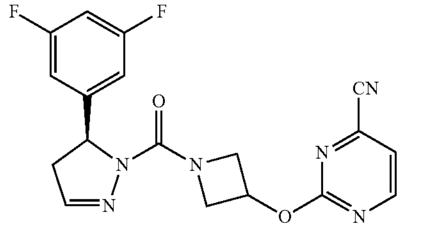 [SMILES: N#Cc1ccnc(OC2CN(C(=O)N3N=CC[C@H]3c3cc(F)cc(F)c3)C2)n1]

The titled compound 333 was prepared in an analogous manner to the preparation of 256 LC-MS (m/z): 385.2 [M+H]$^+$. $^1$H NMR (400 MHz, Chloroform-d) δ 8.77 (d, J=4.7 Hz, 1H), 7.33 (d, J=4.8 Hz, 1H), 6.79 (t, J=1.7 Hz, 1H), 6.77-6.73 (m, 2H), 6.69 (tt, J=8.9, 2.3 Hz, 1H), 5.39 (tt, J=6.6, 4.2 Hz, 1H), 5.28 (dd, J=12.2, 6.5 Hz, 1H), 4.66-4.52 (m, 2H), 4.34-4.19 (m, 2H), 3.35 (ddd, J=18.6, 12.2, 1.7 Hz, 1H), 2.69 (ddd, J=18.6, 6.5, 1.7 Hz, 1H).

Compound 334: (S)-4-((1-(5-(3,5-difluorophenyl)-4,5-dihydro-1H-pyrazole-1-carbonyl)azetidin-3-yl)oxy)pyrimidine-2-carbonitrile

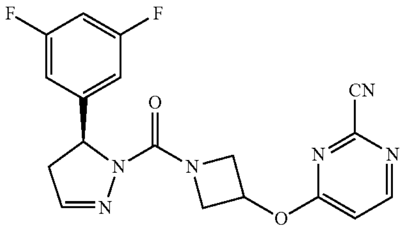 [SMILES: N#Cc1nccc(OC2CN(C(=O)N3N=CC[C@H]3c3cc(F)cc(F)c3)C2)n1]

The titled compound 334 was prepared in an analogous manner to the preparation of 256 LC-MS (m/z): 385.2 [M+H]$^+$. $^1$H NMR (400 MHz, Chloroform-d) δ 8.57 (d, J=5.8 Hz, 1H), 7.00 (d, J=5.8 Hz, 1H), 6.82 (t, J=1.7 Hz, 1H), 6.76-6.73 (m, 2H), 6.70 (tt, J=8.9, 2.3 Hz, 1H), 5.45 (tt, J=6.6, 4.1 Hz, 1H), 5.28 (dd, J=12.2, 6.3 Hz, 1H), 4.71-4.55 (m, 2H), 4.28-4.17 (m, 2H), 3.36 (ddd, J=18.7, 12.2, 1.7 Hz, 1H), 2.71 (ddd, J=18.6, 6.4, 1.7 Hz, 1H).

Compound 335: 6-(((R)-1-((S)-5-(3,5-difluorophenyl)-4,5-dihydro-1H-pyrazole-1-carbonyl)pyrrolidin-3-yl)oxy)pyrazine-2-carbonitrile The titled compound 335 was prepared in an analogous manner to the preparation of 256

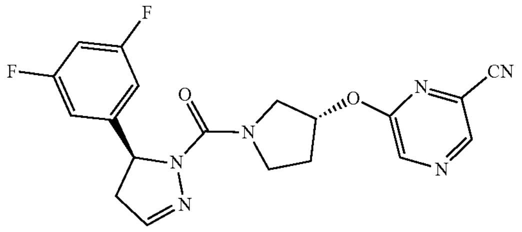 [SMILES: N#Cc1cncc(O[C@@H]2CCN(C(=O)N3N=CC[C@H]3c3cc(F)cc(F)c3)C2)n1]

LC-MS (m/z): 399.2 [M+H]$^+$. $^1$H NMR (400 MHz, Chloroform-d) δ 8.49 (d, J=0.6 Hz, 1H), 8.39 (d, J=0.6 Hz, 1H), 6.85-6.74 (m, 3H), 6.68 (tt, J=8.9, 2.3 Hz, 1H), 5.63-5.58 (m, 1H), 5.32 (dd, J=12.0, 9.0 Hz, 1H), 4.03 (dd, J=13.5, 4.3 Hz, 1H), 3.92-3.82 (m, 1H), 3.81-3.70 (m, 2H), 3.33 (ddd, J=18.4, 12.0, 1.8 Hz, 1H), 2.68 (ddd, J=18.4, 9.1, 1.6 Hz, 1H), 2.25-2.20 (m, 2H).

Compound 336: 2-(((R)-1-((S)-5-(3,5-difluorophenyl)-4,5-dihydro-1H-pyrazole-1-carbonyl)pyrrolidin-3-yl)oxy)isonicotinonitrile

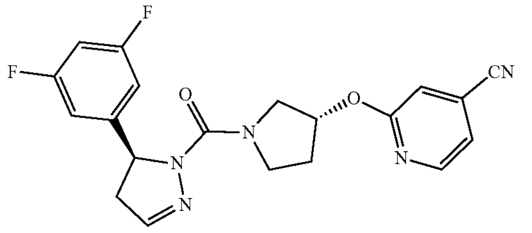 [SMILES: N#Cc1ccnc(O[C@@H]2CCN(C(=O)N3N=CC[C@H]3c3cc(F)cc(F)c3)C2)c1]

The titled compound 336 was prepared in an analogous manner to the preparation of 256 LC-MS (m/z): 398.2 $[M+H]^+$. $^1H$ NMR (400 MHz, Chloroform-d) δ 8.30-8.27 (m, 1H), 7.09-7.07 (m, 1H), 6.99-6.97 (m, 1H), 6.82-6.76 (m, 3H), 6.69 (tt, J=8.9, 2.3 Hz, 1H), 5.61 (t, J=4.3 Hz, 1H), 5.32 (dd, J=12.0, 9.1 Hz, 1H), 3.98 (dd, J=13.2, 4.4 Hz, 1H), 3.87 (td, J=11.0, 6.9 Hz, 1H), 3.73 (d, J=12.5 Hz, 2H), 3.32 (ddd, J=18.4, 12.0, 1.8 Hz, 1H), 2.67 (ddd, J=18.3, 9.1, 1.6 Hz, 1H), 2.25-2.10 (m, 2H).

Compound 337: 6-(((R)-1-((S)-5-(3,5-difluorophenyl)-4,5-dihydro-1H-pyrazole-1-carbonyl)pyrrolidin-3-yl)oxy)picolinonitrile

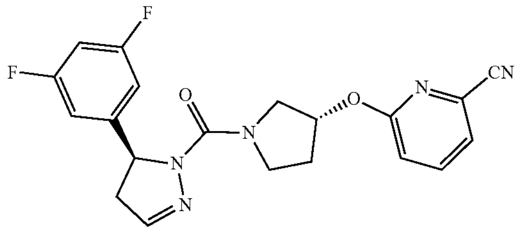 [SMILES: N#Cc1cccc(O[C@@H]2CCN(C(=O)N3N=CC[C@H]3c3cc(F)cc(F)c3)C2)n1]

The titled compound 337 was prepared in an analogous manner to the preparation of 256 LC-MS (m/z): 398.2 $[M+H]^+$. $^1H$ NMR (400 M Hz, Chloroform-d) δ 7.67 (dd, J=8.5, 7.2 Hz, 1H), 7.31 (dd, J=7.2, 0.8 Hz, 1H), 6.94 (dd, J=8.5, 0.8 Hz, 1H), 6.82-6.76 (m, 3H), 6.67 (tt, J=8.9, 2.3 Hz, 1H), 5.62 (t, J=4.2 Hz, 1H), 5.32 (dd, J=12.0, 9.2 Hz, 1H), 4.00 (dd, J=13.3, 4.3 Hz, 1H), 3.85 (td, J=11.0, 7.0 Hz, 1H), 3.79-3.65 (m, 2H), 3.32 (ddd, J=18.3, 12.0, 1.8 Hz, 1H), 2.67 (ddd, J=18.3, 9.2, 1.6 Hz, 1H), 2.27-2.10 (m, 2H).

Compound 338: (S)-(3-((6-chloro-2-fluoropyridin-3-yl)oxy)azetidin-1-yl)(5-(3,5-difluorophenyl)-4,5-dihydro-1H-pyrazol-1-yl)methanone

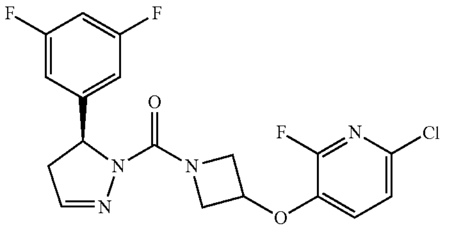 [SMILES: O=C(N1CC(Oc2ccc(Cl)nc2F)C1)N1N=CC[C@H]1c1cc(F)cc(F)c1]

The titled compound 338 was prepared in an analogous manner to the preparation of 256 LC-MS (m/z): 411.1$[M+H]^+$. $^1H$ NMR (400 MHz, Chloroform-d) δ 7.14 (d, J=8.2 Hz, 1H), 7.06 (dd, J=9.5, 8.2 Hz, 1H), 6.80 (t, J=1.7 Hz, 1H), 6.78-6.71 (m, 2H), 6.69 (tt, J=8.8, 2.3 Hz, 1H), 5.27 (dd, J=12.2, 6.4 Hz, 1H), 4.99-4.92 (m, 1H), 4.54 (q, J=8.8, 8.3 Hz, 2H), 4.35-4.19 (m, 2H), 3.36 (ddd, J=18.6, 12.2, 1.7 Hz, 1H), 2.71 (ddd, J=18.6, 6.4, 1.7 Hz, 1H).

Compound 339:3-chloro-6-(((R)-1-((S)-5-(3,5-difluorophenyl)-4,5-dihydro-1H-pyrazole-1-carbonyl)pyrrolidin-3-yl)oxy)picolinonitrile

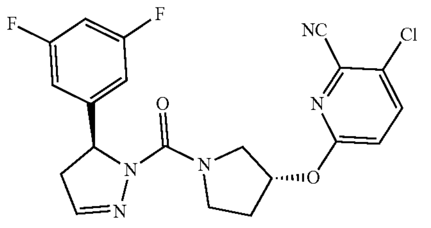 [SMILES: N#Cc1nc(O[C@@H]2CCN(C(=O)N3N=CC[C@H]3c3cc(F)cc(F)c3)C2)ccc1Cl]

The titled compound 339 was prepared in an analogous manner to the preparation of 256 LC-MS (m/z): 432.2 $[M+H]^+$. $^1H$ NMR (400 MHz, Chloroform-d) δ 7.67 (d, J=8.9 Hz, 1H), 6.91 (d, J=9.0 Hz, 1H), 6.82-6.75 (m, 3H), 6.67 (tt, J=8.9, 2.3 Hz, 1H), 5.60-5.55 (m, 1H), 5.31 (dd, J=12.0, 9.2 Hz, 1H), 4.00 (dd, J=13.4, 4.3 Hz, 1H), 3.88-3.78 (m, 1H), 3.78-3.64 (m, 2H), 3.32 (ddd, J=18.4, 12.0, 1.8 Hz, 1H), 2.67 (ddd, J=18.3, 9.2, 1.6 Hz, 1H), 2.26-2.10 (m, 2H).

Compound 340:4-(((R)-1-((S)-5-(3,5-difluorophenyl)-4,5-dihydro-1H-pyrazole-1-carbonyl)pyrrolidin-3-yl)oxy)picolinonitrile

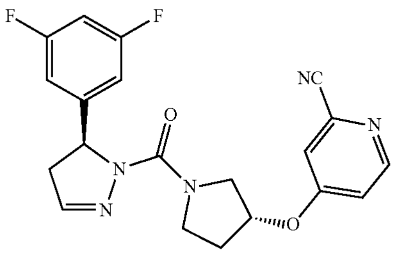 [SMILES: N#Cc1cc(O[C@@H]2CCN(C(=O)N3N=CC[C@H]3c3cc(F)cc(F)c3)C2)ccn1]

The titled compound 340 was prepared in an analogous manner to the preparation of compound 203 LC-MS (m/z): 398.2 $[M+H]^+$. $^1H$ NMR (400 MHz, Chloroform-d) δ 8.51 (d, J=5.8 Hz, 1H), 7.19 (d, J=2.5 Hz, 1H), 6.97 (dd, J=5.8, 2.5 Hz, 1H), 6.82-6.75 (m, 3H), 6.69 (tt, J=8.9, 2.3 Hz, 1H), 5.31 (dd, J=12.0, 9.1 Hz, 1H), 5.00 (t, J=4.3 Hz, 1H), 4.02 (dd, J=13.3, 4.2 Hz, 1H), 3.90-3.81 (m, 1H), 3.81-3.72 (m, 2H), 3.33 (ddd, J=18.4, 12.0, 1.8 Hz, 1H), 2.68 (ddd, J=18.4, 9.1, 1.6 Hz, 1H), 2.29-2.13 (m, 2H).

Compound 341:3-(((R)-1-((S)-5-(3,5-difluorophenyl)-4,5-dihydro-1H-pyrazole-1-carbonyl)pyrrolidin-3-yl)oxy)-4-fluorobenzonitrile

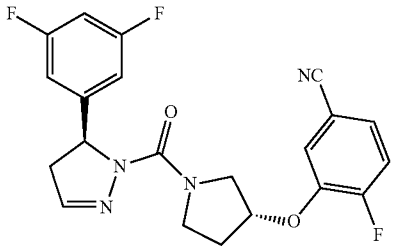 [SMILES: N#Cc1ccc(F)c(O[C@@H]2CCN(C(=O)N3N=CC[C@H]3c3cc(F)cc(F)c3)C2)c1]

The titled compound 341 was prepared in an analogous manner to the preparation of compound 203LC-MS (m/z): 415.2 $[M+H]^+$. $^1H$ NMR (400 MHz, Chloroform-d) δ 7.31-7.27 (m, 1H), 7.23-7.17 (m, 2H), 6.81-6.75 (m, 3H), 6.68 (tt, J=8.9, 2.3 Hz, 1H), 5.31 (dd, J=11.9, 7.5 Hz, 1H), 4.98-4.92 (m, 1H), 4.09-4.03 (m, 1H), 4.02-3.93 (m, 1H), 3.87 (dd, J=13.0, 4.8 Hz, 1H), 3.76-3.66 (m, 1H), 3.32 (ddd, J=18.3, 11.9, 1.7 Hz, 1H), 2.67 (ddd, J=18.3, 7.6, 1.7 Hz, 1H), 2.29-2.13 (m, 2H).

Compound 342: 5-(((R)-1-((S)-5-(3,5-difluorophenyl)-4,5-dihydro-1H-pyrazole-1-carbonyl)pyrrolidin-3-yl)oxy)-2-fluorobenzonitrile

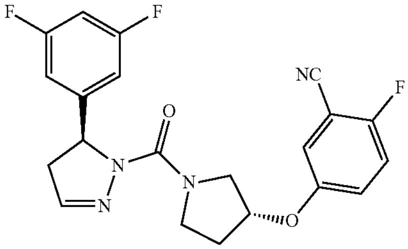 [SMILES: N#Cc1cc(O[C@@H]2CCN(C(=O)N3N=CC[C@H]3c3cc(F)cc(F)c3)C2)ccc1F]

The titled compound 343 was prepared in an analogous manner to the preparation of 203 LC-MS (m/z): 415.2 $[M+H]^+$. $^1H$ NMR (400 MHz, Chloroform-d) δ 7.14-7.08 (m, 2H), 7.06-7.03 (m, 1H), 6.81-6.74 (m, 3H), 6.69 (tt, J=8.9, 2.3 Hz, 1H), 5.30 (dd, J=11.9, 7.7 Hz, 1H), 4.88-4.81 (m, 1H), 4.04-3.91 (m, 2H), 3.84 (dd, J=12.7, 4.9 Hz, 1H), 3.67 (dt, J=11.2, 8.2 Hz, 1H), 3.31 (ddd, J=18.3, 12.0, 1.8 Hz, 1H), 2.67 (ddd, J=18.3, 7.7, 1.7 Hz, 1H), 2.20-2.13 (m, 2H).

Compound 343: 4-(((R)-1-((S)-5-(3,5-difluorophenyl)-4,5-dihydro-1H-pyrazole-1-carbonyl)pyrrolidin-3-yl)oxy)benzonitrile

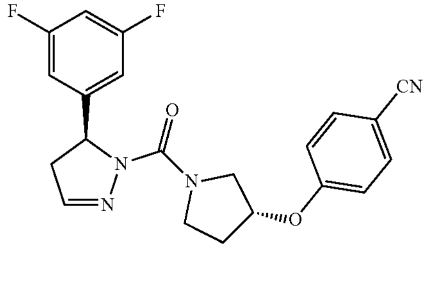 [SMILES: N#Cc1ccc(O[C@@H]2CCN(C(=O)N3N=CC[C@H]3c3cc(F)cc(F)c3)C2)cc1]

The titled compound 343 was prepared in an analogous manner to the preparation of 203. LC-MS (m/z): 397.2 $[M+H]^+$. $^1H$ NMR (400 MHz, Chloroform-d) δ 7.63-7.55 (m, 2H), 6.97-6.89 (m, 2H), 6.81-3.74 (m, 3H), 6.68 (tt, J=8.9, 2.3 Hz, 1H), 5.30 (dd, J=11.9, 7.5 Hz, 1H), 4.99-4.92 (m, 1H), 4.05-3.85 (m, 3H), 3.68 (dt, J=11.2, 8.2 Hz, 1H), 3.31 (ddd, J=18.3, 12.0, 1.8 Hz, 1H), 2.66 (ddd, J=18.3, 7.6, 1.7 Hz, 1H), 2.23-2.16 (m, 2H).

Compound 344: (S)-(5-(3,5-difluorophenyl)-4,5-dihydro-H-pyrazol-1-yl)(3-((5-fluoro-2-((2-hydroxyethyl)amino)pyrimidin-4-yl)oxy)azetidin-1-yl)methanone (SIR-1495D)

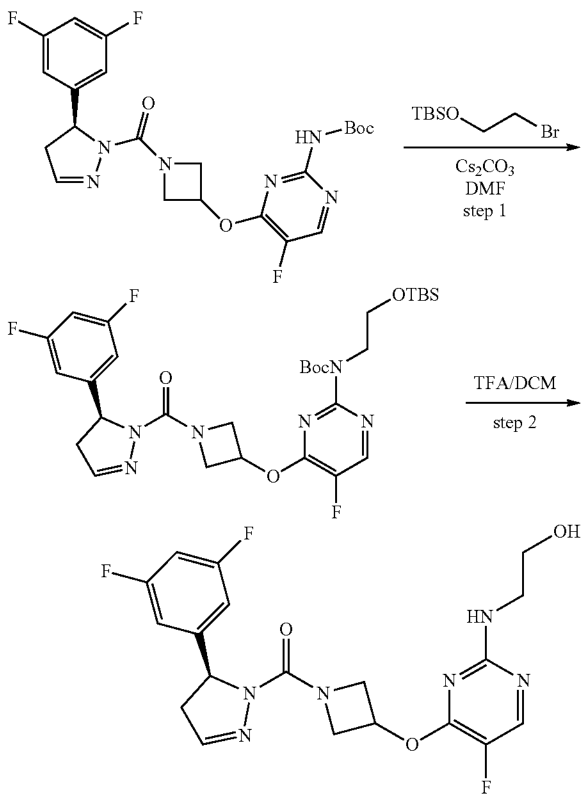

Step 1. (2-bromoethoxy)(tert-butyl)dimethylsilane (29.1 mg, 0.122 mmol) was added to a solution of $Cs_2CO_3$ (66.5 mg, 0.204 mmol) in DMF (1 mL), and (S)-(3-((2-chloro-5-fluoropyrimidin-4-yl)oxy)azetidin-1-yl)(5-(3,5-difluorophenyl)-4,5-dihydro-1H-pyrazol-1-yl)methanone (50 mg, 0.102 mmol) was added. The mixture was stirred at 100° C. for 1 hr. The reaction mixture was then extracted by EtOAc/$H_2O$ (50 mL/50 mL) 3 times. The organic layer was combined, washed with brine, dried over $Na_2SO_4$, concentrated to give tert-butyl (S)-(2-((tert-butyldimethylsilyl)oxy)ethyl)(4-((1-(5-(3,5-difluorophenyl)-4,5-dihydro-1H-pyrazole-1-carbonyl)azetidin-3-yl)oxy)-5-fluoropyrimidin-2-yl)carbamate (60 mg) as a yellow oil Step 2. TFA (5 mL) was added to a solution of tert-butyl (S)-(2-((tert-butyldimethylsilyl)oxy)ethyl)(4-((1-(5-(3,5-difluorophenyl)-4,5-dihydro-1H-pyrazole-1-carbonyl)azetidin-3-yl)oxy)-5-fluoropyrimidin-2-yl)carbamate (60 mg, 0.092 mmol) in DCM (10 mL). the reaction mixture was stirred at room temperature for 0.5 hr. The reaction mixture was concentrated and purified by pre-HPLC to give 16 mg of (S)-(5-(3,5-difluorophenyl)-4,5-dihydro-1H-pyrazol-1-yl)(3-((5-fluoro-2-((2-hydroxyethyl)amino)pyrimidin-4-yl)oxy)azetidin-1-yl)methanone 344 (40%). LC-MS (ESI) m/z $[M+H]^+$: 437.2 $^1H$ NMR (400 MHz, $CDCl_3$): δ 7.82 (d, J=3.4 Hz, 1H), 6.85-6.64 (m, 4H), 5.50 (s, 1H), 5.27 (dd, J=12.1, 6.4 Hz, 1H), 4.60 (br, 2H), 4.38-4.26 ((m, 2H), 3.85 (s, 2H), 3.55 (s, 2H), 3.41-3.33 (m, 1H), 2.77-2.66 (m, 1H).

Compound 345: (S)-(3-((2-chloro-5-fluoropyrimidin-4-yl)oxy)azetidin-1-yl)(5-(3,5-difluorophenyl)-4,5-dihydro-1H-pyrazol-1-yl)methanone

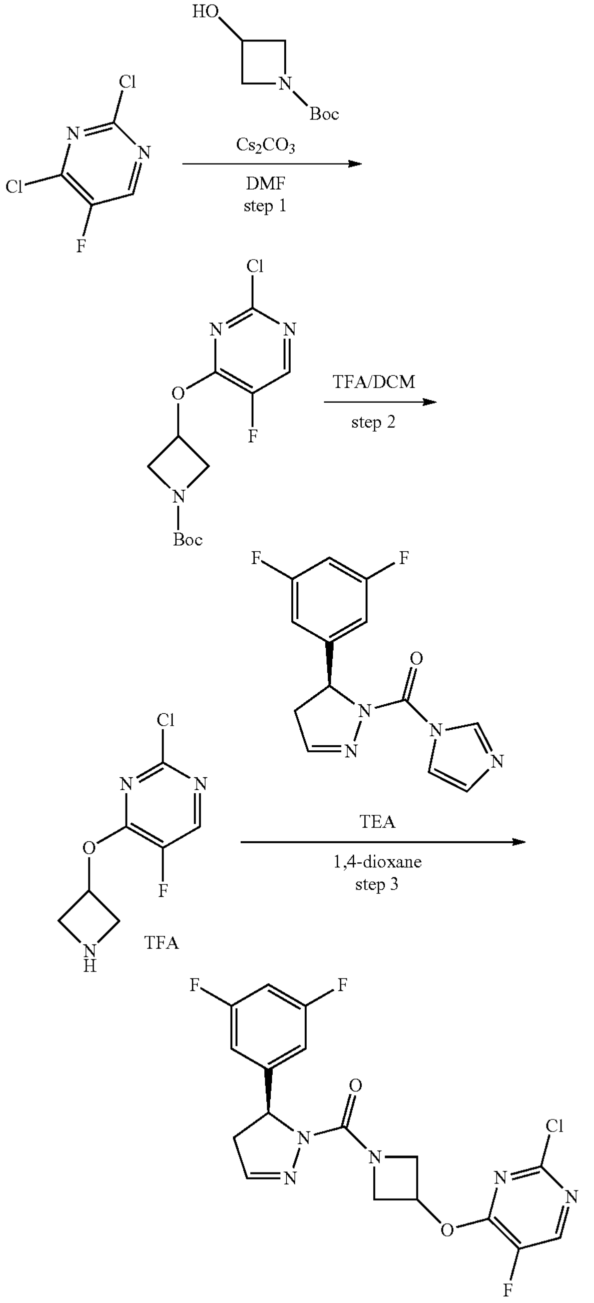

Step 1. Preparation of tert-butyl 3-((2-chloro-5-fluoropyrimidin-4-yl)oxy)azetidine-1-carboxylate 2,4-dichloro-5-fluoropyrimidine (5 g, 29.9 mmol) was added to a solution of $Cs_2CO_3$ (19.5 g, 59.9 mmol) in DMF (100 mL), and tert-butyl 3-hydroxyazetidine-1-carboxylate (5.7 g, 32.9 mmol) was added. The mixture was stirred at 100° C. for 2 hrs. The reaction mixture was then extracted by EtOAc/$H_2O$ (50 mL/50 mL) 3 times. The organic layer was combined, washed with brine, dried over $Na_2SO_4$, concentrated and further purified by silica gel column chromatography (PE/EA=5/1) to give tert-butyl 3-((2-chloro-5-fluoropyrimidin-4-yl)oxy)azetidine-1-carboxylate (3.9 g) as a colorless oil (43%). LC-MS (ESI) m/z $[M+H]^+$:304.1.

Step 2. Preparation of 4-(azetidin-3-yloxy)-2-chloro-5-fluoropyrimidine. TFA (5 mL) was added to a solution of tert-butyl 3-((2-chloro-5-fluoropyrimidin-4-yl)oxy)azetidine-1-carboxylate (3.9 g, 12.9 mmol) in DCM (10 mL). the reaction mixture was stirred at room temperature for 0.5 hr. then the solvent was evaporated in vacuo to give 5.2 g of 4-(azetidin-3-yloxy)-2-chloro-5-fluoropyrimidine as a colorless oil (crude). LC-MS (ESI) m/z $[M+H]^+$:204.1.

Step 3. Preparation of (S)-(3-((2-chloro-5-fluoropyrimidin-4-yl)oxy)azetidin-1-yl)(5-(3,5-difluorophenyl)-4,5-dihydro-1H-pyrazol-1-yl)methanone. (S)-(5-(3,5-difluorophenyl)-4,5-dihydro-1H-pyrazol-1-yl)(1H-imidazol-1-yl)methanone (3.23 g, 11.7 mmol) was added to a solution of 4-(azetidin-3-yloxy)-2-chloro-5-fluoropyrimidine and TEA (3.55 g, 35.1 mmol) in 1,4-dioxane (30 mL). The reaction mixture was stirred at room temperature overnight. Then the solvent was evaporated in vacuo. The oil residue was purified by silica gel column chromatography (PE/EA=1/1) to give 4.35 g of (S)-(3-((2-chloro-5-fluoropyrimidin-4-yl)oxy)azetidin-1-yl)(5-(3,5-difluorophenyl)-4,5-dihydro-1H-pyrazol-1-yl)methanone 154 as a yellow oil (yield=90%). LC-MS (ESI) m/z $[M+H]^+$:412.1. LC-MS (m/z): 412.1$[M+H]^+$. $^1H$ NMR (400 MHz, Chloroform-d) δ 8.25 (d, J=2.1 Hz, 1H), 6.79 (t, J=1.7 Hz, 1H), 6.78-6.73 (m, 2H), 6.69 (tt, J=8.9, 2.3 Hz, 1H), 5.50 (tt, J=6.7, 4.1 Hz, 1H), 5.27 (dd, J=12.2, 6.5 Hz, 1H), 4.69-4.54 (m, 2H), 4.34-4.22 (m, 2H), 3.36 (ddd, J=18.6, 12.2, 1.7 Hz, 1H), 2.70 (ddd, J=18.6, 6.5, 1.7 Hz, 1H).

Compound 346: (S)-(5-(3,5-difluorophenyl)-4,5-dihydro-1H-pyrazol-1-yl)(3-((5-fluoro-2-(methylamino)pyrimidin-4-yl)oxy)azetidin-1-yl)methanone

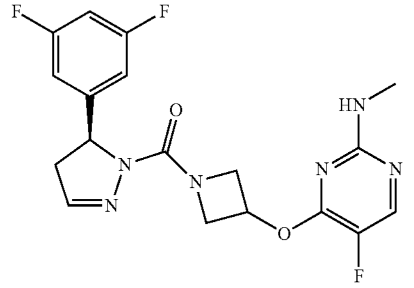 [SMILES: CNc1ncc(F)c(OC2CN(C(=O)N3N=CC[C@H]3c3cc(F)cc(F)c3)C2)n1]

The titled compound 346 was prepared form compound 345 by reacted with methylamine, hydrochloride. LC-MS (m/z): 407.2 $[M+H]^+$. $^1H$ NMR (400 MHz, Chloroform-d) δ 10.25-10.01 (br, 1H), 7.80 (d, J=3.7 Hz, 1H), 6.82 (t, J=1.7 Hz, 1H), 6.78-6.73 (m, 2H), 6.70 (tt, J=8.8, 2.3 Hz, 1H), 5.54 (tt, J=6.7, 4.1 Hz, 1H), 5.28 (dd, J=12.2, 6.4 Hz, 1H), 4.68-4.55 (m, 2H), 4.42-4.33 (m, 1H), 4.33-4.25 (m, 1H), 3.37 (ddd, J=18.6, 12.2, 1.7 Hz, 1H), 3.00 (s, 3H), 2.72 (ddd, J=18.7, 6.4, 1.7 Hz, 1H).

Compound 347: (S)-3-((4-((1-(5-(3,5-difluorophenyl)-4,5-dihydro-1H-pyrazole-1-carbonyl)azetidin-3-yl)oxy)-5-fluoropyrimidin-2-yl)amino)propanenitrile

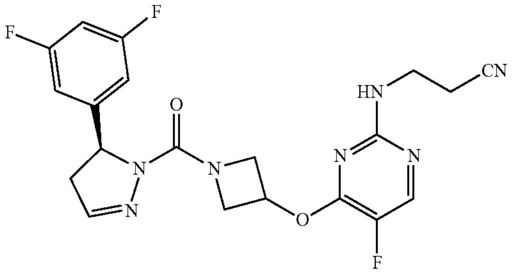 [SMILES: N#CCCNc1ncc(F)c(OC2CN(C(=O)N3N=CC[C@H]3c3cc(F)cc(F)c3)C2)n1]

The titled compound 347 was prepared in an analogous manner to the preparation of 347 Yield 12.4%. $^1$H NMR (400 MHz, Chloroform-d) δ 10.29 (s, 1H), 8.00 (s, 1H), 6.88 (s, 1H), 6.80-6.61 (m, 3H), 5.68-5.57 (m, 1H), 5.30 (dd, J=12.4, 6.0 Hz, 1H), 4.76-4.62 (m, 2H), 4.51-4.30 (m, 2H), 3.84-3.77 (m, 2H), 3.45-3.30 (m, 1H), 2.81-2.64 (m, 3H). LC-MS (m/z) 446.3 (M+H$^+$)

Compound 348: 4-(((R)-1-((S)-5-(3,5-difluorophenyl)-4,5-dihydro-1H-pyrazole-1-carbonyl)pyrrolidin-3-ylamino)pyrimidine-2-carbonitrile

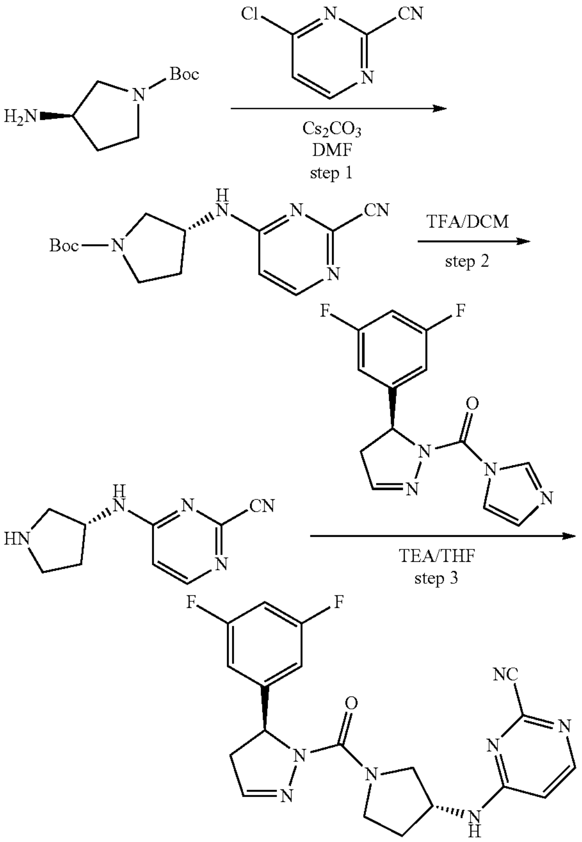

Step 1. Preparation of tert-butyl (R)3-((2-cyanopyrimidin-4-yl)amino)pyrrolidine-1-carboxylate. 100 mL dry single-necked flask tert-butyl (R)-3-aminopyrrolidine-1-carboxylate (187 mg, 1.0 mmol), 4-chloropyrimidine-2-carbonitrile (140 mg, 1.0 mmol), $Cs_2CO_3$ (978 mg, 3.0 mmol) and DMF (5 ml). The reaction system was stirred at 100° C. for 3 hours. The residue was diluted with water (500 mL) and extracted with ethyl acetate (3×500 mL). The combined organic layers were washed with brine, dried over anhydrous sodium sulfate, and filtered. The filtrate was concentrated under vacuum to afford the tert-butyl (R)-3-((2-cyanopyrimidin-4-yl)amino)pyrrolidine-1-carboxylate (yellow solid, 280 mg, Yield: 96.8percent). LC-MS (ESI) m/z: [M+H]=290.2

Step 2. Preparation of (R)-4-(pyrrolidin-3-ylamino)pyrimidine-2-carbonitrile. To a vigorously stirring mixture of tert-butyl (R)-3-((2-cyanopyrimidin-4-yl)amino)pyrrolidine-1-carboxylate (280 mg, 0.97 mmol) in DCM (10 mL) was added TFA (5 mL) dropwise. The resulting mixture was stirred at room temperature for 0.5 hour and concentrated under vacuum to afford the (R)-4-(pyrrolidin-3-ylamino)pyrimidine-2-carbonitrile (180 mg crude) as a yellow solid. LC-MS (ESI) m/z: [M+H]=190.2

Step 3. Preparation of 4-(((R)-1-((S)-5-(3,5-difluorophenyl)-4,5-dihydro-1H-pyrazole-1-carbonyl)pyrrolidin-3-yl)amino)pyrimidine-2-carbonitrile. 50 mL dry single-necked flask (R)-4-(pyrrolidin-3-ylamino)pyrimidine-2-carbonitrile (180 mg, 0.95 mmol), (S)-(5-(3,5-difluorophenyl)-4,5-dihydro-1H-pyrazol-1-yl)(1H-imidazol-1-yl)methanone (193 mg, 0.7 mmol) and TEA (7 mL) in THF (15 ml). The reaction system was refluxed for 2 hours and then concentrated. Crude product Column chromatography (eluent: petroleum ether/ethyl acetate volume ratio: 100/1 to 55/45) to give 4-(((R)-1-((S)-5-(3,5-difluorophenyl)-4,5-dihydro-1H-pyrazole-1-carbonyl)pyrrolidin-3-yl)amino)pyrimidine-2-carbonitrile 348 (white solid, 51 mg, Yield: 18.3percent). $^1$H NMR (400 MHz, Chloroform-d) δ 8.17 (d, J=5.5 Hz, 1H), 6.87 (d, J=1.7 Hz, 1H), 6.76-6.65 (m, 3H), 6.49 (d, J=6.0 Hz, 1H), 5.88 (d, J=7.2 Hz, 1H), 5.30 (dd, J=12.0, 8.5 Hz, 1H), 4.79 (d, J=74.7 Hz, 1H), 3.96 (dd, J=12.5, 4.9 Hz, 1H), 3.80-3.69 (m, 1H), 3.65 (d, J=11.5 Hz, 2H), 3.37 (ddd, J=18.6, 12.0, 1.8 Hz, 1H), 2.72 (ddd, J=18.6, 8.5, 1.6 Hz, 1H), 2.25-2.12 (m, 1H), 2.06-1.97 (m, 1H). LC-MS (ESI) m/z: [M+H]=398.2

Compound 349: 6-((1-((S)-5-(3,5-difluorophenyl)-4,5-dihydro-1H-pyrazole-1-carbonyl)azetidin-3-yl)oxy)-2-methyl-2H-benzo[b][1,4]oxazin-3(4H)-one

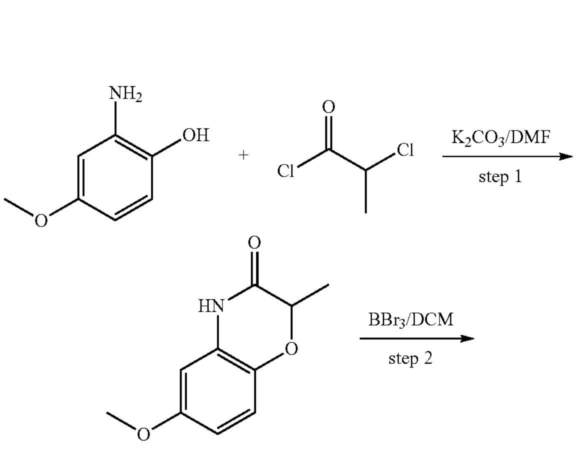

-continued

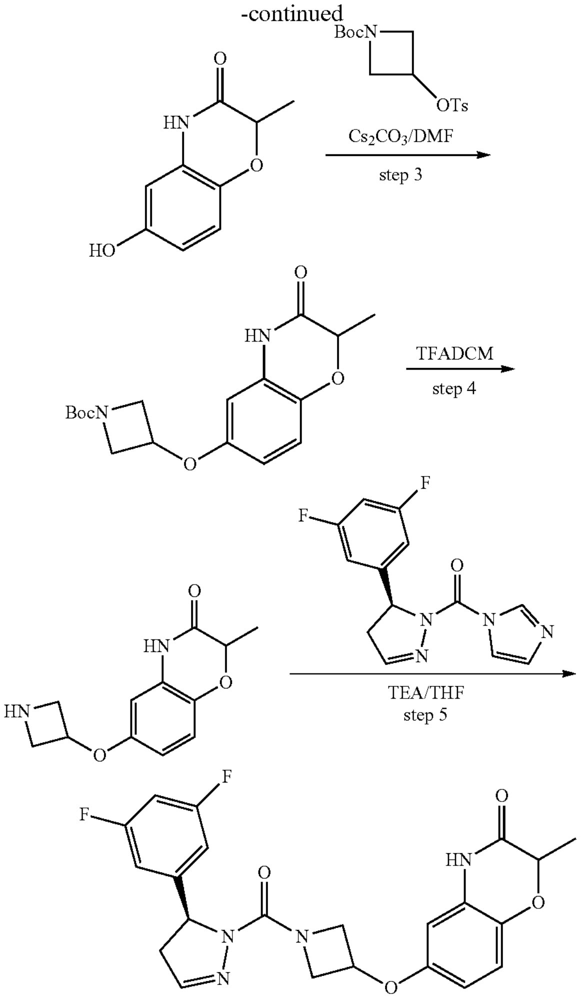

Step1: 2-amino-4-methoxyphenol (800 mg, 5.76 mmol), 2-chloropropanoyl chloride (731 mg, 5.76 mmol) and $K_2CO_3$ (1.59 g, 11.5 mmol) were dissolved in DMF (15 mL). The mixture was stirred at 100° C. overnight. The solvent was evaporated to dryness and purified by flash chromatography (PE/EA=5/1) to give 6-methoxy-2-methyl-2H-benzo[b][1,4]oxazin-3(4H)-one as a yellow solid (850 mg). Yield 76.6%. LC-MS (m/z) 194.2 ($M+H^+$).

Step2: $BBr_3$ (1.6 mL, 1.66 mmol) was added to the solution of 6-methoxy-2-methyl-2H-benzo[b][1,4]oxazin-3(4H)-one (160 mg, 0.83 mmol) in DCM (5 mL) at −78° C. The mixture was stirred at r.t. for 3 hrs. $H_2O$ was added and 90 mg of 6-hydroxy-2-methyl-2H-benzo[b][1,4]oxazin-3(4H)-one as a gray solid was obtained. Yield 60.4%

Step3: 6-hydroxy-2-methyl-2H-benzo[b][1,4]oxazin-3(4H)-one (90 mg, 0.5 mmol), tert-butyl 3-(tosyloxy)azetidine-1-carboxylate (181 mg, 0.55 mmol) and $CS_2CO_3$ (326 mg, 1.0 mmol) were dissolved in DMF (3 mL). The mixture was stirred at 100° C. for 3 hrs. The solvent was evaporated to dryness and purified by flash chromatography (PE/EA=5/1) to give tert-butyl 3-((2-methyl-3-oxo-3,4-dihydro-2H-benzo[b][1,4]oxazin-6-yl)oxy)azetidine-1-carboxylate as an colorless oil (15 mg). Yield 9.0% LC-MS (m/z) 333.2 ($M-H^+$).

Step 4 ad 5: The titled compound 349 was prepared in an analogous manner to the preparation of 192. Yield 23.1% $^1$H NMR (400 MHz, Chloroform-d) δ 8.33 (brs, 1H), 6.87 (d, J=8.8 Hz, 1H), 6.81-6.71 (m, 3H), 6.71-6.59 (m, 1H), 6.33 (dd, J=8.8, 2.8 Hz, 1H), 6.25 (d, J=2.8 Hz, 1H), 5.37-5.31 (m, 1H), 4.89-4.78 (m, 1H), 4.65-4.43 (m, 3H), 4.30-4.05 (m, 2H), 3.41-3.31 (m, 1H), 2.74-2.62 m, 1H), 1.56 (dd, J=6.8, 1.6 Hz, 3H). LC-MS (m/z) 443.2 ($M+H^+$).

Compound 350: 6-((1-((S)-5-(3,5-difluorophenyl)-4,5-dihydro-1H-pyrazole-1-carbonyl)azetidin-3-yl)oxy)-7-fluoro-2-methyl-2H-benzo[b][1,4]oxazin-3(4H)-one The titled compound 350 was prepared in an analogous manner to the preparation of 349. After Chiral HPLC separation to yield two unknown single-enantiomer 350-A and 350-B:

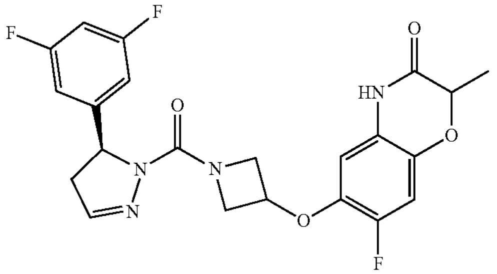 [SMILES: CC1Oc2cc(F)c(OC3CN(C(=O)N4N=CC[C@H]4c4cc(F)cc(F)c4)C3)cc2NC1=O]

(350-B) LC-MS (m/z): 461.3$[M+H]^+$. $^1$H NMR (400 MHz, Chloroform-d) δ 8.33 (s, 1H), 6.81-6.73 (m, 4H), 6.67 (tt, J=8.8, 2.3 Hz, 1H), 6.22 (d, J=7.8 Hz, 1H), 5.41 (dd, J=12.2, 6.3 Hz, 1H), 4.88-4.80 (m, 1H), 4.59 (q, J=6.8 Hz, 1H), 4.55-4.44 (m, 2H), 4.40-4.31 (m, 1H), 4.21-4.11 (m, 1H), 3.38 (ddd, J=18.6, 12.1, 1.7 Hz, 1H), 2.69 (ddd, J=18.6, 6.3, 1.8 Hz, 1H), 1.54 (d, J=6.8 Hz, 3H).

(350-A) LC-MS (m/z): 461.3$[M+H]^+$. $^1$H NMR (400 MHz, Chloroform-d) δ 8.31 (s, 1H), 6.82-6.70 (m, 4H), 6.71-6.64 (m, 1H), 6.23 (d, J=7.8 Hz, 1H), 5.41 (dd, J=12.1, 6.2 Hz, 1H), 4.88-4.80 (m, 1H), 4.57 (q, J=6.8 Hz, 1H), 4.53-4.45 (m, 2H), 4.40-4.32 (m, 1H), 4.20-4.11 (m, 1H), 3.37 (ddd, J=18.5, 12.1, 1.7 Hz, 1H), 2.69 (ddd, J=18.5, 6.2, 1.8 Hz, 1H), 1.56 (d, J=6.8 Hz, 3H).

Compound 351: 3-fluoro-5-((5S)-1(3-((7-fluoro-2-methyl-3-oxo-3,4-dihydro-2H-benzo[b][1,4]oxazin-6-yl)oxy)azetidine-1-carbonyl)-4,5-dihydro-1H-pyrazol-5. yl)benzonitrile

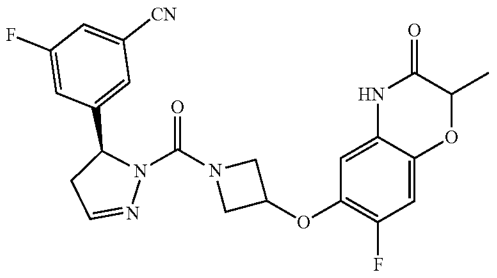 [SMILES: CC1Oc2cc(F)c(OC3CN(C(=O)N4N=CC[C@H]4c4cc(F)cc(C#N)c4)C3)cc2NC1=O]

The titled compound 351 was prepared in an analogous manner to the preparation of compound 349. LC-MS (m/z): 468.2 $[M+H]^+$. $^1$H NMR (400 MHz, Chloroform-d) δ 9.01 (s, 1H), 7.32 (s, 1H), 7.25-7.17 (m, 2H), 6.86-6.84 (m, 1H), 6.78 (d, J=11.1 Hz, 1H), 6.26 (d, J=7.4 Hz, 1H), 5.52-5.42

(m, 1H), 4.90-4.83 (m, 1H), 4.66-4.56 (m, 1H), 4.55-4.45 (m, 2H), 4.43-4.33 (m, 1H), 4.25-4.12 (m, 1H), 3.43 (ddd, J=18.7, 12.2, 1.7 Hz, 1H), 2.70 (ddd, J=18.7, 6.4, 1.7 Hz, 1H), 1.57-1.53 (m, 3H).

Compound 352: 7-fluoro-2-methyl-6-((1-((S)-5-phenyl-4,5-dihydro-1H-pyrazole-1-carbonyl)azetidin-3-yl)oxy)-2H-benzo[b][1,4]oxazin-3(4H)-one

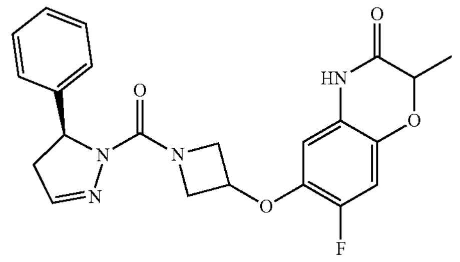 [SMILES: CC1Oc2cc(F)c(OC3CN(C(=O)N4N=CC[C@H]4c4ccccc4)C3)cc2NC1=O]

The titled compound 352 was prepared in an analogous manner to the preparation of compound 349. LC-MS (m/z): 425.2 $[M+H]^+$. $^1H$ NMR (400 MHz, Chloroform-d) δ 8.44 (d, J=10.7 Hz, 1H), 7.33-7.27 (m, 2H), 7.25-7.19 (m, 3H), 6.81 (t, J=1.7 Hz, 1H), 6.76 (d, J=11.2 Hz, 1H), 6.21 (d, J=7.8 Hz, 1H), 5.45-5.38 (m, 1H), 4.84-4.76 (m, 1H), 4.58 (qd, J=6.8, 4.3 Hz, 1H), 4.52-4.42 (m, 2H), 4.36-4.28 (m, 1H), 4.19-4.12 (m, 1H), 3.37 (ddd, J=18.6, 12.1, 1.7 Hz, 1H), 2.74 (ddd, J=18.6, 6.0, 1.7 Hz, 1H), 1.55 (dd, J=6.8, 1.3 Hz, 3H).

Compound 353: 6-((1-((S)-5-(3,5-difluorophenyl)-4,5-dihydro-1H-pyrazole-1-carbonyl)azetidin-3-yl)oxy)-2-methyl-2H-benzo[b][1,4]oxazin-3(4H)-one

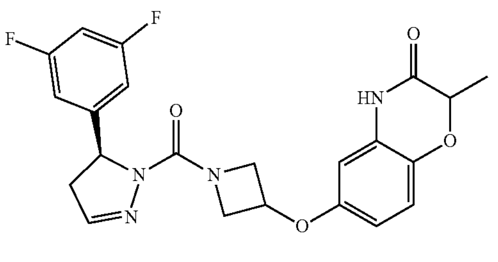 [SMILES: CC1Oc2ccc(OC3CN(C(=O)N4N=CC[C@H]4c4cc(F)cc(F)c4)C3)cc2NC1=O]

The titled compound 353 was prepared in an analogous manner to the preparation of compound 349. LC-MS (m/z): 443.2 $[M+H]^+$. $^1H$ NMR (400 MHz, Chloroform-d) δ 7.99 (s, 1H), 6.88 (d, J=8.7 Hz, 1H), 6.79-6.77 (m, 1H), 6.77-6.72 (m, 2H), 6.68 (tt, J=8.8, 2.3 Hz, 1H), 6.33 (dd, J=8.7, 2.8 Hz, 1H), 6.24 (d, J=2.8 Hz, 1H), 5.36-5.28 (m, 1H), 4.88-4.81 (m, 1H), 4.58 (qd, J=6.8, 2.2 Hz, 1H), 4.54-4.45 (m, 2H), 4.28-4.21 (m, 1H), 4.17-4.10 (m, 1H), 3.35 (ddd, J=18.6, 12.2, 1.7 Hz, 1H), 2.69 (ddd, J=18.6, 6.4, 1.7 Hz, 1H), 1.56 (dd, J=6.8, 1.4 Hz, 3H).

Compound 354: 3-fluoro-5-((5S)-1-(3-((2-methyl-3-oxo-3,4-dihydro-2H-benzo[b][1,4]oxazin-6-yl)oxy)azetidine-1-carbonyl)-4,5-dihydro-1H-pyrazol-5-yl)benzonitrile

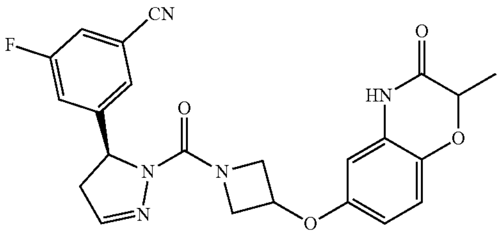 [SMILES: CC1Oc2ccc(OC3CN(C(=O)N4N=CC[C@H]4c4cc(F)cc(C#N)c4)C3)cc2NC1=O]

The titled compound 354 was prepared in an analogous manner to the preparation of compound 349. LC-MS (m/z): 450.4$[M+H]^+$. $^1H$ NMR (400 MHz, Chloroform-d) δ 8.85 (s, 1H), 7.33 (s, 1H), 7.25-7.16 (m, 2H), 6.87 (d, J=8.7 Hz, 1H), 6.82 (s, 1H), 6.36-6.30 (m, 1H), 6.28-6.22 (m, 1H), 5.47-5.36 (m, 1H), 4.89-4.79 (m, 1H), 4.62-4.44 (m, 3H), 4.34-4.21 (m, 1H), 4.20-4.08 (m, 1H), 3.46-3.33 (m, 1H), 2.68 (ddd, J=18.5, 6.5, 1.7 Hz, 1H), 1.58-1.52 (m, 3H).

Compound 355: 2-methyl-6-((1-((S)-5-phenyl-4,5-dihydro-1H-pyrazole-1-carbonyl)azetidin-3-yl)oxy)-2H-benzo[b][1,4]oxazin-3(4H)-one

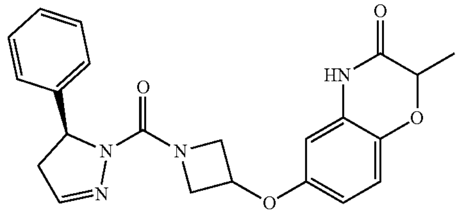 [SMILES: CC1Oc2ccc(OC3CN(C(=O)N4N=CC[C@H]4c4ccccc4)C3)cc2NC1=O]

The titled compound 355 was prepared in an analogous manner to the preparation of compound 349. LC-MS (m/z): 407.2 $[M+H]^+$. $^1H$ NMR (400 MHz, Chloroform-d) δ 8.85-8.78 (br, 1H), 7.33-7.28 (m, 2H), 7.25-7.19 (m, 3H), 6.86 (d, J=8.8 Hz, 1H), 6.80 (t, J=1.7 Hz, 1H), 6.32 (dd, J=8.8, 2.8 Hz, 1H), 6.25 (d, J=2.8 Hz, 1H), 5.38 (ddd, J=12.1, 6.1, 1.9 Hz, 1H), 4.80 (tt, J=6.4, 4.1 Hz, 1H), 4.57 (qd, J=6.8, 1.8 Hz, 1H), 4.49 (q, J=8.3 Hz, 2H), 4.27-4.20 (m, 1H), 4.15-4.08 (m, 1H), 3.36 (ddd, J=18.6, 12.1, 1.7 Hz, 2H), 2.74 (ddd, J=18.6, 6.1, 1.8 Hz, 1H), 1.55 (d, J=6.8 Hz, 3H).

Compound 356: ((S)-5-(3,5-difluorophenyl)-4,5-dihydro-1H-pyrazol-1-yl)((R)-3-((6-methoxypyridin-2-yl)oxy)pyrrolidin-1-yl)methanone

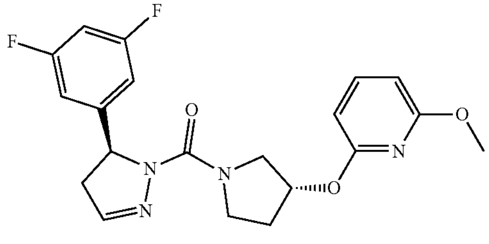 [SMILES: COc1cccc(O[C@@H]2CCN(C(=O)N3N=CC[C@H]3c3cc(F)cc(F)c3)C2)n1]

The titled compound 356 was prepared in an analogous manner to the preparation of 256 yield: 46.3%. $^1$H NMR (400 MHz, Chloroform-d) δ 7.48 (t, J=8.0 Hz, 1H), 6.85-6.75 (m, 2H), 6.71-6.64 (m, 1H), 6.29 (dd, J=9.6, 8.0 Hz, 2H), 5.55 (t, J=4.0 Hz, 1H), 5.32 (dd, J=12.0, 8.8 Hz, 1H), 3.98 (dd, J=13.2, 4.4 Hz, 1H), 3.88 (s, 3H), 3.80-3.59 (m, 2H), 3.36-3.25 (m, 1H), 2.74-2.44 (m, 3H), 2.28-2.19 (m, 1H), 2.17-2.05 (m, 1H). LC-MS (m/z) 403.2 (M+H$^+$).

Compound 357: 6-(((R)-1-((S)-5-(3,5-difluorophenyl)-4,5-dihydro-1H-pyrazole-1-carbonyl)pyrrolidin-3-yl)oxy)pyridin-2(1H)-one

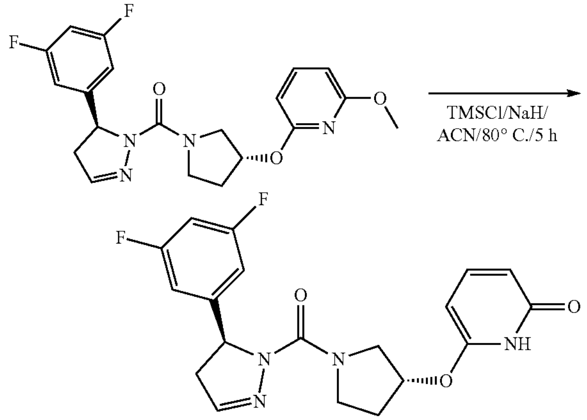

To a solution of ((S)-5-(3,5-difluorophenyl)-4,5-dihydro-1H-pyrazol-1-yl)((R)-3-((6-methoxypyridin-2-yl)oxy)pyrrolidin-1-yl)methanone (10 mg, 0.025 mmol) and NaI (11 mg, 0.075 mmol) in ACN (3 mL) TMSCl (8 mg, 0.075 mmol) was added. The mixture was stirred at 80° C. for 5 hrs. concentrated and the residue was purified by TLC (PE/EA=1/1) to give 6-(((R)-1-((S)-5-(3,5-difluorophenyl)-4,5-dihydro-1H-pyrazole-1-carbonyl)pyrrolidin-3-yl)oxy)pyridin-2(1H)-one 357 as an colorless oil (6 mg., 61.9%). $^1$H NMR (400 MHz, Chloroform-d) δ 7.43 (s, 1H), 6.82-6.75 (m, 2H), 6.72-6.53 (m, 1H), 6.23 (s, 1H), 5.89 (d, J=7.4 Hz, 1H), 5.36-5.25 (m, 1H), 5.18 (s, 1H), 4.07-3.80 (m, 2H), 3.73 (d, J=12.0 Hz, 3H), 3.31 (dd, J=18.4, 11.9 Hz, 1H), 2.65 (dd, J=18.3, 8.9 Hz, 1H), 2.30-2.05 (m, 2H). LC-MS (m/z) 389.3 (M+H$^+$).

Compound 358: ((S)-5-(3,5-difluorophenyl)-4,5-dihydro-1H-pyrazol-1-yl)(R)-3-(6(2-morpholinoethyl)amino)pyridin-2-yl)oxy)pyridin-1-yl)methanone

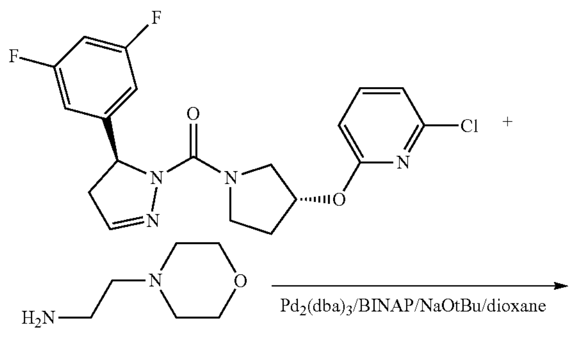

-continued

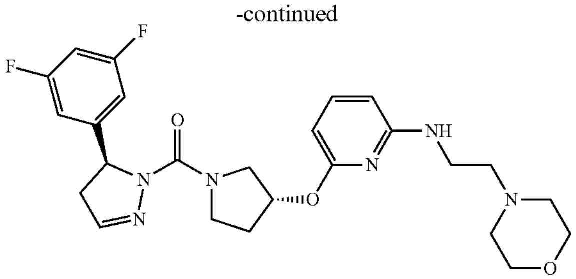

((R)-3-((6-chloropyridin-2-yl)oxy)pyrrolidin-1-yl)((S)-5-(3,5-difluorophenyl)-4,5-dihydro-1H-pyrazol-1-yl)methanone (20 mg, 0.05 mmol), 2-morpholinoethan-1-amine (13 mg, 0.1 mmol), NaOtBu (7.2 mg, 0.075 mmol), $Pd_2(dba)_3$ (4.5 mg, 0.005 mmol) and BINAP (3 mg, 0.005 mmol) were added to dioxane (3 mL) under N2 atmosphere. The mixture was stirred at 90° C. for overnight. concentrated and the residue was purified by TLC (DCM/MeOH=20/1) to give the title compound 358 as brown oil (5 mg, 20.0%)

$^1$H NMR (400 MHz, Chloroform-d) δ 7.43 (t, J=7.6 Hz, 1H), 7.35-7.17 (m, 1H). 6.80 (d, J=6.4 Hz, 2H), 6.68 (t, J=8.4 Hz, 1H), 6.16 (d, J=8.0 Hz, 1H), 6.03 (d, J=7.6 Hz, 1H), 5.37-5.30 (m, 1H), 4.31-3.67 (m, 9H), 3.66-3.42 (m, 3H), 3.41-3.15 (m, 3H), 3.10-2.77 (m, 3H), 2.72-2.58 (m, 1H), 2.30-2.04 (m, 2H).

LC-MS (m/z) 501.3 (M+H$^+$).

Compound 359: 2-(((R)-1-((S)-5-(3,5-difluorophenyl)-4,5-dihydro-1H-pyrazole-1-carbonyl)pyrrolidin-3-yl)oxy)pyrimidine-4-carbonitrile

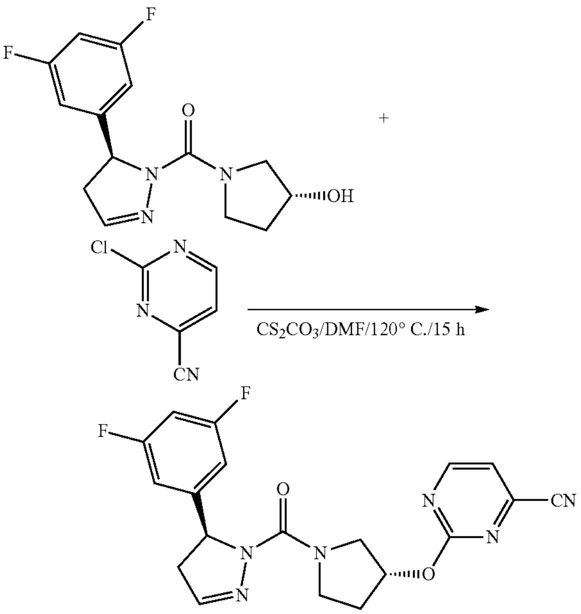

((S)-5-(3,5-difluorophenyl)-4,5-dihydro-1H-pyrazol-1-yl)((R)-3-hydroxypyrrolidin-1-yl)methanone (70 mg, 0.24 mmol), 2-chloropyrimidine-4-carbonitrile (40 mg, 0.29 mmol) and $CS_2CO_3$ (156 mg, 0.48 mmol) were dissolved in DMF (3 mL). the mixture was stirred at 120° C. overnight. concentrated and purified by TLC (DCM/MeOH=25/1) to give the titled compound 359 as colorless oil (12 mg, 12.6%)

$^1$H NMR (400 MHz, Chloroform-d) δ 8.51 (d, J=5.6 Hz, 1H), 6.90 (d, J=5.6 Hz, 1H), 6.83-6.62 (m, 3H), 5.75-5.65 (m, 1H), 5.32 (dd, J=12.0, 8.8 Hz, 1H), 4.13-3.92 (m, 2H), 3.89-3.63 (m, 3H), 3.42-3.24 (m, 1H), 2.74-2.61 (m, 1H), 2.30-2.12 (m, 2H). LC-MS $[M+H]^+$:399.2. LC-MS (m/z) 399.2 ($M+H^+$).

Compound 360: 6-(((R)-1-((S)-5-(3,5-difluorophenyl)-4,5-dihydro-1H-pyrazole-1-carbonyl)pyrrolidin-3-yl)oxy)pyrimidine-4-carbonitrile

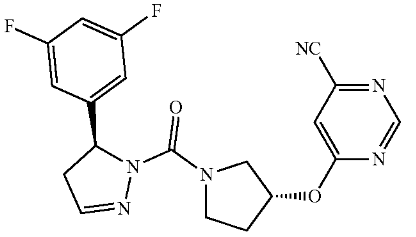 [SMILES: N#Cc1cc(O[C@@H]2CCN(C(=O)N3N=CC[C@H]3c3cc(F)cc(F)c3)C2)ncn1]

The titled compound 360 was prepared in an analogous manner to the preparation of 256. Yield: 12.6%. $^1$H NMR (400 MHz, Chloroform-d) δ 8.84 (d, J=1.1 Hz, 1H), 7.09 (d, J=1.2 Hz, 1H), 6.84-6.66 (m, 3H), 5.71 (t, J=4.6 Hz, 1H), 5.32 (dd, J=12.0, 8.8 Hz, 1H), 4.01 (dd, J=13.6, 4.4 Hz, 1H), 3.93-3.71 (m, 2H), 3.60-3.42 (m, 2H), 3.40-3.26 (m, 1H), 2.73-2.62 (m, 1H), 2.29-2.13 (m, 2H).

LC-MS (m/z) 399.2 ($M+H^+$).

Compound 361: 6-(((R)-1-((S)-5-(3,5-difluorophenyl)-4,5-dihydro-1H-pyrazole-1-carbonyl)pyridin-3-yl)oxy)pyrimidine-4-carboxamide

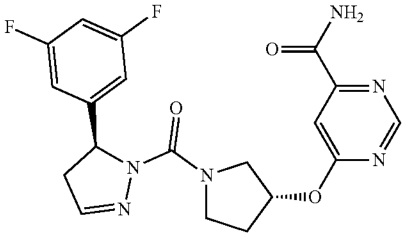 [SMILES: NC(=O)c1cc(O[C@@H]2CCN(C(=O)N3N=CC[C@H]3c3cc(F)cc(F)c3)C2)ncn1]

The titled compound 361 was prepared in an analogous manner to the preparation of 360. yield 14.0% $^1$H NMR (400 MHz, Chloroform-d) δ 8.78 (s, 1H), 7.92 (s, 1H), 7.51 (s, 1H), 6.86-6.59 (m, 4H), 5.70 (t, J=4.4 Hz, 1H), 5.40-5.26 (m, 1H), 4.12-3.85 (m, 2H), 3.83-3.55 (m, 3H), 3.44-3.25 (m, 1H), 2.75-2.63 (m, 1H), 2.33-2.11 (m, 2H). LC-MS (m/z) 417.2 ($M+H^+$).

Compound 362: 4-(((R)-1-((S)-5-(3,5-difluorophenyl)-4,5-dihydro-1H-pyrazole-1-carbonyl)pyrrolidin-3-yl)oxy)pyrimidine-2-carbonitrile

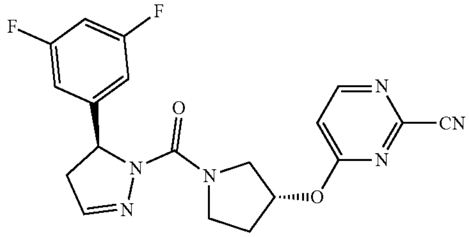 [SMILES: N#Cc1nccc(O[C@@H]2CCN(C(=O)N3N=CC[C@H]3c3cc(F)cc(F)c3)C2)n1]

The titled compound 362 was prepared in an analogous manner to the preparation of 256. yield: 22.2% $^1$H NMR (400 MHz, Chloroform-d) δ 8.51 (d, J=6.0 Hz, 1H), 6.90 (d, J=6.0 Hz, 1H), 6.85-6.72 (m, 2H), 6.72-6.56 (m, 1H), 5.73-5.67 (m, 1H), 5.40-5.24 (m, 1H), 4.03 (dd, J=13.6, 4.4 Hz, 1H), 3.92-3.64 (m, 3H), 3.63-2.3.43 (m, 1H), 3.41-3.28 (m, 1H), 2.714-3.63 (m, 1H), 2.31-2.03 (m, 2H). LC-MS (m/z) 399.2 ($M+H^+$).

Compound 363: ((S)-5-(3,5-difluorophenyl)-4,5-dihydro-1H-pyrazol-1-yl)((R)-3-((5-fluoro-4-methoxypyrimidin-2-yl)oxy)pyrrolidin-1-yl)methanone

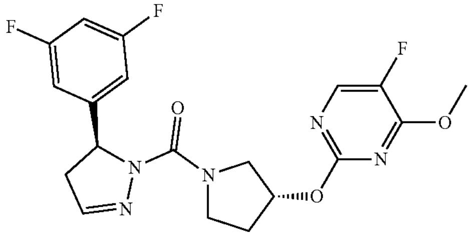 [SMILES: COc1nc(O[C@@H]2CCN(C(=O)N3N=CC[C@H]3c3cc(F)cc(F)c3)C2)ncc1F]

The titled compound 363 was prepared in an analogous manner to the preparation of 256. Yield 3.0%. $^1$H NMR (400 MHz, Chloroform-d) δ 8.07 (d, J=2.4 Hz, 1H), 6.83-6.73 (m, 2H), 6.72-6.60 (m, 1H), 5.46 (t, J=4.4 Hz, 1H), 5.35-5.27 (m, 1H), 4.05 (s, 3H), 3.95-3.85 (m, 1H), 3.82-3.70 (m, 2H), 3.60-3.43 (m, 2H), 3.37-3.26 (m, 1H), 2.72-2.61 (m, 1H), 2.35-2.05 (m, 2H). LC-MS (m/z) 442.3 ($M+H^+$).

Compound 364: 4-(((R)-1-((S)-5-(3,5-difluorophenyl)-4,5-dihydro-1H-pyrazole-1-carbonyl)pyrrolidin-3-yl)oxy)pyrimidine-2-carboxamide

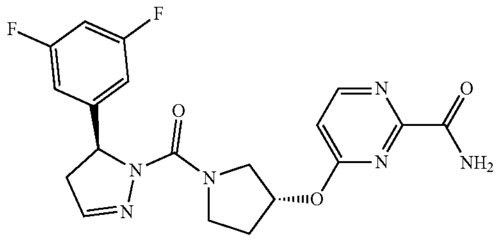 [SMILES: NC(=O)c1nccc(O[C@@H]2CCN(C(=O)N3N=CC[C@H]3c3cc(F)cc(F)c3)C2)n1]

The titled compound 364 was prepared in 50% yield from compound 363 by hydrolyzed using 1N NaOH in MeOH. $^{1}H$ NMR (400 MHz, Chloroform-d) δ 8.56 (d, J=5.6 Hz, 1H), 7.69 (s, 1H), 6.93-6.72 (m, 3H), 6.71-6.54 (m, 1H), 6.08 (s, 1H), 5.87 (s, 1H), 5.36-5.25 (m, 1H), 4.03 (dd, J=13.2, 4.2 Hz, 1H), 3.93-3.76 (m, 2H), 3.76-3.58 (dd, J=17.2, 8.0 Hz, 2H), 3.39-3.26 (m, 1H), 2.72-2.60 (m, 1H), 2.30-2.11 m, 2H). LC-MS (m/z) 417.2 ($M+H^{+}$).

Compound 365:6-chloro-5-(((R)-1-((S)-5-(3,5-difluorophenyl)-4,5-dihydro-1H-pyrazole-1-carbonyl)pyrrolidin-3-yl)oxy)picolinonitrile

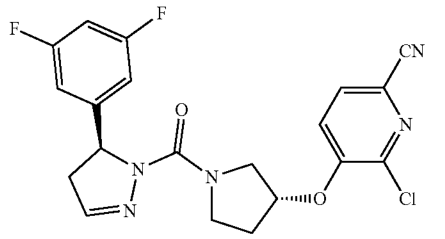 [SMILES: N#Cc1ccc(O[C@@H]2CCN(C(=O)N3N=CC[C@H]3c3cc(F)cc(F)c3)C2)c(Cl)n1]

The titled compound 365 was prepared in an analogous manner to the preparation of 256. Yield 9.3%. $^{1}H$ NMR (400 MHz, Chloroform-d) δ 7.62 (dd, J=8.4, 1.2 Hz, 1H), 7.22 (d, J=8.3 Hz, 1H), 6.88-6.74 (m, 2H), 6.73-6.63 (m, 1H), 5.31 (dd, J=12.0, 8.8 Hz, 1H), 5.01 (t, J=4.4 Hz, 1H), 4.14-3.89 (m, 2H), 3.88-3.58 (m, 3H), 3.39-3.28 (m, 1H), 2.74-2.62 (m, 1H), 2.37-2.10 (m, 2H). LC-MS (m/z) 432.2 ($M+H^{+}$).

Compound 366: tert-butyl (4-(((R)1-((S)-5-(3,5-difluorophenyl)-4,5-dihydro-1H-pyrazole-1-carbonyl)pyrrolidin-3-yl)oxy)pyrimidin-2-yl)(methyl) carbamate

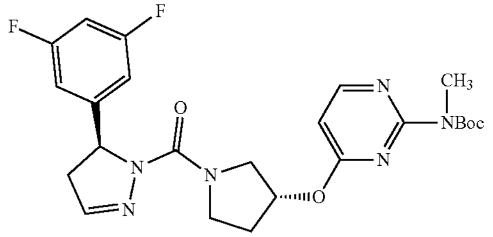 [SMILES: CN(C(=O)OC(C)(C)C)c1nccc(O[C@@H]2CCN(C(=O)N3N=CC[C@H]3c3cc(F)cc(F)c3)C2)n1]

The titled compound 366 was prepared in an analogous manner to the preparation of 256. Yield 66.7% $^{1}H$ NMR (400 MHz, Chloroform-d) δ 8.35 (dd, J=5.6, 0.8 Hz, 1H), 6.89-6.74 (m, 2H), 6.72-6.62 (m, 1H), 6.40 (dd, J=5.6, 0.8 Hz, 1H), 5.65 (t, J=4.4 Hz, 1H), 5.31 (dd, J=12.0, 4.4 Hz, 1H), 3.98 (dd, J=13.2, 4.4 Hz, 1H), 3.93-3.78 (m, 2H), 3.76-3.61 (m, 2H), 3.38 (s, 3H), 3.35-3.26 (m, 1H), 2.72-2.62 (m, 1H), 2.28-2.05 (m, 2H), 1.53 (s, 9H). LC-MS (m/z) 503.3 ($M+H^{+}$)

Compound 367: ((R)-3-((2-aminopyrimidin-4-yl)oxy)pyrrolidin-1-yl)((S)-5-(3,5-difluorophenyl)-4,5-dihydro-1H-pyrazol-1-yl)methanone

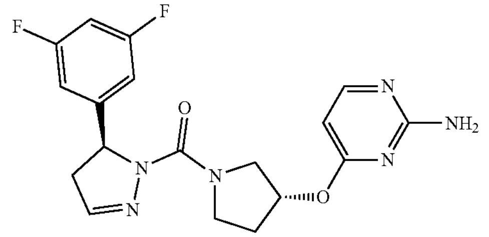 [SMILES: Nc1nccc(O[C@@H]2CCN(C(=O)N3N=CC[C@H]3c3cc(F)cc(F)c3)C2)n1]

The titled compound 367 was prepared in an analogous manner to the preparation of 256. Yield 94.1%. $^{1}H$ NMR (400 MHz, Chloroform-d) δ 8.79 (s, 1H), 7.87 (s, 1H), 6.79 (d, J=8.4 Hz, 2H), 6.69 (t, J=8.8 Hz, 1H), 6.26 (s, 1H), 6.06 (s, 1H), 5.68 (s, 1H), 5.31 (t, J=10.4 Hz, 1H), 4.07-3.96 (m, 1H), 3.94-3.79 (m, 2H), 3.78-3.64 (m, 2H), 3.34 (dd, J=18.4, 11.6 Hz, 1H), 2.70 (dd, J=18.4, 8.4 Hz, 1H), 2.29-2.13 (m, 2H). LC-MS (m/z) 389.2 ($M+H^{+}$)

Compound 368: N-(4-(((R)-1-((S)-5-(3,5-difluorophenyl)-4,5-dihydro-H-pyrazole-1-carbonyl)pyrrolidin-3-yl)oxy)pyrimidin-2-yl)acetamide

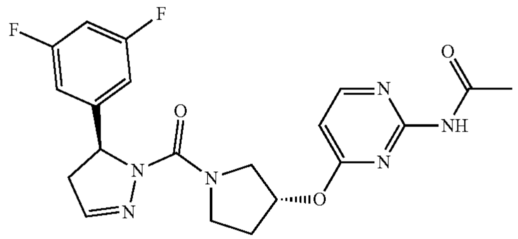 [SMILES: CC(=O)Nc1nccc(O[C@@H]2CCN(C(=O)N3N=CC[C@H]3c3cc(F)cc(F)c3)C2)n1]

The titled compound 368 was prepared in 40% yield from compound 367 by acetylation reaction. LC-MS (m/z) 431.3 ($M+H^{+}$)

Compound 369: N-(4-(((R)-1-((S)-5-(3,5-difluorophenyl)-4,5-dihydro-1H-pyrazole-1-carbonyl)pyrrolidin-3-yl)oxy)pyrimidin-2-yl)cyclopropanecarboxamide

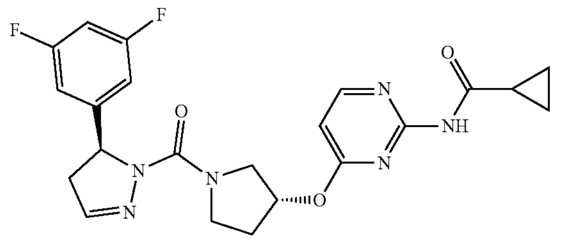 [SMILES: O=C(Nc1nccc(O[C@@H]2CCN(C(=O)N3N=CC[C@H]3c3cc(F)cc(F)c3)C2)n1)C1CC1]

The titled compound 369 was prepared in 67.6% yield from compound 367 by acylation reaction. $^{1}H$ NMR (400 MHz, Chloroform-d) δ 8.45 (s, 1H), 8.25 (d, J=5.8 Hz, 1H), 6.87-6.74 (m, 2H), 6.72-6.62 (m, 1H), 6.40 (d, J=5.8 Hz, 1H), 5.62 (t, J=4.4 Hz, 1H), 5.31 (dd, J=12.0, 9.6 Hz, 1H), 3.97 (dd, J=13.3, 4.4 Hz, 1H), 3.90-3.76 (m, 2H), 3.75-3.55 (m, 2H), 3.37-3.27 (m, 1H), 2.71-2.63 m, 1H), 2.29-2.05 (m, 2H), 1.67-1.57 (m, 1H), 1.20-1.14 (m, 2H), 0.98-0.83 (m, 2H). LC-MS (m/z) 457.3 ($M+H^+$)

Compound 370: ((S)-5-(3,5-difluorophenyl)-4,5-dihydro-1H-pyrazol-1-yl)((R)-3-((2-methylamino)pyrimidin-4-yl)oxy)pyrrolidin-1-yl)methanone

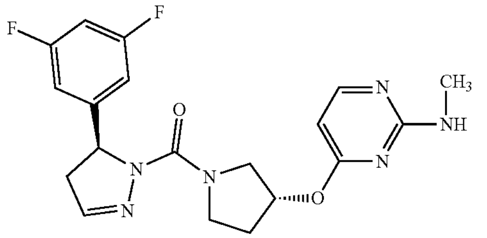 [SMILES: CNc1nccc(O[C@@H]2CCN(C(=O)N3N=CC[C@H]3c3cc(F)cc(F)c3)C2)n1]

The titled compound 370 was prepared in an analogous manner to the preparation of 256 Yield 88.2%. $^1H$ NMR (400 MHz, Chloroform-d) δ 8.85 (s, 1H), 7.83 (d, J=6.4 Hz, 1H), 6.86-6.75 (m, 2H), 6.72-6.64 (m, 1H), 6.15 (d, J=6.0 Hz, 1H), 5.72 (s, 1H), 5.32 (dd, J=12.0, 8.8 Hz, 1H), 4.10-3.99 (m, 1H), 3.95-3.80 (m, 2H), 3.79-3.62 (m, 2H), 3.34 (dd, J=18.4, 11.9 Hz, 1H), 3.07 (d, J=4.0 Hz, 3H), 2.70 (dd, J=18.4, 8.8 Hz, 1H), 2.35-2.16 (m, 2H). LC-MS (m/z) 403.2 ($M+H^+$)

Compound 371: (S)-(5-(3,5-difluorophenyl)-4,5-dihydro-1H-pyrazol-1-yl)(3-(2-fluoro-5-((2-morpholinoethyl)amino)benzylidene)azetidin-1-yl)methanone

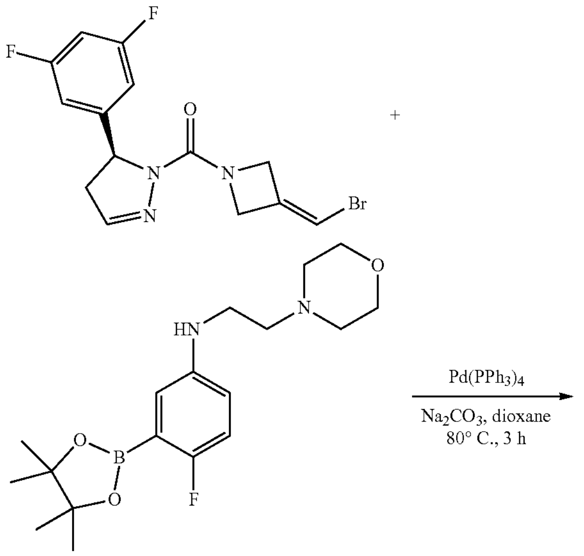

-continued

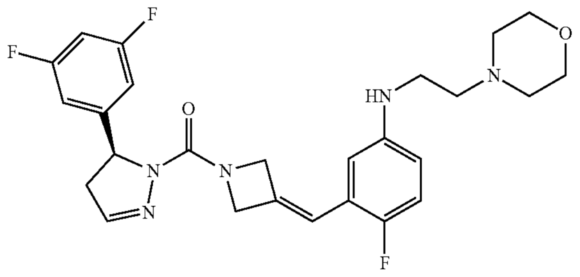

(S)-(3-(bromomethylene)azetidin-1-yl)(5-(3,5-difluorophenyl)-4,5-dihydro-1H-pyrazol-1l-yl)methanone (51 mg, 0.142 mmol) was dissolved in dioxane (3 mL) and water (1.5 mL). Followed by the addition of 4-fluoro-N-(2-morpholinoethyl)-3-(4,4,5,5-tetramethyl-1,3,2-dioxaborolan-2-yl) aniline (50 mg, 0.142 mmol) and $Na_2CO_3$ (30 mg, 0.285 mmol), then the reaction mixture was degassed with argon for three times and stirred at 80° C. for 3 h. EtOAc (150 mL) was added and stirred at 20° C. Followed by $NaHCO_3$ aqueous solution (150 mL). The organic layers were washed with water (100 mL×3) and brine (100 mL), dried with anhydrous $Na_2SO_4$, filtered and concentrated under vacuum. The crude purified by Pre-HPLC to give 10 mg of the titled compound 371 as a white solid. Yield: 14.3%. Mass (ESI): m/z calcd for $C_{26}H_{28}F_3N_5O_2$ 499.2, found 500.1 $[M+H]^+$. $^1H$ NMR (400 MHz, $CDCl_3$) δ (ppm): 7.67 (d, J=1.9 Hz, 1H), 6.99 (dd, J=11.5, 1.9 Hz, 1H), 6.83-6.80 (m, 1H), 6.78-6.62 (m, 3H), 6.10 (s, 1H), 5.30 (dd, J=12.1, 6.4 Hz, 1H), 3.97 (t, J=4.9 Hz, 8H), 3.65-3.46 (m, 1H), 3.44-3.28 (m, 3H), 3.11-2.92 (m, 1H), 2.74-2.67 (m, 1H), 1.24 (s, 6H).

Compound 372: (S)-5-((1-(5-(3,5-difluorophenyl)-4,5-dihydro-1H-pyrazole-1-carbonyl)azetidin-3-yildene)methyl)-6-fluorobenzo[d]oxazol-2(3H)-one

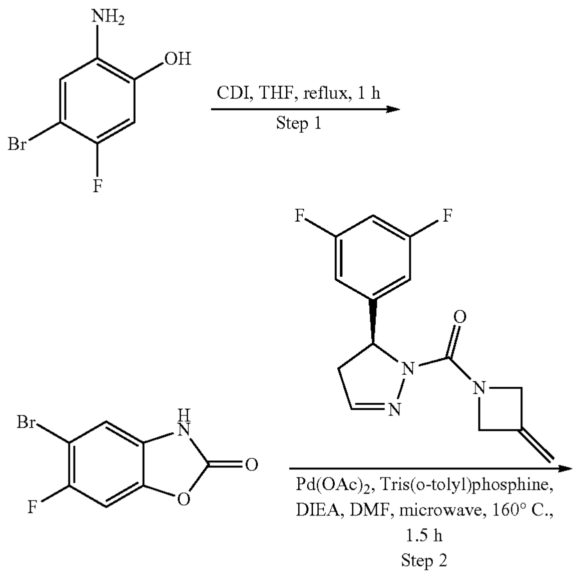

-continued

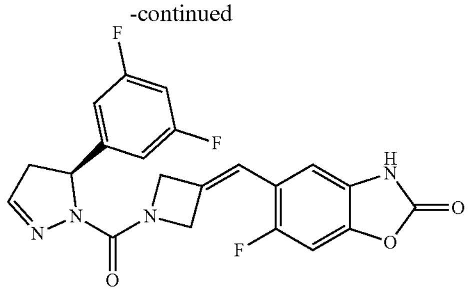

Step 1: 2-amino-4-bromo-5-fluorophenol (300 mg, 1.46 mmol) was dissolved in 12 ml dry THF. CDI (283 mg, 1.75 mmol) was added to the above solution at room temperature. The mixture was heated to reflux for 1 hour. The resulting solution was concentrated in vacuo, purified by silica gel chromatography to afford 300 mg of 5-bromo-6-fluorobenzo [d]oxazol-2(3H)-one as a yellow solid. yield: 89%.

Step 2: The title compound (S)-5-((1-(5-(3,5-difluorophenyl)-4,5-dihydro-1H-pyrazole-1-carbonyl)azetidin-3-ylidene)methyl)-6-fluorobenzo[d]oxazol-2(3H)-one (10 mg) was prepared in a yield of 18% as white solid from 5-bromo-6-fluorobenzo[d]oxazol-2(3H)-one and (S)-(5-(3,5-difluorophenyl)-4,5-dihydro-1H-pyrazol-1-yl)(3-methyleneazetidin-1-yl)methanone according to the procedure outlined for 372. LC-MS (m/z): 429.1[M+H]$^+$. $^1$H NMR (400 MHz, Chloroform-d) δ 9.99-9.63 (br, 1H), 6.97 (d, J=9.2 Hz, 1H), 6.88 (s, 1H), 6.82-6.74 (m, 2H), 6.72-6.63 (m, 2H), 6.49 (s, 1H), 5.66-5.48 (m, 1H), 5.16-4.81 (m, 4H), 3.54-3.36 (m, 1H), 2.82-2.66 (m, 1H).

Compound 373: (S)-3-(1-(3-((5-fluoro-2-oxoindolin-6-yl)methylene)azetidine-1-carbonyl)-4,5-dihydro-1H-pyrazol-5-yl)benzonitrile

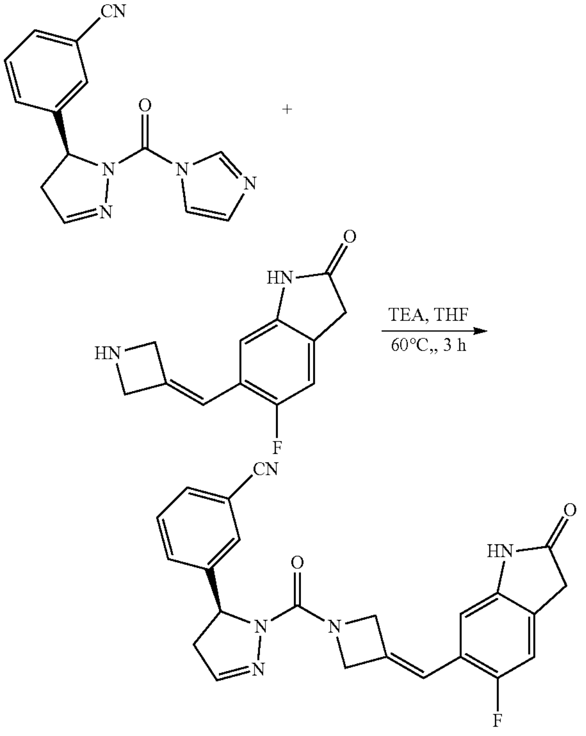

The titled compound 373 was prepare in 28.1% yield from 6-(azetidin-3-ylidenemethyl)-5-fluoroindolin-2-one according to the procedure outlined for compound 203. Mass (ESI): m/z calcd for $C_{23}H_{18}FN_5O_2$ 415.1, found 416.0 [M+H]$^+$.

$^1$H NMR (400 MHz, $CDCl_3$) δ (ppm): 9.77 (s, 1H), 7.60-7.44 (m, 3H), 6.98-6.83 (m, 3H), 6.58 (d, J=6.1 Hz, 1H), 6.43 (s, 1H), 5.39-5.34 (dd, J=12.2, 6.5 Hz, 1H), 4.97-4.85 (m, 2H), 3.66-3.63 (m, 1H), 3.47-3.40 (m, 1H), 2.88-2.70 (m, 2H), 1.47-1.02 (m, 2H).

Compound 374: (S)-5-((1(5-(3,5-difluorophenyl)-4,5-dihydro-1H-pyrazole-1-carbonyl)azetidin-3-ylidene)methyl)benzo[d]oxazol-2(3H)-one

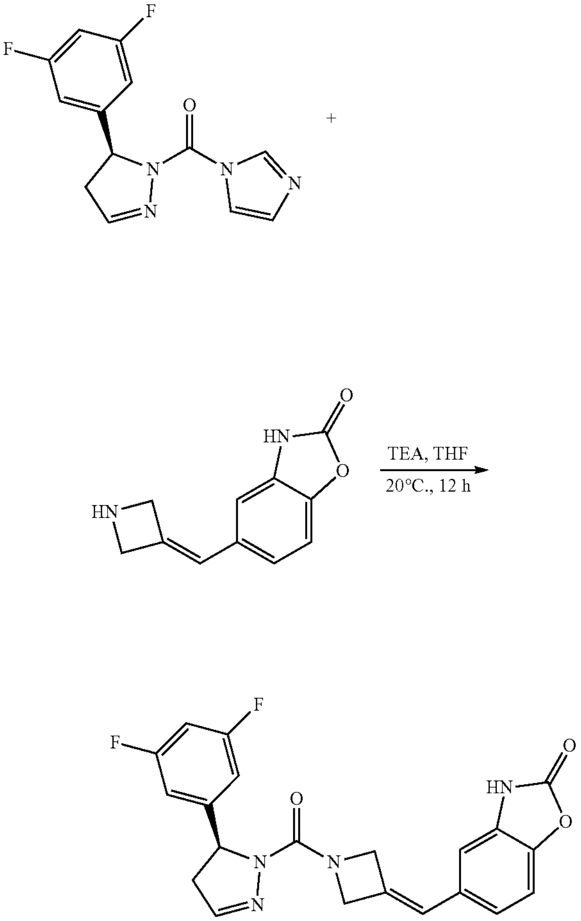

The titled compound 374 was prepare in 47.3% yield from 5-(azetidin-3-ylidenemethyl)benzo[d]oxazol-2(3H)-one according to the procedure outlined for compound 203. Mass (ESI): m/z calcd for $C_{21}H_{16}F_2N_4O_3$ 410.1, found 411.0 [M+H]$^+$.

$^1$H NMR (400 MHz, DMSO-$d_6$) δ (ppm): 11.57 (s, 1H), 7.25 (d, J=8.3 Hz, 1H), 7.13-7.02 (m, 2H), 6.97-6.85 (m, 3H), 6.83 (d, J=1.7 Hz, 1H), 6.36-6.34 (m, 1H), 5.26 (dd, J=12.1, 6.7 Hz, 1H), 4.96 (s, 2H), 4.71 (s, 2H), 3.39 (ddd, J=18.7, 12.2, 1.7 Hz, 1H), 2.64 (ddd, J=18.6, 6.7, 1.8 Hz, 1H).

Compound 375: (S)-(5-(3,5-difluorophenyl)-4,5-dihydro-1H-pyrazol-1-yl)(3-((4,6-dihydropyrrolo[3,4-c]pyrazol-5(1H)-yl)methyl)azetidin-1-yl)methanone

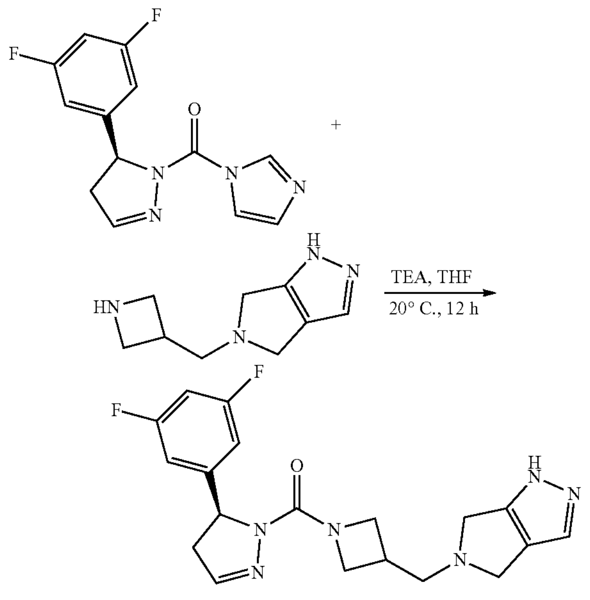

The titled compound 375 was prepare in 45.2% yield from 5-(azetidin-3-ylmethyl)-1,4,5,6-tetrahydropyrrolo[3,4-c]pyrazole according to the procedure outlined for compound 203. Mass (ESI): m/z calcd for $C_{19}H_{20}F_2N_6O$ 386.2, found 386.1 $[M+H]^+$.

$^1H$ NMR (400 MHz, DMSO-$d_6$) δ (ppm): 12.75 (s, 1H), 7.53 (s, 1H), 7.10 (tt, J=9.3, 2.4 Hz, 1H), 7.05-6.94 (m, 1H), 6.94-6.75 (m, 2H), 5.20 (dd, J=12.1, 6.6 Hz, 1H), 4.14 (d, J=7.5 Hz, 6H), 3.85-3.76 (m, 2H), 3.50-3.18 (m, 2H), 3.08 (q, J=7.3 Hz, 2H), 2.95-2.88 (m, 1H), 2.62 (ddd, J=18.7, 6.6, 1.8 Hz, 1H).

Compound 376: (S)-(3-((3,5-difluoro-1H-indazol-6-yl)oxy)azetidin-1-yl)(5-(3,5-difluorophenyl)-4,5-dihydro-1H-pyrazol-1-yl)methanone

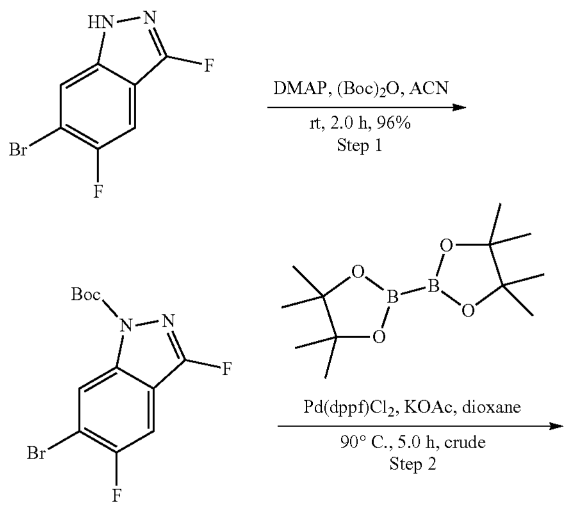

-continued

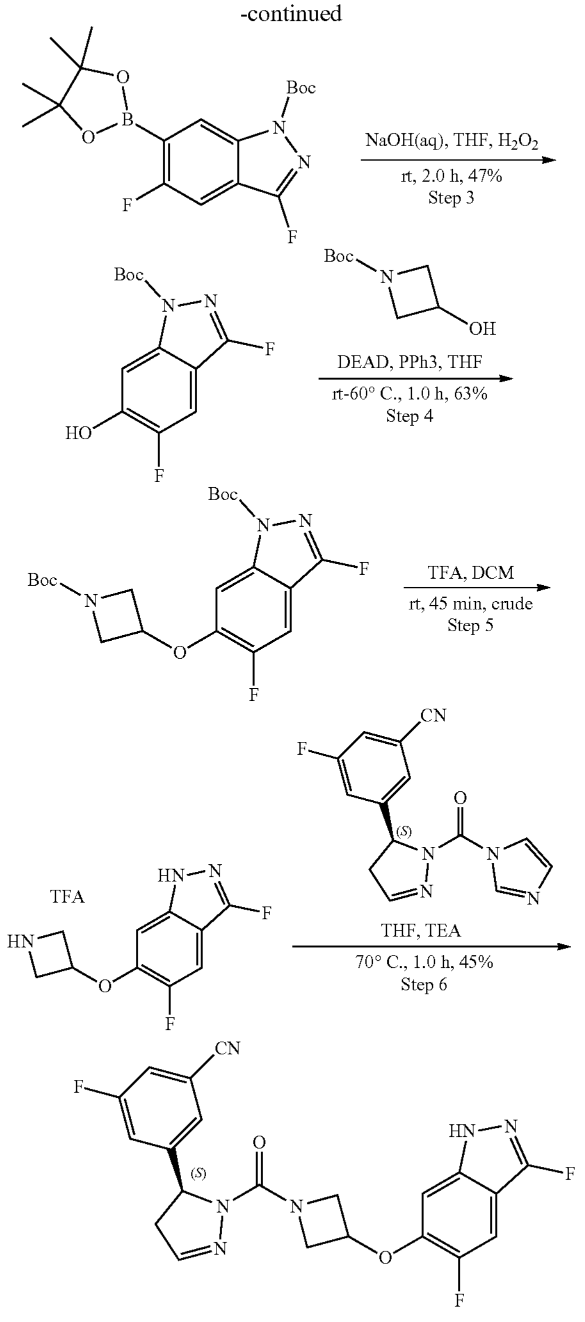

Step 1: tert-butyl 6-bromo-3,5-difluoro-1H-indazole-1-carboxylate. 6-bromo-3,5-difluoro-1H-indazole (4.0 g, 17.16 mmol) was dissolved in 40 ml of dry ACN. $(Boc)_2O$ (5.6 g, 25.57 mmol), DMAP (208 mg, 1.71 mmol) were added to the above solution under nitrogen at room temperature. The mixture was stirred for 1 hour at room temperature. The mixture was extracted with EA, washed with brine, dried ($Na_2SO_4$), and concentrated in vacuo. Purification by silica gel chromatography to give the titled compound (5.5 g, 96%) as a yellow solids. (ES, m/s): 333.1 $[M+H]^+$ Step 2: tert-butyl 3,5-difluoro-6-(4,4,5,5-tetramethyl-1,3,2-dioxaborolan-2-yl)-1H-Indazole-1-carboxylate tert-butyl 6-bromo-3,5-difluoro-1H-indazole-1-carboxylate (5.0 g, 15.01 mmol) was dissolved in 100 ml of dry dioxane. 4,4,4',4',5,5,5',5'-octamethyl-2,2'-bi(1,3,2-dioxaborolane)

(5.7 g, 22.53 mmol), $Pd(dppf)Cl_2$ (1.09 g, 1.49 mmol), KOAc (3.0 g, 30.61 mmol) were added to the above solution under nitrogen at room temperature. The mixture was stirred for 5.0 hours at 90 degrees C. The mixture was extracted with EA, washed with brine, dried ($Na_2SO_4$), and concentrated in vacuo to give the desired compound (9 g, crude) as brown oil which was used for next step without further purification. (ES, m/s): 281.1 $[M+H]^+$ Step 3: tert-butyl 3,5-difluoro-6-hydroxy-1H-indazole-1-carboxylate. tert-butyl 3,5-difluoro-6-(4,4,5,5-tetramethyl-1,3,2-dioxaborolan-2-yl)-1H-indazole-1-carboxylate (9.0 g, crude) was dissolved in 100 ml of dry THF and NaOH(aq) (50 mL, 1 N). $H_2O_2$ (50 mL, 3% in $H_2O$) was added to the above solution at room temperature. The mixture was stirred for 2.0 hours at room temperature. The pH of resulting mixture was adjusted to 3-4 with HCl (aq, 1N). The mixture was extracted with EA, washed with brine, dried ($Na_2SO_4$), and concentrated in vacuo. Purification by silica gel chromatography to give the titled compound (1.9 g, 47%) as a yellow oil. (ES, m/s): 271.2 $[M+H]^+$ Step 4: tert-butyl 6-((1-(tert-butoxycarbonyl)azetidin-3-yl)oxy)-3,5-difluoro-1H-Indazole-1-carboxylate tert-butyl 3,5-difluoro-6-hydroxy-1H-indazole-1-carboxylate (1.5 g, 5.55 mmol) was dissolved in 30 ml of dry THF. DEAD (1.45 g, 8.33 mmol), tert-butyl 3-hydroxyazetidine-1-carboxylate (1.15 g, 6.65 mmol), $PPh_3$ (2.18 g, 8.32 mmol) was added to the above solution at 0 degrees C. under nitrogen. The mixture was stirred for 45 minutes at 60 degrees C. The mixture was extracted with EA, washed with brine, dried ($Na_2SO_4$), and concentrated in vacuo. Purification by silica gel chromatography to give the titled compound (1.5 g, 63%) as a white solid. (ES, m/s): 426.3$[M+H]^+$ Step 5: 6-(azetidin-3-yloxy)-3,5-difluoro-1H-indazole frifluoroacetate tert-butyl 6-((1-(tert-butoxycarbonyl)azetidin-3-yl)oxy)-3,5-difluoro-1H-indazole-1-carboxylate (150 mg, 0.35 mmol) was dissolved in 5 ml of dry DCM. TFA (2 mL) was added to the above solution at room temperature. The mixture was stirred for 45 minutes at room temperature. The mixture was concentrated in vacuo to give the desired compound (300 mg, crude) as brown oil which was used for next step without further purification. (ES, m/s): 225.3$[M-H]^-$ Step 6: (S)-(3-((3,5-difluoro-1H-indazol-6-yl)oxy)azetidin-1-yl)(5-(3,5-difluorophenyl)-4,5-dihydro-1H-pyrazol-1-yl)methanone (S)-(5-(3,5-difluorophenyl)-4,5-dihydro-1H-pyrazol-1-yl)(1H-imidazol-1-yl)methanone was dissolved in 5 ml of dry THF and 2 mL of TEA. 6-(azetidin-3-yloxy)-3,5-difluoro-1H-indazole frifluoroacetate (300 mg, crude) in 5 mL of THF was added to the above solution at room temperature. The mixture was stirred for 1.0 hour at 70 degrees C. The mixture was extracted with EA, washed with brine, dried ($Na_2SO_4$), and concentrated in vacuo. Purification by silica gel chromatography to give the titled compound 376 (69 mg, 45%) as a white solid. (ES, m/s): 434.3$[M+H]^+$ $^1$H NMR (400 MHz, DMSO-$d_6$) δ 12.41 (brs, 1H), 7.60 (d, J=10.4 Hz, 1H), 7.11 (tt, J=9.4, 2.4 Hz, 1H), 7.03-7.00 (m, 1H), 6.95-6.87 (m, 2H), 6.83 (dd, J=6.8, 2.4 Hz, 1H), 5.24 (dd, J=12.2, 6.6 Hz, 1H), 5.20-5.13 (m, 1H), 4.53 (brs, 2H), 4.05 (brs, 2H), 3.43-3.37 (m, 1H), 2.69-2.59 (m, 1H).

Compound 377: (S)-3-(1-(3-((3,5-difluoro-1H-indazol-6-yl)oxy)azetidine-1-carbonyl)-4,5-dihydro-1H-pyrazol-5-yl)-5-fluorobenzonitrile

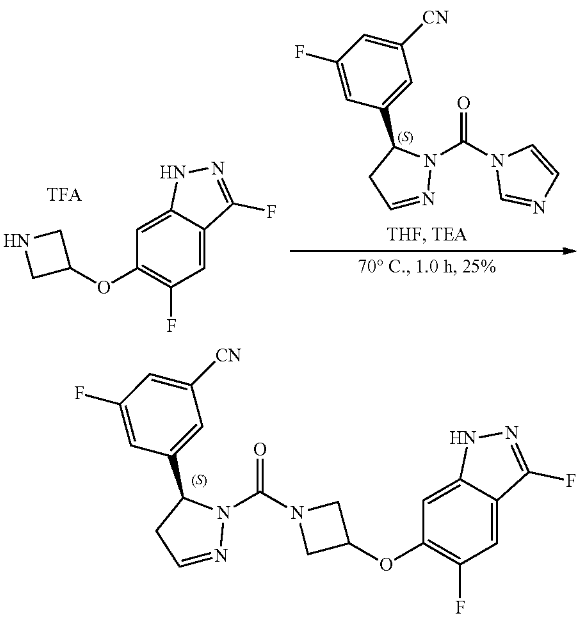

The titled compound 377 as a white solid (13 mg, 25%) was prepare from (S)-3-(1-(1H-imidazole-1-carbonyl)-4,5-dihydro-1H-pyrazol-5-yl)-5-fluorobenzonitrile and 6-(azetidin-3-yloxy)-3,5-difluoro-1H-indazole frifluoroacetate according to the procedure outlined for compound 376 (ES, m/s): 441.4 $[M+H]^+$ $^1$H NMR (400 MHz, DMSO-$d_6$) δ 12.41 (brs, 1H), 7.75 (ddd, J=8.6, 2.6, 1.4 Hz, 1H), 7.63-7.52 (m, 2H), 7.51-7.37 (m, 1H), 7.08-6.98 (m, 1H), 6.82 (dd, J=6.8, 2.2 Hz, 1H), 5.27 (dd, J=12.2, 6.8 Hz, 1H), 5.20-5.12 (m, 1H), 4.53 (brs, 2H), 4.02 (brs, 2H), 3.44-3.37 (m, 1H), 2.70 (ddd, J=18.8, 7.0, 1.6 Hz, 1H).

Compound 378: (3-((3,5-difluoro-1H-indazol-6-yl)oxy)azetidin-1-yl)(5-(5-fluoropyridin-3-yl)-4,5-dihydro-1H-pyrazol-1-yl)methanone

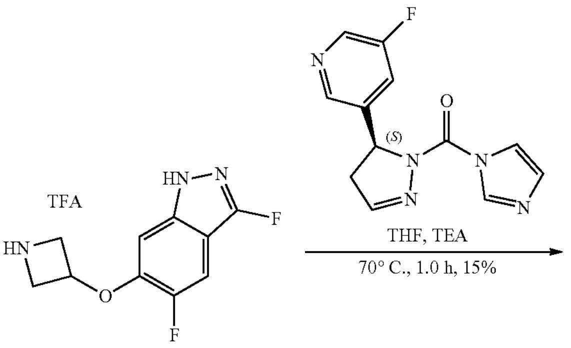

-continued

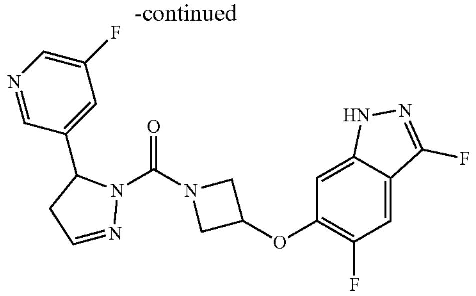

The titled compound 378 as a white solid (10 mg, 15%) was prepare from (S)-(5-(5-fluoropyridin-3-yl)-4,5-dihydro-1H-pyrazol-1-yl)(1H-imidazol-1-yl)methanone and 6-(azetidin-3-yloxy)-3,5-difluoro-1H-indazole frifluoroacetate according to the procedure outlined for compound 376 (ES, m/s): 417.4 $[M+H]^+$ $^1H$ NMR (400 MHz, DMSO-$d_6$) δ 12.40 (brs, 1H), 8.46 (d, J=2.8 Hz, 1H), 8.34 (t, J=1.8 Hz, 1H), 7.59 (d, J=10.4 Hz, 1H), 7.54 (dt, J=9.8, 2.4 Hz, 1H), 7.06-7.03 (m, 1H), 6.81 (dd, J=6.8, 2.4 Hz, 1H), 5.29 (dd, J=12.2, 6.8 Hz, 1H), 5.18-5.10 (m, 1H), 4.51 (brs, 2H), 4.03 (brs, 2H), 3.45-3.36 (m, 1H), 2.76-2.63 (m, 1H).

Compound 379: (3-((3,5-difluoro-1H-indazol-6-yl)oxy)azetidin-1-yl)(5-phenyl-4,5-dihydro-1H-pyrazol-1-yl)methanone

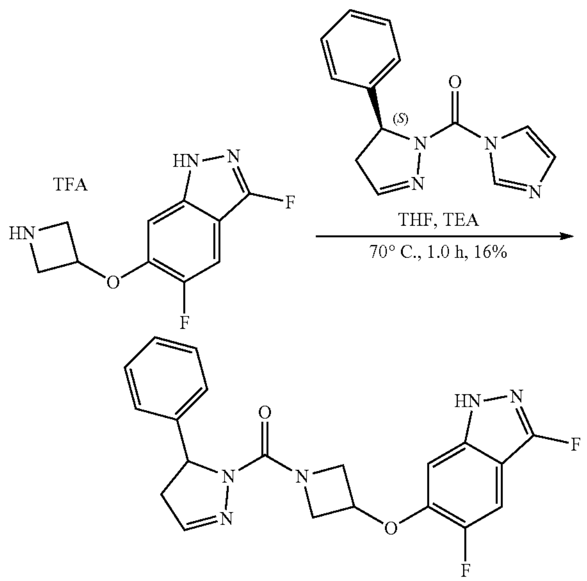

The titled compound 379 as a white solid (10 mg, 16%) was prepare from (S)-(1H-imidazol-1-yl)(5-phenyl-4,5-dihydro-1H-pyrazol-1-yl)methanone and 6-(azetidin-3-yloxy)-3,5-difluoro-1H-indazole frifluoroacetate according to the procedure outlined for compound 376. (ES, m/s): 398.4 $[M+H]^+$ $^1H$ NMR (400 MHz, DMSO-$d_6$) δ 12.40 (brs, 1H), 7.59 (d, J=10.4 Hz, 1H), 7.33-7.28 (m, 2H), 7.25-7.20 (m, 1H), 7.18-7.13 (m, 2H), 7.01-6.99 (m, 1H), 6.82 (dd, J=6.8, 2.4 Hz, 1H), 5.20 (dd, J=12.0, 6.0 Hz, 1H), 5.17-5.12 (m, 1H), 4.50 (brs, 2H), 4.00 (brs, 2H), 3.44-3.35 (m, 1H), 2.61-2.53 (m, 1H).

Compound 380: 3-(1-(3-((3,5-difluoro-1H-indazol-6-yl)oxy)azetidine-1-carbonyl)-4,5-dihydro-1H-pyrazol-5-yl)benzonitrile

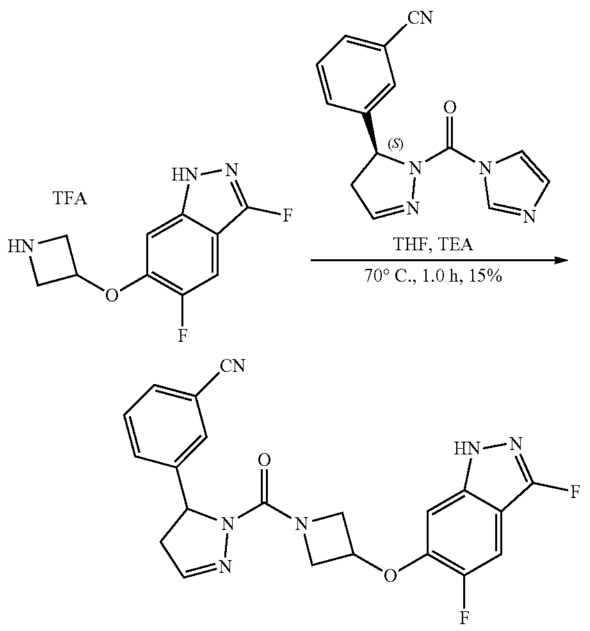

The titled compound 380 as a white solid (10 mg, 15%) was prepare from (S)-3-(1-(1H-imidazole-1-carbonyl)-4,5-dihydro-1H-pyrazol-5-yl)benzonitrile and 6-(azetidin-3-yloxy)-3,5-difluoro-1H-indazole frifluoroacetate according to the procedure outlined for compound 376 (ES, m/s): 423.4 $[M+H]^+$ $^1H$ NMR (400 MHz, DMSO-$d_6$) δ 12.40 (brs, 1H), 7.74-7.70 (m, 1H), 7.64 (brs, 1H), 7.59 (d, J=10.4 Hz, 1H), 7.55-7.51 (m, 2H), 7.05-6.99 (m, 1H), 6.81 (dd, J=6.8, 2.2 Hz, 1H), 5.26 (dd, J=12.2, 6.6 Hz, 1H), 5.18-5.12 (m, 1H), 4.51 (brs, 2H), 4.01 (brs, 1H), 3.44-3.34 (m, 1H), 2.69-2.61 (m, 1H).

Compound 381: 5-(1-(3-((3,5-difluoro-1H-indazol-6-yl)oxy)azetidine-1-carbonyl)-4,5-dihydro-1H-pyrazol-5-yl)nicotinonitrile

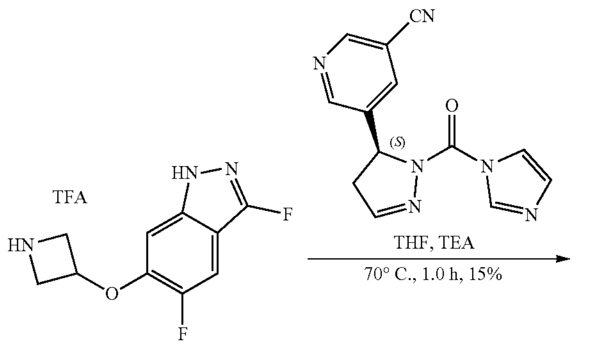

-continued

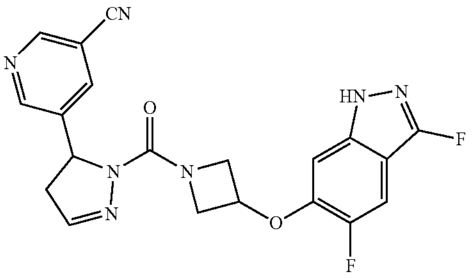

The titled compound 381 as a white solid (10 mg, 15%) was prepare from (S)-5-(1-(1H-imidazole-1-carbonyl)-4,5-dihydro-1H-pyrazol-5-yl)nicotinonitrile and 6-(azetidin-3-yloxy)-3,5-difluoro-1H-indazole frifluoroacetate according to the procedure outlined for compound 376 (ES, m/s): 423.4 $[M+H]^+$ $^1$H NMR (400 MHz, DMSO-$d_6$) δ 12.40 (brs, 1H), 8.91 (d, J=2.0 Hz, 1H), 8.73 (d, J=2.2 Hz, 1H), 8.16 (t, J=2.0 Hz, 1H), 7.59 (d, J=10.6 Hz, 1H), 7.07-7.03 (m, 1H), 6.81 (dd, J=6.8, 2.2 Hz, 1H), 5.30 (dd, J=12.2, 7.2 Hz, 1H), 5.18-5.11 (m, 1H), 4.51 (brs, 2H), 4.04 (brs, 2H), 3.46-3.38 (m, 1H), 2.69-2.61 (m, 1H).

Compound 382: (4-(4-(3-aminoprop-1-yn-1-yl)pyrimidin-2-yl)piperazin-1-yl)(5-(3,5-difluorophenyl)-4,5-dihydro-1H-pyrazol-1-yl)methanone frifluoroacetate

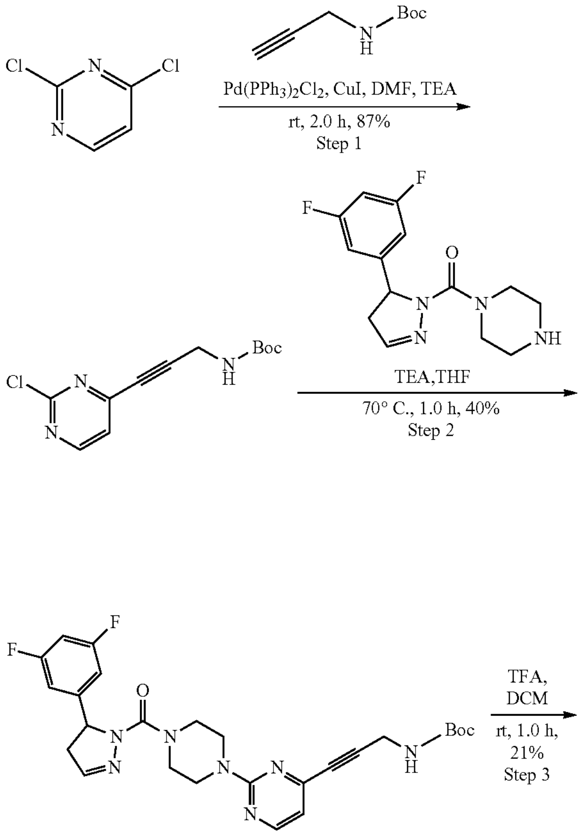

-continued

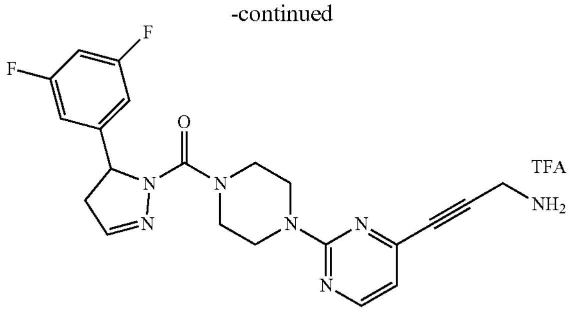

Step 1: tert-butyl (3-(2-chloropyrimidin-4-yl)prop-2-yn-1-yl)carbamate. 2,4-dichloropyrimidine (444 mg, 3.00 mmol) was dissolved in 20 ml of dry DMF and TEA (2 mL). tert-butyl prop-2-yn-1-ylcarbamate (930 mg, 6.00 mmol), $Pd(PPh_3)_2Cl_2$ (210 mg, 0.30 mmol), CuI (114 mg, 0.60 mmol) were added to the above solution under nitrogen at room temperature. The mixture was stirred for 2.0 hours at room temperature. The mixture was extracted with EA, washed with brine, dried ($Na_2SO_4$), and concentrated in vacuo to give the desired compound (700 mg, 87%) as brown solids which was used for next step without further purification. (ES, m/s): 268.5 $[M+H]^+$ Step 2: tert-butyl (3-(2-(4-(5-(3,5-difluorophenyl)-4,5-dihydro-1H-pyrazole-1-carbonyl)piperazin-1-yl)pyrimidin-4-yl)prop-2-yn-1-yl)carbamate (5-(3,5-difluorophenyl)-4,5-dihydro-1H-pyrazol-1-yl)(piperazin-1-yl)methanone (300 mg, 1.12 mmol) was dissolved in 5 ml of dry THF. tert-butyl (3-(2-chloropyrimidin-4-yl)prop-2-yn-1-yl)carbamate (331 mg, 1.12 mmol), TEA (227 mg, 2.24 mmol) was added to the above solution at room temperature. The mixture was stirred for 1.0 hour at 70 degrees C. The mixture was extracted with EA, washed with brine, dried ($Na_2SO_4$), and concentrated in vacuo. Purification by silica gel chromatography to give the titled compound (200 mg, 40%) as a brown solid. (ES, m/s): 526.5$[M+H]^+$ Step 3: (4-(4-(3-aminoprop-1-yn-1-yl)pyrimidin-2-yl)piperazin-1-yl)(5-(3,5-difluorophenyl)-4,5-dihydro-1H-pyrazol-1-yl)methanone frifluoroacetate. tert-butyl (3-(2-(4-(5-(3,5-difluorophenyl)-4,5-dihydro-1H-pyrazole-1-carbonyl)piperazin-1-yl)pyrimidin-4-yl)prop-2-yn-1-yl) carbamate (50 mg, 0.09 mmol) was dissolved in 4 ml of dry DCM. TFA (1 mL) was added to the above solution at room temperature. The mixture was stirred for 1.0 hour at room temperature. The mixture was concentrated in vacuo. Purification by Flash-Prep-HPLC with the following conditions (IntelFlash-1): Column, C18 silica gel; mobile phase, H2O (0.05% TFA)/ACN=100:0 increasing to H2O (0.05% TFA)/ACN=60:40 within 25 min; Detector, UV 254 nm. to give the titled compound 382 (10 mg, 21%) as a yellow solid. (ES, m/s): 426.2 $[M+H]^+$ $^1$H NMR (400 MHz, DMSO-$d_6$) δ 8.45 (d, J=5.0 Hz, 1H), 8.36 (brs, 2H), 7.15-7.07 (m, 2H), 7.00 (d, J=7.6 Hz, 2H), 6.75 (d, J=4.8 Hz, 1H), 5.26 (t, J=10.8 Hz, 1H), 4.07 (brs, 2H), 3.81-3.49 (m, 8H), 3.44-3.34 (m, 1H), 2.70-2.61 (m, 1H).

Compound 383: (S)-6-(4-(5-(3,5-difluorophenyl)-4,5-dihydro-1H-pyrazole-1-carbonyl)piperazin-1-yl)imidazo[1,2-b]pyridazine-3-carbonitrile

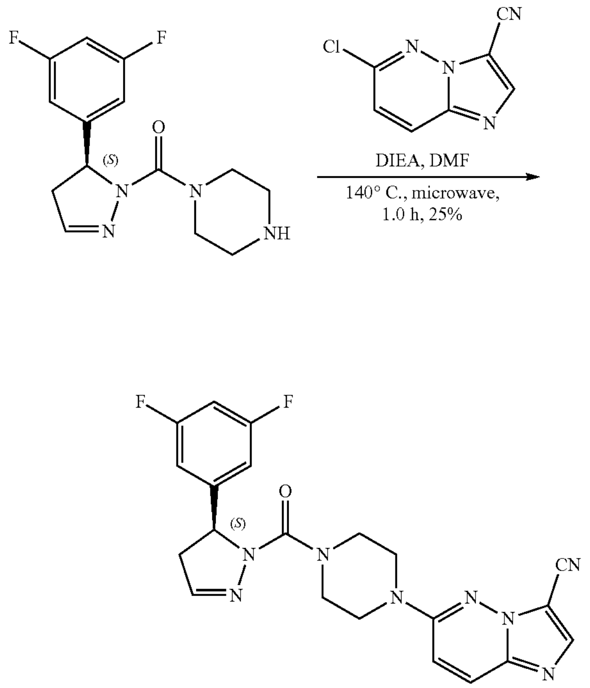

(S)-(5-(3,5-difluorophenyl)-4,5-dihydro-1H-pyrazol-1-yl)(piperazin-1-yl)methanone (165 mg, 0.56 mmol) was dissolved in 4 ml of dry DMF. 6-chloroimidazo[1,2-b]pyridazine-3-carbonitrile (100 mg, 0.56 mmol) and DIEA (145 mg, 1.12 mmol) were added to the above solution under nitrogen at room temperature. The mixture was stirred for 1.0 hour at 140 degrees C. under microwave. The mixture was extracted with EA, washed with brine, dried ($Na_2SO_4$), and concentrated in vacuo. Purification by silica gel chromatography to give the titled compound 383 (60 mg, 25%) as a white solid. (ES, m/s): 437.4[M+H]$^+$ $^1$H NMR (400 MHz, DMSO-$d_6$) δ 8.26 (d, J=0.8 Hz, 1H), 8.07 (d, J=10.0 Hz, 1H), 7.46 (d, J=10.2 Hz, 1H), 7.13-7.06 (m, 2H), 7.02-6.96 (m, 2H), 5.28-5.20 (m, 1H), 3.61 (m, 8H), 3.39-3.32 (m, 1H), 2.68-2.58 (m, 1H).

Compound 384: (S)-(5-(3,5-difluorophenyl)-4,5-dihydro-1H-pyrazol-1-yl)(4-(5-methyl-1,3,4-thiadiazol-2-yl)piperazin-1-yl)methanone

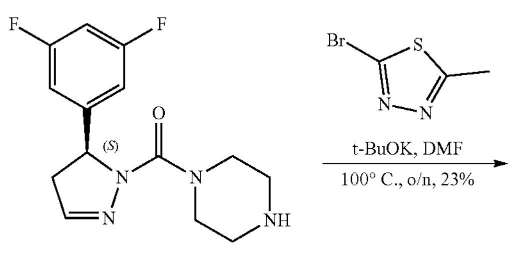

-continued

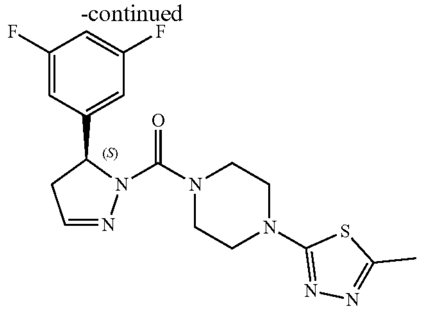

(S)-(5-(3,5-difluorophenyl)-4,5-dihydro-1H-pyrazol-1-yl)(piperazin-1-yl)methanone (100 mg, 0.34 mmol) was dissolved in 10 ml of dry DMF. 2-bromo-5-methyl-1,3,4-thiadiazole (91 mg, 0.51 mmol) and t-BuOK (77 mg, 0.68 mmol) were added to the above solution under nitrogen at room temperature. The mixture was stirred for 1 overnight at 100 degrees C. The mixture was extracted with EA, washed with brine, dried ($Na_2SO_4$), and concentrated in vacuo. Purification by silica gel chromatography to give the titled compound 384 (30 mg, 23%) as a yellow solid. (ES, m/s): 393.2 [M+H]$^+$ $^1$H NMR (400 MHz, DMSO-$d_6$) δ 7.13-7.06 (m, 2H), 6.98 (dt, J=8.7, 2.0 Hz, 2H), 5.24 (dd, J=11.6, 9.8 Hz, 1H), 3.73-3.65 (m, 2H), 3.53-3.47 (m, 2H), 3.45-3.37 (m, 4H), 3.37-3.33 (m, 1H), 2.68-2.58 (m, 1H), 2.50 (s, 3H).

Compound 385: (S)-2-(4-(5-(3,5-difluorophenyl)-4,5-dihydro-1H-pyrazole-1-carbonyl)piperazin-1-yl)pyrimidine-5-carbonitrile

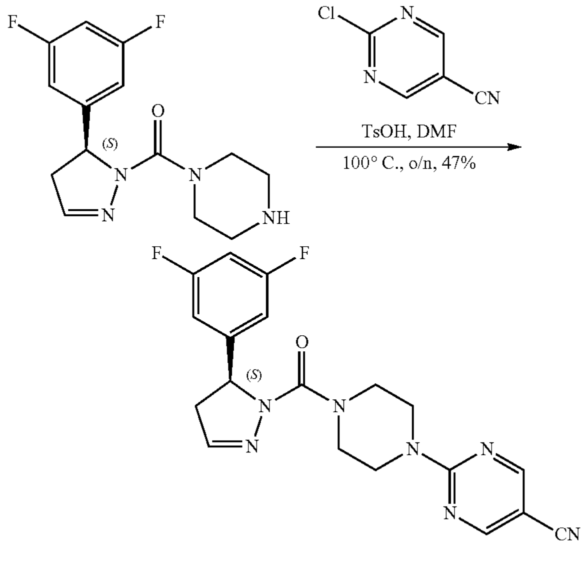

(S)-(5-(3,5-difluorophenyl)-4,5-dihydro-1H-pyrazol-1-yl)(piperazin-1-yl)methanone (200 mg, 0.68 mmol) was dissolved in 10 ml of dry DMF. 2-chloropyrimidine-5-carbonitrile (95 mg, 0.68 mmol) and TsOH (39 mg, 0.20 mmol) were added to the above solution under nitrogen at room temperature. The mixture was stirred for 1 overnight at 100 degrees C. The mixture was extracted with EA, washed with brine, dried ($Na_2SO_4$), and concentrated in vacuo. Purification by silica gel chromatography to give the titled compound 385 (126 mg, 47%) as a white solid. (ES, m/s): 398.2 $[M+H]^+$ $^1H$ NMR (400 MHz, DMSO-$d_6$) δ 8.55-8.53 (m, 2H), 6.91-6.82 (m, 2H), 6.80-6.71 (m, 2H), 5.01 (t, J=10.8 Hz, 1H), 3.73-3.52 (m, 4H), 3.48-3.23 (m, 4H), 3.18-3.10 (m, 1H), 2.46-2.36 (m, 1H).

Compound 386: (S)-2-(4-(5-(3,5-difluorophenyl)-4,5-dihydro-1H-pyrazole-1-carbonyl)piperazin-1-yl)-5,7-dihydro-6H-pyrrolo[2,3-d]pyrimidin-6-one

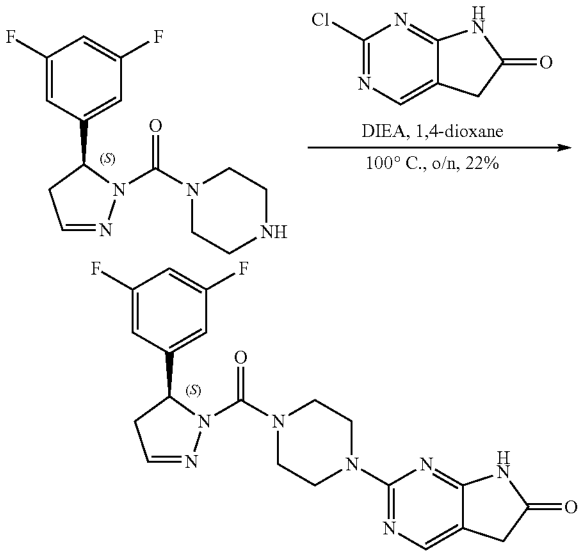

(S)-(5-(3,5-difluorophenyl)-4,5-dihydro-1H-pyrazol-1-yl)(piperazin-1-yl)methanone (100 mg, 0.34 mmol) was dissolved in 10 ml of dry 1,4-dioxane. 2-chloro-5,7-dihydro-6H-pyrrolo[2,3-d]pyrimidin-6-one (86 mg, 0.51 mmol) and DIEA (88 mg, 0.68 mmol) were added to the above solution under nitrogen at room temperature. The mixture was stirred for 1 overnight at 100 degrees C. The mixture was extracted with EA, washed with brine, dried ($Na_2SO_4$), and concentrated in vacuo. Purification by silica gel chromatography to give the titled compound 386 (32 mg, 22%) as a pink solid. (ES, m/s): 428.2 $[M+H]^+$ $^1H$ NMR (400 MHz, DMSO-$d_6$) δ 11.10 (brs, 1H), 7.93 (brs, 1H), 7.13-7.05 (m, 2H), 7.02-6.93 (m, 2H), 5.24 (t, J=10.8 Hz, 1H), 3.77-3.44 (m, 8H), 3.40 (s, 2H), 3.39-3.34 (m, 1H), 2.67-2.58 (m, 1H).

The invention claimed is:

1. A compound of structure:

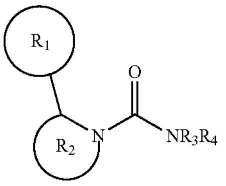

wherein:

$R_1$ is substituted or unsubstituted phenyl or substituted or unsubstituted 2-, 3- or 4-pyridine;

$R_2$ is dihydro-pyrazole or isoxazolidine; and $R_3$ and $R_4$ are linked to form a 4-6 membered N-containing, heterocycloalkyl ring, wherein the 4-6 membered N-containing, heterocycloalkyl ring is fused to phenyl or wherein the 4-6 membered N-containing, heterocycloalkyl ring is linked to $R_5$ through an optional linker selected from —$CH_2$—, —O— and =CH—, wherein $R_5$ is substituted or unsubstituted C3-C9 cycloalkyl with 0-3 heteroatoms, C3-C9 cycloalkenyl with 0-3 heteroatoms, or C3-C9 cycloalkynyl with 0-3 heteroatoms, or substituted or unsubstituted C5-C14 aryl with 0-3 heteroatoms;

or a pharmaceutically acceptable salt, or a hydrate of the compound.

2. The compound of claim 1 wherein:

$R_1$ is fluoro-substituted or unsubstituted phenyl.

3. The compound of claim 1 wherein:

$R_2$ is dihydro-pyrazole.

4. The compound of claim 2 wherein:

$R_2$ is dihydro-pyrazole.

5. The compound of claim 1 wherein:

$R_3$ and $R_4$ are linked to form an azetidine, pyrrolidine or diazinane.

6. The compound of claim 1 wherein:

$R_3$ and $R_4$ are linked to form an azetidine.

7. The compound of claim 4 wherein:

$R_3$ and $R_4$ are linked to form an azetidine.

8. The compound of claim 1 wherein the linker is —O—.

9. The compound of claim 1 wherein:

$R_5$ is (a) substituted or unsubstituted phenyl;

(b) substituted or unsubstituted 2-, 3- or 4-pyridine;

(c) substituted or unsubstituted naphthyl or 3-azanaphthyl;

(d) substituted or unsubstituted 0-3 heteroatoms cyclohexyl, cyclopentyl; or (e) substituted or unsubstituted 0-3 heteroatoms cyclopentene or cyclopentadiene.

10. The compound of claim 1 wherein:

$R_5$ is substituted or unsubstituted 2-, 3- or 4-pyridine.

11. The compound of claim 4 wherein:

$R_5$ is substituted or unsubstituted 2-, 3- or 4-pyridine.

12. The compound of claim 7 wherein:

$R_5$ is substituted or unsubstituted 2-, 3- or 4-pyridine.

13. The compound of claim 1 wherein:

$R_5$ is substituted or unsubstituted: phenyl, cyclohexyl, furan, thiophene or azole.

14. The compound of claim 1 wherein:

$R_5$ is substituted or unsubstituted phenyl.

15. A compound comprising a structure of any one of the following structures:

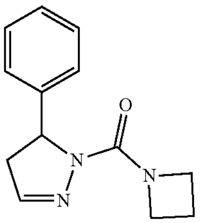

1

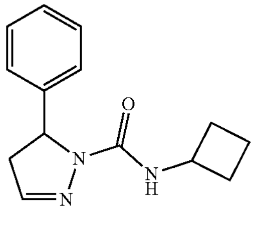

2

3
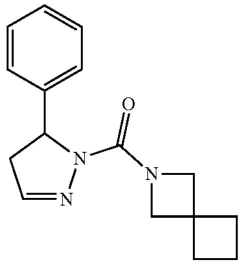
4
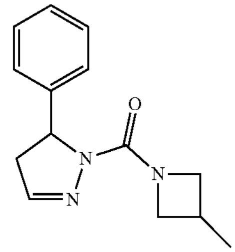
5
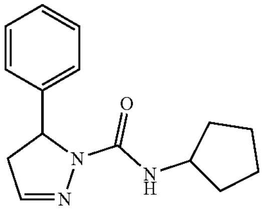
6
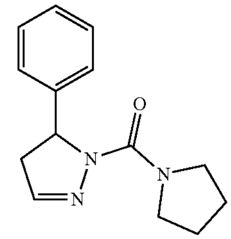
7
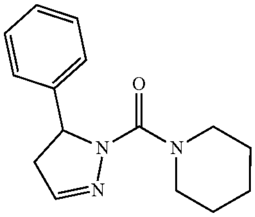
8
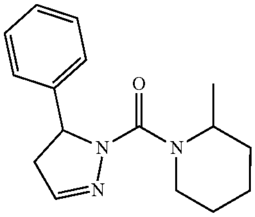
9
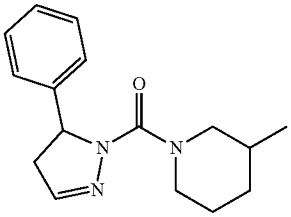
10
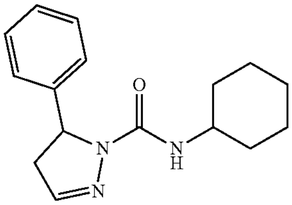
11
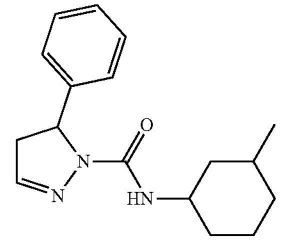
12
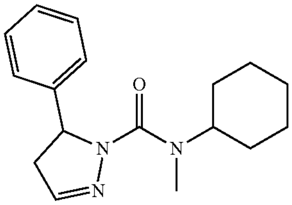
13
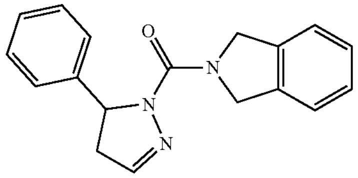
14
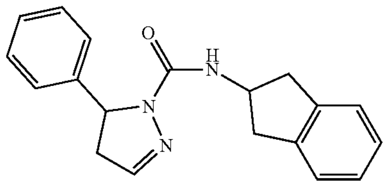
15
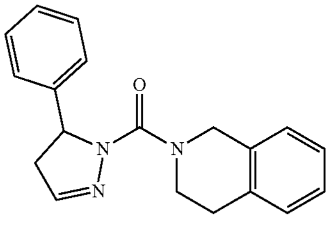

-continued
16
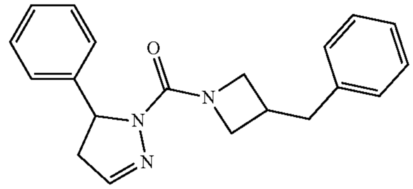
17
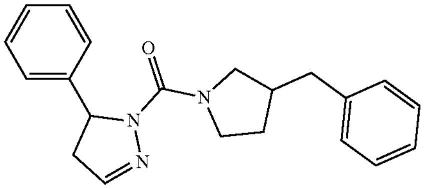
18
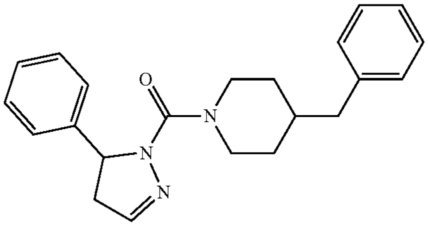
19
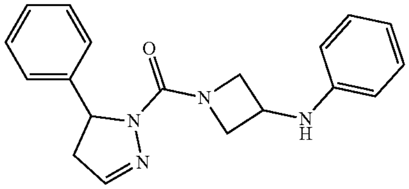
20
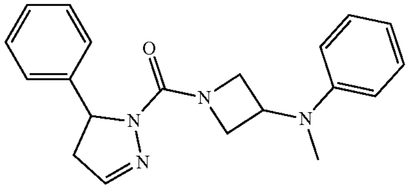
21
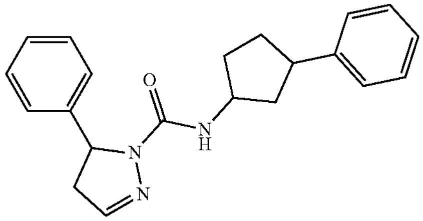
22
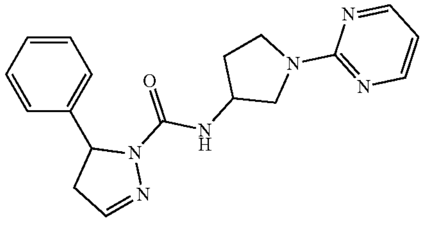
-continued
23
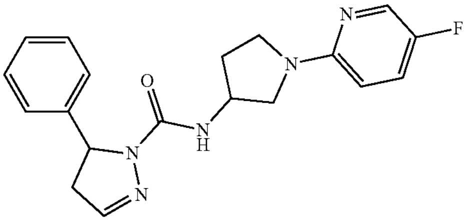
24
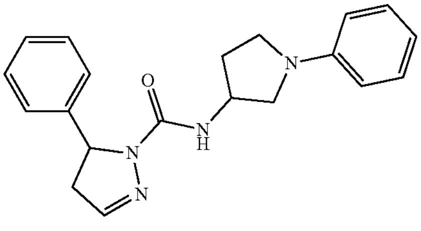
25
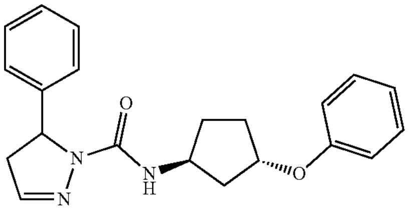
26A
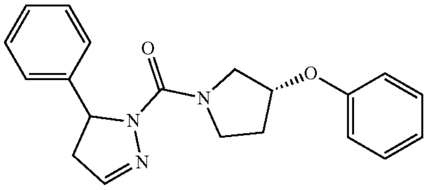
26B
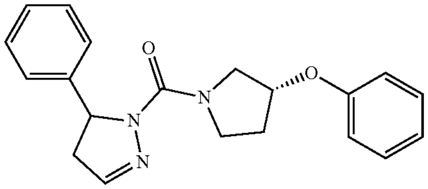
27A
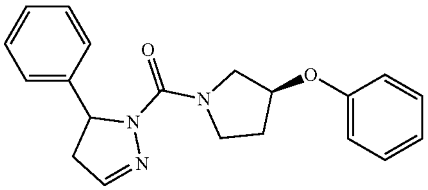
27B
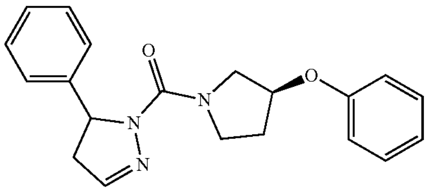

-continued
28
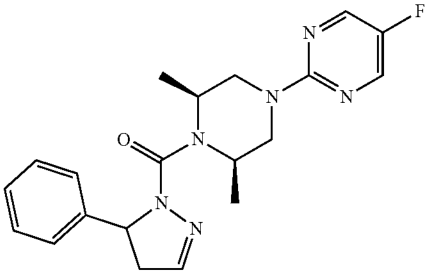
29
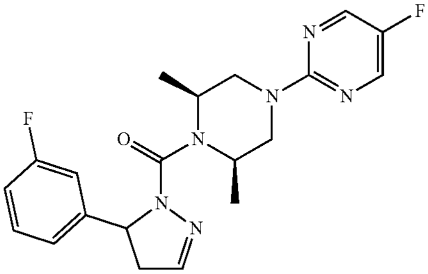
30
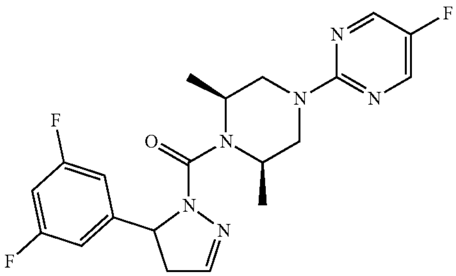
31
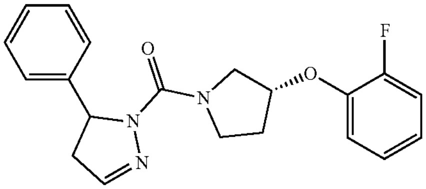
32
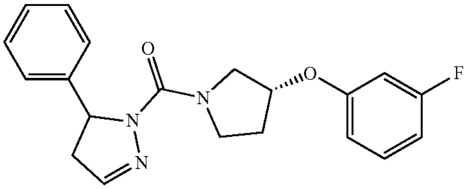
33
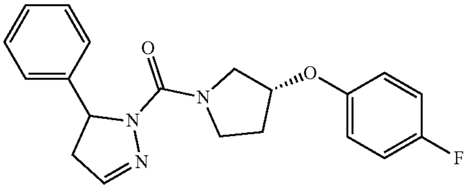
34
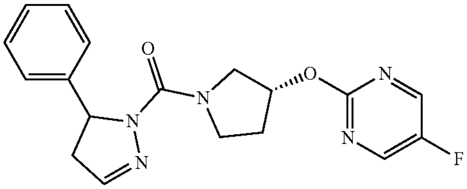
-continued
35
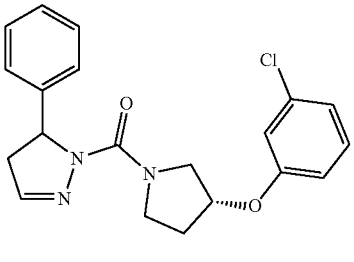
36
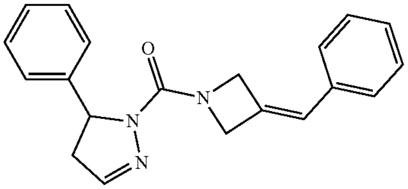
37
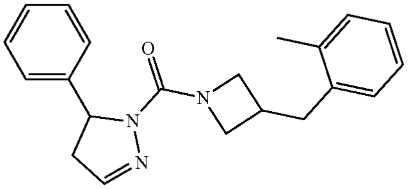
38
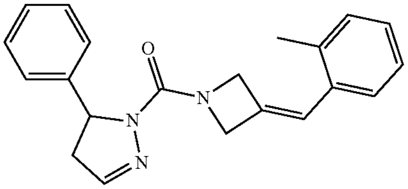
39
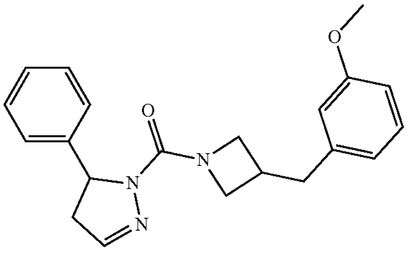
40
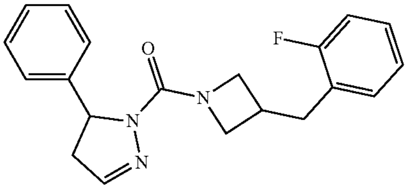
41
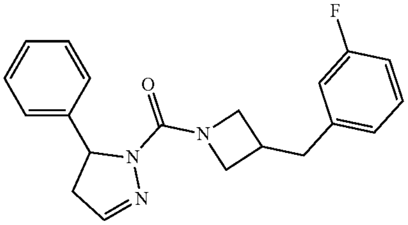

-continued
42
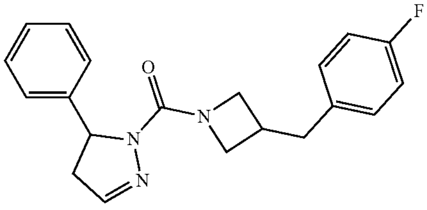
43
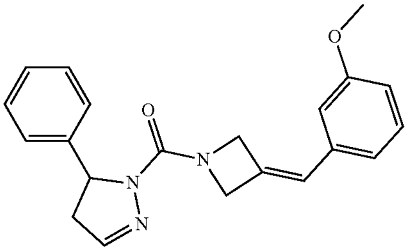
44
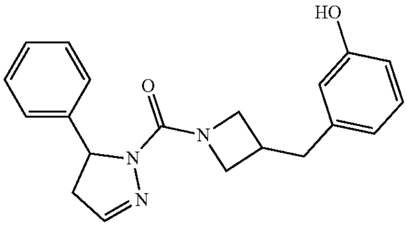
45
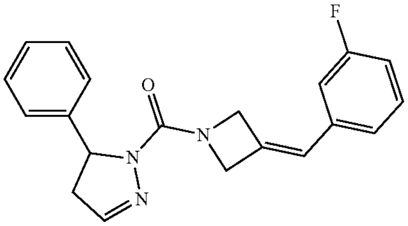
46
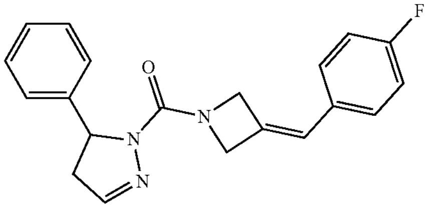
47
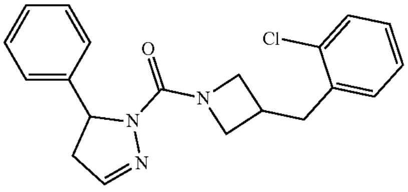
48
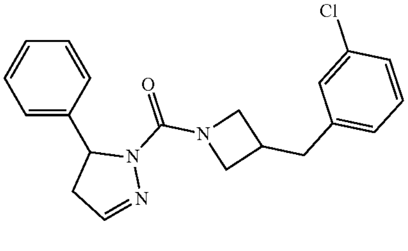
49
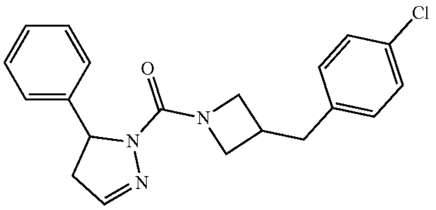
50
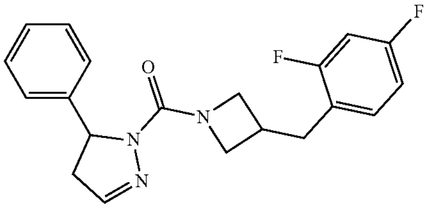
51
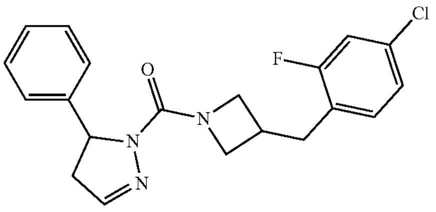
52
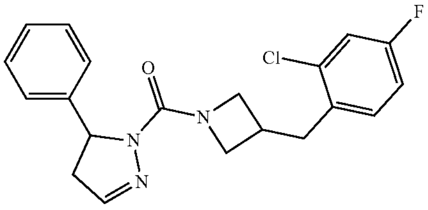
53
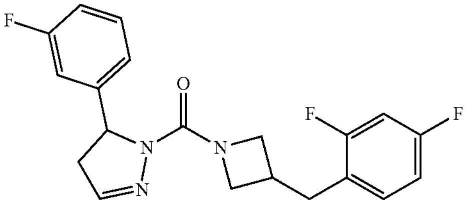
54
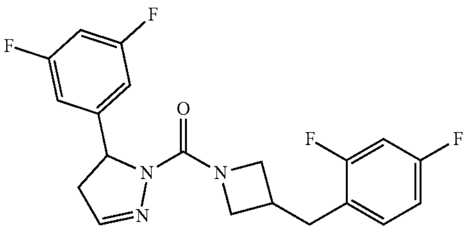
55
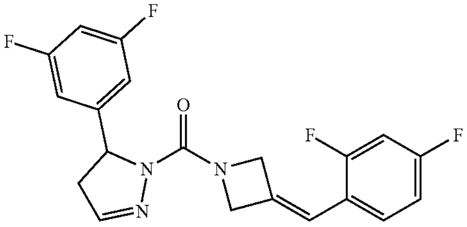

-continued
56
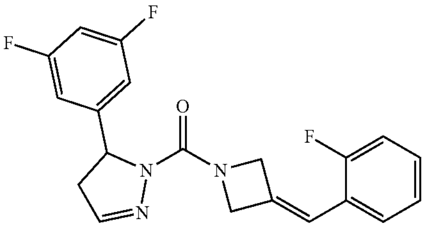
57
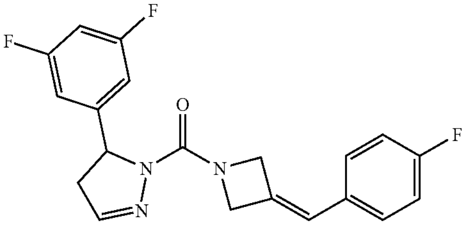
58
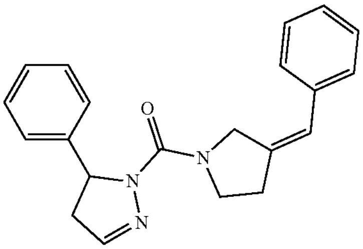
59
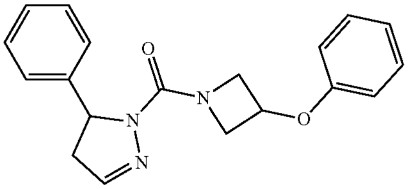
60
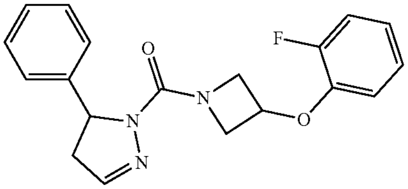
61
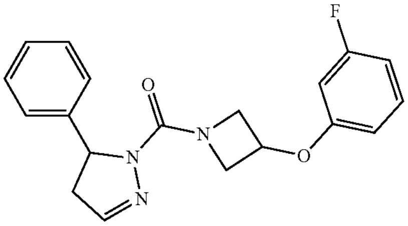
62
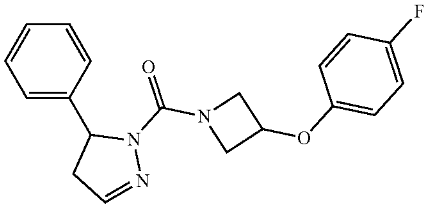
-continued
63
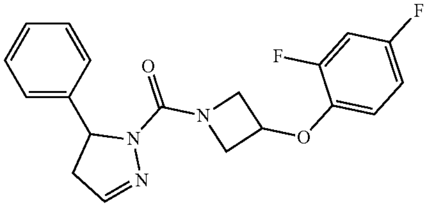
64
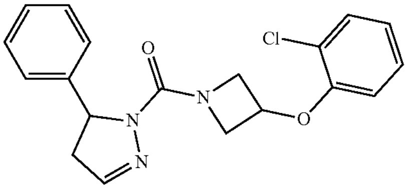
65
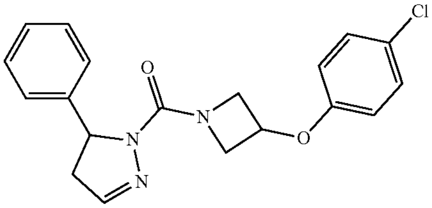
66
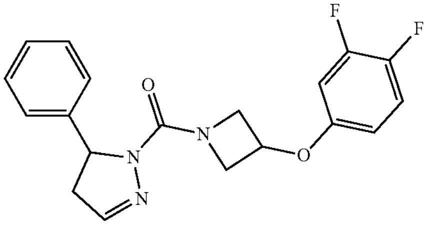
67
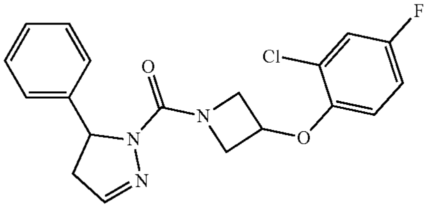
68
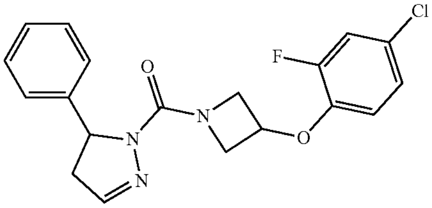
69
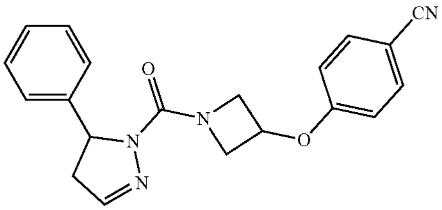

-continued
70
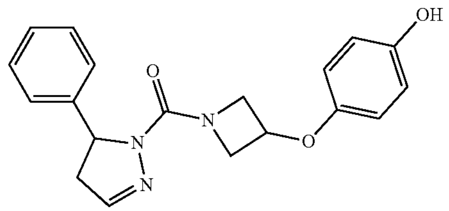
71
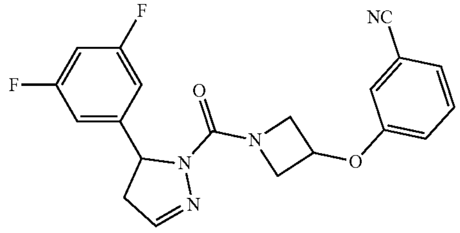
72
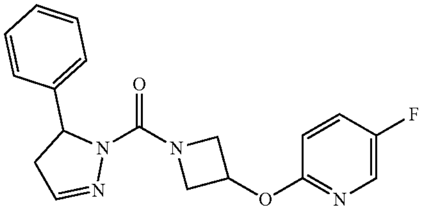
73
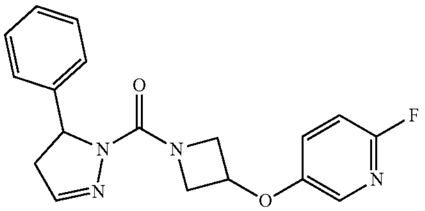
74
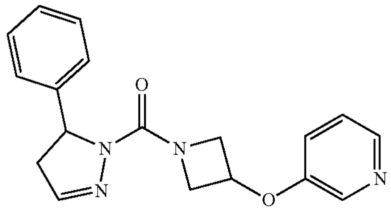
75
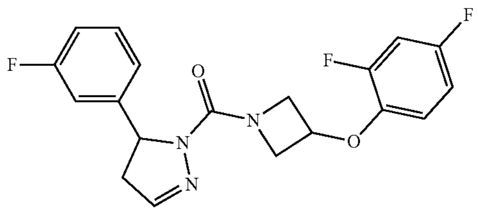
76
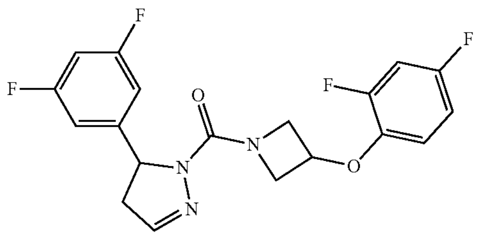
-continued
77
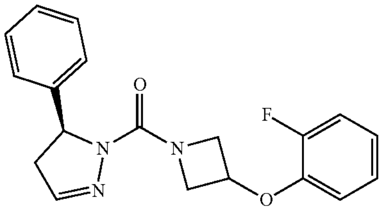
78
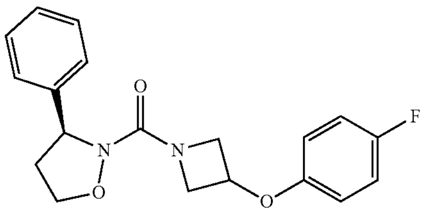
79
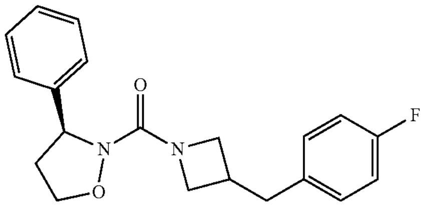
80
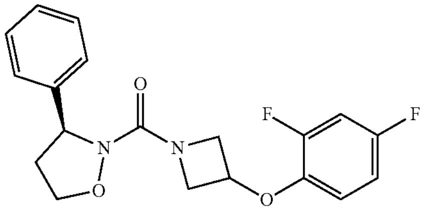
81
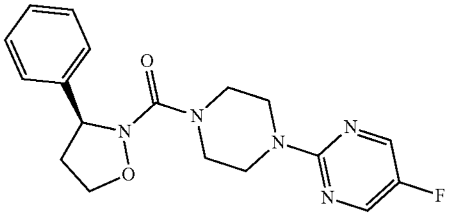
82
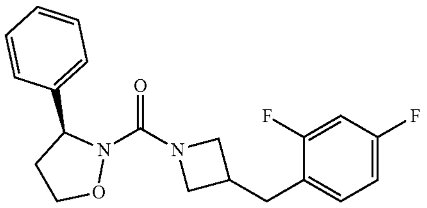
83
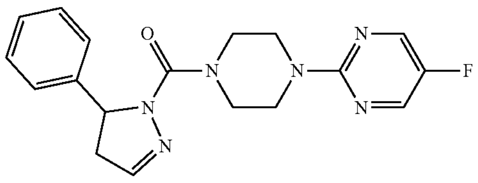

-continued
84
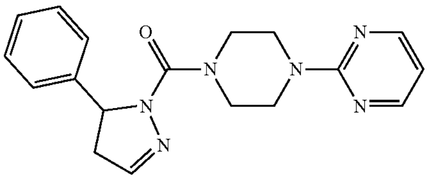
85
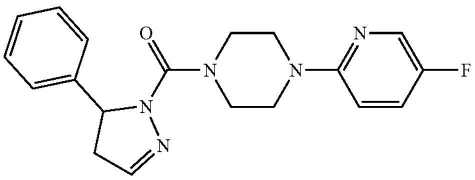
86
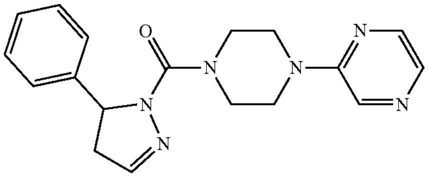
87
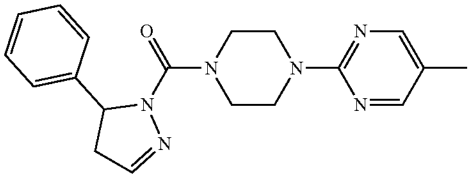
88
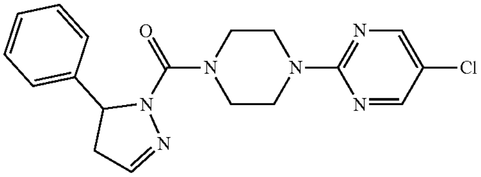
89
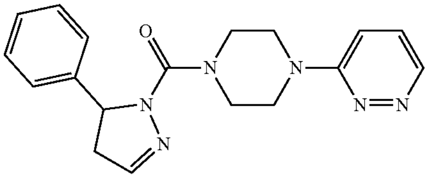
90
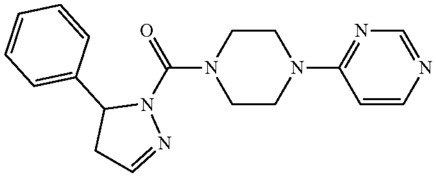
91
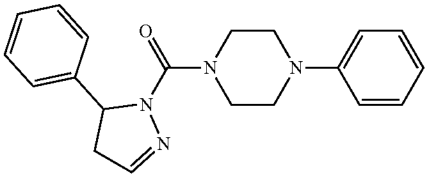
-continued
92
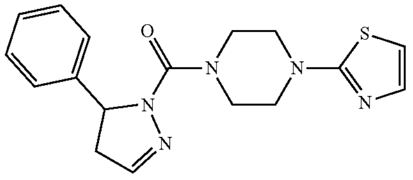
93
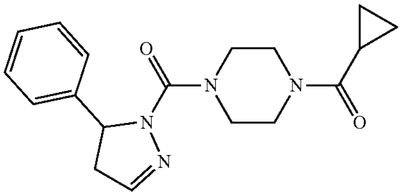
94
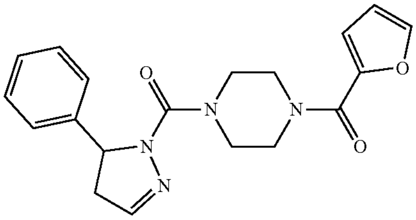
95
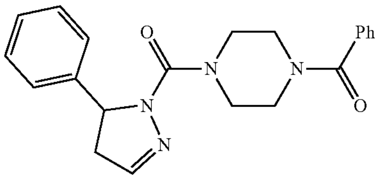
96
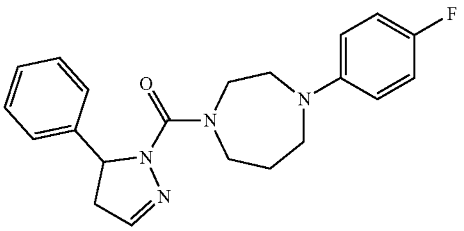
97
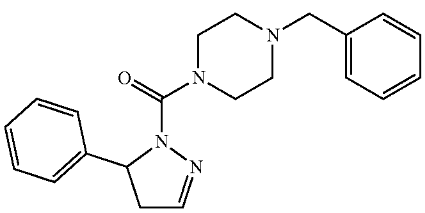
98
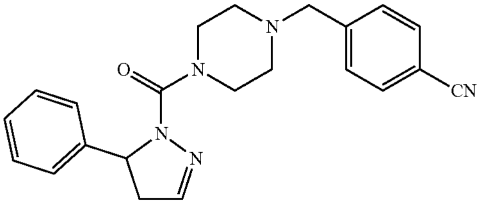

99
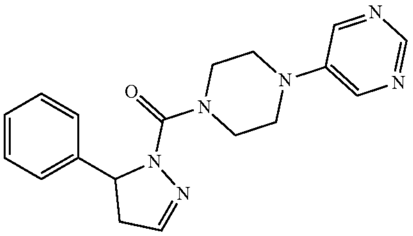
100
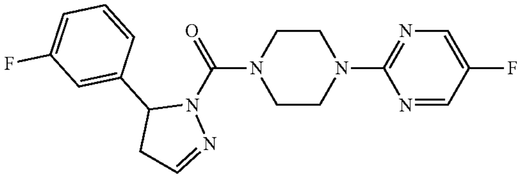
101
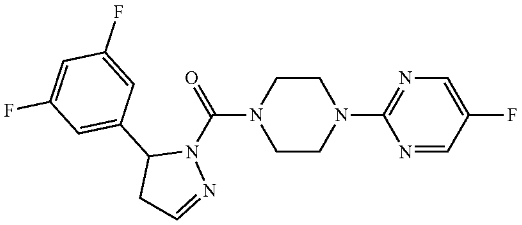
102
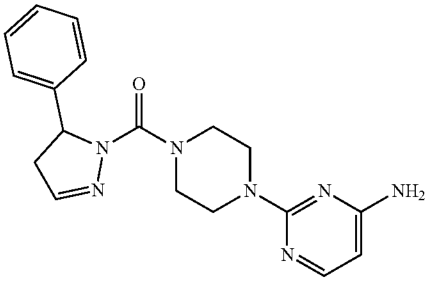
103
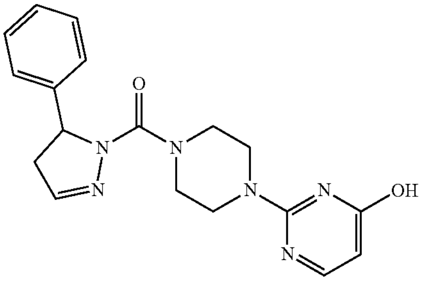
104
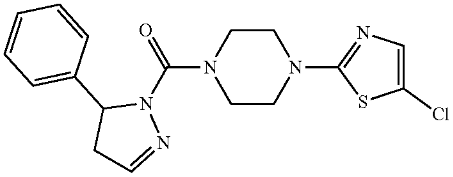
105
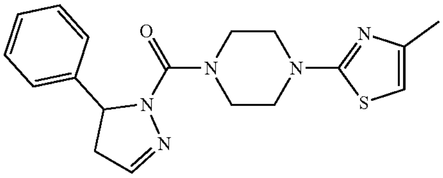
106
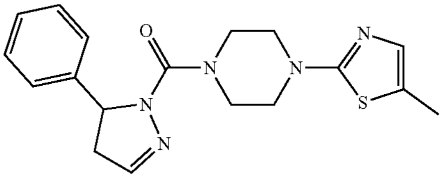
107
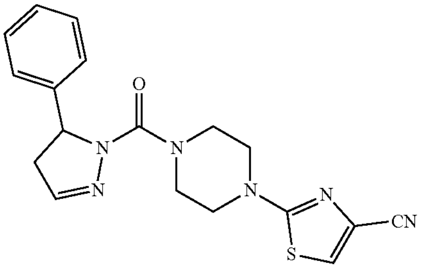
108
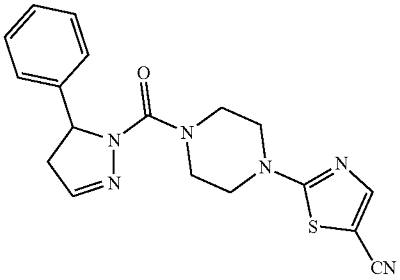
109
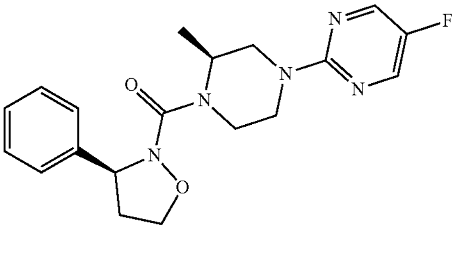
110
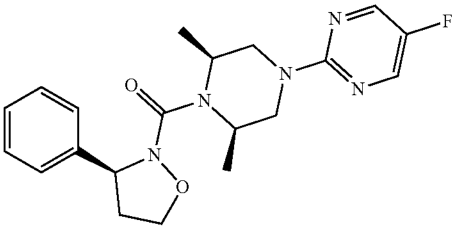
111A
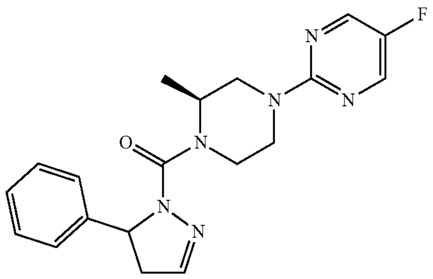

-continued
111B
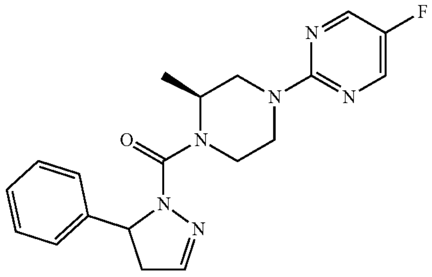
112A
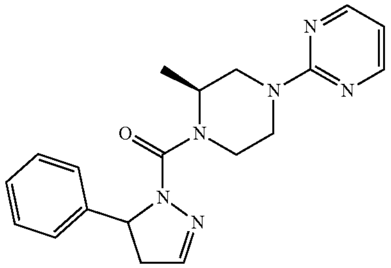
112B
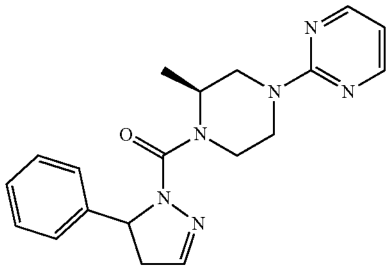
113A
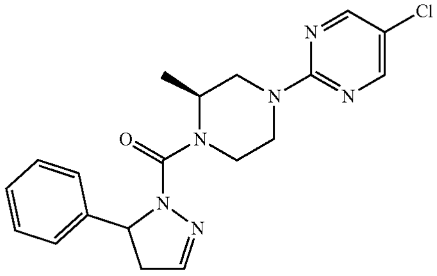
113B
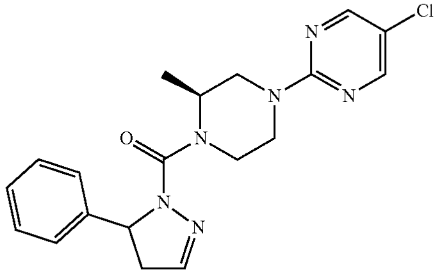
-continued
114A
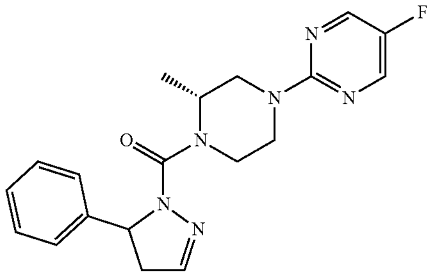
114B
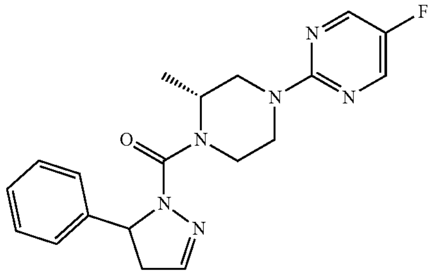
115A
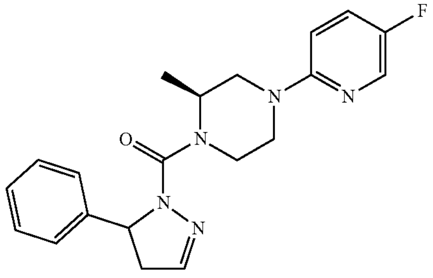
115B
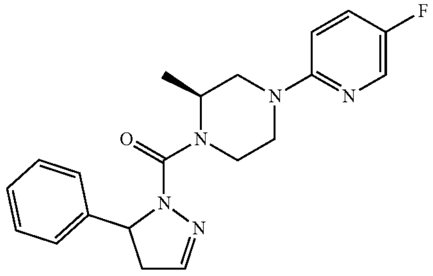
116A
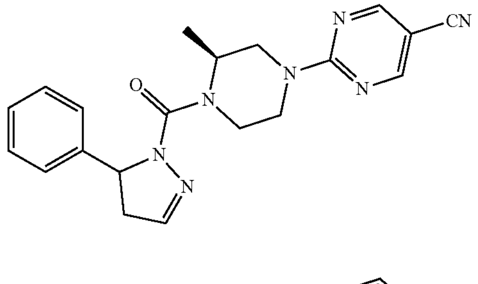
116B
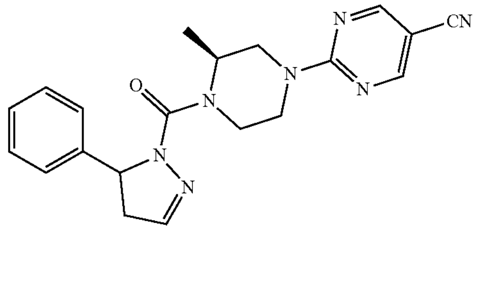

117A
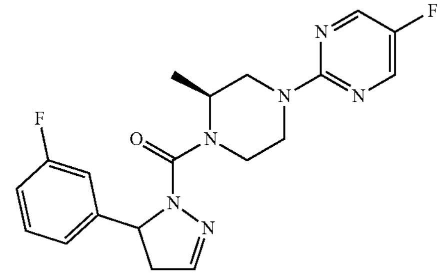
117B
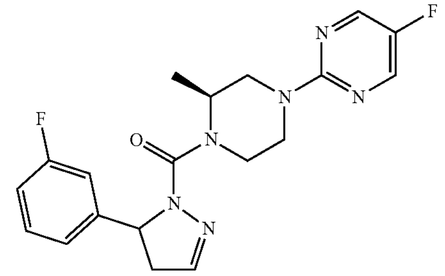
118A
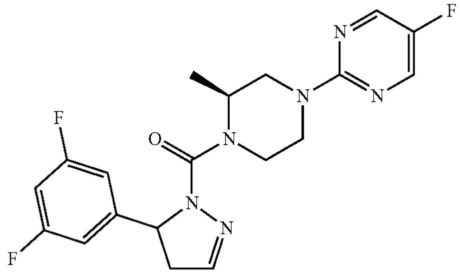
118B
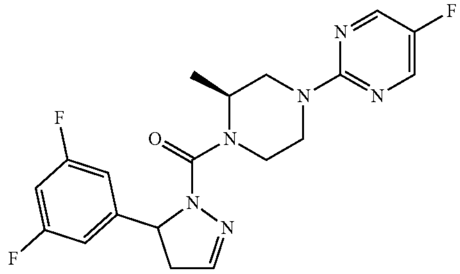
119
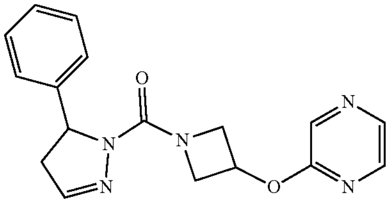
120
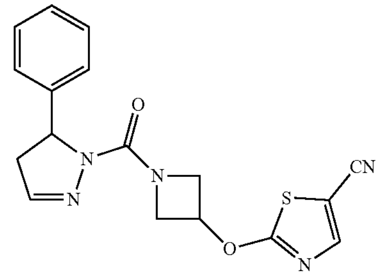
121
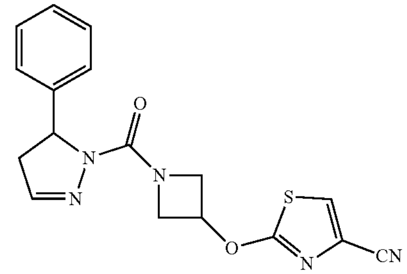
122
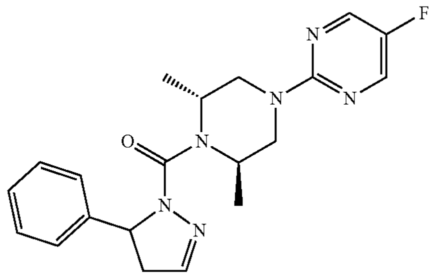
123
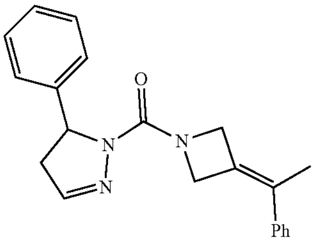
124
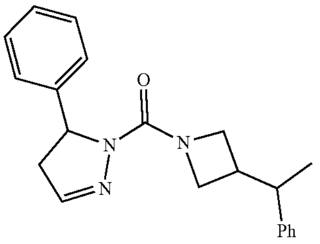
125
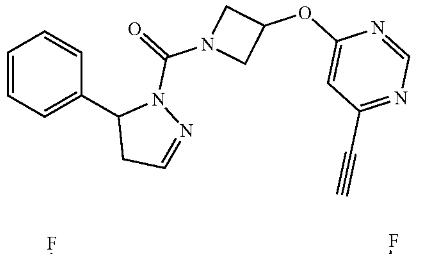
126
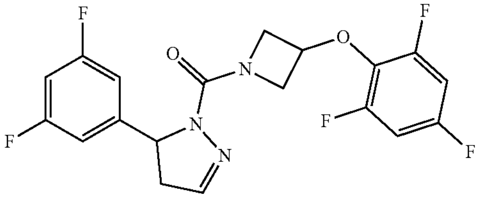

-continued
127
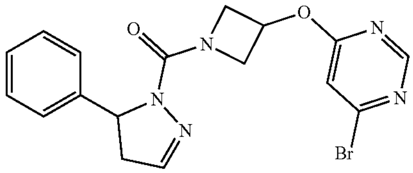
128
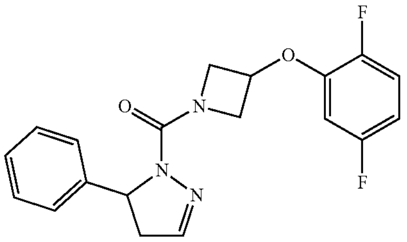
129
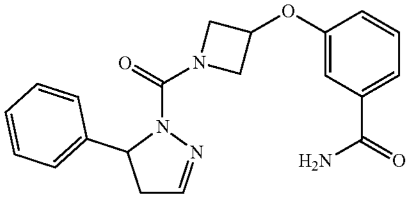
130
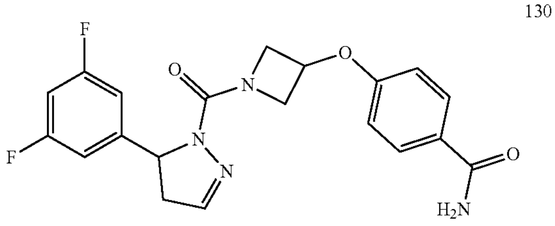
131
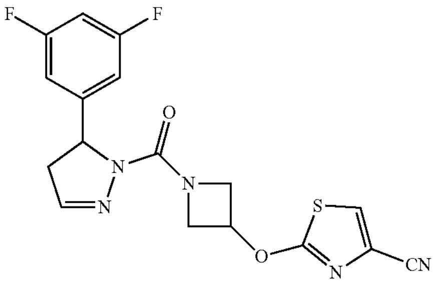
132
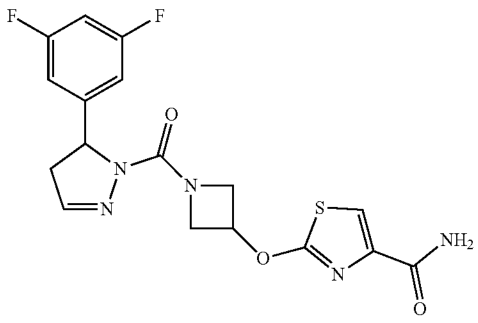
-continued
133
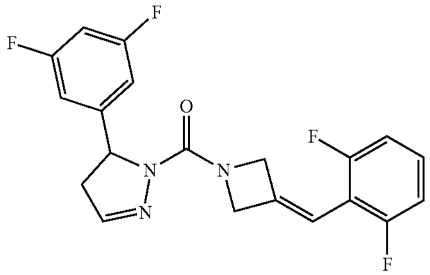
134
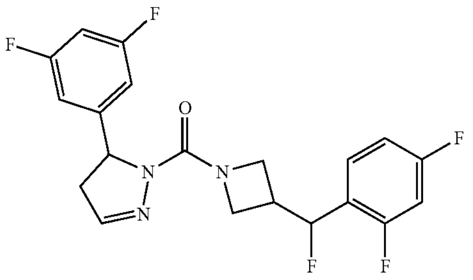
135
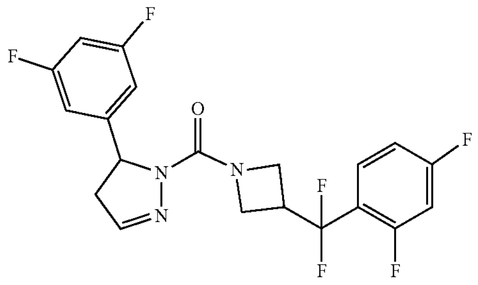
136
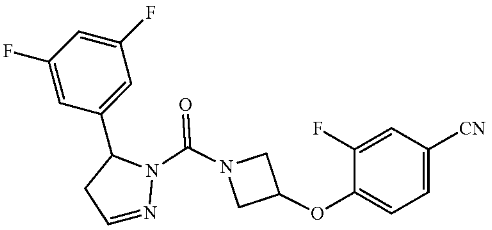
137
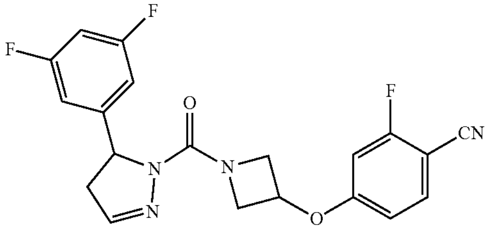
138
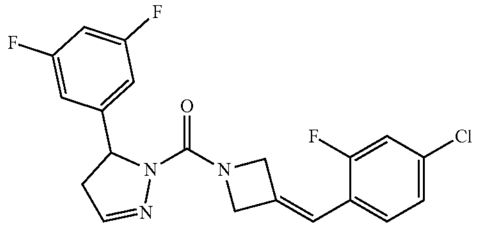

-continued
139
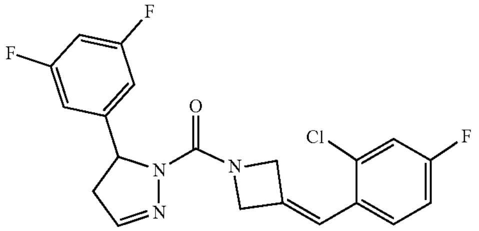
140
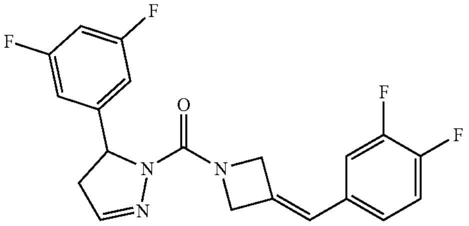
141
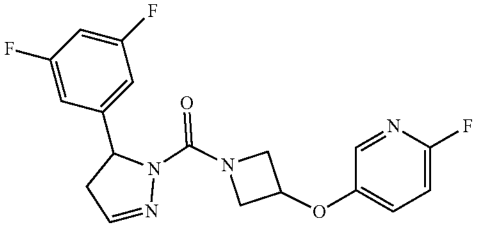
142
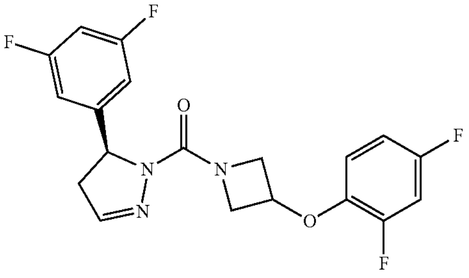
143
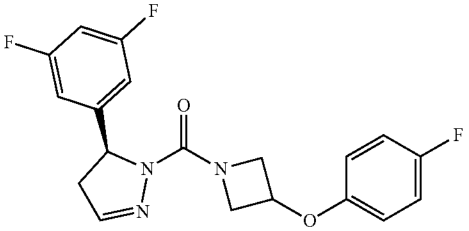
144
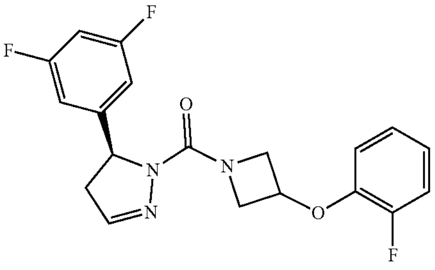
-continued
145
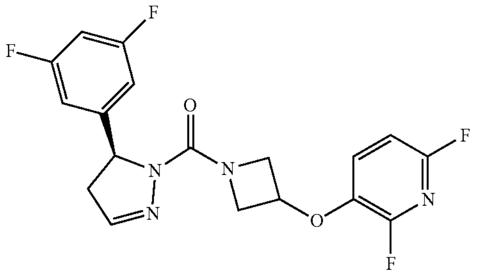
146
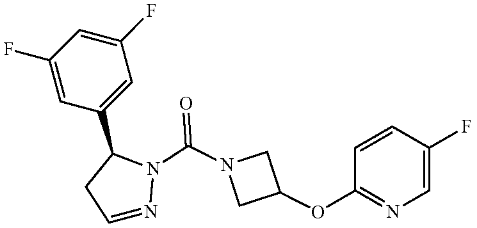
147
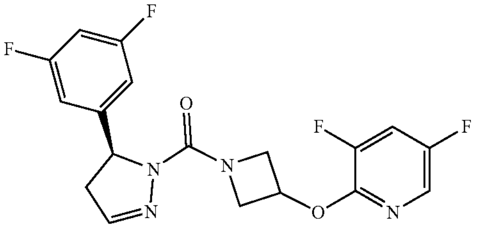
148
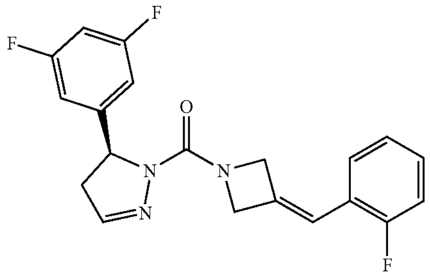
149
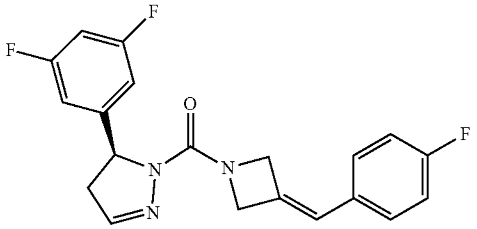
150
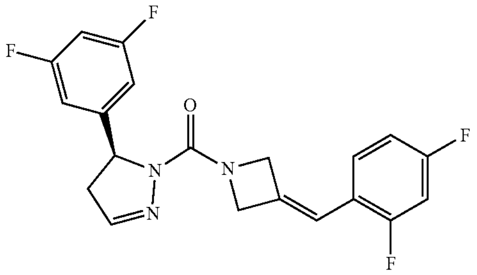

-continued
151
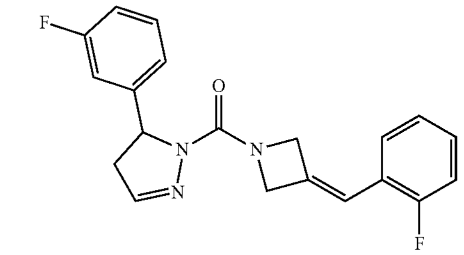
152
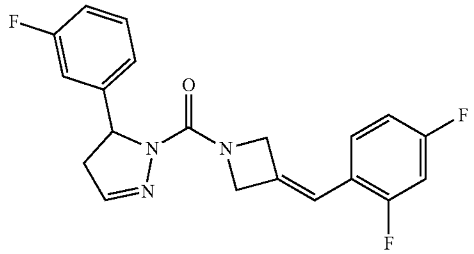
153
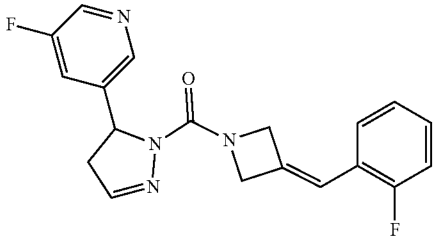
154
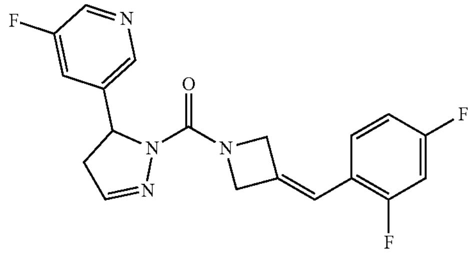
155
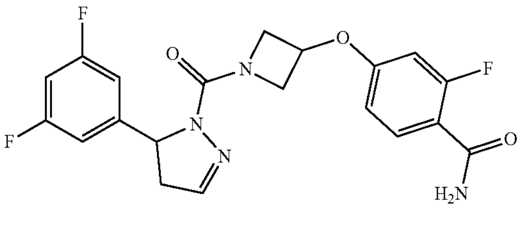
156
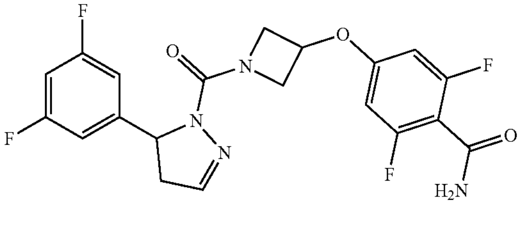
-continued
157
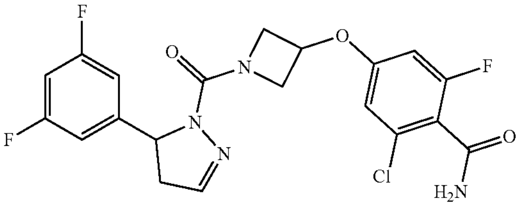
158
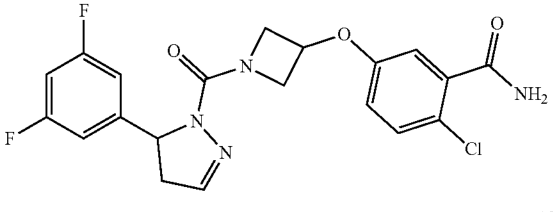
159
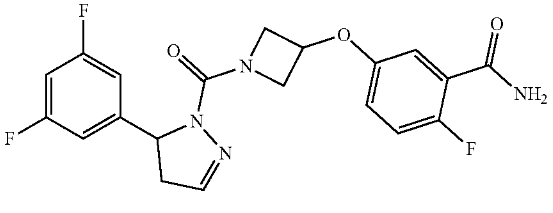
160
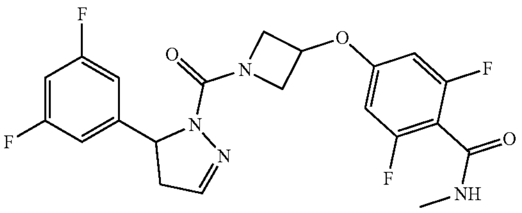
161
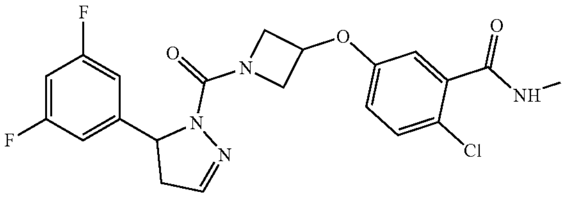
162
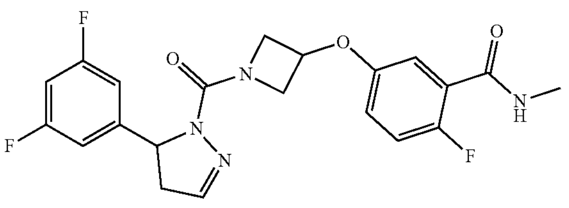

-continued
163
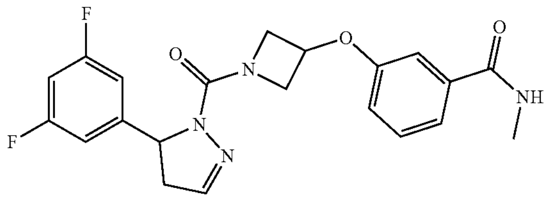
164
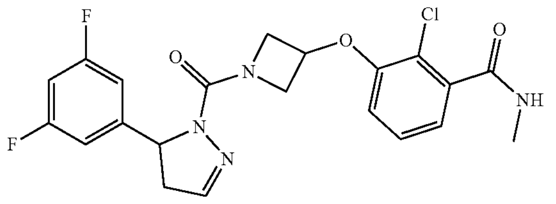
165
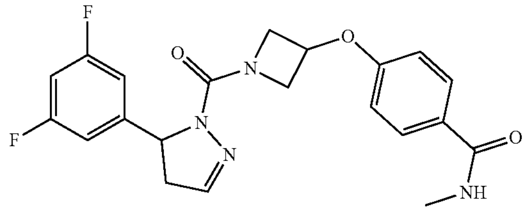
166
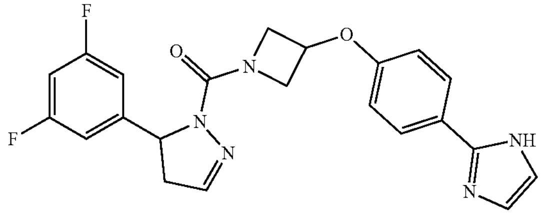
167
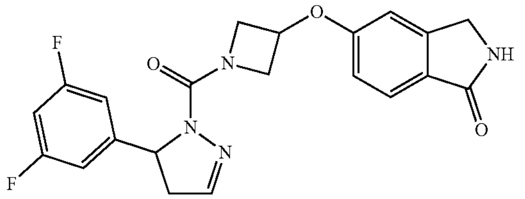
168
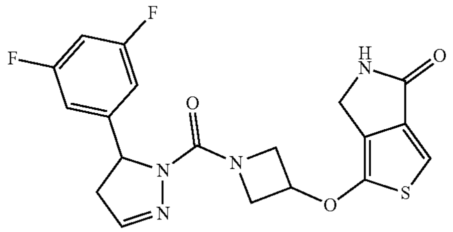
169
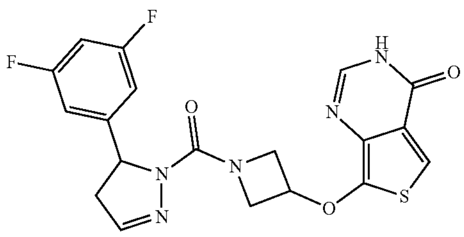
-continued
170
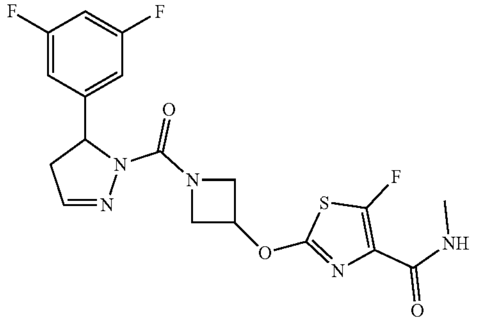
171
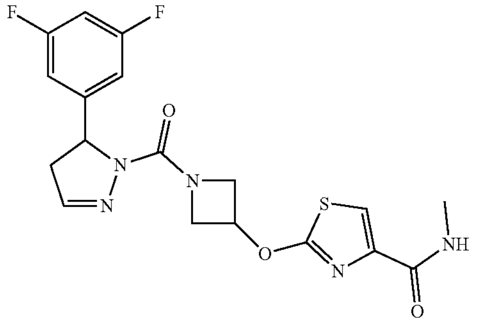
172
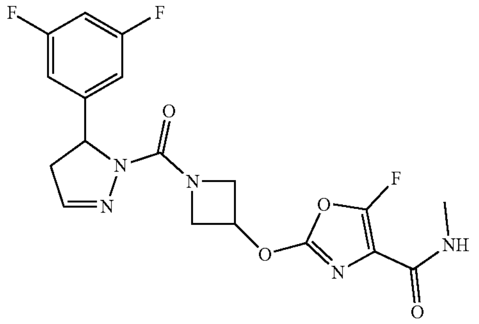
173
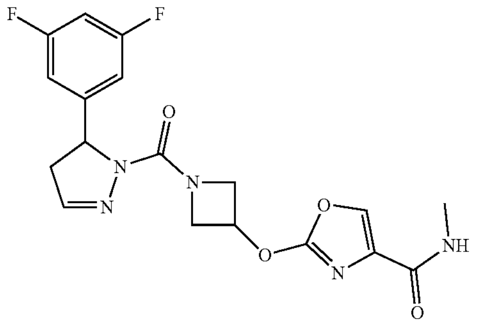

-continued
174
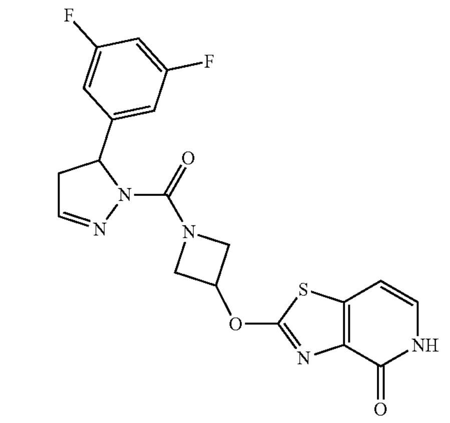
175
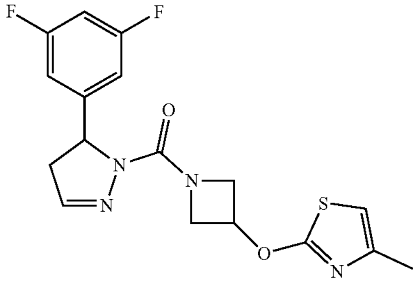
176
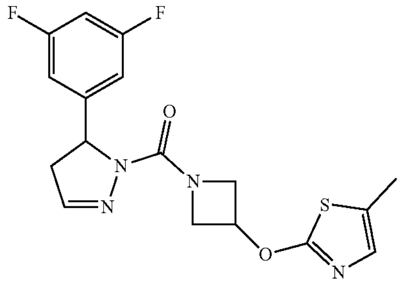
177
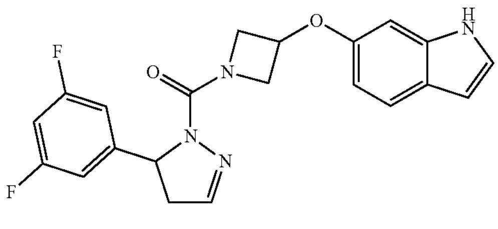
178
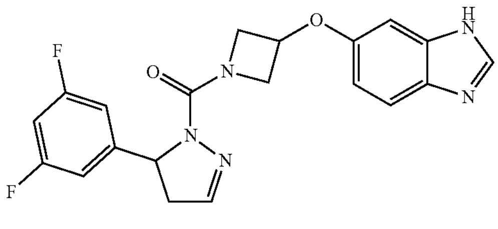
-continued
179
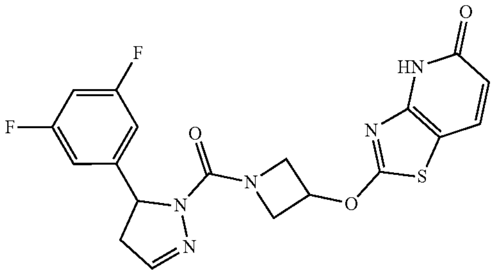
180
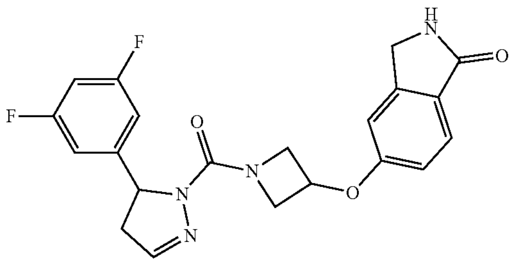
181
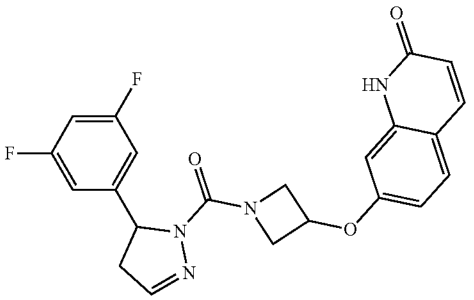
182
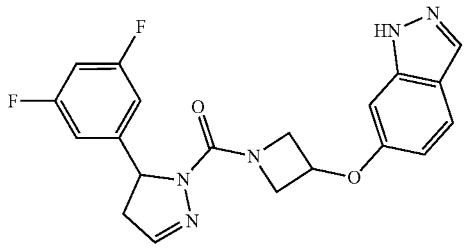
183
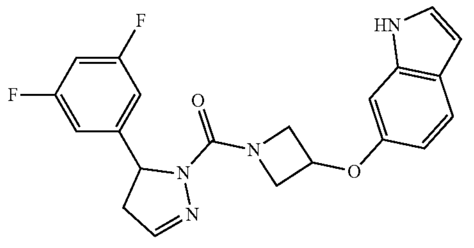
183
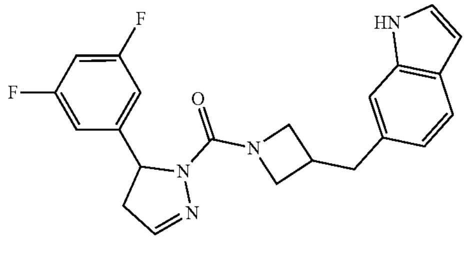

-continued
184
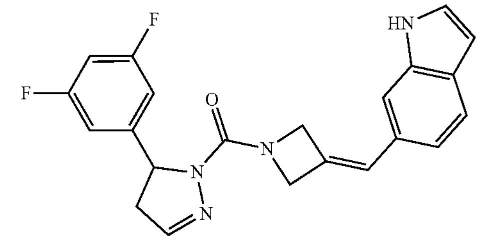
185
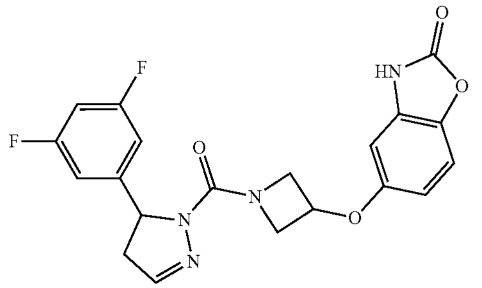
186
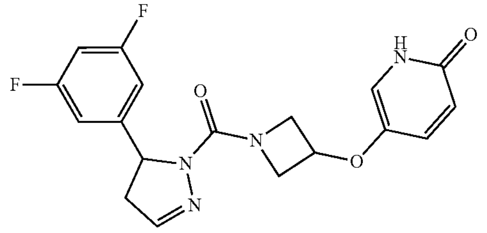
187
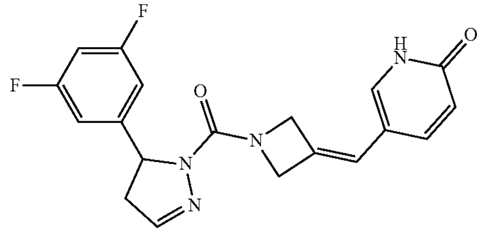
188
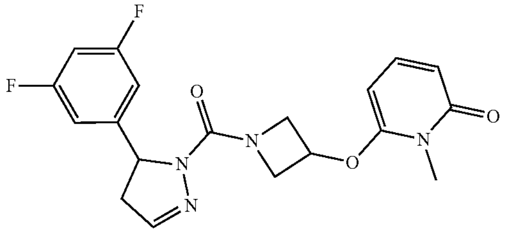
189
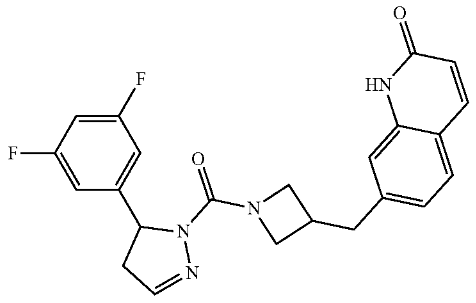
-continued
190
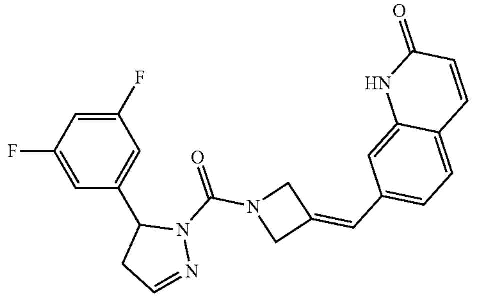
191
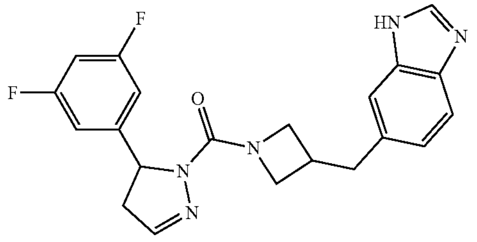
192
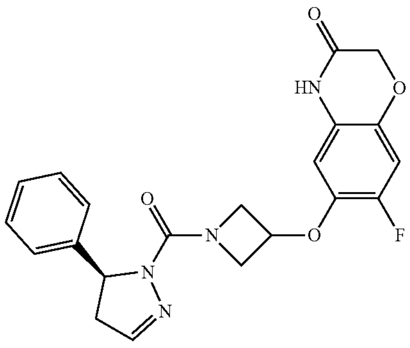
193
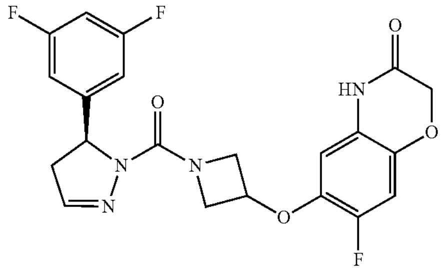
194
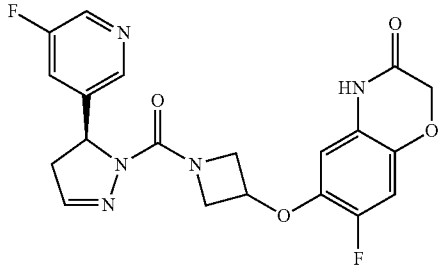

195
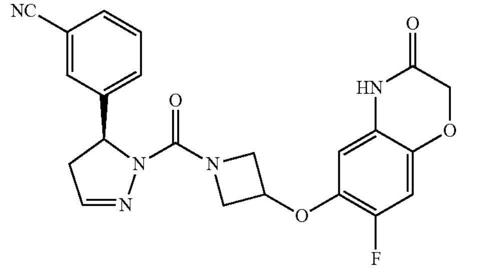
196
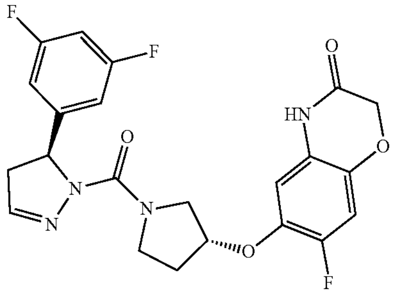
197
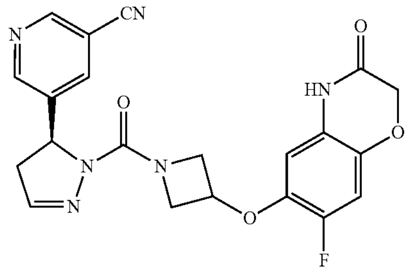
198
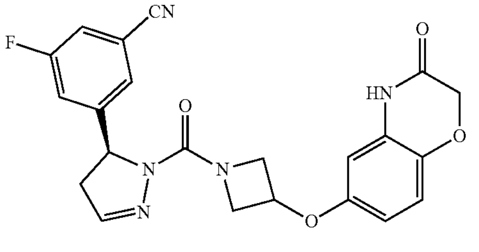
199
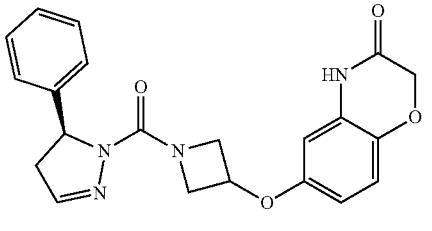
200
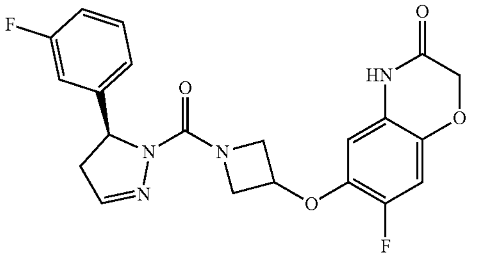
201
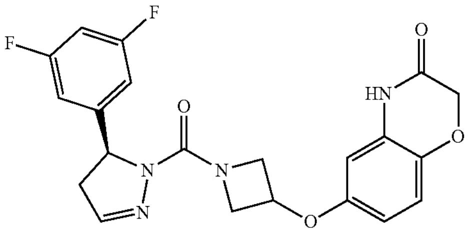
202
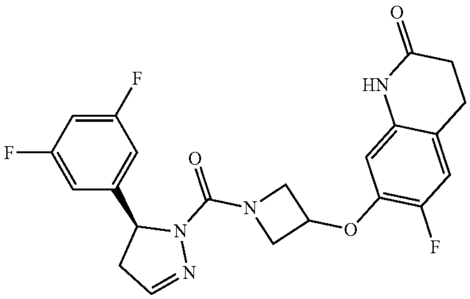
203
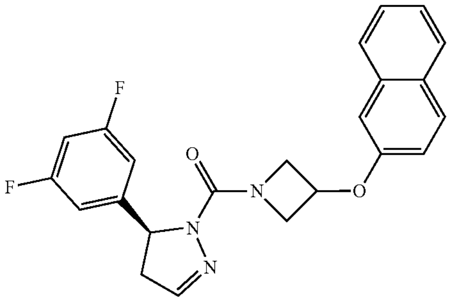
204
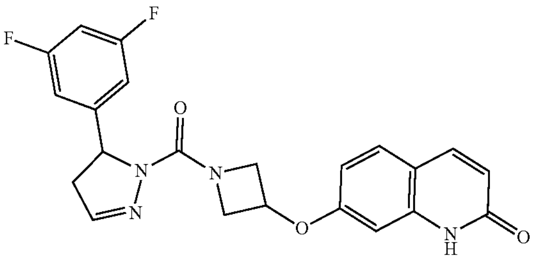
205
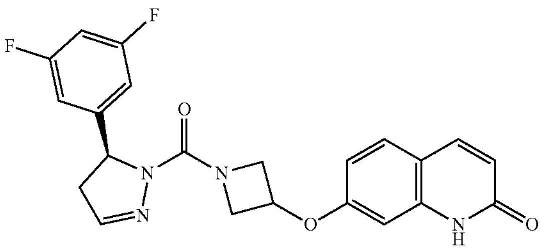

206
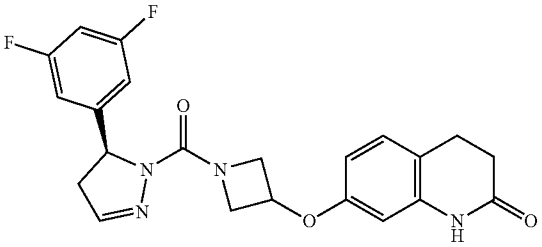
207
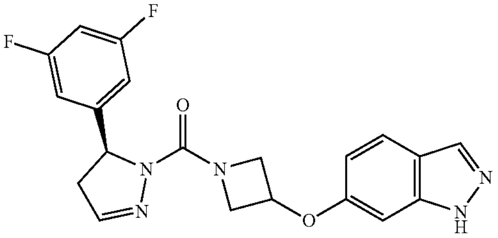
208
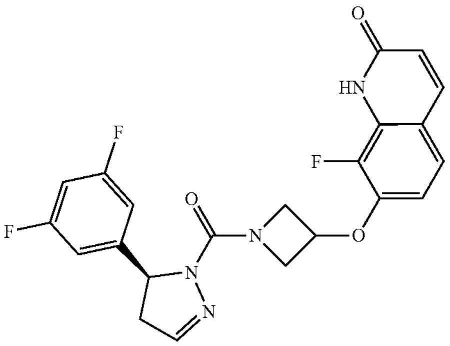
209
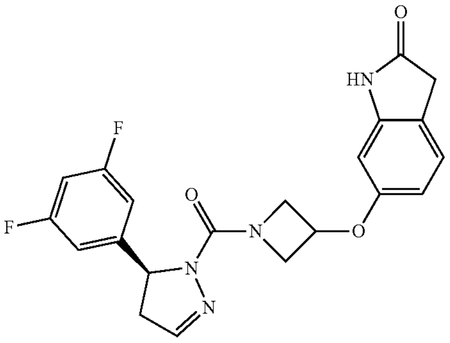
210
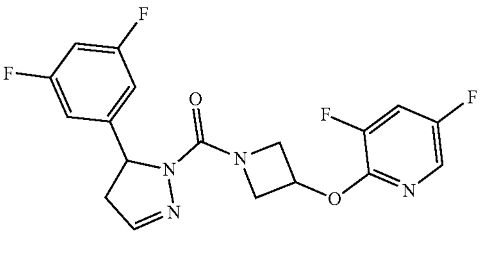
211
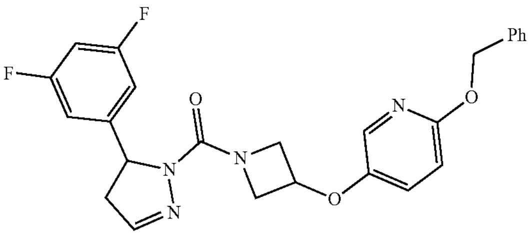
212
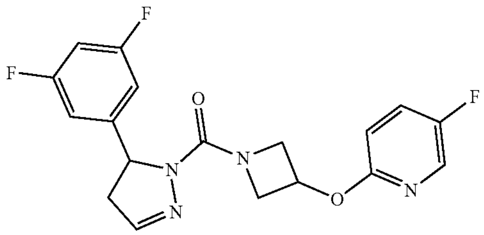
213
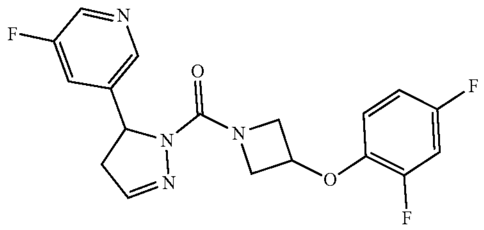
214
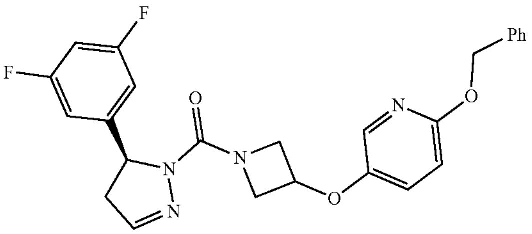
215
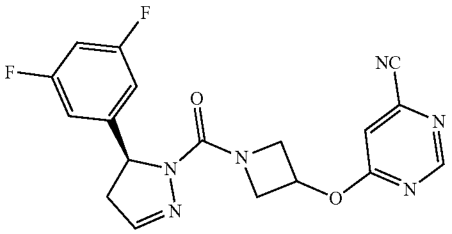
216
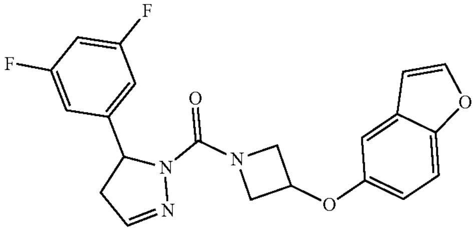

-continued
217
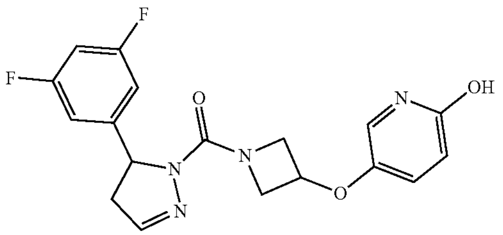
218
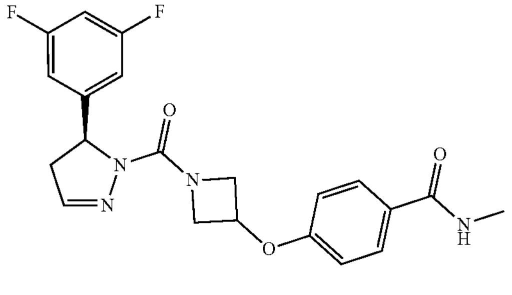
219
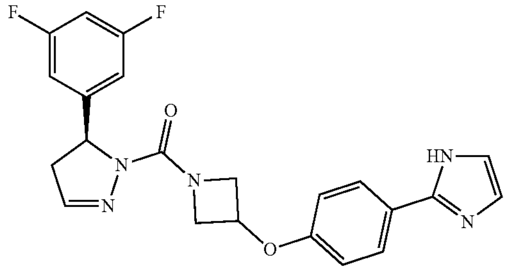
220
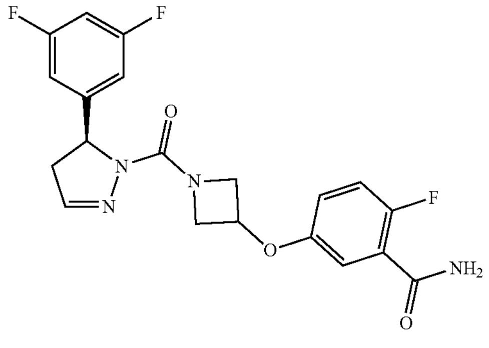
221
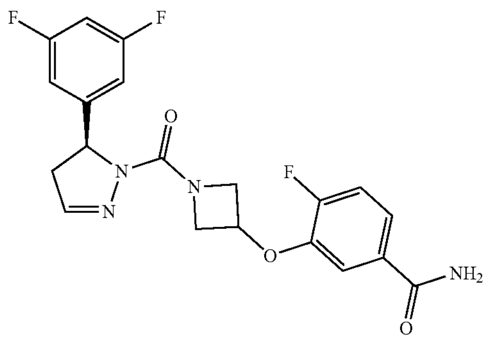
-continued
222
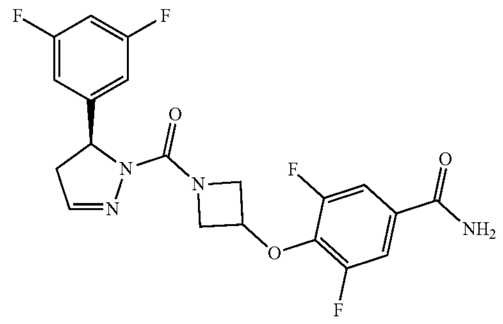
223
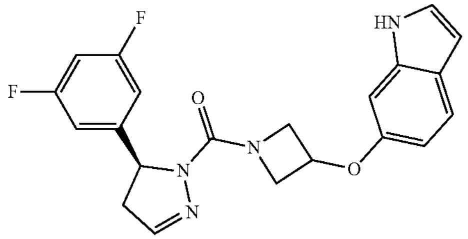
224
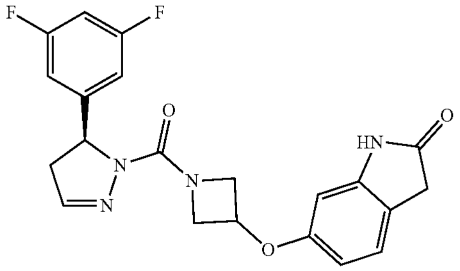
225
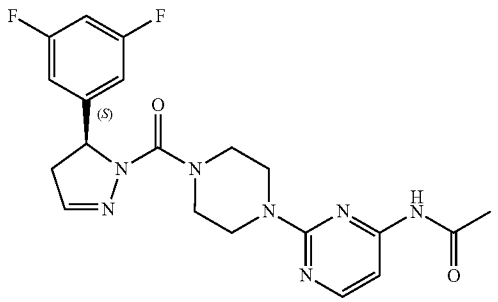
226
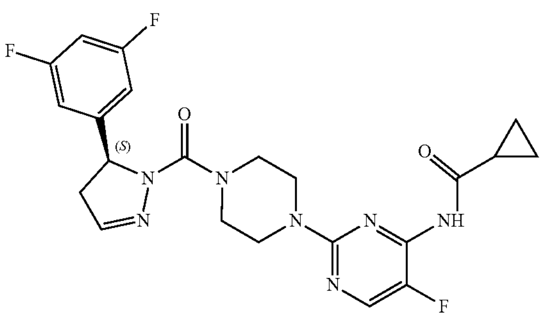

-continued
227
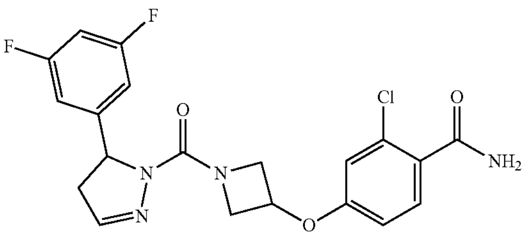
228
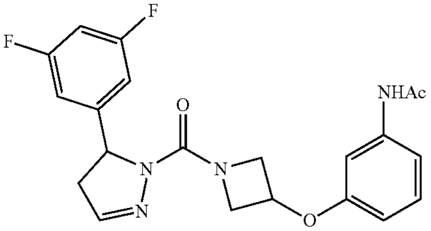
229
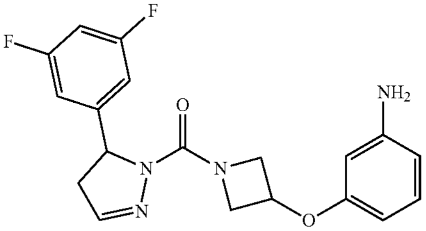
230
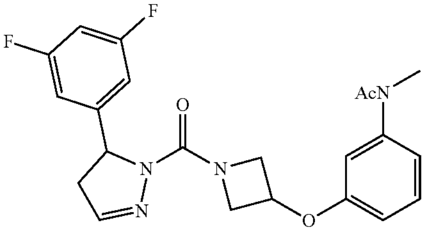
231
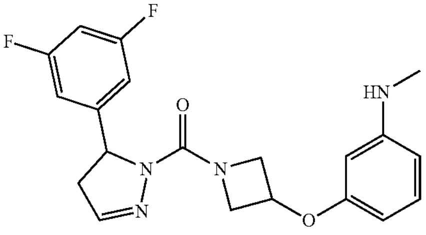
232
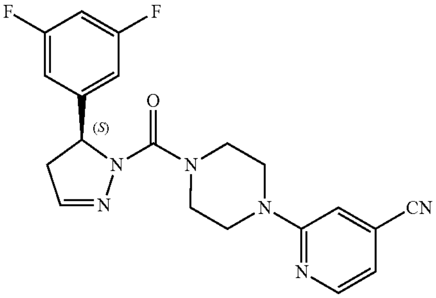
-continued
233
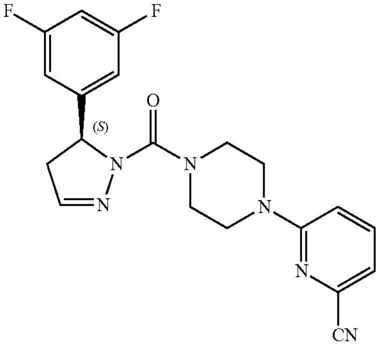
234
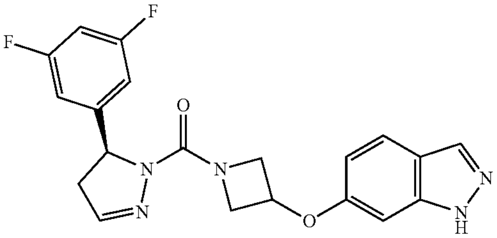
235
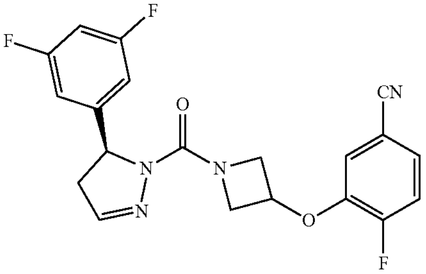
236
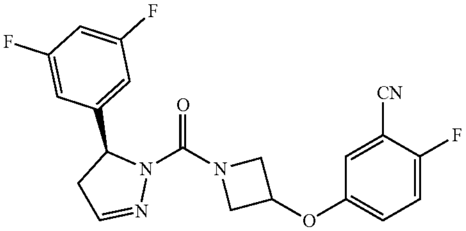
237
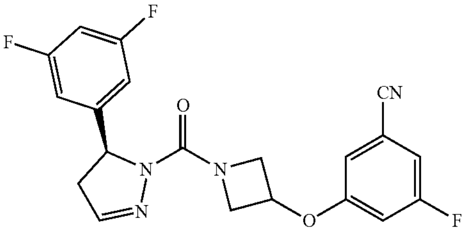
238
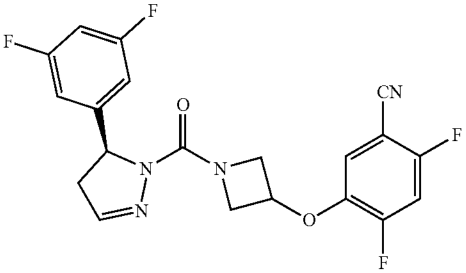

-continued
239
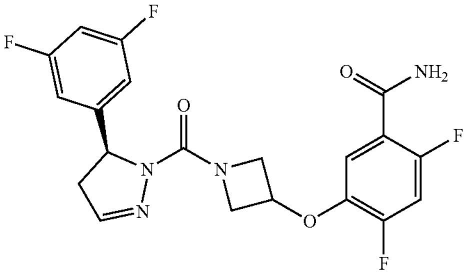
240
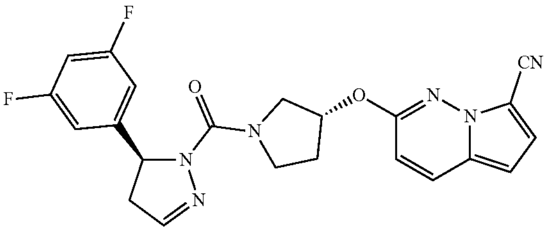
241
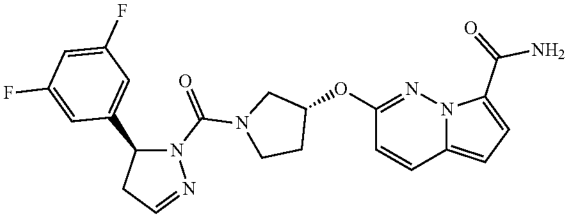
242
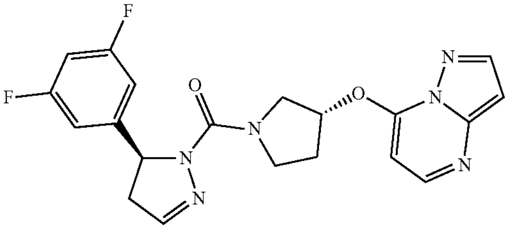
243
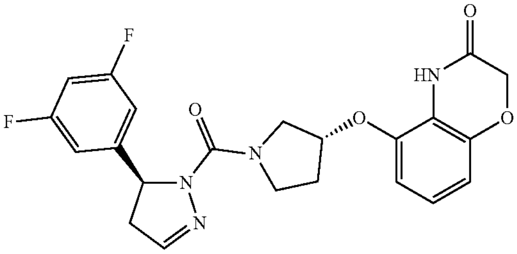
244
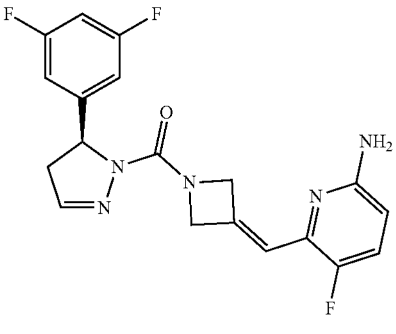
-continued
245
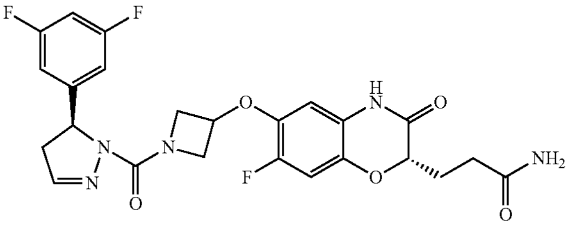
246
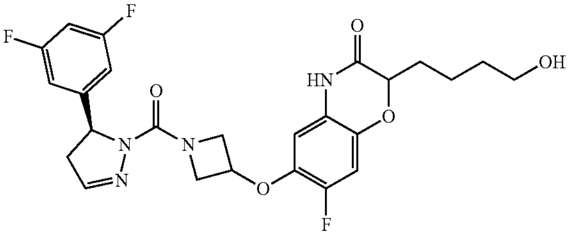
247
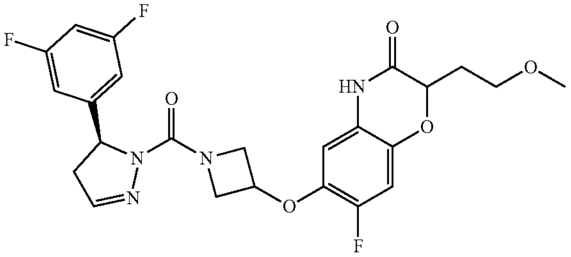
248
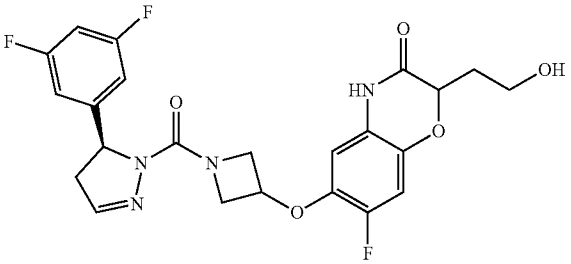
249
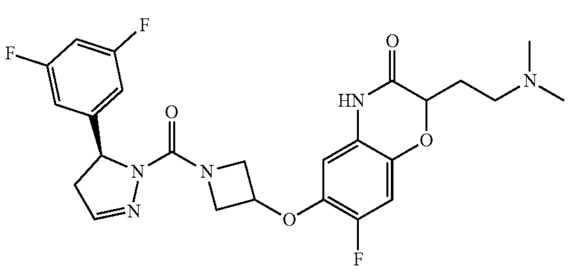

-continued
250
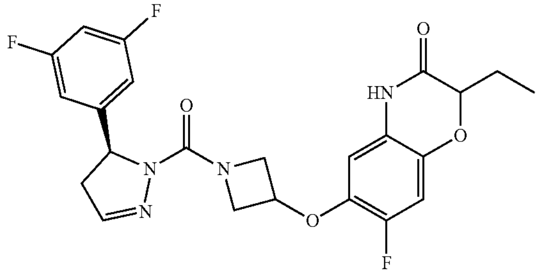
251
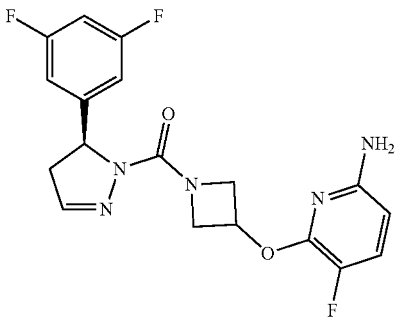
252
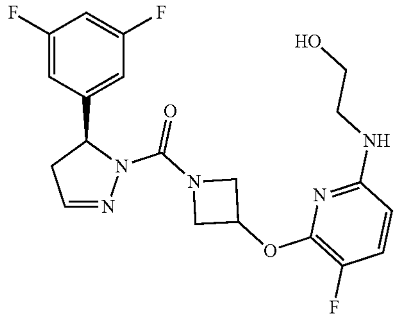
253
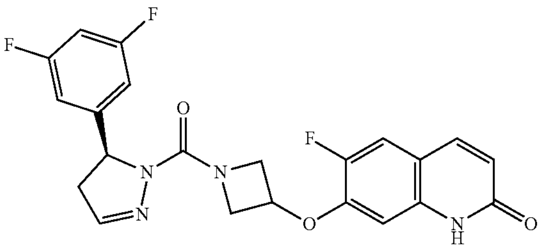
254
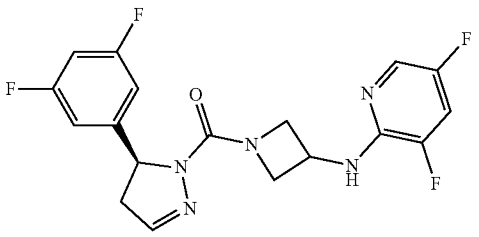
-continued
255
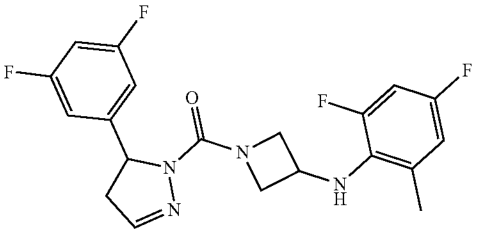
256
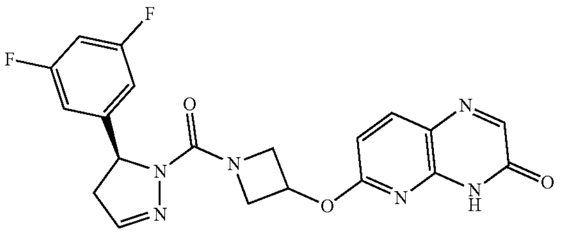
257
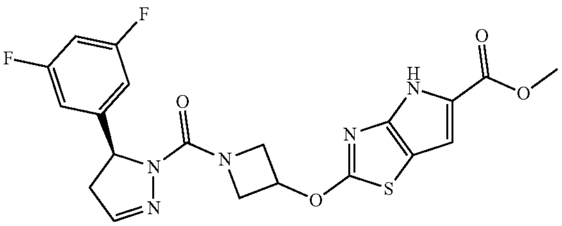
258
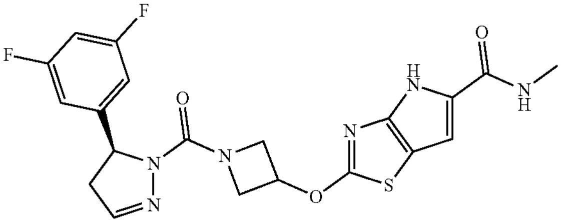
259
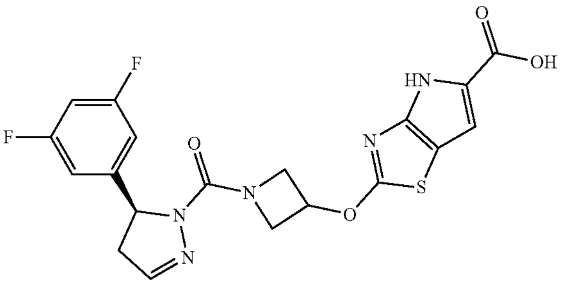
260
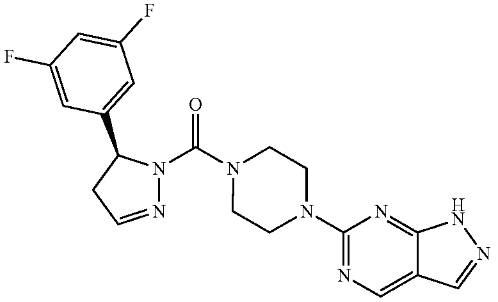

-continued
261
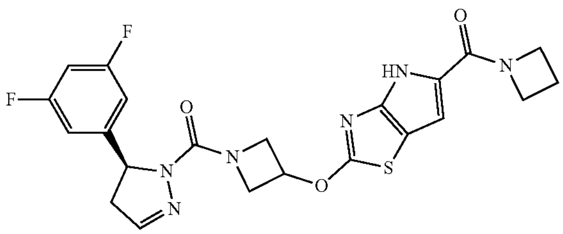
262
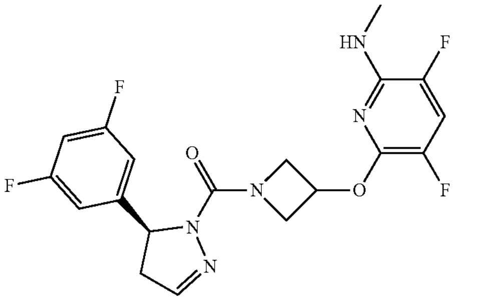
263
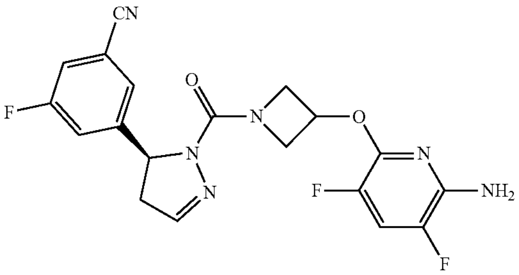
264
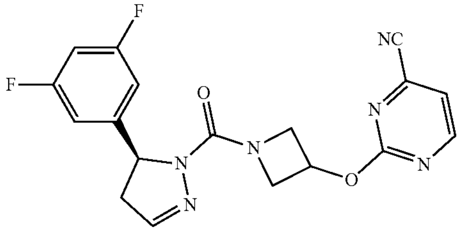
265
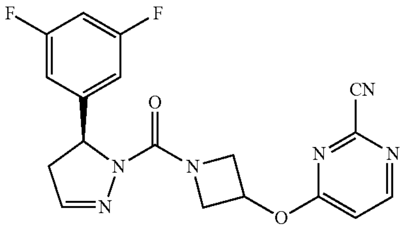
266
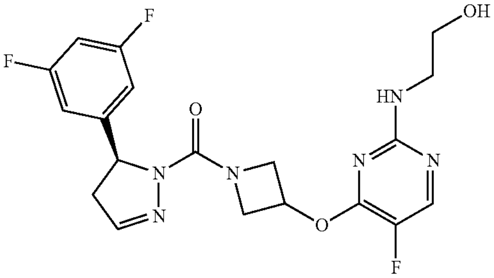
-continued
267
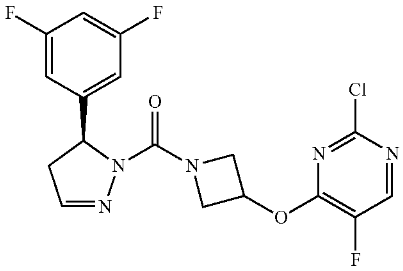
268
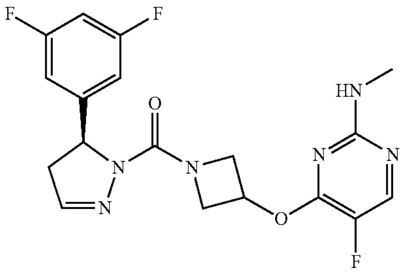
269
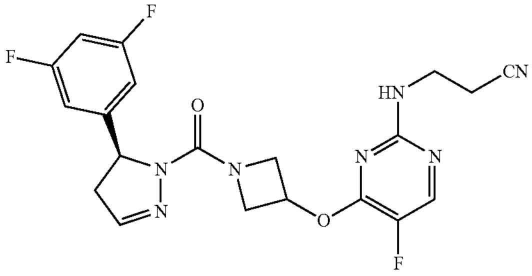
270
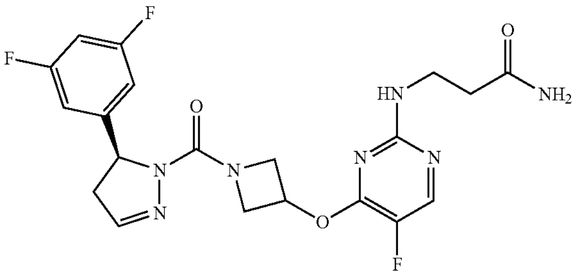
271
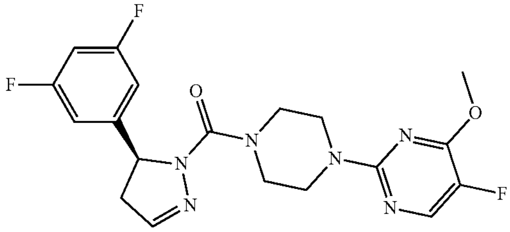

-continued
272
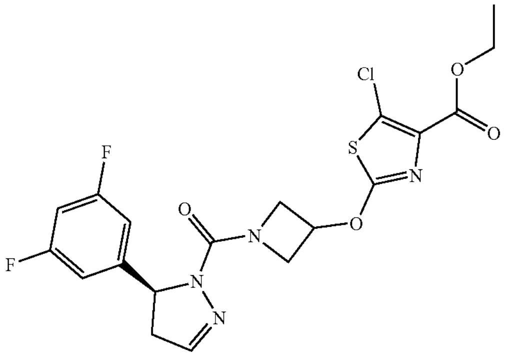
273
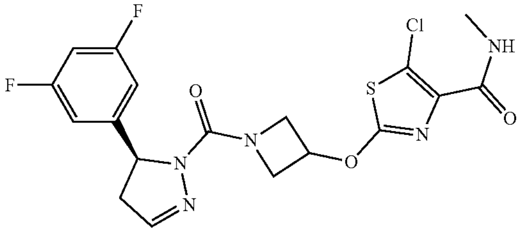
274
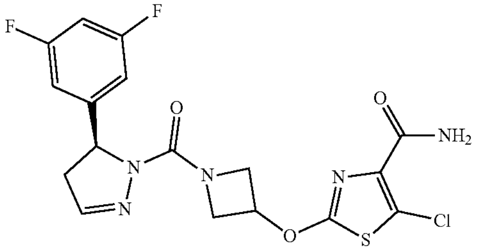
275
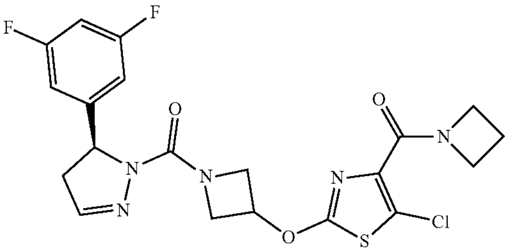
276
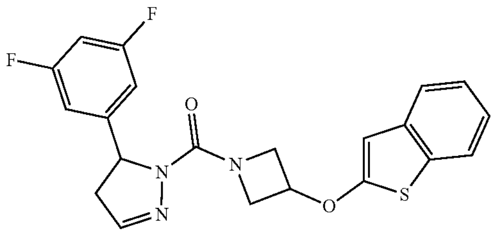
-continued
277
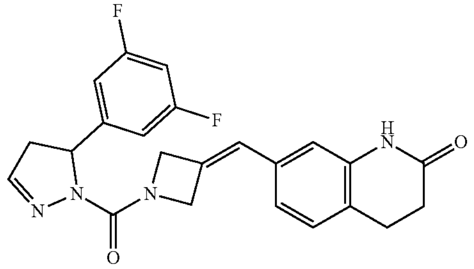
278
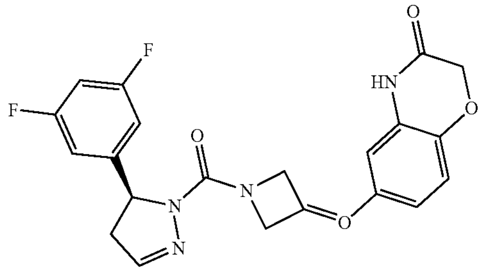
279
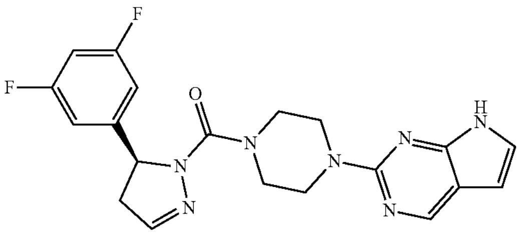
280
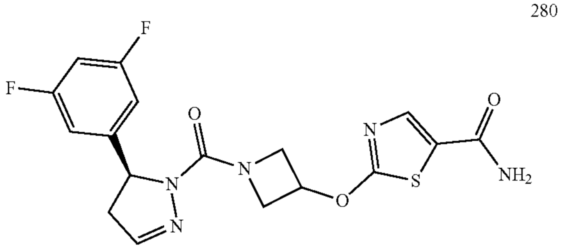
281
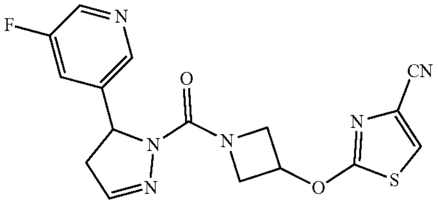
282
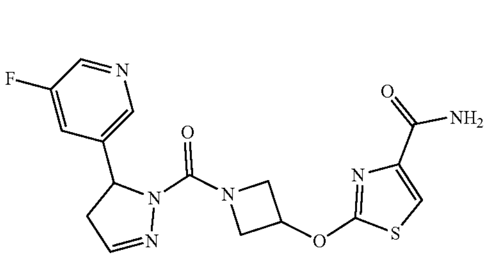

-continued
283
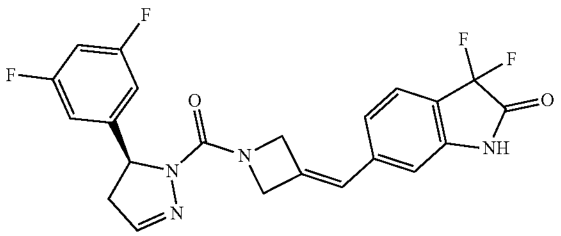
284
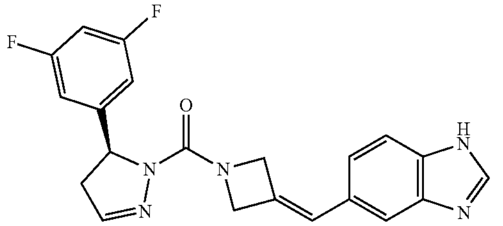
285
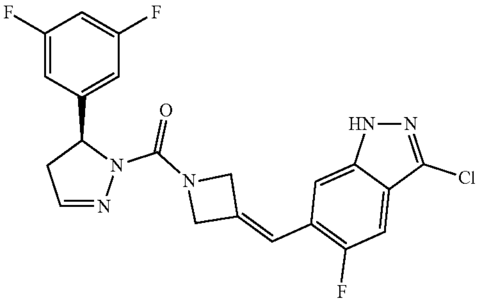
286
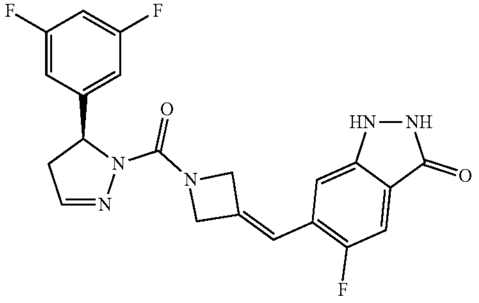
287
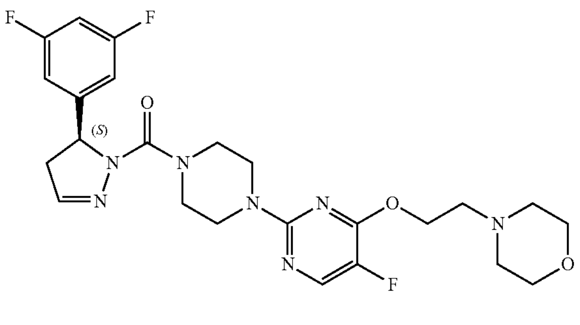
-continued
288
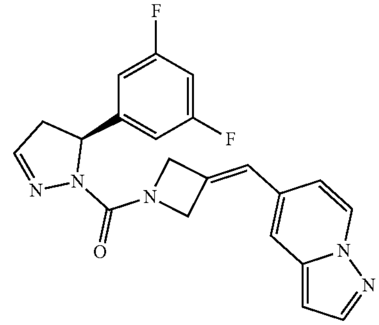
289
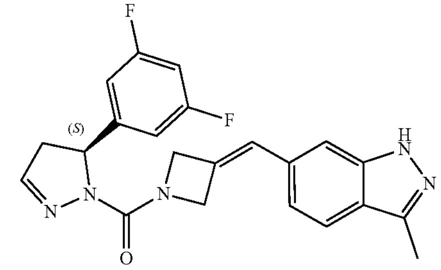
290
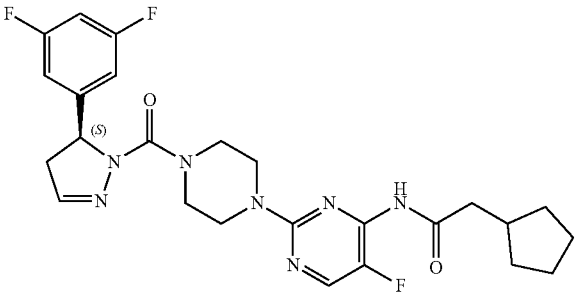
291
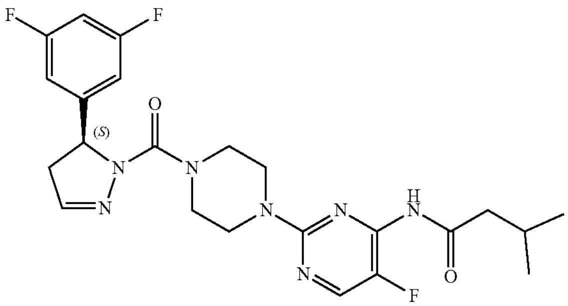
292
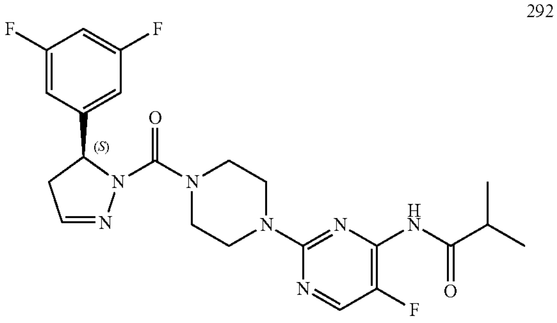

-continued
293
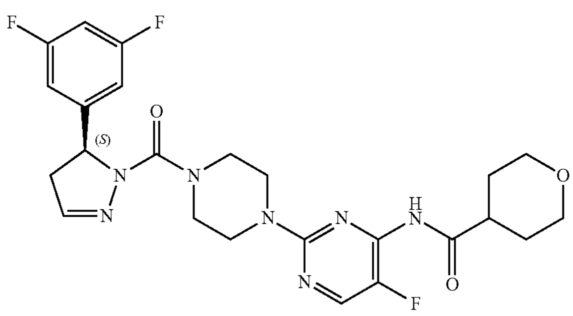
294
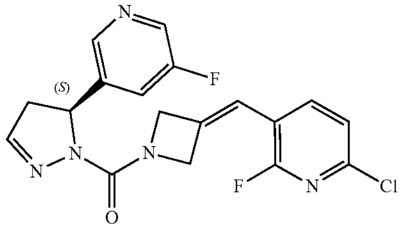
295
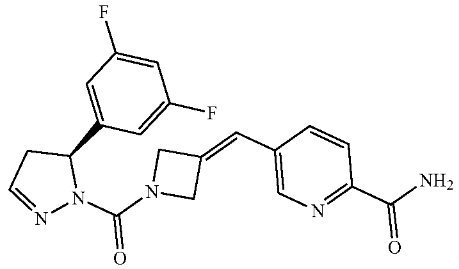
296
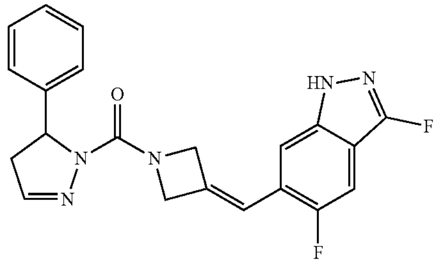
297
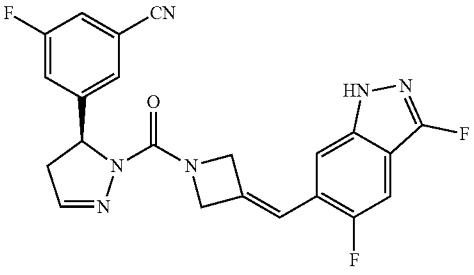
298
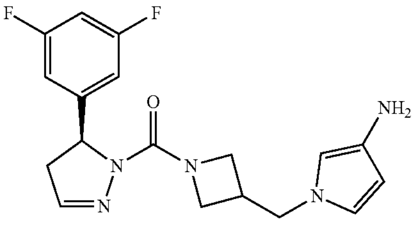
-continued
299
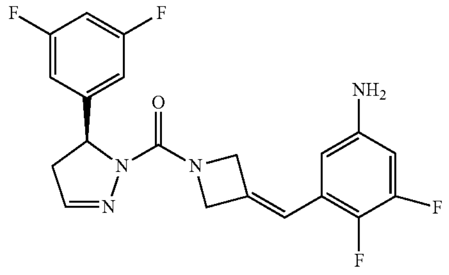
300
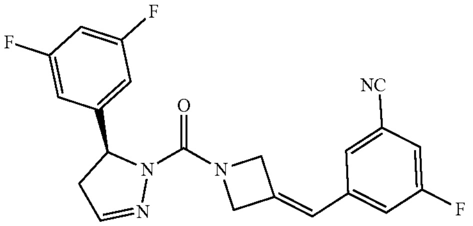
301
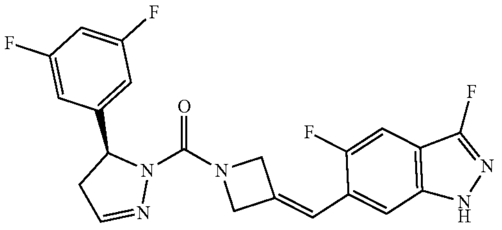
302
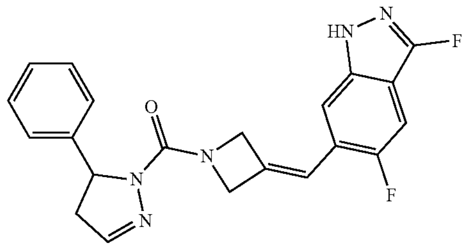
303
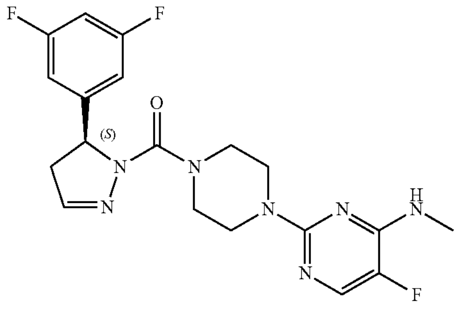
304
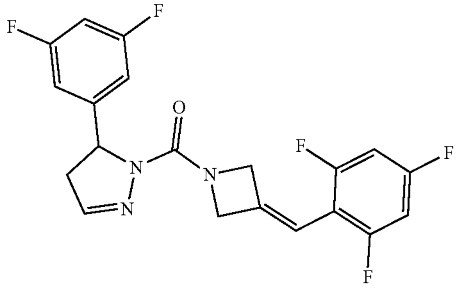

-continued
305
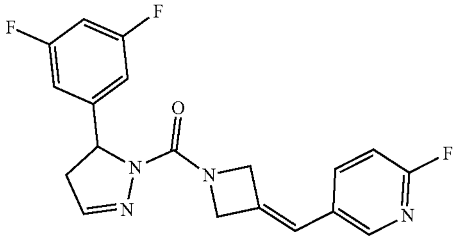
306
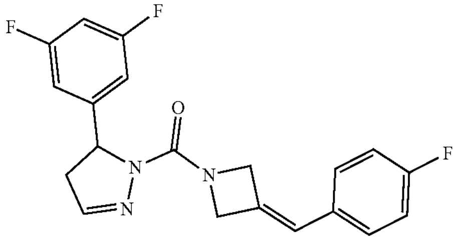
307
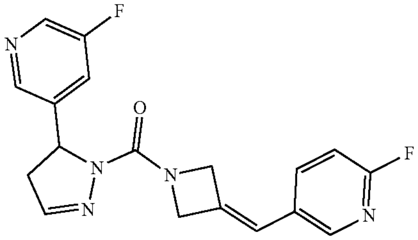
308
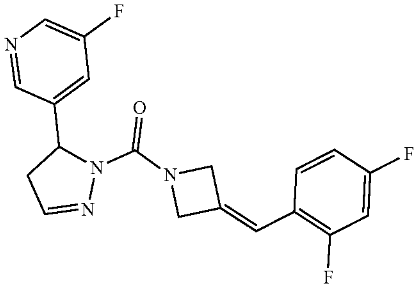
309
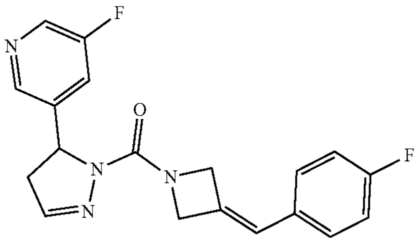
310
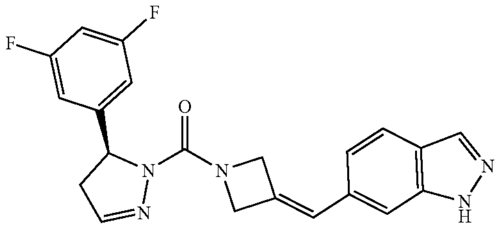
-continued
311
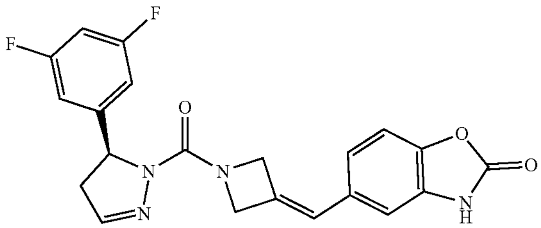
312
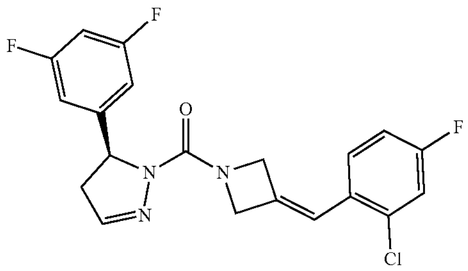
313
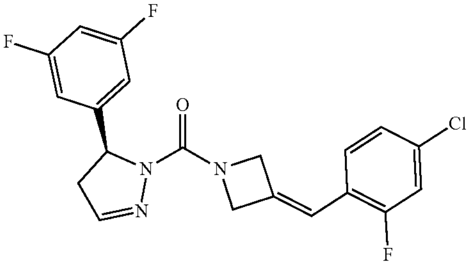
314
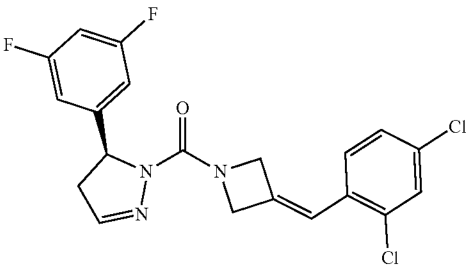
315
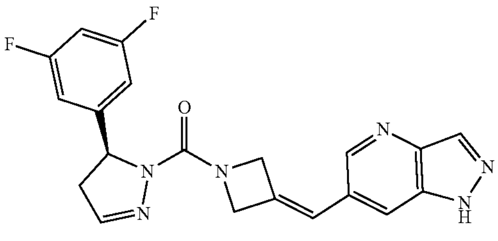
316
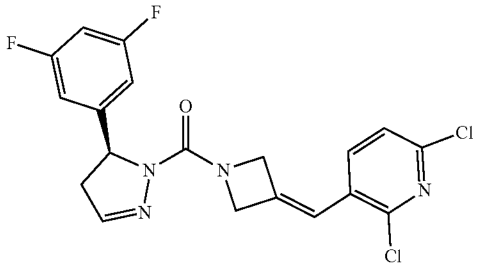

317
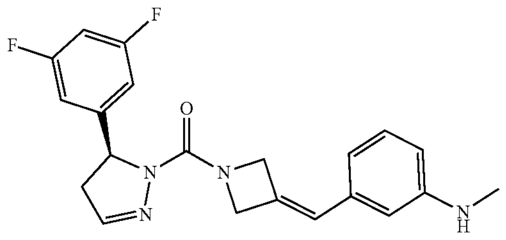
318
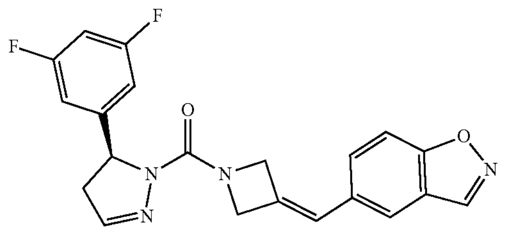
319
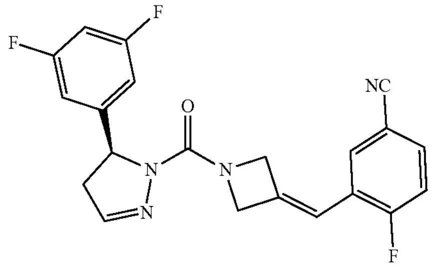
320
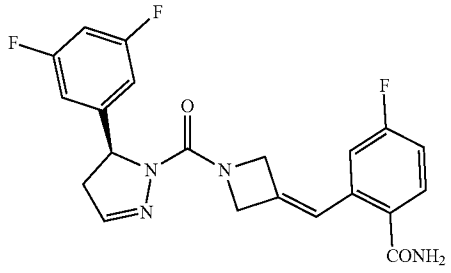
321
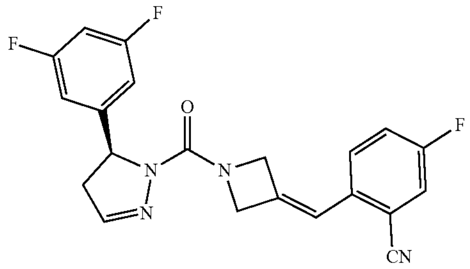
322
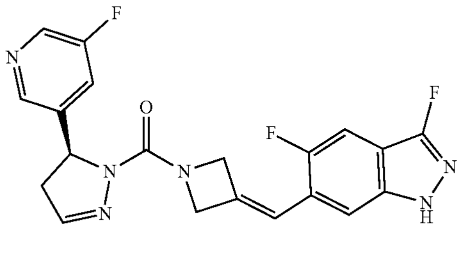
323
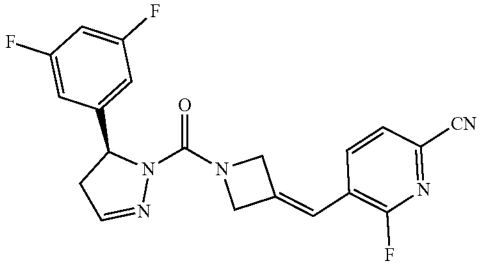
324
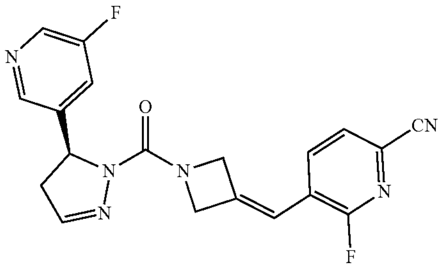
325
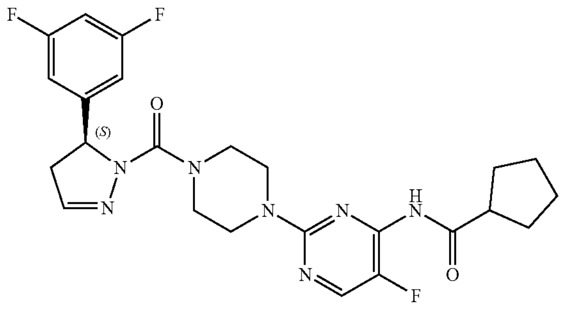
326
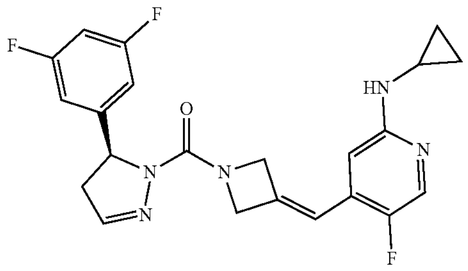
327
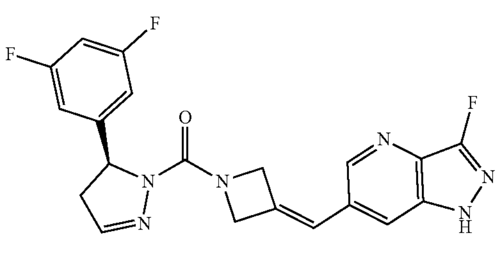

-continued
328
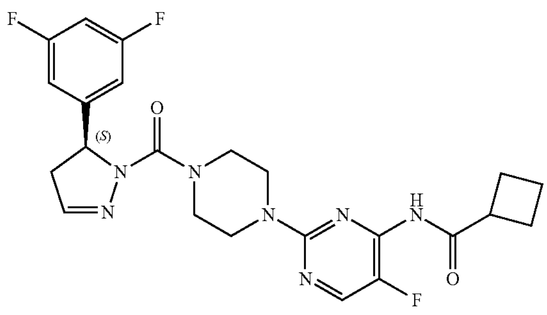
329
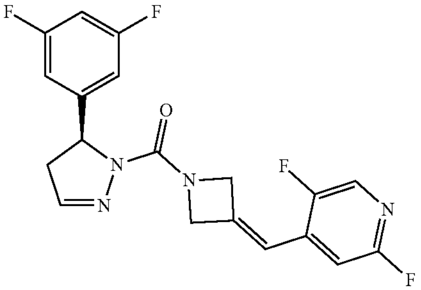
330
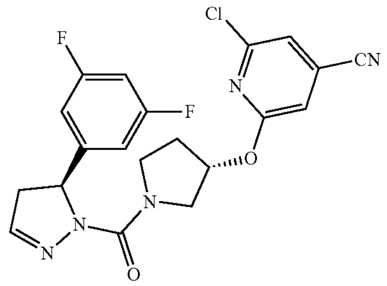
331
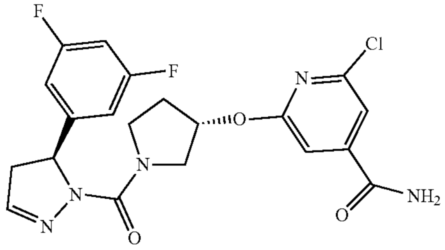
332
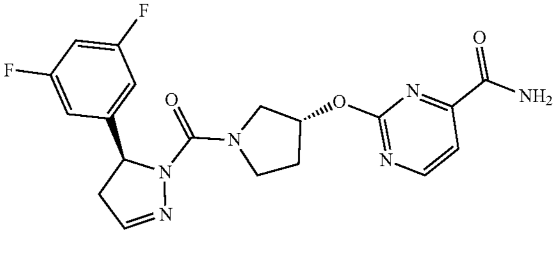
-continued
333
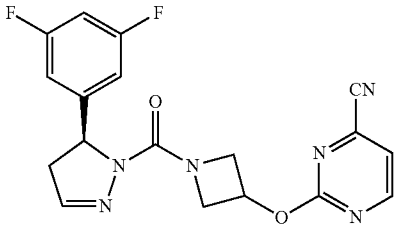
334
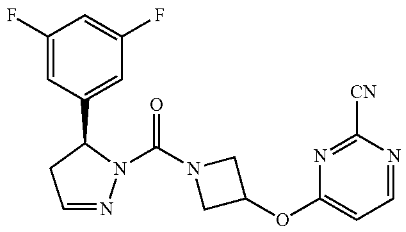
335
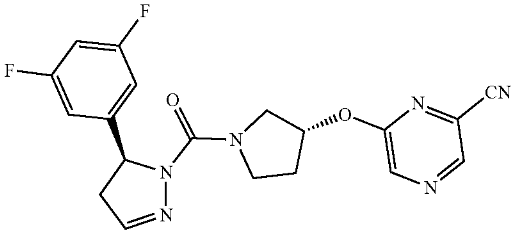
336
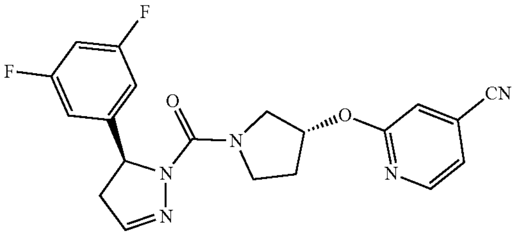
337
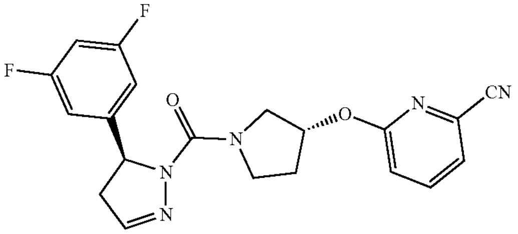
338
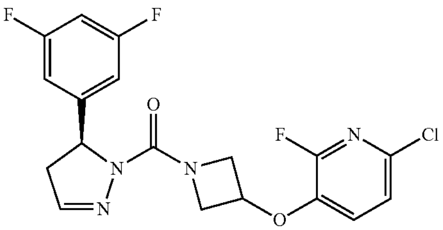

339
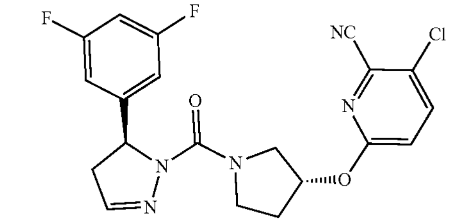
340
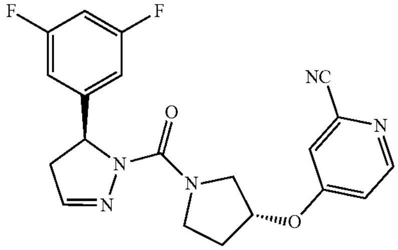
341
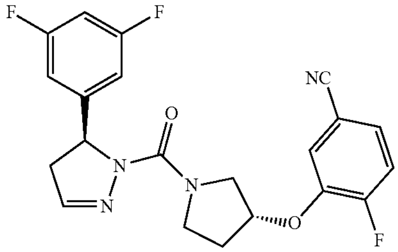
342
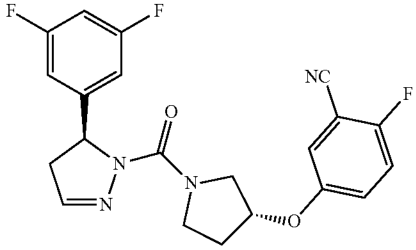
343
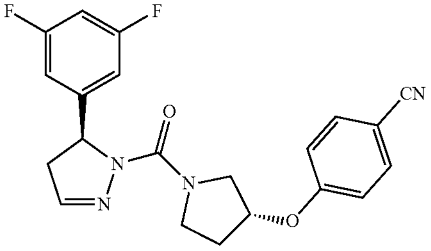
344
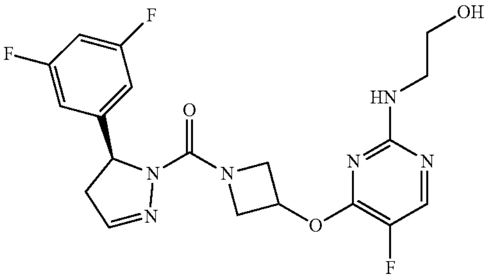
345
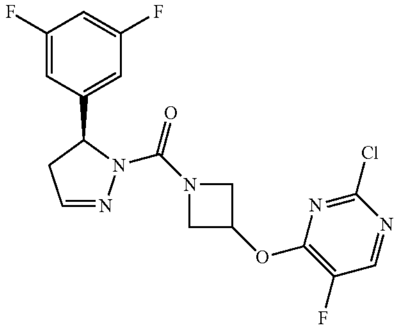
346
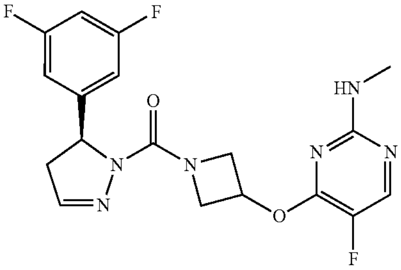
347
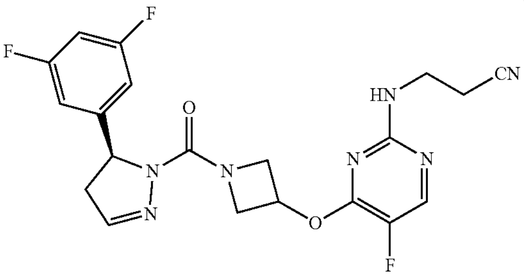
348
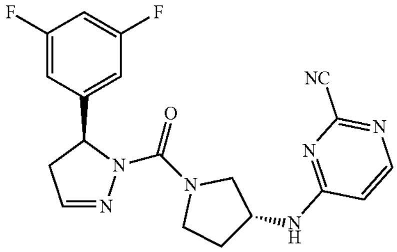
349
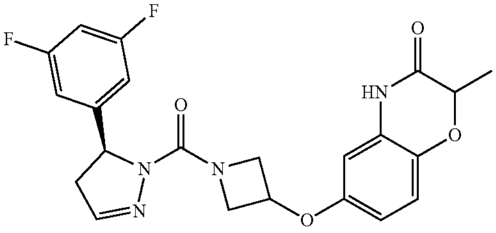

-continued
350
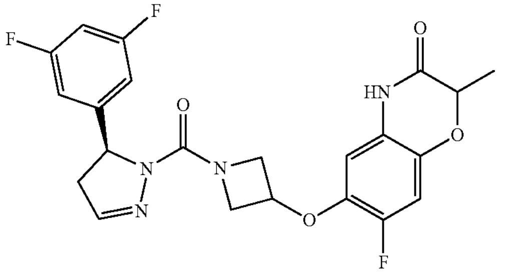
351
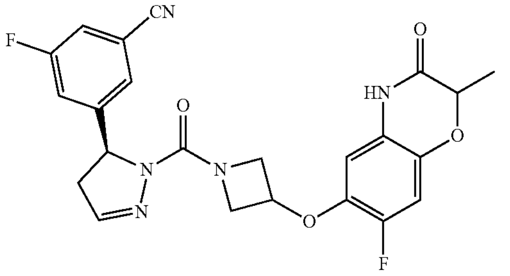
352
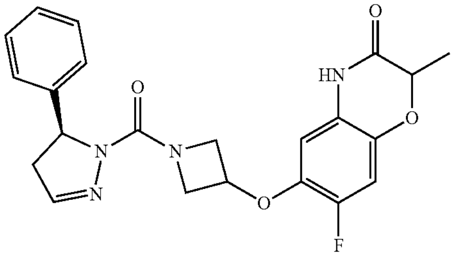
353
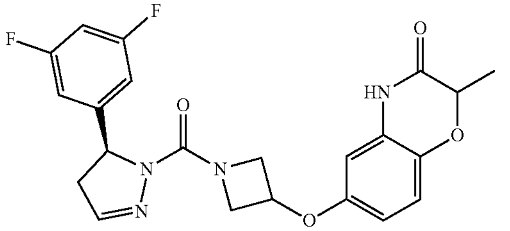
354
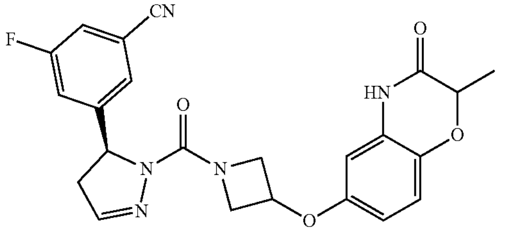
355
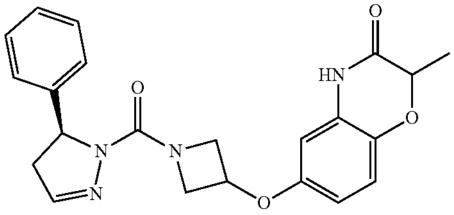
-continued
356
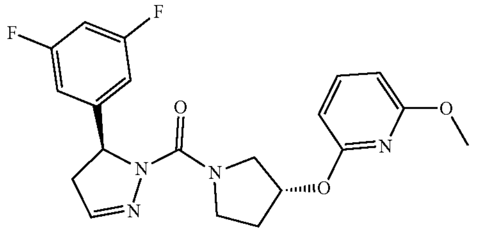
357
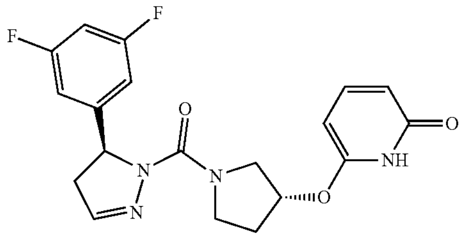
358
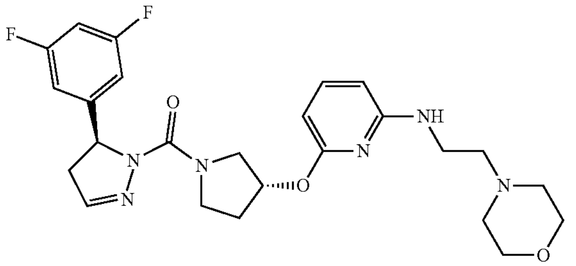
359
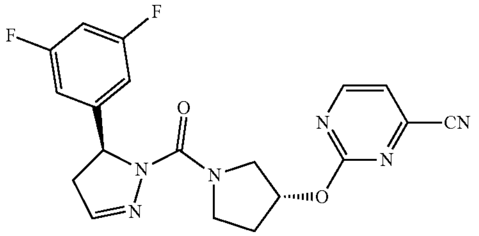
360
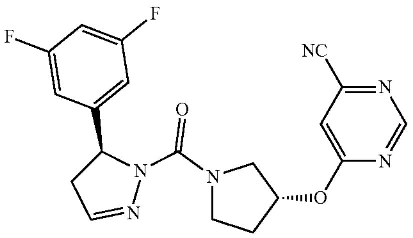
361
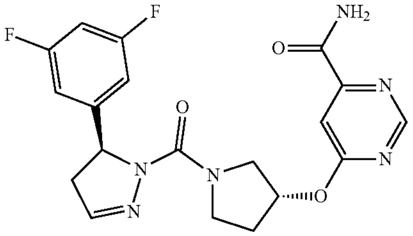

-continued
362
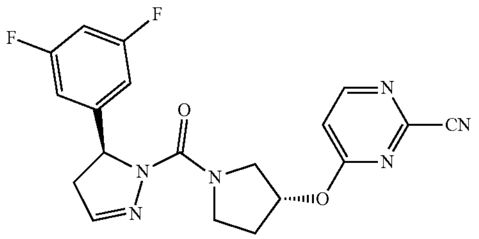
363
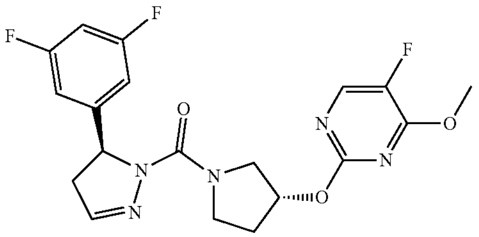
364
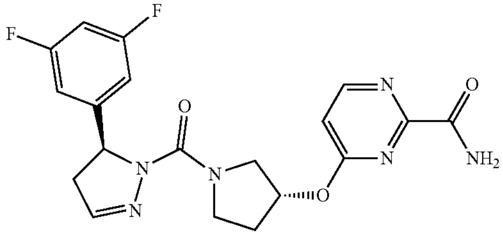
365
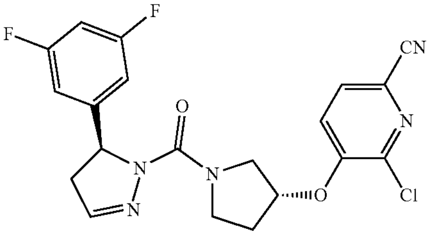
366
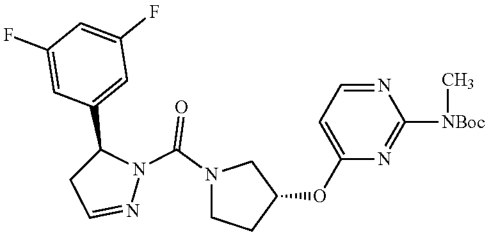
367
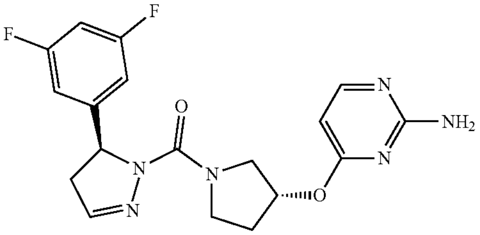
-continued
368
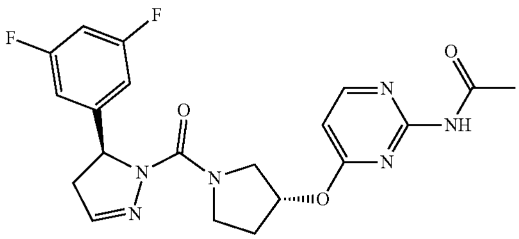
369
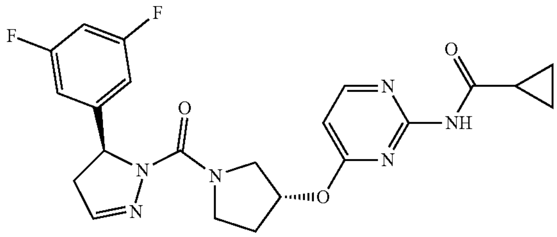
370
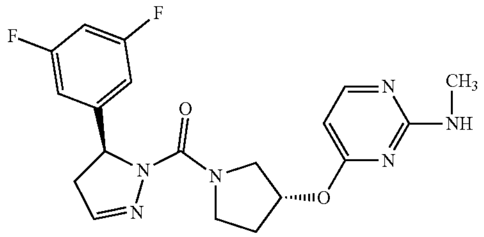
371
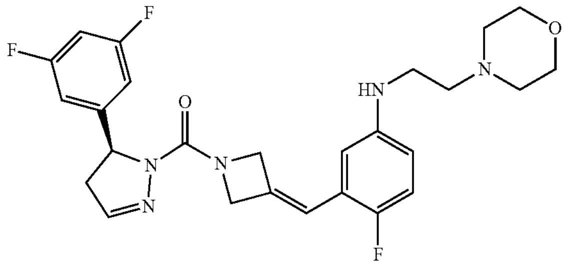
372
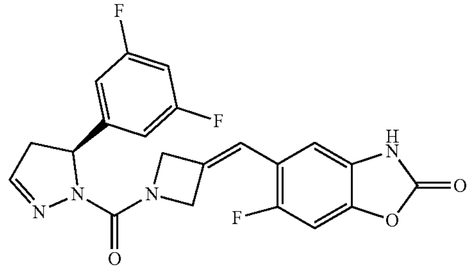
373
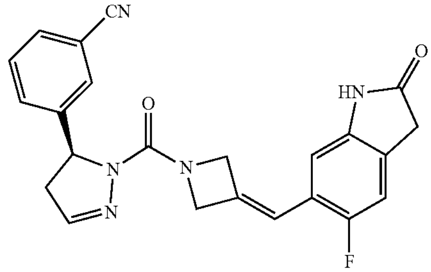

-continued
374
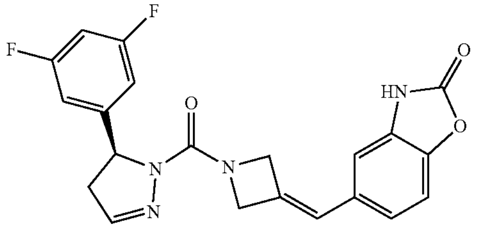
375
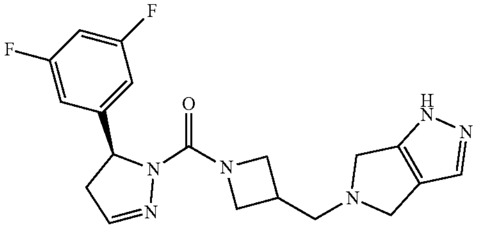
376
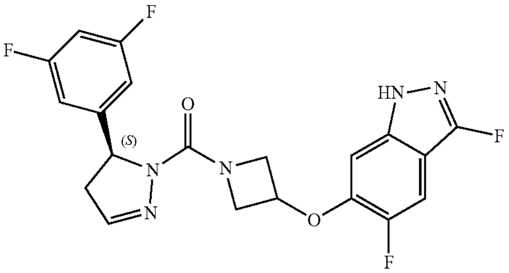
377
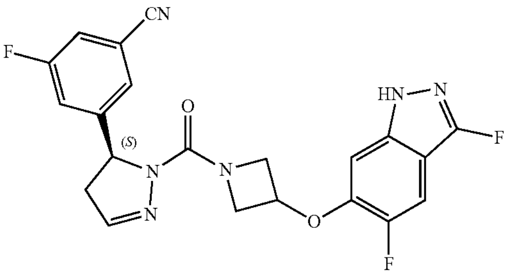
378
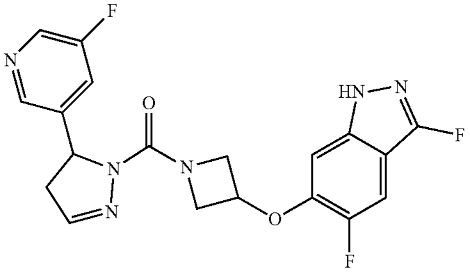
379
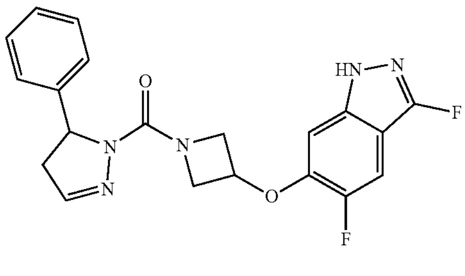
-continued
380
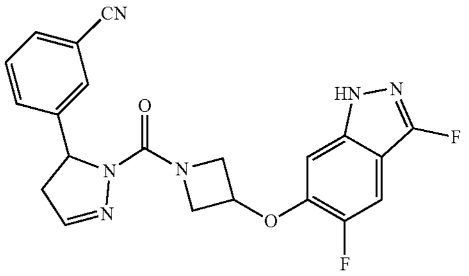
381
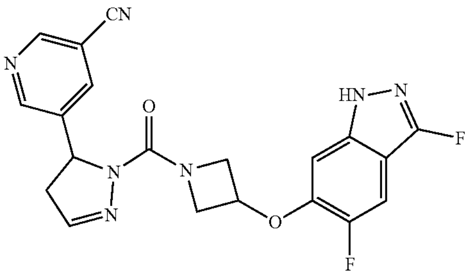
382
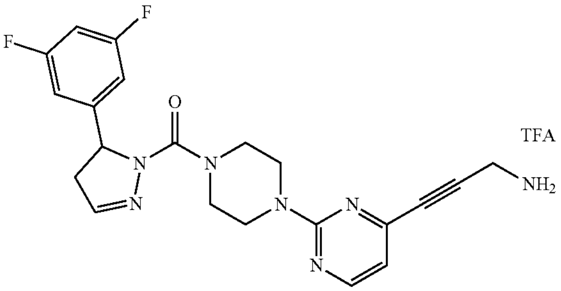
383
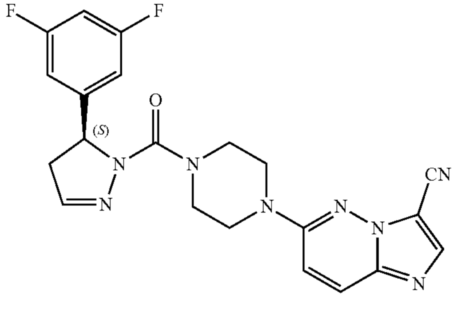
384
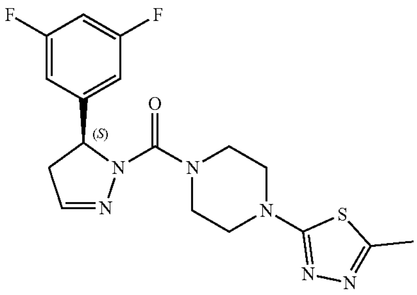

-continued

385

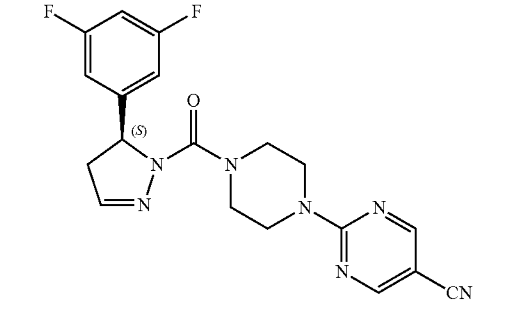

386

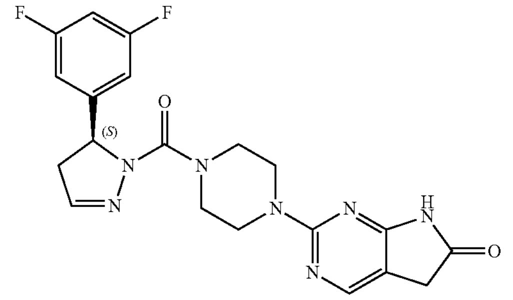

or a pharmaceutically acceptable salt, or a hydrate of the compound.

16. A pharmaceutical composition comprising a therapeutically effective amount of a compound of claim 1 in unit dosage form and one or more pharmaceutically acceptable excipients.

17. A method inhibiting necrosis, ferroptosis or human RIP1, comprising administering to a person in need thereof a compound of claim 1.

18. The compound of claim 1, wherein: the substituent(s) of $R_1$ are selected from halogen and CN; and/or the substituent(s) of $R_5$ are selected from halogen, —R', —OR', =O, —NR'R", —CO2R', —CONR'R", —NR"C(O)R', and —CN, wherein R' and R" are each independently selected from hydrogen, unsubstituted (C1-C4)alkyl, and unsubstituted (C1-C4) heteroalkyl, wherein the (C1-C4) heteroalkyl has at least one heteroatom selected from N, O, and S.

19. A compound of structure:

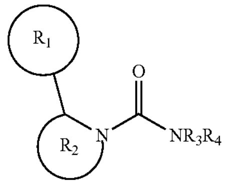

or a pharmaceutically acceptable salt, or a hydrate thereof, wherein:

$R_1$ is substituted or unsubstituted phenyl or substituted or unsubstituted 2-, 3- or 4-pyridyl, wherein the substitute(s) of $R_1$ are selected from halogen and CN;

$R_2$ is dihydro-pyrazole or isoxazolidine; and $R_3$ and $R_4$, together with the nitrogen atom to which they are bound, are linked to form a 4-6 membered N-containing, heterocycloalkyl ring, wherein the formed 4-6 membered N-containing, heterocycloalkyl ring is fused to phenyl, or wherein the 4-6 membered N-containing, heterocycloalkyl ring is linked through a linker to $R_5$;

wherein the linker is —$CH_2$—, —O—, or =CH—; and $R_5$ is (a) substituted or unsubstituted phenyl;

(b) substituted or unsubstituted 2-, 3- or 4-pyridine;

(c) substituted or unsubstituted naphthyl or 3-azanaphthyl;

(d) substituted or unsubstituted 0-3 heteroatoms cyclohexyl, cyclopentyl, wherein the heteroatoms are selected from N, O, and S; or (e) substituted or unsubstituted 0-3 heteroatoms cyclopentene or cyclopentadiene, wherein the heteroatoms are independently selected from N, O, and S; and wherein the substituent(s) of $R_5$ are selected from halogen, —R', —OR', =O, —NR'R", —CO2R', —CONR'R", —NR"C(O)R', and —CN, wherein R' and R" are each independently selected from hydrogen, unsubstituted (C1-C8)alkyl, and unsubstituted (C1-C8) heteroalkyl, wherein the (C1-C8) heteroalkyl has at least one heteroatom selected from N, O, and S.

20. A method inhibiting necrosis, ferroptosis or human RIP1, comprising administering to a person in need thereof a compound of claim 19.

* * * * *